United States Patent [19]
Klinger et al.

[11] Patent Number: 6,071,717
[45] Date of Patent: Jun. 6, 2000

[54] POLYCYSTIC KIDNEY DISEASE GENE AND PROTEIN

[75] Inventors: Katherine Klinger, Sudbury; Timothy Burn, Northborough; Timothy Connors; William Dackowski, both of Hopkinton, all of Mass.; Gregory Germino; Feng Qian, both of Baltimore, Md.; Gregory Landes, Northborough, Mass.

[73] Assignees: Genzyme Corporation, Framingham, Mass.; Johns Hopkins University, Baltimore, Md.

[21] Appl. No.: 08/658,136

[22] Filed: Jun. 4, 1996

Related U.S. Application Data

[63] Continuation-in-part of application No. 08/381,520, Jan. 31, 1995, abandoned.

[51] Int. Cl.[7] .................. C07H 21/04; C07K 14/435; C12N 15/63; C12P 21/02
[52] U.S. Cl. .................. 435/69.1; 435/455; 435/471; 435/325; 435/252.3; 435/320.1; 536/23.5; 536/24.31; 536/24.33; 530/350; 514/44; 514/2; 514/21
[58] Field of Search .................. 435/6, 69.1, 252.3, 435/320.1, 172.3, 455, 471, 325; 536/23.5, 24.31, 24.33; 514/44, 2, 21; 530/350; 935/8, 9, 11, 22, 34, 62, 66

[56] References Cited

FOREIGN PATENT DOCUMENTS

95/34649 12/1995 WIPO .
9584573 12/1995 WIPO .

OTHER PUBLICATIONS

Turco et al, Nephrology Dialysis and Transplantation (1996) 11:10–13.
Van Adelsberg et al, Nature Genetics (Apr. 1995) 1 (4): 359–364.
The EPKDC, Cell (Jun. 1994) 77:881–894.
Hughes et al, Nature Genetics (Jun. 1995) 10: 151–159.
The IPKDC, Cell (Apr. 1995) 81: 289–298.
Sambrook et al, Molecular Cloning: A Laboratory Manual, 1989 Cold Spring Harbor Laboratory Press, NY p. 16.3–16.31.
Orkin et al, 1995, Report and Recommendations to the Panel to Assess the NIH Investment in Research on Gene Therapy.
Burn et al Human Molecular Genetics (1995)4(4):575–582.

*Primary Examiner*—Carla J. Myers

[57] ABSTRACT

The present invention involves isolated nucleic acid encoding human PKD1, and sequences derived therefrom. The invention also encompasses vectors comprising these nucleic acids, host cells transformed with the vectors, and methods for producing PKD1 protein or fragments thereof. In another aspect, the invention involves isolated oligonucleotides that hybridize only to the authentic expressed PKD1 gene, and not to PKD1 homologues. In yet another aspect, the invention involves isolated mutant PKD1 genes, and their cDNA cognates. Further provided are isolated oligonucleotides that discriminate between normal and mutant versions of the PKD1 gene. Methods and compositions for treating APKD or disease conditions having the characteristics of APKD are also provided.

23 Claims, 99 Drawing Sheets

THE PKD1 GENE PRODUCT

FIGURE 1A

```
TGTAAACTTT TTGAGACAGC ATCTCACCCT GTTCCCCAGG CTGGAGTGCA GTGGTGTGAT    60
CATGGCTCAC TGCAGCGTCA ACCTCCTGGG TCTACTTGAT CTGTAAACTT CGAGGGAAGG   120
TGTAATAAAC CCTCCTGCAA TGTCTTTGTT TTTCAAAATC TTTGTATTTC ACAGTTTAGC   180
TTCGTGGGTT GATGTTCTAT TTTGTTTTTG TGTGTGTGTG TGTGTGTTTT GTGTTTTTTT   240
TTGAGACACA GTCTTGCTCT TGTTGCCCAG GCTGGAGTGC AATGGTGTGA TCTTGGCTCA   300
CTGCAACTTC CACCTCTTGG GTTCAAGAGA TTCTCCTGCC TCAGCCTTCC GAGTAGCTAG   360
GATTACAGGC GCCGCCACCA CACCCGCTA ATTTTGTATT TTTAGTAGAG ATGGGGTTTC    420
TCCATATTGG TCAGGCTGGT CTCAAACTCC CGACCTCAGG TGATCCGCCC ACCTCAGCCT   480
CCCAAAATGC TGGGATTACA GGCGTGAGTC ACCGCACCTG GCCAATGTTC TATTTTTGAG   540
AACACAACAG TTCATAATAT ATTCTACATA GACCATACCT GTTATGTGTA GATAAACAGA   600
CTCTTTTCCC ATTTAACACC TTTTGCCTTA GGTTTATTTT TCTGGTATCA ATACTGGCAC   660
ACTTACTTTG TTTGCAGTTT CCTGTCTTTT TTTTTTTTTT TTTTTTTTTT GAGACAGAGT   720
CTCACTCTGT CACCCAGGCT GGAGTGAAGT GGCGGGATCT CGGCTCACTG CAACCTCTAC   780
CTCCTGGGTT CATGCGATTC TCCTGCCTCA GCTTCCCGAA TAGCTGAGAC CACAACTGTG   840
TGCCACCATG CCCAGCCAAT TTTTGTATTT TTAGTAGACA CGGGGTTTCA CCATACTGGC   900
CAGGATGGCT CAATCTCTTG ACCTCGTGAT CCACCTGCCT CCGCCTCCCA AAGTGCTGGG   960
ATTACAGGCA TGAGCCACTG TGCCTGGCCT TTTTTTTTCT TTTTGAGATG GAGTCTCACT  1020
CTGTCACCCA GGCTGGAGTG CAGTGGGGTA ACCTCAGGTC ACTGCGACCT CCGCCTCCCG  1080
GGTTCCAGTG ATTCTCCTGC CTCAGCCTCC CGAGTAGCTG GGATTACAGG CACCCACCAC  1140
CATGCCTGGC TAATTTTTGT ATTTTTAGTA GAGACGGGGT TTGCCACGT TGGCCAGGTT   1200
GGTCTCGAAC TCTTGGCCTC ATGTGACCCG CCTGCCTTGG CCTCCCAAAG TGCTGGGATT  1260
ACAGGTGTGA GCCACTGTGC CTGGCCTGGC TTTCTTGTTT CTTTTCTCCT CTTCTAGTTT  1320
CCCCCTTTTA GGCTAACAAT TATTCACTGT TAATAAAAAC CCTCAGGTCT GTATTTTATC  1380
AAGAAACATT TCCCTCACGT CTTCTTCCCT GAACCAAACA AGATCTCTGG CACATTTTAT  1440
TTGCTCTGTC TCACCACATG GATTTGTTT TTTTGTTTCT TGTTTTTTG AGATGGAGTC    1500
TCACTCTTGT TGCCCAGGCT GGAGTGCCAT GGCACAATCT CAGCTCACTG CAACCTCCAC  1560
CTCCTGGGTT CAAGCGATTC TCCTGTCTCA GCCTCCTGAG TAGCTGGGAT TACAGGCGCG  1620
TGGCACCACC CCCAGCTAAT TTTTGTATTT TTAGTAGAGA CGGGGTTTCA CCATGTTGGT  1680
```

```
CAGGCTGGTC TCGAACTCCT GACCTTGTGA TCTGCCCACC TTGGCCTCCC AAAGTGCTGG    1740

GATTACAGGC ATGAGCCACC ACGCCCGGCC CCCATGGTTT TTCAAATAGT TTAGAATTTC    1800

ATTTCCAGGT AACTAATTTG CTTCTTTAAA CATATGTCTT TTCTATTTAA GAAATCCTTT    1860

CTAAACAATT GCATTTTATT CCACAACCGC CTTCAAACAA TCATTGAGAC TTGGTTAATC    1920

TGTTTTGCTC ATTTGGCAGC AGTTCTTGT GGCTGTTTCT TCCCTCCACT GGAGTCCTTG     1980

AATCTTAAGT CTGTCATTTG ACTGCAATTA AAAGCTGGGT TTGGAATACA ATCGCAGCCT    2040

TACCATCCAC CTGCTGTGTG ACCTGGTAAA TTTCTTTTTT TTTTTTTGAG ACGGAGTCTT    2100

GCTCTGTTGC CCAGGCTGGA GTGCAGTGGC ACAACCTCTG CCTCCCAGGT TCAAGCGATT    2160

CTACTGCCTC AGGCTCCCTA GTAGCTGGGA TTATAGGTGC CTGCCACCAT GCCCAGCTGA    2220

TTTTTGTATT TTTAGTAGAG ATGAGGTTTC ACCATGTTGG CTAGGCTGGT CTCGAACTTC    2280

TGATCTTGTG ATCTGCCCGC CTCGGCCTCC CAAAGTGCTG GGATTACAGG CATGAGCCAC    2340

CACTCCCAGC CAGTTCTTTT TTTCTTTTTT CCATTTTTTT TTTTTTCGAG ACAGGATCTT    2400

ACTCTTTTGC CCAGGCGGGA GTGCAGTGGC ACAATCACGG CTCAGCGCAG CCACTGCCTA    2460

CTGGGCTCAC ACGCTCCTCC GGCCTCAGCC TCTCGAGTAC CTGGGACTAC AAGCGTGAGC    2520

CAGTTTGGCT AATTTTGGCT AATTTTTGTA GAAACGGGGT CTCGCCATGT TGGCCAGGCT    2580

GGTCTCCAAC TCCTGGACTC AAGGGATCCA CCTTCCTCCC CCTCTCAAAG TTCTGGGATT    2640

ACCGGAGTGA GCCACTGTGC CCTGCTGGCA AATTTCTTAA ACTGTCTGTG CCTCAGTGAC    2700

CTCATTTAAT AAAGGGAATA ATTGTAGCAC ACTTTTTCTA GAGCTGTGAA GATTCAATGG    2760

AATAAATAAG GCAATAAATG AATGGATGGG GAATGAAGGA TGTGGGTTTC CTCCCTCTTG    2820

TCTTTCAATA AGCTCTCACC ATCAACCTCC CATTGCCTGT TCTCTCTCTT CCCCCTCTCT    2880

CCCTCTGTCT CTCTCTCAGC CAGGAAACCT GGGGTAGGGA GGCTTGGAGC CAGCGGGTGC    2940

GTCGGGAGGC TGCGGGTACT GACTCGGGCC GCGCACGGAG ATCGCGGGAG AAGGATCCAC    3000

AACCGCGGAA GAAGGATCAG GGTGGAGCCT GTGGCTGCTG CAGGAGGAGG AACCCGCCGC    3060

CTGGCCCACA CCACAGGAGA AGGGCGGAGC AGATGGCACC CTGCCCACCG CTTCCCGCCC    3120

ACGCACTTTA GCCTGCAGCG GGGCGGAGCG TGAAAAATAG CTCGTGCTCC TCGGCCGACT    3180

CTGCAGTGCG ACGGCGGTGC TTCCAGACGC TCCGCCCCAC GTCGCATGCG CCCCGGGAAC    3240

GCGTGGGGCG GAGCTTCCGG AGGCCCCGCC CTGCTGCCGA CCCTGTGGAG CGGAGGGTGA    3300

AGCCTCCGGA TGCCAGTCCC TCATCGCTGG CCCGGTCGCG CTGTGGCGAA GGGGCGGAG    3360

CCTGCACCCG CCCCGCCCCC CCTCGCCCCG TCCGCCCCGC GCCGCGCGGG GAGGAGGAGG    3420
```

| | |
|---|---|
| AGGAGCCGCG GCGGGGCCCG CACTGCAGCG CCAGCGTCCG AGCGGGCGGC CGAGCTCCCG | 3480 |
| GAGCGGCCTG GCCCCGAGCC CCGAGCGGGC GTCGCTCAGC AGCAGGTCGC GGCCGCAGCC | 3540 |
| CCATCCAGCC CGCGCCCGCC ATGCCGTCCG CGGGCCCCGC CTGAGCTGCG GCCTCCGCGC | 3600 |
| GCGGCGGGC CTGGGGACGG CGGGGCCATG CGCGCGCTGC CCTAACGATG CCGCCCGCCG | 3660 |
| CGCCCGCCCG CCTGGCGCTG GCCCTGGGCC TGGGCCTGTG GCTCGGGGCG CTGGCGGGGG | 3720 |
| GCCCCGGGCG CGGCTGCGGG CCCTGCGAGC CCCCCTGCCT CTGCGGCCCA GCGCCCGGCG | 3780 |
| CCGCCTGCCG CGTCAACTGC TCGGGCCGCG GGCTGCGGAC GCTCGGTCCC GCGCTGCGCA | 3840 |
| TCCCCGCGGA CGCCACAGCG CTGTGAGTAG CGGGCCCAGC GGCACCGGG AGAGGCCGCG | 3900 |
| GGACGGGCGG GCGTGGGCGG GTTCCCTGGC CCGGGACGGG AAGCAGGACG CGGGCCAGGA | 3960 |
| CGCTCCCAGG GGCGAGGCTC CGGCGCGGCA CGGCGGGCCC TGCTAAATAA GGAACGCCTG | 4020 |
| GAGCCGCGGT TGGCACGGCC CCGGGGAGCC GAAAAACCCC GGGTCTGGAG ACAGACGTCC | 4080 |
| CACCCGGGGG CTCTGCAGAC GCCAGCGGGG GCGGGGCGCG GAGGCCGCGC TCAGCTGGGA | 4140 |
| GGACAAACAG TCGCTAATTG GAGAGGAATT GGGATCGGCC TGGGGCTGCG GGGTACCCGG | 4200 |
| AGAGGTGGGG ATGGCTGTAG GGGGCGGCAG GGAAGAGTTC CAGGAGGTGT CTGGAAAAGG | 4260 |
| ATTTGATGGA TGTGCAAGAA TTGGGCTGAT GCTTAGGAAG GGGCGATGAG GTGGGTCCAG | 4320 |
| AAGAAGGGGG GTGAACGGTG TGAGCAAAGA CCGTGAGGCT GGAGGCTGGC CACGGGAGGT | 4380 |
| GTGAGGGGTA GGGGCAGGGT GGGAGGTGGG CTCGCGGGTG GCTGGGGTC ATGAAGGGCC | 4440 |
| TCAGGCGCTC TGCTATTGGG TTCCAAGGCT ATCCTGAGAA CAGGGGTGAG GGGGGATTGC | 4500 |
| CGTGGGGGGT TAAAGCCTTG TCATGTTCGC TTTCGGGAGA TAAAAACAAC AGGTGGCCTT | 4560 |
| TATGGAGACG CTGCCCAGAG CCAGGTCTGT GCCAGGCTCC TGTTGGGGGT CGTCATGCGG | 4620 |
| AATCCTGACT CTGACCATCC GAGGCATAGG GACCGTGGAG ATTTGCATTT CACAGATGAG | 4680 |
| GAAACAGGTT TGGAGAGGTG ACACGACCTG TCCCAGGCAT CACAGCCGGG ATGTGCATAG | 4740 |
| CAGGGGTTTG GAACTATGAG GTGCCCAGGA CCCAGGGTTG GATTGAAAAG GGCGGAGGGG | 4800 |
| ACTAAGATAA GCAGACAGTT GTCCCAGCG CTGGGGAGAG TCTTGGGACC AGTCTGATGC | 4860 |
| CTTGTATTTC CCAGGCTCCA GGCTCCTCGC CGGGACAGTG TCTCCTTGGG TGCGTGCTGG | 4920 |
| ATCCCTGGGG GACGTGGCAC ATCCCCAGGC TTGCTAAACA TTGGGTGGGT TCTGGCATTT | 4980 |
| GGTTTTGTAA CGTTTCTGGG TCACTCCCGC CTGTGGCCAC CCTTCCTTAG GGGAGCCGTG | 5040 |
| TGTCCTTGGG GCTTTGCTGG GTGGTCTCGA GGGTGGGAGA AGAATGGGTT CTCCTGGACC | 5100 |
| AATGGAGCCC GTGCCCCTCG GGGCCACATT GCTCCTGCGC TCCCTGACTG CGGACGCGTG | 5160 |

```
TGTCTCGCGG CTGTCTCTGT GGAGATGGCC TCCTCCTGCC TGGCAACAGC ACCCACAGAA    5220

TTGCATCAGA CCTACCCCAC CCGTTGTTTG TGATGCTGTA GCTGAGGGCT CCTCTGTCTG    5280

CCAGGCCGGT CACTGGGGAC TCTGTCCAGG GCCTGGTGGT TCCTGCTTCC CAGCACCTGA    5340

TGGTGTCCAT GAGAGCAGCC CCTCAGGAGC TGTCCGGGAG AGAAGGGCGC TGGTGGCTGC    5400

TGAGCGGAGA GCAAGGCCCG TGTTCTCCAG GCCCTTGGCA CAGCAGTGGA GCCCCGCCC    5460

CTGCCTTGTG TTGTCCTCTT AGGCTCTGGT CCTGGGGTTT GGAGGAGGGG GACCCTGGGA    5520

GTTGGTGGCC TGTCCCAGCC TGAGCTGGCA AGATTCCGAA TGCCAGGCCC CCCAAGTGTG    5580

CAACAGGGCA CAGGGTGACC TCATGTGGGC AGGTGGGTGC TGTTCTGTAC ACCTGGGG     5640

CCGCCGCTGG GAGAGTTCTG GAAGGTGGGG TGAGGGACC CATGGCAAAC TAGGGCCTTA    5700

GGAAGGATGT GAAGGCCCTG GCTGGCCCCC CAGGCCACCC TCTGTGCTGT GGGGCAGCCC    5760

AGCCATTTTG CTGTCTACCC TGCAAACTCC TCCTCGGGGA GACGGCTGGG TTTTCCCCAG    5820

GGAAGAGGGG TCAAGCTGGG AGAGGTGAAG GACACAGATC ACAGCTGCTG GCAGGTGTTC    5880

AAGGGTCCAA GAGCGTTGCT GTCTGGGTGT CACCAGTAGC CTTCCTGGGG GGCTCACGCA    5940

GGTGCCTCTC CACTTGTGGC TCCCTGGCTG CTGAAGCTCA GCAGGGACAG CTGTGTCCAG    6000

TTCCAGGTGG AGGACAGCCG GGGCTTCTGA GGCCACAGCC TGCCTTGGGT TAATGATGCT    6060

GCCGAGAGGT GGTGGCTTTT GGAAAAGATG GCGTACTGCA AAACGTGCTG CTCTGCGTGG    6120

CTCGAAGCTT CGTGGGGAGA CGTGGGCAGA GCCGTGGCTG ACTCACAGAC CCCCCACCCC    6180

AGAGCCTGCC CTGCCCTCCC TGCCCCGACC CTTCTCCCTC CTGACCCATG TGTTTTTTT    6240

TTTTTTTTTT TTTTTTGAGA CAGAGTTCAC TCTTGTTGCC AAGGCTGGAG TGCAATGGCA    6300

CGATCTCGGC TCATGGCAAC CTCCGCCTCC TGGGTTCAAG CGCTTTTTCC TGCCTCAGCC    6360

TCCCGAGTAG CTGGGATTAC AGGCGTGCAC CACCATGCCT GGCTAATTTT GTATTTTAG    6420

TAGAGACAGG GTTTCTCCAT ATTGGTCAGG CTGGTCTTGA ACTCCTGACC TCAGATGATC    6480

CGCCCGCCTC GGCCTCCCAA AGTGCTGGGA TTACAGGCAT GAGCCACCAC GCCCAGCCCT    6540

GACCCATGTT TTGAACCAAA TTCCAGCCAC CCTTTTATCT GCAAGCATTT TGGAGGGCAT    6600

CGCAATACTG CAGACCCACC TAACACAACA GACAGTTCCT TCATGCCACC GAAGGCCTGG    6660

TGTGTTCACA TTTTTGGTTT AATAGTTTGA ATTAAGAGCC AAATAAGGTC CACACACTGC    6720

AATTAGTTGA TGTCTTTTTT TTTTCTTTT TTTTTTTTT TTGAGACGG AGTCTTGCTC    6780

TTGTCTCCAG GCCGCAGTGC AGTGGCATGA TCTCAGCTCA CCGCAACCTC CGACTCCCTG    6840

GTTCAAGCGA TTCTCCTGCC TCAGCCTCCC GAGTACCTGG TAGCTGGGTT TACAGGCATG    6900
```

| | | | | | | |
|---|---|---|---|---|---|---|
| CACCACCGTG | CCCAGCTAAT | TTTTGTATTT | TTAGTAGAGA | CGGGGTTTTA | CTGTGTTGGC | 6960 |
| CAGGATGGTC | TCGATCTCCT | GACCTCGTGA | TCTGCCCACC | TCGGCCTCCC | AAAGTGCTGG | 7020 |
| GATTACAGGC | GTGAGCCACC | GCACCCGGCC | AATGTCTTTT | AAAAATATAT | ACTTTTTTTT | 7080 |
| TTTTTTTGAG | ACGGAGTTTC | GCTCTTGTTG | CCCAGGCTGG | AGTGCAGTGG | CGCGATCTCA | 7140 |
| CCTCACGGCA | ACCTCCGCCT | CCCGGGTTCA | AGTGATTCTC | CTGCCTCAGC | CTCTCCAGTA | 7200 |
| GCTGGGATTA | CAGGCATGTG | CCACCATGCC | TGGCTAATTT | TGTATTTTTA | GGAGAGACGG | 7260 |
| GGTTTCTCCA | CGTTGGTCAG | GCTGGTCTCA | AACTCCTGAC | CTCAGGTGAT | CCGCCTGCCT | 7320 |
| TGGCCTCCCA | AAGTGTTGGG | ATTACAGGTG | TGAGCCAACG | CGCCCAGACA | AAAATATATG | 7380 |
| TGTGTCTTTA | AGGCTGGTCA | AGCAAAGCAG | TAGGACTGGA | GAAAGAATGA | AGAATTCTAC | 7440 |
| CTGGCTGTGA | TCAATTCGTT | GTGAACACCA | CTGTGCTTGG | ACCAGCTAGC | TGATGTCTTT | 7500 |
| TGTTTTGTTT | TGTTTGAGAC | GGAGTCTGGC | TCTGTCACCC | AGGCTGGAGG | ACAATGGTGT | 7560 |
| GATCTCGGCT | CACTGCAGCC | TCCATCTCCC | GGGTTCAAGC | GATTCTCCTG | CCTCAGCCTC | 7620 |
| CTGAGTAGCT | GGGATTAGAG | GCGCGCGCCA | CCACGCCCGG | CTAATTTTTA | AAAATATTTT | 7680 |
| TAGTAGAGAT | GGGGTTTCAC | CATGTTGGTC | AGGCTGGTCT | TGAACTCTTG | GCCTTAGGTG | 7740 |
| ATCTGCTTGC | CTCGGCCTCC | CAAAGTGCTG | GGATTACAGG | TGTGAGTGAT | GTATTTTATT | 7800 |
| TATTTATTTA | TTTATTTATT | TTTATTATTT | GAGATGGAGT | CTCACTCTGT | TGCCCAGGCT | 7860 |
| GGAGTGCAGC | AGTGCCATCT | CAGCTCACTG | CAAGCTCCGC | CTCCTGGGTT | CACGCCATTC | 7920 |
| TCCTGCCTCA | GCCTCCTGAG | TAGCCTGGAC | TGGTGCCCGC | CACCATGCCC | AGCTAATTTT | 7980 |
| TTGTATTTTT | AGTAGAGACG | GGGTTTCACC | GTGTTAGCCA | GGATGGTCTG | GATCTCCTGA | 8040 |
| CCTCGTGATC | CTCCCGCCTC | AGCCTCCCAA | AGTGCTGGGA | TTACAGGCTT | GAGCCACCGC | 8100 |
| CTGTCTTTTA | AATGTCCGAT | GATGTCTAGG | AGCTTCCCTT | CCTCTCTTTT | TCCTTGTGCA | 8160 |
| ATTTGTTGAA | GAAACTGGCT | CCTGCAGCCT | GGATTTCTCG | CTGTGTCTTG | GGGGTGCCAC | 8220 |
| CTCCATGGTG | TCACCTCCGT | GGTGCTGTGA | GTGTGTGCTT | TGTGTTTCTT | GTAAATTGGT | 8280 |
| CGTTGGAGCC | GACATCCCAT | TGTCCCAGAG | GTTGTCCTGG | CTGGCACTGG | CCTAGGTGTA | 8340 |
| GATGTCATCA | GCTCAGGGCC | CCCTGCTCTA | AAGGCCACTT | CTGGTGCTGG | TTGCCACTCA | 8400 |
| CCCTGGCTGG | GGGTCACCTG | GTCTGCTGC | TGTCTCGCAA | ATGCTGGGGT | CCAGGACTGG | 8460 |
| GCACATCGAG | GGACTTGGTA | GGTGCTTGGT | TCACTGATGT | AAAATATAGG | AGCACCCGGG | 8520 |
| GCCTTGCCCT | TTCCCACCTG | CATCCCTGAA | TGACAGGAGA | GTGTGGGAGA | GTGTAGGGAC | 8580 |
| AGCAGGCGCA | GACCCCGGGG | CCCCTGCCTG | GGATTGGCGT | CGGGGAAGAC | AGGCATTCTG | 8640 |

```
GAGCGACCCC TAGGCCTGAT GCCTTAGAGC GCAACTGCCA GAGACACAGC TTCCTTGGGG    8700

GGCTGGCCAG GCCACGGAGG GGCCCTGGCT CCCATTTCTG GTCCCTGGAT CCTGAGAGCG    8760

AGGACTAGGG ATTGTCACCA AGGCCTCCAT GAGCCCTCAG CAGAAGGAGG GCCACCCTCG    8820

AGGGCTCCGT TATCACTGGA GCCCGCGTTC AACCAACACG CAGATGATTC TCCAAGGACA    8880

GAGATGGATG ATGGGGAGGG GGCTGGCCTG GAAGGACCCC CAGTGCAGGT GACATTGAAG    8940

CCAGGTTTCA AAGCTCCCAC AGGGAGCTGC CAGAGAGAG TCCCCAAGGG GCAAGGTGAC     9000

TCGGGGGCAG GGGTAGGGCC TCTGTCAGGA GAGCCTAGGA GAGGCCTGTG TCTTCTAGGA    9060

AGAGCCCTGG CAGCCGAGCG GAGGCAGTGG TGAGGACCTG CATCCTGCAT GTCCAGCTGG    9120

CCTCACCCGG GGTCCCTGAG CCGGGTCTTA CGTGGCTCCC GCACTCGGGC GTTCAGAACG    9180

TGCCTGCGTG AGAAACGGTA GTTTCTTTAT TAGACGCGGA TGCAAACTCG CCAAACTTGT    9240

GGACAAAAAT GTGGACAAGA AGTCACACGC TCACTCCTGT ACGCGATTGC CGGCAGGGGT    9300

GGGGGAAGGG ATGGGGAGGC TTTGGTTGTG TCTGCAGCAG TTGGGAATGT GGGGCACCCG    9360

AGCTCCCACT GCAGAGGCGA CTGTGGAGAC AGAGAGCACC TGCAGGTCAT CCATGCAGTA    9420

TCGGCTTGCA TCCAGATCAT ACAGGGAACA CTATGATTCA ACAACAGACA GGGACCCCGT    9480

TTAAACATGG ACAAGGGGTC ACTCACGCCT GGAATCCCAG CAGTTTGGGA GGCCAGGGTG    9540

GGTGGATCGC TTGAGCCCAG GAGTTTGACA CCAGCCTGGG CAACAGGGTG AGACCCCGGT    9600

CTCTAAAAAA TAAAAGAACA TTGGCCGGGC GTGGTGGTAT GCATCTGTGG TCCCAGCTAT    9660

TCAGGAGACT GAGGTGGGAC ATCACTTGAG CCGAGGAGGT CAAGGCTGCA GTGAGCTGTG    9720

ATCACACCAC TGCACTCCAG GCTGGGTCAC AGAGCAAGAC CCTGTCTCAA AAAAAAAAA    9780

AAAAAAAAA AAAAATCACA GGATCTGAAC AGAGATTTCT CCAAAGAAGA CGCACAGATG     9840

GCCAACAGCG TGTGAGAAGA TGGTCGGCCT CATTAGTCAT GAGGGAAACG TAAATCAAAA    9900

CCACTGTCCA GCCGGGCGCG GTGCCTCACG CCTGTAATCC CAGCACTTTA GGAGAGCAGA    9960

TGGCTTGAGG CCAGGAGTTT GAGGCCAGCC TGGGCAACAT AGCGAGACCA ATAAATAGAT    10020

ATTAGTGGTG GCGCCTGTAG TCCCAGCTAG TTGGGAGGCT GAGGGGGGAG GATTCCCTGA    10080

GTCTATGAGG TTGAGACTGC AGTTAGCTGT GATGGTGCCA CTGCACTCCA GCCTGGGCGA    10140

CTAGGAAACG GTCTTTAAAA AAAAAAAAA AAAACAGGGT GGGCGCGGTG GTTCACGCCT    10200

GTAATCTCAG CACTTTGGGA GGCCAAGGTG GGGGATCAC AAGGTCAGGA GTTTGTGACC    10260

AGCCTGACCA ACATGGTGAA ACCCCGTTCT ACTAAAAATA CAAAAATTAG CGAGGTGTGG    10320

TCGTGGGCGC CTGTAATCCC AGCTAATTAG GAGGCTGAGG CAGGAGAATC ACTTGAACCC    10380
```

```
GGGAGGCGGA GGTTGCAGTG AGCCAATATC ACACCACTGC ACTCTAGCCT GGTCAACAGA    10440

GCGAGACTCT GTCTCAAAAA AAAAAAATGC TGAGCGTGGT GGCGCATGCC TGTAGTCTCA    10500

GCTACTTTGG GGGCTGAGGC AGGAGAATCG CTTGAACCTG GGAGGCAGAG GTCGCAGTGA    10560

GGCAAGATTG CACCATTGCA CTCCAGCCTG GGAGACAGAG TGAAACTCTG TCTCAAAAAG    10620

AAAAGGTCTA GGAAGAGTCC GCACCCTCTC CCGCGGTGG CCACGCCGGG CTCCGCGCTG     10680

AGCCCTCTGT GTTCTTGTCT CTCCATACCT CATCACGGCA CCGCAGGGTT GCAGCCACTC    10740

CTGGTCTCAT TTTACACACC AGGAAATTGA GGCTCTTTGA GAAGCCGTGG TGATGATTTC    10800

ATCAGCATGC TCTGGGGCAG ACCCCTGCAG CCGCACAGGG TGCCTGGGGC CCACACTAGT    10860

GCCCTGGTTT ATAGACAGAC AGAGGTGGCA GTGGCGCTTC CGAGTCGGGC TGCGATGTGC    10920

TTGCACTCCC CGAGGGGCTG AGGGGCCCTG CGCCCAGGTG CAGCTGCTTG GGTGCTGCCA    10980

GCCCCTCCCA CCTCTCCCTC CCTGCCAGCC CCTCCCACCT CTCCCTCCCT GCCAGCCCCT    11040

CCCACCTCTC CCTCCCTGCC AGCCCCTCCC ACCTCTCCCT CCCTGCCAGC CCCTCCCACC    11100

TCTCCCTCCC TGCCAGCCCC TCCCACCTCT CCCTCCCTGC CAGCCCCTCC CACCTCTCCC    11160

TCCCTGCCAG CCCCTCCCAC CTCTCCCTCC CTCCAGCCCC TCCCACCTCT CCCTCCCTGC    11220

CAGCCCCTCC CACCTCTCCC TCCCTGCCAG CCCCTCCCAC CTCTCCCTCC CTGCCAGCCC    11280

CTCCCACCTC TCCCTCCCTG CCAGCCCCTC CCACCTCTCC CTCCCTGCCA GCCCCTCCCA    11340

CCTCTCCCTC CCTGCCAGCC CCTCCCACCT CTCCCTCCCT GGCTCATCCC TGCTGTGTCC    11400

CTTCTCTCTA GTTTCCTGTT CAGTTTCAGG AAGGAGGCTG GGAACCCAGA TGTAGGGAAT    11460

TTGCGCCCTG GAGTCAGACC TGGGTTCACG TCCCAGCGCC TCCACCTCTG GTGTGACCTT    11520

GGTCCAGTCT CTCAGCCTCA GTTTCCTCAC CTGTAAAGTG GCTCCATGA TTAGATGCAC     11580

CCTGCAGGGC AGTGTAGCAG TGACCTGGCT CAGCCACTGG CAGCCCCAAC AATCATACCT    11640

TGTTAAAGTA GCTCTGTCGG TTCCCTCAGG GGTTCCGGGG GCCCATTCCC CTGTCCTCCA    11700

TGCACTGTGA GACCTGCCCT GCCACAGAGC AGAGTGTAAC AGCCTGAGGG TGAGAGCCAG    11760

ACACTGTGCC TGTGCTTAGA CCAGACACTG GACGACGGGA GCCAGTGCAG CCTGGGCGGG    11820

TGGACTCCTA TGGACCCCTC AGCACCCAGC CTCGGTGCCT TCAGCGCAGG GCCGCGTGGC    11880

TGTGGGGGCT CACAAGACCC GGCCCACTCC TGCTTGTGCC TACATCTGGG TGTTTGCCCA    11940

TTGGTGCCTT TTGACGCGTT CTGGTGTGTG TGAGACGTGC GGGGCTGGGA AGTGTTGGCA    12000

GAGCCGCGAG TACCGTCCTC ACTCCTTTTG TTCTTTTGAC GTAAGCTGGC GAGTGGCACT    12060

GCCTGAGTTC CGCTCAGTGC CGCCCTGAT GTGCGGACCC CGCTGCATTC TTGCTGTTAG     12120
```

| | | | | | |
|---|---|---|---|---|---|
|GTGGTGGCGG|TGTGCGCTGT|CGCTGGTGGG|CACCGAGAGT|CTTTGGGAGC|TTTGGGGAGG|12180|
|TTGTGCCAAG|CCTGAGCCTC|GACGTCCCCC|TTCCCGGCTT|TCTGTTGGCT|CTTCTGAGGC|12240|
|CAGGGCATCT|CTATGAGGGC|CTCCTGCTGG|AGCCGTCTCT|GTGGATCTCC|TCTGCCATCC|12300|
|TGGCCCATGA|GTGGGTGATG|CGCTGGCCAC|CATCTGGTGA|CAGTGGCCGG|GCACCGCTGC|12360|
|CAAATGTGGG|TCCCGCATCT|GCAAGCCCCT|CCCTGGGTCC|CCTAGGGTAT|GGGGTGGTTC|12420|
|TGCCACTGCC|CTCGCTCCCC|CACCTTGGGG|TGCCTCTCCC|CCTGCTCGTG|GGGGAGACCC|12480|
|TGCCTGGGAT|CTGCTTTCCA|GCAAGGAATA|TACTTTGGAG|GGAGACACAC|ATGTTCTTTT|12540|
|CTGGAGCTCT|GCAGTGGCCA|CGGCAGCCCA|GCCCGCCAAG|CACCCTGGAA|TGAAAACATC|12600|
|CCGCTGCTGT|CTGGGCCTGG|CCTGCACTCT|GCTGCCTGCG|CTCCAGCTGG|CTGAGGCCGG|12660|
|GCACGTCTGC|GGGCACAGCA|GCGGGGCGC|CACAGTCTCC|CTGCAGAGTG|AGCGCAGCTG|12720|
|GAAAATGCAG|CTCACGCCCT|TTCCCAGAAC|ACCTCGCTCT|TCATGGCTTG|CAGCTGTCC|12780|
|TTGCCTAGGG|GCCAGGGTGC|CCAGGCACTG|GTGGCAGGAG|AAGGGCTACA|TCTGGGGCTG|12840|
|AGGCGGGCTG|GGTCCTTTTC|TCCCTGCAGC|TCCCGAGGCC|CAGCCCTGGC|CCAGCCTGGC|12900|
|ATTCCTGACC|TTAGCAGCGC|CATGATCTGA|AGACAGGCTG|GCTTCTGTGA|GGCCACCTCA|12960|
|GAAAGGGCTT|TGTGCCCAGG|CAGAGGCGGA|AGCCAGCTCT|TCCTTCTGGT|TGAGGCAGGA|13020|
|ATGAGGCCAG|CGCTGGGCAA|GCCCATGCCC|AGGGAACGTC|ACAGCTGTGG|GAGTACAGGG|13080|
|GCTCCGGGTT|CTGAGCCCGT|CCACTGTGCA|TCGTGGCCCT|GGCCTCAGGA|TGGCTCGTAC|13140|
|CATCATTGGC|TGTGCCCACA|GCCGAGTGGG|TGATGGGATT|CCGGCTGCCC|CGCTGGATCT|13200|
|GTGCTGCTGC|CCTCTCCAGG|GCACTGCTGT|GCCCGCACAG|CCGGGCGCAG|ATGGCCAGTT|13260|
|TGCTTGCCCC|CCCCCCCACC|ATCCTCTTCC|TACCTTGGCT|TCCTCCATTG|ACACACTGGA|13320|
|CCCTGCTGGC|TGCCCGGGGA|GGTGTTTGGG|GGATGGTGTT|GGGGGAGGAG|GAGGGCCCCT|13380|
|TGAGCCTCAG|TGTGCCCATC|AGGAGCGTAA|GGṪCAGTGCA|GCACCTGCCC|ACACAGGCTG|13440|
|TGAAGGGTGG|GAGTGGAGAG|GGATGCAAGG|GGGTCACAAC|GCCTGGCTCC|ATGTCAGCTG|13500|
|CGTGCAGGGG|CACCAGGAGC|CGGCCCTCAT|TCTCCCCTTG|AACTGGAAGG|GTGGCCCCGA|13560|
|CCCCAGCGGC|AGGTAGCATA|CGTATGAAGC|GCTCTCCTTC|CTACACCCCA|CAGGTGGGCT|13620|
|CGTCTCCAGA|CGGCCCTTTT|TGAGCTGGCT|GTGTTTTCC|ATCTGTGTAG|GCAAGGACAT|13680|
|CGCAGACTCC|CCTTTCTCAT|CTCCCTCGTT|CAGCCTCCGA|GGCCGGAGTC|TCCATCCCTG|13740|
|TGCCTGCCTG|TGGGTCCCGG|GAGGACCTGA|GGCTGCCCAT|GTCACCCCCG|GCATCTCATC|13800|
|CTGGGGACAG|TTCAGCCGTG|GGAGGGATCT|GTAAGGACAG|AATGCCGCTG|AGCCTGGGGC|13860|

```
TCCCCAGCTA GTCTCACACC CCGTGTCTGG GACCCAGAGA CCCTCGTGCA GGGCTCTGTT    13920

GCTTGGGGCC TGGCAGCCTC GTCCTGTATC AGAGGCTGCC ACCCCCACCC CTCGTGGGGC    13980

CAGGGTTGTG GCCGGCCTCC CTGGCCCTCC CCATGGAAGT GGTAGGCGGA GCCAGCAGCC    14040

ATCTGCCCAG CCCGGGGCTG CACTGTTTTT TTTCAAATGA GCACCGTCCC AAACTGCAGC    14100

CCGTTAATTT AAACAGGATC ATTTCCGGCC CTGGAAGCCG CCTCACTCTC CTTAAATAGA    14160

AAGGAGCACA GCGCAGAGGG AAACAGATGA GGTCATGGCT CGGCTGGCCC AGCGAGGAAG    14220

GGGCCGCAGT GGGGGTGGCA CTGCCGCCTG TCCCTGTCC TCTCCAGCGC CCACACTGCA     14280

GCCCATTTCC TCACCCTGGG CCTGCTCTCG GGAGGGACGG GCCTGGGGGT CCTCTTGCTG    14340

GGCGGAGGGG AACCAGCTCC TCCAGGAGAG GACGGGGCCT GGCAGGGGGC ATGGGCCTC    14400

CCTGGGTCTG GCGTCCTGTC CTGCCCCTGC CGAGGGAGGA GCGGTTACAT AAGCTCCGCA    14460

GGCGGCCCCT CCGAGCCGGT CCCCCAGCC CAGTTTCCAG TGAGGCGGCC AGCGCGGGCG     14520

GGGGTGCCGG GCCTGGCGCA CACCCGCTGC TGACCACACG TGTCTGGAAT GTGCAGATGT    14580

TTCTTTGGGG GCTCCGTCCG GCCCCAGAC CCCACTCAGC ATCTGGTCTG GGGAGTGGGC     14640

GCCTGGGGCA CTCAGCTCTG AGTGTGAGAC TCTGAGGCAG GTCTGGTTTG TCTGGGGCCA    14700

TTCCCTCTGC TGTGGATTGG GAGGGCCCCG GGAGCTGCCC CACACCCAGG GAAGTTCTCC    14760

TCAGTCCCAC TGTTGCATTC CCCGACCCCG GCTCCCCGG CCCAGGAGCG CCTGTGGGGC     14820

AGAAGGCCCA GCCCCAAGAC TTCCCGGCCC TGCCAGCCTC AGGCTTCACC CACCCTCGCG    14880

CCAACTGTGG GCAGAGCCCA GGGGGAGGGC AGGAGAGCCA GCGCCTGGCT GGGAACACCC    14940

CTGAGGGGCC GAGGCTCCAG GGCGAGGGGG CCCGACCTGG GGTTCACACG CCCGGGTGGC    15000

GGGCAGACCC GCTGCAGCAT GAGACACGTG TCAGCTACCT CGGGCCGGCA GGCTGGCCCT    15060

GCTGCCCACA GCCCTGGGAC GTGGCCCCAC CTGTGACGGG TGTGGAGGGG CAGCCTCCAG    15120

GCCTGGCCAC ACCCTCTGCT GTTGCTGCTC CTGCTCCAGG ATTGGCAAGG GTGCTGGGAA    15180

GGGGTGAAGA CCCGTACTGT GGCCACACAC CTGGGACTTC CTTCTCCACC CAGTGGTGCC    15240

CCAGCAGCCG CTAAGGAGCC CGCTGGGTCC CACGCTAGGA TGGTCCTAAC TCCTCCCGCC    15300

TTCCAGATCG GACGCTCGGC GCTGGGGACC CCTTGTGTCC CGGGGCTGGG GCACCGTCCT    15360

GCCCCCATGG GGGTGTACTC CTCCCGACAA GCTTGGCTTC AGCTTCCCTG GGAGCACATC    15420

CTGGCCCTCG GCACCCATC AGGCTGTCCC TGTGCACCTG GCTCCCACCC TTCCAGCTCA     15480

TAGCAGGAAC TGGGGTGAGG AGTGCGTGGG GCAGCAAGGG CCTGGGACCC CAGAGGACCC    15540

TGCACTCTGC TCTGTGCTCT TGCCTGGGCT TAGGGCCGCT CGGTGGTCCT GCTGCCAGAT    15600
```

```
GCCTGGGCCC TGCTGTGTCC CCCATCCTTG CAGGGAACCA GAACGTGGGG GCAGGGCATC    15660
AGACAGCGGC GATGATGTCA CCTGGCGGGT GCAGAGGAAG CCCGAGGGGC GGGGTGGGGG    15720
GGCTGGCGCG AGGCTGCCTG GCTAGGCCTT GGCGTTCCCC CAGAACGGCG ATGGCAAAAG    15780
CAGATGGAGA CGTGAAAAAG TACGGGAGCA AGCGAGGTGA GGACTCCACG GGGACCCCTG    15840
TGCTGTTCCC TGTCCCTGAA GCCCACACCT GAGTCCTGCC CAGGGCAGAT GCTTCCACAC    15900
CCAGGGGGCA CCTGAGTCCT ACCCAGGGCA GACGCTTCCA CACCCTGGGG GCTGGGGAC    15960
TGCACCTGGC TCCTGTCTGG GCCCAGCTT CATTCCACTG CCCTGGGCCC TGGGAGCTCG    16020
GCCGAGCGGG GTCCCCAAGA CCTTGCTGCA TTTCTGGGCC TTGGGCTGGG GTGAGGGCCG    16080
GGAGAAGGAG CCAGCCTGGA GCCTGGCACG CAGGGAGTGC ATGGCCAGAA CCGGTGACAG    16140
GCAGGGCTGC CTGCTGGCGT GGAAGAAGTG TCCATGGCAC CCCCAGGCCT GGTTCACAGT    16200
GGGATGGGCG GGGAGCCGGG GGGCTCTGGG GTCCTCGGCT GACCTGCCCC CACCCCTGCC    16260
CTGGCTTGTC AGCTCCCAGC AGCAGCCACT CTTGATGGAT TTTCCAGAAA ATGAGGTGTG    16320
GCCAAACATC TTCAGGCTTT TCCTTCTTTC CTTTCTCCCG TGGCCTGGGT GGGAGCTGCT    16380
CCCCATGCCT GGGGGCAGGT GCGAGAGCCT GTGCCCCTCC CTGGGGCAGT TTCACAGCTG    16440
TGTCCCTTCC AGGGGGCCTG CCTGTGTTCA CCGTGGCCTC TGCAGCACCT CTCGCCCCTT    16500
AGGGCTCCTG CGCCTCGGGT CCCGGTGCCT CATTTCTCCC TAAAGCATTG GTTCTGCTGC    16560
CGCCGCAGCC GCTGGAAAGT CCCTCCTCAG GTCTAACTGC AGTTCCTCAC GGCACAGTGT    16620
TCCCCCTCGG GCATGGTGCT TGGGCAGTGG GTGTGAGTCC AGCTGCCTCA CCCTGTCTCG    16680
AGAATGGCCT CTTGCTGGTC TCCCAGCCAC CACCCTGTCC CACCCCACGG CGGGGATGGT    16740
GTGGATGCCT AGCAGCGCGG CTGTGGGCCC ACCCATCCTT ATGGGCAGTG GGGAGCACCT    16800
CAGCCCGTGT CCCTACCTTG GTGTAGAGGA GGGGACGGCA GAGAAGCAGG GTTCAGTTAG    16860
GGGGGAAGTG GTGGCCCTGC CGGAGGGGCC GTTCCCTGTG TGCCTGGCCC CCAGATCCTC    16920
TCCCCTCCCG GAGCCCAGGG CACAGGCATA GGCTCTCTGA GTGTCCCACA GCCCCTGGGG    16980
GAAGGGAACT GCACCCCCAA CCGTGCCCTC CATCCGCAGA TGGAACGAGA AGCTCCGGGA    17040
GCCAGTGCCC AGCGTCTCAT CTGTCTGGGC ACCCAGCCCA GGTGAGGGCC TGGCTCCACC    17100
GTCCGTGGCT GGTGCTGCTT CCTGGCACGG AGAAGGCCTC GGCTGCTCTG TCCCCTCAGC    17160
TGGGGTGGCC TCTGGTCCCC TTCTTTGTTG GTTCCCTTCT CAAGCTCTTG CCCTGGCCCC    17220
GGGCCCCACC GGGCAGCCTG TGTGTGCGTC TCTCCTGCGC CGGGTAGGCT CCTGTGGGAG    17280
CGGAGCTCCG GTGGGAGGAG CAGGGCTGGA GGCTGGCAGG GGCTGGGCGG GTGTTCAGGG    17340
```

| | | | | | |
|---|---|---|---|---|---|
| ATGGAGGCCG | CCCCGGCTTG | GGGCTGGCTG | CCGGGTGGTC | ATTGCTGGGA | AGAGCAAGTC | 17400
| TAGGCGGAGG | CACCTGCTGG | GTCACTCGTG | GGGAGGGTGA | CACCTGGGGA | AGTAGAGGCC | 17460
| CGTGGCAGGA | GGTGAGGCCT | CGGGGTCCTG | GGGAGCAGGG | GGGTGGTGTG | CAGACCTGCG | 17520
| GAGCCATAGT | CCTGTGCCAG | GAGCACTACT | GGGAGTGCGT | GGGACCAGGA | GGGGTGCCCA | 17580
| GGGTGGGCGG | CAGAGTGACC | CCCGAGGTGC | TTGAGGCCGA | GGGGAGGTGG | AGTTCTCGGT | 17640
| TTGCCCCAGC | TCTCTGTCTA | CTCACCTCCG | CATCACCAGC | TCCAGGACCT | GGTTTGTAAC | 17700
| TCGGGCAGCT | CTGAAAAGAG | AGACATGCTG | CCGCCCTGTG | GTTTCTGTTG | CTTTTTCTTC | 17760
| ACTGACTACT | GACATGGGAT | GTTTTCCTA | CGGCTGTGAC | CAATTGTGCT | TCTTCTAATT | 17820
| GCCTGGTTTT | TCTTTTTTTG | TTTTTGGAGT | TTTCTCTTTC | TTTCCTCCCT | CCCTCTCACC | 17880
| CTCCATCCTT | TTTTTTTTTA | TTTTTATTTT | TTGAGATGGA | GCTTCACTCT | TGCAGGATGG | 17940
| GGTGCTGGAG | TGCAGGGGTG | CGATCTCAGC | TCACTGCAAC | CTCTGCCTCG | CGGGTTCAAG | 18000
| TGATTCTCCT | GCCTAAGCCT | CCTGAGTAGC | TGGAATTACA | GGTGCTTGCC | ACCACGCCCG | 18060
| ACTAATTCTG | TAGTTTTGGT | AGAGACAGGG | TGTCTCCGTG | TTGGTCGGTC | TGGTCTTGAA | 18120
| CTCCTGACCT | CAGGTGATGC | GCCCGCCTCA | GCCTCCCAAA | GTGCTGGGAT | TACAGGCAGG | 18180
| AGCCATTGCA | CCCGGCTCTT | TCCCCTTCTC | CTTTTCTTCT | CTCTCTCCTC | CCTTTCTTTC | 18240
| TTTTCTTTTC | TTTTTTTTTT | CTTTTGAGAT | GGAGTCTCGC | TCTGTCACCA | GGCTGGATTG | 18300
| CAGTGGCGTG | ATCTTGGCTC | ACTGCAACCT | TCGCCTCCCG | GGTTCACGTG | ATTCTCCTGC | 18360
| CTCAGCCTCC | TGAGTGGCTG | GCACTACAGG | CTCCCGCCGC | CATGCCCGGC | TAATTTTTGC | 18420
| ATTTTTAGTA | GAGACAGGGT | TCACCCTGT | TGGCCAGGAT | GGTCTCGATC | TCTTGATCTC | 18480
| ATGATCCACC | CACCTTGGCC | TCCCAAAGTT | CTGGCATTAC | AGGAGTGAGC | CACCGTGCCC | 18540
| GGCCATCTTT | CTTTCCTTGC | TTTCTCTTTG | TTTTCTTTCG | AGACCGGGTC | TTGCTCTGTC | 18600
| GCCCAGGCTG | GACTGCAGTG | GCACAATCAT | AGCTCACTGC | AGCCTCGACT | TCCCTGGCTC | 18660
| AAGCGATCCT | TCCTCCTCAG | CCCCCCGAGT | AGCTGGAACT | ACAGTTACAC | ACTACCATGC | 18720
| CTGGCTGATT | CTTTTTTTCC | TTGTAGAGAT | GGGGTCTTGC | TATGCTGTCC | ATCCTGGTCT | 18780
| CAAACTCCTG | GCCTTCCCAA | AGCACTGGGT | TTACAGGCAT | AAGCCACCAC | ACCCAGTTTC | 18840
| CTTTTCTTCT | TTTTAACTGG | AATAGTTGAC | GTTTTCTTTA | TTAGCTGTGT | GTCAGGAGGG | 18900
| TATTTTTGGC | CTTTAGTATG | TCGTGTAAGT | TGCTAGTGCT | TTTCTGAGAT | TGTAGTTTGT | 18960
| TTTCTAATTT | TATTTATATT | TTGCGTAGAA | GTTGTGTATT | TTAGATGGAG | TTAGGTCGGC | 19020
| TGGTCTTTGA | TGTTTTATTT | ATTAATTATG | TATGTATTTA | TTTATTTTTG | AGGTAGAGTC | 19080

```
TCGCCGTTTC ACCCAGGCTG GAGTACAGTG ATGCGATCTC AGCTCCCTGT AGCCTTGACC    19140

TCTCTGGGCT CAAGTGATTT TTCTCTCCTC TACCTCCCGA GTACTTGGGA CCCCAGGCGC    19200

ATGCCGCCAT GCCTGGCTAA TGTGTATTTT TTGTAGATAC GGGGTCTCAC TGTGTTGCCC    19260

AGGGTGGTTT CAAAATCCTG GCCCAGGCG ATCCTTCCGT CTCAGCTCCC ACGGTGCTGT     19320

GTTACCGGCG TGTGCCCAGT GCCTGGCCGT CTTGGAGGTC TTGTTTCTCT GGGTTTATGC    19380

CTCGAGGTGG CGCCTGCTCC CCTGTGCTCC CTGGTAGCCT GGTAGTGAGC CTGCTTCTCA    19440

CACAGTCATA CCTGGTTGTG GTCCCACAGT GGGACCACCC TGTTGGGTTC AGAACAGGAG    19500

ATGGGGGCCC CTCGAGTCTG TGTGGGGGCT GTGGACAGGG TTGGGAGACC TTGGCTCTGT    19560

GGGGGACTGT GGACAGGGGA TGGGGGGCCT TGGCCCTGCG TGGGATGGGT TGGGGGTCCG    19620

TGCCCTTCCT GGCCCTGGGT GGACAGGTCC ATGTGGCACT CGGCATAGGG CTGAGATGGG    19680

TGCAGAGGGC TGAGGCCCCC AGGCCTCTCC TGGCTTGGTT TCCCCAGATG AGTGTTCATT    19740

TGGGTCTTCC ATCAGAAAGT CCCCTCCTGA CCTCTGGGAG TGGGGAGCTC AAGGGTGGGA    19800

GGCCATAGCT TGGGGATGCT GGCAATGTGT GGGATGGGCC CAGGGAAGGC CTCTGGCCTA    19860

CTAGGGGCTC TGGCCCTGAC CCACGGCCAC TCACTCCTCA GAGACGTCTC CCACAACCTG    19920

CTCCGGGCGC TGGACGTTGG GCTCCTGGCG AACCTCTCGG CGCTGGCAGA GCTGTGAGTG    19980

TCCCCCAGTC GTGCCAGCAT GCGGGGCTCA CTCCGGGTGG GCTGGCGGCA CCGCCTCTTG    20040

CTGCTCAGCT GTGGGGGCTT CCATCAGCTT TGCCGAATCC CCCGTCTCTT CCAGGGATAT    20100

AAGCAACAAC AAGATTTCTA CGTTAGAAGA AGGAATATTT GCTAATTTAT TTAATTTAAG    20160

TGAAATGTAA GTTGTGGTTC TTTGGGTGGG GTCCTGGCTG ACCCCAGGC CCCCAATATC     20220

CCTTCTGCCC TCCCAGTTGG TCCGTGTCCC CTTCCAGGCT TGAGACCAGA TCCTGGGGGC    20280

AGTTCACTGC CTGCTTGGAG CCCCCCAGTG CCGGCTTGGT TGGGGCAGGG GAGGCGGTGC    20340

TGTCAGGGTG GCTCCAGGGC CTGGTTGCCA GTGGGGGGCT GGCATAGACC CTTCCCACCA    20400

GACCTGGTCC CCAACACCTG CCCCTGCCCT GCAGAAACCT GAGTGGGAAC CCGTTTGAGT    20460

GTGACTGTGG CCTGGCGTGG CTGCCGCGAT GGGCGGAGGA GCAGCAGGTG CGGGTGGTGC    20520

AGCCCGAGGC AGCCACGTGT GCTGGGCCTG GCTCCCTGGC TGGCCAGCCT CTGCTTGGCA    20580

TCCCCTTGCT GGACAGTGGC TGTGGTGAGT GCCGGTGGGT GGGGCCAGCT CTGTCCTTCC    20640

CAGCCAGGTG GGACCTGGGC CCTGCAGACA CTGGGCAGGG CTCAGGAAGG CCTCTCTGGG    20700

GGGGGCCTCC GGGCCAAGGG AACAGCATGG GAGCCTGTGA GTGCGGCGGG CGGATGTGGG    20760

GGCGTGGGGT GGAGCCAGGA GGAGCAGAAC CCGGGGTCCA GTGGCTGCCT CTTCTAGGTG    20820
```

| | | | | | |
|---|---|---|---|---|---|
| AGGAGTATGT | CGCCTGCCTC | CCTGACAACA | GCTCAGGCAC | CGTGGCAGCA | GTGTCCTTTT | 20880 |
| CAGCTGCCCA | CGAAGGCCTG | CTTCAGCCAG | AGGCCTGCAG | CGCCTTCTGC | TTCTCCACCG | 20940 |
| GCCAGGGCCT | CGCAGCCCTC | TCGGAGCAGG | GCTGGTGCCT | GTGTGGGGCG | GCCCAGCCCT | 21000 |
| CCAGTGCCTC | CTTTGCCTGC | CTGTCCCTCT | GCTCCGGCCC | CCCGCCACCT | CCTGCCCCCA | 21060 |
| CCTGTAGGGG | CCCCACCCTC | CTCCAGCACG | TCTTCCCTGC | CTCCCCAGGG | GCCACCCTGG | 21120 |
| TGGGCCCCA | CGGACCTCTG | GCCTCTGGCC | AGCTAGCAGC | CTTCCACATC | GCTGCCCCGC | 21180 |
| TCCCTGTCAC | TGCCACACGC | TGGGACTTCG | GAGACGGCTC | CGCCGAGGTG | GATGCCGCTG | 21240 |
| GGCCGGCTGC | CTCGCATCGC | TATGTGCTGC | CTGGGCGCTA | TCACGTGACG | GCCGTGCTGG | 21300 |
| CCCTGGGGGC | CGGCTCAGCC | CTGCTGGGGA | CAGACGTGCA | GGTGGAAGCG | GCACCTGCCG | 21360 |
| CCCTGGAGCT | CGTGTGCCCG | TCCTCGGTGC | AGAGTGACGA | GAGCCTCGAC | CTCAGCATCC | 21420 |
| AGAACCGCGG | TGGTTCAGGC | CTGGAGGCCG | CCTACAGCAT | CGTGGCCCTG | GGCGAGGAGC | 21480 |
| CGGCCCGAGG | TGAGTGTCTG | CTGCCCACTC | CCCTTCCTCC | CCAGGGCCAT | CCAGATGGGG | 21540 |
| CAGAGCCTGG | TACCCCGTC | TTGGGCCCAC | ACTGACCGTT | GACACCCTCG | TTCCCACCGG | 21600 |
| TCTCCAGCGG | TGCACCCGCT | CTGCCCCTCG | GACACGGAGA | TCTTCCCTGG | CAACGGGCAC | 21660 |
| TGCTACCGCC | TGGTGGTGGA | GAAGGCGGCC | TGGCTGCAGG | CGCAGGAGCA | GTGTCAGGCC | 21720 |
| TGGGCCGGGG | CCGCCCTGGC | AATGGTGGAC | AGTCCCGCCG | TGCAGCGCTT | CCTGGTCTCC | 21780 |
| CGGGTCACCA | GGTGCCTGCC | CCCACCCCCC | GAGGGGCCAT | AGGTTGGGAG | ATCTCTGAAG | 21840 |
| CACTGGGGCA | GAGACTGCGG | CTGGGGAGTC | TCAGGAGGAA | GGAGGTGGGA | GCTGGGCCGG | 21900 |
| CCCTGGTGAG | CAGGTGGCGC | CGGCCGGTGG | GGCCGTTCCT | GTCAGCTCTG | CAGATGCAGA | 21960 |
| GGTGGACATG | AGCTGGGGGC | AGCCTCCGGA | CACTCCTGGG | CACGCCATAC | GGGAGGTGGC | 22020 |
| CTGCACGGGG | ATCCCTGCCG | GTACCCACAG | GCCCCGTGGG | TGGGTGCTGC | TGTGAGCCTG | 22080 |
| GGCTGGTGGG | CCCTGGTCTC | CGGGCTCTGA | GCCTCAGTTT | CCCCATCTGG | AAAGGGGGAC | 22140 |
| AGTGATGGGG | CTCCCAGCGG | GCTGCTGTGA | GGGTGGGAGG | ATGGAGGAGT | GCCCTGAGCC | 22200 |
| CCCTGCCATC | CCACACCCGC | CCCCAGGAGC | CTAGACGTGT | GGATCGGCTT | CTCGACTGTG | 22260 |
| CAGGGGGTGG | AGGTGGGCCC | AGCGCCGCAG | GGCGAGGCCT | TCAGCCTGGA | GAGCTGCCAG | 22320 |
| AACTGGCTGC | CCGGGGAGCC | ACACCCAGCC | ACAGCCGAGC | ACTGCGTCCG | GCTCGGGCCC | 22380 |
| ACCGGGTGGT | GTAACACCGA | CCTGTGCTCA | GCGCCGCACA | GCTACGTCTG | CGAGCTGCAG | 22440 |
| CCCGGAGGTG | TGCGGGGGGC | CAGGCAGGGG | CCTGAGACGC | TGGCTGTGGT | TAGGGGCCTG | 22500 |
| CCGAGCGCCC | GCGGTGGAGC | CTGGGCTGAG | GAGGAGGGGC | TGGTGGGGGG | GTTTTCGGGC | 22560 |

```
GGCTCGGTCC CCAGTCTGTT CGTCCTGGTG TCCTGGGCCC TGGCCCGGCG CCTCACTGTG    22620

CACTCGCCAC CCCAGGCCCA GTGCAGGATG CCGAGAACCT CCTCGTGGGA GCGCCCAGTG    22680

GGGACCTGCA GGGACCCCTG ACGCCTCTGG CACAGCAGGA CGGCCTCTCA GCCCCGCACG    22740

AGCCCGTGGA GGTAGTCGGC CCCCACGTT  CTACAACCTG CCCTCCTGCC TGCCCCTGGA    22800

GGCCTTGCCT GCCCTGCCCA CTGTGGGTCT CGCCAAAAAA CTTGGGGGCC TTAATGTTGC    22860

TTGTGCCCAG TGAAGATGGT TGGGAAAATC CAGAGTGCAG AGAGGAAAGC GTTTACTCAC    22920

ATTACCTCCA GGCCTTTTCT CTGAGCGTGT GTGAGTTATT CCTGAAAGGC AGGTCAGGGG    22980

TCCTGCCCCC CATGGACAGT TTCCACCGGA GTCTTCCTCT CGAGCGACAG GAGCCAGGCC    23040

TGTGGGGGTC TGATGGCTCG CTCTCCTTCC CTCCCCTCTT CCTGGGAAGT TCGGGTAGGG    23100

GGAGTCTGGG CTTCAGGCTG GGATGGGGTC TGTGGAGCTG AGGCGGCCCC CTGCCCACCA    23160

GGTCATGGTA TTCCCGGGCC TGCGTCTGAG CCGTGAAGCC TTCCTCACCA CGGCCGAATT    23220

TGGGACCCAG GAGCTCCGGC GGCCCGCCCA GCTGCGGCTG CAGGTGTACC GGCTCCTCAG    23280

CACAGCAGGT GGGACTCTGG GTGGTGGGTG GTGGGTGGTG GGCGCCGCAG GACTCGGGGT    23340

GGCCTCTCTG AGCTTTCACG TCTGCTGGTC CTGTGGCCAC CAGAGTGGTT CCCAGTCTTA    23400

GGTGGACAGA GCAGGGGTTC CAGAGACACC AGCTCATTCC AGGTGTCCTG GGGGTGGATT    23460

GGGTGGGGCC TGCCTGGGGG CCGGCCTGGG TCAGTCGGCT GGCCGGAGAC GGACGCAGCA    23520

CTGGGCTGGG AGTGCTGCCC AGGTGGGGAG ACCTGTCCTC ACAGCAAGGC CAGGATTGCT    23580

GGTGCAGGCA GTTGGGCATC TCTGACGGTG GCCTGTGGGC AAATCAGGGC CCAACACCC    23640

TCCCCTCCTC ACAGGGACCC CGGAGAACGG CAGCGAGCCT GAGAGCAGGT CCCCGGACAA    23700

CAGGACCCAG CTGGCCCCCG CGTGCATGCC AGGGGACGC  TGGTGCCCTG GAGCCAACAT    23760

CTGCTTGCCG CTGGACGCCT CCTGCCACCC CCAGGCCTGC GCCAATGGCT GCACGTCAGG    23820

GCCAGGGCTA CCCGGGGCCC CCTATGCGCT ATGGAGAGAG TTCCTCTTCT CCGTTCCCGC    23880

GGGGCCCCCC GCGCAGTACT CGGTGTGTGG CCCTGACCTG GGTCTGTTCC CTGCATCTCC    23940

TCAGGCCACC TTCCTGTCTG CTGCCCAGGG TCTGGGTCTG TGCACCAGAC ACACCCAGCC    24000

TGCAGGCCCC TCCCACGTCC TTGCCACCTC TGACCTCCGA CCTCTGCAGT GCCCTCGGCC    24060

CTCTCCCAGT GGGAGAAGCT CTCGCCTGGG CCCTTGGCAC GAGCTGTGCC TCCTCTTCCT    24120

CTCTCCCAGC ACAGCTGCTC CTTCCTGTCT GCCAGGTCTT GGCCTGTGTC CTCTCCCCGT    24180

GTGTCCCCCG GTCTGCAACT GTCCTGCCTG TCCTTGTCAC GAGCACTGTG GGGAGGCTCC    24240

TTGAGGTGTG GCTGACGAAG CGGGGAGCCC TGCGTGTCCA CCCTCATCCG TCGTGCGGGG    24300
```

```
GTCCACGGGC CATGACCGTG AGGACGTGAT GCAGCCCTGC CTCCCTCTCC ACAGGTCACC    24360

CTCCACGGCC AGGATGTCCT CATGCTCCCT GGTGACCTCG TTGGCTTGCA GCACGACGCT    24420

GGCCCTGGCG CCCTCCTGCA CTGCTCGCCG GCTCCCGGCC ACCCTGGTCC CCGGGCCCCG    24480

TACCTCTCCG CCAACGCCTC GTCATGGCTG CCCCACTTGC CAGCCCAGCT GGAGGGCACT    24540

TGGGCCTGCC CTGCCTGTGC CCTGCGGCTG CTTGCAGCCA CGGAACAGCT CACCGTGCTG    24600

CTGGGCTTGA GGCCCAACCC TGGACTGCGG CTGCCTGGGC GCTATGAGGT CCGGGCAGAG    24660

GTGGGCAATG GCGTGTCCAG GCACAACCTC TCCTGCAGCT TTGACGTGGT CTCCCCAGTG    24720

GCTGGGCTGC GGGTCATCTA CCCTGCCCCC CGCGACGGCC GCCTCTACGT GCCCACCAAC    24780

GGCTCAGCCT TGGTGCTCCA GGTGGACTCT GGTGCCAACG CCACGGCCAC GGCTCGCTGG    24840

CCTGGGGGCA GTGTCAGCGC CCGCTTTGAG AATGTCTGCC CTGCCCTGGT GGCCACCTTC    24900

GTGCCCGGCT GCCCCTGGGA GACCAACGAT ACCCTGTTCT CAGTGGTAGC ACTGCCGTGG    24960

CTCAGTGAGG GGGAGCACGT GGTGGACGTG GTGGTGGAAA ACAGCGCCAG CCGGGCCAAC    25020

CTCAGCCTGC GGGTGACGGC GGAGGAGCCC ATCTGTGGCC TCCGCGCCAC GCCCAGCCCC    25080

GAGGCCCGTG TACTGCAGGG AGTCCTAGTG GTGAGTATGG CCGAGGCTCC ACCACCAGCC    25140

CCCAGGCAGG TGCCTGCAGA CAGGGTGCTC ACACAGGGCG TGAGGCCTGG CTTCCCAGTG    25200

AGGGCAGCAG CCCAGTTACT GGGGACGTCG GCCCCGGGCA GGTCCTGCTG GCTGGCTCCT    25260

CGGGCTACCT GGTGGGCTTT AAATTCCTGG AAAGTCACGG CTCTGACAGT GGCTCCGCTA    25320

ACTCATTCCA CTGTCTCATT TCACAAAATG AATTTAAAAC TCTGCTCCCT GACCTCACAC    25380

GAGCCCCCGT GAGTCTCTCA CGCCCTCTGC TGTGTTCTCG CCTGGCTAAA GCGAGTGGCT    25440

TTTGAGGTGG AGTCTGAACC CCTGATGGGA AACTGCGGGC TGCCCGCGGT GCCACCATGC    25500

TGGGTACATG GGGGACAGGG CTGTCTCCAT CTTGCGGGTA CCTGCCTCTT CACCAGGGGC    25560

CTTGGGAGGG GCCATCAGAA ATGGCGTGAC CTGTGCAGCC TGTCCTGGGT TCTGTAAGCC    25620

AGTGTAGGTG CCTCCCCTCA CTGCTCCGAG CTCTCTGGGT GAGGAGCTGG GGCAAGAGCG    25680

CCGGGAGGGT CTGAGAAGAC TCAGAGAGAG GTGGACTCTT TGTAGCTGGT ACTAGGTTTG    25740

CTTTACAGAT GGGGAAACTG AGGCACAGAG AGGTTGAGGC ATTAGTAGTA CTACATGGCT    25800

GGCTGGAGAG CCGGACAGTG AGTGTCCCAG CCCGGGCTTG GCTCCCATGG CATGCAGAGC    25860

CCCGGGCACC TCCTCTCCTC TGTGCCCCGC GTGGGACTCT CCAGCCCGAC GGGAGGTGTG    25920

TCCAGGAGGC GACAGGCTAA GGGCAGAGTC CTCCACAGAG CCCAGGCTGA CACCATTCCC    25980

CCCGCAGAGG TACAGCCCCG TGGTGGAGGC CGGCTCGGAC ATGGTCTTCC GGTGGACCAT    26040
```

| | |
|---|---|
| CAACGACAAG CAGTCCCTGA CCTTCCAGAA CGTGGTCTTC AATGTCATTT ATCAGAGCGC | 26100 |
| GGCGGTCTTC AAGCTCTCAG TAGGTGGGCG GGGGTGGGGA GGGGAGGGGA TGGGGCGGGG | 26160 |
| CAGGGCGGGG GCGGGCTCCA CCTTCACCTC TGCCTTCTGC TCTGCTTCAT GCTGCCCGAG | 26220 |
| GACGCTGCCA TGGCTGTGGG TGAGTGGAGG GAGGGACGCC AATCAGGGCC AGGCCTCTCA | 26280 |
| CCTGCCACCT GGGCTCACTG ACGCCTGTCC CTGCAGCTGA CGGCCTCCAA CCACGTGAGC | 26340 |
| AACGTCACCG TGAACTACAA CGTAACCGTG GAGCGGATGA ACAGGATGCA GGGTCTGCAG | 26400 |
| GTCTCCACAG TGCCGGCCGT GCTGTCCCCC AATGCCACGC TAGCACTGAC GGCGGGCGTG | 26460 |
| CTGGTGGACT CGGCCGTGGA GGTGGCCTTC CTGTGAGTGA CTCGGGGCC GGTTTGGGGT | 26520 |
| GGGCACCAGG CTCTTGTCCC AGCCCCAGCC TCAGCCGAGG GACCCCACA TCACGGGGTT | 26580 |
| GCTTTTCTGA GCCTCGGTTT CCCTGTCTGT TGGGAGGTAA CTGGGTGCAC AGGAGCCCTG | 26640 |
| AGGCTGCACG GGAGCCGGGA GAGGCCTCAG CACAGCCGGG TGGGCCCTGA ATGGAGGCCC | 26700 |
| GGGGCGTGAC TGCAGAGTGG AGCCTCGGCT GGGTCCCAAG CACCCCTGC CCCGCCACCG | 26760 |
| CCCACCCCTG TCCCGGTTCA CTCACTGCGT CCCACCGCCC CGGCAGGTGG ACCTTTGGGG | 26820 |
| ATGGGAGCA GGCCCTCCAC CAGTTCCAGC CTCCGTACAA CGAGTCCTTC CCGGTTCCAG | 26880 |
| ACCCCTCGGT GGCCCAGGTG CTGGTGGAGC ACAATGTCAT GCACACCTAC GCTGCCCCAG | 26940 |
| GTGAGGGATG AGGGGGTGAG GGGGCCACTG CCTTTCAGGC TCTGAGCACG GGTCCCCCCA | 27000 |
| GCTCCCCAGT CAAGCTGCCC CCTTCCTCC CAACAGCCC TCACTGTGAC CTCACCTGGG | 27060 |
| CTGATGGCTT AGGCCCTACT GGGGTGAGGG AGGGGCCAGG CGTGGGGGA GTGGACAGGG | 27120 |
| AAGCTGGGCC CCTGAACTGC GCCCCCGCC CTCCCCGGGC CTGGCTCTTG CTGCTCTGCT | 27180 |
| GCCCCGAGTG CAGCTGCACT TGGAGGCGGT GCGTCCTCGC CAGGCAGCCC TCAGTGCTGC | 27240 |
| TACACCTGTG CTCCGTCCCG CACGTGGCTT GGGAGCCTGG GACCCTTAAG GCTGGGCCGC | 27300 |
| AGGTGCAGCC GTTCACCCCG GCTCCTCAG GCGGGGGCT TCTGCCGAGC GGGTGGGGAG | 27360 |
| CAGGTGGGGG TGCCGCGGCT GCCCCACTCG GGCCTGTCCC CACAGGTGAG TACCTCCTGA | 27420 |
| CCGTGCTGGC ATCTAATGCC TTCGAGAACC GGACGCAGCA GGTGCCTGTG AGCGTGCGCG | 27480 |
| CCTCCCTGCC CTCCGTGGCT GTGGGTGTGA GTGACGGCGT CCTGGTGGCC GGCCGGCCCG | 27540 |
| TCACCTTCTA CCCGCACCCG CTGCCCTCGC CTGGGGGTGT TCTTTACACG TGGGACTTCG | 27600 |
| GGGACGGCTC CCCTGTCCTG ACCCAGAGCC AGCCGGCTGC CAACCACACC TATGCCTCGA | 27660 |
| GGGGCACCTA CCACGTGCGC CTGGAGGTCA ACAACACGGT GAGCGGTGCG GCGGCCCAGG | 27720 |
| CGGATGTGCG CGTCTTTGAG GAGCTCCGCG GACTCAGCGT GGACATGAGC CTGGCCGTGG | 27780 |

```
AGCAGGGCGC CCCCGTGGTG GTCAGCGCCG CGGTGCAGAC GGGCGACAAC ATCACGTGGA    27840

CCTTCGACAT GGGGGACGGC ACCGTGCTGT CGGGCCCGGA GGCAACAGTG GAGCATGTGT    27900

ACCTGCGGGC ACAGAACTGC ACAGTGACCG TGGGTGCGGC CAGCCCCGCC GGCCACCTGG    27960

CCCGGAGCCT GCACGTGCTG GTCTTCGTCC TGGAGGTGCT GCGCGTTGAA CCCGCCGCCT    28020

GCATCCCCAC GCAGCCTGAC GCGCGGCTCA CGGCCTACGT CACCGGGAAC CCGGCCCACT    28080

ACCTCTTCGA CTGGACCTTC GGGGATGGCT CCTCCAACAC GACCGTGCGG GGGTGCCCGA    28140

CGGTGACACA CAACTTCACG CGGAGCGGCA CGTTCCCCCT GGCGCTGGTG CTGTCCAGCC    28200

GCGTGAACAG GGCGCATTAC TTCACCAGCA TCTGCGTGGA GCCAGAGGTG GGCAACGTCA    28260

CCCTGCAGCC AGAGAGGCAG TTTGTGCAGC TCGGGACGA GGCCTGGCTG GTGGCATGTG    28320

CCTGGCCCCC GTTCCCCTAC CGCTACACCT GGGACTTTGG CACCGAGGAA GCCGCCCCCA    28380

CCCGTGCCAG GGGCCCTGAG GTGACGTTCA TCTACCGAGA CCCAGGCTCC TATCTTGTGA    28440

CAGTCACCGC GTCCAACAAC ATCTCTGCTG CCAATGACTC AGCCCTGGTG GAGGTGCAGG    28500

AGCCCGTGCT GGTCACCAGC ATCAAGGTCA ATGGCTCCCT TGGGCTGGAG CTGCAGCAGC    28560

CGTACCTGTT CTCTGCTGTG GGCCGTGGGC GCCCCGCCAG CTACCTGTGG GATCTGGGGG    28620

ACGGTGGGTG GCTCGAGGGT CCGGAGGTCA CCCACGCTTA CAACAGCACA GGTGACTTCA    28680

CCGTTAGGTG GCCGGCTGGA ATGAGGTGAG CCGCAGCGAG GCCTGGCTCA ATGTGACGGT    28740

GAAGCGGCGC GTGCGGGGGC TCGTCGTCAA TGCAAGCCCC ACGGTGGTGC CCCTGAATGG    28800

GAGCGTGAGC TTCAGCACGT CGCTGGAGGC CGGCAGTGAT GTGCGCTATT CCTGGGTGCT    28860

CTGTGACCGC TGCACGCCCA TCCCTGGGGG TCCTACCATC TCTTACACCT TCCGCTCCGT    28920

GGGCACCTTC AATATCATCG TCACGGCTGA GAACGAGGTG GGCTCCGCCC AGGACAGCAT    28980

CTTCGTCTAT GTCCTGCAGC TCATAGAGGG GCTGCAGGTG GTGGGCGGTG GCCGCTACTT    29040

CCCCACCAAC CACACGGTAC AGCTGCAGGC CGTGGTTAGG GATGGCACCA ACGTCTCCTA    29100

CAGCTGGACT GCCTGGAGGG ACAGGGGCCC GGCCCTGGCC GGCAGCGGCA AAGGCTTCTC    29160

GCTCACCGTC TCGAGGCCGG CACCTACCAT GTGCAGCTGC GGGCCACCAA CATGCTGGGC    29220

AGCGCCTGGG CCGACTGCAC CATGGACTTC GTGGAGCCTG TGGGGTGGCT GATGGTGGCC    29280

GCCTCCCCGA ACCCAGCTGC CGTCAACAAA AGCGTCACCC TCAGTGCCGA GCTGGCTGGT    29340

GGCAGTGGTG TCGTATACAC TTGGTCCTTG GAGGAGGGGC TGAGCTGGGA GACCTCCGAG    29400

CCATTTACCA CCCATAGCTT CCCCACACCC GGCCTGCACT TGGTCACCAT GACGGCAGGG    29460

AACCCGCTGG GCTCAGCCAA CGCCACCGTG GAAGTGGATG TGCAGGTGCC TGTGAGTGGC    29520
```

```
CTCAGCATCA GGGCCAGCGA GCCCGGAGGC AGCTTCGTGG CGGCCGGGTC CTCTGTGCCC   29580

TTTTGGGGGC AGCTGGCCAC GGGCACCAAT GTGAGCTGGT GCTGGGCTGT GCCCGGCGGC   29640

AGCAGCAAGC GTGGCCCTCA TGTCACCATG GTCTTCCCGG ATGCTGGCAC CTTCTCCATC   29700

CGGCTCAATG CCTCCAACGC AGTCAGCTGG GTCTCAGCCA CGTACAACCT CACGGCGGAG   29760

GAGCCCATCG TGGGCCTGGT GCTGTGGGCC AGCAGCAAGG TGGTGGCGCC CGGGCAGCTG   29820

GTCCATTTTC AGATCCTGCT GGCTGCCGGC TCAGCTGTCA CCTTCCGCCT GCAGGTCGGC   29880

GGGGCCAACC CCGAGGTGCT CCCCGGGCCC CGTTTCTCCC ACAGCTTCCC CCGCGTCGGA   29940

GACCACGTGG TGAGCGTGCG GGGCAAAAAC CACGTGAGCT GGGCCCAGGC GCAGGTGCGC   30000

ATCGTGGTGC TGGAGGCCGT GAGTGGGCTG CAGGTGCCCA ACTGCTGCGA GCCTGGCATC   30060

GCCACGGGCA CTGAGAGGAA CTTCACAGCC CGCGTGCAGC GCGGCTCTCG GGTCGCCTAC   30120

GCCTGGTACT TCTCGCTGCA GAAGGTCCAG GGCGACTCGC TGGTCATCCT GTCGGGCCGC   30180

GACGTCACCT ACACGCCCGT GGCCGCGGGG CTGTTGGAGA TCCAGGTGCG CGCCTTCAAC   30240

GCCCTGGGCA GTGAGAACCG CACGCTGGTG CTGGAGGTTC AGGACGCCGT CCAGTATGTG   30300

GCCCTGCAGA GCGGCCCCTG CTTCACCAAC CGCTCGGCGC AGTTTGAGGC CGCCACCAGC   30360

CCCAGCCCCC GGCGTGTGGC CTACCACTGG GACTTTGGGG ATGGGTCGCC AGGGCAGGAC   30420

ACAGATGAGC CCAGGGCCGA GCACTCCTAC CTGAGGCCTG GGGACTACCG CGTGCAGGTG   30480

AACGCCTCCA ACCTGGTGAG CTTCTTCGTG GCGCAGGCCA CGGTGACCGT CCAGGTGCTG   30540

GCCTGCCGGG AGCCGGAGGT GGACGTGGTC CTGCCCCTGC AGGTGCTGAT GCGGCGATCA   30600

CAGCGCAACT ACTTGGAGGC CCACGTTGAC CTGCGCGACT GCGTCACCTA CCAGACTGAG   30660

TACCGCTGGG AGGTGTATCG CACCGCCAGC TGCCAGCGGC CGGGGCGCCC AGCGCGTGTG   30720

GCCCTGCCCG GCGTGGACGT GAGCCGGCCT CGGCTGGTGC TGCCGCGGCT GGCGCTGCCT   30780

GTGGGGCACT ACTGCTTTGT GTTTGTCGTG TCATTTGGGG ACACGCCACT GACACAGAGC   30840

ATCCAGGCCA ATGTGACGGT GGCCCCCGAG CGCCTGGTGC CCATCATTGA GGGTGGCTCA   30900

TACCGCGTGT GGTCAGACAC ACGGGACCTG GTGCTGGATG GGAGCGAGTC CTACGACCCC   30960

AACCTGGAGG ACGGCGACCA GACGCCGCTC AGTTTCCACT GGGCCTGTGT GGCTTCGACA   31020

CAGGTCAGTG CGTGGCAGGG CCGTCCTCCA TGCCCCTCAC CGTCCACAC CCATGAGCCC    31080

AGAGAACACC CAGCTTGCCA CCAGGGCTGG CCCGTCCTCA GTGCCTGGTG GGCCCCGTCC   31140

CAGCATGGGG AGGGGGTCTC CCGCGCTGTC TCCTGGGCCG GGCTCTGCTT TAAAACTGGA   31200

TGGGCTCTC AGGCCACGTC GCCCCTTGTT CTCGGCCTGC AGAGGGAGGC TGGCGGGTGT    31260
```

| | |
|---|---|
| GCGCTGAACT TTGGGCCCCG CGGGAGCAGC ACGGTCACCA TTCCACGGGA GCGGCTGGCG | 31320 |
| GCTGGCGTGG AGTACACCTT CAGCCTGACC GTGTGGAAGG CCGGCCGCAA GGAGGAGGCC | 31380 |
| ACCAACCAGA CGGTGGGTGC CGCCCGCCCC TCGGCCACTT GCCTTGGACA GCCCAGCCTC | 31440 |
| CCTGGTCATC TACTGTTTTC CGTGTTTTAG TGCTGGTGGA GGCCGCACGC TCTCCCCTCT | 31500 |
| CTGTTTCTGA TGCAAATTCT ATGTAACACG ACAGCCTGCT TCAGCTTTGC TTCCTTCCAA | 31560 |
| ACCTGCCACA GTTCCACGTA CAGTCTTCAA GCCACATATG CTCTAGTGGC AAAAGCTACA | 31620 |
| CAGTCCCCTA GCAATACCAA CAGTGAGGAA GAGCCCCTTC CCACCCCAGA GGTAGCCACT | 31680 |
| GTCCCCAGCC CATGTCCCTG TTGCTGGATG TGGTGGGCCG GTTCTCACCC TCACGCTCCC | 31740 |
| CTCTCTGGAC CGGCCAGGAG GCTTGGTGAC CCTGAGCCCG TGGTGGCTGC TCCTGCTGCT | 31800 |
| GTCAGGCGGG GCCTGCTGGT GCCCCAGAGT GGGCGTCTGT TCCCCAGTCC CTGCTTTCCT | 31860 |
| CAGCTGGCCT GATTGGGGGT CTTCCCAGAG GGTCGTCTG AGGGGAGGGT GTGGGAGCAG | 31920 |
| GTTCCATCCC AGCTCAGCCT CCTGACCCAG GCCCTGGCTA AGGGCTGCAG GAGTCTGTGA | 31980 |
| GTCAGGCCTA CGTGGCAGCT GCGGTCCTCA CACCCACACA TACGTCTCTT CTCACACGCA | 32040 |
| TCCCCCCAGG GGCCCTCAGT GAGCATTGCC TGCCTCCTGC TAGGGTCCAG CTGGGTCCAG | 32100 |
| TACACCAGAA CGCACACTCC AGTGTCCTCT GCCCTGTGTA TGCCCTTCCG CCGTCCAAGT | 32160 |
| TGGAAGGTGG CAAACCGGAT GAGTATCCTG GGAGGGAGTG AGCTCACCGG CAGTGGCCAG | 32220 |
| GCCCCTGGGA AACCTGGAGT TTGGGAGCAG CATCCTCCAT GGGTCCCCCA GTCCTTCCAG | 32280 |
| CAGGCCAAAT AGACCTGTGT TGGAGGTAAC CCCACTCCCA CGCCAGGTGC TGATCCGGAG | 32340 |
| TGGCCGGGTG CCCATTGTGT CCTTGGAGTG TGTGTCCTGC AAGGCACAGG CCGTGTACGA | 32400 |
| AGTGAGCCGC AGCTCCTACG TGTACTTGGA GGGCCGCTGC CTCAATTGCA GCAGCGGCTC | 32460 |
| CAAGCGAGGG GTGAGTGTTG AGCGGGGTGT GGGCGGGCTG GGGATGGGTC CCATGGCCGA | 32520 |
| GGGGACGGGG CCTGCAGGCA GAAGTGGGGC TGACAGGGCA GAGGGTTGCG CCCCCTCACC | 32580 |
| ACCCCTTCTG CCTGCAGCGG TGGGCTGCAC GTACGTTCAG CAACAAGACG CTGGTGCTGG | 32640 |
| ATGAGACCAC CACATCCACG GGCAGTGCAG GCATGCGACT GGTGCTGCGG CGGGGCGTGC | 32700 |
| TGCGGGACGG CGAGGGATAC ACCTTCACGC TCACGGTGCT GGGCCGCTCT GGCGAGGAGG | 32760 |
| AGGGCTGCGC CTCCATCCGC CTGTCCCCCA ACCGCCGCC GCTGGGGGGC TCTTGCCGCC | 32820 |
| TCTTCCCACT GGGCGCTGTG CACGCCCTCA CCACCAAGGT GCACTTCGAA TGCACGGGTG | 32880 |
| AGTGCAGGCC TGCGTGGGGG GAGCAGCGGG ATCCCCCGAC TCTGTGACGT CACGGAGCCC | 32940 |
| TCCCGTGATG CCGTGGGGAC CGTCCCTCAG GCTGGCATGA CGCGGAGGAT GCTGGCGCCC | 33000 |

```
CGCTGGTGTA CGCCCTGCTG CTGCGGCGCT GTCGCCAGGG CCACTGCGAG GAGTTCTGTG      33060

TCTACAAGGG CAGCCTCTCC AGCTACGGAG CCGTGCTGCC CCCGGGTTTC AGGCCACACT      33120

TCGAGGTGGG CCTGGCCGTG GTGGTGCAGG ACCAGCTGGG AGCCGCTGTG GTCGCCCTCA      33180

ACAGGTGAGC CAGGCCGTGG GAGGGCGCCC CCGAGACTGC CACCTGCTCA CCACCCCCTC      33240

TGCTCGTAGG TCTTTGGCCA TCACCCTCCC AGAGCCCAAC GGCAGCGCAA CGGGGCTCAC      33300

AGTCTGGCTG CACGGGCTCA CCGCTAGTGT GCTCCCAGGG CTGCTGCGGC AGGCCGATCC      33360

CCAGCACGTC ATCGAGTACT CGTTGGCCCT GGTCACCGTG CTGAACGAGG TGAGTGCAGC      33420

CTGGGAGGGG ACGTCACATC TGCTGCATGC GTGCTTGGGA CCAAGACCTG TACCCCTGCC      33480

TGGAGCTTTG CAGAGGGCTC ATCCCGGGCC CCAGAGATAA ATCCCAGTGA CCCTGAAGCA      33540

GCACCCCGAC CTTCCGCTCC CAGCAGCCAC ACCCACGGG CCCTCTCCGG CGTCTGCTTT      33600

CCACAATGCA GCCCCGCCC AGGAGGGCCC ATGTGCTTAC CCTGTTTTGC CCATGAAGAA      33660

ACAGCTCAGT GTTGTGGGTC AGTGCCCGCA TCACACAGCG TCTAGCACGT AACTGCACCC      33720

CGGGAGTCGT GGGCATCTGC TGGCCTCCTG CCGGCCTCCT GCGCTGCTGA CAGCTTGCTG      33780

TGCCCCCTGC CTGCCCCAGT ACGAGCGGGC CCTGGACGTG GCGCAGAGCC CAAGCACGAG      33840

CGGCAGCACC GAGCCCAGAT ACGCAAGAAC ATCACGGAGA CTCTGGTGTC CCTGAGGGTC      33900

CACACTGTGG ATGACATCCA GCAGATCGCT GCTGCGCTGG CCCAGTGCAT GGTAGGATGG      33960

CCCCACCTGC TCACCCTGCC CCGCATGCCT GCCAGGGCAC TGGGTTCAGC CCCCCAGGGC      34020

AGACGGGCAG CTTGGCCGAG GAGCTGAGCC TCCAGCCTGG GCTCCTTCCT GCCATGGCGT      34080

TCCTCGGTCT CTGACCTGCT TCAGTAGCCT CAGCCGTTCT GTCCTGTGTG AACGCAGGGT      34140

GCCTCTCGGG GGACCCAGGG TGTAAAGAGG GGCCCAGATG TGGGGAGGGA CTAAGAAGAT      34200

GCTGCTCTGT GCCCTCCACT CTCCCCTCCC CTCCCCTCCC CCTTCCCTCC CCTAGCCCCT      34260

CCCCTCCTCC CCTCCCCTAG CCCTTCCCCT CCTCCCCTCC CCTAGCCCTT TCCCTTCTTC      34320

CCCCCCAGCC CTTCCCCTCC TCCCCTCCCC TAGCCCTTCC CCTCCTCCCC TCCCCTACCC      34380

CTTCCCCTCC TCCCCTCCCC TAGACCTTCC CCTCACCTCC TCCCGCTGAG CCCCTCCACT      34440

CGTCCCCCAG CCCCTCCCTC CCCTAGCCCC TCCCCTCCCC CTTCCTCCCC TCCTCCCCCT      34500

CCCCTCCTCC CCTCCCTCT TCCTCCCCCT CCCCTCCTCC CCTTCCTCC CCTCTCCTCC       34560

CCCTCCCCTC CTGTCCCCCC TCCTCCCCTC CTCCCTCCTC CCCTCCTCCC CCCTCCTCCT      34620

CCCCCTCCTC CCTCCTCCCT CCTCCCCCTC CTCCTCCTCC CCTCCTCCCT CCTCCCCTCC      34680

TCCCCTCCCC TCCTCCCCCT CCCCCCTCCC TTCCTCCCCC TCCCCCCTCC CCTCCTCCCC      34740
```

```
CTCTCCTCCT CCCATCCCTC CTCCCATCCC TCCTCCCCGT TCCCATTCTC TCCCCTCCCC    34800
CTTCCATTTC TCCCTCCTCC CCCTGCCCTC CTCTCCTCCT CACCTCCCCT TCTCCGCTCC    34860
TTTCTTCTCC TCCCTCCCTT TCTCTCCTCC CTCCCCTTCT CCCCTTCTCC TCTTCTCCCC    34920
TTCTCCTCTC TTTTCATCCT TCCCTTCTTC CCTCCTTTCC TCCTCTTTTC CCTCTTCTCC    34980
CCCCTCCTCC CCTCCTTCCT CCTCCCATTC CCCCTCCTCC CCCCTCCCAT TCCCCCTCCT    35040
CCCCTCCTTC CTCCTCCCAT TACCCCTCCT CTCCTCCCCT CCTCCCACCC CCCTCTCCTC    35100
CCGGCTCCTC TCCTCCCCTC CTCATCCCCC TCCTCTCCTT CCCTCCTAAC CCCCCTCCTC    35160
TCCTCCCCTC CTCATCCCCC TCCTCTCCTT CCCTCCTCCT ATCCCCCTC CTCTCCTCCC    35220
CTCCTCCTAT TCCCCCTCCT CTCCTCCCCT CCTTCCTCCT CCTCTCCTCC CATGCCCCCT    35280
CCTCCCCTCC TCCCATCCCC CTCCTCCCCT CCTCCCTCCT CCCATCCCAT CCCCCTCCTC    35340
TCCTCCCCTT CTCTCCCCTC CTCTCCTCCC CTCCTCTCCT CTCCTCCTCT CCTCCCCTCC    35400
TCCCATCCCC CCTCCTCCCA TCCCCCCTCC TCTCCTCCCC ACTCCTCTCC TCCCCACTCC    35460
TCTCCTCCCC TCATCCCCCT CCTCTCTCCT CCCCTCCCCC TCCTCTCCTT CCCTCCTCCT    35520
TTCCTCCCCT CCCCCTCCTT CCCCCTCCTC CCCCTCCTTC TCCCCATCCC CCTTCCCCTT    35580
CTCCTCCTCT CCCCTCCCCC TTCTCTTTTT CCCTCCTCCT CCCTTCCTCC TCCCCTCTTC    35640
TCCCCTTTTC CCTTTCTCT TCCTCTCCTC CCCTTCTCCC CTCCTGTCCT CCCTCCCTTT    35700
CTCTCTTTCT TTCCTCCCTT TCCTTCTCCC CTGTTCTCCT CCCTTCCCTT CTCCCCTTTT    35760
CTTCCCTCCT CCTTTCCTCC CCTCCTCCTT TTCTCTGTTT CTCTTCCTTT CCCCTCCACT    35820
TTCCCCTTCC TTTCCCCTCT CCTTTCTCCT TCCTTTCCTC TCCCCTTCTC TTCCTTTTCC    35880
TCTCTCCCCT TCTTTTCCCT CTTCCCCTCC CCTCCTCTTC CCCTCCCCTC CTCTTCCCCT    35940
CCCCTCCTCT TCCCCTCCCC TCCTCTTCCC CTCTCCTCCT CTTCCCCTCC CCTCCTCTTT    36000
CCCTCCCCTC TTCTCCTCCC CTCCTCTCCC CTCTTCCCCT CCCCTCCTCT TCCCTCCCCT    36060
TCCCCTCCCC TCCTCTTCCC TCCCCTTCCC CTCCCCTCCT CTTCCCTCCC CTTCCCCTCC    36120
TCTTCCTTCC TCTCTTCCCC TCCCCTCCTC TTCCCTCCCC TCTTCCCCTC CCCTTCTCTT    36180
CTCCTCCCCT TCTCTTCCCC TCCCCTTTTC TTCCCTCTCC TTGTCTTCCC TGCCCTCCTC    36240
TTCCCTCCCC TCCTCTTCCC TCCCCTCTTC CCCTCTCCTC CTCTTCCCTC CCCTCTTCCT    36300
CTTTCCTCTT CCCCTCCCCT CCTCCTCCCT CCCCTTTCCC CTCTTCCCCT CCCCTCCGCT    36360
TCCCTCCCCT TTCTCCCCCT TCTCTCCCCT CCCCTCTCCC CCCTTCTCTC CCTCCCCTC    36420
TCCCCCTTCT CTCCCCTCCC CTCTCCCCCT TCTCTCCCCT CTCCTCTCCC CCTTCTCTCC    36480
```

| | | | | | | |
|---|---|---|---|---|---|---|
| CCCTTCTCTC | CCCCTTCTCT | CTCCCCTTCT | CTCCCCCTTC | TCTCCCCTCC | CCCCTTCTCT | 36540 |
| CCCCTCCCCT | CTCCCCCTTC | TCTCCCCTCC | CCTCTCCCCT | GTCCTCTCCT | CTCCACCCTT | 36600 |
| CTCTCCCCTC | CCCTCTCCTC | TCCCCCTTCC | CTCTCCTCTC | CCCCTTCTCT | CCCCTCCCCT | 36660 |
| CTCCTCTCCC | CCCTTTTCTC | CACTCCCCTC | TCCTCTCTCC | CCTCCTCCTC | CGCTCTCATG | 36720 |
| TGAAGAGGTG | CCTTGTGTGG | TCGGTGGGCT | GCATCACGTG | GTCCCCAGGT | GGAGGCCCTG | 36780 |
| GGTCATGCAG | AGCCACAGAA | AATGCTTAGT | GAGGAGGCTG | TGGGGGTCCA | GTCAAGTGGG | 36840 |
| CTCTCCAGCT | GCAGGGCTGG | GGGTGGGAGC | CAGGTGAGGA | CCCGTGTAGA | GAGGAGGGCG | 36900 |
| TGTGCAAGGA | GTGGGGCCAG | GAGCGGGGCT | GGACACTGCT | GGCTCCACAC | AGGGGCCCAG | 36960 |
| CAGGGAGCTC | GTATGCCGCT | CGTGCCTGAA | GCAGACGCTG | CACAAGCTGG | AGGCCATGAT | 37020 |
| GCTCATCCTG | CAGGCAGAGA | CCACCGCGGG | CACCGTGACG | CCCACCGCCA | TCGGAGACAG | 37080 |
| CATCCTCAAC | ATCACAGGTG | CCGCGGCCCG | TGCCCCATGC | CACCCGCCCG | CCCCGTGCGG | 37140 |
| CCCTTTCCTC | TGCCTCCCTC | CTCCCCCCAA | CCGCGTCGCC | TTTGCCCCAT | CCCATCTTCG | 37200 |
| TCCCCCTCCC | CTCCCCCCAA | TTCCCATCCT | CATCCCCCTC | CCCCAATTCC | CATTCTCCTC | 37260 |
| CCCCTCCCCC | TTCCCTATTA | CCATCCCTTT | TCTCCATCTC | TCTCCCCTTT | TCTCCATTTC | 37320 |
| CCCCCCCGTC | CTCCCCGTCC | TTTTGTCCAT | TCCCCTCATC | TTCCTCATCC | CCCTCATCCC | 37380 |
| CCTTCCCCTC | CCTTATCCCC | CTTCCCCTCC | CTTTCCCCCT | GCTCCTCTTC | TTCTCCCTTC | 37440 |
| TCTTTCTCT | ACCCTTTTCC | TTCCTTTTTC | CTCCCTCTCC | CCATCATCCC | CCTCATCTTC | 37500 |
| GTCCTCATCC | CCATCACCTT | CCCCCTCCCC | CCTCCACCAC | TCTCTCTCCA | GCTTCCCCCT | 37560 |
| TCCTTCTGCC | TGCACCTCGC | TCTCTGCCCC | CTCAGGTTCC | CCCTTTCTCC | CAGCCCCCAC | 37620 |
| CCTCCGGCTC | CCCCTTTTG | CCTGCCCCCA | CCCTCCCTCT | ACCTCCCTGT | CTCTGCACTG | 37680 |
| ACCTCACGCA | TGTCTGCAGG | AGACCTCATC | CACCTGGCCA | GCTCGGACGT | GCGGGCACCA | 37740 |
| CAGCCCTCAG | AGCTGGGAGC | CGAGTCACCA | TCTCGGATGG | TGGCGTCCCA | GGCCTACAAC | 37800 |
| CTGACCTCTG | CCCTCATGCG | CATCCTCATG | CGCTCCCGCG | TGCTCAACGA | GGAGCCCCTG | 37860 |
| ACGCTGGCGG | GCGAGGAGAT | CGTGGCCCAG | GGCAAGCGCT | CGGACCCGCG | GAGCCTGCTG | 37920 |
| TGCTATGGCG | GCGCCCCAGG | GCCTGGCTGC | CACTTCTCCA | TCCCCGAGGC | TTTCAGCGGG | 37980 |
| GCCCTGGCCA | ACCTCAGTGA | CGTGGTGCAG | CTCATCTTTC | TGGTGGACTC | CAATCCCTTT | 38040 |
| CCCTTTGGCT | ATATCAGCAA | CTACACCGTC | TCCACCAAGG | TGGCCTCGAT | GGCATTCCAG | 38100 |
| ACACAGGCCG | GCGCCCAGAT | CCCCATCGAG | CGGCTGGCCT | CAGAGCGCGC | CATCACCGTG | 38160 |
| AAGGTGCCCA | ACAACTCGGA | CTGGGCTGCC | CGGGGCCACC | GCAGCTCCGC | CAACTCCGCC | 38220 |

```
AACTCCGTTG TGGTCCAGCC CCAGGCCTCC GTCGGTGCTG TGGTCACCCT GGACAGCAGC   38280

AACCCTGCGG CCGGGCTGCA TCTGCAGCTC AACTATACGC TGCTGGACGG TGCGTGCAGC   38340

GGGTGGGGCA CACGCGGCCC CCTGGCCTTG TTCTTGGGGG AAGGCGTTT CTCGTAGGGC    38400

TTCCATGGGT GTCTCTGGTG AAATTTGCTT TCTGTTTCAT GGGCTGCTGG GGGCCTGGCC   38460

AGAGAGGAGC TGGGGCCAC GGAGAAGCAG GTGCCAGCTC TGGTGCAGAG GCTCCTATGC    38520

TTTCAGGCCC GTGGCAGAGG GTGGGCTCAG GAGGGCCATC GTGGGTGTCC CCCGGGTGGT   38580

TGAGCTTCCC GGCAGGCGTG TGACCTGCGC GTTCTGCCCC AGGCCACTAC CTGTCTGAGG   38640

AACCTGAGCC CTACCTGGCA GTCTACCTAC ACTCGGAGCC CCGGCCCAAT GAGCACAACT   38700

GCTCGGCTAG CAGGAGGATC CGCCCAGAGT CACTCCAGGG TGCTGACCAC CGGCCCTACA   38760

CCTTCTTCAT TTCCCCGGGG TGAGCTCTGC GGGCCAGCCT GGCAGGGCAG GGCAGGGCAT   38820

CATGGGTCAG CATTGCCTGG GTTACTGGCC CCATGGGGAC GGCAGGCAGC GAGGGGACTG   38880

GACCGGGTAT GGGCTCTGAG ACTGCGACAT CCAACCTGGC GGAGCCTGGG CTCACGTCCG   38940

CTACCCCTTC CCTGCCCAGG AGCAGAGACC CAGCGGGGAG TTACCATCTG AACCTCTCCA   39000

GCCACTTCCG CTGGTCGGCG CTGCAGGTGT CCGTGGGCCT GTACACGTCC CTGTGCCAGT   39060

ACTTCAGCGA GGAGGACATG GTGTGGCGGA CAGAGGGGCT GCTGCCCCTG GAGGAGACCT   39120

CGCCCCGCCA GGCCGTCTGC CTCACCCGCC ACCTCACCGC CTTCGGCGCC AGCCTCTTCG   39180

TGCCCCCAAG CCATGTCCGC TTTGTGTTTC CTGTGAGTGA CCCTGTGCTC CTGGGAGCCT   39240

CTGCAGAGTC GAGGAGGGCC TGGGTGGGCT CGGCTCTATC CTGAGAAGGC ACAGCTTGCA   39300

CGTGACCTCC TGGGCCCGGC GGCTGTGTCC TCACAGGAGC CGACAGCGGA TGTAAACTAC   39360

ATCGTCATGC TGACATGTGC TGTGTGCCTG GTGACCTACA TGGTCATGGC CGCCATCCTG   39420

CACAAGCTGG ACCAGTTGGA TGCCAGCCGG GGCCGCGCCA TCCCTTTCTG TGGGCAGCGG   39480

GGCCGCTTCA AGTACGAGAT CCTCGTCAAG ACAGGCTGGG GCCGGGGCTC AGGTGAGGGG   39540

CGCAGCGGGG TGGCAGGGCC TCCCCTGCTC TCACTGGCTG TGCTGGTTGC ACCCTCTGGG   39600

AGTGAGTCTC GTCGCAGGCG TCAGAACAAG GCAGTTTTTG CAGTGCTGTG TGAAGGGCTC   39660

GTGTGTTCAT CCTGGGAATG ACCTCGTGAG CACTCACTGT CCCTGAGGAC TAGGACAGCT   39720

CCTAGCTGGA AGTAGGTGCC AGTCAGTCAG GGTGGGCAGC CCACGTTCTG CACAGTAGCG   39780

TGGCCCCACA AGTGACGTGA GCATCGCTAC CACTGTGGGA GACTGTGCAT CCACCCGCGA   39840

TCCTGACTGC ATAGCTCGTC TCTCAGACGG AGGCGCCAGC ACCCTCCCCG TGGCTGTTTC   39900

TTCAGTACCT CCATTTTCCT TTCATTGGAA TTGCCCTTCT GGCATTCCCT TTTTGTTTTC   39960
```

```
GTTTTTCTTT TTTTAGAGAC GGAGTCTCAC TCTGTTGCCC AGGCTGGAGT GCAATGGCAT    40020
GATCTTGGCT CACAGCAACT TCCAGCTCCC GGGTTTAAGC CATTCCCCTT AAGCGATTCT    40080
CCTGAGTAGC TGGGAGTACA GGTGCACACC ACCACACCCA GTTAATTTTT CACCATGTCA    40140
GCCAGGCGAA CTCCTGACCT CAGGTGATCC GCCTGCCTCG GCCTGCCAGA GTGCTGGGAT    40200
GACAGGTGTG AGCCACCACA CCTGGCTGTG TTCCCATTTT TTATCTCTGT GCTGCTTTCC    40260
TCTTCATTGC CCAGTTCTTT CTTTTGATTA CCTACTTTTA AAAACTGTCG GCCGGGCGCG    40320
GTGGCTCACA CCTGTAATCC GAGCACTTTG GGAGGCCAGG CAGGCAAATC ACGGGGTCAG    40380
GAGATCGAGA CCATCCTGGC TAACGGTGAA ACCCTGTCTC TAATAAAAAG TACAAAAAAA    40440
TTAGCCCGGC GTAGTGGCAG GCGCCTGTAG TCCCAGCTCC TTGGGAGACT GAGGCAGGAG    40500
AATGGCGTGA ACCCGGGAGG CGGAGCTTGC AGTGAGCTGA GATTGCGCCA CTGCACTCCA    40560
GCCTGGGTGA CACAGCAAGA CTCCATCTCA AAAAAAAAG AAAAAAAATA CTGTCACCTG    40620
GGTCTGTCAC TGGGAGAGGA GGTGACACAG CTTCACGCTT TGCAGTCTGT GCATGAACTG    40680
AGGGACGGGT GTGTGGTGCG GGTCACCGGT TGTGGCATGA CTGAGGCGTG GACAGGTGTG    40740
CAGTGCGGGT CACTGGTTGT GGTGTGGACT GAGGCGTGTG CAGCCATGTT TGCATGTCAC    40800
AAGTTACAGT TCTTTCCATG TAACTTAATC ATGTCCTTGA GGTCCTGCTG TTAATTGGAC    40860
AAATTGCAGT AACCGCAGCT CCTTGTGTAT GGCAGAGCCG TGCAAAGCCG GGACTGCCTG    40920
TGTGGCTCCT TGAGTGCGCA CAGGCCAAAG CTGAGATGAC TTGCCTGGGA TGCCACACGT    40980
GTTGGGCAGC AGACCGAGCC TCCCACCCCT CCCTCTTGCC TCCCAGGTAC CACGGCCCAC    41040
GTGGGCATCA TGCTGTATGG GGTGGACAGC CGGAGCGGCC ACCGGCACCT GGACGGCGAC    41100
AGAGCCTTCC ACCGCAACAG CCTGGACATC TTCCGGATCG CCACCCCGCA CAGCCTGGGT    41160
AGCGTGTGGA AGATCCGAGT GTGGCACGAC AACAAAGGTT TGTGCGGACC CTGCCAAGCT    41220
CTGCCCCTCT GCCCCGCAT TGGGGCGCCC TGCGAGCCTG ACCTCCCTCC TGCGCCTCTG    41280
CAGGGCTCAG CCCTGCCTGG TTCCTGCAGC ACGTCATCGT CAGGGACCTG CAGACGGCAC    41340
GCAGCGCCTT CTTCCTGGTC AATGACTGGC TTTCGGTGGA GACGGAGGCC AACGGGGGCC    41400
TGGTGGAGAA GGAGGTGCTG GCCGCGAGTA AGGCCTCGTT CCATGGTCCC ACTCCGTGGG    41460
AGGTTGGGCA GGGTGGTCCT GCCCCGTGGC CTCCTGCAGT GCGGCCCTCC CTGCCTTCTA    41520
GGCGACGCAG CCCTTTTGCG CTTCCGGCGC CTGCTGGTGG CTGAGCTGCA GCGTGGCTTC    41580
TTTGACAAGC ACATCTGGCT CTCCATATGG GACCGGCCGC CTCGTAGCCG TTTCACTCGC    41640
ATCCAGAGGG CCACCTGCTG CGTTCTCCTC ATCTGCCTCT TCCTGGGCGC CAACGCCGTG    41700
```

```
TGGTACGGGG CTGTTGGCGA CTCTGCCTAC AGGTGGGTGC CGTAGGGGTC GGGGCAGCCT    41760

CTTCCTGCCC AGCCCTTCCT GCCCCTCAGC CTCACCTGTG TGGCCTCCTC TCCTCCACAC    41820

AGCACGGGGC ATGTGTCCAG GCTGAGCCCG CTGAGCGTCG ACACAGTCGC TGTTGGCCTG    41880

GTGTCCAGCG TGGTTGTCTA TCCCGTCTAC CTGGCCATCC TTTTTCTCTT CCGGATGTCC    41940

CGGAGCAAGG TGGGCTGGGG CTGGGGACCC GGGAGTACTG GAATGGAGC CTGGGCCTCG    42000

GCACCATGCC TAGGGCCGCC ACTTTCCAGT GCTGCAGCCA GAGGGAAAGG CGTCCACCAA    42060

AGGCTGCTCG GGAAGGGTCA ACACACTTGA GCAGCCTTAG CTAGACTGAC CAGGGAGAAA    42120

GAGAGAAGAC TCAGAAGCCA GAATGGTGAA AGAACGAGGG CACTTTGCTA AGCAGACGCC    42180

ACGGACGACT GCACAGCAGC ACGCCAGATA ACTCAGAAGA AGCAAGCACG CGGCTGTGCA    42240

CGCTTCCGAA ATGCACTCCA GAAGAAAATC TCAGTACATC TATAGGAAGT GAAGAGGCTG    42300

AGTTAGTCCC TTAGAAACGT CCCAGTGGCC GGGCCGGGTG TGGTGGCTCA CGCCTGTAAT    42360

CCCAACACTT CAGGTGGCCG AGGTGGGCGG ATCTGAGTCC AGGAGTTTGA GACCAGCCTG    42420

GGCAACATAG CAAGACCCCA TCTATATAAA ACATTAAAAA GGGCCAGGCG CGGTGGCTCA    42480

CGCCTGTAAT CCCAGCACTT TGGGAGGCCG AGGCGGGCAG ATCACTTGAG GTCAGGAGTT    42540

CGAGACCAGC CTGGCCAACA CAATGAAACC CCGACTCTAC TACAAATACA AAAACTTAGC    42600

TGGGCATGGT GGCGGGCGCC TGTAGTCCCA GCTACTCGAG AGGCTGAGGC AGGAGAATGG    42660

CATGAACCCA GGAGGCGGAG CTTGCAGTGA GCCGAGATTG CGCCACTGCA CTCCATCCTG    42720

GGCAACGGAG CAAGACTCCA TCTCCAAAAA AAAAAAAAAA AAATCCCACA AGAAAAGCT    42780

CAGGCTCAGA GCCTTCACGA TAGAATTTTT CTAAGCAGTT AAGGAAGAAT TAACACCAAT    42840

CCTTCACAGA CTCTTTCCAA GAATACAGCA GGTGGGAACG CTTCCCATTC ATACGGAAAC    42900

GGGAGGCCGC ACCCCTTAGG AATGCACACG TGGGGTCCTC AAGAGGTTAC ATGCAAACTA    42960

ACCCCAGCAG CACACAGAGA AGGCGCATAA GCCGCGACCA GGAGGGGTTG CTCCCGAGTC    43020

CGTGGCAGGA ACCAGAGGCC ACATGTGGCT GCTCGTATTT AAGTTAATTA AAATGGAACG    43080

ATGGCCGGGT GTGGTGGCTC ACACCTGTAA TCCCAGCACT TGGGAGGCG GAGGCGGGCA    43140

GATCACTTGA GGTCAGGAGT TCCAAGACCA GCCTGGCCAA CACAGTGAAA CCCCGTCTCT    43200

ACTAAAAATA CAAAAAATTA GCTGGGCATG GTGGCAGGCA CCTGTAATCC CAGCTACTCA    43260

GGAGGCTGAG CCAGGACAAT CGCCTGAACG CGGGAGGTGG AGGTTGCAGT GAGCTGAGAT    43320

TGCGCCATTG CACTCCAGCC TGGGTGACAG CGAGACTCCA TCTAAAAAG AAAATATGAA    43380

ATTTAAAACT CTGTTCCTTA GCTGCACCAG TCTGCTGTCA AGTGTTCAGT GGCACACGTC    43440
```

| | | | | | | |
|---|---|---|---|---|---|---|
| GCGAGGGGCT | GCCATCACGG | ACGGTGCAGA | TGTCCCATAT | ATCCAGCATT | CTAGGACATT | 43500 |
| CTGTCAGATG | GCACCGGGCT | CTGTCCTGTC | TGCTGAGGAG | GTGGCTTCTC | ATCCCTGTCC | 43560 |
| TGAGCAGGTC | TGAGCTGCCG | CCCGCTGACC | ACTGCCCTCG | TCCTGCAGGT | GGCTGGGAGC | 43620 |
| CCGAGCCCCA | CACCTGCCGG | GCAGCAGGTG | CTGGACATCG | ACAGCTGCCT | GGACTCGTCC | 43680 |
| GTGCTGGACA | GCTCCTTCCT | CACGTTCTCA | GGCCTCCACG | CTGAGGTGAG | GACTCTACTG | 43740 |
| GGGGTCCTGG | GCTGGGCTGG | GGTCCTGCC | GCCTTGGCGC | AGCTTGGACT | CAAGACACTG | 43800 |
| TGCACCTCTC | AGCAGGCCTT | TGTTGGACAG | ATGAAGAGTG | ACTTGTTTCT | GGATGATTCT | 43860 |
| AAGAGGTGGG | TTCCCTAGAG | AAACCTCGAG | CCCTGGTGCA | GGTCACTGTG | TCTGGGGTGC | 43920 |
| CGGGGGTGTG | CGGGCTGCGT | GTCCTTGCTG | GGTGTCTGTG | GCTCCATGTG | GTCACACCAC | 43980 |
| CCGGGAGCAG | GTTTGCTCGG | AAGCCCAGGG | TGTCCGTGCG | TGACTGGACG | GGGGTGGGCT | 44040 |
| GTGTGTGTGA | CACATCCCCT | GGTACCTTGC | TGACCCGCGC | CACCTGCAGT | CTGGTGTGCT | 44100 |
| GGCCCTCCGG | CGAGGGAACG | CTCAGTTGGC | CGGACCTGCT | CAGTGACCCG | TCCATTGTGG | 44160 |
| GTAGCAATCT | GCGGCAGCTG | GCACGGGGCC | AGGCGGGCCA | TGGGCTGGGC | CCAGAGGAGG | 44220 |
| ACGGCTTCTC | CCTGGCCAGC | CCCTACTCGC | CTGCCAAATC | CTTCTCAGCA | TCAGGTGAGC | 44280 |
| TGGGGTGAGA | GGAGGGGGCT | CTGAAGCTCA | CCCTTGCAGC | TGGGCCCACC | CTATGCCTCC | 44340 |
| TGTACCTCTA | GATGAAGACC | TGATCCAGCA | GGTCCTTGCC | GAGGGGGTCA | GCAGCCCAGC | 44400 |
| CCCTACCCAA | GACACCCACA | TGGAAACGGA | CCTGCTCAGC | AGCCTGTGAG | TGTCCGGCTC | 44460 |
| TCGGGGAGG | GGGGATTGCC | AGAGGAGGG | CCGGGACTCA | GGCCAGGCAG | CCGTGGTTCC | 44520 |
| CGCCTGGGGT | AGGGTGGGGT | GGGGTGCCAG | GGCAGGGCTG | TGGCTGCACC | ACTTCACTTC | 44580 |
| TCTGAACCTC | TGTTGTCTGT | GGAAAGAGCC | TCATGGGATC | CCCAGGGCCC | CAGAACCTTC | 44640 |
| CCTCTAGGGA | GGGAGCAGGC | TCATGGGGCT | TTGTAGGAGC | AGAAAGGCTC | CTGTGTGAGG | 44700 |
| CTGGCCGGGG | CCACGTTTTT | ATCTTGGTCT | CAGAGCAGTG | AGAAATTATG | GGCGGGTTTT | 44760 |
| TAAATACCCC | ATTTTTGGCC | GGGCGCGGTG | GCTCACACGT | GTAATCCCAG | CACTTTGGGA | 44820 |
| GGCCGAGGTG | GGCAGATGAC | CTGAGGTCAG | CAGTTCGAGA | CCAGCCTGGC | CAACATGGCG | 44880 |
| AAACCCCGTC | TCTACTAAAA | ATACAAAAAA | TTAGCCGGGC | ATGCTGGCAG | GCGCCTGTAG | 44940 |
| TCCCAGTTAC | TCGGGAGACT | GAGGTAGGAG | AATCGATTGA | ACCTGGTAGG | TGAAGGTTGT | 45000 |
| AGTGAGCCGA | GATCGCGCCA | CTGCACTCCA | GCCTGGGCAA | CAAGAGCGAA | ACTCCGTCTC | 45060 |
| AAAAACAAAA | AAATTCCTCA | ATTTCTTGGT | TGTTTTGTAA | CTTATCAACA | AATGGTCATA | 45120 |
| TAGAGGTTAC | CTTGTATGTA | GTCACGCACA | TAGTCACGCA | CATGGCAGCC | GGCGGCGGAG | 45180 |

```
CGCACCCACG GCGTGTTCCC ACGCGTGTGA CCCCGGGCTC TGCCATGCCC TCCTATGCTC      45240

AGGTGTGCTG AGGTCCACAC GGCCCTGCCG TTGCACTGCA GCTGCCTGCA GGATTCAGTG      45300

CAGTGGCATG CAGTGCAGGT GCGGTGCCCC GGAGCCACAG GCCACACCAC AGGGCCTGCA      45360

TGCACAGGGG CTGCGGTGTC TGGGTTTGGG TAACTACGCC CTGTGACATT TGCACAGCAA      45420

CAGAATTACC TAATGACGCA TTTCTCAGAA CACATCCCTG GCACTAAGTG GTGCGTGACT      45480

GCTGCTTTTG CATCCACATC TAGTTTGATT TGTGTGTTAT TCCTTTGAGT GCTTCTCATT      45540

GTTAAGCAAC CAAGAACTAA AGAGGTATGA ACTGCCCCTG GACTCAAACA AAAAGGAAAA      45600

CTTCCTGATT TACAAAAGGC AGATAACCAT CACATGAGGG CATCTTTATG AATAAATTGC      45660

TGGTTGGTTT TAAAAATACA GAGTATGGGG AAATCCAGGG GTAGTCACTA CATGCTGACC      45720

AGCCCCAGGT ATCTCCGGCC CAAAGCTCTG TGAAATCCAG ATTCAGTGCT TCCGCGGGGA      45780

TTTCTGACGG CAGCTCAGAC TCCGCATCCA CACAGAGCGC GTGGCCCTCA CCCTCCCGGC      45840

TTCCTCAACC CTTGGCCGTC CCTTGCTCGG ACAGTGCTTC GGGCTGACCA GGTCGGAGGC      45900

TTGGGTTTGT CCTGGACCCC TCTGCGTCCT TCCTCACTGC AGCCTCCAGC GCGTCCCGTG      45960

GCTCCTTTCC CAACGCAGAG CACGGCCTTC CCTGCGCCTG AGCCTGCACC CTCCGTCCTG      46020

GCGGCGCCTC TGCCCTGGCA TTCCCTGCCA CTCCATGCCT CCCTATTGGC CATTCTCCGT      46080

CTCTGCCAGC GAGAGCCTGC TCCCTGAGTC AGACCCTGAG TCATTTGTGT TGCTATAAAG      46140

GAATAGTTGA GGCTGGGTTA TTTTTTATTT TTATTTATTT TTTTGAGATG GAGTCTCTGT      46200

TGCCCAGACT GGAGTGCAGT CGCATGATCT CGGCTCACTG CAAAGTCTGC CTCCCACGTT      46260

CAAGCAGTTA TCTGCCTCAG CCTCCCAAGT AGCTAAGATT ACAGGCGCCC GCCGCCACAG      46320

CCGGCTAATT TTTTGTGTGT GTGTTTTAGT AGAGAGGAGG TTTCACCATC TTAGCCAGGC      46380

TGGTCTTGAA CTCCTGACCT CGTGATCCAC CCATCTCAGC CTCCCAAAAT GCTGAGATTA      46440

CAGGCGTGAG CCACCACGCC TGACCAAGTT GAGGCTAGGT CATTTTTTAA TTTTTTGTAA      46500

AGACAGGGTC TCACTGTCTC CAACTCCTGA GCTCAAGTGA TCCTCCTGCC TCAGCCTCCT      46560

GAAGTGCTGG GATTACAGGC TTGAGACACT GCGCCCAGCC AAGAGTGTCT TTTATCCTCC      46620

GAGAGACAGC AAAACAGGAA GCATTCAGTG CAGTGTGACC CTGGGTCAGG CCGTTCTTTC      46680

GGTGATGGGC TGACGAGGGC GCAGGTACGG GAGAGCGTCC TGAGAGCCCG GGACTCGGCG      46740

TCTCGCAGTT GGTCTCGTCC TCCCCCTCAA CGTGTCTTCG CTGCCTCTGT ACCTCTTCTC      46800

TAGCAGCTCT GGGACCGGGC ATATCAGCAT GGTGGCCCGA TGCAGTGGCA CAGCCTCGGT      46860

GGTCACTGGC TCCTGGAGAC ACAAGCAGAT CTCTGGCCTC AGGGAGCCCT ACACACTGTT      46920
```

```
GGGATTTGAA AGGCATTCAT ATGTTTCCTT GTCCAGAAGT TAATTTTAGG CCATAAACCT    46980

GCATGGGACA GACACACTGG CGTCTCTAGA TTGTAGAGAT GCTTGTTGGA TGGTTGAGAC    47040

CCAATCATAG TTTGCAGGGT TGAAGGGGGG CTCATTGCAC CCTGAGAGAC TGTGCACTGC    47100

TGTAAGGGCA GCTGGTCAGG CTGTGGGCGA TGGGTTTATC AGCAGCAAGC GGGCGGGAGA    47160

GGGACGCAGG CGGACGCCTG ACTTCGGTGC CTGGAGTGGC TCTTGGTTCC CTGGCTCCCA    47220

GCACCACTCC CACTCTCGTT TGGGGTAGGG TCTTCCGGCT TTTTGTCGGG GGGACCCTGT    47280

GACCCAAGAG GCTCAAGAAA CTGCCCGCCC AGGTTAACAT GGGCTTGGCT GCAACTGCCT    47340

CCTGGAGGCC GGGATGAATT CACAGCCTAC CATGTCCCTC AGGTCCAGCA CTCCTGGGA    47400

GAAGACAGAG ACGCTGGCGC TGCAGAGGCT GGGGGAGCTG GGGCCACCCA GCCCAGGCCT    47460

GAACTGGGAA CAGCCCCAGG CAGCGAGGCT GTCCAGGACA GGTGTGCTTG CGTAGCCCCG    47520

GGATGCCCCT AGCCCCTCCC TGTGAGCTGC CTCTCACAGG TCTGTCTCTG CTTCCCCAGG    47580

ACTGGTGGAG GGTCTGCGGA AGCGCCTGCT GCCGGCCTGG TGTGCCTCCC TGGCCCACGG    47640

GCTCAGCCTG CTCCTGGTGG CTGTGGCTGT GGCTGTCTCA GGGTGGGTGG GTGCGAGCTT    47700

CCCCCCGGGC GTGAGTGTTG CGTGGCTCCT GTCCAGCAGC GCCAGCTTCC TGGCCTCATT    47760

CCTCGGCTGG GAGCCACTGA AGGTGAGGGG GCTGCCAGGG GTAGGCTACA GGCCTCCATC    47820

ACGGGGGACC CCTCTGAAGC CACCCCCTCC CCAGGTCTTG CTGGAAGCCC TGTACTTCTC    47880

ACTGGTGGCC AAGCGGCTGC ACCCGGATGA AGATGACACC CTGGTAGAGA GCCCGGCTGT    47940

GACGCCTGTG AGCGCACGTG TGCCCCGCGT ACGGCCACCC CACGGCTTTG CACTCTTCCT    48000

GGCCAAGGAA GAAGCCCGCA AGGTCAAGAG GCTACATGGC ATGCTGCGGG TGAGCCTGGG    48060

TGCGGCCTGT GCCCCTGCCA CCTCCGTCTC TTGTCTCCCA CCTCCCACCC ATGCACGCAG    48120

GACACTCCTG TCCCCCTTTC CTCACCTCAG AAGGCCCTTA GGGGTTCAAT GCTCTGCAGC    48180

CTTTGCCCGG TCTCCCTCCT ACCCCACGCC CCCCACTTGC TGCCCCAGTC CCTGCCAGGG    48240

CCCAGCTCCA ATGCCCACTC CTGCCTGGCC CTGAAGGCCC CTAAGCACCA CTGCAGTGGC    48300

CTGTGTGTCT GCCCCCAGGT GGGGTTCCGG GCAGGGTGTG TGCTGCCATT ACCCTGGCCA    48360

GGTAGAGTCT TGGGGCGCCC CCTGCCAGCT CACCTTCCTG CAGCCACACC TGCCGCAGCC    48420

ATGGCTCCAG CCGTTGCCAA AGCCCTGCTG TCACTGTGGG CTGGGGCCAG GCTGACCACA    48480

GGGCCCCCCC GTCCACCAGA GCCTCCTGGT GTACATGCTT TTTCTGCTGG TGACCCTGCT    48540

GGCCAGCTAT GGGGATGCCT CATGCCATGG GCACGCCTAC CGTCTGCAAA GCGCCATCAA    48600

GCAGGAGCTG CACAGCCGGG CCTTCCTGGC CATCACGCGG TACGGGCATC CGGTGCACTG    48660
```

```
GTCTGTCTTC TGGGCTTTAG TTTTGCCTTT AGTCCAGCCA GACCCTAGGG GACATGTGGA    48720

CATGTGTAGA TACCTTTGTG GCTGCTAGAA CTGGAGGTAG GTGCTGCTGG CATCAGTAGG    48780

CAGAGGGGAG GGACACAGGT CCGTGTCTTG CAGTGCACAG GACGGGCCCA TGACAGACAA    48840

CTGTCTGCCC CAGAACATCC CCAGGATAAG GCTGAGAAGC CCAGGTCTAG CCGTGGCCAG    48900

CAGGGCAGTG GGAGCCATGT TCCCTGGGTC TCTGGTGGCC GCTCACTCGA GGCGGGCATG    48960

GGGCAGTAGG GGCTGGAGCG TGTGACTGAT GCTGTGGCAG GTCTGAGGAG CTCTGGCCAT    49020

GGATGGCCCA CGTGCTGCTG CCCTACGTCC ACGGGAACCA GTCCAGCCCA GAGCTGGGGC    49080

CCCCACGGCT GCGGCAGGTG CGGCTGCAGG AAGGTGAGCT GGCAGGGCGT GCCCCAAGAC    49140

TTAAATCGTT CCTCTTGTTG AGAGAGCAGC CTTTAGCGGA GCTCTGGCAT CAGCCCTGCT    49200

CCCTAGCTGT GTGACCTTTG CCCTCTTAAC ACCGCCGTTT CCTTCTCTGT ATATGAGAGA    49260

TGGTAACGTT GTCTAATTGA TGGCTGCTGG GAGGGTTCCC TGGGGTGGCG CCGAACCAGA    49320

GCTCAGGCGA GCTGGCCAGC AGGAAACACT CCTGTTGGGT TTTGATGAGG CCCTGGCCCC    49380

GGCCTGGGGC TCTGTGTGTT TCAGCACTCT ACCCAGACCC TCCCGGCCCC AGGGTCCACA    49440

CGTGCTCGGC CGCAGGAGGC TTCAGCACCA GCGATTACGA CGTTGGCTGG GAGAGTCCTC    49500

ACAATGGCTC GGGGACGTGG GCCTATTCAG CGCCGGATCT GCTGGGGTGA GCAGAGCGAG    49560

GGCCCCGGGC GTCTACGCCA AGGACAAGGG AGTAGTTCTC CAGGAGTGCC GCGGCCTCCT    49620

GACCAGCCTG GCTCCGGGGT GCCGGAAGGG CTGGGGTGCG GCACCCACGC CACCCCTCTC    49680

CGGCAGGGCA TGGTCCTGGG GCTCCTGTGC CGTGTATGAC AGCGGGGCT ACGTGCAGGA    49740

GCTGGGCCTG AGCCTGGAGG AGAGCCGCGA CCGGCTGCGC TTCCTGCAGC TGCACAACTG    49800

GCTGGACAAC AGGTGGGAGC TCCCTCCCCT GCCCTCTCCG GGTGGCCGC AGTCACCAGC    49860

CAGGAGCCCA CCCTCACTCC TCCGGCCCCC GCTGGCCTAG GCGGCTTCCA CAGCCCCTCA    49920

GCCACGCCTG CACTGCGCGG TCCCCGCAGC TCCCGCCCTG CCACCCGCTC CTACTGACCC    49980

GCACCCTCTG CGCAGGAGCC GCGCTGTGTT CCTGGAGCTC ACGCGCTACA GCCCGGCCGT    50040

GGGGCTGCAC GCCGCCGTCA CGCTGCGCCT CGAGTTCCCG GCGGCCGGCC GCGCCCTGGC    50100

CGCCCTCAGC GTCCGCCCCT TTGCGCTGCG CCGCCTCAGC GCGGGCCTCT CGCTGCCTCT    50160

GCTCACCTCG GTACGCCCGT CCCCGGCCAG ACCCCGCGCC TCCACCGGC AGCGTCCCGC    50220

CCCCTCGCGG GGCCCCGCCC GGCAGCGTCT CACCCCTCGC AGCGCCCCGC CCCCTCGCAG    50280

CGTCCCGCCC CCTCGCAGGG CCCCGCCCCG GCAGCGTCCC GCCCCCTCGT AGGGCCCCGC    50340

CCCGGCAGCG TCCCGCCCCC TCGCAGGGCC CGCCCCGGC AGCGTCCCTC CCGCCCTCCT    50400
```

| | | | | | |
|---|---|---|---|---|---|
|GACCGCGCCC|CCCACAGGTG|TGCCTGCTGC|TGTTCGCCGT|GCACTTCGCC|GTGGCCGAGG|50460|
|CCCGTACTTG|GCACAGGGAA|GGGCGCTGGC|GCGTGCTGCG|GCTCGGAGCC|TGGGCGCGGT|50520|
|GGCTGCTGGT|GGCGCTGACG|GCGGCCACGG|CACTGGTACG|CCTCGCCCAG|CTGGGTGCCG|50580|
|CTGACCGCCA|GTGGACCCGT|TTCGTGCGCG|GCCGCCCGCG|CCGCTTCACT|AGCTTCGACC|50640|
|AGGTGGCGCA|GCTGAGCTCC|GCAGCCCGTG|GCCTGGCGGC|CTCGCTGCTC|TTCCTGCTTT|50700|
|TGGTCAAGGT|GAGGGCTGGG|CCGGTGGGCG|CGGGGCTGGG|CGCACACCCC|AGGGCTGCAA|50760|
|GCAGACAGAT|TTCTCGTCCG|CAGGCTGCCC|AGCAGCTACG|CTTCGTGCGC|CAGTGGTCCG|50820|
|TCTTTGGCAA|GACATTATGC|CGAGCTCTGC|CAGAGCTCCT|GGGGGTCACC|TTGGGCCTGG|50880|
|TGGTGCTCGG|GGTAGCCTAC|GCCCAGCTGG|CCATCCTGGT|AGGTGACTGC|GCGGCCGGGG|50940|
|AGGGCGTCTT|AGCTCAGCTC|AGCTCAGCTG|TACGCCCTCA|CTGGTGTCGC|CTTCCCCGCA|51000|
|GCTCGTGTCT|TCCTGTGTGG|ACTCCCTCTG|GAGCGTGGCC|CAGGCCCTGT|TGGTGCTGTG|51060|
|CCCTGGGACT|GGGCTCTCTA|CCCTGTGTCC|TGCCGAGTCC|TGGCACCTGT|CACCCCTGCT|51120|
|GTGTGTGGGG|CTCTGGGCAC|TGCGGCTGTG|GGGCGCCCTA|CGGCTGGGGG|CTGTTATTCT|51180|
|CCGCTGGCGC|TACCACGCCT|TGCGTGGAGA|GCTGTACCGG|CCGGCCTGGG|AGCCCCAGGA|51240|
|CTACGAGATG|GTGGAGTTGT|TCCTGCGCAG|GCTGCGCCTC|TGGATGGGCC|TCAGCAAGGT|51300|
|CAAGGAGGTG|GGTACGGCCC|AGTGGGGGGG|AGAGGGACAC|GCCCTGGGCT|CTGCCCAGGG|51360|
|TGCAGCCGGA|CTGACTGAGC|CCCTGTGCCG|CCCCAGTTC|CGCCACAAAG|TCCGCTTTGA|51420|
|AGGGATGGAG|CCGCTGCCCT|CTCGCTCCTC|CAGGGGCTCC|AAGGTATCCC|CGGATGTGCC|51480|
|CCCACCCAGC|GCTGGCTCCG|ATGCCTCGCA|CCCCTCCACC|TCCTCCAGCC|AGCTGGATGG|51540|
|GCTGAGCGTG|AGCCTGGGCC|GGCTGGGGAC|AAGGTGTGAG|CCTGAGCCCT|CCCGCCTCCA|51600|
|AGCCGTGTTC|GAGGCCCTGC|TCACCCAGTT|TGACCGACTC|AACCAGGCCA|CAGAGGACGT|51660|
|CTACCAGCTG|GAGCAGCAGC|TGCACAGCCT|GCAAGGCCGC|AGGAGCAGCC|GGGCGCCCGC|51720|
|CGGATCTTCC|CGTGGCCCAT|CCCCGGGCCT|GCGGCCAGCA|CTGCCCAGCC|GCCTTGCCCG|51780|
|GGCCAGTCGG|GGTGTGGACC|TGGCCACTGG|CCCCAGCAGG|ACACCCCTTC|GGGCCAAGAA|51840|
|CAAGGTCCAC|CCCAGCAGCA|CTTAGTCCTC|CTTCCTGGCG|GGGGTGGGCC|GTGGAGTCGG|51900|
|AGTGGACACC|GCTCAGTATT|ACTTTCTGCC|GCTGTCAAGG|CCGAGGGCCA|GGCAGAATGG|51960|
|CTGCACGTAG|GTTCCCCAGA|GAGCAGGCAG|GGGCATCTGT|CTGTCTGTGG|GCTTCAGCAC|52020|
|TTTAAAGAGG|CTGTGTGGCC|AACCAGGACC|CAGGGTCCCC|TCCCCAGCTC|CCTTGGGAAG|52080|
|GACACAGCAG|TATTGGACGG|TTTCTAGCCT|CTGAGATGCT|AATTTATTTC|CCCGAGTCCT|52140|

```
CAGGTACAGC GGGCTGTGCC CGGCCCCACC CCCTGGGCAG ATGTCCCCCA CTGCTAAGGC    52200

TGCTGGCTTC AGGGAGGGTT AGCCTGCACC GCCGCCACCC TGCCCCTAAG TTATTACCTC    52260

TCCAGTTCCT ACCGTACTCC CTGCACCGTC TCACTGTGTG TCTCGTGTCA GTAATTTATA    52320

TGGTGTTAAA ATGTGTATAT TTTTGTATGT CACTATTTTC ACTAGGGCTG AGGGGCCTGC    52380

GCCCAGAGCT GGCCTCCCCC AACACCTGCT GCGCTTGGTA GGTGTGGTGG CGTTATGGCA    52440

GCCCGGCTGC TGCTTGGATG CGAGCTTGGC CTTGGGCCGG TGCTGGGGGC ACAGCTGTCT    52500

GCCAGGCACT CTCATCACCC CAGAGGCCTT GTCATCCTCC CTTGCCCCAG GCCAGGTAGC    52560

AAGAGAGCAG CGCCCAGGCC TGCTGGCATC AGGTCTGGGC AAGTAGCAGG ACTAGGCATG    52620

TCAGAGGACC CCAGGGTGGT TAGAGGAAAA GACTCCTCCT GGGGCTGGC TCCCAGGGTG     52680

GAGGAAGGTG ACTGTGTGTG TGTGTGTGTG CGCGCGCGCA CGCGCGAGTG TGCTGTATGG    52740

CCCAGGCAGC CTCAAGGCCC TCGGAGCTGG CTGTGCCTGC TTCTGTGTAC CACTTCTGTG    52800

GGCATGGCCG CTTCTAGAGC CTCGACACCC CCCCAACCCC CGCACCAAGC AGACAAAGTC    52860

AATAAAAGAG CTGTCTGACT GCAATCTGTG CCTCTATGTC TGTGCACTGG GGTCAGGACT    52920

TTATTTATTT CACTGACAGG CAATACCGTC CAAGGCCAGT GCAGGAGGGA GGGCCCCGGC    52980

CTCACACAAA CTCGGTGAAG TCCTCCACCG AGGAGATGAG GCGCTTCCGC TGGCCCACCT    53040

CATAGCCAGG TGTGGGCTCG GCTGGAGTCT GTGCAGGGGC TTTGCTATGG GACGGAGGGT    53100

GCACCAGAGG TAGGCTGGGG TTGGAGTAGG CGGCTTCCTC GCAGATCTGA AGGCAGAGGC    53160

GGCTTGGGCA GTAAGTCTGG GAGGCGTGGC AACCGCTCTG CCCACACACC CGCCCCACAG    53220

CTTGGGCAGC CAGCACACCC CGCCTGAGGG AGCCCCATAT TCCCTACCCG CTGGCGGAGC    53280

GCTTGATGTG GCGGAGCGGG CAATCCACTT GGAGGGGTAG ATATCGGTGG GGTTGGAGCG    53340

GCTATGATGC ACCTGTGAGG CCATCTGGGG ACGTAGGCAG GGGGTGAGCT CACTATCAGG    53400

TGGCACCTGG GCCTGTCCCA CCAGCTCACG CCTGGACCCA CCCCACTCA CATTTGCGTG     53460

CAGGGCCATC TGGCGGGCCA CGAAGGGCAG GTTGCGGTCA GACACGATCT TGGCCACGCT    53520

GGTGTCCACA AGGCCCTCCA TGTCTGGGGA GACTTGGTGG TCACGCCAGG CCCAGGG       53577
```

FIGURE 1B

| | | | | | |
|---|---|---|---|---|---|
| TGTAAACTTT | TTGAGACAGC | ATCTCACCCT | GTTCCCCAGG | CTGGAGTGCA | GTGGTGTGAT | 60 |
| CATGGCTCAC | TGCAGCGTCA | ACCTCCTGGG | TCTACTTGAT | CTGTAAACTT | CGAGGGAAGG | 120 |
| TGTAATAAAC | CCTCCTGCAA | TGTCTTTGTT | TTTCAAAATC | TTTGTATTTC | ACAGTTTAGC | 180 |
| TTCGTGGGTT | GATGTTCTAT | TTTGTTTTTG | TGTGTGTGTG | TGTGTGTTTT | GTGTTTTTTT | 240 |
| TTGAGACACA | GTCTTGCTCT | TGTTGCCCAG | GCTGGAGTGC | AATGGTGTGA | TCTTGGCTCA | 300 |
| CTGCAACTTC | CACCTCTTGG | GTTCAAGAGA | TTCTCCTGCC | TCAGCCTTCC | GAGTAGCTAG | 360 |
| GATTACAGGC | GCCGCCACCA | CACCCCGCTA | ATTTTGTATT | TTTAGTAGAG | ATGGGGTTTC | 420 |
| TCCATATTGG | TCAGGCTGGT | CTCAAACTCC | CGACCTCAGG | TGATCCGCCC | ACCTCAGCCT | 480 |
| CCCAAAATGC | TGGGATTACA | GGCGTGAGTC | ACCGCACCTG | GCCAATGTTC | TATTTTTGAG | 540 |
| AACACAACAG | TTCATAATAT | ATTCTACATA | GACCATACCT | GTTATGTGTA | GATAAACAGA | 600 |
| CTCTTTTCCC | ATTTAACACC | TTTTGCCTTA | GGTTTATTTT | TCTGGTATCA | ATACTGGCAC | 660 |
| ACTTACTTTG | TTTGCAGTTT | CCTGTCTTTT | TTTTTTTTT | TTTTTTTTT | GAGACAGAGT | 720 |
| CTCACTCTGT | CACCCAGGCT | GGAGTGAAGT | GGCGGGATCT | CGGCTCACTG | CAACCTCTAC | 780 |
| CTCCTGGGTT | CATGCGATTC | TCCTGCCTCA | GCTTCCCGAA | TAGCTGAGAC | CACAACTGTG | 840 |
| TGCCACCATG | CCCAGCCAAT | TTTTGTATTT | TTAGTAGACA | CGGGGTTTCA | CCATACTGGC | 900 |
| CAGGATGGCT | CAATCTCTTG | ACCTCGTGAT | CCACCTGCCT | CCGCCTCCCA | AAGTGCTGGG | 960 |
| ATTACAGGCA | TGAGCCACTG | TGCCTGGCCT | TTTTTTTTCT | TTTGAGATG | GAGTCTCACT | 1020 |
| CTGTCACCCA | GGCTGGAGTG | CAGTGGGGTA | ACCTCAGGTC | ACTGCGACCT | CCGCCTCCCG | 1080 |
| GGTTCCAGTG | ATTCTCCTGC | CTCAGCCTCC | CGAGTAGCTG | GGATTACAGG | CACCCACCAC | 1140 |
| CATGCCTGGC | TAATTTTTGT | ATTTTAGTA | GAGACGGGGT | TTTGCCACGT | TGGCCAGGTT | 1200 |
| GGTCTCGAAC | TCTTGGCCTC | ATGTGACCCG | CCTGCCTTGG | CCTCCCAAAG | TGCTGGGATT | 1260 |
| ACAGGTGTGA | GCCACTGTGC | CTGGCCTGGC | TTTCTTGTTT | CTTTCTCCT | CTTCTAGTTT | 1320 |
| CCCCCTTTTA | GGCTAACAAT | TATTCACTGT | TAATAAAAAC | CCTCAGGTCT | GTATTTTATC | 1380 |
| AAGAAACATT | TCCCTCACGT | CTTCTTCCCT | GAACCAAACA | AGATCTCTGG | CACATTTTAT | 1440 |
| TTGCTCTGTC | TCACCACATG | GATTTGTTT | TTTTGTTTCT | TTGTTTTTTG | AGATGGAGTC | 1500 |
| TCACTCTTGT | TGCCCAGGCT | GGAGTGCCAT | GGCACAATCT | CAGCTCACTG | CAACCTCCAC | 1560 |

```
CTCCTGGGTT CAAGCGATTC TCCTGTCTCA GCCTCCTGAG TAGCTGGGAT TACAGGCGCG   1620

TGGCACCACC CCCAGCTAAT TTTTGTATTT TTAGTAGAGA CGGGGTTTCA CCATGTTGGT   1680

CAGGCTGGTC TCGAACTCCT GACCTTGTGA TCTGCCCACC TTGGCCTCCC AAAGTGCTGG   1740

GATTACAGGC ATGAGCCACC ACGCCCGGCC CCATGGTTT TTCAAATAGT TTAGAATTTC   1800

ATTTCCAGGT AACTAATTTG CTTCTTTAAA CATATGTCTT TTCTATTTAA GAAATCCTTT   1860

CTAAACAATT GCATTTTATT CCACAACCGC CTTCAAACAA TCATTGAGAC TTGGTTAATC   1920

TGTTTTGCTC ATTTGGCAGC AGTTTCTTGT GGCTGTTTCT TCCCTCCACT GGAGTCCTTG   1980

AATCTTAAGT CTGTCATTTG ACTGCAATTA AAAGCTGGGT TTGGAATACA ATCGCAGCCT   2040

TACCATCCAC CTGCTGTGTG ACCTGGTAAA TTTCTTTTTT TTTTTTGAG ACGGAGTCTT    2100

GCTCTGTTGC CCAGGCTGGA GTGCAGTGGC ACAACCTCTG CCTCCCAGGT TCAAGCGATT   2160

CTACTGCCTC AGGCTCCCTA GTAGCTGGGA TTATAGGTGC CTGCCACCAT GCCCAGCTGA   2220

TTTTTGTATT TTTAGTAGAG ATGAGGTTTC ACCATGTTGG CTAGGCTGGT CTCGAACTTC   2280

TGATCTTGTG ATCTGCCCGC CTCGGCCTCC CAAAGTGCTG GGATTACAGG CATGAGCCAC   2340

CACTCCCAGC CAGTTCTTTT TTTCTTTTTT CCATTTTTTT TTTTTTCGAG ACAGGATCTT   2400

ACTCTTTTGC CCAGGCGGGA GTGCAGTGGC ACAATCACGG CTCAGCGCAG CCACTGCCTA   2460

CTGGGCTCAC ACGCTCCTCC GGCCTCAGCC TCTCGAGTAC CTGGGACTAC AAGCGTGAGC   2520

CAGTTTGGCT AATTTTGGCT AATTTTTGTA GAAACGGGGT CTCGCCATGT TGGCCAGGCT   2580

GGTCTCCAAC TCCTGGACTC AAGGGATCCA CCTTCCTCCC CCTCTCAAAG TTCTGGGATT   2640

ACCGGAGTGA GCCACTGTGC CCTGCTGGCA AATTTCTTAA ACTGTCTGTG CCTCAGTGAC   2700

CTCATTTAAT AAAGGGAATA ATTGTAGCAC ACTTTTTCTA GAGCTGTGAA GATTCAATGG   2760

AATAAATAAG GCAATAAATG AATGGATGGG GAATGAAGGA TGTGGGTTTC CTCCCTCTTG   2820

TCTTTCAATA AGCTCTCACC ATCAACCTCC CATTGCCTGT TCTCTCTCTT CCCCCTCTCT   2880

CCCTCTGTCT CTCTCTCAGC CAGGAAACCT GGGGTAGGGA GGCTTGGAGC CAGCGGGTGC   2940

GTCGGGAGGC TGCGGGTACT GACTCGGGCC GCGCACGGAG ATCGCGGGAG AAGGATCCAC   3000

AACCGCGGAA GAAGGATCAG GGTGGAGCCT GTGGCTGCTG CAGGAGGAGG AACCCGCCGC   3060

CTGGCCCACA CCACAGGAGA AGGGCGGAGC AGATGGCACC CTGCCCACCG CTTCCCGCCC   3120

ACGCACTTTA GCCTGCAGCG GGGCGGAGCG TGAAAAATAG CTCGTGCTCC TCGGCCGACT   3180
```

```
CTGCAGTGCG ACGGCGGTGC TTCCAGACGC TCCGCCCCAC GTCGCATGCG CCCCGGGAAC    3240

GCGTGGGGCG GAGCTTCCGG AGGCCCCGCC CTGCTGCCGA CCCTGTGGAG CGGAGGGTGA    3300

AGCCTCCGGA TGCCAGTCCC TCATCGCTGG CCCGGTCGCG CTGTGGCGAA GGGGCGGAG     3360

CCTGCACCCG CCCCGCCCCC CCTCGCCCCG TCCGCCCCGC GCCGCGCGGG GAGGAGGAGG    3420

AGGAGCCGCG GCGGGGCCCG CACTGCAGCG CCAGCGTCCG AGCGGGCGG CGAGCTCCCG     3480

GAGCGGCCTG GCCCCGAGCC CCGAGCGGGC GTCGCTCAGC AGCAGGTCGC GGCCGCAGCC    3540

CCATCCAGCC CGCGCCCGCC ATGCCGTCCG CGGGCCCCGC CTGAGCTGCG GCCTCCGCGC    3600

GCGGGCGGGC CTGGGGACGG CGGGGCCATG CGCGCGCTGC CCTAACGATG CCGCCCGCCG    3660

CGCCCGCCCG CCTGGCGCTG GCCCTGGGCC TGGGCCTGTG GCTCGGGGCG CTGGCGGGGG    3720

GCCCCGGGCG CGGCTGCGGG CCCTGCGAGC CCCCTGCCT CTGCGGCCCA GCGCCCGGCG     3780

CCGCCTGCCG CGTCAACTGC TCGGGCCGCG GGCTGCGGAC GCTCGGTCCC GCGCTGCGCA    3840

TCCCCGCGGA CGCCACAGCG CTGTGAGTAG CGGGCCCAGC GGCACCCGGG AGAGGCCGCG    3900

GGACGGGCGG GCGTGGGCGG GTTCCCTGGC CCGGGACGGG AAGCAGGACG CGGGCCAGGA    3960

CGCTCCCAGG GGCGAGGCTC CGGCGCGGCA CGGCGGGCCC TGCTAAATAA GGAACGCCTG    4020

GAGCCGCGGT TGGCACGGCC CCGGGGAGCC GAAAAACCCC GGGTCTGGAG ACAGACGTCC    4080

CACCCGGGGG CTCTGCAGAC GCCAGCGGGG GCGGGGCGCG GAGGCCGCGC TCAGCTGGGA    4140

GGACAAACAG TCGCTAATTG GAGAGGAATT GGGATGCGGC CTGGGGCTGC GGGGTACCCG    4200

GAGAGGTGGG GATGGCTGTA GGGGGCGGCA GGGAAGAGTT CCAGGAGGTG TCTGGAAAAG    4260

GATTTGATGG ATGTGCAAGA ATTGGGCTGA TGCTTAGGAA GGGGCGATGA GGTGGGTCCA    4320

GAAGAAGGGG GGTGAACGGT GTGAGCAAAG ACCGTGAGGC TGGAGGCTGG CCACGGGAGG    4380

TGTGAGGGGT AGGGCAGGG TGGGAGGTGG GCTCGCGGGT GGGCTGGGGT CATGAAGGGC     4440

CTCAGGCGCT CTGCTATTGG GTTCCAAGGC TATCCTGAGA ACAGGGGTGA GGGGGGATTG    4500

CCGTGGGGGG TTAAAGCCTT GTCATGTTCG CTTTCGGGAG ATAAAAACAA CAGGTGGCCT    4560

TTATGGAGAC GCTGCCCAGA GCCAGGTCTG TGCCAGGCTC CTGTTGGGGG TCGTCATGCG    4620

GAATCCTGAC TCTGACCATC CGAGGCATAG GGACCGTGGA GATTTGCATT TCACAGATGA    4680

GGAAACAGGT TTGGAGAGGT GACACGACCT GTCCCAGGCA TCACAGCCGG GATGTGCATA    4740

GCAGGGGTTT GGAACTATGA GGTGCCCAGG ACCCAGGGTT GGATTGAAAA GGGCGGAGGG    4800
```

| | | | | | |
|---|---|---|---|---|---|
| GACTAAGATA | AGCAGACAGT | TGTCCCCAGC | GCTGGGGAGA | GTCTTGGGAC | CAGTCTGATG | 4860
| CCTTGTATTT | CCCAGGCTCC | AGGCTCCTCG | CCGGGACAGT | GTCTCCTTGG | GTGCGTGCTG | 4920
| GATCCCTGGG | GGACGTGGCA | CATCCCCAGG | CTTGCTAAAC | ATTGGGTGGG | TTCTGGCATT | 4980
| TGGTTTTGTA | ACGTTTCTGG | GTCACTCCCG | CCTGTGGCCA | CCCTTCCTTA | GGGGAGCCGT | 5040
| GTGTCCTTGG | GGCTTTGCTG | GGTGGTCTCG | AGGGTGGGAG | AAGAATGGGT | TCTCCTGGAC | 5100
| CAATGGAGCC | CGTGCCCCTC | GGGGCCACAT | TGCTCCTGCG | CTCCCTGACT | GCGGACGCGT | 5160
| GTGTCTCGCG | GCTGTCTCTG | TGGAGATGGC | CTCCTCCTGC | CTGGCAACAG | CACCCACAGA | 5220
| ATTGCATCAG | ACCTACCCCA | CCCGTTGTTT | GTGATGCTGT | AGCTGAGGGC | TCCTCTGTCT | 5280
| GCCAGGCCGG | TCACTGGGGA | CTCTGTCCAG | GGCCTGGTGG | TTCCTGCTTC | CCAGCACCTG | 5340
| ATGGTGTCCA | TGAGAGCAGC | CCCTCAGGAG | CTGTCCGGGA | GAGAAGGGCG | CTGGTGGCTG | 5400
| CTGAGCGGAG | AGCAAGGCCC | GTGTTCTCCA | GGCCCTTGGC | ACAGCAGTGG | AGCCCCGCC | 5460
| CCTGCCTTGT | GTTGTCCTCT | TAGGCTCTGG | TCCTGGGGTT | TGGAGGAGGG | GGACCCTGGG | 5520
| AGTTGGTGGC | CTGTCCCAGC | CTGAGCTGGC | AAGATTCCGA | ATGCCAGGCC | CCCCAAGTGT | 5580
| GCAACAGGGC | ACAGGGTGAC | CTCATGTGGG | CAGGTGGGTG | CTGTTCTGTA | CACACCTGGG | 5640
| GCCGCCGCTG | GGAGAGTTCT | GGAAGGTGGG | GTGAGGGGAC | CCATGGCAAA | CTAGGGCCTT | 5700
| AGGAAGGATG | TGAAGGCCCT | GGCTGGCCCC | CCAGGCCACC | CTCTGTGCTG | TGGGGCAGCC | 5760
| CAGCCATTTT | GCTGTCTACC | CTGCAAACTC | CTCCTCGGGG | AGACGGCTGG | GTTTTCCCCA | 5820
| GGGAAGAGGG | GTCAAGCTGG | GAGAGGTGAA | GGACACAGAT | CACAGCTGCT | GGCAGGTGTT | 5880
| CAAGGGTCCA | AGAGCGTTGC | TGTCTGGGTG | TCACCAGTAG | CCTTCCTGGG | GGGCTCACGC | 5940
| AGGTGCCTCT | CCACTTGTGG | CTCCCTGGCT | GCTGAAGCTC | AGCAGGGACA | GCTGTGTCCA | 6000
| GTTCCAGGTG | GAGGACAGCC | GGGGCTTCTG | AGGCCACAGC | CTGCCTTGGG | TTAATGATGC | 6060
| TGCCGAGAGG | TGGTGGCTTT | TGGAAAAGAT | GGCGTACTGC | AAAACGTGCT | GCTCTGCGTG | 6120
| GCTCGAAGCT | TCGTGGGGAG | ACGTGGGCAG | AGCCGTGGCT | GACTCACAGA | CCCCCCACCC | 6180
| CAGAGCCTGC | CCTGCCCTCC | CTGCCCCGAC | CCTTCTCCCT | CCTGACCCAT | GTGTTTTTT | 6240
| TTTTTTTTT | TTTTTTGAG | ACAGAGTTCA | CTCTTGTTGC | CAAGGCTGGA | GTGCAATGGC | 6300
| ACGATCTCGG | CTCATGGCAA | CCTCCGCCTC | CTGGGTTCAA | GCGCTTTTTC | CTGCCTCAGC | 6360
| CTCCCGAGTA | GCTGGGATTA | CAGGCGTGCA | CCACCATGCC | TGGCTAATTT | TGTATTTTTA | 6420

```
GTAGAGACAG GGTTTCTCCA TATTGGTCAG GCTGGTCTTG AACTCCTGAC CTCAGATGAT    6480

CCGCCCGCCT CGGCCTCCCA AAGTGCTGGG ATTACAGGCA TGAGCCACCA CGCCCAGCCC    6540

TGACCCATGT TTTGAACCAA ATTCCAGCCA CCCTTTTATC TGCAAGCATT TTGGAGGGCA    6600

TCGCAATACT GCAGACCCAC CTAACACAAC AGACAGTTCC TTCATGCCAC CGAAGGCCTG    6660

GTGTGTTCAC ATTTTTGGTT TAATAGTTTG AATTAAGAGC CAAATAAGGT CCACACACTG    6720

CAATTAGTTG ATGTCTTTTT TTTTTCTTT TTTTTTTTT TTTTGAGACG GAGTCTTGCT    6780

CTTGTCTCCA GGCCGCAGTG CAGTGGCATG ATCTCAGCTC ACCGCAACCT CCGACTCCCT    6840

GGTTCAAGCG ATTCTCCTGC CTCAGCCTCC CGAGTACCTG GTAGCTGGGT TTACAGGCAT    6900

GCACCACCGT GCCCAGCTAA TTTTTGTATT TTTAGTAGAG ACGGGGTTTT ACTGTGTTGG    6960

CCAGGATGGT CTCGATCTCC TGACCTCGTG ATCTGCCCAC CTCGGCCTCC CAAAGTGCTG    7020

GGATTACAGG CGTGAGCCAC CGCACCCGGC CAATGTCTTT TAAAAATATA TACTTTTTTT    7080

TTTTTTTTGA GACGGAGTTT CGCTCTTGTT GCCCAGGCTG GAGTGCAGTG GCGCGATCTC    7140

ACCTCACGGC AACCTCCGCC TCCCGGGTTC AAGTGATTCT CCTGCCTCAG CCTCTCCAGT    7200

AGCTGGGATT ACAGGCATGT GCCACCATGC CTGGCTAATT TTGTATTTTT AGGAGAGACG    7260

GGGTTTCTCC ACGTTGGTCA GGCTGGTCTC AAACTCCTGA CCTCAGGTGA TCCGCCTGCC    7320

TTGGCCTCCC AAAGTGTTGG GATTACAGGT GTGAGCCAAC GCGCCCAGAC AAAAATATAT    7380

GTGTGTCTTT AAGGCTGGTC AAGCAAAGCA GTAGGACTGG AGAAAGAATG AAGAATTCTA    7440

CCTGGCTGTG ATCAATTCGT TGTGAACACC ACTGTGCTTG GACCAGCTAG CTGATGTCTT    7500

TTGTTTTGTT TTGTTTGAGA CGGAGTCTGG CTCTGTCACC CAGGCTGGAG GACAATGGTG    7560

TGATCTCGGC TCACTGCAGC CTCCATCTCC CGGGTTCAAG CGATTCTCCT GCCTCAGCCT    7620

CCTGAGTAGC TGGGATTAGA GGCGCGCGCC ACCACGCCCG GCTAATTTTT AAAAATATTT    7680

TTAGTAGAGA TGGGGTTTCA CCATGTTGGT CAGGCTGGTC TTGAACTCTT GGCCTTAGGT    7740

GATCTGCTTG CCTCGGCCTC CCAAAGTGCT GGGATTACAG GTGTGAGTGA TGTATTTTAT    7800

TTATTTATTT ATTTATTTAT TTTTATTATT TGAGATGGAG TCTCACTCTG TTGCCCAGGC    7860

TGGAGTGCAG CAGTGCCATC TCAGCTCACT GCAAGCTCCG CCTCCTGGGT TCACGCCATT    7920

CTCCTGCCTC AGCCTCCTGA GTAGCCTGGA CTGGTGCCCG CCACCATGCC CAGCTAATTT    7980

TTTGTATTTT TAGTAGAGAC GGGGTTTCAC CGTGTTAGCC AGGATGGTCT GGATCTCCTG    8040
```

```
ACCTCGTGAT CCTCCCGCCT CAGCCTCCCA AAGTGCTGGG ATTACAGGCT TGAGCCACCG    8100

CCTGTCTTTT AAATGTCCGA TGATGTCTAG GAGCTTCCCT TCCTCTCTTT TTCCTTGTGC    8160

AATTTGTTGA AGAAACTGGC TCCTGCAGCC TGGATTTCTC GCTGTGTCTT GGGGGTGCCA    8220

CCTCCATGGT GTCACCTCCG TGGTGCTGTG AGTGTGTGCT TTGTGTTTCT TGTAAATTGG    8280

TCGTTGGAGC CGACATCCCA TTGTCCCAGA GGTTGTCCTG GCTGGCACTG GCCTAGGTGT    8340

AGATGTCATC AGCTCAGGGC CCCCTGCTCT AAAGGCCACT TCTGGTGCTG GTTGCCACTC    8400

ACCCTGGCTG GGGGTCACCT GGGTCTGCTG CTGTCTCGCA AATGCTGGGG TCCAGGACTG    8460

GGCACATCGA GGGACTTGGT AGGTGCTTGG TTCACTGATG TAAAATATAG GAGCACCCGG    8520

GGCCTTGCCC TTTCCCACCT GCATCCCTGA ATGACAGGAG AGTGTGGGAG AGTGTAGGGA    8580

CAGCAGGCGC AGACCCCGGG GCCCCTGCCT GGGATTGGCG TCGGGGAAGA CAGGCATTCT    8640

GGAGCGACCC CTAGGCCTGA TGCCTTAGAG CGCAACTGCC AGAGACACAG CTTCCTTGGG    8700

GGGCTGGCCA GGCCACGGAG GGGCCCTGGC TCCCATTTCT GGTCCCTGGA TCCTGAGAGC    8760

GAGGACTAGG GATTGTCACC AAGGCCTCCA TGAGCCCTCA GCAGAAGGAG GGCCACCCTC    8820

GAGGGCTCCG TTATCACTGG AGCCCGCGTT CAACCAACAC GCAGATGATT CTCCAAGGAC    8880

AGAGATGGAT GATGGGGAGG GGGCTGGCCT GGAAGGACCC CCAGTGCAGG TGACATTGAA    8940

GCCAGGTTTC AAAGCTCCCA CAGGGAGCTG CCCAGAGAGA GTCCCCAAGG GGCAAGGTGA    9000

CTCGGGGGCA GGGGTAGGGC CTCTGTCAGG AGAGCCTAGG AGAGGCCTGT GTCTTCTAGG    9060

AAGAGCCCTG GCAGCCGAGC GGAGGCAGTG GTGAGGACCT GCATCCTGCA TGTCCAGCTG    9120

GCCTCACCCG GGGTCCCTGA GCCGGGTCTT ACGTGGCTCC CGCACTCGGG CGTTCAGAAC    9180

GTGCCTGCGT GAGAAACGGT AGTTTCTTTA TTAGACGCGG ATGCAAACTC GCCAAACTTG    9240

TGGACAAAAA TGTGGACAAG AAGTCACACG CTCACTCCTG TACGCGATTG CCGGCAGGGG    9300

TGGGGGAAGG GATGGGGAGG CTTTGGTTGT GTCTGCAGCA GTTGGGAATG TGGGGCACCC    9360

GAGCTCCCAC TGCAGAGGCG ACTGTGGAGA CAGAGAGCAC CTGCAGGTCA TCCATGCAGT    9420

ATCGGCTTGC ATCCAGATCA TACAGGGAAC ACTATGATTC AACAACAGAC AGGGACCCCG    9480

TTTAAACATG GACAAGGGGT CACTCACGCC TGGAATCCCA GCAGTTTGGG AGGCCAGGGT    9540

GGGTGGATCG CTTGAGCCCA GGAGTTTGAC ACCAGCCTGG GCAACAGGGT GAGACCCCGG    9600

TCTCTAAAAA ATAAAAGAAC ATTGGCCGGG CGTGGTGGTA TGCATCTGTG GTCCCAGCTA    9660
```

| | | | | | |
|---|---|---|---|---|---|
| TTCAGGAGAC | TGAGGTGGGA | CATCACTTGA | GCCGAGGAGG | TCAAGGCTGC | AGTGAGCTGT | 9720 |
| GATCACACCA | CTGCACTCCA | GGCTGGGTCA | CAGAGCAAGA | CCCTGTCTCA | AAAAAAAAAA | 9780 |
| AAAAAAAAAA | AAAAAATCAC | AGGATCTGAA | CAGAGATTTC | TCCAAAGAAG | ACGCACAGAT | 9840 |
| GGCCAACAGC | GTGTGAGAAG | ATGGTCGGCC | TCATTAGTCA | TGAGGGAAAC | GTAAATCAAA | 9900 |
| ACCACTGTCC | AGCCGGGCGC | GGTGCCTCAC | GCCTGTAATC | CCAGCACTTT | AGGAGAGCAG | 9960 |
| ATGGCTTGAG | GCCAGGAGTT | TGAGGCCAGC | CTGGGCAACA | TAGCGAGACC | AATAAATAGA | 10020 |
| TATTAGTGGT | GGCGCCTGTA | GTCCCAGCTA | GTTGGGAGGC | TGAGGGGGGA | GGATTCCCTG | 10080 |
| AGTCTATGAG | GTTGAGACTG | CAGTTAGCTG | TGATGGTGCC | ACTGCACTCC | AGCCTGGGCG | 10140 |
| ACTAGGAAAC | GGTCTTTAAA | AAAAAAAAAA | AAAACAGGG | TGGGCGCGGT | GGTTCACGCC | 10200 |
| TGTAATCTCA | GCACTTTGGG | AGGCCAAGGT | GGGGGGATCA | CAAGGTCAGG | AGTTTGTGAC | 10260 |
| CAGCCTGACC | AACATGGTGA | AACCCCGTTC | TACTAAAAAT | ACAAAAATTA | GCGAGGTGTG | 10320 |
| GTCGTGGGCG | CCTGTAATCC | CAGCTAATTA | GGAGGCTGAG | GCAGGAGAAT | CACTTGAACC | 10380 |
| CGGGAGGCGG | AGGTTGCAGT | GAGCCAATAT | CACACCACTG | CACTCTAGCC | TGGTCAACAG | 10440 |
| AGCGAGACTC | TGTCTCAAAA | AAAAAAAATG | CTGAGCGTGG | TGGCGCATGC | CTGTAGTCTC | 10500 |
| AGCTACTTTG | GGGGCTGAGG | CAGGAGAATC | GCTTGAACCT | GGGAGGCAGA | GGTCGCAGTG | 10560 |
| AGGCAAGATT | GCACCATTGC | ACTCCAGCCT | GGGAGACAGA | GTGAAACTCT | GTCTCAAAAA | 10620 |
| GAAAAGGTCT | AGGAAGAGTC | CGCACCCTCT | CCCCGCGGTG | GCCACGCCGG | GCTCCGCGCT | 10680 |
| GAGCCCTCTG | TGTTCTTGTC | TCTCCATACC | TCATCACGGC | ACCGCAGGGT | TGCAGCCACT | 10740 |
| CCTGGTCTCA | TTTTACACAC | CAGGAAATTG | AGGCTCTTTG | AGAAGCCGTG | GTGATGATTT | 10800 |
| CATCAGCATG | CTCTGGGGCA | GACCCCTGCA | GCCGCACAGG | GTGCCTGGGG | CCCACACTAG | 10860 |
| TGCCCTGGTT | TATAGACAGA | CAGAGGTGGC | AGTGGCGCTT | CCGAGTCGGG | CTGCGATGTG | 10920 |
| CTTGCACTCC | CCGAGGGGCT | GAGGGGCCCT | GCGCCCAGGT | GCAGCTGCTT | GGGTGCTGCC | 10980 |
| AGCCCCTCCC | ACCTCTCCCT | CCCTGCCAGC | CCCTCCCACC | TCTCCCTCCC | TGCCAGCCCC | 11040 |
| TCCCACCTCT | CCCTCCCTGC | CAGCCCCTCC | CACCTCTCCC | TCCCTGCCAG | CCCCTCCCAC | 11100 |
| CTCTCCCTCC | CTGCCAGCCC | CTCCCACCTC | TCCTCCCTG | CCAGCCCCTC | CCACCTCTCC | 11160 |
| CTCCCTGCCA | GCCCCTCCCA | CCTCTCCCTC | CCTCCAGCCC | CTCCCACCTC | TCCCTCCCTG | 11220 |
| CCAGCCCCTC | CCACCTCTCC | CTCCCTGCCA | GCCCCTCCCA | CCTCTCCCTC | CTGCCAGCC | 11280 |

```
CCTCCCACCT CTCCCTCCCT GCCAGCCCCT CCCACCTCTC CCTCCCTGCC AGCCCCTCCC   11340

ACCTCTCCCT CCCTGCCAGC CCCTCCCACC TCTCCCTCCC TGGCTCATCC CTGCTGTGTC   11400

CCTTCTCTCT AGTTTCCTGT TCAGTTTCAG GAAGGAGGCT GGGAACCCAG ATGTAGGGAA   11460

TTTGCGCCCT GGAGTCAGAC CTGGGTTCAC GTCCCAGCGC CTCCACCTCT GGTGTGACCT   11520

TGGTCCAGTC TCTCAGCCTC AGTTTCCTCA CCTGTAAAGT GGGCTCCATG ATTAGATGCA   11580

CCCTGCAGGG CAGTGTAGCA GTGACCTGGC TCAGCCACTG GCAGCCCCAA CAATCATACC   11640

TTGTTAAAGT AGCTCTGTCG GTTCCCTCAG GGGTTCCGGG GGCCCATTCC CCTGTCCTCC   11700

ATGCACTGTG AGACCTGCCC TGCCACAGAG CAGAGTGTAA CAGCCTGAGG GTGAGAGCCA   11760

GACACTGTGC CTGTGCTTAG ACCAGACACT GGACGACGGG AGCCAGTGCA GCCTGGGCGG   11820

GTGGACTCCT ATGGACCCCT CAGCACCCAG CCTCGGTGCC TTCAGCGCAG GGCCGCGTGG   11880

CTGTGGGGGC TCACAAGACC CGGCCCACTC CTGCTTGTGC CTACATCTGG GTGTTTGCCC   11940

ATTGGTGCCT TTTGACGCGT TCTGGTGTGT GTGAGACGTG CGGGGCTGGG AAGTGTTGGC   12000

AGAGCCGCGA GTACCGTCCT CACTCCTTTT GTTCTTTTGA CGTAAGCTGG CGAGTGGCAC   12060

TGCCTGAGTT CCGCTCAGTG CCCGCCCTGA TGTGCGGACC CCGCTGCATT CTTGCTGTTA   12120

GGTGGTGGCG GTGTGCGCTG TCGCTGGTGG GCACCGAGAG TCTTTGGGAG CTTTGGGGAG   12180

GTTGTGCCAA GCCTGAGCCT CGACGTCCCC CTTCCCGGCT TTCTGTTGGC TCTTCTGAGG   12240

CCAGGGCATC TCTATGAGGG CCTCCTGCTG GAGCCGTCTC TGTGGATCTC CTCTGCCATC   12300

CTGGCCCATG AGTGGGTGAT GCGCTGGCCA CCATCTGGTG ACAGTGGCCG GGCACCGCTG   12360

CCAAATGTGG GTCCCGCATC TGCAAGCCCC TCCCTGGGTC CCCTAGGGTA TGGGGTGGTT   12420

CTGCCACTGC CCTCGCTCCC CCACCTTGGG GTGCCTCTCC CCCTGCTCGT GGGGGAGACC   12480

CTGCCTGGGA TCTGCTTTCC AGCAAGGAAT ATACTTTGGA GGGAGACACA CATGTTCTTT   12540

TCTGGAGCTC TGCAGTGGCC ACGGCAGCCC AGCCCGCCAA GCACCCTGGA ATGAAAACAT   12600

CCCGCTGCTG TCTGGGCCTG GCCTGCACTC TGCTGCCTGC GCTCCAGCTG GCTGAGGCCG   12660

GGCACGTCTG CGGGCACAGC AGCGGGGGCG CCACAGTCTC CCTGCAGAGT GAGCGCAGCT   12720

GGAAAATGCA GCTCACGCCC TTTCCCAGAA CACCTCGCTC TTCATGGCTT GGCAGCTGTC   12780

CTTGCCTAGG GGCCAGGGTG CCCAGGCACT GGTGGCAGGA GAAGGGCTAC ATCTGGGGCT   12840

GAGGCGGGCT GGGTCCTTTT CTCCCTGCAG CTCCCGAGGC CCAGCCCTGG CCCAGCCTGG   12900
```

```
CATTCCTGAC CTTAGCAGCG CCATGATCTG AAGACAGGCT GGCTTCTGTG AGGCCACCTC    12960
AGAAAGGGCT TTGTGCCCAG GCAGAGGCGG AAGCCAGCTC TTCCTTCTGG TTGAGGCAGG    13020
AATGAGGCCA GCGCTGGGCA AGCCCATGCC CAGGGAACGT CACAGCTGTG GGAGTACAGG    13080
GGCTCCGGGT TCTGAGCCCG TCCACTGTGC ATCGTGGCCC TGGCCTCAGG ATGGCTCGTA    13140
CCATCATTGG CTGTGCCCAC AGCCGAGTGG GTGATGGGAT TCCGGCTGCC CCGCTGGATC    13200
TGTGCTGCTG CCCTCTCCAG GGCACTGCTG TGCCCGCACA GCCGGGCGCA GATGGCCAGT    13260
TTGCTTGCCC CCCCCCCCAC CATCCTCTTC CTACCTTGGC TTCCTCCATT GACACACTGG    13320
ACCCTGCTGG CTGCCCGGGG AGGTGTTTGG GGATGGTGT  TGGGGAGGA  GGAGGGCCCC    13380
TTGAGCCTCA GTGTGCCCAT CAGGAGCGTA AGGTCAGTGC AGCACCTGCC CACACAGGCT    13440
GTGAAGGGTG GGAGTGGAGA GGGATGCAAG GGGGTCACAA CGCCTGGCTC CATGTCAGCT    13500
GCGTGCAGGG GCACCAGGAG CCGGCCCTCA TTCTCCCCTT GAACTGGAAG GGTGGCCCCG    13560
ACCCCAGCGG CAGGTAGCAT ACGTATGAAG CGCTCTCCTT CCTACACCCC ACAGGTGGGC    13620
TCGTCTCCAG ACGGCCCTTT TTGAGCTGGC TGTGTTTTTC CATCTGTGTA GGCAAGGACA    13680
TCGCAGACTC CCCTTTCTCA TCTCCCTCGT TCAGCCTCCG AGGCGGAGT  CTCCATCCCT    13740
GTGCCTGCCT GTGGGTCCCG GGAGGACCTG AGGCTGCCCA TGTCACCCCC GGCATCTCAT    13800
CCTGGGGACA GTTCAGCCGT GGGAGGGATC TGTAAGGACA GAATGCCGCT GAGCCTGGGG    13860
CTCCCCAGCT AGTCTCACAC CCCGTGTCTG GGACCCAGAG ACCCTCGTGC AGGGCTCTGT    13920
TGCTTGGGGC CTGGCAGCCT CGTCCTGTAT CAGAGGCTGC CACCCCACC  CCTCGTGGGG    13980
CCAGGGTTGT GGCCGGCCTC CCTGGCCCTC CCCATGGAAG TGGTAGGCGG AGCCAGCAGC    14040
CATCTGCCCA GCCCGGGGCT GCACTGTTTT TTTTCAAATG AGCACCGTCC CAAACTGCAG    14100
CCCGTTAATT TAAACAGGAT CATTTCCGGC CCTGGAAGCC GCCTCACTCT CCTTAAATAG    14160
AAAGGAGCAC AGCGCAGAGG GAAACAGATG AGGTCATGGC TCGGCTGGCC CAGCGAGGAA    14220
GGGGCCGCAG TGGGGTGGC  ACTGCCGCCT GTCCCTGTC  CTCTCCAGCG CCCACACTGC    14280
AGCCCATTTC CTCACCCTGG GCCTGCTCTC GGGAGGGACG GGCCTGGGGG TCCTCTTGCT    14340
GGGCGGAGGG GAACCAGCTC CTCCAGGAGA GGACGGGGCC TGGCAGGGGG CATGGGGCCT    14400
CCCTGGGTCT GGCGTCCTGT CCTGCCCCTG CCGAGGGAGG AGCGGTTACA TAAGCTCCGC    14460
AGGCGGCCCC TCCGAGCCGG TCCCCCAGC  CCAGTTTCCA GTGAGGCGGC CAGCGCGGGC    14520
```

```
GGGGGTGCCG GGCCTGGCGC ACACCCGCTG CTGACCACAC GTGTCTGGAA TGTGCAGATG    14580

TTTCTTTGGG GGCTCCGTCC GGCCCCAGA  CCCCACTCAG CATCTGGTCT GGGGAGTGGG    14640

CGCCTGGGGC ACTCAGCTCT GAGTGTGAGA CTCTGAGGCA GGTCTGGTTT GTCTGGGGCC    14700

ATTCCCTCTG CTGTGGATTG GGAGGGCCCC GGGAGCTGCC CCACACCCAG GGAAGTTCTC    14760

CTCAGTCCCA CTGTTGCATT CCCCGACCCC GGCTCCCCCG GCCCAGGAGC GCCTGTGGGG    14820

CAGAAGGCCC AGCCCCAAGA CTTCCCGGCC CTGCCAGCCT CAGGCTTCAC CCACCCTCGC    14880

GCCAACTGTG GGCAGAGCCC AGGGGAGGG  CAGGAGAGCC AGCGCCTGGC TGGGAACACC    14940

CCTGAGGGGC CGAGGCTCCA GGGCGAGGGG GCCCGACCTG GGGTTCACAC GCCCGGGTGG    15000

CGGGCAGACC CGCTGCAGCA TGAGACACGT GTCAGCTACC TCGGGCCGGC AGGCTGGCCC    15060

TGCTGCCCAC AGCCCTGGGA CGTGGCCCCA CCTGTGACGG GTGTGGAGGG GCAGCCTCCA    15120

GGCCTGGCCA CACCCTCTGC TGTTGCTGCT CCTGCTCCAG GATTGGCAAG GGTGCTGGGA    15180

AGGGGTGAAG ACCCGTACTG TGGCCACACA CCTGGGACTT CCTTCTCCAC CCAGTGGTGC    15240

CCCAGCAGCC GCTAAGGAGC CCGCTGGGTC CCACGCTAGG ATGGTCCTAA CTCCTCCCGC    15300

CTTCCAGATC GGACGCTCGG CGCTGGGGAC CCCTTGTGTC CCGGGGCTGG GGCACCGTCC    15360

TGCCCCCATG GGGGTGTACT CCTCCCGACA AGCTTGGCTT CAGCTTCCCT GGGAGCACAT    15420

CCTGGCCCTC GGGCACCCAT CAGGCTGTCC CTGTGCACCT GGCTCCCACC CTTCCAGCTC    15480

ATAGCAGGAA CTGGGGTGAG GAGTGCGTGG GGCAGCAAGG GCCTGGGACC CCAGAGGACC    15540

CTGCACTCTG CTCTGTGCTC TTGCCTGGGC TTAGGGCCGC TCGGTGGTCC TGCTGCCAGA    15600

TGCCTGGGCC CTGCTGTGTC CCCCATCCTT GCAGGGAACC AGAACGTGGG GGCAGGGCAT    15660

CAGACAGCGG CGATGATGTC ACCTGGCGGG TGCAGAGGAA GCCCGAGGGG CGGGGTGGGG    15720

GGGCTGGCGC GAGGCTGCCT GGCTAGGCCT TGGCGTTCCC CCAGAACGGC GATGGCAAAA    15780

GCAGATGGAG ACGTGAAAAA GTACGGGAGC AAGCGAGGTG AGGACTCCAC GGGGACCCCT    15840

GTGCTGTTCC CTGTCCCTGA AGCCCACACC TGAGTCCTGC CCAGGGCAGA TGCTTCCACA    15900

CCCAGGGGGC ACCTGAGTCC TACCCAGGGC AGACGCTTCC ACACCCTGGG GGCTGGGGA    15960

CTGCACCTGG CTCCTGTCTG GGCCCCAGCT TCATTCCACT GCCCTGGGCC CTGGGAGCTC    16020

GGCCGAGCGG GGTCCCCAAG ACCTTGCTGC ATTTCTGGGC CTTGGGCTGG GGTGAGGGCC    16080

GGGAGAAGGA GCCAGCCTGG AGCCTGGCAC GCAGGGAGTG CATGGCCAGA ACCGGTGACA    16140
```

```
GGCAGGGCTG CCTGCTGGCG TGGAAGAAGT GTCCATGGCA CCCCCAGGCC TGGTTCACAG   16200

TGGGATGGGC GGGGAGCCGG GGGGCTCTGG GGTCCTCGGC TGACCTGCCC CCACCCCTGC   16260

CCTGGCTTGT CAGCTCCCAG CAGCAGCCAC TCTTGATGGA TTTTCAGAA  AATGAGGTGT   16320

GGCCAAACAT CTTCAGGCTT TTCCTTCTTT CCTTTCTCCC GTGGCCTGGG TGGGAGCTGC   16380

TCCCCATGCC TGGGGGCAGG TGCGAGAGCC TGTGCCCCTC CCTGGGCAG  TTTCACAGCT   16440

GTGTCCCTTC CAGGGGCCT  GCCTGTGTTC ACCGTGGCCT CTGCAGCACC TCTCGCCCCT   16500

TAGGGCTCCT GCGCCTCGGG TCCCGGTGCC TCATTTCTCC CTAAAGCATT GGTTCTGCTG   16560

CCGCCGCAGC CGCTGGAAAG TCCCTCCTCA GGTCTAACTG CAGTTCCTCA CGGCACAGTG   16620

TTCCCCCTCG GGCATGGTGC TTGGGCAGTG GGTGTGAGTC CAGCTGCCTC ACCCTGTCTC   16680

GAGAATGGCC TCTTGCTGGT CTCCCAGCCA CCACCCTGTC CCACCCCACG GCGGGGATGG   16740

TGTGGATGCC TAGCAGCGCG GCTGTGGGCC CACCCATCCT TATGGGCAGT GGGGAGCACC   16800

TCAGCCCGTG TCCCTACCTT GGTGTAGAGG AGGGGACGGC AGAGAAGCAG GGTTCAGTTA   16860

GGGGGGAAGT GGTGGCCCTG CCGGAGGGGC CGTTCCCTGT GTGCCTGGCC CCCAGATCCT   16920

CTCCCCTCCC GGAGCCCAGG GCACAGGCAT AGGCTCTCTG AGTGTCCCAC AGCCCCTGGG   16980

GGAAGGGAAC TGCACCCCCA ACCGTGCCCT CCATCCGCAG ATGGAACGAG AAGCTCCGGG   17040

AGCCAGTGCC CAGCGTCTCA TCTGTCTGGG CACCCAGCCC AGGTGAGGGC CTGGCTCCAC   17100

CGTCCGTGGC TGGTGCTGCT TCCTGGCACG GAGAAGGCCT CGGCTGCTCT GTCCCCTCAG   17160

CTGGGGTGGC CTCTGGTCCC CTTCTTTGTT GGTTCCCTTC TCAAGCTCTT GCCCTGGCCC   17220

CGGGCCCCAC CGGGCAGCCT GTGTGTGCGT CTCTCCTGCG CCGGGTAGGC TCCTGTGGGA   17280

GCGGAGCTCC GGTGGGAGGA GCAGGGCTGG AGGCTGGCAG GGGCTGGGCG GGTGTTCAGG   17340

GATGGAGGCC GCCCCGGCTT GGGGCTGGCT GCCGGGTGGT CATTGCTGGG AAGAGCAAGT   17400

CTAGGCGGAG GCACCTGCTG GGTCACTCGT GGGGAGGGTG ACACCTGGGG AAGTAGAGGC   17460

CCGTGGCAGG AGGTGAGGCC TCGGGGTCCT GGGGAGCAGG GGGGTGGTGT GCAGACCTGC   17520

GGAGCCATAG TCCTGTGCCA GGAGCACTAC TGGGAGTGCG TGGGACCAGG AGGGGTGCCC   17580

AGGGTGGGCG GCAGAGTGAC CCCCGAGGTG CTTGAGGCCG AGGGGAGGTG GAGTTCTCGG   17640

TTTGCCCCAG CTCTCTGTCT ACTCACCTCC GCATCACCAG CTCCAGGACC TGGTTTGTAA   17700

CTCGGGCAGC TCTGAAAAGA GAGACATGCT GCCGCCCTGT GGTTTCTGTT GCTTTTTCTT   17760
```

```
CACTGACTAC TGACATGGGA TGTTTTTCCT ACGGCTGTGA CCAATTGTGC TTCTTCTAAT   17820
TGCCTGGTTT TTCTTTTTTT GTTTTGGAG  TTTTCTCTTT CTTTCCTCCC TCCCTCTCAC   17880
CCTCCATCCT TTTTTTTTTT ATTTTTATTT TTTGAGATGG AGCTTCACTC TTGCAGGATG   17940
GGGTGCTGGA GTGCAGGGGT GCGATCTCAG CTCACTGCAA CCTCTGCCTC GCGGGTTCAA   18000
GTGATTCTCC TGCCTAAGCC TCCTGAGTAG CTGGAATTAC AGGTGCTTGC CACCACGCCC   18060
GACTAATTCT GTAGTTTTGG TAGAGACAGG GTGTCTCCGT GTTGGTCGGT CTGGTCTTGA   18120
ACTCCTGACC TCAGGTGATG CGCCCGCCTC AGCCTCCCAA AGTGCTGGGA TTACAGGCAG   18180
GAGCCATTGC ACCCGGCTCT TTCCCCTTCT CCTTTTCTTC TCTCTCTCCT CCCTTTCTTT   18240
CTTTTCTTTT CTTTTTTTTT TCTTTTGAGA TGGAGTCTCG CTCTGTCACC AGGCTGGATT   18300
GCAGTGGCGT GATCTTGGCT CACTGCAACC TTCGCCTCCC GGGTTCACGT GATTCTCCTG   18360
CCTCAGCCTC CTGAGTGGCT GGCACTACAG GCTCCCGCCG CCATGCCCGG CTAATTTTTG   18420
CATTTTTAGT AGAGACAGGG TTTCACCCTG TTGGCCAGGA TGGTCTCGAT CTCTTGATCT   18480
CATGATCCAC CCACCTTGGC CTCCCAAAGT TCTGGCATTA CAGGAGTGAG CCACCGTGCC   18540
CGGCCATCTT TCTTTCCTTG CTTTCTCTTT GTTTTCTTTC GAGACCGGGT CTTGCTCTGT   18600
CGCCCAGGCT GGACTGCAGT GGCACAATCA TAGCTCACTG CAGCCTCGAC TTCCCTGGCT   18660
CAAGCGATCC TTCCTCCTCA GCCCCCCGAG TAGCTGGAAC TACAGTTACA CACTACCATG   18720
CCTGGCTGAT TCTTTTTTTC CTTGTAGAGA TGGGGTCTTG CTATGCTGTC CATCCTGGTC   18780
TCAAACTCCT GGCCTTCCCA AAGCACTGGG TTTACAGGCA TAAGCCACCA CACCCAGTTT   18840
CCTTTTCTTC TTTTTAACTG GAATAGTTGA CGTTTTCTTT ATTAGCTGTG TGTCAGGAGG   18900
GTATTTTTGG CCTTTAGTAT GTCGTGTAAG TTGCTAGTGC TTTTCTGAGA TTGTAGTTTG   18960
TTTTCTAATT TTATTTATAT TTTGCGTAGA AGTTGTGTAT TTTAGATGGA GTTAGGTCGG   19020
CTGGTCTTTG ATGTTTTATT TATTAATTAT GTATGTATTT ATTTATTTTT GAGGTAGAGT   19080
CTCGCCGTTT CACCCAGGCT GGAGTACAGT GATGCGATCT CAGCTCCCTG TAGCCTTGAC   19140
CTCTCTGGGC TCAAGTGATT TTTCTCTCCT CTACCTCCCG AGTACTTGGG ACCCCAGGCG   19200
CATGCCGCCA TGCCTGGCTA ATGTGTATTT TTTGTAGATA CGGGGTCTCA CTGTGTTGCC   19260
CAGGGTGGTT TCAAAATCCT GGGCCCAGGC GATCCTTCCG TCTCAGCTCC CACGGTGCTG   19320
TGTTACCGGC GTGTGCCCAG TGCCTGGCCG TCTTGGAGGT CTTGTTTCTC TGGGTTTATG   19380
```

```
CCTCGAGGTG GCGCCTGCTC CCCTGTGCTC CCTGGTAGCC TGGTAGTGAG CCTGCTTCTC    19440

ACACAGTCAT ACCTGGTTGT GGTCCCACAG TGGGACCACC CTGTTGGGTT CAGAACAGGA    19500

GATGGGGGCC CCTCGAGTCT GTGTGGGGGC TGTGGACAGG GTTGGGAGAC CTTGGCTCTG    19560

TGGGGGACTG TGGACAGGGG ATGGGGGGCC TTGGCCCTGC GTGGGATGGG TTGGGGGTCC    19620

GTGCCCTTCC TGGCCCTGGG TGGACAGGTC CATGTGGCAC TCGGCATAGG GCTGAGATGG    19680

GTGCAGAGGG CTGAGGCCCC CAGGCCTCTC CTGGCTTGGT TTCCCCAGAT GAGTGTTCAT    19740

TTGGGTCTTC CATCAGAAAG TCCCCTCCTG ACCTCTGGGA GTGGGGAGCT CAAGGGTGGG    19800

AGGCCATAGC TTGGGGATGC TGGCAATGTG TGGGATGGGC CCAGGGAAGG CCTCTGGCCT    19860

ACTAGGGGCT CTGGCCCTGA CCCACGGCCA CTCACTCCTC AGAGACGTCT CCCACAACCT    19920

GCTCCGGGCG CTGGACGTTG GGCTCCTGGC GAACCTCTCG GCGCTGGCAG AGCTGTGAGT    19980

GTCCCCCAGT CGTGCCAGCA TGCGGGGCTC ACTCCGGGTG GGCTGGCGGC ACCGCCTCTT    20040

GCTGCTCAGC TGTGGGGGCT TCCATCAGCT TTGCCGAATC CCCCGTCTCT TCCAGGGATA    20100

TAAGCAACAA CAAGATTTCT ACGTTAGAAG AAGGAATATT TGCTAATTTA TTTAATTTAA    20160

GTGAAATGTA AGTTGTGGTT CTTTGGGTGG GGTCCTGGCT GGACCCCAGG CCCCCAATAT    20220

CCCTTCTGCC CTCCCAGTTG GTCCGTGTCC CCTTCCAGGC TTGAGACCAG ATCCTGGGGG    20280

CAGTTCACTG CCTGCTTGGA GCCCCCCAGT GCCGGCTTGG TTGGGGCAGG GGAGGCGGTG    20340

CTGTCAGGGT GGCTCCAGGG CCTGGTTGCC AGTGGGGGC TGGCATAGAC CCTTCCCACC    20400

AGACCTGGTC CCCAACACCT GCCCCTGCCC TGCAGAAACC TGAGTGGGAA CCCGTTTGAG    20460

TGTGACTGTG GCCTGGCGTG GCTGCCGCGA TGGGCGGAGG AGCAGCAGGT GCGGGTGGTG    20520

CAGCCCGAGG CAGCCACGTG TGCTGGGCCT GGCTCCCTGG CTGGCCAGCC TCTGCTTGGC    20580

ATCCCCTTGC TGGACAGTGG CTGTGGTGAG TGCCGGTGGG TGGGGCCAGC TCTGTCCTTC    20640

CCAGCCAGGT GGGACCTGGG CCCTGCAGAC ACTGGGCAGG GCTCAGGAAG GCCTCTCTGG    20700

GGGGGGCCTC CGGGCCAAGG GAACAGCATG GGAGCCTGTG AGTGCGGCGG GCGGATGTGG    20760

GGGCGTGGGG TGGAGCCAGG AGGAGCAGAA CCCGGGGTCC AGTGGCTGCC TCTTCTAGGT    20820

GAGGAGTATG TCGCCTGCCT CCCTGACAAC AGCTCAGGCA CCGTGGCAGC AGTGTCCTTT    20880

TCAGCTGCCC ACGAAGGCCT GCTTCAGCCA GAGGCCTGCA GCGCCTTCTG CTTCTCCACC    20940

GGCCAGGGCC TCGCAGCCCT CTCGGAGCAG GGCTGGTGCC TGTGTGGGGC GGCCCAGCCC    21000
```

| | | | | | |
|---|---|---|---|---|---|
| TCCAGTGCCT | CCTTTGCCTG | CCTGTCCCTC | TGCTCCGGCC | CCCGCCACC | TCCTGCCCCC | 21060 |
| ACCTGTAGGG | GCCCCACCCT | CCTCCAGCAC | GTCTTCCCTG | CCTCCCAGG | GGCCACCCTG | 21120 |
| GTGGGGCCCC | ACGGACCTCT | GGCCTCTGGC | CAGCTAGCAG | CCTTCCACAT | CGCTGCCCCG | 21180 |
| CTCCCTGTCA | CTGCCACACG | CTGGGACTTC | GGAGACGGCT | CCGCCGAGGT | GGATGCCGCT | 21240 |
| GGGCCGGCTG | CCTCGCATCG | CTATGTGCTG | CCTGGGCGCT | ATCACGTGAC | GGCCGTGCTG | 21300 |
| GCCCTGGGGG | CCGGCTCAGC | CCTGCTGGGG | ACAGACGTGC | AGGTGGAAGC | GGCACCTGCC | 21360 |
| GCCCTGGAGC | TCGTGTGCCC | GTCCTCGGTG | CAGAGTGACG | AGAGCCTCGA | CCTCAGCATC | 21420 |
| CAGAACCGCG | GTGGTTCAGG | CCTGGAGGCC | GCCTACAGCA | TCGTGGCCCT | GGGCGAGGAG | 21480 |
| CCGGCCCGAG | GTGAGTGTCT | GCTGCCCACT | CCCCTTCCTC | CCCAGGGCCA | TCCAGATGGG | 21540 |
| GCAGAGCCTG | GTACCCCGT | CTTGGGCCCA | CACTGACCGT | TGACACCCTC | GTTCCCACCG | 21600 |
| GTCTCCAGCG | GTGCACCCGC | TCTGCCCCTC | GGACACGGAG | ATCTTCCCTG | GCAACGGGCA | 21660 |
| CTGCTACCGC | CTGGTGGTGG | AGAAGGCGGC | CTGGCTGCAG | GCGCAGGAGC | AGTGTCAGGC | 21720 |
| CTGGGCCGGG | GCCGCCCTGG | CAATGGTGGA | CAGTCCCGCC | GTGCAGCGCT | TCCTGGTCTC | 21780 |
| CCGGGTCACC | AGGTGCCTGC | CCCCACCCCC | CGAGGGGCCA | TAGGTTGGGA | GATCTCTGAA | 21840 |
| GCACTGGGGC | AGAGACTGCG | GCTGGGGAGT | CTCAGGAGGA | AGGAGGTGGG | AGCTGGGCCG | 21900 |
| GCCCTGGTGA | GCAGGTGGCG | CCGGCCGGTG | GGGCCGTTCC | TGTCAGCTCT | GCAGATGCAG | 21960 |
| AGGTGGACAT | GAGCTGGGGG | CAGCCTCCGG | ACACTCCTGG | GCACGCCATA | CGGGAGGTGG | 22020 |
| CCTGCACGGG | GATCCCTGCC | GGTACCCACA | GGCCCCGTGG | GTGGGTGCTG | CTGTGAGCCT | 22080 |
| GGGCTGGTGG | GCCCTGGTCT | CCGGGCTCTG | AGCCTCAGTT | TCCCCATCTG | GAAAGGGGA | 22140 |
| CAGTGATGGG | GCTCCCAGCG | GGCTGCTGTG | AGGGTGGGAG | GATGGAGGAG | TGCCCTGAGC | 22200 |
| CCCCTGCCAT | CCCACACCCG | CCCCCAGGAG | CCTAGACGTG | TGGATCGGCT | TCTCGACTGT | 22260 |
| GCAGGGGGTG | GAGGTGGGCC | CAGCGCCGCA | GGGCGAGGCC | TTCAGCCTGG | AGAGCTGCCA | 22320 |
| GAACTGGCTG | CCCGGGGAGC | CACACCCAGC | CACAGCCGAG | CACTGCGTCC | GGCTCGGGCC | 22380 |
| CACCGGGTGG | TGTAACACCG | ACCTGTGCTC | AGCGCCGCAC | AGCTACGTCT | GCGAGCTGCA | 22440 |
| GCCCGGAGGT | GTGCGGGGGG | CCAGGCAGGG | GCCTGAGACG | CTGGCTGTGG | TTAGGGGCCT | 22500 |
| GCCGAGCGCC | CGCGGTGGAG | CCTGGGCTGA | GGAGGAGGGG | CTGGTGGGGG | GGTTTTCGGG | 22560 |
| CGGCTCGGTC | CCCAGTCTGT | TCGTCCTGGT | GTCCTGGGCC | CTGGCCCGGC | GCCTCACTGT | 22620 |

```
GCACTCGCCA CCCCAGGCCC AGTGCAGGAT GCCGAGAACC TCCTCGTGGG AGCGCCCAGT   22680

GGGGACCTGC AGGGACCCCT GACGCCTCTG GCACAGCAGG ACGGCCTCTC AGCCCCGCAC   22740

GAGCCCGTGG AGGTAGTCGG CCCCCACGT TCTACAACCT GCCCTCCTGC CTGCCCCTGG    22800

AGGCCTTGCC TGCCCTGCCC ACTGTGGGTC TCGCCAAAAA ACTTGGGGGC CTTAATGTTG   22860

CTTGTGCCCA GTGAAGATGG TTGGGAAAAT CCAGAGTGCA GAGAGGAAAG CGTTTACTCA   22920

CATTACCTCC AGGCCTTTTC TCTGAGCGTG TGTGAGTTAT TCCTGAAAGG CAGGTCAGGG   22980

GTCCTGCCCC CCATGGACAG TTTCCACCGG AGTCTTCCTC TCGAGCGACA GGAGCCAGGC   23040

CTGTGGGGGT CTGATGGCTC GCTCTCCTTC CCTCCCCTCT TCCTGGGAAG TTCGGGTAGG   23100

GGGAGTCTGG GCTTCAGGCT GGGATGGGGT CTGTGGAGCT GAGGCGGCCC CCTGCCCACC   23160

AGGTCATGGT ATTCCCGGGC CTGCGTCTGA GCCGTGAAGC CTTCCTCACC ACGGCCGAAT   23220

TTGGGACCCA GGAGCTCCGG CGGCCCGCCC AGCTGCGGCT GCAGGTGTAC CGGCTCCTCA   23280

GCACAGCAGG TGGGACTCTG GGTGGTGGGT GGTGGGTGGT GGGCGCCGCA GGACTCGGGG   23340

TGGCCTCTCT GAGCTTTCAC GTCTGCTGGT CCTGTGGCCA CCAGAGTGGT TCCCAGTCTT   23400

AGGTGGACAG AGCAGGGGTT CCAGAGACAC CAGCTCATTC CAGGTGTCCT GGGGGTGGAT   23460

TGGGTGGGGC CTGCCTGGGG GCCGGCCTGG GTCAGTCGGC TGGCCGGAGA CGGACGCAGC   23520

ACTGGGCTGG GAGTGCTGCC CAGGTGGGGA GACCTGTCCT CACAGCAAGG CCAGGATTGC   23580

TGGTGCAGGC AGTTGGGCAT CTCTGACGGT GGCCTGTGGG CAAATCAGGG CCCCAACACC   23640

CTCCCCTCCT CACAGGGACC CCGGAGAACG GCAGCGAGCC TGAGAGCAGG TCCCCGGACA   23700

ACAGGACCCA GCTGGCCCCC GCGTGCATGC CAGGGGGACG CTGGTGCCCT GGAGCCAACA   23760

TCTGCTTGCC GCTGGACGCC TCCTGCCACC CCCAGGCCTG CGCCAATGGC TGCACGTCAG   23820

GGCCAGGGCT ACCCGGGGCC CCCTATGCGC TATGGAGAGA GTTCCTCTTC TCCGTTCCCG   23880

CGGGGCCCCC CGCGCAGTAC TCGGTGTGTG GCCCTGACCT GGGTCTGTTC CCTGCATCTC   23940

CTCAGGCCAC CTTCCTGTCT GCTGCCCAGG GTCTGGGTCT GTGCACCAGA CACACCCAGC   24000

CTGCAGGCCC CTCCCACGTC CTTGCCACCT CTGACCTCCG ACCTCTGCAG TGCCCTCGGC   24060

CCTCTCCCAG TGGGAGAAGC TCTCGCCTGG GCCCTTGGCA CGAGCTGTGC CTCCTCTTCC   24120

TCTCTCCCAG CACAGCTGCT CCTTCCTGTC TGCCAGGTCT TGGCCTGTGT CCTCTCCCCG   24180

TGTGTCCCCC GGTCTGCAAC TGTCCTGCCT GTCCTTGTCA CGAGCACTGT GGGGAGGCTC   24240
```

| | | | | | |
|---|---|---|---|---|---|
| CTTGAGGTGT | GGCTGACGAA | GCGGGGAGCC | CTGCGTGTCC | ACCCTCATCC | GTCGTGCGGG | 24300
| GGTCCACGGG | CCATGACCGT | GAGGACGTGA | TGCAGCCCTG | CCTCCCTCTC | CACAGGTCAC | 24360
| CCTCCACGGC | CAGGATGTCC | TCATGCTCCC | TGGTGACCTC | GTTGGCTTGC | AGCACGACGC | 24420
| TGGCCCTGGC | GCCCTCCTGC | ACTGCTCGCC | GGCTCCCGGC | CACCCTGGTC | CCCGGGCCCC | 24480
| GTACCTCTCC | GCCAACGCCT | CGTCATGGCT | GCCCCACTTG | CCAGCCCAGC | TGGAGGGCAC | 24540
| TTGGGCCTGC | CCTGCCTGTG | CCCTGCGGCT | GCTTGCAGCC | ACGGAACAGC | TCACCGTGCT | 24600
| GCTGGGCTTG | AGGCCCAACC | CTGGACTGCG | GCTGCCTGGG | CGCTATGAGG | TCCGGGCAGA | 24660
| GGTGGGCAAT | GGCGTGTCCA | GGCACAACCT | CTCCTGCAGC | TTTGACGTGG | TCTCCCCAGT | 24720
| GGCTGGGCTG | CGGGTCATCT | ACCCTGCCCC | CCGCGACGGC | CGCCTCTACG | TGCCCACCAA | 24780
| CGGCTCAGCC | TTGGTGCTCC | AGGTGGACTC | TGGTGCCAAC | GCCACGGCCA | CGGCTCGCTG | 24840
| GCCTGGGGGC | AGTGTCAGCG | CCCGCTTTGA | GAATGTCTGC | CCTGCCCTGG | TGGCCACCTT | 24900
| CGTGCCCGGC | TGCCCCTGGG | AGACCAACGA | TACCCTGTTC | TCAGTGGTAG | CACTGCCGTG | 24960
| GCTCAGTGAG | GGGAGCACG | TGGTGGACGT | GGTGGTGGAA | AACAGCGCCA | GCCGGGCCAA | 25020
| CCTCAGCCTG | CGGGTGACGG | CGGAGGAGCC | CATCTGTGGC | CTCCGCGCCA | CGCCCAGCCC | 25080
| CGAGGCCCGT | GTACTGCAGG | GAGTCCTAGT | GGTGAGTATG | GCCGAGGCTC | CACCACCAGC | 25140
| CCCCAGGCAG | GTGCCTGCAG | ACAGGGTGCT | CACACAGGGC | GTGAGGCCTG | GCTTCCCAGT | 25200
| GAGGGCAGCA | GCCCAGTTAC | TGGGGACGTC | GGCCCCGGGC | AGGTCCTGCT | GGCTGGCTCC | 25260
| TCGGGCTACC | TGGTGGGCTT | TAAATTCCTG | GAAAGTCACG | GCTCTGACAG | TGGCTCCGCT | 25320
| AACTCATTCC | ACTGTCTCAT | TTCACAAAAT | GAATTTAAAA | CTCTGCTCCC | TGACCTCACA | 25380
| CGAGCCCCCG | TGAGTCTCTC | ACGCCCTCTG | CTGTGTTCTC | GCCTGGCTAA | AGCGAGTGGC | 25440
| TTTTGAGGTG | GAGTCTGAAC | CCCTGATGGG | AAACTGCGGG | CTGCCCGCGG | TGCCACCATG | 25500
| CTGGGTACAT | GGGGGACAGG | GCTGTCTCCA | TCTTGCGGGT | ACCTGCCTCT | TCACCAGGGG | 25560
| CCTTGGGAGG | GGCCATCAGA | AATGGCGTGA | CCTGTGCAGC | CTGTCCTGGG | TTCTGTAAGC | 25620
| CAGTGTAGGT | GCCTCCCCTC | ACTGCTCCGA | GCTCTCTGGG | TGAGGAGCTG | GGGCAAGAGC | 25680
| GCCGGGAGGG | TCTGAGAAGA | CTCAGAGAGA | GGTGGACTCT | TTGTAGCTGG | TACTAGGTTT | 25740
| GCTTTACAGA | TGGGGAAACT | GAGGCACAGA | GAGGTTGAGG | CATTAGTAGT | ACTACATGGC | 25800
| TGGCTGGAGA | GCCGGACAGT | GAGTGTCCCA | GCCCGGGCTT | GGCTCCCATG | GCATGCAGAG | 25860

```
CCCCGGGCAC CTCCTCTCCT CTGTGCCCCG CGTGGGACTC TCCAGCCCGA CGGGAGGTGT    25920

GTCCAGGAGG CGACAGGCTA AGGGCAGAGT CCTCCACAGA GCCCAGGCTG ACACCATTCC    25980

CCCCGCAGAG GTACAGCCCC GTGGTGGAGG CCGGCTCGGA CATGGTCTTC CGGTGGACCA    26040

TCAACGACAA GCAGTCCCTG ACCTTCCAGA ACGTGGTCTT CAATGTCATT TATCAGAGCG    26100

CGGCGGTCTT CAAGCTCTCA GTAGGTGGGC GGGGGTGGGG AGGGGAGGGG ATGGGGCGGG    26160

GCAGGGCGGG GGCGGGCTCC ACCTTCACCT CTGCCTTCTG CTCTGCTTCA TGCTGCCCGA    26220

GGACGCTGCC ATGGCTGTGG GTGAGTGGAG GGAGGGACGC CAATCAGGGC CAGGCCTCTC    26280

ACCTGCCACC TGGGCTCACT GACGCCTGTC CCTGCAGCTG ACGGCCTCCA ACCACGTGAG    26340

CAACGTCACC GTGAACTACA ACGTAACCGT GGAGCGGATG AACAGGATGC AGGGTCTGCA    26400

GGTCTCCACA GTGCCGGCCG TGCTGTCCCC CAATGCCACG CTAGCACTGA CGGCGGGCGT    26460

GCTGGTGGAC TCGGCCGTGG AGGTGGCCTT CCTGTGAGTG ACTCGGGGGC CGGTTTGGGG    26520

TGGGCACCAG GCTCTTGTCC CAGCCCCAGC CTCAGCCGAG GGACCCCCAC ATCACGGGGT    26580

TGCTTTTCTG AGCCTCGGTT TCCCTGTCTG TTGGGAGGTA ACTGGGTGCA CAGGAGCCCT    26640

GAGGCTGCAC GGGAGCCGGG AGAGGCCTCA GCACAGCCGG GTGGGCCCTG AATGGAGGCC    26700

CGGGGCGTGA CTGCAGAGTG GAGCCTCGGC TGGGTCCCAA GCACCCCTG CCCCGCCACC    26760

GCCCACCCCT GTCCCGGTTC ACTCACTGCG TCCCACCGCC CCGGCAGGTG GACCTTTGGG    26820

GATGGGAGC AGGCCCTCCA CCAGTTCCAG CCTCCGTACA ACGAGTCCTT CCCGGTTCCA    26880

GACCCCTCGG TGGCCCAGGT GCTGGTGGAG CACAATGTCA TGCACACCTA CGCTGCCCCA    26940

GGTGAGGGAT GAGGGGGTGA GGGGGCCACT GCCTTTCAGG CTCTGAGCAC GGGTCCCCCC    27000

AGCTCCCCAG TCAAGCTGCC CCCCTTCCTC CCCAACAGCC CTCACTGTGA CCTCACCTGG    27060

GCTGATGGCT TAGGCCCTAC TGGGGTGAGG GAGGGGCCAG GCGTGGGGGG AGTGGACAGG    27120

GAAGCTGGGC CCCTGAACTG CGCCCCCGC CCTCCCCGGG CCTGGCTCTT GCTGCTCTGC    27180

TGCCCCGAGT GCAGCTGCAC TTGGAGGCGG TGCCGTCCTC GCCAGGCAGC CCTCAGTGCT    27240

GCTACACCTG TGCTCCGTCC CGCACGTGGC TTGGGAGCCT GGGACCCTTA AGGCTGGGCC    27300

GCAGGTGCAG CCGTTCACCC CGGGCTCCTC AGGCGGGGG CTTCTGCCGA GCGGGTGGGG    27360

AGCAGGTGGG GGTGCCGCGG CTGCCCCACT CGGGCCTGTC CCCACAGGTG AGTACCTCCT    27420

GACCGTGCTG GCATCTAATG CCTTCGAGAA CCTGACGCAG CAGGTGCCTG TGAGCGTGCG    27480
```

```
CGCCTCCCTG CCCTCCGTGG CTGTGGGTGT GAGTGACGGC GTCCTGGTGG CCGGCCGGCC    27540

CGTCACCTTC TACCCGCACC CGCTGCCCTC GCCTGGGGGT GTTCTTTACA CGTGGGACTT    27600

CGGGGACGGC TCCCCTGTCC TGACCCAGAG CCAGCCGGCT GCCAACCACA CCTATGCCTC    27660

GAGGGGCACC TACCACGTGC GCCTGGAGGT CAACAACACG GTGAGCGGTG CGGCGGCCCA    27720

GGCGGATGTG CGCGTCTTTG AGGAGCTCCG CGGACTCAGC GTGGACATGA GCCTGGCCGT    27780

GGAGCAGGGC GCCCCCGTGG TGGTCAGCGC CGCGGTGCAG ACGGGCGACA ACATCACGTG    27840

GACCTTCGAC ATGGGGACG GCACCGTGCT GTCGGGCCCG GAGGCAACAG TGGAGCATGT    27900

GTACCTGCGG GCACAGAACT GCACAGTGAC CGTGGGTGCG GCCAGCCCCG CCGGCCACCT    27960

GGCCCGGAGC CTGCACGTGC TGGTCTTCGT CCTGGAGGTG CTGCGCGTTG AACCCGCCGC    28020

CTGCATCCCC ACGCAGCCTG ACGCGCGGCT CACGGCCTAC GTCACCGGGA ACCCGGCCCA    28080

CTACCTCTTC GACTGGACCT TCGGGGATGG CTCCTCCAAC ACGACCGTGC GGGGGTGCCC    28140

GACGGTGACA CACAACTTCA CGCGGAGCGG CACGTTCCCC CTGGCGCTGG TGCTGTCCAG    28200

CCGCGTGAAC AGGGCGCATT ACTTCACCAG CATCTGCGTG GAGCCAGAGG TGGGCAACGT    28260

CACCCTGCAG CCAGAGAGGC AGTTTGTGCA GCTCGGGGAC GAGGCCTGGC TGGTGGCATG    28320

TGCCTGGCCC CCGTTCCCCT ACCGCTACAC CTGGGACTTT GGCACCGAGG AAGCCGCCCC    28380

CACCCGTGCC AGGGGCCCTG AGGTGACGTT CATCTACCGA GACCCAGGCT CCTATCTTGT    28440

GACAGTCACC GCGTCCAACA ACATCTCTGC TGCCAATGAC TCAGCCCTGG TGGAGGTGCA    28500

GGAGCCCGTG CTGGTCACCA GCATCAAGGT CAATGGCTCC CTTGGGCTGG AGCTGCAGCA    28560

GCCGTACCTG TTCTCTGCTG TGGGCCGTGG GCGCCCCGCC AGCTACCTGT GGGATCTGGG    28620

GGACGGTGGG TGGCTCGAGG GTCCGGAGGT CACCCACGCT TACAACAGCA CAGGTGACTT    28680

CACCGTTAGG GTGGCCGGCT GGAATGAGGT GAGCCGCAGC GAGGCCTGGC TCAATGTGAC    28740

GGTGAAGCGG CGCGTGCGGG GGCTCGTCGT CAATGCAAGC CGCACGGTGG TGCCCCTGAA    28800

TGGGAGCGTG AGCTTCAGCA CGTCGCTGGA GGCCGGCAGT GATGTGCGCT ATTCCTGGGT    28860

GCTCTGTGAC CGCTGCACGC CCATCCCTGG GGTCCTACC ATCTCTTACA CCTTCCGCTC    28920

CGTGGGCACC TTCAATATCA TCGTCACGGC TGAGAACGAG GTGGGCTCCG CCCAGGACAG    28980

CATCTTCGTC TATGTCCTGC AGCTCATAGA GGGGCTGCAG GTGGTGGGCG GTGGCCGCTA    29040

CTTCCCCACC AACCACACGG TACAGCTGCA GGCCGTGGTT AGGGATGGCA CCAACGTCTC    29100
```

```
CTACAGCTGG ACTGCCTGGA GGGACAGGGG CCCGGCCCTG GCCGGCAGCG GCAAAGGCTT    29160
CTCGCTCACC GTGCTCGAGG CCGGCACCTA CCATGTGCAG CTGCGGGCCA CCAACATGCT    29220
GGGCAGCGCC TGGGCCGACT GCACCATGGA CTTCGTGGAG CCTGTGGGGT GGCTGATGGT    29280
GGCCGCCTCC CCGAACCCAG CTGCCGTCAA CACAAGCGTC ACCCTCAGTG CCGAGCTGGC    29340
TGGTGGCAGT GGTGTCGTAT ACACTTGGTC CTTGGAGGAG GGGCTGAGCT GGGAGACCTC    29400
CGAGCCATTT ACCACCCATA GCTTCCCCAC ACCCGGCCTG CACTTGGTCA CCATGACGGC    29460
AGGGAACCCG CTGGGCTCAG CCAACGCCAC CGTGGAAGTG GATGTGCAGG TGCCTGTGAG    29520
TGGCCTCAGC ATCAGGGCCA GCGAGCCCGG AGGCAGCTTC GTGGCGGCCG GTCCTCTGT    29580
GCCCTTTTGG GGGCAGCTGG CCACGGGCAC CAATGTGAGC TGGTGCTGGG CTGTGCCCGG    29640
CGGCAGCAGC AAGCGTGGCC CTCATGTCAC CATGGTCTTC CCGGATGCTG GCACCTTCTC    29700
CATCCGGCTC AATGCCTCCA ACGCAGTCAG CTGGGTCTCA GCCACGTACA ACCTCACGGC    29760
GGAGGAGCCC ATCGTGGGCC TGGTGCTGTG GGCCAGCAGC AAGGTGGTGG CGCCCGGGCA    29820
GCTGGTCCAT TTTCAGATCC TGCTGGCTGC CGGCTCAGCT GTCACCTTCC GCCTGCAGGT    29880
CGGCGGGGCC AACCCCGAGG TGCTCCCCGG GCCCGTTTC TCCCACAGCT TCCCCCGCGT    29940
CGGAGACCAC GTGGTGAGCG TGCGGGGCAA AAACCACGTG AGCTGGGCCC AGGCGCAGGT    30000
GCGCATCGTG GTGCTGGAGG CCGTGAGTGG GCTGCAGGTG CCCAACTGCT GCGAGCCTGG    30060
CATCGCCACG GCACTGAGA GGAACTTCAC AGCCCGCGTG CAGCGCGGCT CTCGGGTCGC    30120
CTACGCCTGG TACTTCTCGC TGCAGAAGGT CCAGGGCGAC TCGCTGGTCA TCCTGTCGGG    30180
CCGCGACGTC ACCTACACGC CCGTGGCCGC GGGGCTGTTG GAGATCCAGG TGCGCGCCTT    30240
CAACGCCCTG GCAGTGAGA ACCGCACGCT GGTGCTGGAG GTTCAGGACG CCGTCCAGTA    30300
TGTGGCCCTG CAGAGCGGCC CCTGCTTCAC CAACCGCTCG GCGCAGTTTG AGGCCGCCAC    30360
CAGCCCCAGC CCCCGGCGTG TGGCCTACCA CTGGGACTTT GGGGATGGGT CGCCAGGGCA    30420
GGACACAGAT GAGCCCAGGG CCGAGCACTC CTACCTGAGG CCTGGGGACT ACCGCGTGCA    30480
GGTGAACGCC TCCAACCTGG TGAGCTTCTT CGTGGCGCAG GCCACGGTGA CCGTCCAGGT    30540
GCTGGCCTGC CGGGAGCCGG AGGTGGACGT GGTCCTGCCC CTGCAGGTGC TGATGCGGCG    30600
ATCACAGCGC AACTACTTGG AGGCCCACGT TGACCTGCGC GACTGCGTCA CCTACCAGAC    30660
TGAGTACCGC TGGGAGGTGT ATCGCACCGC CAGCTGCCAG CGGCCGGGGC GCCCAGCGCG    30720
```

| | |
|---|---:|
| TGTGGCCCTG CCCGGCGTGG ACGTGAGCCG GCCTCGGCTG GTGCTGCCGC GGCTGGCGCT | 30780 |
| GCCTGTGGGG CACTACTGCT TTGTGTTTGT CGTGTCATTT GGGGACACGC CACTGACACA | 30840 |
| GAGCATCCAG GCCAATGTGA CGGTGGCCCC CGAGCGCCTG GTGCCCATCA TTGAGGGTGG | 30900 |
| CTCATACCGC GTGTGGTCAG ACACACGGGA CCTGGTGCTG GATGGGAGCG AGTCCTACGA | 30960 |
| CCCCAACCTG GAGGACGGCG ACCAGACGCC GCTCAGTTTC CACTGGGCCT GTGTGGCTTC | 31020 |
| GACACAGGTC AGTGCGTGGC AGGGCCGTCC TCCATGCCCC TCACCCGTCC ACACCCATGA | 31080 |
| GCCCAGAGAA CACCCAGCTT GCCACCAGGG CTGGCCCGTC CTCAGTGCCT GGTGGGCCCC | 31140 |
| GTCCCAGCAT GGGGAGGGGG TCTCCCGCGC TGTCTCCTGG GCCGGGCTCT GCTTTAAAAC | 31200 |
| TGGATGGGGC TCTCAGGCCA CGTCGCCCCT TGTTCTCGGC CTGCAGAGGG AGGCTGGCGG | 31260 |
| GTGTGCGCTG AACTTTGGGC CCCGCGGGAG CAGCACGGTC ACCATTCCAC GGGAGCGGCT | 31320 |
| GGCGGCTGGC GTGGAGTACA CCTTCAGCCT GACCGTGTGG AAGGCCGGCC GCAAGGAGGA | 31380 |
| GGCCACCAAC CAGACGGTGG GTGCCGCCCG CCCCTCGGCC ACTTGCCTTG ACAGCCCAG | 31440 |
| CCTCCCTGGT CATCTACTGT TTTCCGTGTT TTAGTGCTGG TGGAGGCCGC ACGCTCTCCC | 31500 |
| CTCTCTGTTT CTGATGCAAA TTCTATGTAA CACGACAGCC TGCTTCAGCT TTGCTTCCTT | 31560 |
| CCAAACCTGC CACAGTTCCA CGTACAGTCT TCAAGCCACA TATGCTCTAG TGGCAAAAGC | 31620 |
| TACACAGTCC CCTAGCAATA CCAACAGTGA GGAAGAGCCC CTTCCCACCC CAGAGGTAGC | 31680 |
| CACTGTCCCC AGCCCATGTC CCTGTTGCTG GATGTGGTGG GCCGGTTCTC ACCCTCACGC | 31740 |
| TCCCCTCTCT GGACCGGCCA GGAGGCTTGG TGACCCTGAG CCCGTGGTGG CTGCTCCTGC | 31800 |
| TGCTGTCAGG CGGGGCCTGC TGGTGCCCCA GAGTGGGCGT CTGTTCCCCA GTCCCTGCTT | 31860 |
| TCCTCAGCTG GCCTGATTGG GGGTCTTCCC AGAGGGGTCG TCTGAGGGGA GGGTGTGGGA | 31920 |
| GCAGGTTCCA TCCCAGCTCA GCCTCCTGAC CCAGGCCCTG GCTAAGGGCT GCAGGAGTCT | 31980 |
| GTGAGTCAGG CCTACGTGGC AGCTGCGGTC CTCACACCCA CACATACGTC TCTTCTCACA | 32040 |
| CGCATCCCCC CAGGGGCCCT CAGTGAGCAT TGCCTGCCTC CTGCTAGGGT CCAGCTGGGT | 32100 |
| CCAGTACACC AGAACGCACA CTCCAGTGTC CTCTGCCCTG TGTATGCCCT TCCGCCGTCC | 32160 |
| AAGTTGGAAG GTGGCAAACC GGATGAGTAT CCTGGGAGGG AGTGAGCTCA CCGGCAGTGG | 32220 |
| CCAGGCCCCT GGGAAACCTG GAGTTTGGGA GCAGCATCCT CCATGGGTCC CCCAGTCCTT | 32280 |
| CCAGCAGGCC AAATAGACCT GTGTTGGAGG TAACCCCACT CCCACGCCAG GTGCTGATCC | 32340 |

```
GGAGTGGCCG GGTGCCCATT GTGTCCTTGG AGTGTGTGTC CTGCAAGGCA CAGGCCGTGT    32400

ACGAAGTGAG CCGCAGCTCC TACGTGTACT TGGAGGGCCG CTGCCTCAAT TGCAGCAGCG    32460

GCTCCAAGCG AGGGGTGAGT GTTGAGCGGG GTGTGGGCGG GCTGGGGATG GGTCCCATGG    32520

CCGAGGGGAC GGGGCCTGCA GGCAGAAGTG GGGCTGACAG GGCAGAGGGT TGCGCCCCCT    32580

CACCACCCCT TCTGCCTGCA GCGGTGGGCT GCACGTACGT TCAGCAACAA GACGCTGGTG    32640

CTGGATGAGA CCACCACATC CACGGGCAGT GCAGGCATGC GACTGGTGCT GCGGCGGGGC    32700

GTGCTGCGGG ACGGCGAGGG ATACACCTTC ACGCTCACGG TGCTGGGCCG CTCTGGCGAG    32760

GAGGAGGGCT GCGCCTCCAT CCGCCTGTCC CCCAACCGCC CGCCGCTGGG GGGCTCTTGC    32820

CGCCTCTTCC CACTGGGCGC TGTGCACGCC CTCACCACCA AGGTGCACTT CGAATGCACG    32880

GGTGAGTGCA GGCCTGCGTG GGGGGAGCAG CGGGATCCCC CGACTCTGTG ACGTCACGGA    32940

GCCCTCCCGT GATGCCGTGG GGACCGTCCC TCAGGCTGGC ATGACGCGGA GGATGCTGGC    33000

GCCCCGCTGG TGTACGCCCT GCTGCTGCGG CGCTGTCGCC AGGGCCACTG CGAGGAGTTC    33060

TGTGTCTACA AGGGCAGCCT CTCCAGCTAC GGAGCCGTGC TGCCCCCGGG TTTCAGGCCA    33120

CACTTCGAGG TGGGCCTGGC CGTGGTGGTG CAGGACCAGC TGGGAGCCGC TGTGGTCGCC    33180

CTCAACAGGT GAGCCAGGCC GTGGGAGGGC GCCCCGAGA CTGCCACCTG CTCACCACCC     33240

CCTCTGCTCG TAGGTCTTTG GCCATCACCC TCCCAGAGCC CAACGGCAGC GCAACGGGGC    33300

TCACAGTCTG GCTGCACGGG CTCACCGCTA GTGTGCTCCC AGGGCTGCTG CGGCAGGCCG    33360

ATCCCCAGCA CGTCATCGAG TACTCGTTGG CCCTGGTCAC CGTGCTGAAC GAGGTGAGTG    33420

CAGCCTGGGA GGGGACGTCA CATCTGCTGC ATGCGTGCTT GGGACCAAGA CCTGTACCCC    33480

TGCCTGGAGC TTTGCAGAGG GCTCATCCCG GGCCCAGAG ATAAATCCCA GTGACCCTGA     33540

AGCAGCACCC CGACCTTCCG CTCCCAGCAG CCACACCCAC CGGGCCCTCT CCGGCGTCTG    33600

CTTTCCACAA TGCAGCCCCC GCCCAGGAGG GCCCATGTGC TTACCCTGTT TTGCCCATGA    33660

AGAAACAGCT CAGTGTTGTG GGTCAGTGCC CGCATCACAC AGCGTCTAGC ACGTAACTGC    33720

ACCCCGGGAG TCGTGGGCAT CTGCTGGCCT CCTGCCGGCC TCCTGCGCTG CTGACAGCTT    33780

GCTGTGCCCC CTGCCTGCCC CAGTACGAGC GGGCCCTGGA CGTGGCGGCA GAGCCCAAGC    33840

ACGAGCGGCA GCACCGAGCC CAGATACGCA AGAACATCAC GGAGACTCTG GTGTCCCTGA    33900

GGGTCCACAC TGTGGATGAC ATCCAGCAGA TCGCTGCTGC GCTGGCCCAG TGCATGGTAG    33960
```

```
GATGGCCCCA CCTGCTCACC CTGCCCCGCA TGCCTGCCAG GGCACTGGGT TCAGCCCCCC    34020
AGGGCAGACG GGCAGCTTGG CCGAGGAGCT GAGCCTCCAG CCTGGGCTCC TTCCTGCCAT    34080
GGCGTTCCTC GGTCTCTGAC CTGCTTCAGT AGCCTCAGCC GTTCTGTCCT GTGTGAACGC    34140
AGGGTGCCTC TCGGGGGACC CAGGGTGTAA AGAGGGGCCC AGATGTGGGG AGGGACTAAG    34200
AAGATGCTGC TCTGTGCCCT CCACTCTCCC CTCCCCTCCC CTCCCCCTTC CCTCCCCTAG    34260
CCCCTCCCCT CCTCCCCTCC CCTAGCCCTT CCCCTCCTCC CCTCCCCTAG CCCTTTCCCT    34320
TCTTCCCCCC CAGCCCTTCC CCTCCTCCCC TCCCCTAGCC CTTCCCCTCC TCCCCTCCCC    34380
TACCCCTTCC CCTCCTCCCC TCCCCTAGAC CTTCCCCTCA CCTCCTCCCG CTGAGCCCCT    34440
CCACTCGTCC CCCAGCCCCT CCCTCCCCTA GCCCCTCCCC TCCCCCTTCC TCCCCTCCTC    34500
CCCCTCCCCT CCTCCCCCTC CCTCTTCCTC CCCCTCCCCT CCTCCCCTT CCTCCCCTCT    34560
CCTCCCCCTC CCCTCCTGTC CCCCCTCCTC CCCTCCTCCC TCCTCCCCTC CTCCCCCCTC    34620
CTCCTCCCCC TCCTCCCTCC TCCCTCCTCC CCCTCCTCCT CCTCCCCTCC TCCCTCCTCC    34680
CCTCCTCCCC TCCCCTCCTC CCCCTCCCCC CTCCCTTCCT CCCCCTCCCC CCTCCCCTCC    34740
TCCCCCTCTC CTCCTCCCAT CCCTCCTCCC ATCCCTCCTC CCCGTTCCCA TTCTCTCCCC    34800
TCCCCCTTCC ATTTCTCCCT CCTCCCCCTG CCCTCCTCTC CTCCTCACCT CCCCTTCTCC    34860
GCTCCTTTCT TCTCCTCCCT CCCTTTCTCT CCTCCCTCCC CTTCTCCCCT TCTCCTCTTC    34920
TCCCCTTCTC CTCTCTTTTC ATCCTTCCCT TCTTCCCTCC TTTCCTCCTC TTTTCCCTCT    34980
TCTCCCCCCT CCTCCCCTCC TTCCTCCTCC CATTCCCCCT CCTCCCCCCT CCCATTCCCC    35040
CTCCTCCCCT CCTTCCTCCT CCCATTACCC CTCCTCTCCT CCCCTCCTCC CACCCCCCTC    35100
TCCTCCCGGC TCCTCTCCTC CCCTCCTCAT CCCCCTCCTC TCCTTCCCTC CTAACCCCCC    35160
TCCTCTCCTC CCCTCCTCAT CCCCCTCCTC TCCTTCCCTC CTCCTATCCC CCCTCCTCTC    35220
CTCCCCTCCT CCTATTCCCC CTCCTCTCCT CCCCTCCTTC CTCCTCCTCT CCTCCCATGC    35280
CCCCTCCTCC CCTCCTCCCA TCCCCCTCCT CCCCTCCTCC CTCCTCCCAT CCCATCCCCC    35340
TCCTCTCCTC CCCTTCTCTC CCCTCCTCTC CTCCCCTCCT CCTCTCCT CCTCTCCTCC    35400
CCTCCTCCCA TCCCCCCTCC TCCCATCCCC CCTCCTCTCC TCCCCACTCC TCTCCTCCCC    35460
ACTCCTCTCC TCCCCTCATC CCCCTCCTCT CTCCTCCCCT CCCCCTCCTC TCCTTCCCTC    35520
CTCCTTTCCT CCCCTCCCCC TCCTTCCCCC TCCTCCCCCT CCTTCTCCCC ATCCCCCTTC    35580
```

| | |
|---|---|
| CCCTTCTCCT CCTCTCCCCT CCCCCTTCTC TTTTTCCCTC CTCCTCCCTT CCTCCTCCCC | 35640 |
| TCTTCTCCCC TTTTCCCTTT TCTCTTCCTC TCCTCCCCTT CTCCCTCCT GTCCTCCCTC | 35700 |
| CCTTTCTCTC TTTCTTTCCT CCCTTTCCTT CTCCCTGTT CTCCTCCCTT CCCTTCTCCC | 35760 |
| CTTTTCTTCC CTCCTCCTTT CCTCCCCTCC TCCTTTTCTC TGTTTCTCTT CCTTTCCCCT | 35820 |
| CCACTTTCCC CTTCCTTTCC CCTCTCCTTT CTCCTTCCTT TCCTCTCCCC TTCTCTTCCT | 35880 |
| TTTCCTCTCT CCCCTTCTTT CCCTCTTCC CCTCCCCTCC TCTTCCCCTC CCCTCCTCTT | 35940 |
| CCCCTCCCCT CCTCTTCCCC TCCCCTCCTC TTCCCTCTC CTCCTCTTCC CCTCCCCTCC | 36000 |
| TCTTTCCCTC CCCTCTTCTC CTCCCCTCCT CTCCCTCTT CCCCTCCCCT CCTCTTCCCT | 36060 |
| CCCCTTCCCC TCCCCTCCTC TTCCCTCCCC TTCCCTCCC CTCCTCTTCC CTCCCCTTCC | 36120 |
| CCTCCTCTTC CTTCCTCTCT TCCCCTCCCC TCCTCTTCCC TCCCCTCTTC CCTCCCCTT | 36180 |
| CTCTTCTCCT CCCCTTCTCT TCCCCTCCCC TTTTCTTCCC TCTCCTTGTC TTCCCTGCCC | 36240 |
| TCCTCTTCCC TCCCCTCCTC TTCCCTCCCC TCTTCCCCTC TCCTCCTCTT CCCTCCCCTC | 36300 |
| TTCCTCTTTC CTCTTCCCCT CCCCTCCTCC TCCCTCCCCT TTCCCCTCTT CCCCTCCCCT | 36360 |
| CCGCTTCCCT CCCCTTTCTC CCCCTTCTCT CCCCTCCCCT CTCCCCCCTT CTCTCCCCTC | 36420 |
| CCCTCTCCCC CTTCTCTCCC CTCCCCTCTC CCCCTTCTCT CCCCTCTCCT CTCCCCCTTC | 36480 |
| TCTCCCCCTT CTCTCCCCCT TCTCTCTCCC CTTCTCTCCC CCTTCTCTCC CCTCCCCCCT | 36540 |
| TCTCTCCCCT CCCCTCTCCC CCTTCTCTCC CCTCCCCTCT CCCCTGTCCT CTCCTCTCCA | 36600 |
| CCCTTCTCTC CCCTCCCCTC TCCTCTCCCC CTTCCCTCTC CTCTCCCCCT TCTCTCCCCT | 36660 |
| CCCCTCTCCT CTCCCCCCTT TTCTCCACTC CCCTCTCCTC TCTCCCCTCC TCCTCCGCTC | 36720 |
| TCATGTGAAG AGGTGCCTTG TGTGGTCGGT GGGCTGCATC ACGTGGTCCC CAGGTGGAGG | 36780 |
| CCCTGGGTCA TGCAGAGCCA CAGAAAATGC TTAGTGAGGA GGCTGTGGGG GTCCAGTCAA | 36840 |
| GTGGGCTCTC CAGCTGCAGG GCTGGGGGTG GGAGCCAGGT GAGGACCCGT GTAGAGAGGA | 36900 |
| GGGCGTGTGC AAGGAGTGGG GCCAGGAGCG GGGCTGGACA CTGCTGGCTC CACACAGGGG | 36960 |
| CCCAGCAGGG AGCTCGTATG CCGCTCGTGC CTGAAGCAGA CGCTGCACAA GCTGGAGGCC | 37020 |
| ATGATGCTCA TCCTGCAGGC AGAGACCACC GCGGGCACCG TGACGCCCAC CGCCATCGGA | 37080 |
| GACAGCATCC TCAACATCAC AGGTGCCGCG GCCCGTGCCC CATGCCACCC GCCCGCCCCG | 37140 |
| TGCGGCCCTT TCCTCTGCCT CCCTCCTCCC CCCAACCGCG TCGCCTTTGC CCCATCCCAT | 37200 |

```
CTTCGTCCCC CTCCCCTCCC CCCAATTCCC ATCCTCATCC CCCTCCCCCA ATTCCCATTC  37260

TCCTCCCCCT CCCCCTTCCC TATTACCATC CCTTTTCTCC ATCTCTCTCC CCTTTTCTCC  37320

ATTTCCCCCC CCGTCCTCCC CGTCCTTTTG TCCATTCCCC TCATCTTCCT CATCCCCCTC  37380

ATCCCCCTTC CCCTCCCTTA TCCCCCTTCC CCTCCCTTTC CCCTGCTCC TCTTCTTCTC   37440

CCTTCTCTTT TCTCTACCCT TTTCCTTCCT TTTTCCTCCC TCTCCCCATC ATCCCCCTCA  37500

TCTTCGTCCT CATCCCCATC ACCTTCCCCC TCCCCCCTCC ACCACTCTCT CTCCAGCTTC  37560

CCCCTTCCTT CTGCCTGCAC CTCGCTCTCT GCCCCCTCAG GTTCCCCCTT TCTCCCAGCC  37620

CCCACCCTCC GGCTCCCCCT TTTTGCCTGC CCCCACCCTC CCTCTACCTC CCTGTCTCTG  37680

CACTGACCTC ACGCATGTCT GCAGGAGACC TCATCCACCT GGCCAGCTCG GACGTGCGGG  37740

CACCACAGCC CTCAGAGCTG GGAGCCGAGT CACCATCTCG GATGGTGGCG TCCCAGGCCT  37800

ACAACCTGAC CTCTGCCCTC ATGCGCATCC TCATGCGCTC CCGCGTGCTC AACGAGGAGC  37860

CCCTGACGCT GGCGGGCGAG GAGATCGTGG CCCAGGGCAA GCGCTCGGAC CCGCGGAGCC  37920

TGCTGTGCTA TGGCGGCGCC CCAGGGCCTG GCTGCCACTT CTCCATCCCC GAGGCTTTCA  37980

GCGGGCCCT GGCCAACCTC AGTGACGTGG TGCAGCTCAT CTTTCTGGTG GACTCCAATC   38040

CCTTTCCCTT TGGCTATATC AGCAACTACA CCGTCTCCAC CAAGGTGGCC TCGATGGCAT  38100

TCCAGACACA GGCCGGCGCC CAGATCCCCA TCGAGCGGCT GGCCTCAGAG CGCGCCATCA  38160

CCGTGAAGGT GCCCAACAAC TCGGACTGGG CTGCCCGGGG CCACCGCAGC TCCGCCAACT  38220

CCGCCAACTC CGTTGTGGTC CAGCCCCAGG CCTCCGTCGG TGCTGTGGTC ACCCTGGACA  38280

GCAGCAACCCC TGCGGCCGGG CTGCATCTGC AGCTCAACTA TACGCTGCTG GACGGTGCGT  38340

GCAGCGGGTG GGGCACACGC GGCCCCCTGG CCTTGTTCTT GGGGGGAAGG CGTTTCTCGT  38400

AGGGCTTCCA TGGGTGTCTC TGGTGAAATT TGCTTTCTGT TTCATGGGCT GCTGGGGGCC  38460

TGGCCAGAGA GGAGCTGGGG GCCACGGAGA AGCAGGTGCC AGCTCTGGTG CAGAGGCTCC  38520

TATGCTTTCA GGCCCGTGGC AGAGGGTGGG CTCAGGAGGG CCATCGTGGG TGTCCCCCGG  38580

GTGGTTGAGC TTCCCGGCAG GCGTGTGACC TGCGCGTTCT GCCCCAGGCC ACTACCTGTC  38640

TGAGGAACCT GAGCCCTACC TGGCAGTCTA CCTACACTCG GAGCCCCGGC CCAATGAGCA  38700

CAACTGCTCG GCTAGCAGGA GGATCCGCCC AGAGTCACTC CAGGGTGCTG ACCACCGGCC  38760

CTACACCTTC TTCATTTCCC CGGGGTGAGC TCTGCGGGCC AGCCTGGCAG GGCAGGGCAG  38820
```

```
GGCATCATGG GTCAGCATTG CCTGGGTTAC TGGCCCCATG GGGACGGCAG GCAGCGAGGG      38880

GACTGGACCG GGTATGGGCT CTGAGACTGC GACATCCAAC CTGGCGGAGC CTGGGCTCAC      38940

GTCCGCTACC CCTTCCCTGC CCAGGAGCAG AGACCCAGCG GGGAGTTACC ATCTGAACCT      39000

CTCCAGCCAC TTCCGCTGGT CGGCGCTGCA GGTGTCCGTG GCCTGTACA  CGTCCCTGTG      39060

CCAGTACTTC AGCGAGGAGG ACATGGTGTG GCGGACAGAG GGGCTGCTGC CCTGGAGGA      39120

GACCTCGCCC CGCCAGGCCG TCTGCCTCAC CCGCCACCTC ACCGCCTTCG GCGCCAGCCT      39180

CTTCGTGCCC CCAAGCCATG TCCGCTTTGT GTTTCCTGTG AGTGACCCTG TGCTCCTGGG      39240

AGCCTCTGCA GAGTCGAGGA GGGCCTGGGT GGGCTCGGCT CTATCCTGAG AAGGCACAGC      39300

TTGCACGTGA CCTCCTGGGC CCGGCGGCTG TGTCCTCACA GGAGCCGACA GCGGATGTAA      39360

ACTACATCGT CATGCTGACA TGTGCTGTGT GCCTGGTGAC CTACATGGTC ATGGCCGCCA      39420

TCCTGCACAA GCTGGACCAG TTGGATGCCA GCCGGGGCCG CGCCATCCCT TTCTGTGGGC      39480

AGCGGGGCCG CTTCAAGTAC GAGATCCTCG TCAAGACAGG CTGGGGCCGG GGCTCAGGTG      39540

AGGGGCGCAG CGGGGTGGCA GGGCCTCCCC TGCTCTCACT GGCTGTGCTG GTTGCACCCT      39600

CTGGGAGTGA GTCTCGTCGC AGGCGTCAGA ACAAGGCAGT TTTTGCAGTG CTGTGTGAAG      39660

GGCTCGTGTG TTCATCCTGG GAATGACCTC GTGAGCACTC ACTGTCCCTG AGGACTAGGA      39720

CAGCTCCTAG CTGGAAGTAG GTGCCAGTCA GTCAGGGTGG GCAGCCCACG TTCTGCACAG      39780

TAGCGTGGCC CCACAAGTGA CGTGAGCATC GCTACCACTG TGGGAGACTG TGCATCCACC      39840

CGCGATCCTG ACTGCATAGC TCGTCTCTCA GACGGAGGCG CCAGCACCCT CCCCGTGGCT      39900

GTTTCTTCAG TACCTCCATT TTCCTTTCAT TGGAATTGCC CTTCTGGCAT TCCCTTTTTG      39960

TTTTCGTTTT TCTTTTTTTA GAGACGGAGT CTCACTCTGT TGCCCAGGCT GGAGTGCAAT      40020

GGCATGATCT TGGCTCACAG CAACTTCCAG CTCCCGGGTT TAAGCCATTC CCCTTAAGCG      40080

ATTCTCCTGA GTAGCTGGGA GTACAGGTGC ACACCACCAC ACCCAGTTAA TTTTTCACCA      40140

TGTCAGCCAG GCGAACTCCT GACCTCAGGT GATCCGCCTG CCTCGGCCTG CCAGAGTGCT      40200

GGGATGACAG GTGTGAGCCA CCACACCTGG CTGTGTTCCC ATTTTTTATC TCTGTGCTGC      40260

TTTCCTCTTC ATTGCCCAGT TCTTTCTTTT GATTACCTAC TTTTAAAAAC TGTCGGCCGG      40320

GCGCGGTGGC TCACACCTGT AATCCGAGCA CTTTGGGAGG CCAGGCAGGC AAATCACGGG      40380

GTCAGGAGAT CGAGACCATC CTGGCTAACG GTGAAACCCT GTCTCTAATA AAAGTACAA       40440
```

| | | | | | |
|---|---|---|---|---|---|
| AAAAATTAGC | CCGGCGTAGT | GGCAGGCGCC | TGTAGTCCCA | GCTCCTTGGG | AGACTGAGGC | 40500 |
| AGGAGAATGG | CGTGAACCCG | GGAGGCGGAG | CTTGCAGTGA | GCTGAGATTG | CGCCACTGCA | 40560 |
| CTCCAGCCTG | GGTGACACAG | CAAGACTCCA | TCTCAAAAAA | AAAAGAAAAA | AAATACTGTC | 40620 |
| ACCTGGGTCT | GTCACTGGGA | GAGGAGGTGA | CACAGCTTCA | CGCTTTGCAG | TCTGTGCATG | 40680 |
| AACTGAGGGA | CGGGTGTGTG | GTGCGGGTCA | CCGGTTGTGG | CATGACTGAG | GCGTGGACAG | 40740 |
| GTGTGCAGTG | CGGGTCACTG | GTTGTGGTGT | GGACTGAGGC | GTGTGCAGCC | ATGTTTGCAT | 40800 |
| GTCACAAGTT | ACAGTTCTTT | CCATGTAACT | TAATCATGTC | CTTGAGGTCC | TGCTGTTAAT | 40860 |
| TGGACAAATT | GCAGTAACCG | CAGCTCCTTG | TGTATGGCAG | AGCCGTGCAA | AGCCGGGACT | 40920 |
| GCCTGTGTGG | CTCCTTGAGT | GCGCACAGGC | CAAAGCTGAG | ATGACTTGCC | TGGGATGCCA | 40980 |
| CACGTGTTGG | GCAGCAGACC | GAGCCTCCCA | CCCCTCCCTC | TTGCCTCCCA | GGTACCACGG | 41040 |
| CCCACGTGGG | CATCATGCTG | TATGGGGTGG | ACAGCCGGAG | CGGCCACCGG | CACCTGGACG | 41100 |
| GCGACAGAGC | CTTCCACCGC | AACAGCCTGG | ACATCTTCCG | GATCGCCACC | CCGCACAGCC | 41160 |
| TGGGTAGCGT | GTGGAAGATC | CGAGTGTGGC | ACGACAACAA | AGGTTTGTGC | GGACCCTGCC | 41220 |
| AAGCTCTGCC | CCTCTGCCCC | CGCATTGGGG | CGCCCTGCGA | GCCTGACCTC | CCTCCTGCGC | 41280 |
| CTCTGCAGGG | CTCAGCCCTG | CCTGGTTCCT | GCAGCACGTC | ATCGTCAGGG | ACCTGCAGAC | 41340 |
| GGCACGCAGC | GCCTTCTTCC | TGGTCAATGA | CTGGCTTTCG | GTGGAGACGG | AGGCCAACGG | 41400 |
| GGGCCTGGTG | GAGAAGGAGG | TGCTGGCCGC | GAGTAAGGCC | TCGTTCCATG | GTCCCACTCC | 41460 |
| GTGGGAGGTT | GGGCAGGGTG | GTCCTGCCCC | GTGGCCTCCT | GCAGTGCGGC | CCTCCCTGCC | 41520 |
| TTCTAGGCGA | CGCAGCCCTT | TTGCGCTTCC | GGCGCCTGCT | GGTGGCTGAG | CTGCAGCGTG | 41580 |
| GCTTCTTTGA | CAAGCACATC | TGGCTCTCCA | TATGGGACCG | GCCGCCTCGT | AGCCGTTTCA | 41640 |
| CTCGCATCCA | GAGGGCCACC | TGCTGCGTTC | TCCTCATCTG | CCTCTTCCTG | GGCGCCAACG | 41700 |
| CCGTGTGGTA | CGGGGCTGTT | GGCGACTCTG | CCTACAGGTG | GGTGCCGTAG | GGTCGGGGC | 41760 |
| AGCCTCTTCC | TGCCCAGCCC | TTCCTGCCCC | TCAGCCTCAC | CTGTGTGGCC | TCCTCTCCTC | 41820 |
| CACACAGCAC | GGGGCATGTG | TCCAGGCTGA | GCCCGCTGAG | CGTCGACACA | GTCGCTGTTG | 41880 |
| GCCTGGTGTC | CAGCGTGGTT | GTCTATCCCG | TCTACCTGGC | CATCCTTTTT | CTCTTCCGGA | 41940 |
| TGTCCCGGAG | CAAGGTGGGC | TGGGGCTGGG | GACCCGGGAG | TACTGGGAAT | GGAGCCTGGG | 42000 |
| CCTCGGCACC | ATGCCTAGGG | CCGCCACTTT | CCAGTGCTGC | AGCCAGAGGG | AAAGGCGTCC | 42060 |

```
ACCAAAGGCT GCTCGGGAAG GGTCAACACA CTTGAGCAGC CTTAGCTAGA CTGACCAGGG    42120

AGAAAGAGAG AAGACTCAGA AGCCAGAATG GTGAAAGAAC GAGGGCACTT TGCTAAGCAG    42180

ACGCCACGGA CGACTGCACA GCAGCACGCC AGATAACTCA GAAGAAGCAA GCACGCGGCT    42240

GTGCACGCTT CCGAAATGCA CTCCAGAAGA AAATCTCAGT ACATCTATAG GAAGTGAAGA    42300

GGCTGAGTTA GTCCCTTAGA AACGTCCAG TGGCCGGGCC GGGTGTGGTG GCTCACGCCT     42360

GTAATCCCAA CACTTCAGGT GGCCGAGGTG GGCGGATCTG AGTCCAGGAG TTTGAGACCA    42420

GCCTGGGCAA CATAGCAAGA CCCCATCTAT ATAAAACATT AAAAAGGGCC AGGCGCGGTG    42480

GCTCACGCCT GTAATCCCAG CACTTTGGGA GGCCGAGGCG GGCAGATCAC TTGAGGTCAG    42540

GAGTTCGAGA CCAGCCTGGC CAACACAATG AAACCCCGAC TCTACTACAA ATACAAAAAC    42600

TTAGCTGGGC ATGGTGGCGG GCGCCTGTAG TCCCAGCTAC TCGAGAGGCT GAGGCAGGAG    42660

AATGGCATGA ACCCAGGAGG CGGAGCTTGC AGTGAGCCGA GATTGCGCCA CTGCACTCCA    42720

TCCTGGGCAA CGGAGCAAGA CTCCATCTCC AAAAAAAAAA AAAAAAAATC CCACAAAGAA    42780

AAGCTCAGGC TCAGAGCCTT CACGATAGAA TTTTTCTAAG CAGTTAAGGA AGAATTAACA    42840

CCAATCCTTC ACAGACTCTT TCCAAGAATA CAGCAGGTGG GAACGCTTCC CATTCATACG    42900

GAAACGGGAG GCCGCACCCC TTAGGAATGC ACACGTGGGG TCCTCAAGAG GTTACATGCA    42960

AACTAACCCC AGCAGCACAC AGAGAAGGCG CATAAGCCGC GACCAGGAGG GGTTGCTCCC    43020

GAGTCCGTGG CAGGAACCAG AGGCCACATG TGGCTGCTCG TATTTAAGTT AATTAAAATG    43080

GAACGATGGC CGGGTGTGGT GGCTCACACC TGTAATCCCA GCACTTTGGG AGGCGGAGGC    43140

GGGCAGATCA CTTGAGGTCA GGAGTTCCAA GACCAGCCTG GCCAACACAG TGAAACCCCG    43200

TCTCTACTAA AAATACAAAA AATTAGCTGG GCATGGTGGC AGGCACCTGT AATCCCAGCT    43260

ACTCAGGAGG CTGAGCCAGG ACAATCGCCT GAACGCGGGA GGTGGAGGTT GCAGTGAGCT    43320

GAGATTGCGC CATTGCACTC CAGCCTGGGT GACAGCGAGA CTCCATCTAA AAAGAAAAT    43380

ATGAAATTTA AAACTCTGTT CCTTAGCTGC ACCAGTCTGC TGTCAAGTGT TCAGTGGCAC    43440

ACGTCGCGAG GGGCTGCCAT CACGGACGGT GCAGATGTCC CATATATCCA GCATTCTAGG    43500

ACATTCTGTC AGATGGCACC GGGCTCTGTC CTGTCTGCTG AGGAGGTGGC TTCTCATCCC    43560

TGTCCTGAGC AGGTCTGAGC TGCCGCCCGC TGACCACTGC CCTCGTCCTG CAGGTGGCTG    43620

GGAGCCCGAG CCCCACACCT GCCGGGCAGC AGGTGCTGGA CATCGACAGC TGCCTGGACT    43680
```

```
CGTCCGTGCT GGACAGCTCC TTCCTCACGT TCTCAGGCCT CCACGCTGAG GTGAGGACTC    43740

TACTGGGGGT CCTGGGCTGG GCTGGGGGTC CTGCCGCCTT GGCGCAGCTT GGACTCAAGA    43800

CACTGTGCAC CTCTCAGCAG GCCTTTGTTG GACAGATGAA GAGTGACTTG TTTCTGGATG    43860

ATTCTAAGAG GTGGGTTCCC TAGAGAAACC TCGAGCCCTG GTGCAGGTCA CTGTGTCTGG    43920

GGTGCCGGGG GTGTGCGGGC TGCGTGTCCT TGCTGGGTGT CTGTGGCTCC ATGTGGTCAC    43980

ACCACCCGGG AGCAGGTTTG CTCGGAAGCC CAGGGTGTCC GTGCGTGACT GGACGGGGGT    44040

GGGCTGTGTG TGTGACACAT CCCCTGGTAC CTTGCTGACC CGCGCCACCT GCAGTCTGGT    44100

GTGCTGGCCC TCCGGCGAGG GAACGCTCAG TTGGCCGGAC CTGCTCAGTG ACCCGTCCAT    44160

TGTGGGTAGC AATCTGCGGC AGCTGGCACG GGGCCAGGCG GGCCATGGGC TGGGCCCAGA    44220

GGAGGACGGC TTCTCCCTGG CCAGCCCCTA CTCGCCTGCC AAATCCTTCT CAGCATCAGG    44280

TGAGCTGGGG TGAGAGGAGG GGGCTCTGAA GCTCACCCTT GCAGCTGGGC CCACCCTATG    44340

CCTCCTGTAC CTCTAGATGA AGACCTGATC CAGCAGGTCC TTGCCGAGGG GGTCAGCAGC    44400

CCAGCCCCTA CCCAAGACAC CCACATGGAA ACGGACCTGC TCAGCAGCCT GTGAGTGTCC    44460

GGCTCTCGGG GGAGGGGGGA TTGCCAGAGG AGGGGCCGGG ACTCAGGCCA GGCAGCCGTG    44520

GTTCCCGCCT GGGGTAGGGT GGGGTGGGGT GCCAGGGCAG GGCTGTGGCT GCACCACTTC    44580

ACTTCTCTGA ACCTCTGTTG TCTGTGGAAA GAGCCTCATG GGATCCCCAG GGCCCCAGAA    44640

CCTTCCCTCT AGGGAGGGAG CAGGCTCATG GGGCTTTGTA GGAGCAGAAA GGCTCCTGTG    44700

TGAGGCTGGC CGGGGCCACG TTTTTATCTT GGTCTCAGAG CAGTGAGAAA TTATGGGCGG    44760

GTTTTTAAAT ACCCCATTTT TGGCCGGGCG CGGTGGCTCA CACGTGTAAT CCCAGCACTT    44820

TGGGAGGCCG AGGTGGGCAG ATGACCTGAG GTCAGCAGTT CGAGACCAGC CTGGCCAACA    44880

TGGCGAAACC CCGTCTCTAC TAAAAATACA AAAAATTAGC CGGGCATGCT GGCAGGCGCC    44940

TGTAGTCCCA GTTACTCGGG AGACTGAGGT AGGAGAATCG ATTGAACCTG GTAGGTGAAG    45000

GTTGTAGTGA GCCGAGATCG CGCCACTGCA CTCCAGCCTG GCAACAAGA GCGAAACTCC    45060

GTCTCAAAAA CAAAAAAATT CCTCAATTTC TTGGTTGTTT TGTAACTTAT CAACAAATGG    45120

TCATATAGAG GTTACCTTGT ATGTAGTCAC GCACATAGTC ACGCACATGG CAGCCGGCGG    45180

CGGAGCGCAC CCACGGCGTG TTCCCACGCG TGTGACCCCG GGCTCTGCCA TGCCCTCCTA    45240

TGCTCAGGTG TGCTGAGGTC CACACGGCCC TGCCGTTGCA CTGCAGCTGC CTGCAGGATT    45300
```

```
CAGTGCAGTG GCATGCAGTG CAGGTGCGGT GCCCCGGAGC CACAGGCCAC ACCACAGGGC   45360
CTGCATGCAC AGGGGCTGCG GTGTCTGGGT TTGGGTAACT ACGCCCTGTG ACATTTGCAC   45420
AGCAACAGAA TTACCTAATG ACGCATTTCT CAGAACACAT CCCTGGCACT AAGTGGTGCG   45480
TGACTGCTGC TTTTGCATCC ACATCTAGTT TGATTTGTGT GTTATTCCTT TGAGTGCTTC   45540
TCATTGTTAA GCAACCAAGA ACTAAAGAGG TATGAACTGC CCCTGGACTC AAACAAAAAG   45600
GAAAACTTCC TGATTTACAA AAGGCAGATA ACCATCACAT GAGGGCATCT TTATGAATAA   45660
ATTGCTGGTT GGTTTTAAAA ATACAGAGTA TGGGGAAATC CAGGGGTAGT CACTACATGC   45720
TGACCAGCCC CAGGTATCTC CGGCCCAAAG CTCTGTGAAA TCCAGATTCA GTGCTTCCGC   45780
GGGGATTTCT GACGGCAGCT CAGACTCCGC ATCCACACAG AGCGCGTGGC CCTCACCCTC   45840
CCGGCTTCCT CAACCCTTGG CCGTCCCTTG CTCGGACAGT GCTTCGGGCT GACCAGGTCG   45900
GAGGCTTGGG TTTGTCCTGG ACCCCTCTGC GTCCTTCCTC ACTGCAGCCT CCAGCGCGTC   45960
CCGTGGCTCC TTTCCCAACG CAGAGCACGG CCTTCCCTGC GCCTGAGCCT GCACCCTCCG   46020
TCCTGGCGGC GCCTCTGCCC TGGCATTCCC TGCCACTCCA TGCCTCCCTA TTGGCCATTC   46080
TCCGTCTCTG CCAGCGAGAG CCTGCTCCCT GAGTCAGACC CTGAGTCATT TGTGTTGCTA   46140
TAAAGGAATA GTTGAGGCTG GGTTATTTTT TATTTTTATT TATTTTTTTG AGATGGAGTC   46200
TCTGTTGCCC AGACTGGAGT GCAGTCGCAT GATCTCGGCT CACTGCAAAG TCTGCCTCCC   46260
ACGTTCAAGC AGTTATCTGC CTCAGCCTCC CAAGTAGCTA AGATTACAGG CGCCCGCCGC   46320
CACAGCCGGC TAATTTTTTG TGTGTGTGTT TTAGTAGAGA GGAGGTTTCA CCATCTTAGC   46380
CAGGCTGGTC TTGAACTCCT GACCTCGTGA TCCACCCATC TCAGCCTCCC AAAATGCTGA   46440
GATTACAGGC GTGAGCCACC ACGCCTGACC AAGTTGAGGC TAGGTCATTT TTTAATTTTT   46500
TGTAAAGACA GGGTCTCACT GTCTCCAACT CCTGAGCTCA AGTGATCCTC CTGCCTCAGC   46560
CTCCTGAAGT GCTGGGATTA CAGGCTTGAG ACACTGCGCC CAGCCAAGAG TGTCTTTTAT   46620
CCTCCGAGAG ACAGCAAAAC AGGAAGCATT CAGTGCAGTG TGACCCTGGG TCAGGCCGTT   46680
CTTTCGGTGA TGGGCTGACG AGGGCGCAGG TACGGGAGAG CGTCCTGAGA GCCCGGGACT   46740
CGGCGTCTCG CAGTTGGTCT CGTCCTCCCC CTCAACGTGT CTTCGCTGCC TCTGTACCTC   46800
TTCTCTAGCA GCTCTGGGAC CGGGCATATC AGCATGGTGG CCCGATGCAG TGGCACAGCC   46860
TCGGTGGTCA CTGGCTCCTG GAGACACAAG CAGATCTCTG GCCTCAGGGA GCCCTACACA   46920
```

```
CTGTTGGGAT TTGAAAGGCA TTCATATGTT TCCTTGTCCA GAAGTTAATT TTAGGCCATA    46980
AACCTGCATG GGACAGACAC ACTGGCGTCT CTAGATTGTA GAGATGCTTG TTGGATGGTT    47040
GAGACCCAAT CATAGTTTGC AGGGTTGAAG GGGGGCTCAT TGCACCCTGA GAGACTGTGC    47100
ACTGCTGTAA GGGCAGCTGG TCAGGCTGTG GGCGATGGGT TTATCAGCAG CAAGCGGGCG    47160
GGAGAGGGAC GCAGGCGGAC GCCTGACTTC GGTGCCTGGA GTGGCTCTTG GTTCCCTGGC    47220
TCCCAGCACC ACTCCCACTC TCGTTTGGGG TAGGGTCTTC CGGCTTTTTG TCGGGGGAC     47280
CCTGTGACCC AAGAGGCTCA AGAAACTGCC CGCCCAGGTT AACATGGGCT TGGCTGCAAC    47340
TGCCTCCTGG AGGCCGGGAT GAATTCACAG CCTACCATGT CCCTCAGGTC CAGCACTCCT    47400
GGGGAGAAGA CAGAGACGCT GGCGCTGCAG AGGCTGGGGG AGCTGGGGCC ACCCAGCCCA    47460
GGCCTGAACT GGGAACAGCC CCAGGCAGCG AGGCTGTCCA GGACAGGTGT GCTTGCGTAG    47520
CCCCGGGATG CCCCTAGCCC CTCCCTGTGA GCTGCCTCTC ACAGGTCTGT CTCTGCTTCC    47580
CCAGGACTGG TGGAGGGTCT GCGGAAGCGC CTGCTGCCGG CCTGGTGTGC CTCCCTGGCC    47640
CACGGGCTCA GCCTGCTCCT GGTGGCTGTG GCTGTGGCTG TCTCAGGGTG GGTGGGTGCG    47700
AGCTTCCCCC CGGGCGTGAG TGTTGCGTGG CTCCTGTCCA GCAGCGCCAG CTTCCTGGCC    47760
TCATTCCTCG GCTGGGAGCC ACTGAAGGTG AGGGGCTGC CAGGGGTAGG CTACAGGCCT     47820
CCATCACGGG GGACCCCTCT GAAGCCACCC CCTCCCCAGG TCTTGCTGGA AGCCCTGTAC    47880
TTCTCACTGG TGGCCAAGCG GCTGCACCCG GATGAAGATG ACACCCTGGT AGAGAGCCCG    47940
GCTGTGACGC CTGTGAGCGC ACGTGTGCCC CGCGTACGGC CACCCCACGG CTTTGCACTC    48000
TTCCTGGCCA AGGAAGAAGC CCGCAAGGTC AAGAGGCTAC ATGGCATGCT GCGGGTGAGC    48060
CTGGGTGCGG CCTGTGCCCC TGCCACCTCC GTCTCTTGTC TCCCACCTCC CACCCATGCA    48120
CGCAGGACAC TCCTGTCCCC CTTTCCTCAC CTCAGAAGGC CCTTAGGGGT TCAATGCTCT    48180
GCAGCCTTTG CCCGGTCTCC CTCCTACCCC ACGCCCCCA CTTGCTGCCC CAGTCCCTGC     48240
CAGGGCCCAG CTCCAATGCC CACTCCTGCC TGGCCCTGAA GGCCCCTAAG CACCACTGCA    48300
GTGGCCTGTG TGTCTGCCCC CAGGTGGGGT TCCGGGCAGG GTGTGTGCTG CCATTACCCT    48360
GGCCAGGTAG AGTCTTGGGG CGCCCCCTGC CAGCTCACCT TCCTGCAGCC ACACCTGCCG    48420
CAGCCATGGC TCCAGCCGTT GCCAAAGCCC TGCTGTCACT GTGGGCTGGG GCCAGGCTGA    48480
CCACAGGGCC CCCCCGTCCA CCAGAGCCTC CTGGTGTACA TGCTTTTTCT GCTGGTGACC    48540
```

```
CTGCTGGCCA GCTATGGGGA TGCCTCATGC CATGGGCACG CCTACCGTCT GCAAAGCGCC    48600

ATCAAGCAGG AGCTGCACAG CCGGGCCTTC CTGGCCATCA CGCGGTACGG GCATCCGGTG    48660

CACTGGTCTG TCTTCTGGGC TTTAGTTTTG CCTTTAGTCC AGCCAGACCC TAGGGGACAT    48720

GTGGACATGT GTAGATACCT TTGTGGCTGC TAGAACTGGA GGTAGGTGCT GCTGGCATCA    48780

GTAGGCAGAG GGGAGGGACA CAGGTCCGTG TCTTGCAGTG CACAGGACGG GCCCATGACA    48840

GACAACTGTC TGCCCCAGAA CATCCCCAGG ATAAGGCTGA GAAGCCCAGG TCTAGCCGTG    48900

GCCAGCAGGG CAGTGGGAGC CATGTTCCCT GGGTCTCTGG TGGCCGCTCA CTCGAGGCGG    48960

GCATGGGGCA GTAGGGGCTG GAGCGTGTGA CTGATGCTGT GGCAGGTCTG AGGAGCTCTG    49020

GCCATGGATG GCCCACGTGC TGCTGCCCTA CGTCCACGGG AACCAGTCCA GCCCAGAGCT    49080

GGGGCCCCCA CGGCTGCGGC AGGTGCGGCT GCAGGAAGGT GAGCTGGCAG GGCGTGCCCC    49140

AAGACTTAAA TCGTTCCTCT TGTTGAGAGA GCAGCCTTTA GCGGAGCTCT GGCATCAGCC    49200

CTGCTCCCTA GCTGTGTGAC CTTTGCCCTC TTAACACCGC CGTTTCCTTC TCTGTATATG    49260

AGAGATGGTA ACGTTGTCTA ATTGATGGCT GCTGGGAGGG TTCCCTGGGG TGGCGCCGAA    49320

CCAGAGCTCA GGCGAGCTGG CCAGCAGGAA ACACTCCTGT GGGTTTTGA TGAGGCCCTG    49380

GCCCCGGCCT GGGGCTCTGT GTGTTTCAGC ACTCTACCCA GACCCTCCCG GCCCCAGGGT    49440

CCACACGTGC TCGGCCGCAG GAGGCTTCAG CACCAGCGAT TACGACGTTG CTGGGAGAG    49500

TCCTCACAAT GGCTCGGGGA CGTGGGCCTA TTCAGCGCCG GATCTGCTGG GGTGAGCAGA    49560

GCGAGGGCCC CGGGCGTCTA CGCCAAGGAC AAGGGAGTAG TTCTCCAGGA GTGCCGCGGC    49620

CTCCTGACCA GCCTGGCTCC GGGGTGCCGG AAGGGCTGGG GTGCGGCACC CACGCCACCC    49680

CTCTCCGGCA GGGCATGGTC CTGGGGCTCC TGTGCCGTGT ATGACAGCGG GGGCTACGTG    49740

CAGGAGCTGG GCCTGAGCCT GGAGGAGAGC CGCGACCGGC TGCGCTTCCT GCAGCTGCAC    49800

AACTGGCTGG ACAACAGGTG GGAGCTCCCT CCCCTGCCCT CTCCGGGGTG GCCGCAGTCA    49860

CCAGCCAGGA GCCCACCCTC ACTCCTCCGG CCCCGCTGG CCTAGGCGGC TTCCACAGCC    49920

CCTCAGCCAC GCCTGCACTG CGCGGTCCCC GCAGCTCCCG CCCTGCCACC CGCTCCTACT    49980

GACCCGCACC CTCTGCGCAG GAGCCGCGCT GTGTTCCTGG AGCTCACGCG CTACAGCCCG    50040

GCCGTGGGGC TGCACGCCGC CGTCACGCTG CGCCTCGAGT TCCCGGCGGC CGGCCGCGCC    50100

CTGGCCGCCC TCAGCGTCCG CCCCTTTGCG CTGCGCCGCC TCAGCGCGGG CCTCTCGCTG    50160
```

```
CCTCTGCTCA CCTCGGTACG CCCGTCCCCG GCCAGACCCC GCGCCTCCCA CCGGCAGCGT    50220

CCCGCCCCCT CGCGGGGCCC CGCCCGGCAG CGTCTCACCC CTCGCAGCGC CCCGCCCCCT    50280

CGCAGCGTCC CGCCCCCTCG CAGGGCCCCG CCCCGGCAGC GTCCCGCCCC CTCGTAGGGC    50340

CCCGCCCCGG CAGCGTCCCG CCCCCTCGCA GGGCCCCGCC CCGGCAGCGT CCCTCCCGCC    50400

CTCCTGACCG CGCCCCCCAC AGGTGTGCCT GCTGCTGTTC GCCGTGCACT TCGCCGTGGC    50460

CGAGGCCCGT ACTTGGCACA GGGAAGGGCG CTGGCGCGTG CTGCGGCTCG GAGCCTGGGC    50520

GCGGTGGCTG CTGGTGGCGC TGACGGCGGC CACGGCACTG GTACGCCTCG CCCAGCTGGG    50580

TGCCGCTGAC CGCCAGTGGA CCCGTTTCGT GCGCGGCCGC CCGCGCCGCT TCACTAGCTT    50640

CGACCAGGTG GCGCAGCTGA GCTCCGCAGC CCGTGGCCTG GCGGCCTCGC TGCTCTTCCT    50700

GCTTTTGGTC AAGGTGAGGG CTGGGCCGGT GGGCGCGGGG CTGGGCGCAC ACCCCAGGGC    50760

TGCAAGCAGA CAGATTTCTC GTCCGCAGGC TGCCCAGCAG CTACGCTTCG TGCGCCAGTG    50820

GTCCGTCTTT GGCAAGACAT TATGCCGAGC TCTGCCAGAG CTCCTGGGGG TCACCTTGGG    50880

CCTGGTGGTG CTCGGGGTAG CCTACGCCCA GCTGGCCATC CTGGTAGGTG ACTGCGCGGC    50940

CGGGGAGGGC GTCTTAGCTC AGCTCAGCTC AGCTGTACGC CCTCACTGGT GTCGCCTTCC    51000

CCGCAGCTCG TGTCTTCCTG TGTGGACTCC CTCTGGAGCG TGGCCCAGGC CCTGTTGGTG    51060

CTGTGCCCTG GGACTGGGCT CTCTACCCTG TGTCCTGCCG AGTCCTGGCA CCTGTCACCC    51120

CTGCTGTGTG TGGGGCTCTG GGCACTGCGG CTGTGGGGCG CCCTACGGCT GGGGGCTGTT    51180

ATTCTCCGCT GGCGCTACCA CGCCTTGCGT GGAGAGCTGT ACCGGCCGGC CTGGGAGCCC    51240

CAGGACTACG AGATGGTGGA GTTGTTCCTG CGCAGGCTGC GCCTCTGGAT GGGCCTCAGC    51300

AAGGTCAAGG AGGTGGGTAC GGCCCAGTGG GGGGGAGAGG GACACGCCCT GGGCTCTGCC    51360

CAGGGTGCAG CCGGACTGAC TGAGCCCCTG TGCCGCCCCC AGTTCCGCCA CAAAGTCCGC    51420

TTTGAAGGGA TGGAGCCGCT GCCCTCTCGC TCCTCCAGGG GCTCCAAGGT ATCCCCGGAT    51480

GTGCCCCCAC CCAGCGCTGG CTCCGATGCC TCGCACCCCT CCACCTCCTC CAGCCAGCTG    51540

GATGGGCTGA GCGTGAGCCT GGGCCGGCTG GGGACAAGGT GTGAGCCTGA GCCCTCCCGC    51600

CTCCAAGCCG TGTTCGAGGC CCTGCTCACC CAGTTTGACC GACTCAACCA GGCCACAGAG    51660

GACGTCTACC AGCTGGAGCA GCAGCTGCAC AGCCTGCAAG GCCGCAGGAG CAGCCGGGCG    51720

CCCGCCGGAT CTTCCCGTGG CCCATCCCCG GGCCTGCGGC CAGCACTGCC CAGCCGCCTT    51780
```

```
GCCCGGGCCA GTCGGGGTGT GGACCTGGCC ACTGGCCCCA GCAGGACACC CCTTCGGGCC    51840

AAGAACAAGG TCCACCCCAG CAGCACTTAG TCCTCCTTCC TGGCGGGGGT GGGCCGTGGA    51900

GTCGGAGTGG ACACCGCTCA GTATTACTTT CTGCCGCTGT CAAGGCCGAG GGCCAGGCAG    51960

AATGGCTGCA CGTAGGTTCC CCAGAGAGCA GGCAGGGGCA TCTGTCTGTC TGTGGGCTTC    52020

AGCACTTTAA AGAGGCTGTG TGGCCAACCA GGACCCAGGG TCCCCTCCCC AGCTCCCTTG    52080

GGAAGGACAC AGCAGTATTG GACGGTTTCT AGCCTCTGAG ATGCTAATTT ATTTCCCCGA    52140

GTCCTCAGGT ACAGCGGGCT GTGCCCGGCC CCACCCCCTG GGCAGATGTC CCCCACTGCT    52200

AAGGCTGCTG GCTTCAGGGA GGGTTAGCCT GCACCGCCGC CACCCTGCCC CTAAGTTATT    52260

ACCTCTCCAG TTCCTACCGT ACTCCCTGCA CCGTCTCACT GTGTGTCTCG TGTCAGTAAT    52320

TTATATGGTG TTAAAATGTG TATATTTTTG TATGTCACTA TTTTCACTAG GGCTGAGGGG    52380

CCTGCGCCCA GAGCTGGCCT CCCCCAACAC CTGCTGCGCT TGGTAGGTGT GGTGGCGTTA    52440

TGGCAGCCCG GCTGCTGCTT GGATGCGAGC TTGGCCTTGG GCCGGTGCTG GGGGCACAGC    52500

TGTCTGCCAG GCACTCTCAT CACCCCAGAG GCCTTGTCAT CCTCCCTTGC CCCAGGCCAG    52560

GTAGCAAGAG AGCAGCGCCC AGGCCTGCTG GCATCAGGTC TGGGCAAGTA GCAGGACTAG    52620

GCATGTCAGA GGACCCCAGG GTGGTTAGAG GAAAAGACTC CTCCTGGGGG CTGGCTCCCA    52680

GGGTGGAGGA AGGTGACTGT GTGTGTGTGT GTGTGCGCGC GCGCACGCGC GAGTGTGCTG    52740

TATGGCCCAG GCAGCCTCAA GGCCCTCGGA GCTGGCTGTG CCTGCTTCTG TGTACCACTT    52800

CTGTGGGCAT GGCCGCTTCT AGAGCCTCGA CACCCCCCCA ACCCCGCAC CAAGCAGACA     52860

AAGTCAATAA AAGAGCTGTC TGACTGCAAT CTGTGCCTCT ATGTCTGTGC ACTGGGGTCA    52920

GGACTTTATT TATTTCACTG ACAGGCAATA CCGTCCAAGG CCAGTGCAGG AGGGAGGGCC    52980

CCGGCCTCAC ACAAACTCGG TGAAGTCCTC CACCGAGGAG ATGAGGCGCT TCCGCTGGCC    53040

CACCTCATAG CCAGGTGTGG GCTCGGCTGG AGTCTGTGCA GGGGCTTTGC TATGGGACGG    53100

AGGGTGCACC AGAGGTAGGC TGGGGTTGGA GTAGGCGGCT TCCTCGCAGA TCTGAAGGCA    53160

GAGGCGGCTT GGGCAGTAAG TCTGGGAGGC GTGGCAACCG CTCTGCCCAC ACACCCGCCC    53220

CACAGCTTGG GCAGCCAGCA CACCCCGCTG AGGGAGCCCC ATATTCCCTA CCCGCTGGCG    53280

GAGCGCTTGA TGTGGCGGAG CGGGCAATCC ACTTGGAGGG GTAGATATCG GTGGGGTTGG    53340

AGCGGCTATG ATGCACCTGT GAGGCCATCT GGGGACGTAG GCAGGGGGTG AGCTCACTAT    53400
```

```
CAGGTGGCAC CTGGGCCTGT CCCACCAGCT CACGCCTGGA CCCACCCCCA CTCACATTTG    53460

CGTGCAGGGC CATCTGGCGG GCCACGAAGG GCAGGTTGCG GTCAGACACG ATCTTGGCCA    53520

CGCTGG                                                                53526
```

```
GGTGTGAGGGGTAGGGGCAGGGTGGGAGGTGGGAGCTCGCGGGTGGGCTGGG       50
GTCATGAAGGGCCTCAGGCGCTCTGCTATTGGGTTCCAAGGCTATCCTGA         100
GAACAGGGGTGAGGGGGATTGCCGTGGGGGGTTAAAGCCTTGTCATGTT          150
CGCTTTCGGGAGATAAAAACAACAGGTGGCCTTTATGGAGACGCTGCCCA         200
GAGCCAGGTCTGTGCCAGGCTCCTGTTGGGGGTCGTCATGCGGAATCCTG         250
ACTCTGACCATCCGAGGCATAGGGACCGTGGAGATTTGCATTTCACAGAT         300
GAGGAAACAGGTTTGGAGAGGTGACACGACCTGTCCCAGGCATCACAGCC         350
GGGATGTGCATAGCAGGGTTTGGAACTATGAGGTGCCCAGGACCCAGGG          400
TTGGATTGAAAAGGGCGGAGGGACTAAGATCTGATGCCTTGTATTCCCCA         450
GCGCTGGGGGAGAGTCTTGGGACCAGTGTCTCCTTGGGTGCTGCTGGCT          500
CCAGGCTCCTCGCGGGACAGTGTCTCCTTGGGTGCTGGATCCCTG              550
GGGGACGTGGCACATCCCCAGGCTTGCTAAACATTGGGTGGGTTCTGGCA         600
TTTGGTTTTGTAACGTTTCTGGGTCACTCCCGCCTGTGCCACCCTTCCT          650
TAGGGGAGCCGTGTCCTTGGGGCTTTGCTGGTGGTCTCGAGGGTGGG            700
AGAAGAATGGGTTCTCCTGACCAATGGAGCCCGTGCCCCTCGGGGCCAC          750
ATTGCTCCTGCGCTCCCTGCCTCGCGGACGCGTGTCTCGCGGCTGTCTC          800
TGTGGAGATGGCCTCCTCCTGCCTGGCAACAGCACCCACAGAATTGCATC         850
AGACCTACCCCACCCGTTGTTTGTGATGCTGTAGCTGAGGGCTC               894
```

```
GCTCAGCAGC AGGTCGCGGC CGCAGCCCCA TCCAGCCCGC GCCCGCCATG CCGTCCGCGG       60

GCCCCGCCTG AGCTGCGGCC TCCGCGCGCG GGCGGGCCTG GGACGGCGG GGCCATGCGC        120
```

| GCGCTGCCCT AACG | ATG | CCG | CCC | GCC | GCG | CCC | GCC | CGC | CTG | GCG | CTG | GCC | 170 |
|---|---|---|---|---|---|---|---|---|---|---|---|---|---|
| | Met | Pro | Pro | Ala | Ala | Pro | Ala | Arg | Leu | Ala | Leu | Ala | |
| | 1 | | | 5 | | | | | | 10 | | | |

| CTG | GGC | CTG | GGC | CTG | TGG | CTC | GGG | GCG | CTG | GCG | GGG | GGC | CCC | GGG | CGC | 218 |
|---|---|---|---|---|---|---|---|---|---|---|---|---|---|---|---|---|
| Leu | Gly | Leu | Gly | Leu | Trp | Leu | Gly | Ala | Leu | Ala | Gly | Gly | Pro | Gly | Arg | |
| | | | 15 | | | | 20 | | | | | 25 | | | | |

| GGC | TGC | GGG | CCC | TGC | GAG | CCC | CCC | TGC | CTC | TGC | GGC | CCA | GCG | CCC | GGC | 266 |
|---|---|---|---|---|---|---|---|---|---|---|---|---|---|---|---|---|
| Gly | Cys | Gly | Pro | Cys | Glu | Pro | Pro | Cys | Leu | Cys | Gly | Pro | Ala | Pro | Gly | |
| | | 30 | | | | | 35 | | | | | 40 | | | | |

| GCC | GCC | TGC | CGC | GTC | AAC | TGC | TCG | GGC | CGC | GGG | CTG | CGG | ACG | CTC | GGT | 314 |
|---|---|---|---|---|---|---|---|---|---|---|---|---|---|---|---|---|
| Ala | Ala | Cys | Arg | Val | Asn | Cys | Ser | Gly | Arg | Gly | Leu | Arg | Thr | Leu | Gly | |
| 45 | | | | | 50 | | | | | 55 | | | | | 60 | |

| CCC | GCG | CTG | CGC | ATC | CCC | GCG | GAC | GCC | ACA | GCG | CTA | GAC | GTC | TCC | CAC | 362 |
|---|---|---|---|---|---|---|---|---|---|---|---|---|---|---|---|---|
| Pro | Ala | Leu | Arg | Ile | Pro | Ala | Asp | Ala | Thr | Ala | Leu | Asp | Val | Ser | His | |
| | | | | 65 | | | | | 70 | | | | | 75 | | |

| AAC | CTG | CTC | CGG | GCG | CTG | GAC | GTT | GGG | CTC | CTG | GCG | AAC | CTC | TCG | GCG | 410 |
|---|---|---|---|---|---|---|---|---|---|---|---|---|---|---|---|---|
| Asn | Leu | Leu | Arg | Ala | Leu | Asp | Val | Gly | Leu | Leu | Ala | Asn | Leu | Ser | Ala | |
| | | | 80 | | | | | 85 | | | | | 90 | | | |

| CTG | GCA | GAG | CTG | GAT | ATA | AGC | AAC | AAC | AAG | ATT | TCT | ACG | TTA | GAA | GAA | 458 |
|---|---|---|---|---|---|---|---|---|---|---|---|---|---|---|---|---|
| Leu | Ala | Glu | Leu | Asp | Ile | Ser | Asn | Asn | Lys | Ile | Ser | Thr | Leu | Glu | Glu | |
| | | 95 | | | | | 100 | | | | | 105 | | | | |

| GGA | ATA | TTT | GCT | AAT | TTA | TTT | AAT | TTA | AGT | GAA | ATA | AAC | CTG | AGT | GGG | 506 |
|---|---|---|---|---|---|---|---|---|---|---|---|---|---|---|---|---|
| Gly | Ile | Phe | Ala | Asn | Leu | Phe | Asn | Leu | Ser | Glu | Ile | Asn | Leu | Ser | Gly | |
| | 110 | | | | | 115 | | | | | 120 | | | | | |

| AAC | CCG | TTT | GAG | TGT | GAC | TGT | GGC | CTG | GCG | TGG | CTG | CCG | CGA | TGG | GCG | 554 |
|---|---|---|---|---|---|---|---|---|---|---|---|---|---|---|---|---|
| Asn | Pro | Phe | Glu | Cys | Asp | Cys | Gly | Leu | Ala | Trp | Leu | Pro | Arg | Trp | Ala | |
| 125 | | | | | 130 | | | | | 135 | | | | | 140 | |

| GAG | GAG | CAG | CAG | GTG | CGG | GTG | GTG | CAG | CCC | GAG | GCA | GCC | ACG | TGT | GCT | 602 |
|---|---|---|---|---|---|---|---|---|---|---|---|---|---|---|---|---|
| Glu | Glu | Gln | Gln | Val | Arg | Val | Val | Gln | Pro | Glu | Ala | Ala | Thr | Cys | Ala | |
| | | | | 145 | | | | | 150 | | | | | 155 | | |

| GGG | CCT | GGC | TCC | CTG | GCT | GGC | CAG | CCT | CTG | CTT | GGC | ATC | CCC | TTG | CTG | 650 |
|---|---|---|---|---|---|---|---|---|---|---|---|---|---|---|---|---|
| Gly | Pro | Gly | Ser | Leu | Ala | Gly | Gln | Pro | Leu | Leu | Gly | Ile | Pro | Leu | Leu | |
| | | | 160 | | | | | 165 | | | | | 170 | | | |

| GAC | AGT | GGC | TGT | GGT | GAG | GAG | TAT | GTC | GCC | TGC | CTC | CCT | GAC | AAC | AGC | 698 |
|---|---|---|---|---|---|---|---|---|---|---|---|---|---|---|---|---|
| Asp | Ser | Gly | Cys | Gly | Glu | Glu | Tyr | Val | Ala | Cys | Leu | Pro | Asp | Asn | Ser | |
| | | | 175 | | | | | 180 | | | | | 185 | | | |

| TCA | GGC | ACC | GTG | GCA | GCA | GTG | TCC | TTT | TCA | GCT | GCC | CAC | GAA | GGC | CTG | 746 |
|---|---|---|---|---|---|---|---|---|---|---|---|---|---|---|---|---|
| Ser | Gly | Thr | Val | Ala | Ala | Val | Ser | Phe | Ser | Ala | Ala | His | Glu | Gly | Leu | |
| | 190 | | | | | 195 | | | | | 200 | | | | | |

```
CTT CAG CCA GAG GCC TGC AGC GCC TTC TGC TTC TCC ACC GGC CAG GGC        794
Leu Gln Pro Glu Ala Cys Ser Ala Phe Cys Phe Ser Thr Gly Gln Gly
205                 210                 215                 220

CTC GCA GCC CTC TCG GAG CAG GGC TGG TGC CTG TGT GGG GCG GCC CAG        842
Leu Ala Ala Leu Ser Glu Gln Gly Trp Cys Leu Cys Gly Ala Ala Gln
                225                 230                 235

CCC TCC AGT GCC TCC TTT GCC TGC CTG TCC CTC TGC TCC GGC CCC CCG        890
Pro Ser Ser Ala Ser Phe Ala Cys Leu Ser Leu Cys Ser Gly Pro Pro
            240                 245                 250

CCA CCT CCT GCC CCC ACC TGT AGG GGC CCC ACC CTC CTC CAG CAC GTC        938
Pro Pro Pro Ala Pro Thr Cys Arg Gly Pro Thr Leu Leu Gln His Val
                255                 260                 265

TTC CCT GCC TCC CCA GGG GCC ACC CTG GTG GGG CCC CAC GGA CCT CTG        986
Phe Pro Ala Ser Pro Gly Ala Thr Leu Val Gly Pro His Gly Pro Leu
        270                 275                 280

GCC TCT GGC CAG CTA GCA GCC TTC CAC ATC GCT GCC CCG CTC CCT GTC       1034
Ala Ser Gly Gln Leu Ala Ala Phe His Ile Ala Ala Pro Leu Pro Val
285                 290                 295                 300

ACT GCC ACA CGC TGG GAC TTC GGA GAC GGC TCC GCC GAG GTG GAT GCC       1082
Thr Ala Thr Arg Trp Asp Phe Gly Asp Gly Ser Ala Glu Val Asp Ala
                305                 310                 315

GCT GGG CCG GCT GCC TCG CAT CGC TAT GTG CTG CCT GGG CGC TAT CAC       1130
Ala Gly Pro Ala Ala Ser His Arg Tyr Val Leu Pro Gly Arg Tyr His
            320                 325                 330

GTG ACG GCC GTG CTG GCC CTG GGG GCC GGC TCA GCC CTG CTG GGG ACA       1178
Val Thr Ala Val Leu Ala Leu Gly Ala Gly Ser Ala Leu Leu Gly Thr
                335                 340                 345

GAC GTG CAG GTG GAA GCG GCA CCT GCC GCC CTG GAG CTC GTG TGC CCG       1226
Asp Val Gln Val Glu Ala Ala Pro Ala Ala Leu Glu Leu Val Cys Pro
350                 355                 360

TCC TCG GTG CAG AGT GAC GAG AGC CTC GAC CTC AGC ATC CAG AAC CGC       1274
Ser Ser Val Gln Ser Asp Glu Ser Leu Asp Leu Ser Ile Gln Asn Arg
365                 370                 375                 380

GGT GGT TCA GGC CTG GAG GCC GCC TAC AGC ATC GTG GCC CTG GGC GAG       1322
Gly Gly Ser Gly Leu Glu Ala Ala Tyr Ser Ile Val Ala Leu Gly Glu
                385                 390                 395

GAG CCG GCC CGA GCG GTG CAC CCG CTC TGC CCC TCG GAC ACG GAG ATC       1370
Glu Pro Ala Arg Ala Val His Pro Leu Cys Pro Ser Asp Thr Glu Ile
            400                 405                 410

TTC CCT GGC AAC GGG CAC TGC TAC CGC CTG GTG GTG GAG AAG GCG GCC       1418
Phe Pro Gly Asn Gly His Cys Tyr Arg Leu Val Val Glu Lys Ala Ala
            415                 420                 425
```

```
TGG CTG CAG GCG CAG GAG CAG TGT CAG GCC TGG GCC GGG GCC GCC CTG      1466
Trp Leu Gln Ala Gln Glu Gln Cys Gln Ala Trp Ala Gly Ala Ala Leu
    430             435             440

GCA ATG GTG GAC AGT CCC GCC GTG CAG CGC TTC CTG GTC TCC CGG GTC      1514
Ala Met Val Asp Ser Pro Ala Val Gln Arg Phe Leu Val Ser Arg Val
445             450             455             460

ACC AGG TGC CTA GAC GTG TGG ATC GGC TTC TCG ACT GTG CAG GGG GTG      1562
Thr Arg Cys Leu Asp Val Trp Ile Gly Phe Ser Thr Val Gln Gly Val
                465             470             475

GAG GTG GGC CCA GCG CCG CAG GGC GAG GCC TTC AGC CTG GAG AGC TGC      1610
Glu Val Gly Pro Ala Pro Gln Gly Glu Ala Phe Ser Leu Glu Ser Cys
            480             485             490

CAG AAC TGG CTG CCC GGG GAG CCA CAC CCA GCC ACA GCC GAG CAC TGC      1658
Gln Asn Trp Leu Pro Gly Glu Pro His Pro Ala Thr Ala Glu His Cys
        495             500             505

GTC CGG CTC GGG CCC ACC GGG TGG TGT AAC ACC GAC CTG TGC TCA GCG      1706
Val Arg Leu Gly Pro Thr Gly Trp Cys Asn Thr Asp Leu Cys Ser Ala
    510             515             520

CCG CAC AGC TAC GTC TGC GAG CTG CAG CCC GGA GGC CCA GTG CAG GAT      1754
Pro His Ser Tyr Val Cys Glu Leu Gln Pro Gly Gly Pro Val Gln Asp
525             530             535             540

GCC GAG AAC CTC CTC GTG GGA GCG CCC AGT GGG GAC CTG CAG GGA CCC      1802
Ala Glu Asn Leu Leu Val Gly Ala Pro Ser Gly Asp Leu Gln Gly Pro
                545             550             555

CTG ACG CCT CTG GCA CAG CAG GAC GGC CTC TCA GCC CCG CAC GAG CCC      1850
Leu Thr Pro Leu Ala Gln Gln Asp Gly Leu Ser Ala Pro His Glu Pro
            560             565             570

GTG GAG GTC ATG GTA TTC CCG GGC CTG CGT CTG AGC CGT GAA GCC TTC      1898
Val Glu Val Met Val Phe Pro Gly Leu Arg Leu Ser Arg Glu Ala Phe
        575             580             585

CTC ACC ACG GCC GAA TTT GGG ACC CAG GAG CTC CGG CGG CCC GCC CAG      1946
Leu Thr Thr Ala Glu Phe Gly Thr Gln Glu Leu Arg Arg Pro Ala Gln
    590             595             600

CTG CGG CTG CAG GTG TAC CGG CTC CTC AGC ACA GCA GGG ACC CCG GAG      1994
Leu Arg Leu Gln Val Tyr Arg Leu Leu Ser Thr Ala Gly Thr Pro Glu
605             610             615             620

AAC GGC AGC GAG CCT GAG AGC AGG TCC CCG GAC AAC AGG ACC CAG CTG      2042
Asn Gly Ser Glu Pro Glu Ser Arg Ser Pro Asp Asn Arg Thr Gln Leu
                625             630             635

GCC CCC GCG TGC ATG CCA GGG GGA CGC TGG TGC CCT GGA GCC AAC ATC      2090
Ala Pro Ala Cys Met Pro Gly Gly Arg Trp Cys Pro Gly Ala Asn Ile
            640             645             650
```

```
TGC TTG CCG CTG GAC GCC TCC TGC CAC CCC CAG GCC TGC GCC AAT GGC        2138
Cys Leu Pro Leu Asp Ala Ser Cys His Pro Gln Ala Cys Ala Asn Gly
        655                 660                 665

TGC ACG TCA GGG CCA GGG CTA CCC GGG GCC CCC TAT GCG CTA TGG AGA        2186
Cys Thr Ser Gly Pro Gly Leu Pro Gly Ala Pro Tyr Ala Leu Trp Arg
        670                 675                 680

GAG TTC CTC TTC TCC GTT CCC GCG GGG CCC CCC GCG CAG TAC TCG GTC        2234
Glu Phe Leu Phe Ser Val Pro Ala Gly Pro Pro Ala Gln Tyr Ser Val
685                 690                 695                 700

ACC CTC CAC GGC CAG GAT GTC CTC ATG CTC CCT GGT GAC CTC GTT GGC        2282
Thr Leu His Gly Gln Asp Val Leu Met Leu Pro Gly Asp Leu Val Gly
                705                 710                 715

TTG CAG CAC GAC GCT GGC CCT GGC GCC CTC CTG CAC TGC TCG CCG GCT        2330
Leu Gln His Asp Ala Gly Pro Gly Ala Leu Leu His Cys Ser Pro Ala
                720                 725                 730

CCC GGC CAC CCT GGT CCC CGG GCC CCG TAC CTC TCC GCC AAC GCC TCG        2378
Pro Gly His Pro Gly Pro Arg Ala Pro Tyr Leu Ser Ala Asn Ala Ser
        735                 740                 745

TCA TGG CTG CCC CAC TTG CCA GCC CAG CTG GAG GGC ACT TGG GCC TGC        2426
Ser Trp Leu Pro His Leu Pro Ala Gln Leu Glu Gly Thr Trp Ala Cys
        750                 755                 760

CCT GCC TGT GCC CTG CGG CTG CTT GCA GCC ACG GAA CAG CTC ACC GTG        2474
Pro Ala Cys Ala Leu Arg Leu Leu Ala Ala Thr Glu Gln Leu Thr Val
765                 770                 775                 780

CTG CTG GGC TTG AGG CCC AAC CCT GGA CTG CGG CTG CCT GGG CGC TAT        2522
Leu Leu Gly Leu Arg Pro Asn Pro Gly Leu Arg Leu Pro Gly Arg Tyr
                785                 790                 795

GAG GTC CGG GCA GAG GTG GGC AAT GGC GTG TCC AGG CAC AAC CTC TCC        2570
Glu Val Arg Ala Glu Val Gly Asn Gly Val Ser Arg His Asn Leu Ser
                800                 805                 810

TGC AGC TTT GAC GTG GTC TCC CCA GTG GCT GGG CTG CGG GTC ATC TAC        2618
Cys Ser Phe Asp Val Val Ser Pro Val Ala Gly Leu Arg Val Ile Tyr
        815                 820                 825

CCT GCC CCC CGC GAC GGC CGC CTC TAC GTG CCC ACC AAC GGC TCA GCC        2666
Pro Ala Pro Arg Asp Gly Arg Leu Tyr Val Pro Thr Asn Gly Ser Ala
        830                 835                 840

TTG GTG CTC CAG GTG GAC TCT GGT GCC AAC GCC ACG GCC ACG GCT CGC        2714
Leu Val Leu Gln Val Asp Ser Gly Ala Asn Ala Thr Ala Thr Ala Arg
845                 850                 855                 860

TGG CCT GGG GGC AGT GTC AGC GCC CGC TTT GAG AAT GTC TGC CCT GCC        2762
Trp Pro Gly Gly Ser Val Ser Ala Arg Phe Glu Asn Val Cys Pro Ala
                865                 870                 875
```

```
CTG GTG GCC ACC TTC GTG CCC GGC TGC CCC TGG GAG ACC AAC GAT ACC    2810
Leu Val Ala Thr Phe Val Pro Gly Cys Pro Trp Glu Thr Asn Asp Thr
        880                 885                 890

CTG TTC TCA GTG GTA GCA CTG CCG TGG CTC AGT GAG GGG GAG CAC GTG    2858
Leu Phe Ser Val Val Ala Leu Pro Trp Leu Ser Glu Gly Glu His Val
        895                 900                 905

GTG GAC GTG GTG GTG GAA AAC AGC GCC AGC CGG GCC AAC CTC AGC CTG    2906
Val Asp Val Val Val Glu Asn Ser Ala Ser Arg Ala Asn Leu Ser Leu
        910                 915                 920

CGG GTG ACG GCG GAG GAG CCC ATC TGT GGC CTC CGC GCC ACG CCC AGC    2954
Arg Val Thr Ala Glu Glu Pro Ile Cys Gly Leu Arg Ala Thr Pro Ser
925                 930                 935                 940

CCC GAG GCC CGT GTA CTG CAG GGA GTC CTA GTG AGG TAC AGC CCC GTG    3002
Pro Glu Ala Arg Val Leu Gln Gly Val Leu Val Arg Tyr Ser Pro Val
                945                 950                 955

GTG GAG GCC GGC TCG GAC ATG GTC TTC CGG TGG ACC ATC AAC GAC AAG    3050
Val Glu Ala Gly Ser Asp Met Val Phe Arg Trp Thr Ile Asn Asp Lys
        960                 965                 970

CAG TCC CTG ACC TTC CAG AAC GTG GTC TTC AAT GTC ATT TAT CAG AGC    3098
Gln Ser Leu Thr Phe Gln Asn Val Val Phe Asn Val Ile Tyr Gln Ser
        975                 980                 985

GCG GCG GTC TTC AAG CTC TCA CTG ACG GCC TCC AAC CAC GTG AGC AAC    3146
Ala Ala Val Phe Lys Leu Ser Leu Thr Ala Ser Asn His Val Ser Asn
        990                 995                 1000

GTC ACC GTG AAC TAC AAC GTA ACC GTG GAG CGG ATG AAC AGG ATG CAG    3194
Val Thr Val Asn Tyr Asn Val Thr Val Glu Arg Met Asn Arg Met Gln
1005                1010                1015                1020

GGT CTG CAG GTC TCC ACA GTG CCG GCC GTG CTG TCC CCC AAT GCC ACG    3242
Gly Leu Gln Val Ser Thr Val Pro Ala Val Leu Ser Pro Asn Ala Thr
                1025                1030                1035

CTA GCA CTG ACG GCG GGC GTG CTG GTG GAC TCG GCC GTG GAG GTG GCC    3290
Leu Ala Leu Thr Ala Gly Val Leu Val Asp Ser Ala Val Glu Val Ala
                1040                1045                1050

TTC CTG TGG ACC TTT GGG GAT GGG GAG CAG GCC CTC CAC CAG TTC CAG    3338
Phe Leu Trp Thr Phe Gly Asp Gly Glu Gln Ala Leu His Gln Phe Gln
                1055                1060                1065

CCT CCG TAC AAC GAG TCC TTC CCG GTT CCA GAC CCC TCG GTG GCC CAG    3386
Pro Pro Tyr Asn Glu Ser Phe Pro Val Pro Asp Pro Ser Val Ala Gln
        1070                1075                1080

GTG CTG GTG GAG CAC AAT GTC ATG CAC ACC TAC GCT GCC CCA GGT GAG    3434
Val Leu Val Glu His Asn Val Met His Thr Tyr Ala Ala Pro Gly Glu
1085                1090                1095                1100
```

| | |
|---|---|
| TAC CTC CTG ACC GTG CTG GCA TCT AAT GCC TTC GAG AAC CTG ACG CAG<br>Tyr Leu Leu Thr Val Leu Ala Ser Asn Ala Phe Glu Asn Leu Thr Gln<br>　　　　　　　　1105　　　　　　　　1110　　　　　　　　1115 | 3482 |
| CAG GTG CCT GTG AGC GTG CGC GCC TCC CTG CCC TCC GTG GCT GTG GGT<br>Gln Val Pro Val Ser Val Arg Ala Ser Leu Pro Ser Val Ala Val Gly<br>　　　　　　1120　　　　　　　　1125　　　　　　　　1130 | 3530 |
| GTG AGT GAC GGC GTC CTG GTG GCC GGC CGG CCC GTC ACC TTC TAC CCG<br>Val Ser Asp Gly Val Leu Val Ala Gly Arg Pro Val Thr Phe Tyr Pro<br>　　　　　　1135　　　　　　　　1140　　　　　　　　1145 | 3578 |
| CAC CCG CTG CCC TCG CCT GGG GGT GTT CTT TAC ACG TGG GAC TTC GGG<br>His Pro Leu Pro Ser Pro Gly Gly Val Leu Tyr Thr Trp Asp Phe Gly<br>　　　　　　1150　　　　　　　　1155　　　　　　　　1160 | 3626 |
| GAC GGC TCC CCT GTC CTG ACC CAG AGC CAG CCG GCT GCC AAC CAC ACC<br>Asp Gly Ser Pro Val Leu Thr Gln Ser Gln Pro Ala Ala Asn His Thr<br>1165　　　　　　　　1170　　　　　　　　1175　　　　　　　　1180 | 3674 |
| TAT GCC TCG AGG GGC ACC TAC CAC GTG CGC CTG GAG GTC AAC AAC ACG<br>Tyr Ala Ser Arg Gly Thr Tyr His Val Arg Leu Glu Val Asn Asn Thr<br>　　　　　　1185　　　　　　　　1190　　　　　　　　1195 | 3722 |
| GTG AGC GGT GCG GCG GCC CAG GCG GAT GTG CGC GTC TTT GAG GAG CTC<br>Val Ser Gly Ala Ala Ala Gln Ala Asp Val Arg Val Phe Glu Glu Leu<br>　　　　　　1200　　　　　　　　1205　　　　　　　　1210 | 3770 |
| CGC GGA CTC AGC GTG GAC ATG AGC CTG GCC GTG GAG CAG GGC GCC CCC<br>Arg Gly Leu Ser Val Asp Met Ser Leu Ala Val Glu Gln Gly Ala Pro<br>　　　　　　1215　　　　　　　　1220　　　　　　　　1225 | 3818 |
| GTG GTG GTC AGC GCC GCG GTG CAG ACG GGC GAC AAC ATC ACG TGG ACC<br>Val Val Val Ser Ala Ala Val Gln Thr Gly Asp Asn Ile Thr Trp Thr<br>　　　　　　1230　　　　　　　　1235　　　　　　　　1240 | 3866 |
| TTC GAC ATG GGG GAC GGC ACC GTG CTG TCG GGC CCG GAG GCA ACA GTG<br>Phe Asp Met Gly Asp Gly Thr Val Leu Ser Gly Pro Glu Ala Thr Val<br>1245　　　　　　　　1250　　　　　　　　1255　　　　　　　　1260 | 3914 |
| GAG CAT GTG TAC CTG CGG GCA CAG AAC TGC ACA GTG ACC GTG GGT GCG<br>Glu His Val Tyr Leu Arg Ala Gln Asn Cys Thr Val Thr Val Gly Ala<br>　　　　　　1265　　　　　　　　1270　　　　　　　　1275 | 3962 |
| GCC AGC CCC GCC GGC CAC CTG GCC CGG AGC CTG CAC GTG CTG GTC TTC<br>Ala Ser Pro Ala Gly His Leu Ala Arg Ser Leu His Val Leu Val Phe<br>　　　　　　1280　　　　　　　　1285　　　　　　　　1290 | 4010 |
| GTC CTG GAG GTG CTG CGC GTT GAA CCC GCC GCC TGC ATC CCC ACG CAG<br>Val Leu Glu Val Leu Arg Val Glu Pro Ala Ala Cys Ile Pro Thr Gln<br>　　　　　　1295　　　　　　　　1300　　　　　　　　1305 | 4058 |
| CCT GAC GCG CGG CTC ACG GCC TAC GTC ACC GGG AAC CCG GCC CAC TAC<br>Pro Asp Ala Arg Leu Thr Ala Tyr Val Thr Gly Asn Pro Ala His Tyr<br>1310　　　　　　　　1315　　　　　　　　1320 | 4106 |

```
CTC TTC GAC TGG ACC TTC GGG GAT GGC TCC TCC AAC ACG ACC GTG CGG    4154
Leu Phe Asp Trp Thr Phe Gly Asp Gly Ser Ser Asn Thr Thr Val Arg
1325                1330                1335                1340

GGG TGC CCG ACG GTG ACA CAC AAC TTC ACG CGG AGC GGC ACG TTC CCC    4202
Gly Cys Pro Thr Val Thr His Asn Phe Thr Arg Ser Gly Thr Phe Pro
                1345                1350                1355

CTG GCG CTG GTG CTG TCC AGC CGC GTG AAC AGG GCG CAT TAC TTC ACC    4250
Leu Ala Leu Val Leu Ser Ser Arg Val Asn Arg Ala His Tyr Phe Thr
            1360                1365                1370

AGC ATC TGC GTG GAG CCA GAG GTG GGC AAC GTC ACC CTG CAG CCA GAG    4298
Ser Ile Cys Val Glu Pro Glu Val Gly Asn Val Thr Leu Gln Pro Glu
        1375                1380                1385

AGG CAG TTT GTG CAG CTC GGG GAC GAG GCC TGG CTG GTG GCA TGT GCC    4346
Arg Gln Phe Val Gln Leu Gly Asp Glu Ala Trp Leu Val Ala Cys Ala
    1390                1395                1400

TGG CCC CCG TTC CCC TAC CGC TAC ACC TGG GAC TTT GGC ACC GAG GAA    4394
Trp Pro Pro Phe Pro Tyr Arg Tyr Thr Trp Asp Phe Gly Thr Glu Glu
1405                1410                1415                1420

GCC GCC CCC ACC CGT GCC AGG GGC CCT GAG GTG ACG TTC ATC TAC CGA    4442
Ala Ala Pro Thr Arg Ala Arg Gly Pro Glu Val Thr Phe Ile Tyr Arg
                1425                1430                1435

GAC CCA GGC TCC TAT CTT GTG ACA GTC ACC GCG TCC AAC AAC ATC TCT    4490
Asp Pro Gly Ser Tyr Leu Val Thr Val Thr Ala Ser Asn Asn Ile Ser
            1440                1445                1450

GCT GCC AAT GAC TCA GCC CTG GTG GAG GTG CAG GAG CCC GTG CTG GTC    4538
Ala Ala Asn Asp Ser Ala Leu Val Glu Val Gln Glu Pro Val Leu Val
        1455                1460                1465

ACC AGC ATC AAG GTC AAT GGC TCC CTT GGG CTG GAG CTG CAG CAG CCG    4586
Thr Ser Ile Lys Val Asn Gly Ser Leu Gly Leu Glu Leu Gln Gln Pro
    1470                1475                1480

TAC CTG TTC TCT GCT GTG GGC CGT GGG CGC CCC GCC AGC TAC CTG TGG    4634
Tyr Leu Phe Ser Ala Val Gly Arg Gly Arg Pro Ala Ser Tyr Leu Trp
1485                1490                1495                1500

GAT CTG GGG GAC GGT GGG TGG CTC GAG GGT CCG GAG GTC ACC CAC GCT    4682
Asp Leu Gly Asp Gly Gly Trp Leu Glu Gly Pro Glu Val Thr His Ala
                1505                1510                1515

TAC AAC AGC ACA GGT GAC TTC ACC GTT AGG GTG GCC GGC TGG AAT GAG    4730
Tyr Asn Ser Thr Gly Asp Phe Thr Val Arg Val Ala Gly Trp Asn Glu
            1520                1525                1530

GTG AGC CGC AGC GAG GCC TGG CTC AAT GTG ACG GTG AAG CGG CGC GTG    4778
Val Ser Arg Ser Glu Ala Trp Leu Asn Val Thr Val Lys Arg Arg Val
        1535                1540                1545
```

| | |
|---|---|
| CGG GGG CTC GTC GTC AAT GCA AGC CGC ACG GTG GTG CCC CTG AAT GGG<br>Arg Gly Leu Val Val Asn Ala Ser Arg Thr Val Val Pro Leu Asn Gly<br>      1550                 1555                   1560 | 4826 |
| AGC GTG AGC TTC AGC ACG TCG CTG GAG GCC GGC AGT GAT GTG CGC TAT<br>Ser Val Ser Phe Ser Thr Ser Leu Glu Ala Gly Ser Asp Val Arg Tyr<br>1565               1570                 1575                 1580 | 4874 |
| TCC TGG GTG CTC TGT GAC CGC TGC ACG CCC ATC CCT GGG GGT CCT ACC<br>Ser Trp Val Leu Cys Asp Arg Cys Thr Pro Ile Pro Gly Gly Pro Thr<br>               1585                 1590                 1595 | 4922 |
| ATC TCT TAC ACC TTC CGC TCC GTG GGC ACC TTC AAT ATC ATC GTC ACG<br>Ile Ser Tyr Thr Phe Arg Ser Val Gly Thr Phe Asn Ile Ile Val Thr<br>             1600                 1605                 1610 | 4970 |
| GCT GAG AAC GAG GTG GGC TCC GCC CAG GAC AGC ATC TTC GTC TAT GTC<br>Ala Glu Asn Glu Val Gly Ser Ala Gln Asp Ser Ile Phe Val Tyr Val<br>          1615                 1620                 1625 | 5018 |
| CTG CAG CTC ATA GAG GGG CTG CAG GTG GTG GGC GGT GGC CGC TAC TTC<br>Leu Gln Leu Ile Glu Gly Leu Gln Val Val Gly Gly Gly Arg Tyr Phe<br>       1630                 1635                 1640 | 5066 |
| CCC ACC AAC CAC ACG GTA CAG CTG CAG GCC GTG GTT AGG GAT GGC ACC<br>Pro Thr Asn His Thr Val Gln Leu Gln Ala Val Val Arg Asp Gly Thr<br>1645               1650                 1655                 1660 | 5114 |
| AAC GTC TCC TAC AGC TGG ACT GCC TGG AGG GAC AGG GGC CCG GCC CTG<br>Asn Val Ser Tyr Ser Trp Thr Ala Trp Arg Asp Arg Gly Pro Ala Leu<br>               1665                 1670                 1675 | 5162 |
| GCC GGC AGC GGC AAA GGC TTC TCG CTC ACC GTG CTC GAG GCC GGC ACC<br>Ala Gly Ser Gly Lys Gly Phe Ser Leu Thr Val Leu Glu Ala Gly Thr<br>          1680                 1685                 1690 | 5210 |
| TAC CAT GTG CAG CTG CGG GCC ACC AAC ATG CTG GGC AGC GCC TGG GCC<br>Tyr His Val Gln Leu Arg Ala Thr Asn Met Leu Gly Ser Ala Trp Ala<br>          1695                 1700                 1705 | 5258 |
| GAC TGC ACC ATG GAC TTC GTG GAG CCT GTG GGG TGG CTG ATG GTG GCC<br>Asp Cys Thr Met Asp Phe Val Glu Pro Val Gly Trp Leu Met Val Ala<br>       1710                 1715                 1720 | 5306 |
| GCC TCC CCG AAC CCA GCT GCC GTC AAC ACA AGC GTC ACC CTC AGT GCC<br>Ala Ser Pro Asn Pro Ala Ala Val Asn Thr Ser Val Thr Leu Ser Ala<br>1725               1730                 1735                 1740 | 5354 |
| GAG CTG GCT GGT GGC AGT GGT GTC GTA TAC ACT TGG TCC TTG GAG GAG<br>Glu Leu Ala Gly Gly Ser Gly Val Val Tyr Thr Trp Ser Leu Glu Glu<br>               1745                 1750                 1755 | 5402 |
| GGG CTG AGC TGG GAG ACC TCC GAG CCA TTT ACC ACC CAT AGC TTC CCC<br>Gly Leu Ser Trp Glu Thr Ser Glu Pro Phe Thr Thr His Ser Phe Pro<br>             1760                 1765                 1770 | 5450 |

```
ACA CCC GGC CTG CAC TTG GTC ACC ATG ACG GCA GGG AAC CCG CTG GGC    5498
Thr Pro Gly Leu His Leu Val Thr Met Thr Ala Gly Asn Pro Leu Gly
        1775                1780                1785

TCA GCC AAC GCC ACC GTG GAA GTG GAT GTG CAG GTG CCT GTG AGT GGC    5546
Ser Ala Asn Ala Thr Val Glu Val Asp Val Gln Val Pro Val Ser Gly
        1790                1795                1800

CTC AGC ATC AGG GCC AGC GAG CCC GGA GGC AGC TTC GTG GCG GCC GGG    5594
Leu Ser Ile Arg Ala Ser Glu Pro Gly Gly Ser Phe Val Ala Ala Gly
1805                1810                1815                1820

TCC TCT GTG CCC TTT TGG GGG CAG CTG GCC ACG GGC ACC AAT GTG AGC    5642
Ser Ser Val Pro Phe Trp Gly Gln Leu Ala Thr Gly Thr Asn Val Ser
                1825                1830                1835

TGG TGC TGG GCT GTG CCC GGC GGC AGC AGC AAG CGT GGC CCT CAT GTC    5690
Trp Cys Trp Ala Val Pro Gly Gly Ser Ser Lys Arg Gly Pro His Val
            1840                1845                1850

ACC ATG GTC TTC CCG GAT GCT GGC ACC TTC TCC ATC CGG CTC AAT GCC    5738
Thr Met Val Phe Pro Asp Ala Gly Thr Phe Ser Ile Arg Leu Asn Ala
        1855                1860                1865

TCC AAC GCA GTC AGC TGG GTC TCA GCC ACG TAC AAC CTC ACG GCG GAG    5786
Ser Asn Ala Val Ser Trp Val Ser Ala Thr Tyr Asn Leu Thr Ala Glu
        1870                1875                1880

GAG CCC ATC GTG GGC CTG GTG CTG TGG GCC AGC AGC AAG GTG GTG GCG    5834
Glu Pro Ile Val Gly Leu Val Leu Trp Ala Ser Ser Lys Val Val Ala
1885                1890                1895                1900

CCC GGG CAG CTG GTC CAT TTT CAG ATC CTG CTG GCT GCC GGC TCA GCT    5882
Pro Gly Gln Leu Val His Phe Gln Ile Leu Leu Ala Ala Gly Ser Ala
                1905                1910                1915

GTC ACC TTC CGC CTG CAG GTC GGC GGG GCC AAC CCC GAG GTG CTC CCC    5930
Val Thr Phe Arg Leu Gln Val Gly Gly Ala Asn Pro Glu Val Leu Pro
            1920                1925                1930

GGG CCC CGT TTC TCC CAC AGC TTC CCC CGC GTC GGA GAC CAC GTG GTG    5978
Gly Pro Arg Phe Ser His Ser Phe Pro Arg Val Gly Asp His Val Val
        1935                1940                1945

AGC GTG CGG GGC AAA AAC CAC GTG AGC TGG GCC CAG GCG CAG GTG CGC    6026
Ser Val Arg Gly Lys Asn His Val Ser Trp Ala Gln Ala Gln Val Arg
        1950                1955                1960

ATC GTG GTG CTG GAG GCC GTG AGT GGG CTG CAG GTG CCC AAC TGC TGC    6074
Ile Val Val Leu Glu Ala Val Ser Gly Leu Gln Val Pro Asn Cys Cys
1965                1970                1975                1980

GAG CCT GGC ATC GCC ACG GGC ACT GAG AGG AAC TTC ACA GCC CGC GTG    6122
Glu Pro Gly Ile Ala Thr Gly Thr Glu Arg Asn Phe Thr Ala Arg Val
                1985                1990                1995
```

```
CAG CGC GGC TCT CGG GTC GCC TAC GCC TGG TAC TTC TCG CTG CAG AAG      6170
Gln Arg Gly Ser Arg Val Ala Tyr Ala Trp Tyr Phe Ser Leu Gln Lys
            2000                2005                2010

GTC CAG GGC GAC TCG CTG GTC ATC CTG TCG GGC CGC GAC GTC ACC TAC      6218
Val Gln Gly Asp Ser Leu Val Ile Leu Ser Gly Arg Asp Val Thr Tyr
            2015                2020                2025

ACG CCC GTG GCC GCG GGG CTG TTG GAG ATC CAG GTG CGC GCC TTC AAC      6266
Thr Pro Val Ala Ala Gly Leu Leu Glu Ile Gln Val Arg Ala Phe Asn
            2030                2035                2040

GCC CTG GGC AGT GAG AAC CGC ACG CTG GTG CTG GAG GTT CAG GAC GCC      6314
Ala Leu Gly Ser Glu Asn Arg Thr Leu Val Leu Glu Val Gln Asp Ala
2045                2050                2055                2060

GTC CAG TAT GTG GCC CTG CAG AGC GGC CCC TGC TTC ACC AAC CGC TCG      6362
Val Gln Tyr Val Ala Leu Gln Ser Gly Pro Cys Phe Thr Asn Arg Ser
            2065                2070                2075

GCG CAG TTT GAG GCC GCC ACC AGC CCC AGC CCC CGG CGT GTG GCC TAC      6410
Ala Gln Phe Glu Ala Ala Thr Ser Pro Ser Pro Arg Arg Val Ala Tyr
            2080                2085                2090

CAC TGG GAC TTT GGG GAT GGG TCG CCA GGG CAG GAC ACA GAT GAG CCC      6458
His Trp Asp Phe Gly Asp Gly Ser Pro Gly Gln Asp Thr Asp Glu Pro
            2095                2100                2105

AGG GCC GAG CAC TCC TAC CTG AGG CCT GGG GAC TAC CGC GTG CAG GTG      6506
Arg Ala Glu His Ser Tyr Leu Arg Pro Gly Asp Tyr Arg Val Gln Val
            2110                2115                2120

AAC GCC TCC AAC CTG GTG AGC TTC TTC GTG GCG CAG GCC ACG GTG ACC      6554
Asn Ala Ser Asn Leu Val Ser Phe Phe Val Ala Gln Ala Thr Val Thr
2125                2130                2135                2140

GTC CAG GTG CTG GCC TGC CGG GAG CCG GAG GTG GAC GTG GTC CTG CCC      6602
Val Gln Val Leu Ala Cys Arg Glu Pro Glu Val Asp Val Val Leu Pro
            2145                2150                2155

CTG CAG GTG CTG ATG CGG CGA TCA CAG CGC AAC TAC TTG GAG GCC CAC      6650
Leu Gln Val Leu Met Arg Arg Ser Gln Arg Asn Tyr Leu Glu Ala His
            2160                2165                2170

GTT GAC CTG CGC GAC TGC GTC ACC TAC CAG ACT GAG TAC CGC TGG GAG      6698
Val Asp Leu Arg Asp Cys Val Thr Tyr Gln Thr Glu Tyr Arg Trp Glu
            2175                2180                2185

GTG TAT CGC ACC GCC AGC TGC CAG CGG CCG GGG CGC CCA GCG CGT GTG      6746
Val Tyr Arg Thr Ala Ser Cys Gln Arg Pro Gly Arg Pro Ala Arg Val
            2190                2195                2200

GCC CTG CCC GGC GTG GAC GTG AGC CGG CCT CGG CTG GTG CTG CCG CGG      6794
Ala Leu Pro Gly Val Asp Val Ser Arg Pro Arg Leu Val Leu Pro Arg
2205                2210                2215                2220
```

```
CTG GCG CTG CCT GTG GGG CAC TAC TGC TTT GTG TTT GTC GTG TCA TTT         6842
Leu Ala Leu Pro Val Gly His Tyr Cys Phe Val Phe Val Val Ser Phe
                2225            2230            2235

GGG GAC ACG CCA CTG ACA CAG AGC ATC CAG GCC AAT GTG ACG GTG GCC         6890
Gly Asp Thr Pro Leu Thr Gln Ser Ile Gln Ala Asn Val Thr Val Ala
                2240            2245            2250

CCC GAG CGC CTG GTG CCC ATC ATT GAG GGT GGC TCA TAC CGC GTG TGG         6938
Pro Glu Arg Leu Val Pro Ile Ile Glu Gly Gly Ser Tyr Arg Val Trp
                2255            2260            2265

TCA GAC ACA CGG GAC CTG GTG CTG GAT GGG AGC GAG TCC TAC GAC CCC         6986
Ser Asp Thr Arg Asp Leu Val Leu Asp Gly Ser Glu Ser Tyr Asp Pro
                2270            2275            2280

AAC CTG GAG GAC GGC GAC CAG ACG CCG CTC AGT TTC CAC TGG GCC TGT         7034
Asn Leu Glu Asp Gly Asp Gln Thr Pro Leu Ser Phe His Trp Ala Cys
2285            2290            2295            2300

GTG GCT TCG ACA CAG AGG GAG GCT GGC GGG TGT GCG CTG AAC TTT GGG         7082
Val Ala Ser Thr Gln Arg Glu Ala Gly Gly Cys Ala Leu Asn Phe Gly
                2305            2310            2315

CCC CGC GGG AGC AGC ACG GTC ACC ATT CCA CGG GAG CGG CTG GCG GCT         7130
Pro Arg Gly Ser Ser Thr Val Thr Ile Pro Arg Glu Arg Leu Ala Ala
                2320            2325            2330

GGC GTG GAG TAC ACC TTC AGC CTG ACC GTG TGG AAG GCC GGC CGC AAG         7178
Gly Val Glu Tyr Thr Phe Ser Leu Thr Val Trp Lys Ala Gly Arg Lys
                2335            2340            2345

GAG GAG GCC ACC AAC CAG ACG GTG CTG ATC CGG AGT GGC CGG GTG CCC         7226
Glu Glu Ala Thr Asn Gln Thr Val Leu Ile Arg Ser Gly Arg Val Pro
                2350            2355            2360

ATT GTG TCC TTG GAG TGT GTG TCC TGC AAG GCA CAG GCC GTG TAC GAA         7274
Ile Val Ser Leu Glu Cys Val Ser Cys Lys Ala Gln Ala Val Tyr Glu
2365            2370            2375            2380

GTG AGC CGC AGC TCC TAC GTG TAC TTG GAG GGC CGC TGC CTC AAT TGC         7322
Val Ser Arg Ser Ser Tyr Val Tyr Leu Glu Gly Arg Cys Leu Asn Cys
                2385            2390            2395

AGC AGC GGC TCC AAG CGA GGG CGG TGG GCT GCA CGT ACG TTC AGC AAC         7370
Ser Ser Gly Ser Lys Arg Gly Arg Trp Ala Ala Arg Thr Phe Ser Asn
                2400            2405            2410

AAG ACG CTG GTG CTG GAT GAG ACC ACC ACA TCC ACG GGC AGT GCA GGC         7418
Lys Thr Leu Val Leu Asp Glu Thr Thr Thr Ser Thr Gly Ser Ala Gly
                2415            2420            2425

ATG CGA CTG GTG CTG CGG CGG GGC GTG CTG CGG GAC GGC GAG GGA TAC         7466
Met Arg Leu Val Leu Arg Arg Gly Val Leu Arg Asp Gly Glu Gly Tyr
                2430            2435            2440
```

```
ACC TTC ACG CTC ACG GTG CTG GGC CGC TCT GGC GAG GAG GAG GGC TGC       7514
Thr Phe Thr Leu Thr Val Leu Gly Arg Ser Gly Glu Glu Glu Gly Cys
2445                2450                2455                2460

GCC TCC ATC CGC CTG TCC CCC AAC CGC CCG CCG CTG GGG GGC TCT TGC       7562
Ala Ser Ile Arg Leu Ser Pro Asn Arg Pro Pro Leu Gly Gly Ser Cys
                    2465                2470                2475

CGC CTC TTC CCA CTG GGC GCT GTG CAC GCC CTC ACC ACC AAG GTG CAC       7610
Arg Leu Phe Pro Leu Gly Ala Val His Ala Leu Thr Thr Lys Val His
                2480                2485                2490

TTC GAA TGC ACG GGC TGG CAT GAC GCG GAG GAT GCT GGC GCC CCG CTG       7658
Phe Glu Cys Thr Gly Trp His Asp Ala Glu Asp Ala Gly Ala Pro Leu
            2495                2500                2505

GTG TAC GCC CTG CTG CTG CGG CGC TGT CGC CAG GGC CAC TGC GAG GAG       7706
Val Tyr Ala Leu Leu Leu Arg Arg Cys Arg Gln Gly His Cys Glu Glu
2510                2515                2520

TTC TGT GTC TAC AAG GGC AGC CTC TCC AGC TAC GGA GCC GTG CTG CCC       7754
Phe Cys Val Tyr Lys Gly Ser Leu Ser Ser Tyr Gly Ala Val Leu Pro
2525                2530                2535                2540

CCG GGT TTC AGG CCA CAC TTC GAG GTG GGC CTG GCC GTG GTG GTG CAG       7802
Pro Gly Phe Arg Pro His Phe Glu Val Gly Leu Ala Val Val Val Gln
                    2545                2550                2555

GAC CAG CTG GGA GCC GCT GTG GTC GCC CTC AAC AGG TCT TTG GCC ATC       7850
Asp Gln Leu Gly Ala Ala Val Val Ala Leu Asn Arg Ser Leu Ala Ile
                2560                2565                2570

ACC CTC CCA GAG CCC AAC GGC AGC GCA ACG GGG CTC ACA GTC TGG CTG       7898
Thr Leu Pro Glu Pro Asn Gly Ser Ala Thr Gly Leu Thr Val Trp Leu
            2575                2580                2585

CAC GGG CTC ACC GCT AGT GTG CTC CCA GGG CTG CTG CGG CAG GCC GAT       7946
His Gly Leu Thr Ala Ser Val Leu Pro Gly Leu Leu Arg Gln Ala Asp
        2590                2595                2600

CCC CAG CAC GTC ATC GAG TAC TCG TTG GCC CTG GTC ACC GTG CTG AAC       7994
Pro Gln His Val Ile Glu Tyr Ser Leu Ala Leu Val Thr Val Leu Asn
2605                2610                2615                2620

GAG TAC GAG CGG GCC CTG GAC GTG GCG GCA GAG CCC AAG CAC GAG CGG       8042
Glu Tyr Glu Arg Ala Leu Asp Val Ala Ala Glu Pro Lys His Glu Arg
                2625                2630                2635

CAG CAC CGA GCC CAG ATA CGC AAG AAC ATC ACG GAG ACT CTG GTG TCC       8090
Gln His Arg Ala Gln Ile Arg Lys Asn Ile Thr Glu Thr Leu Val Ser
                2640                2645                2650

CTG AGG GTC CAC ACT GTG GAT GAC ATC CAG CAG ATC GCT GCT GCG CTG       8138
Leu Arg Val His Thr Val Asp Asp Ile Gln Gln Ile Ala Ala Ala Leu
            2655                2660                2665
```

```
GCC CAG TGC ATG GGG CCC AGC AGG GAG CTC GTA TGC CGC TCG TGC CTG        8186
Ala Gln Cys Met Gly Pro Ser Arg Glu Leu Val Cys Arg Ser Cys Leu
    2670            2675            2680

AAG CAG ACG CTG CAC AAG CTG GAG GCC ATG ATG CTC ATC CTG CAG GCA        8234
Lys Gln Thr Leu His Lys Leu Glu Ala Met Met Leu Ile Leu Gln Ala
2685            2690            2695            2700

GAG ACC ACC GCG GGC ACC GTG ACG CCC ACC GCC ATC GGA GAC AGC ATC        8282
Glu Thr Thr Ala Gly Thr Val Thr Pro Thr Ala Ile Gly Asp Ser Ile
            2705            2710            2715

CTC AAC ATC ACA GGA GAC CTC ATC CAC CTG GCC AGC TCG GAC GTG CGG        8330
Leu Asn Ile Thr Gly Asp Leu Ile His Leu Ala Ser Ser Asp Val Arg
        2720            2725            2730

GCA CCA CAG CCC TCA GAG CTG GGA GCC GAG TCA CCA TCT CGG ATG GTG        8378
Ala Pro Gln Pro Ser Glu Leu Gly Ala Glu Ser Pro Ser Arg Met Val
    2735            2740            2745

GCG TCC CAG GCC TAC AAC CTG ACC TCT GCC CTC ATG CGC ATC CTC ATG        8426
Ala Ser Gln Ala Tyr Asn Leu Thr Ser Ala Leu Met Arg Ile Leu Met
    2750            2755            2760

CGC TCC CGC GTG CTC AAC GAG GAG CCC CTG ACG CTG GCG GGC GAG GAG        8474
Arg Ser Arg Val Leu Asn Glu Glu Pro Leu Thr Leu Ala Gly Glu Glu
2765            2770            2775            2780

ATC GTG GCC CAG GGC AAG CGC TCG GAC CCG CGG AGC CTG CTG TGC TAT        8522
Ile Val Ala Gln Gly Lys Arg Ser Asp Pro Arg Ser Leu Leu Cys Tyr
            2785            2790            2795

GGC GGC GCC CCA GGG CCT GGC TGC CAC TTC TCC ATC CCC GAG GCT TTC        8570
Gly Gly Ala Pro Gly Pro Gly Cys His Phe Ser Ile Pro Glu Ala Phe
        2800            2805            2810

AGC GGG GCC CTG GCC AAC CTC AGT GAC GTG GTG CAG CTC ATC TTT CTG        8618
Ser Gly Ala Leu Ala Asn Leu Ser Asp Val Val Gln Leu Ile Phe Leu
    2815            2820            2825

GTG GAC TCC AAT CCC TTT CCC TTT GGC TAT ATC AGC AAC TAC ACC GTC        8666
Val Asp Ser Asn Pro Phe Pro Phe Gly Tyr Ile Ser Asn Tyr Thr Val
    2830            2835            2840

TCC ACC AAG GTG GCC TCG ATG GCA TTC CAG ACA CAG GCC GGC GCC CAG        8714
Ser Thr Lys Val Ala Ser Met Ala Phe Gln Thr Gln Ala Gly Ala Gln
2845            2850            2855            2860

ATC CCC ATC GAG CGG CTG GCC TCA GAG CGC GCC ATC ACC GTG AAG GTG        8762
Ile Pro Ile Glu Arg Leu Ala Ser Glu Arg Ala Ile Thr Val Lys Val
            2865            2870            2875

CCC AAC AAC TCG GAC TGG GCT GCC CGG GGC CAC CGC AGC TCC GCC AAC        8810
Pro Asn Asn Ser Asp Trp Ala Ala Arg Gly His Arg Ser Ser Ala Asn
            2880            2885            2890
```

```
TCC GCC AAC TCC GTT GTG GTC CAG CCC CAG GCC TCC GTC GGT GCT GTG    8858
Ser Ala Asn Ser Val Val Val Gln Pro Gln Ala Ser Val Gly Ala Val
        2895            2900            2905

GTC ACC CTG GAC AGC AGC AAC CCT GCG GCC GGG CTG CAT CTG CAG CTC    8906
Val Thr Leu Asp Ser Ser Asn Pro Ala Ala Gly Leu His Leu Gln Leu
    2910            2915            2920

AAC TAT ACG CTG CTG GAC GGC CAC TAC CTG TCT GAG GAA CCT GAG CCC    8954
Asn Tyr Thr Leu Leu Asp Gly His Tyr Leu Ser Glu Glu Pro Glu Pro
2925            2930            2935            2940

TAC CTG GCA GTC TAC CTA CAC TCG GAG CCC CGG CCC AAT GAG CAC AAC    9002
Tyr Leu Ala Val Tyr Leu His Ser Glu Pro Arg Pro Asn Glu His Asn
        2945            2950            2955

TGC TCG GCT AGC AGG AGG ATC CGC CCA GAG TCA CTC CAG GGT GCT GAC    9050
Cys Ser Ala Ser Arg Arg Ile Arg Pro Glu Ser Leu Gln Gly Ala Asp
            2960            2965            2970

CAC CGG CCC TAC ACC TTC TTC ATT TCC CCG GGG AGC AGA GAC CCA GCG    9098
His Arg Pro Tyr Thr Phe Phe Ile Ser Pro Gly Ser Arg Asp Pro Ala
        2975            2980            2985

GGG AGT TAC CAT CTG AAC CTC TCC AGC CAC TTC CGC TGG TCG GCG CTG    9146
Gly Ser Tyr His Leu Asn Leu Ser Ser His Phe Arg Trp Ser Ala Leu
    2990            2995            3000

CAG GTG TCC GTG GGC CTG TAC ACG TCC CTG TGC CAG TAC TTC AGC GAG    9194
Gln Val Ser Val Gly Leu Tyr Thr Ser Leu Cys Gln Tyr Phe Ser Glu
3005            3010            3015            3020

GAG GAC ATG GTG TGG CGG ACA GAG GGG CTG CTG CCC CTG GAG GAG ACC    9242
Glu Asp Met Val Trp Arg Thr Glu Gly Leu Leu Pro Leu Glu Glu Thr
            3025            3030            3035

TCG CCC CGC CAG GCC GTC TGC CTC ACC CGC CAC CTC ACC GCC TTC GGC    9290
Ser Pro Arg Gln Ala Val Cys Leu Thr Arg His Leu Thr Ala Phe Gly
        3040            3045            3050

GCC AGC CTC TTC GTG CCC CCA AGC CAT GTC CGC TTT GTG TTT CCT GAG    9338
Ala Ser Leu Phe Val Pro Pro Ser His Val Arg Phe Val Phe Pro Glu
    3055            3060            3065

CCG ACA GCG GAT GTA AAC TAC ATC GTC ATG CTG ACA TGT GCT GTG TGC    9386
Pro Thr Ala Asp Val Asn Tyr Ile Val Met Leu Thr Cys Ala Val Cys
3070            3075            3080

CTG GTG ACC TAC ATG GTC ATG GCC GCC ATC CTG CAC AAG CTG GAC CAG    9434
Leu Val Thr Tyr Met Val Met Ala Ala Ile Leu His Lys Leu Asp Gln
3085            3090            3095            3100

TTG GAT GCC AGC CGG GGC CGC GCC ATC CCT TTC TGT GGG CAG CGG GGC    9482
Leu Asp Ala Ser Arg Gly Arg Ala Ile Pro Phe Cys Gly Gln Arg Gly
            3105            3110            3115
```

```
CGC TTC AAG TAC GAG ATC CTC GTC AAG ACA GGC TGG GGC CGG GGC TCA    9530
Arg Phe Lys Tyr Glu Ile Leu Val Lys Thr Gly Trp Gly Arg Gly Ser
            3120                3125                3130

GGT ACC ACG GCC CAC GTG GGC ATC ATG CTG TAT GGG GTG GAC AGC CGG    9578
Gly Thr Thr Ala His Val Gly Ile Met Leu Tyr Gly Val Asp Ser Arg
        3135                3140                3145

AGC GGC CAC CGG CAC CTG GAC GGC GAC AGA GCC TTC CAC CGC AAC AGC    9626
Ser Gly His Arg His Leu Asp Gly Asp Arg Ala Phe His Arg Asn Ser
    3150                3155                3160

CTG GAC ATC TTC CGG ATC GCC ACC CCG CAC AGC CTG GGT AGC GTG TGG    9674
Leu Asp Ile Phe Arg Ile Ala Thr Pro His Ser Leu Gly Ser Val Trp
3165                3170                3175                3180

AAG ATC CGA GTG TGG CAC GAC AAC AAA GGG CTC AGC CCT GCC TGG TTC    9722
Lys Ile Arg Val Trp His Asp Asn Lys Gly Leu Ser Pro Ala Trp Phe
                3185                3190                3195

CTG CAG CAC GTC ATC GTC AGG GAC CTG CAG ACG GCA CGC AGC GCC TTC    9770
Leu Gln His Val Ile Val Arg Asp Leu Gln Thr Ala Arg Ser Ala Phe
            3200                3205                3210

TTC CTG GTC AAT GAC TGG CTT TCG GTG GAG ACG GAG GCC AAC GGG GGC    9818
Phe Leu Val Asn Asp Trp Leu Ser Val Glu Thr Glu Ala Asn Gly Gly
            3215                3220                3225

CTG GTG GAG AAG GAG GTG CTG GCC GCG AGC GAC GCA GCC CTT TTG CGC    9866
Leu Val Glu Lys Glu Val Leu Ala Ala Ser Asp Ala Ala Leu Leu Arg
        3230                3235                3240

TTC CGG CGC CTG CTG GTG GCT GAG CTG CAG CGT GGC TTC TTT GAC AAG    9914
Phe Arg Arg Leu Leu Val Ala Glu Leu Gln Arg Gly Phe Phe Asp Lys
3245                3250                3255                3260

CAC ATC TGG CTC TCC ATA TGG GAC CGG CCG CCT CGT AGC CGT TTC ACT    9962
His Ile Trp Leu Ser Ile Trp Asp Arg Pro Pro Arg Ser Arg Phe Thr
                3265                3270                3275

CGC ATC CAG AGG GCC ACC TGC TGC GTT CTC CTC ATC TGC CTC TTC CTG   10010
Arg Ile Gln Arg Ala Thr Cys Cys Val Leu Leu Ile Cys Leu Phe Leu
            3280                3285                3290

GGC GCC AAC GCC GTG TGG TAC GGG GCT GTT GGC GAC TCT GCC TAC AGC   10058
Gly Ala Asn Ala Val Trp Tyr Gly Ala Val Gly Asp Ser Ala Tyr Ser
        3295                3300                3305

ACG GGG CAT GTG TCC AGG CTG AGC CCG CTG AGC GTC GAC ACA GTC GCT   10106
Thr Gly His Val Ser Arg Leu Ser Pro Leu Ser Val Asp Thr Val Ala
    3310                3315                3320

GTT GGC CTG GTG TCC AGC GTG GTT GTC TAT CCC GTC TAC CTG GCC ATC   10154
Val Gly Leu Val Ser Ser Val Val Val Tyr Pro Val Tyr Leu Ala Ile
3325                3330                3335                3340
```

```
CTT TTT CTC TTC CGG ATG TCC CGG AGC AAG GTG GCT GGG AGC CCG AGC    10202
Leu Phe Leu Phe Arg Met Ser Arg Ser Lys Val Ala Gly Ser Pro Ser
                3345                3350                3355

CCC ACA CCT GCC GGG CAG CAG GTG CTG GAC ATC GAC AGC TGC CTG GAC    10250
Pro Thr Pro Ala Gly Gln Gln Val Leu Asp Ile Asp Ser Cys Leu Asp
                3360                3365                3370

TCG TCC GTG CTG GAC AGC TCC TTC CTC ACG TTC TCA GGC CTC CAC GCT    10298
Ser Ser Val Leu Asp Ser Ser Phe Leu Thr Phe Ser Gly Leu His Ala
                3375                3380                3385

GAG GCC TTT GTT GGA CAG ATG AAG AGT GAC TTG TTT CTG GAT GAT TCT    10346
Glu Ala Phe Val Gly Gln Met Lys Ser Asp Leu Phe Leu Asp Asp Ser
                3390                3395                3400

AAG AGT CTG GTG TGC TGG CCC TCC GGC GAG GGA ACG CTC AGT TGG CCG    10394
Lys Ser Leu Val Cys Trp Pro Ser Gly Glu Gly Thr Leu Ser Trp Pro
3405                3410                3415                3420

GAC CTG CTC AGT GAC CCG TCC ATT GTG GGT AGC AAT CTG CGG CAG CTG    10442
Asp Leu Leu Ser Asp Pro Ser Ile Val Gly Ser Asn Leu Arg Gln Leu
                3425                3430                3435

GCA CGG GGC CAG GCG GGC CAT GGG CTG GGC CCA GAG GAG GAC GGC TTC    10490
Ala Arg Gly Gln Ala Gly His Gly Leu Gly Pro Glu Glu Asp Gly Phe
                3440                3445                3450

TCC CTG GCC AGC CCC TAC TCG CCT GCC AAA TCC TTC TCA GCA TCA GAT    10538
Ser Leu Ala Ser Pro Tyr Ser Pro Ala Lys Ser Phe Ser Ala Ser Asp
                3455                3460                3465

GAA GAC CTG ATC CAG CAG GTC CTT GCC GAG GGG GTC AGC AGC CCA GCC    10586
Glu Asp Leu Ile Gln Gln Val Leu Ala Glu Gly Val Ser Ser Pro Ala
                3470                3475                3480

CCT ACC CAA GAC ACC CAC ATG GAA ACG GAC CTG CTC AGC AGC CTG TCC    10634
Pro Thr Gln Asp Thr His Met Glu Thr Asp Leu Leu Ser Ser Leu Ser
3485                3490                3495                3500

AGC ACT CCT GGG GAG AAG ACA GAG ACG CTG GCG CTG CAG AGG CTG GGG    10682
Ser Thr Pro Gly Glu Lys Thr Glu Thr Leu Ala Leu Gln Arg Leu Gly
                3505                3510                3515

GAG CTG GGG CCA CCC AGC CCA GGC CTG AAC TGG GAA CAG CCC CAG GCA    10730
Glu Leu Gly Pro Pro Ser Pro Gly Leu Asn Trp Glu Gln Pro Gln Ala
                3520                3525                3530

GCG AGG CTG TCC AGG ACA GGA CTG GTG GAG GGT CTG CGG AAG CGC CTG    10778
Ala Arg Leu Ser Arg Thr Gly Leu Val Glu Gly Leu Arg Lys Arg Leu
                3535                3540                3545

CTG CCG GCC TGG TGT GCC TCC CTG GCC CAC GGG CTC AGC CTG CTC CTG    10826
Leu Pro Ala Trp Cys Ala Ser Leu Ala His Gly Leu Ser Leu Leu Leu
                3550                3555                3560
```

```
GTG GCT GTG GCT GTG GCT GTC TCA GGG TGG GTG GGT GCG AGC TTC CCC      10874
Val Ala Val Ala Val Ala Val Ser Gly Trp Val Gly Ala Ser Phe Pro
3565            3570                3575                3580

CCG GGC GTG AGT GTT GCG TGG CTC CTG TCC AGC AGC GCC AGC TTC CTG      10922
Pro Gly Val Ser Val Ala Trp Leu Leu Ser Ser Ser Ala Ser Phe Leu
                3585                3590                3595

GCC TCA TTC CTC GGC TGG GAG CCA CTG AAG GTC TTG CTG GAA GCC CTG      10970
Ala Ser Phe Leu Gly Trp Glu Pro Leu Lys Val Leu Leu Glu Ala Leu
            3600                3605                3610

TAC TTC TCA CTG GTG GCC AAG CGG CTG CAC CCG GAT GAA GAT GAC ACC      11018
Tyr Phe Ser Leu Val Ala Lys Arg Leu His Pro Asp Glu Asp Asp Thr
        3615                3620                3625

CTG GTA GAG AGC CCG GCT GTG ACG CCT GTG AGC GCA CGT GTG CCC CGC      11066
Leu Val Glu Ser Pro Ala Val Thr Pro Val Ser Ala Arg Val Pro Arg
    3630                3635                3640

GTA CGG CCA CCC CAC GGC TTT GCA CTC TTC CTG GCC AAG GAA GAA GCC      11114
Val Arg Pro Pro His Gly Phe Ala Leu Phe Leu Ala Lys Glu Glu Ala
3645                3650                3655                3660

CGC AAG GTC AAG AGG CTA CAT GGC ATG CTG CGG AGC CTC CTG GTG TAC      11162
Arg Lys Val Lys Arg Leu His Gly Met Leu Arg Ser Leu Leu Val Tyr
                3665                3670                3675

ATG CTT TTT CTG CTG GTG ACC CTG CTG GCC AGC TAT GGG GAT GCC TCA      11210
Met Leu Phe Leu Leu Val Thr Leu Leu Ala Ser Tyr Gly Asp Ala Ser
            3680                3685                3690

TGC CAT GGG CAC GCC TAC CGT CTG CAA AGC GCC ATC AAG CAG GAG CTG      11258
Cys His Gly His Ala Tyr Arg Leu Gln Ser Ala Ile Lys Gln Glu Leu
        3695                3700                3705

CAC AGC CGG GCC TTC CTG GCC ATC ACG CGG TCT GAG GAG CTC TGG CCA      11306
His Ser Arg Ala Phe Leu Ala Ile Thr Arg Ser Glu Glu Leu Trp Pro
    3710                3715                3720

TGG ATG GCC CAC GTG CTG CTG CCC TAC GTC CAC GGG AAC CAG TCC AGC      11354
Trp Met Ala His Val Leu Leu Pro Tyr Val His Gly Asn Gln Ser Ser
3725                3730                3735                3740

CCA GAG CTG GGG CCC CCA CGG CTG CGG CAG GTG CGG CTG CAG GAA GCA      11402
Pro Glu Leu Gly Pro Pro Arg Leu Arg Gln Val Arg Leu Gln Glu Ala
                3745                3750                3755

CTC TAC CCA GAC CCT CCC GGC CCC AGG GTC CAC ACG TGC TCG GCC GCA      11450
Leu Tyr Pro Asp Pro Pro Gly Pro Arg Val His Thr Cys Ser Ala Ala
            3760                3765                3770

GGA GGC TTC AGC ACC AGC GAT TAC GAC GTT GGC TGG GAG AGT CCT CAC      11498
Gly Gly Phe Ser Thr Ser Asp Tyr Asp Val Gly Trp Glu Ser Pro His
        3775                3780                3785
```

```
AAT GGC TCG GGG ACG TGG GCC TAT TCA GCG CCG GAT CTG CTG GGG GCA    11546
Asn Gly Ser Gly Thr Trp Ala Tyr Ser Ala Pro Asp Leu Leu Gly Ala
    3790                3795                3800

TGG TCC TGG GGC TCC TGT GCC GTG TAT GAC AGC GGG GGC TAC GTG CAG    11594
Trp Ser Trp Gly Ser Cys Ala Val Tyr Asp Ser Gly Gly Tyr Val Gln
3805            3810                3815                    3820

GAG CTG GGC CTG AGC CTG GAG GAG AGC CGC GAC CGG CTG CGC TTC CTG    11642
Glu Leu Gly Leu Ser Leu Glu Glu Ser Arg Asp Arg Leu Arg Phe Leu
                3825                3830                3835

CAG CTG CAC AAC TGG CTG GAC AAC AGG AGC CGC GCT GTG TTC CTG GAG    11690
Gln Leu His Asn Trp Leu Asp Asn Arg Ser Arg Ala Val Phe Leu Glu
                3840                3845                3850

CTC ACG CGC TAC AGC CCG GCC GTG GGG CTG CAC GCC GCC GTC ACG CTG    11738
Leu Thr Arg Tyr Ser Pro Ala Val Gly Leu His Ala Ala Val Thr Leu
            3855                3860                3865

CGC CTC GAG TTC CCG GCG GCC GGC CGC GCC CTG GCC GCC CTC AGC GTC    11786
Arg Leu Glu Phe Pro Ala Ala Gly Arg Ala Leu Ala Ala Leu Ser Val
    3870                3875                3880

CGC CCC TTT GCG CTG CGC CGC CTC AGC GCG GGC CTC TCG CTG CCT CTG    11834
Arg Pro Phe Ala Leu Arg Arg Leu Ser Ala Gly Leu Ser Leu Pro Leu
3885                3890                3895                3900

CTC ACC TCG GTG TGC CTG CTG CTG TTC GCC GTG CAC TTC GCC GTG GCC    11882
Leu Thr Ser Val Cys Leu Leu Leu Phe Ala Val His Phe Ala Val Ala
                3905                3910                3915

GAG GCC CGT ACT TGG CAC AGG GAA GGG CGC TGG CGC GTG CTG CGG CTC    11930
Glu Ala Arg Thr Trp His Arg Glu Gly Arg Trp Arg Val Leu Arg Leu
                3920                3925                3930

GGA GCC TGG GCG CGG TGG CTG CTG GTG GCG CTG ACG GCG GCC ACG GCA    11978
Gly Ala Trp Ala Arg Trp Leu Leu Val Ala Leu Thr Ala Ala Thr Ala
            3935                3940                3945

CTG GTA CGC CTC GCC CAG CTG GGT GCC GCT GAC CGC CAG TGG ACC CGT    12026
Leu Val Arg Leu Ala Gln Leu Gly Ala Ala Asp Arg Gln Trp Thr Arg
    3950                3955                3960

TTC GTG CGC GGC CGC CCG CGC CGC TTC ACT AGC TTC GAC CAG GTG GCG    12074
Phe Val Arg Gly Arg Pro Arg Arg Phe Thr Ser Phe Asp Gln Val Ala
3965                3970                3975                3980

CAG CTG AGC TCC GCA GCC CGT GGC CTG GCG GCC TCG CTG CTC TTC CTG    12122
Gln Leu Ser Ser Ala Ala Arg Gly Leu Ala Ala Ser Leu Leu Phe Leu
                3985                3990                3995

CTT TTG GTC AAG GCT GCC CAG CAG CTA CGC TTC GTG CGC CAG TGG TCC    12170
Leu Leu Val Lys Ala Ala Gln Gln Leu Arg Phe Val Arg Gln Trp Ser
                4000                4005                4010
```

```
GTC TTT GGC AAG ACA TTA TGC CGA GCT CTG CCA GAG CTC CTG GGG GTC       12218
Val Phe Gly Lys Thr Leu Cys Arg Ala Leu Pro Glu Leu Leu Gly Val
        4015                4020                4025

ACC TTG GGC CTG GTG GTG CTC GGG GTA GCC TAC GCC CAG CTG GCC ATC       12266
Thr Leu Gly Leu Val Val Leu Gly Val Ala Tyr Ala Gln Leu Ala Ile
        4030                4035                4040

CTG CTC GTG TCT TCC TGT GTG GAC TCC CTC TGG AGC GTG GCC CAG GCC       12314
Leu Leu Val Ser Ser Cys Val Asp Ser Leu Trp Ser Val Ala Gln Ala
4045                4050                4055                4060

CTG TTG GTG CTG TGC CCT GGG ACT GGG CTC TCT ACC CTG TGT CCT GCC       12362
Leu Leu Val Leu Cys Pro Gly Thr Gly Leu Ser Thr Leu Cys Pro Ala
                4065                4070                4075

GAG TCC TGG CAC CTG TCA CCC CTG CTG TGT GTG GGG CTC TGG GCA CTG       12410
Glu Ser Trp His Leu Ser Pro Leu Leu Cys Val Gly Leu Trp Ala Leu
                    4080                4085                4090

CGG CTG TGG GGC GCC CTA CGG CTG GGG GCT GTT ATT CTC CGC TGG CGC       12458
Arg Leu Trp Gly Ala Leu Arg Leu Gly Ala Val Ile Leu Arg Trp Arg
            4095                4100                4105

TAC CAC GCC TTG CGT GGA GAG CTG TAC CGG CCG GCC TGG GAG CCC CAG       12506
Tyr His Ala Leu Arg Gly Glu Leu Tyr Arg Pro Ala Trp Glu Pro Gln
        4110                4115                4120

GAC TAC GAG ATG GTG GAG TTG TTC CTG CGC AGG CTG CGC CTC TGG ATG       12554
Asp Tyr Glu Met Val Glu Leu Phe Leu Arg Arg Leu Arg Leu Trp Met
4125                4130                4135                4140

GGC CTC AGC AAG GTC AAG GAG TTC CGC CAC AAA GTC CGC TTT GAA GGG       12602
Gly Leu Ser Lys Val Lys Glu Phe Arg His Lys Val Arg Phe Glu Gly
                4145                4150                4155

ATG GAG CCG CTG CCC TCT CGC TCC TCC AGG GGC TCC AAG GTA TCC CCG       12650
Met Glu Pro Leu Pro Ser Arg Ser Ser Arg Gly Ser Lys Val Ser Pro
                    4160                4165                4170

GAT GTG CCC CCA CCC AGC GCT GGC TCC GAT GCC TCG CAC CCC TCC ACC       12698
Asp Val Pro Pro Pro Ser Ala Gly Ser Asp Ala Ser His Pro Ser Thr
            4175                4180                4185

TCC TCC AGC CAG CTG GAT GGG CTG AGC GTG AGC CTG GGC CGG CTG GGG       12746
Ser Ser Ser Gln Leu Asp Gly Leu Ser Val Ser Leu Gly Arg Leu Gly
        4190                4195                4200

ACA AGG TGT GAG CCT GAG CCC TCC CGC CTC CAA GCC GTG TTC GAG GCC       12794
Thr Arg Cys Glu Pro Glu Pro Ser Arg Leu Gln Ala Val Phe Glu Ala
4205                4210                4215                4220

CTG CTC ACC CAG TTT GAC CGA CTC AAC CAG GCC ACA GAG GAC GTC TAC       12842
Leu Leu Thr Gln Phe Asp Arg Leu Asn Gln Ala Thr Glu Asp Val Tyr
                4225                4230                4235
```

```
CAG CTG GAG CAG CAG CTG CAC AGC CTG CAA GGC CGC AGG AGC AGC CGG          12890
Gln Leu Glu Gln Gln Leu His Ser Leu Gln Gly Arg Arg Ser Ser Arg
        4240                4245                4250

GCG CCC GCC GGA TCT TCC CGT GGC CCA TCC CCG GGC CTG CGG CCA GCA          12938
Ala Pro Ala Gly Ser Ser Arg Gly Pro Ser Pro Gly Leu Arg Pro Ala
        4255                4260                4265

CTG CCC AGC CGC CTT GCC CGG GCC AGT CGG GGT GTG GAC CTG GCC ACT          12986
Leu Pro Ser Arg Leu Ala Arg Ala Ser Arg Gly Val Asp Leu Ala Thr
        4270                4275                4280

GGC CCC AGC AGG ACA CCC CTT CGG GCC AAG AAC AAG GTC CAC CCC AGC          13034
Gly Pro Ser Arg Thr Pro Leu Arg Ala Lys Asn Lys Val His Pro Ser
4285                4290                4295                4300

AGC ACT TAGTCCTCCT TCCTGGCGGG GGTGGGCCGT GGAGTCGGAG TGGACACCGC           13090
Ser Thr

TCAGTATTAC TTTCTGCCGC TGTCAAGGCC GAGGGCCAGG CAGAATGGCT GCACGTAGGT        13150

TCCCCAGAGA GCAGGCAGGG GCATCTGTCT GTCTGTGGGC TTCAGCACTT TAAAGAGGCT        13210

GTGTGGCCAA CCAGGACCCA GGGTCCCCTC CCCAGCTCCC TTGGGAAGGA CACAGCAGTA        13270

TTGGACGGTT TCTAGCCTCT GAGATGCTAA TTTATTTCCC CGAGTCCTCA GGTACAGCGG        13330

GCTGTGCCCG GCCCCACCCC CTGGGCAGAT GTCCCCCACT GCTAAGGCTG CTGGCTTCAG        13390

GGAGGGTTAG CCTGCACCGC CGCCACCCTG CCCCTAAGTT ATTACCTCTC CAGTTCCTAC        13450

CGTACTCCCT GCACCGTCTC ACTGTGTGTC TCGTGTCAGT AATTTATATG GTGTTAAAAT        13510

GTGTATATTT TTGTATGTCA CTATTTTCAC TAGGGCTGAG GGGCCTGCGC CCAGAGCTGG        13570

CCTCCCCCAA CACCTGCTGC GCTTGGTAGG TGTGGTGGCG TTATGGCAGC CCGGCTGCTG        13630

CTTGGATGCG AGCTTGGCCT TGGGCCGGTG CTGGGGCAC AGCTGTCTGC CAGGCACTCT         13690

CATCACCCCA GAGGCCTTGT CATCCTCCCT TGCCCCAGGC CAGGTAGCAA GAGAGCAGCG        13750

CCCAGGCCTG CTGGCATCAG GTCTGGGCAA GTAGCAGGAC TAGGCATGTC AGAGGACCCC        13810

AGGGTGGTTA GAGGAAAAGA CTCCTCCTGG GGGCTGGCTC CCAGGGTGGA GGAAGGTGAC        13870

TGTGTGTGTG TGTGTGTGCG CGCGCGCACG CGCGAGTGTG CTGTATGGCC CAGGCAGCCT        13930

CAAGGCCCTC GGAGCTGGCT GTGCCTGCTT CTGTGTACCA CTTCTGTGGG CATGGCCGCT        13990

TCTAGAGCCT CGACACCCCC CCAACCCCCG CACCAAGCAG ACAAAGTCAA TAAAGAGCT         14050

GTCTGACTGC                                                               14060
```

FIGURE 4A

```
Homologue  5' GGAAACAGGT TTGGAGAGGT GACACGACCT GTCCCAGGCA TCACAGCCAG
Authentic  5' GGAAACAGGT TTGGAGAGGT GACACGACCT GTC::::::: ::::::::::

Homologue     GACAGGACCT GTCCAGGCAT CACAGCCGGG ATGTGCATAG CAGGGGTTTG
Authentic     ::::::::::  ::CCAGGCAT CACAGCCGGG ATGTGCATAG CAGGGGTTTG Homologue     GAACTATGAG GTGCCCAGGA CCCAGGGTTG GATTGAAAAG GGCGCAGGGG ACTAAGATAA-3' (SEQ ID NO:18)
Authentic     GAACTATGAG GTGCCCAGGA CCCAGGGTTG GATTGAAAAG GGCGCAGGGG ACTAAGATAA-3' (SEQ ID NO:19)
```

FIGURE 4B

5'-AGGACCTGTCCAGGCATC*-3'    (SEQ ID NO:10)

FIGURE 7

```
3601 CGCCCGCGCCGCCGCTTCACTAGCTTCGACCAGTGGCGCACgTGAGCTCCGCAGCCCGTGGC  3660  (SEQ ID NO:20)
1201  R  P  R  R  R  F  T  S  F  D  Q  V  A  h  v  S  S  A  A  R  G         1220  (SEQ ID NO:21)
      :  :  :  :  :  :  :  :  :  :  :  :  :  X  X  :  :  :  :  :  :
      R  P  R  R  R  F  T  S  F  D  Q  V  A  Q  L  S  S  A  A  R  G                (SEQ ID NO:23)
      CGCCCGCGCCGCCGCTTCACTAGCTTCGACCAGTGGCGCAGTGAGCTCCGCAGCCCGTGGC               (SEQ ID NO:22)

3697 GCTGCCCCAGCACgTACGCTTCGTGCGCCAGTGGTCCGTCTTTGGCAAGACATTATGCCGA  3756  (SEQ ID NO:24)
1233  A  A  Q  H  V  R  F  V  R  Q  W  S  V  F  G  K  T  L  C  R         1252  (SEQ ID NO:25)
      :  :  X  X  :  :  :  :  :  :  :  :  :  :  :  :  :  :  :  :
      A  A  Q  Q  L  R  F  V  R  Q  W  S  V  F  G  K  T  L  C  R                (SEQ ID NO:27)
      GCTGCCCCAGCAGCTACGCTTCGTGCGCCAGTGGTCCGTCTTTGGCAAGACATTATGCCGA               (SEQ ID NO:26)

4540 CTGGCCACTGGCCCCCAGCAGGACACCTTCGGGCCAAGAACAAGGTCCACCCCAGCAGCACTTAGTCCTCTCCTTCCTGGGGG  4620  (SEQ ID NO:28)
1514  L  A  T  G  P  P  S  R  T  P  s  g  q  e  q  g  p  p  q  h  l  v  l  l  p  g  g    1540  (SEQ ID NO:29)
      :  :  :  :  :  :  :  :  :  :                                                        
      L  A  T  G  P  S  R  T  P  L  R  A  K  N  K  V  H  P  S  S  T                      (SEQ ID NO:31)
      CTGGCCACTGGCCCCCAGCAGGACACCCCTTCGGGCCAAGAACAAGGTCCACCCCAGCAGCACTTAGTCCTCCTTCCTGGCG      (SEQ ID NO:30)
```

FIGURE 13

|  |  | SEQ ID NO: |
|---|---|---|
| Exon 3: | ALTHGHSLLRDVSHNLLRALDVGLLANLSALAEL | 32 |
| LRG: | LHGLKALGHLDLSGNRLRKLPPGLLANFTLLRTL | 33 |
| GPIX: | PALPARTRHLLLANNSLQSVPPGAFDHLPQLQTL | 34 |
| GPIa: | GQTLPALTVLDVSFNRLTSLPLGALRGLGELQEL | 35 |
| GPIb: | TAFPVDTTELVLTGNNLTALPPGLLDALPALRTA | 36 |
| Toll (LRR 8): | LEHQVNLLSLDLSNNALTHLPDSLFAHTTNLTDL | 37 |
| SLIT (LRR 4): | IRHLRSLTRLDLSNNQITILSNYTFANLTKLSTL | 38 |
| Chaoptin: | FGNMPHLQWLDLSYNWIHELDFDAFKNTKQLQLV | 39 |
| CONSENSUS: | ---------LDLS-N-LT-LP-GLLA-L--L-TL | 40 |
|  |          I        AF |  |

|  |  |  |
|---|---|---|
| Exon 4: | GPQHLPLPCRNLSGNPFECDCGLAWLPRWAEE | 41 |
| LRG: | QPNWDMRDGFDISGNPWICDQNLSDLYRWLQA | 42 |
| TRKA: | TVQGLSLQELVLSGNPLHCSCALRWLQRWEEE | 43 |
| GPIX: | FDHLPQLQTLDVTQNPWHCDCSLTYLRLWLED | 44 |
| GPIa: | FFGSHLLPFAFLHGNPWLCNCEILYFRRWLQD | 45 |
| GPIb: | LDALPALRTAHLGANPWRCDCRLVPLRAWLAG | 46 |
| Toll: | LNRTMKWRSVKLSGNPWMCDCTAKPLLLFTQD | 47 |
| Slit (4): | FEDLKSLTHIALGSNPLYCDCGLKWFSDWIKL | 48 |
| CONSENSUS: | ------L----LSGNPW-CDC-L-WL-RW--- | 49 |

|  |  |  |
|---|---|---|
| EXON 8: | TATRWDFGDGSAEVDAAGPAASHRYVLPGRYHVTA | 50 |
| EXON 19: | VLYTWDFGDGSPVLTQSQPAANHTYASRGTYHVRL | 51 |
| EXON 21: | VAYHWDFGDGSPGQDTDEPRAEHSYLRPGDYRVQV | 52 |
| Pmel-17: | LSYTWDFGDSSGTLISRAPVVTHTYLEPGPVTAQV | 53 |
| RPE-1: | LSYTWDFGDSTGTLISRALTVTHTYLESGPVTAQV | 54 |
| CONSENSUS: | --YTWDFGDGS--L----P-A-HTYL-PG-Y-VQV | 55 |

Exon Trapping of the PKD1 Locus

POLYCYSTIC KIDNEY DISEASE GENE AND PROTEIN

This application is a continuation-in-part of U.S. patent application Ser. No. 08/381,520, filed Jan. 31, 1995 now abandoned.

FIELD OF THE INVENTION

The present invention pertains to the diagnosis and treatment of polycystic kidney disease in humans, using DNA sequences derived from the human PKD1 gene and the protein or proteins encoded by that gene.

BACKGROUND OF THE INVENTION

Autosomal dominant polycystic kidney disease (APKD), also called adult-onset polycystic kidney disease, is one of the most common hereditary disorders in humans, affecting approximately one individual in a thousand. The prevalence in the United States is greater than 500,000, with 6,000 to 7,000 new cases detected yearly (Striker et al., *Am. J. Nephrol.*, 6:161–164, 1986; Iglesias et al., *Am. J. Kid. Dis.*, 2:630–639, 1983). The disease is considered to be a systemic disorder, characterized by cyst formation in the ductal organs such as kidney, liver, and pancreas, as well as by gastrointestinal, cardiovascular, and musculoskeletal abnormalities, including colonic diverticulitis, berry aneurysms, hernias, and mitral valve prolapse (Gabow et al., *Adv. Nephrol.*, 18:19–32, 1989; Gabow, *New Eng. J. Med.*, 329:332–342, 1993).

The most prevalent and obvious symptom of APKD, however, is the formation of kidney cysts, which result in grossly enlarged kidneys and a decrease in renal-concentrating ability. Hypertension and endocrine abnormalities are also common in APKD patients, appearing even before symptoms of renal insufficiency. In approximately half of APKD patients, the disease progresses to end-stage renal disease; accordingly, APKD is responsible for 4–8% of the renal dialysis and transplantation cases in the United States and Europe (*Proc. European Dialysis and Transplant Assn.*, Robinson and Hawkins, eds., 17:20, 1981). Thus, there is a need in the art for diagnostic and therapeutic tools to reduce the incidence and severity of this disease.

APKD exhibits a transmission pattern typical of autosomal dominant inheritance, i.e., each offspring of an affected individual has a 50% chance of inheriting the causative gene. Linkage studies indicated that a causative gene is present on the short arm of chromosome 16, near the α-globin cluster; this locus was designated PKD1 (Reeders et al., *Nature*, 317:542, 1985). Though other PKD-associated genes exist, such as, for example, PKD2, PKD1 defects appear to cause APKD in about 85–90% of affected families (Parfrey et al., *New Eng. J. Med.*, 323:1085–1090, 1990; Peters et al., *Contrib. Nephrol.*, 97:128–139, 1992).

The PKD1 gene has been localized to chromosomal position 16p13.3. Using extensive linkage analysis, in conjunction with the identification of new markers and restriction enzyme analysis, the gene has been further localized to an interval of approximately 700 kb between the markers ATPL (ATP6C) and CMM65 (D16S84). The region is rich in CpG islands that are thought to flank transcribed sequences, and it has been estimated that this interval contains at least 20 genes. The precise location of the PKD1 gene was pinpointed by the finding of a PKD family whose affected members carry a translocation that disrupts a 14 kb RNA transcript associated with this region, as reported in the European PKD Consortium (EPKDC), *Cell*, 77:881, 1994, describing approximately 5631 bp of DNA sequence corresponding to the 3' end of the putative PKD1 cDNA sequence.

Notwithstanding knowledge of the partial PKD1 3' cDNA sequence, several significant impediments stand in the way of determining the complete sequence of the PKD1 gene. For the most part, these impediments arise from the complex organization of the PKD1 locus. One serious obstacle is that sequences related to the PKD1 transcript are duplicated at least three times on chromosome 16 proximal to the PKD1 locus, forming PKD1 homologues. Another obstacle is that the PKD1 genomic interval also contains repeat elements that are present in other genomic regions. Both of these types of sequence duplications interfere with "chromosome walking" techniques that are widely used for identification of genomic DNA. This is because these techniques rely on hybridization to identify clones containing overlapping fragments of genomic DNA; thus, there is a high likelihood of "walking" into clones derived from PKD1 homologues instead of clones derived from the authentic PKD1 gene. In a similar manner, the PKD1 duplications and chromosome 16-specific repeats also interfere with the unambiguous determination of a complete cDNA sequence that encodes the PKD1 protein. Thus, there is a need in the art for genomic and cDNA sequences corresponding to the authentic PKD1 gene. This includes identification of segments of these sequences that are unique to the expressed PKD1 and not are present in the duplicated homologous sequences also present on chromosome 16.

SUMMARY OF THE INVENTION

The present invention involves an isolated normal human PKD1 gene having the sequence set forth in FIG. 1, sequences derived therefrom such as the sequence set forth in FIG. 2, an isolated nucleic acid having the PKD1 cDNA sequence set forth in FIG. 3, and sequences derived therefrom. The PKD1 gene is a genomic DNA sequence whose altered, defective, or non-functional expression leads to adult-onset polycystic kidney disease. The invention also encompasses DNA vectors comprising these nucleic acids, cells transformed with the vectors, and methods for producing PKD1 protein or fragments thereof.

In another aspect, the invention involves isolated oligonucleotides that hybridize only to the authentic expressed PKD1 gene, and not to PKD1 homologues.

In yet another aspect, the invention involves isolated mutant PKD1 genes, and their cDNA cognates, which contain alterations in nucleotide sequence relative to the normal PKD1 gene, and whose presence in one or more copies in the genome of a human individual is associated with adult-onset polycystic kidney disease.

In still another aspect, the invention involves isolated oligonucleotides that discriminate between normal and mutant versions of the PKD1 gene.

In still another aspect, the invention involves methods for identifying a human subject carrying a mutant PKD1 gene in a human subject, comprising:

a) obtaining a sample of biological material from the subject, and b) detecting the presence of the mutant gene or its protein product.

In still another aspect, the invention involves methods and compositions for treating APKD or disease conditions having the characteristics of APKD. Such methods encompass administering an isolated human PKD1 gene, or fragments of the gene, under conditions that result in expression of therapeutically effective amounts of all, or part of, the PKD1 protein. The invention also encompasses compositions for treating APKD that comprise all or part of the PKD1 DNA of FIGS. 1, 2 and 3, or the PKD1 protein encoded by the DNA of FIGS. 1, 2 or 3.

BRIEF DESCRIPTION OF THE DRAWINGS

FIG. 1A shows the DNA sequence of the human PKD1 locus between chromosomal markers ATPL (ATP6C) and D16S84. (SEQ ID NO:1).

FIG. 1B shows the DNA sequence of 53,526 bases comprising the normal human PKD1 gene. (SEQ ID NO:2).

FIG. 2 shows a partial DNA sequence of 894 bases within the 5' region of normal human PKD1 DNA. (SEQ ID NO:3)

FIG. 3 shows the full-length sequence of normal human PKD1 cDNA and corresponding amino acid sequence. (SEQ ID NOS:4–5).

FIG. 4A shows a comparison of the DNA sequence of the 5' region of DNAs derived from the authentic PKD1 gene (SEQ ID NO:19) and PKD1 homologues (SEQ ID NO:18). A 29-base pair gap must be introduced into the sequence of the authentic gene to align the two sequences. In addition, the authentic PKD1 and the PKD1 homologue differ at position 418 of this figure.

FIG. 4B shows the DNA sequence of an oligonucleotide that can be used to discriminate between the authentic PKD1 sequence and PKD1 homologues. The star denotes a polymerization-blocking modification. (SEQ ID NO:10).

FIG. 7 shows a comparison between the previously reported (EPKDC) partial PKD1 cDNA (SEQ ID NOS:20, 21, 24, 25,28 and 29) sequence and the sequence reported herein (SEQ ID NOS: 22,23,26, 27, 30 and 31). The upper sequence is that reported for the cDNA (EPKDC), while the lower sequence is the genomic sequence of the present invention. Discrepancies are highlighted by lower case in the cDNA (EPKDC) sequence and by boxes in the genomic sequence with the corresponding changes in amino acids denoted with X's. The altered carboxy-terminal residues resulting from the frame shift are shown above the genomic sequence and the previously predicted residues are shown in lowercase. An in-frame termination codon is indicated by an underline in the genomic sequence.

FIG. 13 shows regions of homology in the PKD1 gene between sequences encoded by GRAIL2-predicted exons and proteins present in SwissProt and PIR databases. (SEQ ID NOS: 32–55). Positions where the PKD1 sequence matches the consensus sequence are shaded.

DETAILED DESCRIPTION OF THE INVENTION

Figure 5:
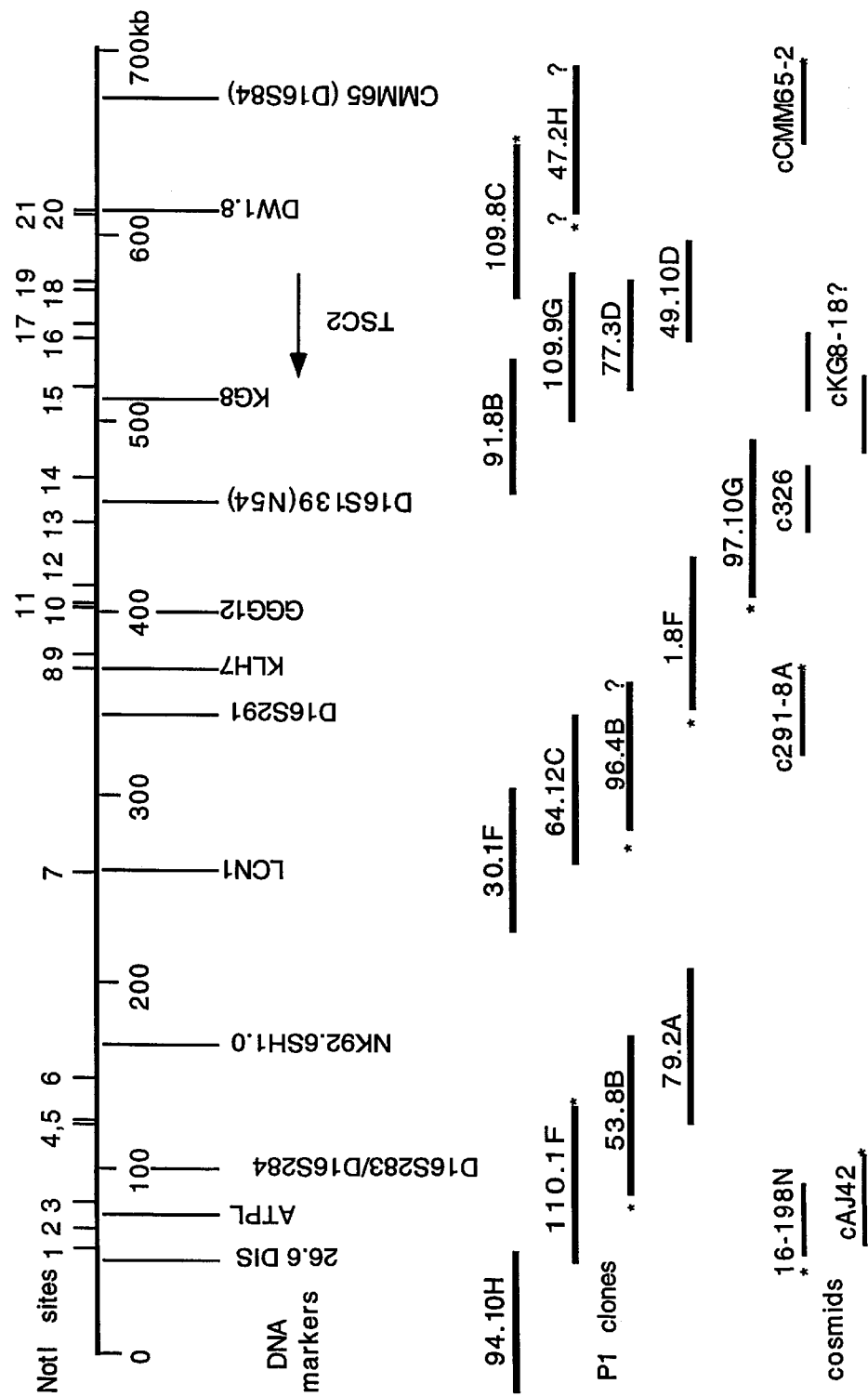
FIG. 5 shows the region of chromosome 16 containing the PKD1 locus. The upper panel shows NotI restriction sites, as well as previously identified genetic markers in this region. The bottom panel shows P1 clones covering this region.

All patent applications, patents, and literature references cited in this specification are hereby incorporated by reference in their entirety. In case of conflict or inconsistency, the present description, including definitions, will control.

Definitions:

1. "APKD" as used herein denotes adult-onset polycystic kidney disease, which is characterized by the development of renal cysts and, ultimately, renal failure, and may alternatively or in addition involve cysts in other organs including liver and spleen, as well as gastrointestinal, cardiovascular, and musculoskeletal abnormalities.

2. The term "PKD1 gene" refers to a genomic DNA sequence which maps to chromosomal position 16p13.3 and gives rise to a messenger RNA molecule encoding the PKD1 protein. The PKD1 gene encompasses the sequences shown in FIGS. 1 and 2, which includes introns and putative regulatory sequences. The term "authentic" is used herein to denote the genomic sequence at this location, as well as sequences derived therefrom, and serves to distinguish these authentic sequences from "PKD1 homologues" (see below).

3. "PKD1 complementary DNA (cDNA)" is defined herein as a single-stranded or double-stranded intronless DNA molecule encompassing the sequence shown in FIG. 3, that is derived from the authentic PKD1 gene and whose sequence, or complement thereof, encodes the PKD1 protein shown in FIG. 3.

4. A "normal" PKD1 gene is defined herein as a PKD1 gene whose altered, defective, or non-functional expression leads to adult-onset polycystic kidney disease. A normal PKD1 gene is not associated with disease and thus is considered to be a wild-type version of the gene. Included in this category are allelic variants in the PKD1 gene, also denoted allelic polymorphisms, i.e. alternate versions of the PKD1 gene, not associated with disease, that may be represented at any frequency in the population. Also included are alterations in DNA sequence, whether recombinant or naturally occurring, that have no apparent effect on expression or function of the PKD1 gene product.

5. A "mutant" PKD1 gene is defined herein as a PKD1 gene whose sequence has been modified by transitions, transversions, deletions, insertions, or other modifications relative to the normal PKD1 gene, which modifications cause detectable changes in the expression or function of the PKD1 gene product, including causing disease. The modifications may involve from one to as many as several thousand nucleotides, and result in one or more of a variety of changes in PKD1 gene expression, such as, for example, decreased or increased rates of expression, or expression of a defective RNA transcript or protein product. Mutant PKD1 genes encompass those genes whose presence in one or more copies in the genome of a human individual is associated with APKD.

6. A "PKD1 homologue" is a sequence which is closely related to PKD1, but which does not encode the authentic expressed PKD1 gene product. Several examples of such homologues that map to chromosomal location 16p13.1 have been identified and sequenced by the present inventors.

7. A "PKD1 carrier" is defined herein as an individual who carries at least one copy of a disease-producing mutant PKD1 gene. Since the disease generally exhibits an autosomal dominant pattern of transmission, PKD1 carriers have a high probability of developing some symptom of PKD. Thus, a PKD1 carrier is likely to be a "PKD patient."

8. As referred to herein, a "contig" is a continuous stretch of DNA or DNA sequence, which may be represented by multiple, overlapping, clones or sequences.

9. As referred to herein, a "cosmid" is a DNA plasmid that can replicate in bacterial cells and that accommodates large DNA inserts from about 30 to about 45 kb in length.

10. The term "P1 clones" refers to genomic DNAs cloned into vectors based on the P1 phage replication mechanisms. These vectors generally accommodate inserts of about 70 to about 105 kb (Pierce et al., *Proc. Natl. Acad. Sci., USA*, 89:2056–2060, 1992).

11. As used herein, the term "exon trapping" refers to a method for isolating genomic DNA sequences that are flanked by donor and acceptor splice sites for RNA processing.

12. The term "single-strand conformational polymorphism analysis" (SSCP) refers to a method for detecting sequence differences between two DNAs, comprising hybridization of the two species with subsequent mismatch detection by gel electrophoresis. (Ravnik-Glavac et al., *Hum. Mol. Genet.*, 3:801, 1994).

13. "HOT cleavage" is defined herein as a method for detecting sequence differences between two DNAs, comprising hybridization of the two species with subsequent mismatch detection by chemical cleavage (Cotton, et al., *Proc. Natl. Acad. Sci., USA*, 85:4397, 1988).

14. "Denaturing gradient gel electrophoresis" (DDGE) refers to a method for resolving two DNA fragments of identical length on the basis of sequence differences as small as a single base pair change, using electrophoresis through a gel containing varying concentrations of denaturant (Guldberg et al., *Nuc. Acids Res.*, 22:880, 1994).

15. As used herein, "sequence-specific oligonucleotides" refers to related sets of oligonucleotides that can be used to detect allelic variations or mutations in the PKD1 gene.

16. As used herein, "PKD1-specific oligonucleotides" refers to oligonucleotides that hybridize to sequences present in the authentic expressed PKD1 gene and not to PKD1 homologues or other sequences.

17. "Amplification" of DNA as used herein denotes a reaction that serves to increase the concentration of a particular DNA sequence within a mixture of DNA sequences. Amplification may be carried out using polymerase chain reaction (PCR) (Saiki et al., *Science*, 239:487, 1988), ligase chain reaction (LCR), nucleic acid-specific based amplification (NSBA), or any method known in the art.

18. "RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

19. A PKD1 gene or PKD1 cDNA, whether normal or mutant, corresponding to a particular sequence is understood to include alterations in the particular sequence that do not change the inherent properties of the sequence. It will be understood that additional nucleotides may be added to the 5'- and/or 3'-terminus of the PKD1 gene shown in FIG. 1B, or the PKD1 cDNA shown in FIG. 3, as part of routine recombinant DNA manipulations. Furthermore, conservative DNA substitutions, i.e. changes in the sequence of the protein-coding region that do not change the encoded amino acid sequence, may also be accommodated.

The present invention encompasses the human gene for PKD1. Mutations in this gene are associated with the occurrence of adult-onset polycystic kidney disease. A "normal" version of the genomic sequence, corresponding to 53,526 bases of the PKD1 gene is shown in FIG. 1B.

The PKD1 gene sequence was determined using the strategy described in Example 1. Briefly, a series of cosmid and P1 DNA clones was assembled containing overlapping human genomic DNA sequences that collectively cover a 700 kilobase segment of chromosome 16 known to contain the PKD1 locus. To identify transcribed sequences within this 700 kb segment, including those sequences encoding PKD1, both exon trapping and cDNA selection techniques were employed. At the same time, direct DNA sequencing of the human DNA sequences contained in the genomic clones was performed, using techniques that are well-known in the art. These included the isolation of subclones from particular cosmid or P1 clones. Nested deletions were created from selected subclones, and the nested deletions were then subjected to direct DNA sequencing using the ALF™ automated sequencer (Pharmacia, Uppsala, Sweden).

The full-length sequence of PKD1 cDNA is shown in FIG. 3.

The present invention encompasses isolated oligonucleotides corresponding to sequences within the PKD1 gene, or within PKD1 cDNA, which, alone or together, can be used to discriminate between the authentic expressed PKD1 gene and PKD1 homologues or other repeated sequences. These oligonucleotides may be from about 12 to about 60 nucleotides in length, preferably about 18 nucleotides, may be single- or double-stranded, and may be labelled or modified as described below. An example of an oligonucleotide that can be used in this manner is shown in FIG. 4B. The discrimination function of this oligonucleotide is based on a comparison of the sequence of the authentic PKD1 gene with three cDNAs derived from the PKD1 homologues, which revealed that homologue cDNAs contain a 29 bp insertion relative to the authentic PKD1 sequence (FIG. 4A). The oligonucleotide shown in FIG. 4B is modified at its 3' terminus so that it does not support polymerization reactions, and is designed to hybridize specifically to the homologue sequence and not to the authentic PKD1 sequence. When this oligonucleotide is included in amplification reactions, it selectively prevents the amplification of PKD1 homologue sequences. In this manner, authentic PKD1 sequences are selectively amplified and PKD1 homologues are not. These oligonucleotides or their functional equivalents thus provide a basis for testing for the presence of mutations in the authentic PKD1 gene in a human patient (see Example 5 below).

The present invention encompasses isolated DNA and RNA sequences, including sense and antisense sequences, derived from the sequences shown in FIGS. 1, 2, and 3. The particular sequences may represent "normal" alleles of PKD1, including allelic variants, or "mutant" alleles, which are associated with disease symptoms. PKD1-derived sequences may also be associated with heterologous sequences, including promoters, enhancers, response elements, signal sequences, polyadenylation sequences, and the like. Furthermore, the nucleic acids can be modified to alter stability, solubility, binding affinity, and specificity. For example, PKD1-derived sequences can be selectively methylated.

The DNA may comprise antisense oligonucleotides, and may further include nuclease-resistant phosphorothioate, phosphoroamidate, and methylphosphonate derivatives, as well as "protein nucleic acid" (PNA) formed by conjugating bases to an amino acid backbone as described in Nielsen et al., *Science,* 254: 1497, 1991. The DNA may be derivatized by linkage of the a-anomer nucleotide, or by formation of a methyl or ethyl phosphotriester or an alkyl phosphoramidate linkage. Furthermore, the nucleic acid sequences of the present invention may also be modified with a label capable of providing a detectable signal, either directly or indirectly.

Exemplary labels include radioisotopes, fluorescent molecules, biotin, and the like.

In general, nucleic acid manipulations according to the present invention use methods that are well known in the art, as disclosed in, for example, *Molecular Cloning, A Laboratory Manual* (2nd Ed., Sambrook, Fritsch and Maniatis, Cold Spring Harbor), or *Current Protocols in Molecular Biology* (Eds. Ausubel, Brent, Kingston, More, Feidman, Smith and Struhl, Greene Publ. Assoc., Wiley-Interscience, NY, N.Y., 1992).

The invention also provides vectors comprising nucleic acids having PKD1 or PKD1-related sequences. A large number of vectors, including plasmid, phage, viral and fungal vectors, have been described for expression in a variety of eukaryotic and prokaryotic hosts, and may be used for gene therapy as well as for simple protein expression. Advantageously, vectors may also include a promoter operably linked to the PKD1-encoding portion, particularly when the PKD1-encoding portion comprises the cDNA shown in FIG. 3 or derivatives or fragments thereof. The encoded PKD1 may be expressed by using any suitable vectors, such as pREP4, pREP8, or pCEP4 (InVitrogen, San Diego, Calif.), and any suitable host cells, using methods disclosed or cited herein or otherwise known to those skilled in the relevant art. The particular choice of vector/host is not critical to the operation of the invention.

Recombinant cloning vectors will often include one or more replication systems for cloning or expression, one or more markers for selection in the host, e.g. antibiotic resistance, and one or more expression cassettes. The inserted PKD1 coding sequences may be synthesized, isolated from natural sources, or prepared as hybrids, for example. Ligation of the PKD1 coding sequences to transcriptional regulatory elements and/or to other amino acid coding sequences may be achieved by known methods. Suitable host cells may be transformed/transfected/infected by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *E. coli, B. Subtilis, Saccharomyces cerevisiae,* SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, artificial chromosomes, and the like. A large number of transcription initiation and termination regulatory regions have been isolated and shown to be effective in the transcription and translation of heterologous proteins in the various hosts. Examples of these regions, methods of isolation, manner of manipulation, and the like, are known in the art. Under appropriate expression conditions, host cells can be used as a source of recombinantly produced PKD1.

This invention also contemplates the use of unicellular or multicellular organisms whose genome has been transfected or transformed by the introduction of PKD1 coding sequences through any suitable method, in order to obtain recombinantly produced PKD1 protein or peptides derived therefrom.

Nucleic acids encoding PKD1 polypeptides may also be incorporated into the genome of recipient cells by recombination events. For example, such a sequence can be microinjected into a cell, and thereby effect homologous recombination at the site of an endogenous gene encoding PKD1, an analog or pseudogene thereof, or a sequence with substantial identity to a PKD1-encoding gene. Other recombination-based methods such as nonhomologous recombinations or deletion of endogenous gene by homologous recombination, especially in pluripotent cells, may also be used.

The present invention also encompasses an isolated polypeptide having a sequence encoded by the authentic PKD1 gene, as well as peptides of six or more amino acids derived therefrom. The polypeptide(s) may be isolated from human tissues obtained by biopsy or autopsy, or may be produced in a heterologous cell by recombinant DNA methods as described above. Standard protein purification methods may be used to isolate PKD1-related polypeptides, including but not limited to detergent extraction, and chromatographic methods including molecular sieve, ion-exchange, and affinity chromatography using e.g. PKD1-specific antibodies or ligands. When the PKD1 polypeptide to be purified is produced in a recombinant system, the recombinant expression vector may comprise additional sequences that encode additional amino-terminal or carboxy-terminal amino acids; these extra amino acids act as "tags" for immunoaffinity purification using immobilized antibodies or for affinity purification using immobilized ligands.

Peptides comprising PKD1-specific sequences may be derived from isolated larger PKD1 polypeptides described above, using proteolytic cleavages by e.g. proteases such as trypsin and chemical treatments such as cyanogen bromide that are well-known in the art. Alternatively, peptides up to 60 residues in length can be routinely synthesized in milligram quantities using commercially available peptide synthesizers.

The present invention encompasses antibodies that specifically recognize the PKD1 polypeptide(s) encoded by the gene shown in FIGS. 1 and 2 or the cDNA shown in FIG. 3, and/or fragments or portions thereof. The antibodies may be polyclonal or monoclonal, may be produced in response to the native PKD1 polypeptide or to synthetic peptides as described above. Such antibodies are conveniently made using the methods and compositions disclosed in Harlow and Lane, *Antibodies, A Laboratory Manual,* Cold Spring Harbor Laboratory, 1988, other references cited herein, as well as immunological and hybridoma technologies known to those in the art. Where natural or synthetic PKD1-derived peptides are used to induce a PKD1-specific immune response, the peptides may be conveniently coupled to an suitable carrier such as KLH and administered in a suitable adjuvant such as Freund's. Preferably, selected peptides are coupled to a lysine core carrier substantially according to the methods of Tam, *Proc.Natl.Acad.Sci,USA* 85:5409–5413, 1988. The resulting antibodies may be modified to a monovalent form, such as, for example, Fab, $Fab_2$, FAB', or FV. Anti-idiotypic antibodies may also be prepared using known methods.

In one embodiment, normal or mutant PKD1 polypeptides are used to immunize mice, after which their spleens are removed, and splenocytes used to form cell hybrids with myeloma cells and obtain clones of antibody-secreted cells according to techniques that are standard in the art. The resulting monoclonal antibodies are screened for specific binding to PKD1 proteins or PKD1-related peptides.

In another embodiment, antibodies are screened for selective binding to normal or mutant PKD1 sequences. Antibodies that distinguish between normal and mutant forms of PKD1 may be used in diagnostic tests (see below) employing ELISA, EMIT, CEDIA, SLIFA, and the like. Anti-PKD1 antibodies may also be used to perform subcellular and histochemical localization studies. Finally, antibodies may be used to block the function of the PKD1 polypeptide, whether normal or mutant, or to perform rational drug design studies to identify and test inhibitors of the function (e.g., using an anti-idiotypic antibody approach).

Identification of Disease-Causing Mutations in PKD1

In one mode of practice of the present invention, the isolated and sequenced PKD1 gene is utilized to identify previously unknown or mutant versions of the PKD1 gene. First, human subjects with inherited polycystic kidney disease are identified by clinical testing, pedigree analysis, and linkage analysis, using standard diagnostic criteria and interview procedures, and DNA or RNA samples are obtained from the subjects (see below).

A variety of techniques are then employed to pinpoint new mutant sequences. First, PKD1 DNA may be subjected to direct DNA sequencing, using methods that are standard in the art. Furthermore, deletions may be detected using a PCR-based assay, in which pairs of oligonucleotides are used to prime amplification reactions and the sizes of the amplification products are compared with those of control products. Other useful techniques include Single-Strand Conformation Polymorphism analysis (SSCP), HOT cleavage, denaturing gradient gel electrophoresis, and two-dimensional gel electrophoresis.

A confounding and complicating factor in the detection of a PKD1 mutation is the presence of PKD1 homologues at several sites on chromosome 16 proximal to the transcribed gene. In analysis of mutations in PKD1, it is critical to distinguish between sequences derived from the authentic PKD1 gene and sequences derived from any of the homologues. Thus, an important feature of the present invention is the provision of oligonucleotide primers that discriminate between authentic PKD1 and the homologues. A detailed comparison of the sequences of the authentic PKD1 gene and the homologues enables the design of primers that discriminate between the authentic PKD1 gene or cDNA and the homologues. Primers that conform to this criterion, such as those disclosed in FIG. 4B, may be used in conjunction with any of the analytical methods described below.

For SSCP, primers are designed that amplify DNA products of about 250–300 bp in length across non-duplicated segments of the PKD1 gene. For each amplification product, one gel system and two running conditions are used. Each amplification product is applied to a 10% polyacrylamide gel containing 10% glycerol. Separate aliquots of each amplimer are subjected to electrophoresis at 8w at room temperature for 16 hours and at 30 W at 4° C. for 5.4 hours. These conditions were previously shown to identify 98% of the known mutations in the CFTR gene (Ravnik-Glavac et al., *Hum. Mol. Genet.,* 3:801, 1994).

For "HOT" cleavage, amplification reactions are performed using radiolabelled PKD1-specific primers. Each radiolabelled amplification product is then mixed with a 10-fold to 100-fold molar excess of unlabelled amplification products produced using the identical primers and DNA from APKD-affected or -unaffected subjects. Heteroduplex formation, chemical cleavage, and gel analysis are then performed as described (Cotton, et al., *Proc. Natl. Acad. Sci., USA,* 85:4397, 1988). Bands on the gel that are smaller than the homoduplex result from chemical cleavage of heteroduplexes at base pair mismatches involving cytidine or thymidine. Once a mutation has been identified by this procedure, the exact location of the mismatch(es) is determined by direct DNA sequencing.

Mutations are also identified by "broad range" DDGE (Guldberg et al., *Nuc. Acids Res.,* 22:880, 1994). The use of GC-clamped PCR primers and a very broad denaturant gradient enables the efficient detection of mutant sequences. This method can also be combined with non-denaturing size fractionation in a two-dimensional system. An apparatus is used that permits automated two-dimensional electrophoresis, and the second dimension considerably increases the resolution of mutations.

After the presence of a mutation is detected by any of the above techniques, the specific nucleic acid alteration comprising the mutation is identified by direct DNA sequence analysis. In this manner, previously unidentified PKD1 mutations may be defined.

Once a previously unidentified PKD1 mutation is defined, methods for detecting the particular mutation in other affected individuals can be devised, using a variety of methods that are standard in the art. For example, oligonucleotide probes may be prepared that allow the detection and discrimination of the particular mutation. It will be understood that such probes may comprise either the mutant sequence itself, or, alternatively, may flank the mutant sequence. Furthermore, the oligonucleotide sequence can be used to design a peptide immunogen comprising the mutant amino acid sequence. These peptides are then used to elicit antibodies that distinguish between normal and mutant PKD1 polypeptides.

Diagnostic Tests for PKD1 Mutations

Mutant PKD1 genes, whether identified by the methods described above or by other means, find use in the design and operation of diagnostic tests. Tests that detect the presence of mutant PKD1 genes, including those described below and in Example 5, can be applied in the following ways:

(1) To determine donor suitability for kidney transplants. In general, it is desirable to use a close relative of the transplant recipient. When the recipient is a patient suffering from familial APKD, it is important to ascertain that the donor relative does not also carry the familial mutant PKD1 gene.

(2) To screen for at-risk individuals in APKD-affected families. Presymptomatic individuals who have a high probability of developing APKD can be identified, allowing them to be monitored and to avail themselves of preventive therapies.

(3) To target hypertensive patients for antihypertensive treatment. Hypertension is also linked to APKD. Screening of hypertensive patients for the presence of mutant PKD1 genes can be used to identify patients for preemptive regulation of blood pressure to prevent later kidney damage.

(4) To perform prenatal screening. Most PKD1-linked PKD is of the adult-onset type. In a small subset of families carrying a mutation in PKD1 genes, however, juvenile onset is common and signifies a more severe form of the disease. In these families, prenatal screening can be useful for genetic counselling purposes.

In general, the diagnostic tests according to the present invention involve obtaining a biological sample from a subject, and screening the sample, using all or part of the PKD1 gene of this invention, for the presence of one or more mutant versions of the PKD1 gene or its protein product. The subject may be a fetus in utero, or a human patient of any age.

In one embodiment, a sample of genomic DNA is obtained from a human subject and assayed for the presence of one or more disease-associated PKD1 mutations. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, amniotic fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $3 \times 10^9$ base pairs).

In this embodiment, the assay used to detect the presence of mutations may comprise restriction enzyme digestion, direct DNA sequencing, hybridization with sequence-specific oligonucleotides, amplification by PCR, single-stranded conformational polymorphism analysis, denaturating gradient gel electrophoresis (DDGE), two-dimensional gel electrophoresis, in situ hybridization, and combinations thereof.

In a preferred embodiment, RNA is isolated from a PKD1-expressing cell or tissue, preferably lymphocytes, using standard techniques including automated systems such as that marketed by Applied Biosystems, Inc. (Foster City, Calif.). The RNA is then subjected to coupled reverse-transcription and PCR amplification (RT-PCR). The resulting DNA may then be screened for the presence of mutant sequences by any of the methods outlined above (see Example 5 below).

As discussed above, any nucleic-acid-based screening method for PKD1 mutations must be able to discriminate between the authentic PKD1 gene present at chromosome location 16p13.3 and PKD1 homologues present at 16p13.1 and other locations. The oligonucleotides (i.e., SEQ ID Nos:10 and 13–15) are examples of primers that discriminate between the authentic and homologue sequences, and these oligonucleotides or their equivalents form an important part of any such diagnostic test. Furthermore, nucleotides 43,823 through 52,887 of the PKD1 sequence of FIG. 1B represent a sequence that is unique to the authentic PKD1 gene and is not present in the homologues. Thus, oligonucleotides derived from this region can be used in a screening method to insure that the authentic PKD1 gene, and not the homologues, are detected.

In another embodiment, the assay used to detect the presence of a mutant PKD1 gene involves testing for mutant gene products by an immunological assay, using one of many methods known in the art, such as, for example, radioimmunoassay, ELISA, immunofluorescence, and the like. In this embodiment, the biological sample is preferably derived from a PKD1-expressing tissue such as kidney. The PKD1 polypeptide may be extracted from the sample. Alternatively, the sample may be treated to allow detection or visualization of specifically bound antibodies in situ as occurs in, for example, cryosectioning followed by immunofluorescent staining.

The antibodies may be monoclonal or polyclonal, may be raised against intact PKD1 protein, or natural or synthetic peptides derived from PKD1. In a preferred embodiment, the antibodies discriminate between "normal" and "mutant" PKD1 sequences, and possess a sufficiently high affinity for PKD1 polypeptides so that they can be used in routine assays.

It will be understood that the particular method or combination of methods used will depend on the particular application. For example, high-throughput screening methods preferably involve extraction of DNA or RNA from an easily available tissue, followed by amplification of particular PKD1 sequences and hybridization of the amplification products with a panel of specific oligonucleotides.

Therapeutic Applications

The present invention encompasses the treatment of PKD using the methods and compositions disclosed herein. All or part of the normal PKD1 gene disclosed above can be delivered to kidney cells or other affected cells using a variety of known methods, including e.g. liposomes, viral vectors, recombinant viruses, and the like. The gene can be incorporated into DNA vectors that additionally comprise tissue-specific regulatory elements, allowing PKD1 expression in a tissue-specific manner. This approach is feasible if a particular mutant PKD1 allele, when present in a single copy, merely causes the level of the PKD1 protein to diminish below a threshold level necessary for normal function; in this case, increasing the gene dosage by supplementing with additional normal copies of the PKD1 gene should correct the functional defect. In another embodiment, a mixture of isolated nucleic acids, such as that set forth in FIG. 2 and at least a portion of the normal PKD1 gene, may be delivered to kidney or other affected cells in order to treat APKD. Alternatively, it may be desired to limit the expression of a mutant PKD1 gene, using, for example, antisense sequences. In this embodiment, antisense oligonucleotides may be delivered to kidney or other cells.

For therapeutic uses, PKD1-related DNA may be administered in any convenient way, for example, parenterally in a physiologically acceptable carrier such as phosphate buffered saline, saline, deionized water, or the like. Typically, the compositions are added to a retained physiological fluid such as blood or synovial fluid. The amount administered will be empirically determined using routine experimentation. Other additives, such as stabilizers, bactericides, and the like, may be included in conventional amounts.

This invention also encompasses the treatment of APKD by protein replacement. In one embodiment, protein produced by host cells transformed or transfected with DNA encoding the PKD1 polypeptide of the present invention is introduced into the cells of an individual suffering from altered, defective, or non-functional expression of the PKD1 gene. This approach augments the absence of PKD1 protein, or the presence of a defective PKD1 protein, by adding functional PKD1 protein. The PKD1 protein used in augmentation may comprise a subcellular fragment or fraction, or may be partially or substantially purified. In any case, the PKD1 protein is formulated in an appropriate vehicle, such as, for example, liposomes, that may additionally include conventional carriers, excipients, stabilizers, and the like.

It will be understood that the therapeutic compositions of the present invention need not in themselves constitute an effective amount, since such effective amounts can be reached by administering a plurality of such therapeutic compositions.

The following examples are intended to illustrate the invention without limiting its scope thereof.

EXAMPLE 1

Cloning and Sequencing of the Human PKD1 gene

A. Methods:

Employing an ordered sequencing approach, restriction fragments from cDEB11 and cGGG10.2 cosmids were subcloned into either pBLUESCRIPT (Stratagene, La Jolla, Calif.) or pGEM (Promega, Madison, Wis.). Plasmids were purified by CsCl density centrifugation in the presence of ethidium bromide. Nested deletions were generated from each plasmid using ExoIII (Henikoff, S., Methods Enzymol. 155: 156–165, 1987) and additional enzymatic reagents provided by the Erase-A-Base kit (Promega, Madison, Wis.). The resulting nested clones were analyzed electrophoretically after appropriate restriction enzyme digestion and were ordered into a nested set of templates for sequencing. A minimum tiling series of plasmids, each differing by approximately 250 bp from flanking clones, were identified and used for sequencing.

Plasmid DNAs were prepared for sequencing in one of two ways. Initially, all clones of interest were cultured in 2 mL of Super Broth (Tartof et al., BRL Focus 9: 12, 1987) for 20 hours at 37° C. Sets of 12–24 were processed simultaneously using a modified alkaline SDS procedure followed by ion-exchange chromatography as described by the manufacturer (Easy-Prep, Pharmacia, Piscataway, N.J.). Plasmid DNA yields ranged from 2.5 to 25 $\mu$g. Poor growing clones, or those whose plasmids generated sequence of unacceptable quality, were recultured in 100 mL of Luria's Broth and the plasmid DNA isolated using Qiagen columns (Qiagen, San Diego, Calif.).

Dideoxy sequencing reactions were performed on deletion clones using the Auto-Read Sequencing Kit (Pharmacia, Piscataway, N.J.) and fluorescein-labeled vector primers (M13 universal, M13 reverse, T3, T7 and SP6). Reaction products were separated on 6% denaturing acrylamide gels using the ALF™ DNA Sequencer (Pharmacia, Piscataway, N.J.).

Second strand sequencing was performed using either an opposing set of nested deletions or primer walking. For primer walking, custom 17-mers, staggered every 250 bp, were purchased from a commercial supplier (Protogene, Palo Alto, Calif.). Template DNAs prepared by Qiagen or CsCl density gradients were sequenced using the unlabeled 17-mers by inclusion of fluor-dATP labeling mix in the sequencing reactions as described by the manufacturer (Pharmacia, Piscataway, N.J.). In all cases, except the 2.5kb GC-rich region, single-stranded DNA was rescued from deletion clones using helper phage VCSM13 (Stratagene) as described by the manufacturer.

Single-stranded templates from the 2.5 kb GC-rich region were sequenced using fluorescein-labeled universal primer and the Sequitherm Long Read cycle sequencing kit (Epicentre Technologies, Madison, Wis.) (Zimmerman et al., Biotechniques 17: 303–307, 1994). All processed sequencing data was transferred to a Quadra 700 Macintosh computer and assembled using the SEQUENCHER (Gene Codes, Ann Arbor, Mich.) sequencing assembly program. For differences that would not be resolved by examining the chromatograms, templates were either resequenced or primers proximal to the ambiguity were designed and used for resolution of the sequence difference.

Cycle sequencing was performed using the Sequitherm cycle sequencing kit as described by the manufacturer (Epicentre Technologies, Madison, Wis.). Reaction products were separated on denaturing acrylamide gels and subsequently detected by autoradiography.

Figure 6:
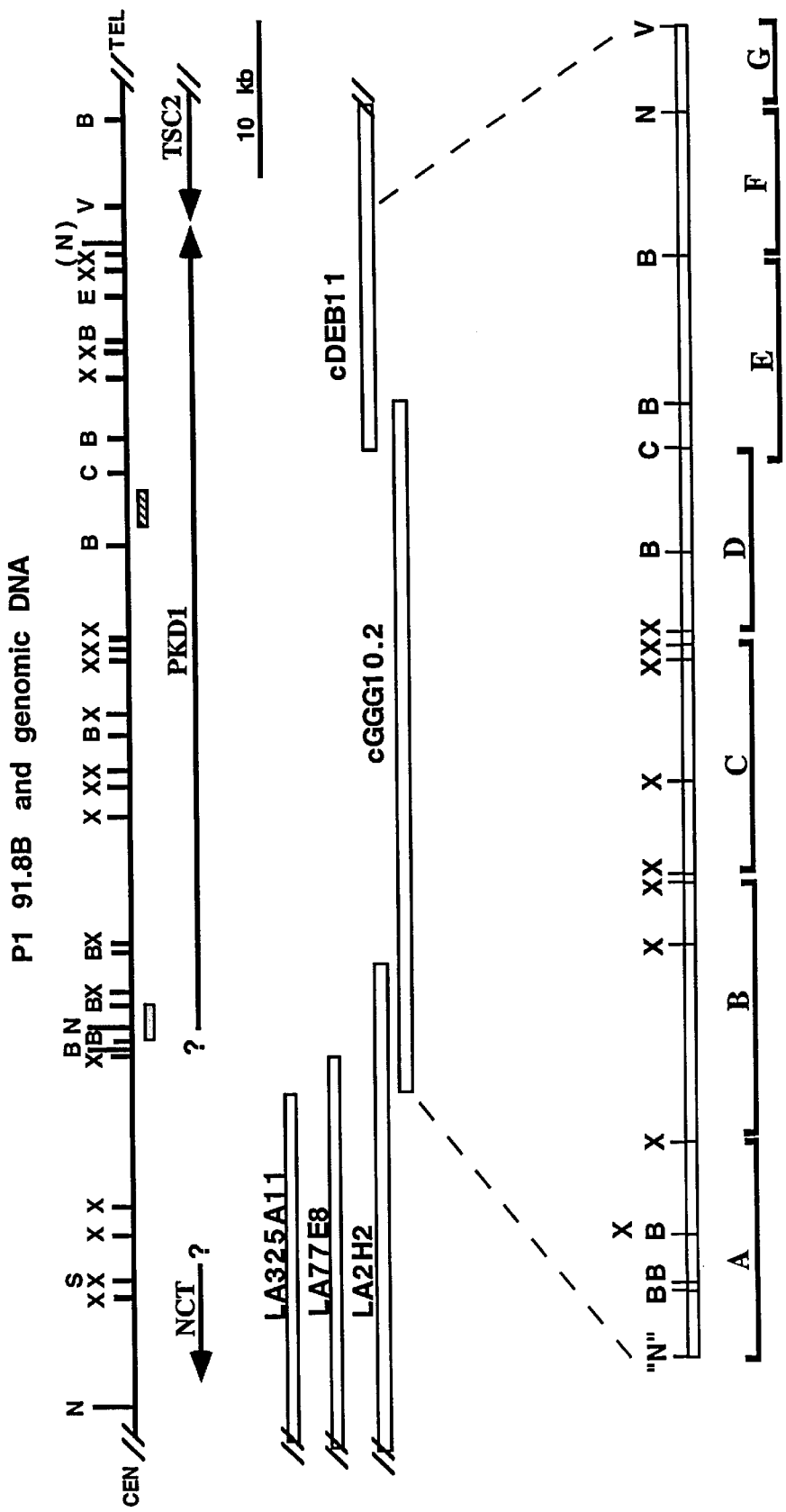
FIG. 6 shows the restriction map of the 91.8B P1 clone containing the PKD1 gene and flanking regions with only the relevant sites indicated (B=BamHI, C=SacI, E=EcoRI, N=NotI, S=SalI, X=XhoI and V=EcoRV). The NotI site in parenthesis is methylated in genomic DNA. The position of the 1.9 kb BamHI-BamHI fragment is shown by the shaded box, the striped box denotes the location of the 2.5 kb polypurine/polypyrimidine tract. The arrows indicate the position and orientation of the next most centromeric transcript (NCT), TSC-2 and PKD1 genes. The location of relevant cosmid clones is shown by open boxes. Restriction fragments used to generate sequencing templates are shown at the bottom with quotation marks denoting that the site is vector derived. Pools used in fluorescence in situ hybridization (FISH) are indicated by brackets at the bottom.

B. Sequencing Strategy:

A 700 kb region of chromosome 16 containing the PKD1 locus is shown in FIG. 5 (top panel). A contig covering this region was assembled from overlapping P1 clones (shown in the middle panel). The contig was assembled by unidirectional chromosomal walking from the ends of the interval (ATPL and D16S84) and bidirectional walking from several internal loci (D16S139 and KG8). One of the clones, 91.8B (ATCC Accession No. 98056), spans the entire PKD1 interval and includes cosmids cDEB11 (ATCC Accession No. 98057), cGGG10.2 (ATCC Accession No. 98058), and substantial portions of cosmids 2H2 and 325All (Stallings, R. L. et al., Genomics 13:1031, 1992). The P1 clone 91.8B (shown schematically in FIG. 6) was used as a second genomic template to confirm discrepancies between the published cDNA sequence (EPKDC, Cell, 1994, supra) and the cosmid-derived genomic sequence.

Preliminary experiments revealed the presence of multiple repetitive elements in the cGGG10.2 cosmid. Therefore, an ordered approach based on nested deletions, rather than random shotgun subcloning, was used to sequence the PKD1 gene. Restriction fragments derived from the inserts of both cGGG10.2 and cDEB11 were subcloned into high-copy number plasmids as a preliminary step to the generation of nested deletions. Unidirectional deletions were prepared and sequenced, using the ALF™ automated sequencing system (Pharmacia, Uppsala, Sweden).

Figure 8:
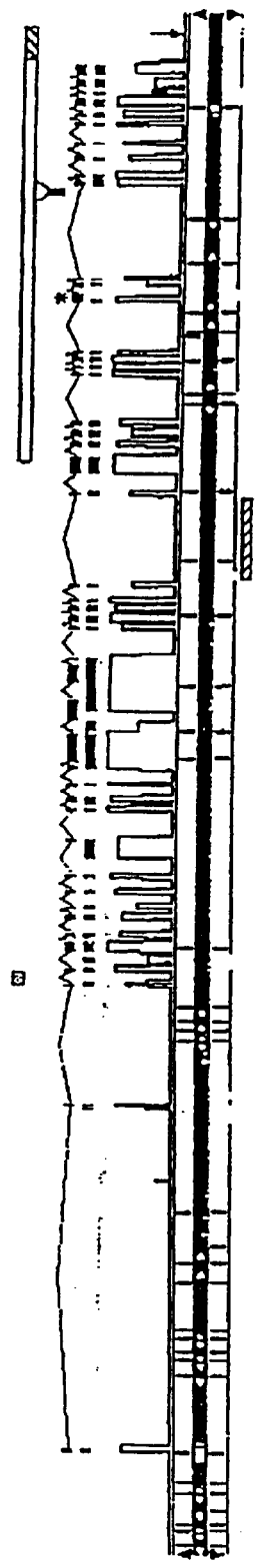
FIG. 8 shows an illustration of the PKD1 genomic structure as predicted by GRAIL2. The predicted exons are represented as boxes along the genomic sequence. The reported cDNA is at the top right. The position of the 2.5 kb GC-rich region is indicated by the striped box at the bottom. The stippled box above exons 3 and 4 in the gene model indicate the position of the predicted LRR and carboxy-flanking region. The extent of the published cDNA is shown by the open (coding region) and cross hatched boxes (3' untranslated region). The filled black box indicates the relative position of the exon which was absent in the predicted gene model, while the asterisk designates the exon which contains an unspliced intron. The position of the 2.5 kb GC-rich region is marked by the striped box below the GC-content bar.

C. Primary Structure of the PKD1 Locus:

The primary sequence of the locus encompassing the PKD1 gene is 53,577 bp in length. This locus is GC-rich (62.4%), with a CpG/GpC dinucleotide ratio of 0.485. The primary sequence of the PKD1 gene within this locus is 53,526 bp in length. The present sequence was analyzed for transcriptional elements and CpG islands using GRAIL2 (Uberbacher, E. C. et al., *Proc. Natl. Acad. Sci., USA* 88:11261, 1991) and XGrail client server (Shah et al., *User's Guide to GRAIL and GENQUEST*, Client-Server Systems, available by anonymous ftp to arthur.epm.omi.gov (128.219.9.76) from directory pub/xgrail or pub/xgenquest, as file manual.grail-genquest, 1994). Ten CpG islands were identified (FIG. 8). Forty-eight exons were predicted on the coding strand by the GRAIL program. The quality of 39 of the 48 exons was "excellent", six were considered "good", and three were deemed "marginal". These data were analyzed using the gene model feature of GRAIL2. The final gene model contained 46 exons.

Comparison of the present genomic sequence with the previously reported partial cDNA sequence (EPKDC, *Cell*, 1994, supra) revealed several differences (FIG. 7). The first and most significant difference is the presence of two additional cytosine residues at position 4566 of the reported sequence. The presence of these two cytosine residues results in a frame shift in the predicted protein coding sequence, leading to the replacement of 92 carboxy-terminal amino acids with a novel 12-amino acid carboxy terminus. Seven of the twelve amino acids of the new carboxy terminus are charged or polar. Additional sequence differences are located at positions 3639–3640 and 3708–3709 of the published EPKDC sequence (FIG. 7). A GC dinucleotide pair is present at each of these positions in the present sequence, while a CG pair is found in the reported sequence. In each case, histidine and valine residues would replace the previously predicted glutamine and leucine residues, respectively.

D. Identification of Protein Coding Regions:

Exons predicted by the GRAIL2 program with an "excellent" score were used to search the SwissProt and PIR databases (Bairoch and Boeckmann, *Nuc. Acids Res.* 20:2019–2022, 1992) using the BLASTP program (Altschul et al., *J. Mol. Biol.* 215:403–410, 1990). Exons 3 and 4 of the gene model were predicted to encode peptides with homology to a number of leucine-rich repeat (LRR)-containing proteins involved in protein-protein interactions (FIG. 13). In addition to the LRR itself, sequences amino- and carboxy-flanking to the LRR may also be conserved in proteins of the leucine-rich glycoprotein (LRG) family, either singly or together.

Exon 3 encodes residues homologous to the LRR from leucine-rich α2 glycoprotein, members of the GP1b.IX complex which comprise the von Willebrand factor receptor, as well as to the Drosophila proteins chaoptin, toll, and slit. The latter are involved in adhesion, dorsal-ventral polarity, and morphogenesis, respectively.

Sequences predicted by GRAIL2 to be encoded by exon 4 were found to have homology to the conserved region carboxy terminal to the LRR in all of the above proteins except chaoptin, which lacks this conserved region. Homology was also observed between the exon 4-encoded sequences and the trk proto-oncogene, which encodes a receptor for nerve growth factor. Further examination of the predicted PKD1 peptide revealed additional regions of weaker homology with conserved regions of the trk tyrosine kinase domain. None of the more proximal exons in the gene model appear to encode a peptide with homology to the conserved amino-flanking region seen in a subset of the LRR-containing proteins.

Exon trapping, RT-PCR, and Northern blot analysis revealed that GRAIL2-predicted exons 3 and 4 are present in expressed sequences. During initial exon trapping experiments using genomic P1 and cosmid clones from the PKD1 locus, an exon trap was identified that contained both of these exons. In separate experiments, the presence of the LRR-carboxy-flanking motif in transcribed sequences was confirmed by RT-PCR using as a template RNA from fetal kidney and from adult brain. On a Northern blot, an RT-PCR fragment containing this motif detected the 14kb PKD1 transcript and several other transcripts of 21 kb, 17 kb, and 8.5 kb.

A region of homology was also observed between the GRAIL2-predicted peptide and the human gp100/Pmel17 gene products, as well as with bovine RPE1. Three copies of a 34 amino acid segment that is also present in the Pmel-17 and gp100 gene products was deduced (Kwon et al, *Proc. Natl. Acad. Sci., USA* 88:9228–9232, 1991; Adema et al., *J. Biol. Chem.* 269:20126–33, 1994) within the larger context of immunoglobulin repeat motifs. The RPE1 gene product has significant homology to gp100 and may represent the bovine homolog (Kim and Wistow, *Exp. Eye Res.* 55:657–662, 1992).

GRAIL2-predicted exons 9, 22, and 28, upstream of the 3' cDNA, showed strong homology to EST T03080 (85%, 255 bp), EST T04943 (98%, 189 bp) and EST T05931 (94%, 233 bp). In addition, nucleotides 10378–10625 of GRAIL-predicted intron 1 showed strong homology to a region of the Apo CII gene (81%, 263 bp).

Figure 9:
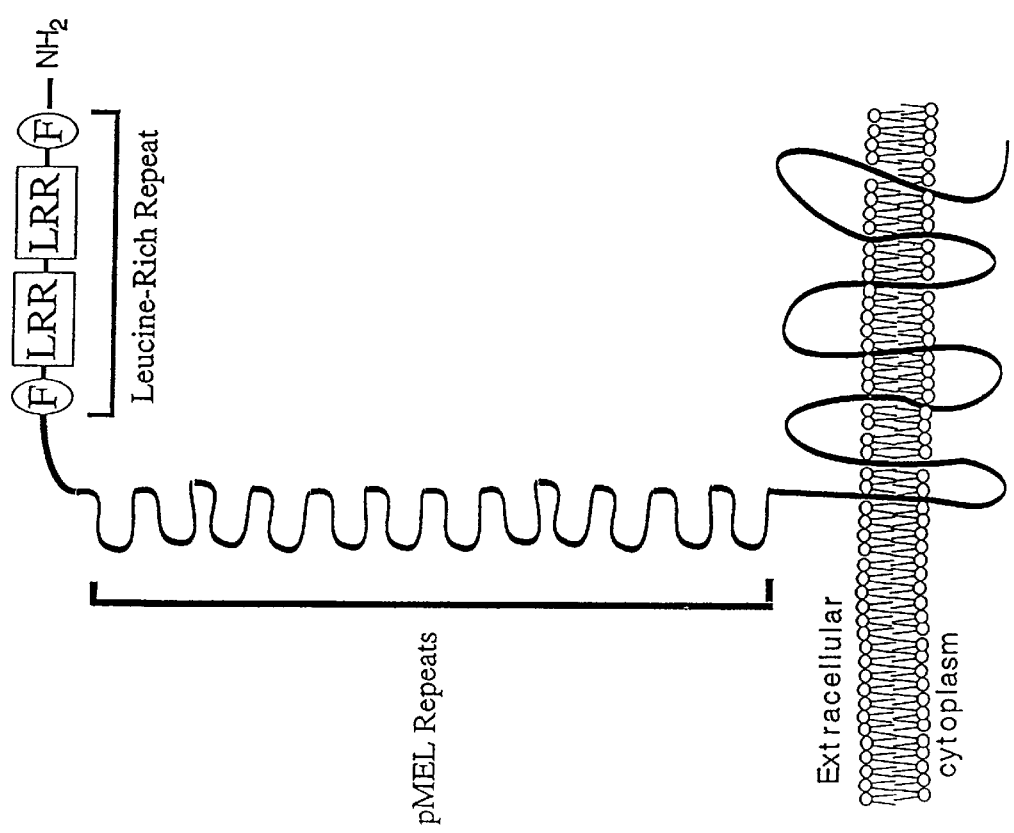
FIG. 9 shows a schematic structure of the predicted PKD1 protein. Multiple domains are depicted based on sequence homology including two copies of a leucine-rich repeat (LRR) near the N-terminal which is flanked by a cysteine-rich cluster (F). Three perfect copies and 12 related copies of a domain of unknown function (Pmel-17 or Ig-like repeat) are shown. The predicted 7 (or more) membrane-spanning domains are indicated. The exons encoding the various domains are listed.

The identification of a number of transmembrane domains and a leucine-rich repeat motif possessing conserved carboxy-flanking regions, raises interesting speculations about potential protein function. LRR motifs have been shown to be involved in protein-protein interactions, while the conserved carboxy-flanking region is associated with proteins which interact with the extracellular matrix. These data suggest that the PKD1 gene product may be a membrane glycoprotein that functions in cell-matrix or cell—cell interactions. Less commonly, LRR motifs have been identified in receptors involved in signal transduction (McFarland et al., *Science* 245:494–499, 1989). Thus an alternative hypothesis is that the gene product is a receptor for a soluble factor(s). In either case, PKD1 would function to mediate interactions with the extracellular environment. If so, ligands for the gene product as well as downstream intracellular effectors are obvious candidates for the non-chromosome 16-linked forms of the disease. A model of the predicted PKD1 protein structure is shown in FIG. 9.

E. Repeated Sequences:

The PKD1 locus was searched for known classes of repetitive DNA by FASTA comparison against the repeat database of Jurka et al., *J.Mol.Evol.* 35:286–291, 1992. This search identified 23 Alu repeats but no other repetitive elements. The Alu repeats are organized into three clusters of four or more Alu repeats, three clusters of two Alu repeats, and two singlet Alu repeats (FIG. 8).

The PKD1 sequence interval contained two dinucleotide repeats (>(TG)8) and a single tetranucleotide repeat ((TTTA)6). The TG dinucleotide repeats are present at positions 209–224 and 52,698–52,715. The tetranucleotide repeat is located at position 7796–7819. No trinucleotide repeats >5 were identified. Only the most 3' TG8 repeat is known to be polymorphic.

In addition to the more usual repetitive elements, the PKD1 gene contains several types of repeated sequences that either do not appear in existing data bases, or do not appear in the extreme form seen at this locus. The most striking repeat is a 2.5 kb segment within the 4 kb BamHI-SacI fragment. A significantly shorter C-T rich region is also found in the adjoining 1.8 kb SacI-BamHI fragment. These regions proved very difficult to sequence unambiguously due to the high GC content (65%), to the purine asymmetry with respect to each strand and to the length of the repeat. The coding strand in this region has an extreme pyrimidine bias, being 96% C-T, and could not be sequenced using T7 DNA polymerase or Sequenase. This was true regardless of the template type (plasmid, single-stranded phage, or strand-separated single-stranded DNA). In both cases, the non-coding strand, which is G-A rich, was successfully sequenced with both T7 DNA polymerase and Sequenase, although run lengths were noticeably abbreviated compared to all other regions sequenced. Compressions on the non-coding strand were resolved by conventional and cycle sequencing using single-stranded template. The extreme purine asymmetry of strands in this segment may promote localized triple strand conformation under the appropriate conditions (pH, divalent cations, supercoiling), and may be a major cause of the difficulty in sequencing this segment.

The other unusual repeat was located in the 7.6 kb XhoI fragment. This repeat is 459 bp in length and consists of 17 tandem copies of a perfect 27 bp repeat.

EXAMPLE 2
PKD1 cDNA Sequences Obtained Through Exon Trapping and cDNA Selection Techniques The 700 kb interval of chromosome 16 that includes the PKD1 gene appears to be particularly rich in CpG islands and, by association, is most likely rich in expressed sequences as well. To purify and sequence expressed PKD1 sequences, an exon-rescue vector, pSPL3, was used to recover sequences from cosmids that contain both a splice acceptor and splice donor element; this method is designated "exon trapping."

Exon trapping is a highly efficient method for isolating expressed sequences from genomic DNA. The procedure utilizes the pSPL3 plasmid, which contains rabbit β-globin coding sequences separated by a portion of the HIV-tat gene, or improved derivatives of SPL3 lacking cryptic (interfering) splice sites. Fragments of cloned PKD1 genomic DNA were cloned into the intron of the tat gene, and the resulting subclones were transfected into COS-7 cells. SV40 sequences in the vector allow for both relaxed episomal replication of the transfected vectors, as well as transcription of the cloned genomic DNAS. Exons within the subcloned genomic DNAs spliced into the globin/tat transcript were recovered using RT-PCR, using primers containing tat splice donor and acceptor sequences. A major advantage of exon trapping is that expression of the cloned DNA is directed by a viral promoter; thus, developmental or tissue-specific expression of gene products is not a concern.

PKD1-containing genomic clones, in the form of either cosmid or P1 DNA, were either double digested with BamHI and BglII or partially digested with Sau3A and shotgun cloned into BamHI-digested and dephosphorylated pSPL3 (GIBCO BRL, Bethesda, Md.) or its derivatives. Plasmid minipreps were electroporated into COS-7 cells, and trapped exons were recovered by RT-PCR, followed by subcloning, using standard procedures.

Figure 14:
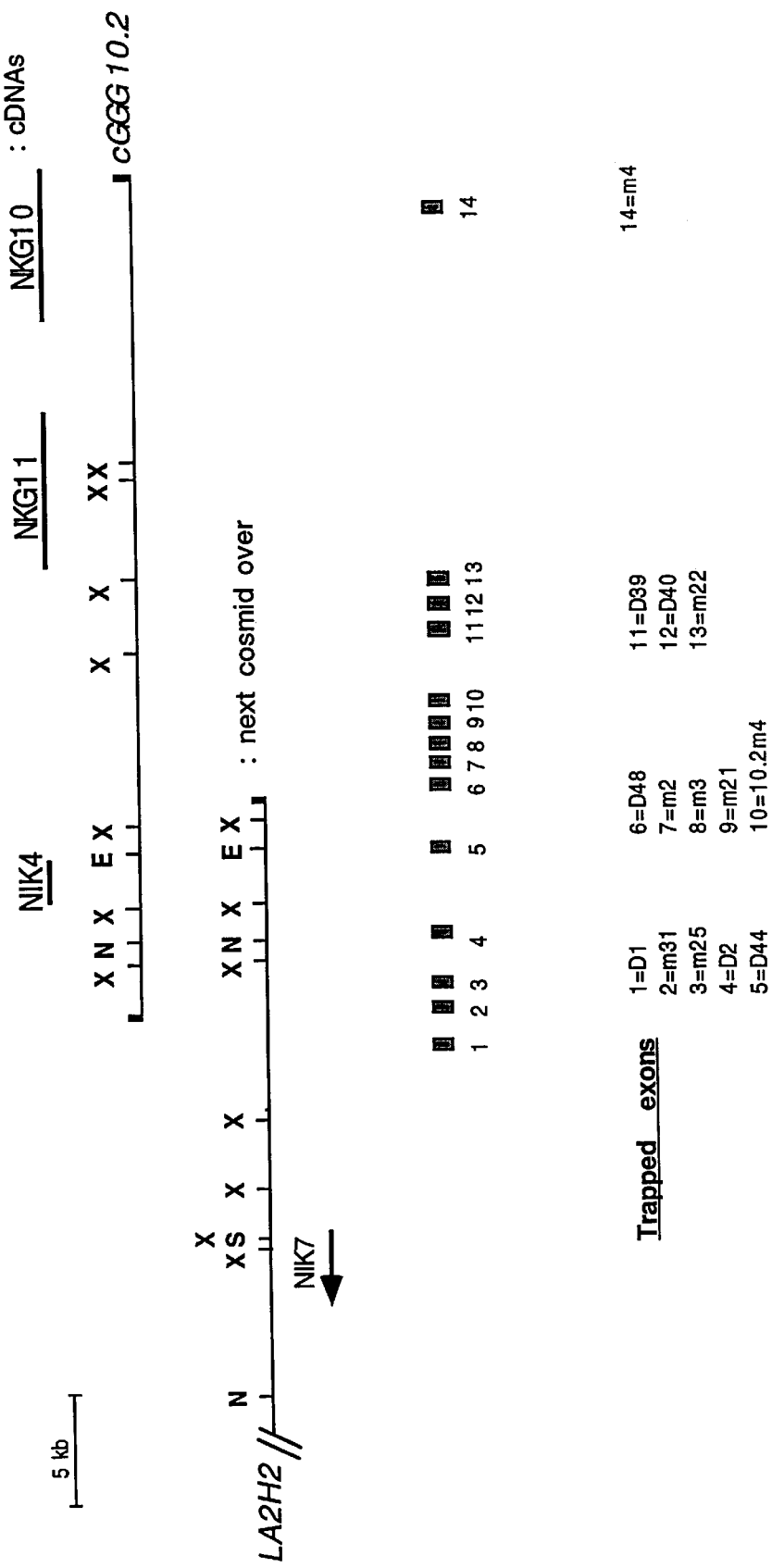
FIG. 14 shows the results of exon trapping within the PKD1 locus.

Trapped exons from the PKD1 locus are shown in FIG. 14 (bottom). The trapped exons were subjected to automated DNA sequencing as above, allowing their alignment with the genomic PKD1 DNA.

EXAMPLE 3
Construction of Full-length PKD1 cDNA

In the case of PKD1, the identification of a DNAs which are specific for the 5' end of the PKD1 locus is particularly difficult since multiple transcribed copies of homologous sequences are also present at 16p13.1 (EPKDC, *Cell*, 1994 supra). Regions of both genomic DNA and cDNA derived from the homologues were sequenced and compared with the present PKD1 sequence. In this data set, the PKD1 and homologous sequences were greater than 97% identical at the nucleotide level. Therefore, direct comparisons of potential PKD1 cDNAs and genomic sequence are required to definitively map a cDNA to the PKD1 locus, and to verify that the correct sequence is encoded by the cDNA.

Multiple approaches were required to assemble the full-length PKD1 cDNA. Seven cDNAs were used to construct the full-length cDNA. Five of these cDNAs were recovered from screening cDNA libraries: the BRL Gene-Trapper brain library, and cDNA libraries constructed from fetal brain, and constructed from the somatic cell hybrid 145.19. The 145.19 cell line contains the PKD1 locus, but does not include the PKD1 homologs in its human component.

A. cDNA Library Construction and Screening

The somatic cell hybrid library was constructed using both oligo(dT) and random hexamer priming and poly(A)-containing RNA from the 145.19 cell line. The duplex cDNA was linked and then ligated into lambda ZAP EXPRESS (Stratagene, La Jolla, Calif.) to yield a library consisting of several million independent plaques. Fourteen clones were positive by colony hybridization using a PKD1 specific probe, with inserts ranging in size from 2.6 to 9 kb. Consistent with the RT-PCR products derived from the 145.19 cell line, substantial alternative splicing or incomplete splicing was evident. Interestingly, the missing exons appeared to comprise one or more distinct protein domains.

Two additional libraries were constructed using fetal brain cDNA cloned into lambda ZAP EXPRESS and the replacement vector, lambda DASH (Stratagene, La Jolla, Calif.).

Additionally, a variation of the cDNA selection methodology was used to screen oligo(dT)-primed, unidirectional cDNA libraries (in phagemids). Briefly, single-stranded library DNA was prepared from cultures of the adult brain cDNA library. A single biotinylated 17-mer derived from the sense-strand from the gene-specific portion of the predicted PKD1 cDNA was used for hybrid selection.

Hybrid-bound cDNAs released by denaturation were made double-stranded using the same oligonucleotide as a gene-specific primer and Klenow and then introduced into *E. coli* by electroporation. Colony hybridization was used to identify the PKD1 clones from the enriched brain cDNA population. The cloned brain inserts ranged in size from 0.7 to 2.5 kb. The sequence of the two largest cDNAs was virtually identical to each other as well as to the genomic sequence.

EXAMPLE 4
Expression of Full-Length PKD1 cDNA

Figure 11:
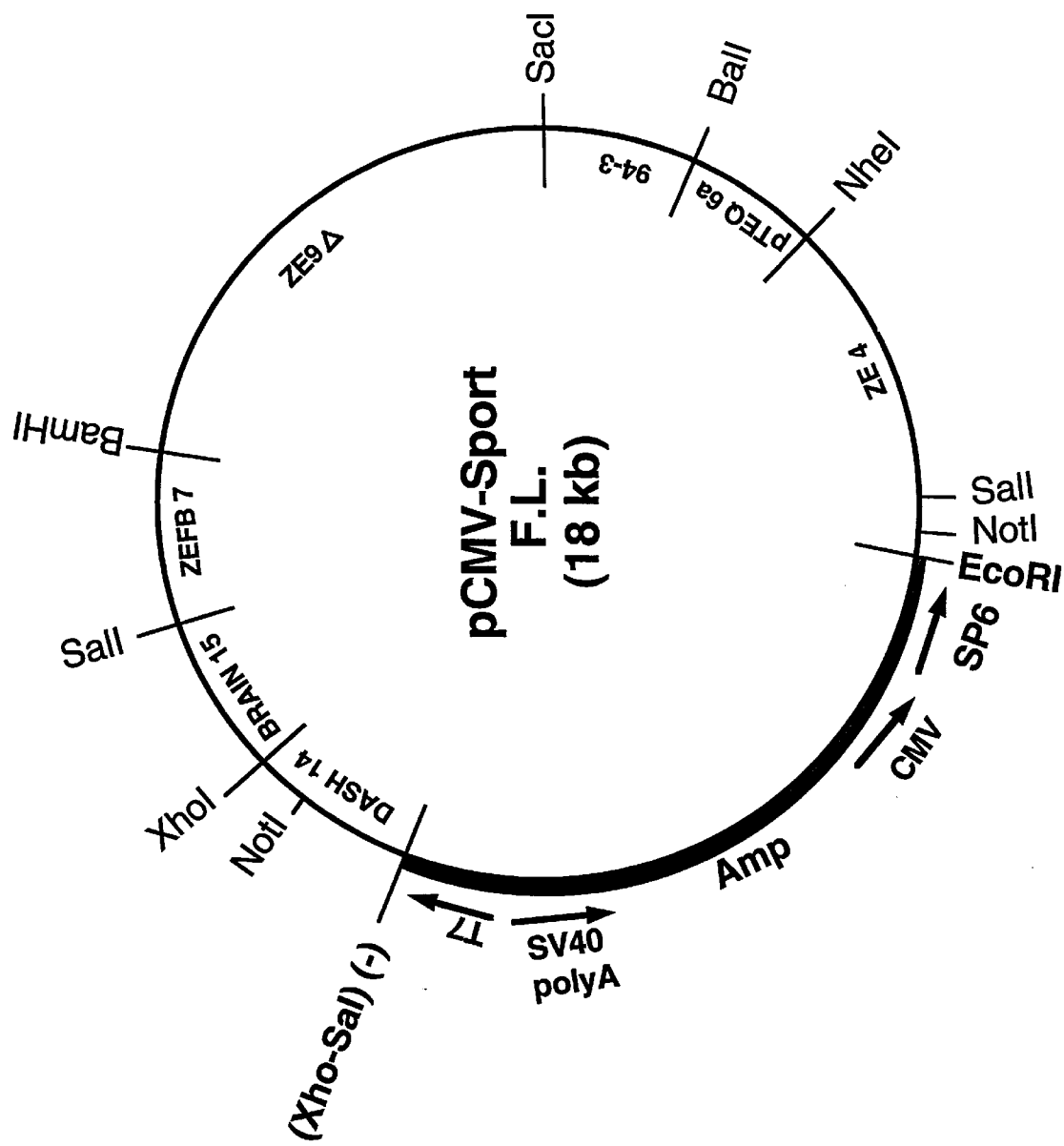
FIG. 11 shows a schematic structure of the full length PKD1 cDNA in pCMV-SPORT vector. Thin line represents PKD1 cDNA with restriction sites used to assemble individual cDNA clones. Thick line represents pCMV-SPORT vector which contains SP6 and T7 RNA polymerase promoters to generate RNA for in vitro translations, CMV promoter, SV40 origin of replication and polyadenylation signal for expression in mammalian cells.
Figure 12:
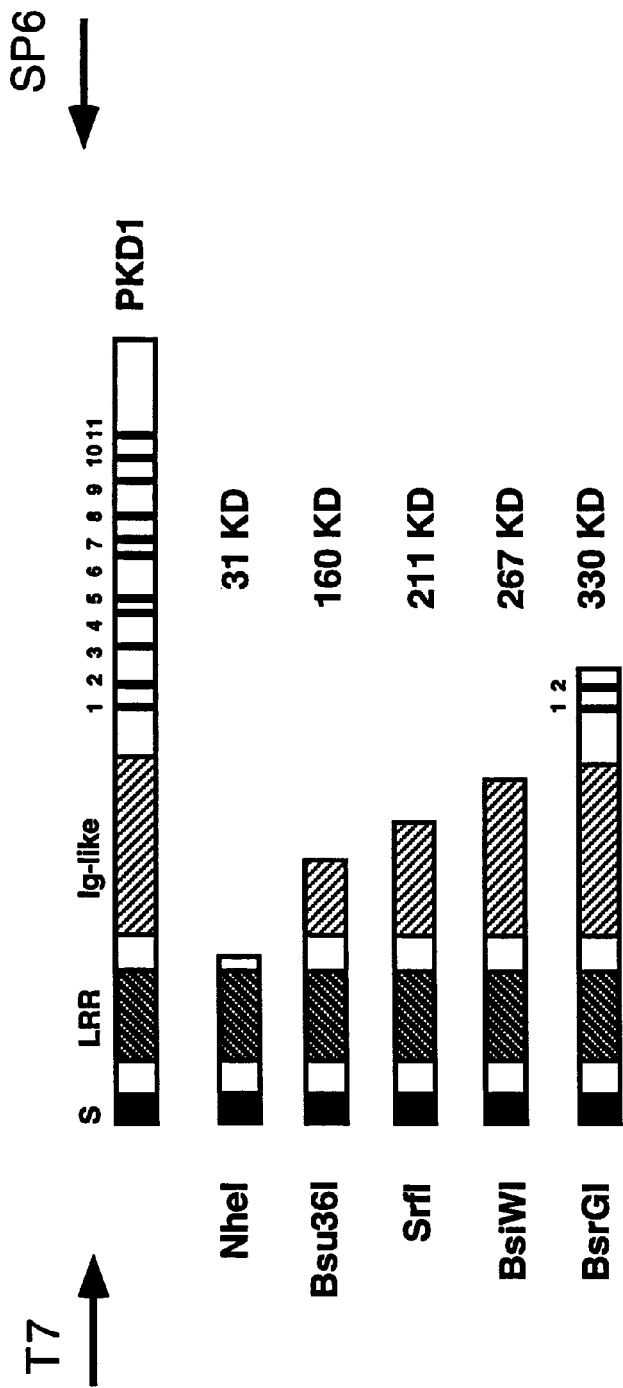
FIG. 12 shows a schematic of the full-length PKD1 product and its truncated products. Black box represents signal peptide (S), Leucine rich repeat (LRR) and Ig-like (Ig-like) domains are indicated by shaded boxes. The eleven predicted transmembrane regions are also indicated by black bars and numbered.

Full-length PKD1 cDNA was cloned into three expression vectors, pCMV-SPORT, pcDNA3, and pCEP4 (total construct sizes ranging from 18–24.2 kb). The schematic structure of full-length PKD1 cDNA in pCMV-SPORT is shown in FIG. 11. pCMV-SPORT and pcDNA3 have small differences in cloning sites and some other small features, but share the basic features of flanking T7 and SP6 promoters, CMV enhancer-promoter sequences for high level transcription, and eukaryotic polyadenylation and transcription sequences which enhance RNA stability. The SV40 origin of replication allows growth in eukaryotic cells, while the ColE1 origin allows growth in E. coli. The vector pcDNA3 confers neomycin resistance in eukaryotes, while ampicillin resistance is used for selection in E. coli.

pCEP4 is an EBV-based vector which is maintained extrachromosomally in primate cells. Like pCMV-SPORT and pcDNA3, pCEP4 contains the CMV enhancer and promoter, and the ColE1 origin of replication and ampicillin resistance are used for maintenance. However, hygromycin resistance is used for selection in eukaryotic cells. The use of the EBV origin of replication and hygromycin resistance are important features for studies of PKD1 transformed cell lines, since as a function of the transformation procedure they already contain SV40 large T antigen, and are G418 resistant.

A. In vitro Expression

The T7 promoter feature of pcDNA3 was used to analyze the protein product encoded by the PKD1 cDNA employing the TNT Coupled Reticulocyte Lysate System, (Promega, Madison, Wis.). This system enables large amounts of RNA to be synthesized from the T7 promoter, and the RNA to be translated into protein in the rabbit reticulocyte lysate.

Figure 10:
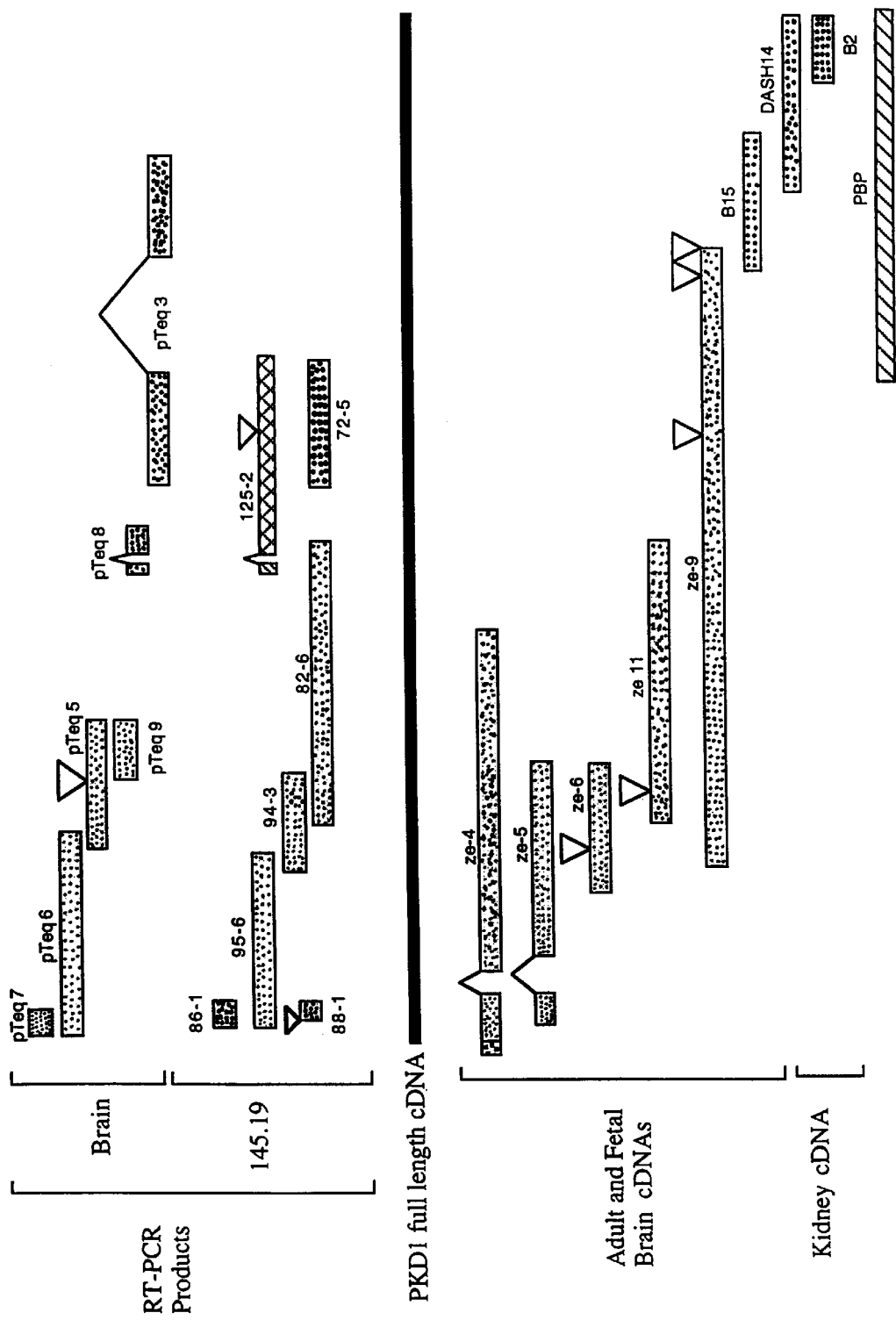
FIG. 10 shows the RT-PCR and cDNA products comprising the PKD1 cDNA. The EPKDC 3' cDNA sequence is shown by the striped box. The full-length cDNA is shown in black. Shaded boxes denote individual cDNAs and RT-PCR products. The cross hatched box denotes the RT-PCR products containing alternatively spliced exons and an unspliced exon which do not maintain the open reading frame. Alternatively spliced exons and insertions are designated by thin lines and inverted triangles, respectively. Open boxes designate the position of open reading frames. The stippled box denotes the 5' untranslated region.

Since conventional molecular weight standards only extend up to ~216 kD, the size estimates of in vitro synthesized polycystin, ~462 kD (non-glycosylated), would be speculative at best. For this reason, a series of 3' deleted PKD1 cDNA plasmid templates encoding truncated proteins of predicted size were constructed (FIG. 10). The protein products of these deletion clones as well as the full-length PKD1 cDNA were analyzed using the TNT system.

Newly synthesized protein was labeled by inclusion of radioactive amino acids, initially $^{35}$S-methionine. The synthesized proteins were then resolved by electrophoresis on a 3–12% gradient SDS-PAGE gel. The mobility of the protein product produced from each of the truncated clones was consistent with its predicted molecular size. These results are consistent with assembled PKD1 cDNA expression vectors directing in vitro synthesis of polycystin.

B. In vivo Expression: PKD1 cDNA Transfection in Human Embryonic Kidney (HEK) 293 cells cDNA constructs containing full-length PKD1 cDNA or portions thereof were transfected into HEK 293 cells and assayed for PKD1 expression using Northern analysis, 48 hours post-transfection. An insertless vector, pcDNA3, was used in parallel as a control for transfection. A Northern blot was probed with a PKD1-specific probe and then subsequently re-probed with a β-actin cDNA to normalize the respective lanes. The results showed that the PKD1 mRNA is increased at least two-fold in HEK 293 which received the PKD1 cDNA construct.

EXAMPLE 5
Diagnostic Tests for PKD1 Mutations

Whole blood samples collected in high glucose ACD Vacutainers™ (yellow top) were centrifuged and the buffy coat collected. The white cells were lysed with two washed of a 10:1 (v/v) mixture of 14 mM NH$_4$Cl and 1 mM NaHCO$_3$, their nuclei were resuspended in nuclei-lysis buffer (10 mM Tris, pH 8.0, 0.4M NaCl, 2 mM EDTA, 0.5% SDS, 500 μg/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA).

A. Test I

Long PCR conditions were used with a 4-part reaction mixture. Part 1 containing the following components:

| | |
|---|---|
| 3.3X XL Buffer | 12 μl |
| dNTPs (2 mM each) | 8 μl |
| Forward primer (20 μM) | 1–5 μl |
| Reverse primer (20 μM) | 1–5 μl |
| Blocking oligo (2 mM) | 1.5 μl |
| Mg(OAc)2, (25 mM) | 4.4 μl |
| water to | 40 μl |

Part 1 can be assembled as a single reaction component or in batch (10, 50, 100 reaction equivalents) and then dispensed as 40 μl aliquots into individual reaction tubes.

Part 2 comprises carefully adding 1 AmpliWaxPCR Gem 100 (or comparable product to each Part 1 reaction tube). The tubes were incubated at 75–80° C. for 5 min. to melt the wax bead. The reactions were cooled allowing the wax to solidify.

In Part 3, the following components were added to the cooled reaction mixture of Part 2:

| | |
|---|---|
| 3.3X XL Buffer | 18 μl |
| rTth DNA Polymerase, XL | 2 μl |

In Part 4, the following components are added to the reaction mixture of Part 3:

| | |
|---|---|
| human DNA | 0.2–1 μg |
| water to | 40 μl |

The forward primer used in the reaction described above comprises an oligonucleotide that hybridizes to both authentic PKD1 and PKD1 homologue sequences. An example of such a primer is:

5'-CACGACCTGTCCCAGGCAT-3' (SEQ ID NO:6) (corresponding to nucleotides 4702–4720 of SEQ ID NO:1).

The reverse primer comprises a sequence derived from a 3' region of the authentic PKD1 gene, which may or may not be present in the PKD1 homologues. Examples of such 3' regions and corresponding reverse primers are:

| 3' sequence: | reverse primer: |
|---|---|
| 5'-CTGGCGGGCGAGGAGAT-3' (SEQ ID NO:7) | 5'-ATCTCCTCGCCCGCCAG-3' (SEQ ID NO:56) |
| 5'-CTTTGACAAGCACATCT-3' (SEQ ID NO:8) | 5'-AGATGTGCTTGTCAAAG-3' (SEQ ID NO:57) |
| 5'-CAACTGGCTGGACAACA-3' (SEQ ID NO:9) | 5'-TGTTGTCCAGCCAGTTG-3' (SEQ ID NO:58) |

The blocking oligonucleotide comprises:

```
5'-AGGACCTGTCCAGGCATC-3'    (SEQ ID NO:10).
```

Importantly, this oligonucleotide must be incapable of supporting polymerization. One example is an oligonucleotide in which the 3' terminal nucleotide comprises a dideoxynucleotide. It will be understood that any modification that achieves this effect may be used in practicing the invention. Under appropriate conditions, the blocking oligonucleotide hybridizes efficiently to PKD1 homologues but inefficiently to the authentic PKD1 sequence. Thus, the amplification products in this diagnostic test are derived only from the authentic PKD1 gene.

Twenty-five to thirty-eight cycles of amplification were performed, using a standard DNA thermal cycler the following primer-dependent conditions for each cycle:

SEQ ID NO:56: 94° C., 30 seconds; 62° C., 30 seconds; and 72° C., 34 minutes.
SEQ ID NO:57: 94° C., 30 seconds; 56° C., 30 seconds; and 72° C., 37 minutes.
SEQ ID NO:58: 94° C., 30 seconds; 58° C., 30 seconds; and 72° C., 45 minutes.

The 72° C. extension cycle was lengthened 5 seconds each subsequent cycle. The primary PCR product can be analyzed immediately for mutations or alternatively, can be used as a template for secondary PCR using a collection of paired amplimers to generate an overlapping set of smaller amplicons. The smaller amplicons can then be analyzed for mutations.

B. Test II

Long PCR conditions were used with a 4-part reaction mixture. Part 1 containing the following components:

| | |
|---|---|
| 3.3X XL Buffer | 12 µl |
| dNTPs (2 mM each) | 8 µl |
| Forward primer (20 µM) | 1–5 µl |
| Reverse primer (20 µM) | 1–5 µl |
| Mg(OAc)2, (25 mM) | 4.4 µl |
| water to | 40 µl |

Part 1 can be assembled as a single reaction component or in batch (10, 50, 100 reaction equivalents) and then dispensed as 40µl aliquots into individual reaction tubes.

Part 2 comprises carefully adding 1 AmpliWaxPCR Gem 100 (or comparable product to each Part 1 reaction tube. The tubes were incubated at 75–80° C. for 5 min. To melt the wax bead. The reactions were cooled allowing the wax to solidify.

In Part 3, the following components were added to the cooled reaction mixture of Part 2:

| | |
|---|---|
| 3.3X XL Buffer | 18 µl |
| rTth DNA Polymerase, XL | 2 µl |

In Part 4, the following components are added to the reaction mixture of Part 3:

| | |
|---|---|
| human DNA | 0.2–1 µg |
| water to | 40 µl |

Twenty-five to thirty-eight cycles of amplification were performed, using a standard DNA thermal cycler the following protocol for each cycle: 94° C., 30 seconds; 61° C., 30 seconds; and 72° C., 11 minutes. The 72° C. extension cycle was lengthened 5 seconds each subsequent cycle. The primary PCR product can be analyzed immediately for mutations or alternatively, can be used as a template for secondary PCR using a collection of paired amplimers to generate an overlapping set of smaller amplicons. The smaller amplicons can then be analyzed for mutations.

The forward primer used in the reaction described above comprises an oligonucleotide that hybridizes to both authentic PKD1 and PKD1 homologue sequences. An Example of such a primer is: 1

```
5'-CTGCACTGACCTCACGCATGT-3'    (SEQ ID NO:11)
0
```

The reverse primer comprises a sequence derived from the authentic PKD1 gene and is not present in the PKD1 homologues. Thus, the amplification product in this diagnostic test is derived only from the authentic PKD1 gene. An example of a suitable reverse primer is: 1

```
5'-GCGCTTTGCAGACGGTAGGCG-3'    (SEQ ID NO:14)
0
```

C. Test III

Long PCR conditions were used with a 4-part reaction mixture. Part 1 containing the following components:

| | |
|---|---|
| 3.3X XL Buffer | 12 µl |
| dNTPs (2 mM each) | 8 µl |
| Forward primer (20 µM) | 1–5 µl |
| Reverse primer (20 µM) | 1–5 µl |
| Mg(OAc)2, (25 mM) | 4.4 µl |
| water to | 40 µl |

Part 1 can be assembled as a single reaction component or in batch (10, 50, 100 reaction equivalents) and then dispensed as 40 µl aliquots into individual reaction tubes.

Part 2 comprises carefully adding 1 AmpliWaxPCR Gem 100 (or comparable product to each Part 1 reaction tube. The tubes were incubated at 75–80° C. for 5 min. To melt the wax bead. The reactions were cooled allowing the wax to solidify.

In Part 3, the following components were added to the cooled reaction mixture of Part 2:

| | |
|---|---|
| 3.3X XL Buffer | 18 µl |
| rTth DNA Polymerase, XL | 2 µl |

In Part 4, the following components are added to the reaction mixture of Part 3:

| | |
|---|---|
| human DNA | 0.2–1 µg |
| water to | 40 µl |

Twenty-five to thirty-eight cycles of amplification were performed, using a standard DNA thermal cycler the following protocol for each cycle: 94° C., 30 seconds; 65° C., 30 seconds; and 72° C., 11 minutes. The 72° C. extension cycle was lengthened 5 seconds each subsequent cycle. The primary PCR product can be analyzed immediately for mutations or alternatively, can be used as a template for secondary PCR using a collection of paired amplimers to generate an overlapping set of smaller amplicons. The smaller amplicons can then be analyzed for mutations.

The forward primer used in the reaction described above comprises an oligonucleotide that hybridizes to both authentic PKD1 and PKD1 homologue sequences. An Example of such a primer is:

5'-ACGTTGGGCTCCTGGGCAACC-3'    (SEQ ID NO:12)

The reverse primer comprises a sequence derived from the authentic PKD1 gene and is not present in the PKD1 homologues. Thus, the amplification product in this diagnostic test is derived only from the authentic PKD1 gene. An example of a suitable reverse primer is:

5'-AGGTCAACGTGGGCCTCCAAGTAGT-3'    (SEQ ID NO:13)

For RT-PCR, first strand cDNA synthesis is performed using the reverse primer (SEQ ID NO:14) and Superscript II™ according to manufacturer's recommended conditions (Life Technologies, Inc., Gaithersburg, Md.). PCR is then performed using 1–50% of the first strand reaction under the reaction conditions described above, with the modification that the extension cycle is conducted at 72° C. for only 6 min.(due to the smaller product size).

D. Test IV

To analyze PKD1 mRNA for mutations, RNA is isolated from the white blood cells as a requisite template for RT-PCR. Whole blood samples collected in high glucose ACD Vacutainers™ (yellow top) were centrifuged and the buffy coat collected (4–20×10$^6$ cells/10 ml of blood). RNA can be isolated directly from white blood cells or after standard short-term culturing of white blood cells in the presence of a mitogen such as phytohemagglutinin (48–72 hours). RNA is isolated as described using standard conditions such as guanidium isothiocyanate:acid phenol extraction (Chomczynski and Sacchi, *Anal. Biochem.* 162:156–159, 1987).

For RT-PCR, first strand cDNA synthesis is performed using the reverse primer (below) and a commercially available reverse transcriptase, such as, for example, Superscript II™ according to manufacturer's recommended conditions (Life Technologies, Inc., Gaithersburg, Md.). PCR is then performed using 1–50% of the first strand reaction under the reaction conditions described below.

The reverse primer comprises a sequence derived from both the authentic PKD1 gene and the PKD1 homologues. In contrast, the forward primer is specific for the authentic PKD1 locus and will not allow amplification of cDNAs derived from the homologous loci. Thus, the resulting RT-PCR amplification product in this diagnostic test is derived only from authentic PKD1 RNA.

The forward primer used in this reaction comprises an oligonucleotide that hybridizes only to authentic PKD1 and not to homologue sequences. An example of such a primer is:

5'-AGCGCAACTACTTGGAGGCCC-3'    (SEQ ID NO:15)

An example of a suitable reverse primer is:

5'-GCCAAAGGGAAAGGGATTGGA-3'    (SEQ ID NO:16)

The amplification aspect of the RT-PCR reactions was performed using standard conditions as described below including a "hot-start" step:

| | |
|---|---|
| 10X Taq Buffer | 8 µl |
| dNTPs (2 mM each) | 7 µl |
| Forward Primer (100 µM) | 0.4–1.5 µl |
| Reverse Primer (100 µM) | 0.4–1.5 µl |
| DNA | 0.2–1.0 µg |
| water to | 80 µl |

Amplification was initiated using a single "hot-start" step, followed by twenty-five to thirty-eight cycles of amplification using a standard DNA thermal cycler. The single "hot-start" step consisted of 80° C. for 3–5 minutes after which time 1 µl of Taq polymerase was added to each reaction tube. "Hot-start" was proceeded by 25–38 cycles with each cycle consisting of the following specifications: 94° C., 20 seconds; 64° C., 30 seconds; and 72° C., 2 minutes.

The primary PCR product can be analyzed immediately for mutations or alternatively, can be used as a template for secondary PCR using a collection of paired amplimers to generate an overlapping set of smaller amplicons. The smaller amplicons can then be analyzed for mutations.

The PCR and RT-PCR products obtained above were analyzed for the presence of specific PKD1 mutations as follows:

8 µl of the amplified products were added to 50 µl of a denaturing solution (0.5 mM NaOH, 2.0M NaCl, 25 mM EDTA) and spotted onto nylon membrane filters (INC Biotrans). The denatured DNA was then fixed to the nylon filters by baking the filters at 80° C. for 15 minutes under vacuum.

Oligonucleotides that detect PKD1 mutations were chemically synthesized using an automated synthesizer and radiolabeled with $\gamma^{32}P$ with polynucleotide kinase, using methods that are standard in the art.

Hybridizations were carried out in plastic bags containing the filters prepared above, to which one or more labeled oligonucleotides were added in a hybridization buffer (3.0M Tetramethylammonium chloride (TMAC), 0.6% SDS, 1 mM EDTA, 10 mM sodium phosphate pH 6.8, 5× Denhardt's Solution, and 40 µg/ml yeast RNA). Oligonucleotide concentrations in the pools ranged from 0.03 to 0.15 pmol/ml hybridization solution.

Hybridizations were allowed to proceed overnight at 52° C., with agitation. The filters were then removed from the bags and washed for 20 min. at room temperature with wash buffer (3.0M TMAC, 0.6% SDS, 1 mM EDTA, 10 mM sodium phosphate pH 6.8), followed by a second wash in the same buffer for 20 min. at 52° C. The filters were dried and exposed to Kodak X-OMAT™ film.

It will be understood that the enzymes and nucleotides used in the above reactions may be obtained from any manufacturer, such as GIBCO-BRL, Promega, New England Biolabs, and the like.

EXAMPLE 6

Antipolycystin Antibodies

A. Production and Characterization of Polyclonal Antisera Against Synthetic C-Terminal Peptide.

A peptide (C)SRTPLRAKNKVHPSST (SEQ ID NO:17) representing the last 16 carboxy-terminal amino acids of the predicted PKD1 gene product was synthesized. A cysteine residue that is not predicted from the DNA sequence was appended to the amino terminus to facilitate coupling to KLH carrier protein. Two rabbits (A and B) were immunized with the peptide as described in Cheng et al., *EMBO J.* 7:3845–3855, 1988.

Polyclonal anti-peptide antisera were diluted from 1:10 up to 1:10,000, and immunoreactivity was determined by ELISA according to conventional procedures (Cheng et al., *EMBO J.*, 1988 supra.). Antisera produced by both rabbits were epitope mapped by the SPOTs method (Blankenmeyer-Menge and Frank, in *INNOVATION AND PERSPECTIVES IN SOLID PHASE SYNTHESIS*, Epton, R. Ed., Chapman and Hall Medical, London, 1990, pp. 1–10). Briefly, overlapping 8 amino acid long peptides were synthesized simultaneously on a cellulose membrane and assayed for immunological reactivity. Positive peptides were aligned and the epitope was identified by determining sequence homologies. Interestingly, antisera A and B had at least 2 non-overlapping epitopes each, thus increasing the possibility that these antibodies will recognize the PKD1 gene product.

B. Domain Specific Fusion Proteins

Figure 15:
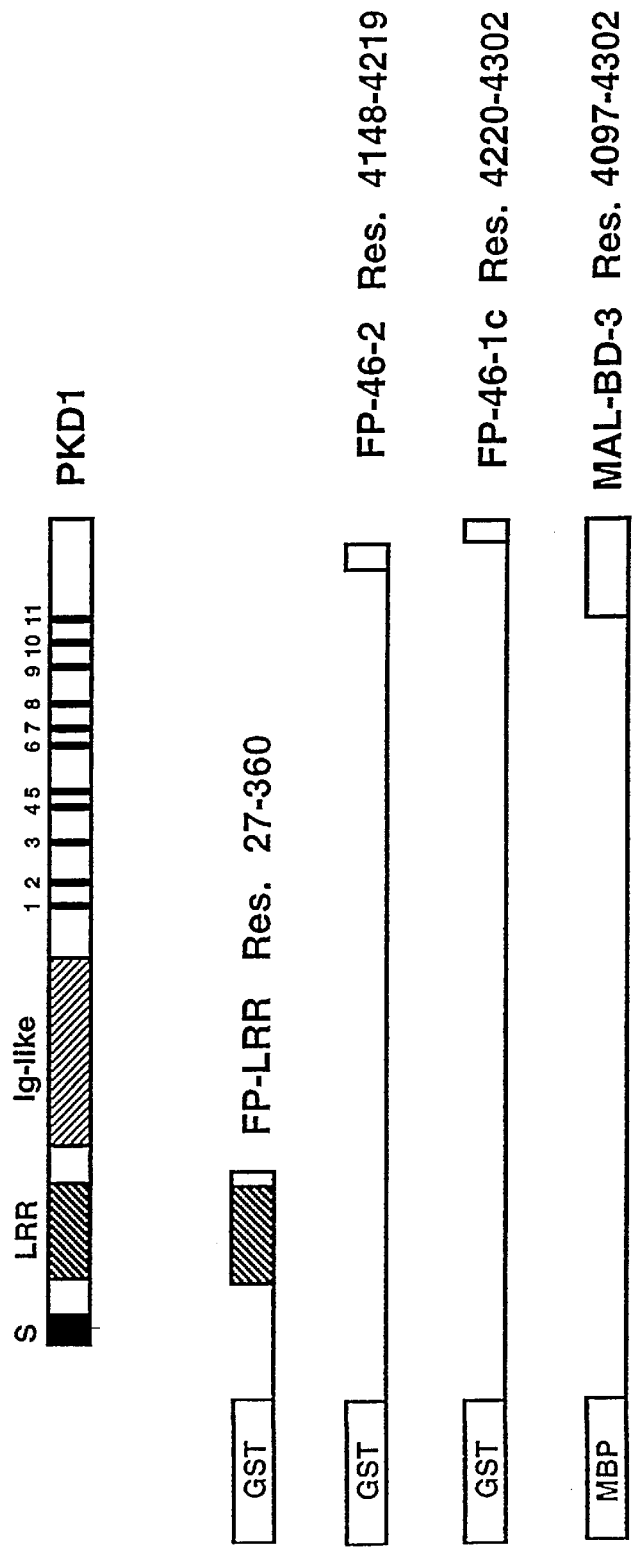
FIG. 15 shows the regions of PKD1 protein used as fusion proteins for generation of domain specific polyclonal antibodies. The predicted structure of the PKD1 protein is shown above. Each fusion protein consists of the carrier glutathione-S-transferase (GST) or maltose binding protein (MBP) and the indicated region of PKD1 polypeptide. PKD1 corresponding residues of each fusion protein are shown.

Four fusion clones were constructed to contain different domains of polycystin such that the correct open reading frame was maintained, as shown in FIG. 15. Three of the expression constructs were cloned in the pGEX vectors designed for the expression of foreign sequences as glutathione S-transferase (GST) fusion proteins in E. coli. These are FP-LRR, which contained the leucine-rich repeat (LRR); FP-46-1c, containing 83 C-terminal amino acids and FP46-2 which has 77 amino acids internal to the FP-46-1c. The fourth fusion construct was cloned into a maltose binding protein (MBP) vector, and encoded 205 amino acids at the carboxy terminus, thus overlapping two of the GST fusion proteins. The overlapping carboxy-fusion products provide an additional layer of antibody reagent confirmation. They allow one to verify that positive antibody reactions are not artifactual, since similar, if not identical, patterns of antibody reactivity should be seen with antibodies raised against these overlapping proteins. Two different 'carrier' fusion proteins also allows one to purify antibody raised against a fusion product using the alternate carrier protein as the affinity ligand. This helps to eliminate antibodies raised against the carrier protein itself.

GST fusion proteins were purified from extracts of transformed bacteria using glutathione-Sepharose (Pharmacia) as described in Smith and Johnson, *Gene* 67:31–40, 1988. MBP fusion proteins were purified on amylose resin (NEB, Beverly, Mass.).

C. Generation and characterization of polyclonal antibodies to domain specific polycystin fusion proteins.

Antibodies against the fusion proteins were raised in rabbits using published procedures (Cheng et al., *EMBO J.* 1988 supra.) with 200 μg of protein. These respective antibodies specifically recognized PKD1 protein as part of the fusion protein construct used as immunogen (i.e., FP-LRR, FP46-1c, FP-46-2 and MAL-BD-3). Further, these antibodies did not bind the irrelevant antigens GST or MBP, nor cross-react to polycystin domains not present in the immunogen included as controls after sufficient antibody purification.

Figure 16:
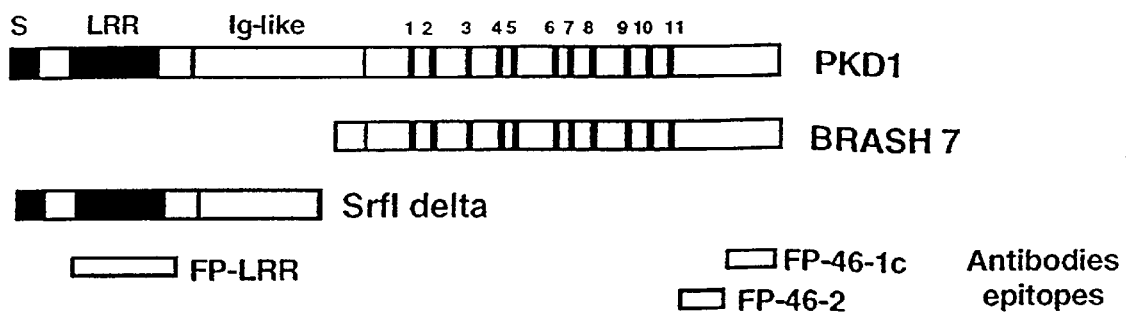
FIG. 16 shows the two constructs used for immunoprecipitation, SrfIΔ, which corresponds to the N-terminal half of the PKD1 protein and BRASH 7, which corresponds to the C-terminal half of the PKD1 protein as shown. Epitopes for anti-fusion proteins FP-LRR, FP-46-1c and FP-46-2 polyclonal antibodies used for immunoprecipitations are also indicated.

In vitro synthesized polycystin protein was used to test the domain specific antibodies. In addition to the full-length PKD1 cDNA, two shorter clones which each expressed only a subset of the PKD1 domains were constructed in expression vectors as shown in FIG. 16. The BRASH 7 clone contains the carboxy terminal epitopes, as well as the transmembrane domains, while SrfIΔ contains the amino terminus, the LRR, and the majority of the Ig-like domains. Both are efficiently expressed in the TNT in vitro transcription/translation system.

D. Immunoprecipitation

Antipolycystin antibodies were incubated with either protein A Sepharose or Protein G Sepharose to generate antibody coupled beads. These beads were then incubated with $^{35}$S-labeled protein synthesized in vitro from the expression clones. The void and retained fractions were collected and analyzed by SDS gel electrophoresis. Sepharose alone was included as a control against artifactual binding, a concern due to the large size of polycystin, the presence of the large number of Ig-like repeats, and the lectin domain. Antibodies to irrelevant antigens were also included as controls. If the antibody specifically bound the antigen, a protein species of the correct molecular mass will be detected on the gel in the bead fraction. If not, the expressed protein will appear in the void volume on the gel.

Each of the anti-fusion protein antibodies coupled to Sepharose A specifically immunoprecipitated protein expressed by clones which contained the matching antigenic domain. The antibodies did not immunoprecipitate protein expressed from irrelevant domains of polycystin (i.e. domains not used as immunogen to generate that particular antibody), nor did they recognize other irrelevant antigens (e.g., luciferase). These results confirm that these polyclonal antibodies specifically recognize the carboxy terminus and LRR domains of polycystin.

EXAMPLE 7

Identification of Proteins that Interact with PKD1

Further characterization of the PKD1 protein can be accomplished through identification of other proteins which normally interact with the PKD1 protein. Those of skill in the art are familiar with a variety of approaches useful for such purposes, including, but not limited to, immunoprecipitation of protein complexes using antipolycystin antibodies, screening of expression libraries with labeled in vitro synthesized polycystin, and use of yeast systems that exploit the interaction of DNA binding and activation domains.

For example, one such approach is the two-hybrid yeast system (Fields and Song, *Nature* 340:245–6, 1989; Finley and Brent, *Proc. Natl. Acad. Sci., USA* 91:12980–84, 1994) which enables the identification of genes which encode proteins that interact with PKD1. This technique relies on the fact that eukaryotic transcriptional activators, such as GAL4, function utilizing two essential and discrete domains, i.e., an amino terminal DNA binding domain and a carboxy terminal transcriptional activation domain (Ma and Ptashne, *Cell* 51:113–119, 1987). The two-hybrid system exploits the observation that a functional transcriptional activator can be generated even when the two domains are encoded by different hybrid polypeptides, so long as the spatial relationship between the two essential domains is similar to the native transcriptional activator. The yeast two hybrid system has been used successfully to screen cDNA expression libraries in search of proteins that interact with Yin-Yang-1 (Shrivastava et al., *Science* 262:1889–92, 1993), E12 (Staudinger et al., *J. Biol. Chem.* 268:4608–11, 1993), H-Ras (Vojtek et al., *Cell* 74:205–214, 1993), Pr55gag (Luban et al., *Cell* 73:1067–78, 1993), p11ORB (Durfee et al., *Genes Dev.* 7:555–69, 1993), and p53 (Iwabuchi et al., *Oncogene* 8:1693–96, 1993).

A. Hybrid Construction

Several constructs of the PKD1 regions as fusion proteins with the GAL4 DNA binding domain were prepared. The constructs were: a BD-3 fusion between the GAL4 DNA-binding domain and the cytoplasmic tail of the PKD1 protein (amino acid residues 4097–4302) using pGBT9 vector, a BD-1 clone containing a DNA-binding domain and the LRR region of polycystin (amino acid residues 27–360), and a BD-2 clone which contains DNA-binding domain and region of Ig-like repeats (amino acid residues 713–2324).

B. Transformation of constructs into yeast

Competent yeast cells HF7c, containing the lacZ reporter gene are obtained by the LiAc method. Briefly, overnight cultures are diluted to OD600=0.2 and continue to grow for an additional 3 hr. Cells are collected, washed in $H_2O$ and resuspended in 0.1M LiAc in TE. Competent cells (0.1 ml) are mixed with 0.1 mg of plasmid-construct DNA and 100 mg of carrier DNA. 50% PEG400 (0.6 ml) is added and incubated at 30° C. for 1 h. Following this incubation, the cells are heated to 42° C. for 10 min. and plated on minimal medium (Difco Yeast Nitrogen Base without amino acids, supplemented with auxotrophic requirements). Yeast transformants are selected after 3 days of culture.

B. Colony lift filter assay for β-galactosidase

VWR grade 410 filters are layered over agar plates containing transformants on selection medium and transferred to a pool of liquid nitrogen for 10 sec. Filters, colony side up are placed on another filter that is presoaked in X-gal solution. After two hours, filters are analyzed for the presence of blue, β-galactosidase producing colonies (not shown). Alternatively, individual colonies from different transformations can be streaked onto the same plate and processed for β-galactosidase activity.

While the present invention has been described with respect to what are presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An isolated gene encoding human PKD1 polypeptide.

2. Isolated human PKD1 gene according to claim 1 comprising the sequence set forth in SEQ ID NO:2.

3. Isolated RNA transcript expressed by the gene of claim 1.

4. Isolated cDNA comprising the sequence set forth in SEQ ID NO:4.

5. An isolated polynucleotide fragment consisting of the sequence set forth in SEQ ID NO:3.

6. Isolated polypeptide comprising the amino acid sequence set forth in SEQ ID NO:5.

7. A vector comprising the isolated gene of claim 1.

8. A vector according to claim 7 further comprising a transcriptional regulatory element operably linked to said gene, said element having the ability to direct the expression of genes of prokaryotic or eukaryotic cells and their viruses or combinations thereof.

9. A host cell comprising the vector of claim 7.

10. A method for producing PKD1 protein, which comprises:
    (a) culturing the host cell of claim 9 in a medium and under conditions suitable for expression of said protein, and
    (b) isolating said expressed protein.

11. Isolated human PKD1 gene, comprising modifications selected from the group consisting of: transitions, transversions, deletions and insertions.

12. A recombinant vector comprising the DNA sequence of claim 11.

13. The vector of claim 12 further comprising a transcriptional regulatory element operably linked to said gene, said element having the ability to direct the expression of genes of prokaryotic or eukaryotic cells and their viruses or combinations thereof.

14. A host cell comprising the vector of claim 12.

15. A method for producing mutant PKD1 protein, which comprises:
   (a) culturing the host cell of claim 14 in a medium and under conditions suitable for expression of said protein, and
   (b) isolating said expressed protein.

16. An isolated nucleic acid of a length of about 12 to 60 nucleotides comprising: 5'-GCGCTTTGCAGACGGTAGGCG-3' (SEQ ID NO:14).

17. An isolated nucleic acid of a length of about 12 to 60 nucleotides comprising: 5'-AGGTCAACGTGGGCCTCCAAGTAGT-3' (SEQ ID NO:13).

18. An isolated nucleic acid of a length of about 12 to 60 nucleotides comprising: 5'-AGCGCAACTACTTGGAGGCCC-3' (SEQ ID NO:15).

19. A composition comprising an isolated human PKD1 gene having the DNA sequence of SEQ ID NO:2 and a carrier or diluent.

20. A composition comprising a vector containing a PKD1 gene having the DNA sequence of SEQ ID NO:2 and a carrier or diluent.

21. A composition comprising the cDNA sequence of SEQ ID NO:4 and a carrier or diluent.

22. A composition comprising a normal PKD1 protein encoded by the DNA sequence of SEQ ID NO:2, or fragments thereof, and a carrier or diluent.

23. A composition comprising a normal PKD1 polypeptide encoded by the DNA sequence of SEQ ID NO:4, or fragments thereof, and a carrier or diluent.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 53577 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
TGTAAACTTT TTGAGACAGC ATCTCACCCT GTTCCCCAGG CTGGAGTGCA GTGGTGTGAT      60

CATGGCTCAC TGCAGCGTCA ACCTCCTGGG TCTACTTGAT CTGTAAACTT CGAGGGAAGG     120

TGTAATAAAC CCTCCTGCAA TGTCTTTGTT TTTCAAAATC TTTGTATTTC ACAGTTTAGC     180

TTCGTGGGTT GATGTTCTAT TTTGTTTTTG TGTGTGTGTG TGTGTGTTTT GTGTTTTTTT     240

TTGAGACACA GTCTTGCTCT TGTTGCCCAG GCTGGAGTGC AATGGTGTGA TCTTGGCTCA     300

CTGCAACTTC CACCTCTTGG GTTCAAGAGA TTCTCCTGCC TCAGCCTTCC GAGTAGCTAG     360

GATTACAGGC GCCGCCACCA CACCCCGCTA ATTTTGTATT TTTAGTAGAG ATGGGGTTTC     420

TCCATATTGG TCAGGCTGGT CTCAAACTCC CGACCTCAGG TGATCCGCCC ACCTCAGCCT     480

CCCAAAATGC TGGGATTACA GGCGTGAGTC ACCGCACCTG GCCAATGTTC TATTTTTGAG     540

AACACAACAG TTCATAATAT ATTCTACATA GACCATACCT GTTATGTGTA GATAAACAGA     600

CTCTTTTCCC ATTTAACACC TTTTGCCTTA GGTTTATTTT TCTGGTATCA ATACTGGCAC     660

ACTTACTTTG TTTGCAGTTT CCTGTCTTTT TTTTTTTTTT TTTTTTTTTT GAGACAGAGT     720

CTCACTCTGT CACCCAGGCT GGAGTGAAGT GGCGGGATCT CGGCTCACTG CAACCTCTAC     780

CTCCTGGGTT CATGCGATTC TCCTGCCTCA GCTTCCCGAA TAGCTGAGAC CACAACTGTG     840
```

```
TGCCACCATG CCCAGCCAAT TTTTGTATTT TTAGTAGACA CGGGGTTTCA CCATACTGGC    900
CAGGATGGCT CAATCTCTTG ACCTCGTGAT CCACCTGCCT CCGCCTCCCA AAGTGCTGGG    960
ATTACAGGCA TGAGCCACTG TGCCTGGCCT TTTTTTTTCT TTTTGAGATG GAGTCTCACT   1020
CTGTCACCCA GGCTGGAGTG CAGTGGGGTA ACCTCAGGTC ACTGCGACCT CCGCCTCCCG   1080
GGTTCCAGTG ATTCTCCTGC CTCAGCCTCC CGAGTAGCTG GGATTACAGG CACCCACCAC   1140
CATGCCTGGC TAATTTTTGT ATTTTTAGTA GAGACGGGGT TTTGCCACGT TGGCCAGGTT   1200
GGTCTCGAAC TCTTGGCCTC ATGTGACCCG CCTGCCTTGG CCTCCCAAAG TGCTGGGATT   1260
ACAGGTGTGA GCCACTGTGC CTGGCCTGGC TTTCTTGTTT CTTTTCTCCT CTTCTAGTTT   1320
CCCCCTTTTA GGCTAACAAT TATTCACTGT TAATAAAAAC CCTCAGGTCT GTATTTTATC   1380
AAGAAACATT TCCCTCACGT CTTCTTCCCT GAACCAAACA AGATCTCTGG CACATTTTAT   1440
TTGCTCTGTC TCACCACATG GATTTTGTTT TTTTGTTTCT TTGTTTTTTG AGATGGAGTC   1500
TCACTCTTGT TGCCCAGGCT GGAGTGCCAT GGCACAATCT CAGCTCACTG CAACCTCCAC   1560
CTCCTGGGTT CAAGCGATTC TCCTGTCTCA GCCTCCTGAG TAGCTGGGAT TACAGGCGCG   1620
TGGCACCACC CCCAGCTAAT TTTTGTATTT TTAGTAGAGA CGGGGTTTCA CCATGTTGGT   1680
CAGGCTGGTC TCGAACTCCT GACCTTGTGA TCTGCCCACC TTGGCCTCCC AAAGTGCTGG   1740
GATTACAGGC ATGAGCCACC ACGCCCGGCC CCCATGGTTT TTCAAATAGT TTAGAATTTC   1800
ATTTCCAGGT AACTAATTTG CTTCTTTAAA CATATGTCTT TTCTATTTAA GAAATCCTTT   1860
CTAAACAATT GCATTTTATT CCACAACCGC CTTCAAACAA TCATTGAGAC TTGGTTAATC   1920
TGTTTTGCTC ATTTGGCAGC AGTTTCTTGT GGCTGTTTCT TCCCTCCACT GGAGTCCTTG   1980
AATCTTAAGT CTGTCATTTG ACTGCAATTA AAAGCTGGGT TTGGAATACA ATCGCAGCCT   2040
TACCATCCAC CTGCTGTGTG ACCTGGTAAA TTTCTTTTTT TTTTTTGAG ACGGAGTCTT   2100
GCTCTGTTGC CCAGGCTGGA GTGCAGTGGC ACAACCTCTG CCTCCCAGGT TCAAGCGATT   2160
CTACTGCCTC AGGCTCCCTA GTAGCTGGGA TTATAGGTGC CTGCCACCAT GCCCAGCTGA   2220
TTTTTGTATT TTTAGTAGAG ATGAGGTTTC ACCATGTTGG CTAGGCTGGT CTCGAACTTC   2280
TGATCTTGTG ATCTGCCCGC CTCGGCCTCC CAAAGTGCTG GGATTACAGG CATGAGCCAC   2340
CACTCCCAGC CAGTTCTTTT TTTCTTTTTT CCATTTTTTT TTTTTCGAG ACAGGATCTT   2400
ACTCTTTTGC CCAGGCGGGA GTGCAGTGGC ACAATCACGG CTCAGCGCAG CCACTGCCTA   2460
CTGGGCTCAC ACGCTCCTCC GGCCTCAGCC TCTCGAGTAC CTGGGACTAC AAGCGTGAGC   2520
CAGTTTGGCT AATTTTGGCT AATTTTTGTA GAAACGGGGT CTCGCCATGT TGGCCAGGCT   2580
GGTCTCCAAC TCCTGGACTC AAGGGATCCA CCTTCCTCCC CCTCTCAAAG TTCTGGGATT   2640
ACCGGAGTGA GCCACTGTGC CCTGCTGGCA AATTTCTTAA ACTGTCTGTG CCTCAGTGAC   2700
CTCATTTAAT AAAGGGAATA ATTGTAGCAC ACTTTTTCTA GAGCTGTGAA GATTCAATGG   2760
AATAAATAAG GCAATAAATG AATGGATGGG GAATGAAGGA TGTGGGTTTC CTCCCTCTTG   2820
TCTTTCAATA AGCTCTCACC ATCAACCTCC CATTGCCTGT TCTCTCTCTT CCCCCTCTCT   2880
CCCTCTGTCT CTCTCTCAGC CAGGAAACCT GGGGTAGGGA GGCTTGGAGC CAGCGGGTGC   2940
GTCGGGAGGC TGCGGGTACT GACTCGGCCG CGCACGGAGA TCGCGGGAG AAGGATCCAC   3000
AACCGCGGAA GAAGGATCAG GGTGGAGCCT GTGGCTGCTG CAGGAGGAGG AACCCGCCGC   3060
CTGGCCCACA CCACAGGAGA AGGGCGGAGC AGATGGCACC CTGCCCACCG CTTCCCGCCC   3120
ACGCACTTTA GCCTGCAGCG GGGCGGAGCG TGAAAAATAG CTCGTGCTCC TCGGCCGACT   3180
```

```
CTGCAGTGCG ACGGCGGTGC TTCCAGACGC TCCGCCCCAC GTCGCATGCG CCCCGGGAAC      3240

GCGTGGGGCG GAGCTTCCGG AGGCCCCGCC CTGCTGCCGA CCCTGTGGAG CGGAGGGTGA      3300

AGCCTCCGGA TGCCAGTCCC TCATCGCTGG CCCGGTCGCG CTGTGGCGAA GGGGGCGGAG      3360

CCTGCACCCG CCCCGCCCCC CCTCGCCCCG TCCGCCCCGC GCCGCGCGGG GAGGAGGAGG      3420

AGGAGCCGCG GCGGGGCCCG CACTGCAGCG CCAGCGTCCG AGCGGGCGGC CGAGCTCCCG      3480

GAGCGGCCTG GCCCCGAGCC CCGAGCGGGC GTCGCTCAGC AGCAGGTCGC GGCCGCAGCC      3540

CCATCCAGCC CGCGCCCGCC ATGCCGTCCG CGGGCCCCGC CTGAGCTGCG GCCTCCGCGC      3600

GCGGCGGGC CTGGGACGG CGGGGCCATG CGCGCGCTGC CCTAACGATG CCGCCCGCCG        3660

CGCCCGCCCC CCTGGCGCTG GCCCTGGGCC TGGGCCTGTG GCTCGGGCG CTGGCGGGGG       3720

GCCCCGGGCG CGGCTGCGGG CCCTGCGAGC CCCCCTGCCT CTGCGGCCCA GCGCCCGGCG      3780

CCGCCTGCCG CGTCAACTGC TCGGGCCGCG GGCTGCGGAC GCTCGGTCCC GCGCTGCGCA      3840

TCCCCGCGGA CGCCACAGCG CTGTGAGTAG CGGGCCCAGC GGCACCCGGG AGAGGCCGCG      3900

GGACGGGCGG GCGTGGGCGG GTTCCCTGGC CCGGGACGGG AAGCAGGACG CGGGCCAGGA      3960

CGCTCCCAGG GGCGAGGCTC CGGCGCGGCA CGGCGGGCCC TGCTAAATAA GGAACGCCTG      4020

GAGCCGCGGT TGGCACGGCC CCGGGGAGCC GAAAAACCCC GGGTCTGGAG ACAGACGTCC      4080

CACCCGGGGG CTCTGCAGAC GCCAGCGGGG GCGGGCGCG GAGGCCGCGC TCAGCTGGGA       4140

GGACAAACAG TCGCTAATTG GAGAGGAATT GGGATCGGCC TGGGGCTGCG GGTACCCGG       4200

AGAGGTGGGG ATGGCTGTAG GGGGCGGCAG GGAAGAGTTC CAGGAGGTGT CTGGAAAAGG      4260

ATTTGATGGA TGTGCAAGAA TTGGGCTGAT GCTTAGGAAG GGGCGATGAG GTGGGTCCAG      4320

AAGAAGGGGG GTGAACGGTG TGAGCAAAGA CCGTGAGGCT GGAGGCTGGC CACGGGAGGT      4380

GTGAGGGGTA GGGGCAGGGT GGGAGGTGGG CTCGCGGGTG GGCTGGGGTC ATGAAGGGCC      4440

TCAGGCGCTC TGCTATTGGG TTCCAAGGCT ATCCTGAGAA CAGGGGTGAG GGGGGATTGC      4500

CGTGGGGGGT TAAAGCCTTG TCATGTTCGC TTTCGGGAGA TAAAAACAAC AGGTGGCCTT      4560

TATGGAGACG CTGCCCAGAG CCAGGTCTGT GCCAGGCTCC TGTTGGGGGT CGTCATGCGG      4620

AATCCTGACT CTGACCATCC GAGGCATAGG GACCGTGGAG ATTTGCATTT CACAGATGAG      4680

GAAACAGGTT TGGAGAGGTG ACACGACCTG TCCCAGGCAT CACAGCCGGG ATGTGCATAG      4740

CAGGGGTTTG GAACTATGAG GTGCCCAGGA CCCAGGGTTG GATTGAAAAG GGCGGAGGGG      4800

ACTAAGATAA GCAGACAGTT GTCCCCAGCG CTGGGGAGAG TCTTGGGACC AGTCTGATGC      4860

CTTGTATTTC CCAGGCTCCA GGCTCCTCGC CGGGACAGTG TCTCCTTGGG TGCGTGCTGG      4920

ATCCCTGGGG GACGTGGCAC ATCCCCAGGC TTGCTAAACA TTGGGTGGGT CTGGCATTT       4980

GGTTTTGTAA CGTTTCTGGG TCACTCCCGC CTGTGGCCAC CCTTCCTTAG GGGAGCCGTG      5040

TGTCCTTGGG GCTTTGCTGG GTGGTCTCGA GGGTGGGAGA AGAATGGGTT CTCCTGGACC     5100

AATGGAGCCC GTGCCCCTCG GGGCCACATT GCTCCTGCGC TCCCTGACTG CGGACGCGTG     5160

TGTCTCGCGG CTGTCTCTGT GGAGATGGCC TCCTCCTGCC TGGCAACAGC ACCCACAGAA     5220

TTGCATCAGA CCTACCCCAC CCGTTGTTTG TGATGCTGTA GCTGAGGGCT CCTCTGTCTG     5280

CCAGGCCGGT CACTGGGAC TCTGTCCAGG GCCTGGTGGT TCCTGCTTCC CAGCACCTGA      5340

TGGTGTCCAT GAGAGCAGCC CCTCAGGAGC TGTCCGGGAG AGAAGGGCGC TGGTGGCTGC     5400

TGAGCGGAGA GCAAGGCCCG TGTTCTCCAG GCCCTTGGCA CAGCAGTGGA GCCCCCGCCC     5460

CTGCCTTGTG TTGTCCTCTT AGGCTCTGGT CCTGGGGTTT GGAGGAGGGG GACCCTGGGA     5520

GTTGGTGGCC TGTCCCAGCC TGAGCTGGCA AGATTCCGAA TGCCAGGCCC CCCAAGTGTG     5580
```

```
CAACAGGGCA CAGGGTGACC TCATGTGGGC AGGTGGGTGC TGTTCTGTAC ACACCTGGGG      5640

CCGCCGCTGG GAGAGTTCTG GAAGGTGGGG TGAGGGACC  CATGGCAAAC TAGGGCCTTA      5700

GGAAGGATGT GAAGGCCCTG GCTGGCCCCC CAGGCCACCC TCTGTGCTGT GGGGCAGCCC      5760

AGCCATTTTG CTGTCTACCC TGCAAACTCC TCCTCGGGGA GACGGCTGGG TTTTCCCCAG      5820

GGAAGAGGGG TCAAGCTGGG AGAGGTGAAG GACACAGATC ACAGCTGCTG GCAGGTGTTC      5880

AAGGGTCCAA GAGCGTTGCT GTCTGGGTGT CACCAGTAGC CTTCCTGGGG GGCTCACGCA      5940

GGTGCCTCTC CACTTGTGGC TCCCTGGCTG CTGAAGCTCA GCAGGGACAG CTGTGTCCAG      6000

TTCCAGGTGG AGGACAGCCG GGGCTTCTGA GGCCACAGCC TGCCTTGGGT TAATGATGCT      6060

GCCGAGAGGT GGTGGCTTTT GGAAAAGATG GCGTACTGCA AAACGTGCTG CTCTGCGTGG      6120

CTCGAAGCTT CGTGGGGAGA CGTGGGCAGA GCCGTGGCTG ACTCACAGAC CCCCCACCCC      6180

AGAGCCTGCC CTGCCCTCCC TGCCCCGACC CTTCTCCCTC CTGACCCATG TGTTTTTTTT      6240

TTTTTTTTTT TTTTTTGAGA CAGAGTTCAC TCTTGTTGCC AAGGCTGGAG TGCAATGGCA      6300

CGATCTCGGC TCATGGCAAC CTCCGCCTCC TGGGTTCAAG CGCTTTTTCC TGCCTCAGCC      6360

TCCCGAGTAG CTGGGATTAC AGGCGTGCAC CACCATGCCT GGCTAATTTT GTATTTTTAG      6420

TAGAGACAGG GTTTCTCCAT ATTGGTCAGG CTGGTCTTGA ACTCCTGACC TCAGATGATC      6480

CGCCCGCCTC GGCCTCCCAA AGTGCTGGGA TTACAGGCAT GAGCCACCAC GCCCAGCCCT      6540

GACCCATGTT TTGAACCAAA TTCCAGCCAC CCTTTTATCT GCAAGCATTT GGAGGGCAT       6600

CGCAATACTG CAGACCCACC TAACACAACA GACAGTTCCT TCATGCCACC GAAGGCCTGG      6660

TGTGTTCACA TTTTTGGTTT AATAGTTTGA ATTAAGAGCC AAATAAGGTC CACACACTGC      6720

AATTAGTTGA TGTCTTTTTT TTTTTCTTTT TTTTTTTTT  TTTGAGACGG AGTCTTGCTC      6780

TTGTCTCCAG GCCGCAGTGC AGTGGCATGA TCTCAGCTCA CCGCAACCTC CGACTCCCTG      6840

GTTCAAGCGA TTCTCCTGCC TCAGCCTCCC GAGTACCTGG TAGCTGGGTT TACAGGCATG      6900

CACCACCGTG CCCAGCTAAT TTTTGTATTT TTAGTAGAGA CGGGGTTTTA CTGTGTTGGC      6960

CAGGATGGTC TCGATCTCCT GACCTCGTGA TCTGCCCACC TCGGCCTCCC AAAGTGCTGG      7020

GATTACAGGC GTGAGCCACC GCACCCGGCC AATGTCTTTT AAAAATATAT ACTTTTTTTT      7080

TTTTTTTGAG ACGGAGTTTC GCTCTTGTTG CCCAGGCTGG AGTGCAGTGG CGCGATCTCA      7140

CCTCACGGCA ACCTCCGCCT CCCGGGTTCA AGTGATTCTC CTGCCTCAGC CTCTCCAGTA      7200

GCTGGGATTA CAGGCATGTG CCACCATGCC TGGCTAATTT TGTATTTTTA GGAGAGACGG      7260

GGTTTCTCCA CGTTGGTCAG GCTGGTCTCA AACTCCTGAC CTCAGGTGAT CCGCCTGCCT      7320

TGGCCTCCCA AAGTGTTGGG ATTACAGGTG TGAGCCAACG CGCCCAGACA AAAATATATG      7380

TGTGTCTTTA AGGCTGGTCA AGCAAAGCAG TAGGACTGGA GAAAGAATGA AGAATTCTAC      7440

CTGGCTGTGA TCAATTCGTT GTGAACACCA CTGTGCTTGG ACCAGCTAGC TGATGTCTTT      7500

TGTTTTGTTT TGTTTGAGAC GGAGTCTGGC TCTGTCACCC AGGCTGGAGG ACAATGGTGT      7560

GATCTCGGCT CACTGCAGCC TCCATCTCCC GGGTTCAAGC GATTCTCCTG CCTCAGCCTC      7620

CTGAGTAGCT GGGATTAGAG GCGCGCGCCA CCACGCCCGG CTAATTTTTA AAAATATTTT      7680

TAGTAGAGAT GGGGTTTCAC CATGTTGGTC AGGCTGGTCT TGAACTCTTG GCCTTAGGTG      7740

ATCTGCTTGC CTCGGCCTCC CAAAGTGCTG GGATTACAGG TGTGAGTGAT GTATTTTATT      7800

TATTTATTTA TTTATTTATT TTTATTATTT GAGATGGAGT CTCACTCTGT TGCCCAGGCT      7860

GGAGTGCAGC AGTGCCATCT CAGCTCACTG CAAGCTCCGC CTCCTGGGTT CACGCCATTC      7920
```

```
TCCTGCCTCA GCCTCCTGAG TAGCCTGGAC TGGTGCCCGC CACCATGCCC AGCTAATTTT     7980

TTGTATTTTT AGTAGAGACG GGGTTTCACC GTGTTAGCCA GGATGGTCTG GATCTCCTGA     8040

CCTCGTGATC CTCCCGCCTC AGCCTCCCAA AGTGCTGGGA TTACAGGCTT GAGCCACCGC     8100

CTGTCTTTTA AATGTCCGAT GATGTCTAGG AGCTTCCCTT CCTCTCTTTT TCCTTGTGCA     8160

ATTTGTTGAA GAAACTGGCT CCTGCAGCCT GGATTTCTCG CTGTGTCTTG GGGGTGCCAC     8220

CTCCATGGTG TCACCTCCGT GGTGCTGTGA GTGTGTGCTT TGTGTTTCTT GTAAATTGGT     8280

CGTTGGAGCC GACATCCCAT TGTCCCAGAG GTTGTCCTGG CTGGCACTGG CCTAGGTGTA     8340

GATGTCATCA GCTCAGGGCC CCCTGCTCTA AAGGCCACTT CTGGTGCTGG TTGCCACTCA     8400

CCCTGGCTGG GGGTCACCTG GGTCTGCTGC TGTCTCGCAA ATGCTGGGGT CCAGGACTGG     8460

GCACATCGAG GGACTTGGTA GGTGCTTGGT TCACTGATGT AAAATATAGG AGCACCCGGG     8520

GCCTTGCCCT TTCCCACCTG CATCCCTGAA TGACAGGAGA GTGTGGGAGA GTGTAGGGAC     8580

AGCAGGCGCA GACCCCGGGG CCCCTGCCTG GGATTGGCGT CGGGGAAGAC AGGCATTCTG     8640

GAGCGACCCC TAGGCCTGAT GCCTTAGAGC GCAACTGCCA GAGACACAGC TTCCTTGGGG     8700

GGCTGGCCAG GCCACGGAGG GGCCCTGGCT CCCATTTCTG GTCCCTGGAT CCTGAGAGCG     8760

AGGACTAGGG ATTGTCACCA AGGCCTCCAT GAGCCCTCAG CAGAAGGAGG GCCACCCTCG     8820

AGGGCTCCGT TATCACTGGA GCCCGCGTTC AACCAACACG CAGATGATTC TCCAAGGACA     8880

GAGATGGATG ATGGGGAGGG GGCTGGCCTG GAAGGACCCC CAGTGCAGGT GACATTGAAG     8940

CCAGGTTTCA AAGCTCCCAC AGGGAGCTGC CCAGAGAGAG TCCCCAAGGG GCAAGGTGAC     9000

TCGGGGGCAG GGGTAGGGCC TCTGTCAGGA GAGCCTAGGA GAGGCCTGTG TCTTCTAGGA     9060

AGAGCCCTGG CAGCCGAGCG GAGGCAGTGG TGAGGACCTG CATCCTGCAT GTCCAGCTGG     9120

CCTCACCCGG GGTCCCTGAG CCGGGTCTTA CGTGGCTCCC GCACTCGGGC GTTCAGAACG     9180

TGCCTGCGTG AGAAACGGTA GTTTCTTTAT TAGACGCGGA TGCAAACTCG CCAAACTTGT     9240

GGACAAAAAT GTGGACAAGA AGTCACACGC TCACTCCTGT ACGCGATTGC CGGCAGGGGT     9300

GGGGGAAGGG ATGGGGAGGC TTTGGTTGTG TCTGCAGCAG TTGGGAATGT GGGGCACCCG     9360

AGCTCCCACT GCAGAGGCGA CTGTGGAGAC AGAGAGCACC TGCAGGTCAT CCATGCAGTA     9420

TCGGCTTGCA TCCAGATCAT ACAGGGAACA CTATGATTCA ACAACAGACA GGGACCCCGT     9480

TTAAACATGG ACAAGGGGTC ACTCACGCCT GGAATCCCAG CAGTTTGGGA GGCCAGGGTG     9540

GGTGGATCGC TTGAGCCCAG GAGTTTGACA CCAGCCTGGG CAACAGGGTG AGACCCCGGT     9600

CTCTAAAAAA TAAAAGAACA TTGGCCGGGC GTGGTGGTAT GCATCTGTGG TCCCAGCTAT     9660

TCAGGAGACT GAGGTGGGAC ATCACTTGAG CCGAGGAGGT CAAGGCTGCA GTGAGCTGTG     9720

ATCACACCAC TGCACTCCAG GCTGGGTCAC AGAGCAAGAC CCTGTCTCAA AAAAAAAAA     9780

AAAAAAAAAA AAAAATCACA GGATCTGAAC AGAGATTTCT CCAAAGAAGA CGCACAGATG     9840

GCCAACAGCG TGTGAGAAGA TGGTCGGCCT CATTAGTCAT GAGGGAAACG TAAATCAAAA     9900

CCACTGTCCA GCCGGGCGCG GTGCCTCACG CCTGTAATCC CAGCACTTTA GGAGAGCAGA     9960

TGGCTTGAGG CCAGGAGTTT GAGGCCAGCC TGGGCAACAT AGCGAGACCA ATAAATAGAT    10020

ATTAGTGGTG GCGCCTGTAG TCCCAGCTAG TTGGGAGGCT GAGGGGGGAG GATTCCCTGA    10080

GTCTATGAGG TTGAGACTGC AGTTAGCTGT GATGGTGCCA CTGCACTCCA GCCTGGGCGA    10140

CTAGGAAACG GTCTTTAAAA AAAAAAAAA AAAACAGGGT GGGCGCGGTG GTTCACGCCT    10200

GTAATCTCAG CACTTTGGGA GGCCAAGGTG GGGGATCAC AAGGTCAGGA GTTTGTGACC    10260

AGCCTGACCA ACATGGTGAA ACCCCGTTCT ACTAAAAATA CAAAAATTAG CGAGGTGTGG    10320
```

-continued

```
TCGTGGGCGC CTGTAATCCC AGCTAATTAG GAGGCTGAGG CAGGAGAATC ACTTGAACCC    10380

GGGAGGCGGA GGTTGCAGTG AGCCAATATC ACACCACTGC ACTCTAGCCT GGTCAACAGA    10440

GCGAGACTCT GTCTCAAAAA AAAAAAATGC TGAGCGTGGT GGCGCATGCC TGTAGTCTCA    10500

GCTACTTTGG GGGCTGAGGC AGGAGAATCG CTTGAACCTG GGAGGCAGAG GTCGCAGTGA    10560

GGCAAGATTG CACCATTGCA CTCCAGCCTG GGAGACAGAG TGAAACTCTG TCTCAAAAAG    10620

AAAAGGTCTA GGAAGAGTCC GCACCCTCTC CCCGCGGTGG CCACGCCGGG CTCCGCGCTG    10680

AGCCCTCTGT GTTCTTGTCT CTCCATACCT CATCACGGCA CCGCAGGGTT GCAGCCACTC    10740

CTGGTCTCAT TTTACACACC AGGAAATTGA GGCTCTTTGA GAAGCCGTGG TGATGATTTC    10800

ATCAGCATGC TCTGGGCAG ACCCCTGCAG CCGCACAGGG TGCCTGGGGC CCACACTAGT    10860

GCCCTGGTTT ATAGACAGAC AGAGGTGGCA GTGGCGCTTC CGAGTCGGGC TGCGATGTGC    10920

TTGCACTCCC CGAGGGCTG AGGGGCCCTG CGCCCAGGTG CAGCTGCTTG GGTGCTGCCA    10980

GCCCCTCCCA CCTCTCCCTC CCTGCCAGCC CCTCCCACCT CTCCCTCCCT GCCAGCCCCT    11040

CCCACCTCTC CCTCCCTGCC AGCCCCTCCC ACCTCTCCCT CCCTGCCAGC CCCTCCCACC    11100

TCTCCCTCCC TGCCAGCCCC TCCCACCTCT CCCTCCCTGC CAGCCCCTCC CACCTCTCCC    11160

TCCCTGCCAG CCCCTCCCAC CTCTCCCTCC CTCCAGCCCC TCCCACCTCT CCCTCCCTGC    11220

CAGCCCCTCC CACCTCTCCC TCCCTGCCAG CCCCTCCCAC CTCTCCCTCC CTGCCAGCCC    11280

CTCCCACCTC TCCCTCCCTG CCAGCCCCTC CCACCTCTCC CTCCCTGCCA GCCCCTCCCA    11340

CCTCTCCCTC CCTGCCAGCC CCTCCCACCT CTCCCTCCCT GGCTCATCCC TGCTGTGTCC    11400

CTTCTCTCTA GTTTCCTGTT CAGTTTCAGG AAGGAGGCTG GGAACCCAGA TGTAGGGAAT    11460

TTGCGCCCTG GAGTCAGACC TGGGTTCACG TCCCAGCGCC TCCACCTCTG GTGTGACCTT    11520

GGTCCAGTCT CTCAGCCTCA GTTTCCTCAC CTGTAAAGTG GGCTCCATGA TTAGATGCAC    11580

CCTGCAGGGC AGTGTAGCAG TGACCTGGCT CAGCCACTGG CAGCCCCAAC AATCATACCT    11640

TGTTAAAGTA GCTCTGTCGG TTCCCTCAGG GGTTCCGGGG GCCCATTCCC CTGTCCTCCA    11700

TGCACTGTGA GACCTGCCCT GCCACAGAGC AGAGTGTAAC AGCCTGAGGG TGAGAGCCAG    11760

ACACTGTGCC TGTGCTTAGA CCAGACACTG GACGACGGGA GCCAGTGCAG CCTGGGCGGG    11820

TGGACTCCTA TGGACCCCTC AGCACCCAGC CTCGGTGCCT TCAGCGCAGG GCCGCGTGGC    11880

TGTGGGGGCT CACAAGACCC GGCCCACTCC TGCTTGTGCC TACATCTGGG TGTTTGCCCA    11940

TTGGTGCCTT TTGACGCGTT CTGGTGTGTG TGAGACGTGC GGGGCTGGGA AGTGTTGGCA    12000

GAGCCGCGAG TACCGTCCTC ACTCCTTTTG TTCTTTTGAC GTAAGCTGGC GAGTGGCACT    12060

GCCTGAGTTC CGCTCAGTGC CCGCCCTGAT GTGCGGACCC CGCTGCATTC TTGCTGTTAG    12120

GTGGTGGCGG TGTGCGCTGT CGCTGGTGGG CACCGAGAGT CTTTGGGAGC TTTGGGGAGG    12180

TTGTGCCAAG CCTGAGCCTC GACGTCCCCC TTCCCGGCTT TCTGTTGGCT CTTCTGAGGC    12240

CAGGGCATCT CTATGAGGGC CTCCTGCTGG AGCCGTCTCT GTGGATCTCC TCTGCCATCC    12300

TGGCCCATGA GTGGGTGATG CGCTGGCCAC CATCTGGTGA CAGTGGCCGG GCACCGCTGC    12360

CAAATGTGGG TCCCGCATCT GCAAGCCCCT CCCTGGGTCC CCTAGGGTAT GGGGTGGTTC    12420

TGCCACTGCC CTCGCTCCCC CACCTTGGGG TGCCTCTCCC CCTGCTCGTG GGGGAGACCC    12480

TGCCTGGGAT CTGCTTTCCA GCAAGGAATA TACTTTGGAG GGAGACACAC ATGTTCTTTT    12540

CTGGAGCTCT GCAGTGGCCA CGGCAGCCCA GCCCGCCAAG CACCCTGGAA TGAAAACATC    12600

CCGCTGCTGT CTGGGCCTGG CCTGCACTCT GCTGCCTGCG CTCCAGCTGG CTGAGGCCGG    12660
```

-continued

```
GCACGTCTGC GGGCACAGCA GCGGGGCGC CACAGTCTCC CTGCAGAGTG AGCGCAGCTG   12720

GAAAATGCAG CTCACGCCCT TTCCCAGAAC ACCTCGCTCT TCATGGCTTG GCAGCTGTCC   12780

TTGCCTAGGG GCCAGGGTGC CCAGGCACTG GTGGCAGGAG AAGGGCTACA TCTGGGGCTG   12840

AGGCGGGCTG GGTCCTTTTC TCCCTGCAGC TCCCGAGGCC CAGCCCTGGC CCAGCCTGGC   12900

ATTCCTGACC TTAGCAGCGC CATGATCTGA AGACAGGCTG GCTTCTGTGA GGCCACCTCA   12960

GAAAGGGCTT TGTGCCCAGG CAGAGGCGGA AGCCAGCTCT TCCTTCTGGT TGAGGCAGGA   13020

ATGAGGCCAG CGCTGGGCAA GCCCATGCCC AGGGAACGTC ACAGCTGTGG GAGTACAGGG   13080

GCTCCGGGTT CTGAGCCCGT CCACTGTGCA TCGTGGCCCT GGCCTCAGGA TGGCTCGTAC   13140

CATCATTGGC TGTGCCCACA GCCGAGTGGG TGATGGGATT CCGGCTGCCC CGCTGGATCT   13200

GTGCTGCTGC CCTCTCCAGG GCACTGCTGT GCCCGCACAG CCGGGCGCAG ATGGCCAGTT   13260

TGCTTGCCCC CCCCCCCACC ATCCTCTTCC TACCTTGGCT TCCTCCATTG ACACACTGGA   13320

CCCTGCTGGC TGCCCGGGGA GGTGTTTGGG GGATGGTGTT GGGGGAGGAG GAGGGCCCCT   13380

TGAGCCTCAG TGTGCCCATC AGGAGCGTAA GGTCAGTGCA GCACCTGCCC ACACAGGCTG   13440

TGAAGGGTGG GAGTGGAGAG GGATGCAAGG GGGTCACAAC GCCTGGCTCC ATGTCAGCTG   13500

CGTGCAGGGG CACCAGGAGC CGGCCCTCAT TCTCCCCTTG AACTGGAAGG GTGGCCCCGA   13560

CCCCAGCGGC AGGTAGCATA CGTATGAAGC GCTCTCCTTC CTACACCCCA CAGGTGGGCT   13620

CGTCTCCAGA CGGCCCTTTT TGAGCTGGCT GTGTTTTTCC ATCTGTGTAG CAAGGACAT    13680

CGCAGACTCC CCTTTCTCAT CTCCCTCGTT CAGCCTCCGA GGCCGGAGTC TCCATCCCTG   13740

TGCCTGCCTG TGGGTCCCGG GAGGACCTGA GGCTGCCCAT GTCACCCCCG GCATCTCATC   13800

CTGGGGACAG TTCAGCCGTG GGAGGGATCT GTAAGGACAG AATGCCGCTG AGCCTGGGGC   13860

TCCCCAGCTA GTCTCACACC CCGTGTCTGG GACCCAGAGA CCCTCGTGCA GGGCTCTGTT   13920

GCTTGGGGCC TGGCAGCCTC GTCCTGTATC AGAGGCTGCC ACCCCACCC CTCGTGGGGC    13980

CAGGGTTGTG GCCGGCCTCC CTGGCCCTCC CCATGGAAGT GGTAGGCGGA GCCAGCAGCC   14040

ATCTGCCCAG CCCGGGGCTG CACTGTTTTT TTTCAAATGA GCACCGTCCC AAACTGCAGC   14100

CCGTTAATTT AAACAGGATC ATTTCCGGCC CTGGAAGCCG CCTCACTCTC CTTAAATAGA   14160

AAGGAGCACA CGCAGAGGG AAACAGATGA GGTCATGGCT CGGCTGGCCC AGCGAGGAAG    14220

GGGCCGCAGT GGGGGTGGCA CTGCCGCCTG TCCCCTGTCC TCTCCAGCGC CCACACTGCA   14280

GCCCATTTCC TCACCCTGGG CCTGCTCTCG GGAGGGACGG GCCTGGGGGT CCTCTTGCTG   14340

GGCGGAGGGG AACCAGCTCC TCCAGGAGAG GACGGGGCCT GGCAGGGGGC ATGGGCCTC    14400

CCTGGGTCTG GCGTCCTGTC CTGCCCCTGC CGAGGGAGGA GCGGTTACAT AAGCTCCGCA   14460

GGCGGCCCCT CCGAGCCGGT CCCCCCAGCC CAGTTTCCAG TGAGGCGGCC AGCGCGGGCG   14520

GGGGTGCCGG GCCTGGCGCA CACCCGCTGC TGACCACACG TGTCTGGAAT GTGCAGATGT   14580

TTCTTTGGGG GCTCCGTCCG GCCCCAGAC CCCACTCAGC ATCTGGTCTG GGGAGTGGGC    14640

GCCTGGGCA CTCAGCTCTG AGTGTGAGAC TCTGAGGCAG GTCTGGTTTG TCTGGGGCCA    14700

TTCCCTCTGC TGTGGATTGG GAGGGCCCCG GGAGCTGCCC CACACCCAGG GAAGTTCTCC   14760

TCAGTCCCAC TGTTGCATTC CCCGACCCCG GCTCCCCGG CCCAGGAGCG CCTGTGGGGC    14820

AGAAGGCCCA GCCCCAAGAC TTCCCGGCCC TGCCAGCCTC AGGCTTCACC CACCCTCGCG   14880

CCAACTGTGG GCAGAGCCCA GGGGGAGGGC AGGAGAGCCA GCGCCTGGCT GGGAACACCC   14940

CTGAGGGGCC GAGGCTCCAG GGCGAGGGGG CCCGACCTGG GGTTCACACG CCCGGGTGGC   15000

GGGCAGACCC GCTGCAGCAT GAGACACGTG TCAGCTACCT CGGGCCGGCA GGCTGGCCCT   15060
```

-continued

```
GCTGCCCACA GCCCTGGGAC GTGGCCCCAC CTGTGACGGG TGTGGAGGGG CAGCCTCCAG    15120

GCCTGGCCAC ACCCTCTGCT GTTGCTGCTC CTGCTCCAGG ATTGGCAAGG GTGCTGGGAA    15180

GGGGTGAAGA CCCGTACTGT GGCCACACAC CTGGGACTTC CTTCTCCACC CAGTGGTGCC    15240

CCAGCAGCCG CTAAGGAGCC CGCTGGGTCC CACGCTAGGA TGGTCCTAAC TCCTCCCGCC    15300

TTCCAGATCG GACGCTCGGC GCTGGGGACC CCTTGTGTCC CGGGGCTGGG GCACCGTCCT    15360

GCCCCCATGG GGGTGTACTC CTCCCGACAA GCTTGGCTTC AGCTTCCCTG GGAGCACATC    15420

CTGGCCCTCG GGCACCCATC AGGCTGTCCC TGTGCACCTG GCTCCCACCC TTCCAGCTCA    15480

TAGCAGGAAC TGGGGTGAGG AGTGCGTGGG GCAGCAAGGG CCTGGGACCC CAGAGGACCC    15540

TGCACTCTGC TCTGTGCTCT TGCCTGGGCT TAGGGCCGCT CGGTGGTCCT GCTGCCAGAT    15600

GCCTGGGCCC TGCTGTGTCC CCCATCCTTG CAGGGAACCA GAACGTGGGG CAGGGCATC     15660

AGACAGCGGC GATGATGTCA CCTGGCGGGT GCAGAGGAAG CCCGAGGGGC GGGGTGGGGG    15720

GGCTGGCGCG AGGCTGCCTG GCTAGGCCTT GGCGTTCCCC CAGAACGGCG ATGGCAAAAG    15780

CAGATGGAGA CGTGAAAAAG TACGGGAGCA AGCGAGGTGA GGACTCCACG GGGACCCCTG    15840

TGCTGTTCCC TGTCCCTGAA GCCCACACCT GAGTCCTGCC CAGGGCAGAT GCTTCCACAC    15900

CCAGGGGCA CCTGAGTCCT ACCCAGGGCA GACGCTTCCA CACCCTGGGG GCTGGGGGAC     15960

TGCACCTGGC TCCTGTCTGG GCCCCAGCTT CATTCCACTG CCCTGGGCCC TGGGAGCTCG    16020

GCCGAGCGGG GTCCCCAAGA CCTTGCTGCA TTTCTGGGCC TTGGGCTGGG GTGAGGGCCG    16080

GGAGAAGGAG CCAGCCTGGA GCCTGGCACG CAGGGAGTGC ATGGCCAGAA CCGGTGACAG    16140

GCAGGGCTGC CTGCTGGCGT GGAAGAAGTG TCCATGGCAC CCCCAGGCCT GGTTCACAGT    16200

GGGATGGGCG GGGAGCCGGG GGGCTCTGGG GTCCTCGGCT GACCTGCCCC CACCCCTGCC    16260

CTGGCTTGTC AGCTCCCAGC AGCAGCCACT CTTGATGGAT TTTCCAGAAA ATGAGGTGTG    16320

GCCAAACATC TTCAGGCTTT TCCTTCTTTC CTTTCTCCCG TGGCCTGGGT GGGAGCTGCT    16380

CCCCATGCCT GGGGGCAGGT GCGAGAGCCT GTGCCCCTCC CTGGGGCAGT TTCACAGCTG    16440

TGTCCCTTCC AGGGGGCCTG CCTGTGTTCA CCGTGGCCTC TGCAGCACCT CTCGCCCCTT    16500

AGGGCTCCTG CGCCTCGGGT CCCGGTGCCT CATTTCTCCC TAAAGCATTG GTTCTGCTGC    16560

CGCCGCAGCC GCTGGAAAGT CCCTCCTCAG GTCTAACTGC AGTTCCTCAC GGCACAGTGT    16620

TCCCCCTCGG GCATGGTGCT TGGGCAGTGG GTGTGAGTCC AGCTGCCTCA CCCTGTCTCG    16680

AGAATGGCCT CTTGCTGGTC TCCCAGCCAC CACCCTGTCC CACCCCACGG CGGGGATGGT    16740

GTGGATGCCT AGCAGCGCGG CTGTGGGCCC ACCCATCCTT ATGGGCAGTG GGGAGCACCT    16800

CAGCCCGTGT CCCTACCTTG GTGTAGAGGA GGGGACGGCA GAGAAGCAGG GTTCAGTTAG    16860

GGGGGAAGTG GTGGCCCTGC CGGAGGGGCC GTTCCCTGTG TGCCTGGCCC CCAGATCCTC    16920

TCCCCTCCCG GAGCCCAGGG CACAGGCATA GGCTCTCTGA GTGTCCCACA GCCCCTGGGG    16980

GAAGGGAACT GCACCCCCAA CCGTGCCCTC CATCCGCAGA TGGAACGAGA AGCTCCGGGA    17040

GCCAGTGCCC AGCGTCTCAT CTGTCTGGGC ACCCAGCCCA GGTGAGGGCC TGGCTCCACC    17100

GTCCGTGGCT GGTGCTGCTT CCTGGCACGG AGAAGGCCTC GGCTGCTCTG TCCCCTCAGC    17160

TGGGGTGGCC TCTGGTCCCC TTCTTTGTTG GTTCCCTTCT CAAGCTCTTG CCCTGGCCCC    17220

GGGCCCCACC GGGCAGCCTG TGTGTGCGTC TCTCCTGCGC CGGGTAGGCT CCTGTGGGAG    17280

CGGAGCTCCG GTGGGAGGAG CAGGGCTGGA GGCTGGCAGG GGCTGGGCGG GTGTTCAGGG    17340

ATGGAGGCCG CCCCGGCTTG GGGCTGGCTG CCGGGTGGTC ATTGCTGGGA AGAGCAAGTC    17400
```

-continued

```
TAGGCGGAGG CACCTGCTGG GTCACTCGTG GGGAGGGTGA CACCTGGGGA AGTAGAGGCC   17460

CGTGGCAGGA GGTGAGGCCT CGGGGTCCTG GGGAGCAGGG GGGTGGTGTG CAGACCTGCG   17520

GAGCCATAGT CCTGTGCCAG GAGCACTACT GGGAGTGCGT GGGACCAGGA GGGGTGCCCA   17580

GGGTGGGCGG CAGAGTGACC CCCGAGGTGC TTGAGGCCGA GGGGAGGTGG AGTTCTCGGT   17640

TTGCCCCAGC TCTCTGTCTA CTCACCTCCG CATCACCAGC TCCAGGACCT GGTTTGTAAC   17700

TCGGGCAGCT CTGAAAAGAG AGACATGCTG CCGCCCTGTG GTTTCTGTTG CTTTTTCTTC   17760

ACTGACTACT GACATGGGAT GTTTTTCCTA CGGCTGTGAC CAATTGTGCT TCTTCTAATT   17820

GCCTGGTTTT TCTTTTTTTG TTTTTGGAGT TTTCTCTTTC TTTCCTCCCT CCCTCTCACC   17880

CTCCATCCTT TTTTTTTTTA TTTTTATTTT TTGAGATGGA GCTTCACTCT TGCAGGATGG   17940

GGTGCTGGAG TGCAGGGGTG CGATCTCAGC TCACTGCAAC CTCTGCCTCG CGGGTTCAAG   18000

TGATTCTCCT GCCTAAGCCT CCTGAGTAGC TGGAATTACA GGTGCTTGCC ACCACGCCCG   18060

ACTAATTCTG TAGTTTTGGT AGAGACAGGG TGTCTCCGTG TTGGTCGGTC TGGTCTTGAA   18120

CTCCTGACCT CAGGTGATGC GCCCGCCTCA GCCTCCCAAA GTGCTGGGAT TACAGGCAGG   18180

AGCCATTGCA CCCGGCTCTT TCCCCTTCTC CTTTTCTTCT CTCTCTCCTC CCTTTCTTTC   18240

TTTTCTTTTC TTTTTTTTTT CTTTTGAGAT GGAGTCTCGC TCTGTCACCA GGCTGGATTG   18300

CAGTGGCGTG ATCTTGGCTC ACTGCAACCT TCGCCTCCCG GGTTCACGTG ATTCTCCTGC   18360

CTCAGCCTCC TGAGTGGCTG GCACTACAGG CTCCCGCCGC CATGCCCGGC TAATTTTTGC   18420

ATTTTTAGTA GAGACAGGGT TTCACCCTGT TGGCCAGGAT GGTCTCGATC TCTTGATCTC   18480

ATGATCCACC CACCTTGGCC TCCCAAAGTT CTGGCATTAC AGGAGTGAGC CACCGTGCCC   18540

GGCCATCTTT CTTTCCTTGC TTTCTCTTTG TTTTCTTTCG AGACCGGGTC TTGCTCTGTC   18600

GCCCAGGCTG GACTGCAGTG GCACAATCAT AGCTCACTGC AGCCTCGACT TCCCTGGCTC   18660

AAGCGATCCT TCCTCCTCAG CCCCCCGAGT AGCTGGAACT ACAGTTACAC ACTACCATGC   18720

CTGGCTGATT CTTTTTTTCC TTGTAGAGAT GGGGTCTTGC TATGCTGTCC ATCCTGGTCT   18780

CAAACTCCTG GCCTTCCCAA AGCACTGGGT TTACAGGCAT AAGCCACCAC ACCCAGTTTC   18840

CTTTTCTTCT TTTTAACTGG AATAGTTGAC GTTTTCTTTA TTAGCTGTGT GTCAGGAGGG   18900

TATTTTTGGC CTTTAGTATG TCGTGTAAGT TGCTAGTGCT TTTCTGAGAT TGTAGTTTGT   18960

TTTCTAATTT TATTTATATT TTGCGTAGAA GTTGTGTATT TTAGATGGAG TTAGGTCGGC   19020

TGGTCTTTGA TGTTTTATTT ATTAATTATG TATGTATTTA TTTATTTTTG AGGTAGAGTC   19080

TCGCCGTTTC ACCCAGGCTG GAGTACAGTG ATGCGATCTC AGCTCCCTGT AGCCTTGACC   19140

TCTCTGGGCT CAAGTGATTT TTCTCTCCTC TACCTCCCGA GTACTGGGA CCCCAGGCGC   19200

ATGCCGCCAT GCCTGGCTAA TGTGTATTTT TTGTAGATAC GGGGTCTCAC TGTGTTGCCC   19260

AGGGTGGTTT CAAAATCCTG GCCCAGGCG ATCCTTCCGT CTCAGCTCCC ACGGTGCTGT   19320

GTTACCGGCG TGTGCCCAGT GCCTGGCCGT CTTGGAGGTC TTGTTTCTCT GGGTTTATGC   19380

CTCGAGGTGG CGCCTGCTCC CCTGTGCTCC CTGGTAGCCT GGTAGTGAGC CTGCTTCTCA   19440

CACAGTCATA CCTGGTTGTG GTCCCACAGT GGGACCACCC TGTTGGGTTC AGAACAGGAG   19500

ATGGGGCCC CTCGAGTCTG TGTGGGGCT GTGGACAGGG TTGGGAGACC TTGGCTCTGT   19560

GGGGGACTGT GGACAGGGA TGGGGGCCT TGGCCCTGCG TGGGATGGGT TGGGGGTCCG   19620

TGCCCTTCCT GGCCCTGGGT GGACAGGTCC ATGTGGCACT CGGCATAGGG CTGAGATGGG   19680

TGCAGAGGGC TGAGGCCCCC AGGCCTCTCC TGGCTTGGTT TCCCCAGATG AGTGTTCATT   19740

TGGGTCTTCC ATCAGAAAGT CCCCTCCTGA CCTCTGGGAG TGGGGAGCTC AAGGGTGGGA   19800
```

```
GGCCATAGCT TGGGGATGCT GGCAATGTGT GGGATGGGCC CAGGGAAGGC CTCTGGCCTA    19860

CTAGGGCTC  TGGCCCTGAC CCACGGCCAC TCACTCCTCA GAGACGTCTC CCACAACCTG    19920

CTCCGGGCGC TGGACGTTGG GCTCCTGGCG AACCTCTCGG CGCTGGCAGA GCTGTGAGTG    19980

TCCCCCAGTC GTGCCAGCAT GCGGGGCTCA CTCCGGGTGG GCTGGCGGCA CCGCCTCTTG    20040

CTGCTCAGCT GTGGGGCTT  CCATCAGCTT TGCCGAATCC CCCGTCTCTT CCAGGGATAT    20100

AAGCAACAAC AAGATTTCTA CGTTAGAAGA AGGAATATTT GCTAATTTAT TTAATTTAAG    20160

TGAAATGTAA GTTGTGGTTC TTTGGGTGGG GTCCTGGCTG GACCCCAGGC CCCCAATATC    20220

CCTTCTGCCC TCCCAGTTGG TCCGTGTCCC CTTCCAGGCT TGAGACCAGA TCCTGGGGGC    20280

AGTTCACTGC CTGCTTGGAG CCCCCCAGTG CCGGCTTGGT TGGGGCAGGG GAGGCGGTGC    20340

TGTCAGGGTG GCTCCAGGGC CTGGTTGCCA GTGGGGGGCT GGCATAGACC CTTCCCACCA    20400

GACCTGGTCC CCAACACCTG CCCCTGCCCT GCAGAAACCT GAGTGGGAAC CCGTTTGAGT    20460

GTGACTGTGG CCTGGCGTGG CTGCCGCGAT GGGCGGAGGA GCAGCAGGTG CGGGTGGTGC    20520

AGCCCGAGGC AGCCACGTGT GCTGGGCCTG GCTCCCTGGC TGGCCAGCCT CTGCTTGGCA    20580

TCCCCTTGCT GGACAGTGGC TGTGGTGAGT GCCGGTGGGT GGGGCCAGCT CTGTCCTTCC    20640

CAGCCAGGTG GGACCTGGGC CCTGCAGACA CTGGGCAGGG CTCAGGAAGG CCTCTCTGGG    20700

GGGGCCTCC  GGGCCAAGGG AACAGCATGG GAGCCTGTGA GTGCGGCGGG CGGATGTGGG    20760

GGCGTGGGGT GGAGCCAGGA GGAGCAGAAC CCGGGGTCCA GTGGCTGCCT CTTCTAGGTG    20820

AGGAGTATGT CGCCTGCCTC CCTGACAACA GCTCAGGCAC CGTGGCAGCA GTGTCCTTTT    20880

CAGCTGCCCA CGAAGGCCTG CTTCAGCCAG AGGCCTGCAG CGCCTTCTGC TTCTCCACCG    20940

GCCAGGGCCT CGCAGCCCTC TCGGAGCAGG GCTGGTGCCT GTGTGGGGCG GCCCAGCCCT    21000

CCAGTGCCTC CTTTGCCTGC CTGTCCCTCT GCTCCGGCCC CCGCCACCT  CCTGCCCCCA    21060

CCTGTAGGGG CCCCACCCTC CTCCAGCACG TCTTCCCTGC CTCCCCAGGG GCCACCCTGG    21120

TGGGCCCCA  CGGACCTCTG GCCTCTGGCC AGCTAGCAGC CTTCCACATC GCTGCCCCGC    21180

TCCCTGTCAC TGCCACACGC TGGGACTTCG GAGACGGCTC CGCCGAGGTG GATGCCGCTG    21240

GGCCGGCTGC CTCGCATCGC TATGTGCTGC CTGGGCGCTA TCACGTGACG GCCGTGCTGG    21300

CCCTGGGGGC CGGCTCAGCC CTGCTGGGGA CAGACGTGCA GGTGGAAGCG GCACCTGCCG    21360

CCCTGGAGCT CGTGTGCCCG TCCTCGGTGC AGAGTGACGA GAGCCTCGAC CTCAGCATCC    21420

AGAACCGCGG TGGTTCAGGC CTGGAGGCCG CCTACAGCAT CGTGGCCCTG GGCGAGGAGC    21480

CGGCCCGAGG TGAGTGTCTG CTGCCCACTC CCCTTCCTCC CCAGGGCCAT CCAGATGGGG    21540

CAGAGCCTGG TACCCCGTC  TTGGGCCCAC ACTGACCGTT GACACCCTCG TTCCCACCGG    21600

TCTCCAGCGG TGCACCCGCT CTGCCCCTCG GACACGGAGA TCTTCCCTGG CAACGGGCAC    21660

TGCTACCGCC TGGTGGTGGA GAAGGCGGCC TGGCTGCAGG CGCAGGAGCA GTGTCAGGCC    21720

TGGGCCGGGG CCGCCCTGGC AATGGTGGAC AGTCCCGCCG TGCAGCGCTT CCTGGTCTCC    21780

CGGGTCACCA GGTGCCTGCC CCCACCCCCC GAGGGGCCAT AGGTTGGGAG ATCTCTGAAG    21840

CACTGGGGCA GAGACTGCGG CTGGGGAGTC TCAGGAGGAA GGAGGTGGGA GCTGGGCCGG    21900

CCCTGGTGAG CAGGTGGCGC CGGCCGGTGG GGCCGTTCCT GTCAGCTCTG CAGATGCAGA    21960

GGTGGACATG AGCTGGGGGC AGCCTCCGGA CACTCCTGGG CACGCCATAC GGGAGGTGGC    22020

CTGCACGGGG ATCCCTGCCG GTACCCACAG GCCCCGTGGG TGGGTGCTGC TGTGAGCCTG    22080

GGCTGGTGGG CCCTGGTCTC CGGGCTCTGA GCCTCAGTTT CCCCATCTGG AAAGGGGAC    22140
```

```
AGTGATGGGG CTCCCAGCGG GCTGCTGTGA GGGTGGGAGG ATGGAGGAGT GCCCTGAGCC    22200

CCCTGCCATC CCACACCCGC CCCCAGGAGC CTAGACGTGT GGATCGGCTT CTCGACTGTG    22260

CAGGGGGTGG AGGTGGGCCC AGCGCCGCAG GGCGAGGCCT TCAGCCTGGA GAGCTGCCAG    22320

AACTGGCTGC CCGGGGAGCC ACACCCAGCC ACAGCCGAGC ACTGCGTCCG GCTCGGGCCC    22380

ACCGGGTGGT GTAACACCGA CCTGTGCTCA GCGCCGCACA GCTACGTCTG CGAGCTGCAG    22440

CCCGGAGGTG TGCGGGGGGC CAGGCAGGGG CCTGAGACGC TGGCTGTGGT TAGGGCCTG    22500

CCGAGCGCCC GCGGTGGAGC CTGGGCTGAG GAGGAGGGGC TGGTGGGGGG GTTTTCGGGC    22560

GGCTCGGTCC CCAGTCTGTT CGTCCTGGTG TCCTGGGCCC TGGCCCGGCG CCTCACTGTG    22620

CACTCGCCAC CCCAGGCCCA GTGCAGGATG CCGAGAACCT CCTCGTGGGA GCGCCCAGTG    22680

GGGACCTGCA GGGACCCCTG ACGCCTCTGG CACAGCAGGA CGGCCTCTCA GCCCCGCACG    22740

AGCCCGTGGA GGTAGTCGGC CCCCCACGTT CTACAACCTG CCCTCCTGCC TGCCCCTGGA    22800

GGCCTTGCCT GCCCTGCCCA CTGTGGGTCT CGCCAAAAAA CTTGGGGGCC TTAATGTTGC    22860

TTGTGCCCAG TGAAGATGGT TGGGAAAATC CAGAGTGCAG AGAGGAAAGC GTTTACTCAC    22920

ATTACCTCCA GGCCTTTTCT CTGAGCGTGT GTGAGTTATT CCTGAAAGGC AGGTCAGGGG    22980

TCCTGCCCCC CATGGACAGT TTCCACCGGA GTCTTCCTCT CGAGCGACAG GAGCCAGGCC    23040

TGTGGGGGTC TGATGGCTCG CTCTCCTTCC CTCCCCTCTT CCTGGGAAGT TCGGGTAGGG    23100

GGAGTCTGGG CTTCAGGCTG GGATGGGGTC TGTGGAGCTG AGGCGGCCCC CTGCCCACCA    23160

GGTCATGGTA TTCCCGGGCC TGCGTCTGAG CCGTGAAGCC TTCCTCACCA CGGCCGAATT    23220

TGGGACCCAG GAGCTCCGGC GGCCCGCCCA GCTGCGGCTG CAGGTGTACC GGCTCCTCAG    23280

CACAGCAGGT GGGACTCTGG GTGGTGGGTG GTGGGTGGTG GGCGCCGCAG GACTCGGGGT    23340

GGCCTCTCTG AGCTTTCACG TCTGCTGGTC CTGTGGCCAC CAGAGTGGTT CCCAGTCTTA    23400

GGTGGACAGA GCAGGGGTTC CAGAGACACC AGCTCATTCC AGGTGTCCTG GGGGTGGATT    23460

GGGTGGGGCC TGCCTGGGGG CCGGCCTGGG TCAGTCGGCT GGCCGGAGAC GGACGCAGCA    23520

CTGGGCTGGG AGTGCTGCCC AGGTGGGGAG ACCTGTCCTC ACAGCAAGGC CAGGATTGCT    23580

GGTGCAGGCA GTTGGGCATC TCTGACGGTG GCCTGTGGGC AAATCAGGGC CCCAACACCC    23640

TCCCCTCCTC ACAGGGACCC CGGAGAACGG CAGCGAGCCT GAGAGCAGGT CCCCGGACAA    23700

CAGGACCCAG CTGGCCCCCG CGTGCATGCC AGGGGACGC TGGTGCCCTG GAGCCAACAT    23760

CTGCTTGCCG CTGGACGCCT CCTGCCACCC CCAGGCCTGC GCCAATGGCT GCACGTCAGG    23820

GCCAGGGCTA CCCGGGGCCC CCTATGCGCT ATGGAGAGAG TTCCTCTTCT CCGTTCCCGC    23880

GGGGCCCCCC GCGCAGTACT CGGTGTGTGG CCCTGACCTG GGTCTGTTCC CTGCATCTCC    23940

TCAGGCCACC TTCCTGTCTG CTGCCCAGGG TCTGGGTCTG TGCACCAGAC ACACCCAGCC    24000

TGCAGGCCCC TCCCACGTCC TTGCCACCTC TGACCTCCGA CCTCTGCAGT GCCCTCGGCC    24060

CTCTCCCAGT GGGAGAAGCT CTCGCCTGGG CCCTTGGCAC GAGCTGTGCC TCCTCTTCCT    24120

CTCTCCCAGC ACAGCTGCTC CTTCCTGTCT GCCAGGTCTT GGCCTGTGTC CTCTCCCCGT    24180

GTGTCCCCCG GTCTGCAACT GTCCTGCCTG TCCTTGTCAC GAGCACTGTG GGGAGGCTCC    24240

TTGAGGTGTG GCTGACGAAG CGGGGAGCCC TGCGTGTCCA CCCTCATCCG TCGTGCGGGG    24300

GTCCACGGGC CATGACCGTG AGGACGTGAT GCAGCCCTGC CTCCCTCTCC ACAGGTCACC    24360

CTCCACGGCC AGGATGTCCT CATGCTCCCT GGTGACCTCG TTGGCTTGCA GCACGACGCT    24420

GGCCCTGGCG CCCTCCTGCA CTGCTCGCCG GCTCCCGGCC ACCCTGGTCC CCGGGCCCCG    24480

TACCTCTCCG CCAACGCCTC GTCATGGCTG CCCCACTTGC CAGCCCAGCT GGAGGGCACT    24540
```

```
TGGGCCTGCC CTGCCTGTGC CCTGCGGCTG CTTGCAGCCA CGGAACAGCT CACCGTGCTG    24600

CTGGGCTTGA GGCCCAACCC TGGACTGCGG CTGCCTGGGC GCTATGAGGT CCGGGCAGAG    24660

GTGGGCAATG GCGTGTCCAG GCACAACCTC TCCTGCAGCT TTGACGTGGT CTCCCCAGTG    24720

GCTGGGCTGC GGGTCATCTA CCCTGCCCCC CGCGACGGCC GCCTCTACGT GCCCACCAAC    24780

GGCTCAGCCT TGGTGCTCCA GGTGGACTCT GGTGCCAACG CCACGGCCAC GGCTCGCTGG    24840

CCTGGGGGCA GTGTCAGCGC CCGCTTTGAG AATGTCTGCC CTGCCCTGGT GGCCACCTTC    24900

GTGCCCGGCT GCCCCTGGGA GACCAACGAT ACCCTGTTCT CAGTGGTAGC ACTGCCGTGG    24960

CTCAGTGAGG GGGAGCACGT GGTGGACGTG GTGGTGGAAA ACAGCGCCAG CCGGGCCAAC    25020

CTCAGCCTGC GGGTGACGGC GGAGGAGCCC ATCTGTGGCC TCCGCGCCAC GCCCAGCCCC    25080

GAGGCCCGTG TACTGCAGGG AGTCCTAGTG GTGAGTATGG CCGAGGCTCC ACCACCAGCC    25140

CCCAGGCAGG TGCCTGCAGA CAGGGTGCTC ACACAGGGCG TGAGGCCTGG CTTCCCAGTG    25200

AGGGCAGCAG CCCAGTTACT GGGGACGTCG GCCCCGGGCA GGTCCTGCTG GCTGGCTCCT    25260

CGGGCTACCT GGTGGGCTTT AAATTCCTGG AAAGTCACGG CTCTGACAGT GGCTCCGCTA    25320

ACTCATTCCA CTGTCTCATT TCACAAAATG AATTTAAAAC TCTGCTCCCT GACCTCACAC    25380

GAGCCCCCGT GAGTCTCTCA CGCCCTCTGC TGTGTTCTCG CCTGGCTAAA GCGAGTGGCT    25440

TTTGAGGTGG AGTCTGAACC CCTGATGGGA AACTGCGGGC TGCCCGCGGT GCCACCATGC    25500

TGGGTACATG GGGGACAGGG CTGTCTCCAT CTTGCGGGTA CCTGCCTCTT CACCAGGGGC    25560

CTTGGGAGGG GCCATCAGAA ATGGCGTGAC CTGTGCAGCC TGTCCTGGGT TCTGTAAGCC    25620

AGTGTAGGTG CCTCCCCTCA CTGCTCCGAG CTCTCTGGGT GAGGAGCTGG GGCAAGAGCG    25680

CCGGGAGGGT CTGAGAAGAC TCAGAGAGAG GTGGACTCTT TGTAGCTGGT ACTAGGTTTG    25740

CTTTACAGAT GGGGAAACTG AGGCACAGAG AGGTTGAGGC ATTAGTAGTA CTACATGGCT    25800

GGCTGGAGAG CCGGACAGTG AGTGTCCCAG CCCGGGCTTG GCTCCCATGG CATGCAGAGC    25860

CCCGGGCACC TCCTCTCCTC TGTGCCCCGC GTGGGACTCT CCAGCCCGAC GGGAGGTGTG    25920

TCCAGGAGGC GACAGGCTAA GGGCAGAGTC CTCCACAGAG CCCAGGCTGA CACCATTCCC    25980

CCCGCAGAGG TACAGCCCCG TGGTGGAGGC CGGCTCGGAC ATGGTCTTCC GGTGGACCAT    26040

CAACGACAAG CAGTCCCTGA CCTTCCAGAA CGTGGTCTTC AATGTCATTT ATCAGAGCGC    26100

GGCGGTCTTC AAGCTCTCAG TAGGTGGGCG GGGGTGGGGA GGGGAGGGGA TGGGGCGGGG    26160

CAGGGCGGGG GCGGGCTCCA CCTTCACCTC TGCCTTCTGC TCTGCTTCAT GCTGCCCGAG    26220

GACGCTGCCA TGGCTGTGGG TGAGTGGAGG GAGGGACGCC AATCAGGGCC AGGCCTCTCA    26280

CCTGCCACCT GGGCTCACTG ACGCCTGTCC CTGCAGCTGA CGGCCTCCAA CCACGTGAGC    26340

AACGTCACCG TGAACTACAA CGTAACCGTG GAGCGGATGA ACAGGATGCA GGGTCTGCAG    26400

GTCTCCACAG TGCCGGCCGT GCTGTCCCCC AATGCCACGC TAGCACTGAC GGCGGGCGTG    26460

CTGGTGGACT CGGCCGTGGA GGTGGCCTTC CTGTGAGTGA CTCGGGGGCC GGTTTGGGGT    26520

GGGCACCAGG CTCTTGTCCC AGCCCCAGCC TCAGCCGAGG GACCCCACA TCACGGGGTT     26580

GCTTTTCTGA GCCTCGGTTT CCCTGTCTGT TGGGAGGTAA CTGGGTGCAC AGGAGCCCTG    26640

AGGCTGCACG GGAGCCGGGA GAGGCCTCAG CACAGCCGGG TGGGCCCTGA ATGGAGGCCC    26700

GGGGCGTGAC TGCAGAGTGG AGCCTCGGCT GGGTCCCAAG CACCCCCTGC CCCGCCACCG    26760

CCCACCCCTG TCCCGGTTCA CTCACTGCGT CCCACCGCCC CGGCAGGTGG ACCTTTGGGG    26820

ATGGGGAGCA GGCCCTCCAC CAGTTCCAGC CTCCGTACAA CGAGTCCTTC CCGGTTCCAG    26880
```

```
ACCCCTCGGT GGCCCAGGTG CTGGTGGAGC ACAATGTCAT GCACACCTAC GCTGCCCCAG     26940

GTGAGGGATG AGGGGGTGAG GGGGCCACTG CCTTTCAGGC TCTGAGCACG GGTCCCCCCA     27000

GCTCCCCAGT CAAGCTGCCC CCCTTCCTCC CCAACAGCCC TCACTGTGAC CTCACCTGGG     27060

CTGATGGCTT AGGCCCTACT GGGGTGAGGG AGGGGCCAGG CGTGGGGGA GTGGACAGGG      27120

AAGCTGGGCC CCTGAACTGC GCCCCCCGCC CTCCCCGGGC CTGGCTCTTG CTGCTCTGCT     27180

GCCCCGAGTG CAGCTGCACT TGGAGGCGGT GCGTCCTCGC CAGGCAGCCC TCAGTGCTGC     27240

TACACCTGTG CTCCGTCCCG CACGTGGCTT GGGAGCCTGG GACCCTTAAG CTGGGCCGC     27300

AGGTGCAGCC GTTCACCCCG GGCTCCTCAG GCGGGGGGCT TCTGCCGAGC GGGTGGGGAG     27360

CAGGTGGGGG TGCCGCGGCT GCCCCACTCG GGCCTGTCCC CACAGGTGAG TACCTCCTGA     27420

CCGTGCTGGC ATCTAATGCC TTCGAGAACC GGACGCAGCA GGTGCCTGTG AGCGTGCGCG     27480

CCTCCCTGCC CTCCGTGGCT GTGGGTGTGA GTGACGGCGT CCTGGTGGCC GGCCGGCCCG     27540

TCACCTTCTA CCCGCACCCG CTGCCCTCGC CTGGGGTGT TCTTTACACG TGGGACTTCG      27600

GGGACGGCTC CCCTGTCCTG ACCCAGAGCC AGCCGGCTGC CAACCACACC TATGCCTCGA     27660

GGGGCACCTA CCACGTGCGC CTGGAGGTCA ACAACACGGT GAGCGGTGCG GCGGCCCAGG     27720

CGGATGTGCG CGTCTTTGAG GAGCTCCGCG GACTCAGCGT GGACATGAGC CTGGCCGTGG     27780

AGCAGGGCGC CCCCGTGGTG GTCAGCGCCG CGGTGCAGAC GGGCGACAAC ATCACGTGGA     27840

CCTTCGACAT GGGGGACGGC ACCGTGCTGT CGGGCCCGGA GGCAACAGTG GAGCATGTGT     27900

ACCTGCGGGC ACAGAACTGC ACAGTGACCG TGGGTGCGGC CAGCCCCGCC GGCCACCTGG     27960

CCCGGAGCCT GCACGTGCTG GTCTTCGTCC TGGAGGTGCT GCGCGTTGAA CCCGCCGCCT     28020

GCATCCCCAC GCAGCCTGAC GCGCGGCTCA CGGCCTACGT CACCGGGAAC CCGGCCCACT     28080

ACCTCTTCGA CTGGACCTTC GGGGATGGCT CCTCCAACAC GACCGTGCGG GGGTGCCCGA     28140

CGGTGACACA CAACTTCACG CGGAGCGGCA CGTTCCCCCT GGCGCTGGTG CTGTCCAGCC     28200

GCGTGAACAG GGCGCATTAC TTCACCAGCA TCTGCGTGGA GCCAGAGGTG GGCAACGTCA     28260

CCCTGCAGCC AGAGAGGCAG TTTGTGCAGC TCGGGGACGA GGCCTGGCTG GTGGCATGTG     28320

CCTGGCCCCC GTTCCCCTAC CGCTACACCT GGGACTTTGG CACCGAGGAA GCCGCCCCCA     28380

CCCGTGCCAG GGGCCCTGAG GTGACGTTCA TCTACCGAGA CCCAGGCTCC TATCTTGTGA     28440

CAGTCACCGC GTCCAACAAC ATCTCTGCTG CCAATGACTC AGCCCTGGTG GAGGTGCAGG     28500

AGCCCGTGCT GGTCACCAGC ATCAAGGTCA ATGGCTCCCT TGGGCTGGAG CTGCAGCAGC     28560

CGTACCTGTT CTCTGCTGTG GGCCGTGGGC GCCCCGCCAG CTACCTGTGG GATCTGGGGG     28620

ACGGTGGGTG GCTCGAGGGT CCGGAGGTCA CCCACGCTTA CAACAGCACA GGTGACTTCA     28680

CCGTTAGGTG GCCGGCTGGA ATGAGGTGAG CCGCAGCGAG GCCTGGCTCA ATGTGACGGT     28740

GAAGCGGCGC GTGCGGGGGC TCGTCGTCAA TGCAAGCCCC ACGGTGGTGC CCCTGAATGG     28800

GAGCGTGAGC TTCAGCACGT CGCTGGAGGC CGGCAGTGAT GTGCGCTATT CCTGGGTGCT     28860

CTGTGACCGC TGCACGCCCA TCCCTGGGGG TCCTACCATC TCTTACACCT TCCGCTCCGT     28920

GGGCACCTTC AATATCATCG TCACGGCTGA GAACGAGGTG GGCTCCGCCC AGGACAGCAT     28980

CTTCGTCTAT GTCCTGCAGC TCATAGAGGG GCTGCAGGTG GTGGGCGGTG GCCGCTACTT     29040

CCCCACCAAC CACACGGTAC AGCTGCAGGC CGTGGTTAGG GATGGCACCA ACGTCTCCTA     29100

CAGCTGGACT GCCTGGAGGG ACAGGGGCCC GGCCCTGGCC GGCAGCGGCA AAGGCTTCTC     29160

GCTCACCGTC TCGAGGCCGG CACCTACCAT GTGCAGCTGC GGGCCACCAA CATGCTGGGC     29220

AGCGCCTGGG CCGACTGCAC CATGGACTTC GTGGAGCCTG TGGGGTGGCT GATGGTGGCC     29280
```

```
GCCTCCCCGA ACCCAGCTGC CGTCAACAAA AGCGTCACCC TCAGTGCCGA GCTGGCTGGT       29340

GGCAGTGGTG TCGTATACAC TTGGTCCTTG GAGGAGGGGC TGAGCTGGGA GACCTCCGAG       29400

CCATTTACCA CCCATAGCTT CCCCACACCC GGCCTGCACT TGGTCACCAT GACGGCAGGG       29460

AACCCGCTGG GCTCAGCCAA CGCCACCGTG GAAGTGGATG TGCAGGTGCC TGTGAGTGGC       29520

CTCAGCATCA GGGCCAGCGA GCCCGGAGGC AGCTTCGTGG CGGCCGGGTC CTCTGTGCCC       29580

TTTTGGGGGC AGCTGGCCAC GGGCACCAAT GTGAGCTGGT GCTGGGCTGT GCCCGGCGGC       29640

AGCAGCAAGC GTGGCCCTCA TGTCACCATG GTCTTCCCGG ATGCTGGCAC CTTCTCCATC       29700

CGGCTCAATG CCTCCAACGC AGTCAGCTGG GTCTCAGCCA CGTACAACCT CACGGCGGAG       29760

GAGCCCATCG TGGGCCTGGT GCTGTGGGCC AGCAGCAAGG TGGTGGCGCC CGGGCAGCTG       29820

GTCCATTTTC AGATCCTGCT GGCTGCCGGC TCAGCTGTCA CCTTCCGCCT GCAGGTCGGC       29880

GGGGCCAACC CCGAGGTGCT CCCCGGGCCC CGTTTCTCCC ACAGCTTCCC CCGCGTCGGA       29940

GACCACGTGG TGAGCGTGCG GGGCAAAAAC CACGTGAGCT GGGCCCAGGC GCAGGTGCGC       30000

ATCGTGGTGC TGGAGGCCGT GAGTGGGCTG CAGGTGCCCA ACTGCTGCGA GCCTGGCATC       30060

GCCACGGGCA CTGAGAGGAA CTTCACAGCC CGCGTGCAGC GCGGCTCTCG GGTCGCCTAC       30120

GCCTGGTACT TCTCGCTGCA GAAGGTCCAG GGCGACTCGC TGGTCATCCT GTCGGGCCGC       30180

GACGTCACCT ACACGCCCGT GGCCGCGGGG CTGTTGGAGA TCCAGGTGCG CGCCTTCAAC       30240

GCCCTGGGCA GTGAGAACCG CACGCTGGTG CTGGAGGTTC AGGACGCCGT CCAGTATGTG       30300

GCCCTGCAGA GCGGCCCCTG CTTCACCAAC CGCTCGGCGC AGTTTGAGGC CGCCACCAGC       30360

CCCAGCCCCC GGCGTGTGGC CTACCACTGG GACTTTGGGG ATGGGTCGCC AGGGCAGGAC       30420

ACAGATGAGC CCAGGGCCGA GCACTCCTAC CTGAGGCCTG GGGACTACCG CGTGCAGGTG       30480

AACGCCTCCA ACCTGGTGAG CTTCTTCGTG GCGCAGGCCA CGGTGACCGT CCAGGTGCTG       30540

GCCTGCCGGG AGCCGGAGGT GGACGTGGTC CTGCCCCTGC AGGTGCTGAT GCGGCGATCA       30600

CAGCGCAACT ACTTGGAGGC CCACGTTGAC CTGCGCGACT GCGTCACCTA CCAGACTGAG       30660

TACCGCTGGG AGGTGTATCG CACCGCCAGC TGCCAGCGGC CGGGGCGCCC AGCGCGTGTG       30720

GCCCTGCCCG GCGTGGACGT GAGCCGGCCT CGGCTGGTGC TGCCGCGGCT GGCGCTGCCT       30780

GTGGGGCACT ACTGCTTTGT GTTTGTCGTG TCATTTGGGG ACACGCCACT GACACAGAGC       30840

ATCCAGGCCA ATGTGACGGT GGCCCCCGAG CGCCTGGTGC CCATCATTGA GGGTGGCTCA       30900

TACCGCGTGT GGTCAGACAC ACGGGACCTG GTGCTGGATG GGAGCGAGTC CTACGACCCC       30960

AACCTGGAGG ACGGCGACCA GACGCCGCTC AGTTTCCACT GGGCCTGTGT GGCTTCGACA       31020

CAGGTCAGTG CGTGGCAGGG CCGTCCTCCA TGCCCCTCAC CCGTCCACAC CCATGAGCCC       31080

AGAGAACACC CAGCTTGCCA CCAGGGCTGG CCCGTCCTCA GTGCCTGGTG GGCCCCGTCC       31140

CAGCATGGGG AGGGGTCTC CCGCGCTGTC TCCTGGGCCG GGCTCTGCTT TAAAACTGGA        31200

TGGGCTCTC AGGCCACGTC GCCCCTTGTT CTCGGCCTGC AGAGGGAGGC TGGCGGGTGT        31260

GCGCTGAACT TTGGGCCCCG CGGGAGCAGC ACGGTCACCA TTCCACGGGA GCGGCTGGCG       31320

GCTGGCGTGG AGTACACCTT CAGCCTGACC GTGTGGAAGG CCGGCCGCAA GGAGGAGGCC       31380

ACCAACCAGA CGGTGGGTGC CGCCCGCCCC TCGGCCACTT GCCTTGGACA GCCCAGCCTC       31440

CCTGGTCATC TACTGTTTTC CGTGTTTTAG TGCTGGTGGA GGCCGCACGC TCTCCCCTCT       31500

CTGTTTCTGA TGCAAATTCT ATGTAACACG ACAGCCTGCT TCAGCTTTGC TTCCTTCCAA       31560

ACCTGCCACA GTTCCACGTA CAGTCTTCAA GCCACATATG CTCTAGTGGC AAAAGCTACA       31620
```

-continued

```
CAGTCCCCTA GCAATACCAA CAGTGAGGAA GAGCCCCTTC CCACCCCAGA GGTAGCCACT    31680
GTCCCCAGCC CATGTCCCTG TTGCTGGATG TGGTGGGCCG GTTCTCACCC TCACGCTCCC    31740
CTCTCTGGAC CGGCCAGGAG GCTTGGTGAC CCTGAGCCCG TGGTGGCTGC TCCTGCTGCT    31800
GTCAGGCGGG GCCTGCTGGT GCCCCAGAGT GGGCGTCTGT TCCCCAGTCC CTGCTTTCCT    31860
CAGCTGGCCT GATTGGGGGT CTTCCCAGAG GGGTCGTCTG AGGGGAGGGT GTGGGAGCAG    31920
GTTCCATCCC AGCTCAGCCT CCTGACCCAG GCCCTGGCTA AGGGCTGCAG GAGTCTGTGA    31980
GTCAGGCCTA CGTGGCAGCT GCGGTCCTCA CACCCACACA TACGTCTCTT CTCACACGCA    32040
TCCCCCCAGG GGCCCTCAGT GAGCATTGCC TGCCTCCTGC TAGGGTCCAG CTGGGTCCAG    32100
TACACCAGAA CGCACACTCC AGTGTCCTCT GCCCTGTGTA TGCCCTTCCG CCGTCCAAGT    32160
TGGAAGGTGG CAAACCGGAT GAGTATCCTG GGAGGGAGTG AGCTCACCGG CAGTGGCCAG    32220
GCCCCTGGGA AACCTGGAGT TTGGGAGCAG CATCCTCCAT GGGTCCCCCA GTCCTTCCAG    32280
CAGGCCAAAT AGACCTGTGT TGGAGGTAAC CCCACTCCCA CGCCAGGTGC TGATCCGGAG    32340
TGGCCGGGTG CCCATTGTGT CCTTGGAGTG TGTGTCCTGC AAGGCACAGG CCGTGTACGA    32400
AGTGAGCCGC AGCTCCTACG TGTACTTGGA GGGCCGCTGC CTCAATTGCA GCAGCGGCTC    32460
CAAGCGAGGG GTGAGTGTTG AGCGGGGTGT GGGCGGGCTG GGGATGGGTC CCATGGCCGA    32520
GGGGACGGGG CCTGCAGGCA GAAGTGGGGC TGACAGGGCA GAGGGTTGCG CCCCCTCACC    32580
ACCCCTTCTG CCTGCAGCGG TGGGCTGCAC GTACGTTCAG CAACAAGACG CTGGTGCTGG    32640
ATGAGACCAC CACATCCACG GGCAGTGCAG GCATGCGACT GGTGCTGCGG CGGGGCGTGC    32700
TGCGGGACGG CGAGGGATAC ACCTTCACGC TCACGGTGCT GGGCCGCTCT GGCGAGGAGG    32760
AGGGCTGCGC CTCCATCCGC CTGTCCCCCA ACCGCCCGCC GCTGGGGGGC TCTTGCCGCC    32820
TCTTCCCACT GGGCGCTGTG CACGCCCTCA CCACCAAGGT GCACTTCGAA TGCACGGGTG    32880
AGTGCAGGCC TGCGTGGGGG GAGCAGCGGG ATCCCCCGAC TCTGTGACGT CACGGAGCCC    32940
TCCCGTGATG CCGTGGGGAC CGTCCCTCAG GCTGGCATGA CGCGGAGGAT GCTGGCGCCC    33000
CGCTGGTGTA CGCCCTGCTG CTGCGGCGCT GTCGCCAGGG CCACTGCGAG GAGTTCTGTG    33060
TCTACAAGGG CAGCCTCTCC AGCTACGGAG CCGTGCTGCC CCCGGGTTTC AGGCCACACT    33120
TCGAGGTGGG CCTGGCCGTG GTGGTGCAGG ACCAGCTGGG AGCCGCTGTG GTCGCCCTCA    33180
ACAGGTGAGC CAGGCCGTGG GAGGGCGCCC CCGAGACTGC CACCTGCTCA CCACCCCCTC    33240
TGCTCGTAGG TCTTTGGCCA TCACCCTCCC AGAGCCCAAC GGCAGCGCAA CGGGGCTCAC    33300
AGTCTGGCTG CACGGGCTCA CCGCTAGTGT GCTCCCAGGG CTGCTGCGGC AGGCCGATCC    33360
CCAGCACGTC ATCGAGTACT CGTTGGCCCT GGTCACCGTG CTGAACGAGG TGAGTGCAGC    33420
CTGGGAGGGG ACGTCACATC TGCTGCATGC GTGCTTGGGA CCAAGACCTG TACCCCTGCC    33480
TGGAGCTTTG CAGAGGGCTC ATCCCGGGCC CCAGAGATAA ATCCCAGTGA CCCTGAAGCA    33540
GCACCCCGAC CTTCCGCTCC CAGCAGCCAC ACCCACCGGG CCCTCTCCGG CGTCTGCTTT    33600
CCACAATGCA GCCCCCGCCC AGGAGGGCCC ATGTGCTTAC CCTGTTTTGC CCATGAAGAA    33660
ACAGCTCAGT GTTGTGGGTC AGTGCCCGCA TCACACAGCG TCTAGCACGT AACTGCACCC    33720
CGGGAGTCGT GGGCATCTGC TGGCCTCCTG CCGGCCTCCT GCGCTGCTGA CAGCTTGCTG    33780
TGCCCCCTGC CTGCCCCAGT ACGAGCGGGC CCTGGACGTG GCGCAGAGCC AAGCACGAG    33840
CGGCAGCACC GAGCCCAGAT ACGCAAGAAC ATCACGGAGA CTCTGGTGTC CCTGAGGGTC    33900
CACACTGTGG ATGACATCCA GCAGATCGCT GCTGCGCTGG CCCAGTGCAT GGTAGGATGG    33960
CCCCACCTGC TCACCCTGCC CCGCATGCCT GCCAGGGCAC TGGGTTCAGC CCCCCAGGGC    34020
```

-continued

```
AGACGGGCAG CTTGGCCGAG GAGCTGAGCC TCCAGCCTGG GCTCCTTCCT GCCATGGCGT    34080
TCCTCGGTCT CTGACCTGCT TCAGTAGCCT CAGCCGTTCT GTCCTGTGTG AACGCAGGGT    34140
GCCTCTCGGG GGACCCAGGG TGTAAAGAGG GGCCCAGATG TGGGGAGGGA CTAAGAAGAT    34200
GCTGCTCTGT GCCCTCCACT CTCCCCTCCC CTCCCCTCCC CCTTCCCTCC CCTAGCCCCT    34260
CCCCTCCTCC CCTCCCCTAG CCCTTCCCCT CCTCCCCTCC CCTAGCCCTT TCCCTTCTTC    34320
CCCCCCAGCC CTTCCCCTCC TCCCCTCCCC TAGCCCTTCC CCTCCTCCCC TCCCCTACCC    34380
CTTCCCCTCC TCCCCTCCCC TAGACCTTCC CCTCACCTCC TCCCGCTGAG CCCCTCCACT    34440
CGTCCCCCAG CCCCTCCCTC CCCTAGCCCC TCCCCTCCCC CTTCCTCCCC TCCTCCCCCT    34500
CCCCTCCTCC CCCTCCCTCT TCCTCCCCCT CCCCTCCTCC CCCTTCCTCC CCTCTCCTCC    34560
CCCTCCCCTC CTGTCCCCCC TCCTCCCCTC CTCCCTCCTC CCCTCCTCCC CCCTCCTCCT    34620
CCCCTCCTCC CCTCCTCCCT CCTCCCCCTC CTCCTCCTCC CCTCCTCCCT CCTCCCCTCC    34680
TCCCCTCCCC TCCTCCCCCT CCCCCCTCCC TTCCTCCCCC TCCCCCCTCC CCTCCTCCCC    34740
CTCTCCTCCT CCCATCCCTC CTCCCATCCC TCCTCCCCGT TCCCATTCTC TCCCCTCCCC    34800
CTTCCATTTC TCCCTCCTCC CCCTGCCCTC CTCTCCTCCT CACCTCCCCT TCTCCGCTCC    34860
TTTCTTCTCC TCCCTCCCTT TCTCTCCTCC CTCCCCTTCT CCCCTTCTCC TCTTCTCCCC    34920
TTCTCCTCTC TTTTCATCCT TCCCTTCTTC CCTCCTTTCC TCCTCTTTTC CCTCTTCTCC    34980
CCCTCCTCC CCTCCTTCCT CCTCCCATTC CCCCTCCTCC CCCCTCCCAT TCCCCCTCCT    35040
CCCCTCCTTC CTCCTCCCAT TACCCCTCCT CTCCTCCCCT CCTCCCACCC CCCTCTCCTC    35100
CCGGCTCCTC TCCTCCCCTC CTCATCCCCC TCCTCTCCTT CCCTCCTAAC CCCCCTCCTC    35160
TCCTCCCCTC CTCATCCCCC TCCTCTCCTT CCCTCCTCCT ATCCCCCCTC CTCTCCTCCC    35220
CTCCTCCTAT TCCCCCTCCT CTCCTCCCCT CCTTCCTCCT CCTCTCCTCC CATGCCCCCT    35280
CCTCCCCTCC TCCCATCCCC CTCCTCCCCT CCTCCCTCCT CCCATCCCAT CCCCCTCCTC    35340
TCCTCCCCTT CTCTCCCCTC CTCTCCTCCC CTCCTCTCCT CTCCTCCTCT CCTCCCCTCC    35400
TCCCATCCCC CCTCCTCCCA TCCCCCCTCC TCTCCTCCCC ACTCCTCTCC TCCCCACTCC    35460
TCTCCTCCCC TCATCCCCCT CCTCTCTCCT CCCCTCCCCC TCCTCTCCTT CCCTCCTCCT    35520
TTCCTCCCCT CCCCCTCCTT CCCCCTCCTC CCCCTCCTTC TCCCCATCCC CCTTCCCCTT    35580
CTCCTCCTCT CCCCTCCCCC TTCTCTTTTT CCCTCCTCCT CCCTTCCTCC TCCCCTCTTC    35640
TCCCCTTTTC CCTTTTCTCT TCCTCTCCTC CCCTTCTCCC CTCCTGTCCT CCCTCCCTTT    35700
CTCTCTTTCT TTCCTCCCTT TCCTTCTCCC CTGTTCTCCT CCCTTCCCTT CTCCCCTTTT    35760
CTTCCCTCCT CCTTTCCTCC CCTCCTCCTT TTCTCTGTTT TCTTCCTTT CCCCTCCACT    35820
TTCCCCTTCC TTTCCCCTCT CCTTTCTCCT TCCTTTCCTC TCCCCTTCTC TTCCTTTTCC    35880
TCTCTCCCCT TCTTTTCCCT CTTCCCCTCC CCTCCTCTTC CCCTCCCCTC CTCTTCCCCT    35940
CCCCTCCTCT TCCCCTCCCC TCCTCTTCCC CTCTCCTCCT CTTCCCCTCC CCTCCTCTTT    36000
CCCTCCCCTC TTCTCCTCCC CTCCTCTCCC CTCTTCCCCT CCCCTCCTCT TCCCTCCCCT    36060
TCCCCTCCCC TCCTCTTCCC TCCCCTTCCC CTCCCCTCCT CTTCCCTCCC CTTCCCCTCC    36120
TCTTCCTTCC TCTCTTCCCC TCCCCTCCTC TTCCCTCCCC TCTTCCCCTC CCCTTCTCTT    36180
CTCCTCCCCT TCTCTTCCCC TCCCCTTTTC TTCCCTCTCC TTGTCTTCCC TGCCCTCCTC    36240
TTCCCTCCCC TCCTCTTCCC TCCCCTCTTC CCCTCTCCTC CTCTTCCCTC CCCTCTTCCT    36300
CTTTCCTCTT CCCCTCCCCT CCTCCTCCCT CCCCTTTCCC CTCTTCCCCT CCCCTCCGCT    36360
```

```
TCCCTCCCCT TTCTCCCCCT TCTCTCCCCT CCCCTCTCCC CCCTTCTCTC CCCTCCCCTC    36420

TCCCCCTTCT CTCCCCTCCC CTCTCCCCCT TCTCTCCCCT CTCCTCTCCC CCTTCTCTCC    36480

CCCTTCTCTC CCCCTTCTCT CTCCCCTTCT CTCCCCCTTC TCTCCCCTCC CCCCTTCTCT    36540

CCCCTCCCCT CTCCCCCTTC TCTCCCCTCC CCTCTCCCCT GTCCTCTCCT CTCCACCCTT    36600

CTCTCCCCTC CCCTCTCCTC TCCCCCTTCC CTCTCCTCTC CCCCTTCTCT CCCCTCCCCT    36660

CTCCTCTCCC CCCTTTTCTC CACTCCCCTC TCCTCTCTCC CCTCCTCCTC CGCTCTCATG    36720

TGAAGAGGTG CCTTGTGTGG TCGGTGGGCT GCATCACGTG GTCCCCAGGT GGAGGCCCTG    36780

GGTCATGCAG AGCCACAGAA AATGCTTAGT GAGGAGGCTG TGGGGGTCCA GTCAAGTGGG    36840

CTCTCCAGCT GCAGGGCTGG GGGTGGGAGC CAGGTGAGGA CCCGTGTAGA GAGGAGGGCG    36900

TGTGCAAGGA GTGGGGCCAG GAGCGGGGCT GGACACTGCT GGCTCCACAC AGGGGCCCAG    36960

CAGGGAGCTC GTATGCCGCT CGTGCCTGAA GCAGACGCTG CACAAGCTGG AGGCCATGAT    37020

GCTCATCCTG CAGGCAGAGA CCACCGCGGG CACCGTGACG CCCACCGCCA TCGGAGACAG    37080

CATCCTCAAC ATCACAGGTG CCGCGGCCCG TGCCCCATGC CACCCGCCCG CCCCGTGCGG    37140

CCCTTTCCTC TGCCTCCCTC CTCCCCCCAA CCGCGTCGCC TTTGCCCCAT CCCATCTTCG    37200

TCCCCCTCCC CTCCCCCCAA TTCCCATCCT CATCCCCCTC CCCCAATTCC CATTCTCCTC    37260

CCCCTCCCCC TTCCCTATTA CCATCCCTTT TCTCCATCTC TCTCCCCTTT TCTCCATTTC    37320

CCCCCCCGTC CTCCCCGTCC TTTTGTCCAT TCCCCTCATC TTCCTCATCC CCCTCATCCC    37380

CCTTCCCCTC CCTTATCCCC CTTCCCCTCC CTTTCCCCCT GCTCCTCTTC TTCTCCCTTC    37440

TCTTTTCTCT ACCCTTTTCC TTCCTTTTTC CTCCCTCTCC CCATCATCCC CCTCATCTTC    37500

GTCCTCATCC CCATCACCTT CCCCCTCCCC CCTCCACCAC TCTCTCTCCA GCTTCCCCCT    37560

TCCTTCTGCC TGCACCTCGC TCTCTGCCCC CTCAGGTTCC CCCTTTCTCC CAGCCCCCAC    37620

CCTCCGGCTC CCCCTTTTTG CCTGCCCCCA CCCTCCCTCT ACCTCCTGT CTCTGCACTG    37680

ACCTCACGCA TGTCTGCAGG AGACCTCATC CACCTGGCCA GCTCGGACGT GCGGGCACCA    37740

CAGCCCTCAG AGCTGGGAGC CGAGTCACCA TCTCGGATGG TGGCGTCCCA GGCCTACAAC    37800

CTGACCTCTG CCCTCATGCG CATCCTCATG CGCTCCCGCG TGCTCAACGA GGAGCCCCTG    37860

ACGCTGGCGG GCGAGGAGAT CGTGGCCCAG GGCAAGCGCT CGGACCCGCG GAGCCTGCTG    37920

TGCTATGGCG GCGCCCCAGG GCCTGGCTGC CACTTCTCCA TCCCCGAGGC TTTCAGCGGG    37980

GCCCTGGCCA ACCTCAGTGA CGTGGTGCAG CTCATCTTTC TGGTGGACTC CAATCCCTTT    38040

CCCTTTGGCT ATATCAGCAA CTACACCGTC TCCACCAAGG TGGCCTCGAT GGCATTCCAG    38100

ACACAGGCCG CGCGCCCAGAT CCCCATCGAG CGGCTGGCCT CAGAGCGCGC CATCACCGTG    38160

AAGGTGCCCA ACAACTCGGA CTGGGCTGCC CGGGGCCACC GCAGCTCCGC CAACTCCGCC    38220

AACTCCGTTG TGGTCCAGCC CCAGGCCTCC GTCGGTGCTG TGGTCACCCT GGACAGCAGC    38280

AACCCTGCGG CCGGGCTGCA TCTGCAGCTC AACTATACGC TGCTGGACGG TGCGTGCAGC    38340

GGGTGGGGCA CACGCGGCCC CCTGGCCTTG TTCTTGGGGG GAAGGCGTTT CTCGTAGGGC    38400

TTCCATGGGT GTCTCTGGTG AAATTTGCTT TCTGTTTCAT GGGCTGCTGG GGGCCTGGCC    38460

AGAGAGGAGC TGGGGGCCAC GGAGAAGCAG GTGCCAGCTC TGGTGCAGAG GCTCCTATGC    38520

TTTCAGGCCC GTGGCAGAGG GTGGGCTCAG GAGGGCCATC GTGGGTGTCC CCCGGGTGGT    38580

TGAGCTTCCC GGCAGGCGTG TGACCTGCGC GTTCTGCCCC AGGCCACTAC CTGTCTGAGG    38640

AACCTGAGCC CTACCTGGCA GTCTACCTAC ACTCGGAGCC CCGCCCAAT GAGCACAACT    38700

GCTCGGCTAG CAGGAGGATC CGCCCAGAGT CACTCCAGGG TGCTGACCAC CGGCCCTACA    38760
```

-continued

```
CCTTCTTCAT TTCCCCGGGG TGAGCTCTGC GGGCCAGCCT GGCAGGGCAG GGCAGGGCAT    38820
CATGGGTCAG CATTGCCTGG GTTACTGGCC CCATGGGGAC GGCAGGCAGC GAGGGGACTG    38880
GACCGGGTAT GGGCTCTGAG ACTGCGACAT CCAACCTGGC GGAGCCTGGG CTCACGTCCG    38940
CTACCCCTTC CCTGCCCAGG AGCAGAGACC CAGCGGGGAG TTACCATCTG AACCTCTCCA    39000
GCCACTTCCG CTGGTCGGCG CTGCAGGTGT CCGTGGGCCT GTACACGTCC CTGTGCCAGT    39060
ACTTCAGCGA GGAGGACATG GTGTGGCGGA CAGAGGGGCT GCTGCCCCTG GAGGAGACCT    39120
CGCCCCGCCA GGCCGTCTGC CTCACCCGCC ACCTCACCGC CTTCGGCGCC AGCCTCTTCG    39180
TGCCCCCAAG CCATGTCCGC TTTGTGTTTC CTGTGAGTGA CCCTGTGCTC CTGGGAGCCT    39240
CTGCAGAGTC GAGGAGGGCC TGGGTGGGCT CGGCTCTATC CTGAGAAGGC ACAGCTTGCA    39300
CGTGACCTCC TGGGCCCGGC GGCTGTGTCC TCACAGGAGC CGACAGCGGA TGTAAACTAC    39360
ATCGTCATGC TGACATGTGC TGTGTGCCTG GTGACCTACA TGGTCATGGC CGCCATCCTG    39420
CACAAGCTGG ACCAGTTGGA TGCCAGCCGG GGCCGCGCCA TCCCTTTCTG TGGGCAGCGG    39480
GGCCGCTTCA AGTACGAGAT CCTCGTCAAG ACAGGCTGGG GCCGGGGCTC AGGTGAGGGG    39540
CGCAGCGGGG TGGCAGGGCC TCCCCTGCTC TCACTGGCTG TGCTGGTTGC ACCCTCTGGG    39600
AGTGAGTCTC GTCGCAGGCG TCAGAACAAG GCAGTTTTTG CAGTGCTGTG TGAAGGGCTC    39660
GTGTGTTCAT CCTGGGAATG ACCTCGTGAG CACTCACTGT CCCTGAGGAC TAGGACAGCT    39720
CCTAGCTGGA AGTAGGTGCC AGTCAGTCAG GGTGGGCAGC CCACGTTCTG CACAGTAGCG    39780
TGGCCCCACA AGTGACGTGA GCATCGCTAC CACTGTGGGA GACTGTGCAT CCACCCGCGA    39840
TCCTGACTGC ATAGCTCGTC TCTCAGACGG AGGCGCCAGC ACCCTCCCCG TGGCTGTTTC    39900
TTCAGTACCT CCATTTTCCT TTCATTGGAA TTGCCCTTCT GGCATTCCCT TTTTGTTTTC    39960
GTTTTTCTTT TTTTAGAGAC GGAGTCTCAC TCTGTTGCCC AGGCTGGAGT GCAATGGCAT    40020
GATCTTGGCT CACAGCAACT TCCAGCTCCC GGGTTTAAGC CATTCCCCTT AAGCGATTCT    40080
CCTGAGTAGC TGGGAGTACA GGTGCACACC ACCACACCCA GTTAATTTTT CACCATGTCA    40140
GCCAGGCGAA CTCCTGACCT CAGGTGATCC GCCTGCCTCG GCCTGCCAGA GTGCTGGGAT    40200
GACAGGTGTG AGCCACCACA CCTGGCTGTG TTCCCATTTT TTATCTCTGT GCTGCTTTCC    40260
TCTTCATTGC CCAGTTCTTT CTTTTGATTA CCTACTTTTA AAAACTGTCG GCCGGGCGCG    40320
GTGGCTCACA CCTGTAATCC GAGCACTTTG GGAGGCCAGG CAGGCAAATC ACGGGGTCAG    40380
GAGATCGAGA CCATCCTGGC TAACGGTGAA ACCCTGTCTC TAATAAAAAG TACAAAAAAA    40440
TTAGCCCGGC GTAGTGGCAG GCGCCTGTAG TCCCAGCTCC TTGGGAGACT GAGGCAGGAG    40500
AATGGCGTGA ACCCGGGAGG CGGAGCTTGC AGTGAGCTGA GATTGCGCCA CTGCACTCCA    40560
GCCTGGGTGA CACAGCAAGA CTCCATCTCA AAAAAAAAG AAAAAAAATA CTGTCACCTG    40620
GGTCTGTCAC TGGGAGAGGA GGTGACACAG CTTCACGCTT TGCAGTCTGT GCATGAACTG    40680
AGGGACGGGT GTGTGGTGCG GGTCACCGGT TGTGGCATGA CTGAGGCGTG GACAGGTGTG    40740
CAGTGCGGGT CACTGGTTGT GGTGTGGACT GAGGCGTGTG CAGCCATGTT TGCATGTCAC    40800
AAGTTACAGT TCTTTCCATG TAACTTAATC ATGTCCTTGA GGTCCTGCTG TTAATTGGAC    40860
AAATTGCAGT AACCGCAGCT CCTTGTGTAT GGCAGAGCCG TGCAAAGCCG GGACTGCCTG    40920
TGTGGCTCCT TGAGTGCGCA CAGGCCAAAG CTGAGATGAC TTGCCTGGGA TGCCACACGT    40980
GTTGGGCAGC AGACCGAGCC TCCCACCCCT CCCTCTTGCC TCCCAGGTAC CACGGCCCAC    41040
GTGGGCATCA TGCTGTATGG GGTGGACAGC CGGAGCGGCC ACCGGCACCT GGACGGCGAC    41100
```

-continued

```
AGAGCCTTCC ACCGCAACAG CCTGGACATC TTCCGGATCG CCACCCCGCA CAGCCTGGGT    41160

AGCGTGTGGA AGATCCGAGT GTGGCACGAC AACAAAGGTT TGTGCGGACC CTGCCAAGCT    41220

CTGCCCCTCT GCCCCCGCAT TGGGGCGCCC TGCGAGCCTG ACCTCCCTCC TGCGCCTCTG    41280

CAGGGCTCAG CCCTGCCTGG TTCCTGCAGC ACGTCATCGT CAGGGACCTG CAGACGGCAC    41340

GCAGCGCCTT CTTCCTGGTC AATGACTGGC TTTCGGTGGA GACGGAGGCC AACGGGGGCC    41400

TGGTGGAGAA GGAGGTGCTG GCCGCGAGTA AGGCCTCGTT CCATGGTCCC ACTCCGTGGG    41460

AGGTTGGGCA GGGTGGTCCT GCCCCGTGGC CTCCTGCAGT GCGGCCCTCC CTGCCTTCTA    41520

GGCGACGCAG CCCTTTTGCG CTTCCGGCGC CTGCTGGTGG CTGAGCTGCA GCGTGGCTTC    41580

TTTGACAAGC ACATCTGGCT CTCCATATGG GACCGGCCGC CTCGTAGCCG TTTCACTCGC    41640

ATCCAGAGGG CCACCTGCTG CGTTCTCCTC ATCTGCCTCT TCCTGGGCGC CAACGCCGTG    41700

TGGTACGGGG CTGTTGGCGA CTCTGCCTAC AGGTGGGTGC CGTAGGGGTC GGGGCAGCCT    41760

CTTCCTGCCC AGCCCTTCCT GCCCCTCAGC CTCACCTGTG TGGCCTCCTC TCCTCCACAC    41820

AGCACGGGGC ATGTGTCCAG GCTGAGCCCG CTGAGCGTCG ACACAGTCGC TGTTGGCCTG    41880

GTGTCCAGCG TGGTTGTCTA TCCCGTCTAC CTGGCCATCC TTTTTCTCTT CCGGATGTCC    41940

CGGAGCAAGG TGGGCTGGGG CTGGGGACCC GGGAGTACTG GGAATGGAGC CTGGGCCTCG    42000

GCACCATGCC TAGGGCCGCC ACTTTCCAGT GCTGCAGCCA GAGGGAAAGG CGTCCACCAA    42060

AGGCTGCTCG GGAAGGGTCA ACACACTTGA GCAGCCTTAG CTAGACTGAC CAGGGAGAAA    42120

GAGAGAAGAC TCAGAAGCCA GAATGGTGAA AGAACGAGGG CACTTTGCTA AGCAGACGCC    42180

ACGGACGACT GCACAGCAGC ACGCCAGATA ACTCAGAAGA AGCAAGCACG CGGCTGTGCA    42240

CGCTTCCGAA ATGCACTCCA GAAGAAAATC TCAGTACATC TATAGGAAGT GAAGAGGCTG    42300

AGTTAGTCCC TTAGAAACGT CCCAGTGGCC GGGCCGGGTG TGGTGGCTCA CGCCTGTAAT    42360

CCCAACACTT CAGGTGGCCG AGGTGGGCGG ATCTGAGTCC AGGAGTTTGA GACCAGCCTG    42420

GGCAACATAG CAAGACCCCA TCTATATAAA ACATTAAAAA GGGCCAGGCG CGGTGGCTCA    42480

CGCCTGTAAT CCCAGCACTT TGGGAGGCCG AGGCGGGCAG ATCACTTGAG GTCAGGAGTT    42540

CGAGACCAGC CTGGCCAACA CAATGAAACC CCGACTCTAC TACAAATACA AAAACTTAGC    42600

TGGGCATGGT GGCGGGCGCC TGTAGTCCCA GCTACTCGAG AGGCTGAGGC AGGAGAATGG    42660

CATGAACCCA GGAGGCGGAG CTTGCAGTGA GCCGAGATTG CGCCACTGCA CTCCATCCTG    42720

GGCAACGGAG CAAGACTCCA TCTCCAAAAA AAAAAAAAA AAATCCCACA AGAAAAAGCT    42780

CAGGCTCAGA GCCTTCACGA TAGAATTTTT CTAAGCAGTT AAGGAAGAAT TAACACCAAT    42840

CCTTCACAGA CTCTTTCCAA GAATACAGCA GGTGGGAACG CTTCCCATTC ATACGGAAAC    42900

GGGAGGCCGC ACCCCTTAGG AATGCACACG TGGGGTCCTC AAGAGGTTAC ATGCAAACTA    42960

ACCCCAGCAG CACACAGAGA AGGCGCATAA GCCGCGACCA GGAGGGGTTG CTCCCGAGTC    43020

CGTGGCAGGA ACCAGAGGCC ACATGTGGCT GCTCGTATTT AAGTTAATTA AAATGGAACG    43080

ATGGCCGGGT GTGGTGGCTC ACACCTGTAA TCCCAGCACT TGGGAGGCG GAGGCGGGCA    43140

GATCACTTGA GGTCAGGAGT TCCAAGACCA GCCTGGCCAA CACAGTGAAA CCCCGTCTCT    43200

ACTAAAAATA CAAAAAATTA GCTGGGCATG GTGGCAGGCA CCTGTAATCC CAGCTACTCA    43260

GGAGGCTGAG CCAGGACAAT CGCCTGAACG CGGGAGGTGG AGGTTGCAGT GAGCTGAGAT    43320

TGCGCCATTG CACTCCAGCC TGGGTGACAG CGAGACTCCA TCTAAAAAAG AAAATATGAA    43380

ATTTAAAACT CTGTTCCTTA GCTGCACCAG TCTGCTGTCA AGTGTTCAGT GGCACACGTC    43440

GCGAGGGGCT GCCATCACGG ACGGTGCAGA TGTCCCATAT ATCCAGCATT CTAGGACATT    43500
```

-continued

```
CTGTCAGATG GCACCGGGCT CTGTCCTGTC TGCTGAGGAG GTGGCTTCTC ATCCCTGTCC    43560

TGAGCAGGTC TGAGCTGCCG CCCGCTGACC ACTGCCCTCG TCCTGCAGGT GGCTGGGAGC    43620

CCGAGCCCCA CACCTGCCGG GCAGCAGGTG CTGGACATCA ACAGCTGCCT GGACTCGTCC    43680

GTGCTGGACA GCTCCTTCCT CACGTTCTCA GGCCTCCACG CTGAGGTGAG GACTCTACTG    43740

GGGGTCCTGG GCTGGGCTGG GGGTCCTGCC GCCTTGGCGC AGCTTGGACT CAAGACACTG    43800

TGCACCTCTC AGCAGGCCTT TGTTGGACAG ATGAAGAGTG ACTTGTTTCT GGATGATTCT    43860

AAGAGGTGGG TTCCCTAGAG AAACCTCGAG CCCTGGTGCA GGTCACTGTG TCTGGGGTGC    43920

CGGGGGTGTG CGGGCTGCGT GTCCTTGCTG GGTGTCTGTG GCTCCATGTG GTCACACCAC    43980

CCGGGAGCAG GTTTGCTCGG AAGCCCAGGG TGTCCGTGCG TGACTGGACG GGGGTGGGCT    44040

GTGTGTGTGA CACATCCCCT GGTACCTTGC TGACCCGCGC CACCTGCAGT CTGGTGTGCT    44100

GGCCCTCCGG CGAGGGAACG CTCAGTTGGC CGGACCTGCT CAGTGACCCG TCCATTGTGG    44160

GTAGCAATCT GCGGCAGCTG GCACGGGGCC AGGCGGGCCA TGGGCTGGGC CCAGAGGAGG    44220

ACGGCTTCTC CCTGGCCAGC CCCTACTCGC CTGCCAAATC CTTCTCAGCA TCAGGTGAGC    44280

TGGGGTGAGA GGAGGGGGCT CTGAAGCTCA CCCTTGCAGC TGGGCCCACC CTATGCCTCC    44340

TGTACCTCTA GATGAAGACC TGATCCAGCA GGTCCTTGCC GAGGGGGTCA GCAGCCCAGC    44400

CCCTACCCAA GACACCCACA TGGAAACGGA CCTGCTCAGC AGCCTGTGAG TGTCCGGCTC    44460

TCGGGGAGG GGGGATTGCC AGAGGAGGGG CCGGGACTCA GGCCAGGCAG CCGTGGTTCC    44520

CGCCTGGGGT AGGGTGGGGT GGGGTGCCAG GGCAGGGCTG TGGCTGCACC ACTTCACTTC    44580

TCTGAACCTC TGTTGTCTGT GGAAAGAGCC TCATGGATC CCCAGGGCCC CAGAACCTTC    44640

CCTCTAGGGA GGGAGCAGGC TCATGGGGCT TTGTAGGAGC AGAAAGGCTC CTGTGTGAGG    44700

CTGGCCGGGG CCACGTTTTT ATCTTGGTCT CAGAGCAGTG AGAAATTATG GGCGGGTTTT    44760

TAAATACCCC ATTTTTGGCC GGGCGCGGTG GCTCACACGT GTAATCCCAG CACTTTGGGA    44820

GGCCGAGGTG GGCAGATGAC CTGAGGTCAG CAGTTCGAGA CCAGCCTGGC CAACATGGCG    44880

AAACCCCGTC TCTACTAAAA ATACAAAAAA TTAGCCGGGC ATGCTGGCAG GCGCCTGTAG    44940

TCCCAGTTAC TCGGGAGACT GAGGTAGGAG AATCGATTGA ACCTGGTAGG TGAAGGTTGT    45000

AGTGAGCCGA GATCGCGCCA CTGCACTCCA GCCTGGGCAA CAAGAGCGAA ACTCCGTCTC    45060

AAAAACAAAA AAATTCCTCA ATTTCTTGGT TGTTTTGTAA CTTATCAACA AATGGTCATA    45120

TAGAGGTTAC CTTGTATGTA GTCACGCACA TAGTCACGCA CATGGCAGCC GGCGGCGGAG    45180

CGCACCCACG GCGTGTTCCC ACGCGTGTGA CCCCGGGCTC TGCCATGCCC TCCTATGCTC    45240

AGGTGTGCTG AGGTCCACAC GGCCCTGCCG TTGCACTGCA GCTGCCTGCA GGATTCAGTG    45300

CAGTGGCATG CAGTGCAGGT GCGGTGCCCC GGAGCCACAG GCCACACCAC AGGGCCTGCA    45360

TGCACAGGGG CTGCGGTGTC TGGGTTTGGG TAACTACGCC CTGTGACATT TGCACAGCAA    45420

CAGAATTACC TAATGACGCA TTTCTCAGAA CACATCCCTG GCACTAAGTG GTGCGTGACT    45480

GCTGCTTTTG CATCCACATC TAGTTTGATT TGTGTGTTAT TCCTTTGAGT GCTTCTCATT    45540

GTTAAGCAAC CAAGAACTAA AGAGGTATGA ACTGCCCCTG GACTCAAACA AAAGGAAAA    45600

CTTCCTGATT TACAAAAGGC AGATAACCAT CACATGAGGG CATCTTTATG AATAAATTGC    45660

TGGTTGGTTT TAAAAATACA GAGTATGGGG AAATCCAGGG GTAGTCACTA CATGCTGACC    45720

AGCCCCAGGT ATCTCCGGCC CAAAGCTCTG TGAAATCCAG ATTCAGTGCT TCCGCGGGGA    45780

TTTCTGACGG CAGCTCAGAC TCCGCATCCA CACAGAGCGC GTGGCCCTCA CCCTCCCGGC    45840
```

```
-continued

TTCCTCAACC CTTGGCCGTC CCTTGCTCGG ACAGTGCTTC GGGCTGACCA GGTCGGAGGC    45900

TTGGGTTTGT CCTGGACCCC TCTGCGTCCT TCCTCACTGC AGCCTCCAGC GCGTCCCGTG    45960

GCTCCTTTCC CAACGCAGAG CACGGCCTTC CCTGCGCCTG AGCCTGCACC CTCCGTCCTG    46020

GCGGCGCCTC TGCCCTGGCA TTCCCTGCCA CTCCATGCCT CCCTATTGGC CATTCTCCGT    46080

CTCTGCCAGC GAGAGCCTGC TCCCTGAGTC AGACCCTGAG TCATTTGTGT TGCTATAAAG    46140

GAATAGTTGA GGCTGGGTTA TTTTTTATTT TTATTTATTT TTTTGAGATG GAGTCTCTGT    46200

TGCCCAGACT GGAGTGCAGT CGCATGATCT CGGCTCACTG CAAAGTCTGC CTCCCACGTT    46260

CAAGCAGTTA TCTGCCTCAG CCTCCCAAGT AGCTAAGATT ACAGGCGCCC GCCGCCACAG    46320

CCGGCTAATT TTTTGTGTGT GTGTTTTAGT AGAGAGGAGG TTTCACCATC TTAGCCAGGC    46380

TGGTCTTGAA CTCCTGACCT CGTGATCCAC CCATCTCAGC CTCCCAAAAT GCTGAGATTA    46440

CAGGCGTGAG CCACCACGCC TGACCAAGTT GAGGCTAGGT CATTTTTTAA TTTTTTGTAA    46500

AGACAGGGTC TCACTGTCTC CAACTCCTGA GCTCAAGTGA TCCTCCTGCC TCAGCCTCCT    46560

GAAGTGCTGG GATTACAGGC TTGAGACACT GCGCCCAGCC AAGAGTGTCT TTTATCCTCC    46620

GAGAGACAGC AAAACAGGAA GCATTCAGTG CAGTGTGACC CTGGGTCAGG CCGTTCTTTC    46680

GGTGATGGGC TGACGAGGGC GCAGGTACGG GAGAGCGTCC TGAGAGCCCG GGACTCGGCG    46740

TCTCGCAGTT GGTCTCGTCC TCCCCCTCAA CGTGTCTTCG CTGCCTCTGT ACCTCTTCTC    46800

TAGCAGCTCT GGGACCGGGC ATATCAGCAT GGTGGCCCGA TGCAGTGGCA CAGCCTCGGT    46860

GGTCACTGGC TCCTGGAGAC ACAAGCAGAT CTCTGGCCTC AGGGAGCCCT ACACACTGTT    46920

GGGATTTGAA AGGCATTCAT ATGTTTCCTT GTCCAGAAGT TAATTTTAGG CCATAAACCT    46980

GCATGGGACA GACACACTGG CGTCTCTAGA TTGTAGAGAT GCTTGTTGGA TGGTTGAGAC    47040

CCAATCATAG TTTGCAGGGT TGAAGGGGGG CTCATTGCAC CCTGAGAGAC TGTGCACTGC    47100

TGTAAGGGCA GCTGGTCAGG CTGTGGGCGA TGGGTTTATC AGCAGCAAGC GGGCGGGAGA    47160

GGGACGCAGG CGGACGCCTG ACTTCGGTGC CTGGAGTGGC TCTTGGTTCC CTGGCTCCCA    47220

GCACCACTCC CACTCTCGTT TGGGGTAGGG TCTTCCGGCT TTTTGTCGGG GGACCCTGT     47280

GACCCAAGAG GCTCAAGAAA CTGCCCGCCC AGGTTAACAT GGGCTTGGCT GCAACTGCCT    47340

CCTGGAGGCC GGGATGAATT CACAGCCTAC CATGTCCCTC AGGTCCAGCA CTCCTGGGGA    47400

GAAGACAGAG ACGCTGGCGC TGCAGAGGCT GGGGGAGCTG GGGCCACCCA GCCCAGGCCT    47460

GAACTGGGAA CAGCCCCAGG CAGCGAGGCT GTCCAGGACA GGTGTGCTTG CGTAGCCCCG    47520

GGATGCCCCT AGCCCCTCCC TGTGAGCTGC CTCTCACAGG TCTGTCTCTG CTTCCCCAGG    47580

ACTGGTGGAG GGTCTGCGGA AGCGCCTGCT GCCGGCCTGG TGTGCCTCCC TGGCCCACGG    47640

GCTCAGCCTG CTCCTGGTGG CTGTGGCTGT GGCTGTCTCA GGGTGGGTGG GTGCGAGCTT    47700

CCCCCCGGGC GTGAGTGTTG CGTGGCTCCT GTCCAGCAGC GCCAGCTTCC TGGCCTCATT    47760

CCTCGGCTGG GAGCCACTGA AGGTGAGGGG GCTGCCAGGG GTAGGCTACA GGCCTCCATC    47820

ACGGGGACC CCTCTGAAGC CACCCCCTCC CCAGGTCTTG CTGGAAGCCC TGTACTTCTC     47880

ACTGGTGGCC AAGCGGCTGC ACCCGGATGA AGATGACACC CTGGTAGAGA GCCCGGCTGT    47940

GACGCCTGTG AGCGCACGTG TGCCCCGCGT ACGGCCACCC CACGGCTTTG CACTCTTCCT    48000

GGCCAAGGAA GAAGCCCGCA AGGTCAAGAG GCTACATGGC ATGCTGCGGG TGAGCCTGGG    48060

TGCGGCCTGT GCCCCTGCCA CCTCCGTCTC TTGTCTCCCA CCTCCCACCC ATGCACGCAG    48120

GACACTCCTG TCCCCCTTTC CTCACCTCAG AAGGCCCTTA GGGGTTCAAT GCTCTGCAGC    48180

CTTTGCCCGG TCTCCCTCCT ACCCCACGCC CCCCACTTGC TGCCCCAGTC CCTGCCAGGG    48240
```

```
CCCAGCTCCA ATGCCCACTC CTGCCTGGCC CTGAAGGCCC CTAAGCACCA CTGCAGTGGC   48300

CTGTGTGTCT GCCCCCAGGT GGGGTTCCGG GCAGGGTGTG TGCTGCCATT ACCCTGGCCA   48360

GGTAGAGTCT TGGGGCGCCC CCTGCCAGCT CACCTTCCTG CAGCCACACC TGCCGCAGCC   48420

ATGGCTCCAG CCGTTGCCAA AGCCCTGCTG TCACTGTGGG CTGGGGCCAG GCTGACCACA   48480

GGGCCCCCCC GTCCACCAGA GCCTCCTGGT GTACATGCTT TTTCTGCTGG TGACCCTGCT   48540

GGCCAGCTAT GGGGATGCCT CATGCCATGG GCACGCCTAC CGTCTGCAAA GCGCCATCAA   48600

GCAGGAGCTG CACAGCCGGG CCTTCCTGGC CATCACGCGG TACGGGCATC CGGTGCACTG   48660

GTCTGTCTTC TGGGCTTTAG TTTTGCCTTT AGTCCAGCCA GACCCTAGGG GACATGTGGA   48720

CATGTGTAGA TACCTTTGTG GCTGCTAGAA CTGGAGGTAG GTGCTGCTGG CATCAGTAGG   48780

CAGAGGGGAG GGACACAGGT CCGTGTCTTG CAGTGCACAG GACGGGCCCA TGACAGACAA   48840

CTGTCTGCCC CAGAACATCC CCAGGATAAG GCTGAGAAGC CCAGGTCTAG CCGTGGCCAG   48900

CAGGGCAGTG GGAGCCATGT TCCCTGGGTC TCTGGTGGCC GCTCACTCGA GGCGGGCATG   48960

GGGCAGTAGG GGCTGGAGCG TGTGACTGAT GCTGTGGCAG GTCTGAGGAG CTCTGGCCAT   49020

GGATGGCCCA CGTGCTGCTG CCCTACGTCC ACGGGAACCA GTCCAGCCCA GAGCTGGGGC   49080

CCCCACGGCT GCGGCAGGTG CGGCTGCAGG AAGGTGAGCT GGCAGGGCGT GCCCCAAGAC   49140

TTAAATCGTT CCTCTTGTTG AGAGAGCAGC CTTTAGCGGA GCTCTGGCAT CAGCCCTGCT   49200

CCCTAGCTGT GTGACCTTTG CCCTCTTAAC ACCGCCGTTT CCTTCTCTGT ATATGAGAGA   49260

TGGTAACGTT GTCTAATTGA TGGCTGCTGG GAGGGTTCCC TGGGGTGGCG CCGAACCAGA   49320

GCTCAGGCGA GCTGGCCAGC AGGAAACACT CCTGTTGGGT TTTGATGAGG CCCTGGCCCC   49380

GGCCTGGGGC TCTGTGTGTT TCAGCACTCT ACCCAGACCC TCCCGGCCCC AGGGTCCACA   49440

CGTGCTCGGC CGCAGGAGGC TTCAGCACCA GCGATTACGA CGTTGGCTGG GAGAGTCCTC   49500

ACAATGGCTC GGGGACGTGG GCCTATTCAG CGCCGGATCT GCTGGGGTGA GCAGAGCGAG   49560

GGCCCCGGGC GTCTACGCCA AGGACAAGGG AGTAGTTCTC CAGGAGTGCC GCGGCCTCCT   49620

GACCAGCCTG GCTCCGGGGT GCCGGAAGGG CTGGGGTGCG GCACCCACGC CACCCCTCTC   49680

CGGCAGGGCA TGGTCCTGGG GCTCCTGTGC CGTGTATGAC AGCGGGGGCT ACGTGCAGGA   49740

GCTGGGCCTG AGCCTGGAGG AGAGCCGCGA CCGGCTGCGC TTCCTGCAGC TGCACAACTG   49800

GCTGGACAAC AGGTGGGAGC TCCCTCCCCT GCCCTCTCCG GGGTGGCCGC AGTCACCAGC   49860

CAGGAGCCCA CCCTCACTCC TCCGGCCCCC GCTGGCCTAG GCGGCTTCCA CAGCCCCTCA   49920

GCCACGCCTG CACTCGCGGG TCCCCGCAGC TCCCGCCCTG CCACCCGCTC CTACTGACCC   49980

GCACCCTCTG CGCAGGAGCC GCGCTGTGTT CCTGGAGCTC ACGCGCTACA GCCCGGCCGT   50040

GGGGCTGCAC GCCGCCGTCA CGCTGCGCCT CGAGTTCCCG GCGGCCGGCC GCGCCCTGGC   50100

CGCCCTCAGC GTCCGCCCCT TTGCGCTGCG CCGCCTCAGC GCGGGCCTCT CGCTGCCTCT   50160

GCTCACCTCG GTACGCCCGT CCCCGGCCAG ACCCCGCGCC TCCCACCGGC AGCGTCCCGC   50220

CCCCTCGCGG GGCCCCGCCC GGCAGCGTCT CACCCCTCGC AGCGCCCCGC CCCCTCGCAG   50280

CGTCCCGCCC CCTCGCAGGG CCCCGCCCCG GCAGCGTCCC GCCCCCTCGT AGGGCCCCGC   50340

CCCGGCAGCG TCCCGCCCCC TCGCAGGGCC CCGCCCGGC AGCGTCCCTC CCGCCCTCCT   50400

GACCGCGCCC CCCACAGGTG TGCCTGCTGC TGTTCGCCGT GCACTTCGCC GTGGCCGAGG   50460

CCCGTACTTG GCACAGGGAA GGGCGCTGGC GCGTGCTGCG GCTCGGAGCC TGGGCGCGGT   50520

GGCTGCTGGT GGCGCTGACG GCGGCCACGG CACTGGTACG CCTCGCCCAG CTGGGTGCCG   50580
```

-continued

```
CTGACCGCCA GTGGACCCGT TTCGTGCGCG GCCGCCCGCG CCGCTTCACT AGCTTCGACC    50640

AGGTGGCGCA GCTGAGCTCC GCAGCCCGTG GCCTGGCGGC CTCGCTGCTC TTCCTGCTTT    50700

TGGTCAAGGT GAGGGCTGGG CCGGTGGGCG CGGGGCTGGG CGCACACCCC AGGGCTGCAA    50760

GCAGACAGAT TTCTCGTCCG CAGGCTGCCC AGCAGCTACG CTTCGTGCGC CAGTGGTCCG    50820

TCTTTGGCAA GACATTATGC CGAGCTCTGC CAGAGCTCCT GGGGGTCACC TTGGGCCTGG    50880

TGGTGCTCGG GGTAGCCTAC GCCCAGCTGG CCATCCTGGT AGGTGACTGC GCGGCCGGGG    50940

AGGGCGTCTT AGCTCAGCTC AGCTCAGCTG TACGCCCTCA CTGGTGTCGC CTTCCCCGCA    51000

GCTCGTGTCT TCCTGTGTGG ACTCCCTCTG GAGCGTGGCC CAGGCCCTGT TGGTGCTGTG    51060

CCCTGGGACT GGGCTCTCTA CCCTGTGTCC TGCCGAGTCC TGGCACCTGT CACCCCTGCT    51120

GTGTGTGGGG CTCTGGGCAC TGCGGCTGTG GGGCGCCCTA CGGCTGGGGG CTGTTATTCT    51180

CCGCTGGCGC TACCACGCCT TGCGTGGAGA GCTGTACCGG CCGGCCTGGG AGCCCCAGGA    51240

CTACGAGATG GTGGAGTTGT TCCTGCGCAG GCTGCGCCTC TGGATGGGCC TCAGCAAGGT    51300

CAAGGAGGTG GGTACGGCCC AGTGGGGGGG AGAGGGACAC GCCCTGGGCT CTGCCCAGGG    51360

TGCAGCCGGA CTGACTGAGC CCCTGTGCCG CCCCCAGTTC CGCCACAAAG TCCGCTTTGA    51420

AGGGATGGAG CCGCTGCCCT CTCGCTCCTC CAGGGGCTCC AAGGTATCCC CGGATGTGCC    51480

CCCACCCAGC GCTGGCTCCG ATGCCTCGCA CCCCTCCACC TCCTCCAGCC AGCTGGATGG    51540

GCTGAGCGTG AGCCTGGGCC GGCTGGGGAC AAGGTGTGAG CCTGAGCCCT CCCGCCTCCA    51600

AGCCGTGTTC GAGGCCCTGC TCACCCAGTT TGACCGACTC AACCAGGCCA CAGAGGACGT    51660

CTACCAGCTG GAGCAGCAGC TGCACAGCCT GCAAGGCCGC AGGAGCAGCC GGGCGCCCGC    51720

CGGATCTTCC CGTGGCCCAT CCCCGGGCCT GCGGCCAGCA CTGCCCAGCC GCCTTGCCCG    51780

GGCCAGTCGG GGTGTGGACC TGGCCACTGG CCCCAGCAGG ACACCCCTTC GGGCCAAGAA    51840

CAAGGTCCAC CCCAGCAGCA CTTAGTCCTC CTTCCTGGCG GGGGTGGGCC GTGGAGTCGG    51900

AGTGGACACC GCTCAGTATT ACTTTCTGCC GCTGTCAAGG CCGAGGGCCA GGCAGAATGG    51960

CTGCACGTAG GTTCCCCAGA GAGCAGGCAG GGGCATCTGT CTGTCTGTGG GCTTCAGCAC    52020

TTTAAAGAGG CTGTGTGGCC AACCAGGACC CAGGGTCCCC TCCCCAGCTC CCTTGGGAAG    52080

GACACAGCAG TATTGGACGG TTTCTAGCCT CTGAGATGCT AATTTATTTC CCCGAGTCCT    52140

CAGGTACAGC GGGCTGTGCC CGGCCCCACC CCCTGGGCAG ATGTCCCCCA CTGCTAAGGC    52200

TGCTGGCTTC AGGGAGGGTT AGCCTGCACC GCCGCCACCC TGCCCCTAAG TTATTACCTC    52260

TCCAGTTCCT ACCGTACTCC CTGCACCGTC TCACTGTGTG TCTCGTGTCA GTAATTTATA    52320

TGGTGTTAAA ATGTGTATAT TTTTGTATGT CACTATTTTC ACTAGGGCTG AGGGGCCTGC    52380

GCCCAGAGCT GGCCTCCCCC AACACCTGCT GCGCTTGGTA GGTGTGGTGG CGTTATGGCA    52440

GCCCGGCTGC TGCTTGGATG CGAGCTTGGC CTTGGGCCGG TGCTGGGGGC ACAGCTGTCT    52500

GCCAGGCACT CTCATCACCC CAGAGGCCTT GTCATCCTCC CTTGCCCCAG GCCAGGTAGC    52560

AAGAGAGCAG CGCCCAGGCC TGCTGGCATC AGGTCTGGGC AAGTAGCAGG ACTAGGCATG    52620

TCAGAGGACC CCAGGGTGGT TAGAGGAAAA GACTCCTCCT GGGGGCTGGC TCCCAGGGTG    52680

GAGGAAGGTG ACTGTGTGTG TGTGTGTGTG CGCGCGCGCA CGCGCGAGTG TGCTGTATGG    52740

CCCAGGCAGC CTCAAGGCCC TCGGAGCTGG CTGTGCCTGC TTCTGTGTAC CACTTCTGTG    52800

GGCATGGCCG CTTCTAGAGC CTCGACACCC CCCAACCCC CGCACCAAGC AGACAAAGTC    52860

AATAAAAGAG CTGTCTGACT GCAATCTGTG CCTCTATGTC TGTGCACTGG GGTCAGGACT    52920

TTATTTATTT CACTGACAGG CAATACCGTC CAAGGCCAGT GCAGGAGGGA GGGCCCCGGC    52980
```

```
CTCACACAAA CTCGGTGAAG TCCTCCACCG AGGAGATGAG GCGCTTCCGC TGGCCCACCT    53040

CATAGCCAGG TGTGGGCTCG GCTGGAGTCT GTGCAGGGGC TTTGCTATGG ACGGAGGGT    53100

GCACCAGAGG TAGGCTGGGG TTGGAGTAGG CGGCTTCCTC GCAGATCTGA AGGCAGAGGC    53160

GGCTTGGGCA GTAAGTCTGG GAGGCGTGGC AACCGCTCTG CCCACACACC CGCCCCACAG    53220

CTTGGGCAGC CAGCACACCC CGCCTGAGGG AGCCCCATAT TCCCTACCCG CTGGCGGAGC    53280

GCTTGATGTG GCGGAGCGGG CAATCCACTT GGAGGGGTAG ATATCGGTGG GGTTGGAGCG    53340

GCTATGATGC ACCTGTGAGG CCATCTGGGG ACGTAGGCAG GGGGTGAGCT CACTATCAGG    53400

TGGCACCTGG GCCTGTCCCA CCAGCTCACG CCTGGACCCA CCCCCACTCA CATTTGCGTG    53460

CAGGGCCATC TGGCGGGCCA CGAAGGGCAG GTTGCGGTCA GACACGATCT TGGCCACGCT    53520

GGTGTCCACA AGGCCCTCCA TGTCTGGGGA GACTTGGTGG TCACGCCAGG CCCAGGG      53577
```

(2) INFORMATION FOR SEQ ID NO:2:

(i) SEQUENCE CHARACTERISTICS:
        (A) LENGTH: 53526 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
TGTAAACTTT TTGAGACAGC ATCTCACCCT GTTCCCCAGG CTGGAGTGCA GTGGTGTGAT      60

CATGGCTCAC TGCAGCGTCA ACCTCCTGGG TCTACTTGAT CTGTAAACTT CGAGGGAAGG     120

TGTAATAAAC CCTCCTGCAA TGTCTTTGTT TTTCAAAATC TTTGTATTTC ACAGTTTAGC     180

TTCGTGGGTT GATGTTCTAT TTTGTTTTTG TGTGTGTGTG TGTGTGTTTT GTGTTTTTTT     240

TTGAGACACA GTCTTGCTCT TGTTGCCCAG GCTGGAGTGC AATGGTGTGA TCTTGGCTCA     300

CTGCAACTTC CACCTCTTGG GTTCAAGAGA TTCTCCTGCC TCAGCCTTCC GAGTAGCTAG     360

GATTACAGGC GCCGCCACCA CACCCCGCTA ATTTTGTATT TTTAGTAGAG ATGGGGTTTC     420

TCCATATTGG TCAGGCTGGT CTCAAACTCC CGACCTCAGG TGATCCGCCC ACCTCAGCCT     480

CCCAAAATGC TGGGATTACA GGCGTGAGTC ACCGCACCTG GCCAATGTTC TATTTTTGAG     540

AACACAACAG TTCATAATAT ATTCTACATA GACCATACCT GTTATGTGTA GATAAACAGA     600

CTCTTTTCCC ATTTAACACC TTTTGCCTTA GGTTTATTTT TCTGGTATCA ATACTGGCAC     660

ACTTACTTTG TTTGCAGTTT CCTGTCTTTT TTTTTTTTTT TTTTTTTTTT GAGACAGAGT     720

CTCACTCTGT CACCCAGGCT GGAGTGAAGT GGCGGGATCT CGGCTCACTG CAACCTCTAC     780

CTCCTGGGTT CATGCGATTC TCCTGCCTCA GCTTCCCGAA TAGCTGAGAC CACAACTGTG     840

TGCCACCATG CCCAGCCAAT TTTTGTATTT TTAGTAGACA CGGGGTTTCA CCATACTGGC     900

CAGGATGGCT CAATCTCTTG ACCTCGTGAT CCACCTGCCT CCGCCTCCCA AAGTGCTGGG     960

ATTACAGGCA TGAGCCACTG TGCCTGGCCT TTTTTTTTCT TTTTGAGATG GAGTCTCACT    1020

CTGTCACCCA GGCTGGAGTG CAGTGGGGTA ACCTCAGGTC ACTGCGACCT CCGCCTCCCG    1080

GGTTCCAGTG ATTCTCCTGC CTCAGCCTCC CGAGTAGCTG GGATTACAGG CACCCACCAC    1140

CATGCCTGGC TAATTTTTGT ATTTTTAGTA GAGACGGGGT TTTGCCACGT TGGCCAGGTT    1200

GGTCTCGAAC TCTTGGCCTC ATGTGACCCG CCTGCCTTGG CCTCCCAAAG TGCTGGGATT    1260

ACAGGTGTGA GCCACTGTGC CTGGCCTGGC TTTCTTGTTT CTTTTCTCCT CTTCTAGTTT    1320

CCCCCTTTTA GGCTAACAAT TATTCACTGT TAATAAAAAC CCTCAGGTCT GTATTTTATC    1380
```

```
AAGAAACATT TCCCTCACGT CTTCTTCCCT GAACCAAACA AGATCTCTGG CACATTTTAT    1440

TTGCTCTGTC TCACCACATG GATTTTGTTT TTTTGTTTCT TTGTTTTTTG AGATGGAGTC    1500

TCACTCTTGT TGCCCAGGCT GGAGTGCCAT GGCACAATCT CAGCTCACTG CAACCTCCAC    1560

CTCCTGGGTT CAAGCGATTC TCCTGTCTCA GCCTCCTGAG TAGCTGGGAT TACAGGCGCG    1620

TGGCACCACC CCCAGCTAAT TTTTGTATTT TTAGTAGAGA CGGGGTTTCA CCATGTTGGT    1680

CAGGCTGGTC TCGAACTCCT GACCTTGTGA TCTGCCCACC TTGGCCTCCC AAAGTGCTGG    1740

GATTACAGGC ATGAGCCACC ACGCCCGGCC CCCATGGTTT TTCAAATAGT TTAGAATTTC    1800

ATTTCCAGGT AACTAATTTG CTTCTTTAAA CATATGTCTT TTCTATTTAA GAAATCCTTT    1860

CTAAACAATT GCATTTTATT CCACAACCGC CTTCAAACAA TCATTGAGAC TTGGTTAATC    1920

TGTTTTGCTC ATTTGGCAGC AGTTTCTTGT GGCTGTTTCT TCCCTCCACT GGAGTCCTTG    1980

AATCTTAAGT CTGTCATTTG ACTGCAATTA AAAGCTGGGT TTGGAATACA ATCGCAGCCT    2040

TACCATCCAC CTGCTGTGTG ACCTGGTAAA TTTCTTTTTT TTTTTTTGAG ACGGAGTCTT    2100

GCTCTGTTGC CCAGGCTGGA GTGCAGTGGC ACAACCTCTG CCTCCCAGGT TCAAGCGATT    2160

CTACTGCCTC AGGCTCCCTA GTAGCTGGGA TTATAGGTGC CTGCCACCAT GCCCAGCTGA    2220

TTTTTGTATT TTTAGTAGAG ATGAGGTTTC ACCATGTTGG CTAGGCTGGT CTCGAACTTC    2280

TGATCTTGTG ATCTGCCCGC CTCGGCCTCC CAAAGTGCTG GGATTACAGG CATGAGCCAC    2340

CACTCCCAGC CAGTTCTTTT TTTCTTTTTT CCATTTTTTT TTTTTTCGAG ACAGGATCTT    2400

ACTCTTTTGC CCAGGCGGGA GTGCAGTGGC ACAATCACGG CTCAGCGCAG CCACTGCCTA    2460

CTGGGCTCAC ACGCTCCTCC GGCCTCAGCC TCTCGAGTAC CTGGGACTAC AAGCGTGAGC    2520

CAGTTTGGCT AATTTTGGCT AATTTTTGTA GAAACGGGGT CTCGCCATGT TGGCCAGGCT    2580

GGTCTCCAAC TCCTGGACTC AAGGGATCCA CCTTCCTCCC CCTCTCAAAG TTCTGGGATT    2640

ACCGGAGTGA GCCACTGTGC CCTGCTGGCA AATTTCTTAA ACTGTCTGTG CCTCAGTGAC    2700

CTCATTTAAT AAAGGGAATA ATTGTAGCAC ACTTTTTCTA GAGCTGTGAA GATTCAATGG    2760

AATAAATAAG GCAATAAATG AATGGATGGG GAATGAAGGA TGTGGGTTTC CTCCCTCTTG    2820

TCTTTCAATA AGCTCTCACC ATCAACCTCC CATTGCCTGT TCTCTCTCTT CCCCCTCTCT    2880

CCCTCTGTCT CTCTCTCAGC CAGGAAACCT GGGGTAGGGA GGCTTGGAGC CAGCGGGTGC    2940

GTCGGGAGGC TGCGGGTACT GACTCGGGCC GCGCACGGAG ATCGCGGGAG AAGGATCCAC    3000

AACCGCGGAA GAAGGATCAG GGTGGAGCCT GTGGCTGCTG CAGGAGGAGG AACCCGCCGC    3060

CTGGCCCACA CCACAGGAGA AGGGCGGAGC AGATGGCACC CTGCCCACCG CTTCCCGCCC    3120

ACGCACTTTA GCCTGCAGCG GGGCGGAGCG TGAAAAATAG CTCGTGCTCC TCGGCCGACT    3180

CTGCAGTGCG ACGGCGGTGC TTCCAGACGC TCCGCCCCAC GTCGCATGCG CCCCGGGAAC    3240

GCGTGGGGCG GAGCTTCCGG AGGCCCCGCC CTGCTGCCGA CCCTGTGGAG CGGAGGGTGA    3300

AGCCTCCGGA TGCCAGTCCC TCATCGCTGG CCCGGTCGCG CTGTGGCGAA GGGGGCGGAG    3360

CCTGCACCCG CCCCGCCCCC CCTCGCCCCG TCCGCCCCGC GCCGCGCGGG GAGGAGGAGG    3420

AGGAGCCGCG GCGGGCCCCG CACTGCAGCG CCAGCGTCCG AGCGGGCGGC CGAGCTCCCG    3480

GAGCGGCCTG GCCCCGAGCC CCGAGCGGGC GTCGCTCAGC AGCAGGTCGC GGCCGCAGCC    3540

CCATCCAGCC CGCGCCCGCC ATGCCGTCCG CGGGCCCCGC CTGAGCTGCG GCCTCCGCGC    3600

GCGGGCGGGC CTGGGGACGG CGGGGCCATG CGCGCGCTGC CCTAACGATG CCGCCCGCCC    3660

CGCCCGCCCG CCTGGCGCTG GCCCTGGGCC TGGGCCTGTG GCTCGGGGCG CTGGCGGGGG    3720
```

```
GCCCCGGGCG CGGCTGCGGG CCCTGCGAGC CCCCCTGCCT CTGCGGCCCA GCGCCCGGCG      3780

CCGCCTGCCG CGTCAACTGC TCGGGCCGCG GGCTGCGGAC GCTCGGTCCC GCGCTGCGCA      3840

TCCCCGCGGA CGCCACAGCG CTGTGAGTAG CGGGCCCAGC GGCACCCGGG AGAGGCCGCG      3900

GGACGGGCGG GCGTGGGCGG GTTCCCTGGC CCGGGACGGG AAGCAGGACG CGGGCCAGGA      3960

CGCTCCCAGG GGCGAGGCTC CGGCGCGGCA CGGCGGGCCC TGCTAAATAA GGAACGCCTG      4020

GAGCCGCGGT TGGCACGGCC CCGGGGAGCC GAAAAACCCC GGGTCTGGAG ACAGACGTCC      4080

CACCCGGGGG CTCTGCAGAC GCCAGCGGGG GCGGGGCGCG GAGGCCGCGC TCAGCTGGGA      4140

GGACAAACAG TCGCTAATTG GAGAGGAATT GGGATGCGGC CTGGGCTGC GGGGTACCCG       4200

GAGAGGTGGG GATGGCTGTA GGGGGCGGCA GGGAAGAGTT CCAGGAGGTG TCTGGAAAAG      4260

GATTTGATGG ATGTGCAAGA ATTGGGCTGA TGCTTAGGAA GGGGCGATGA GGTGGGTCCA      4320

GAAGAAGGGG GGTGAACGGT GTGAGCAAAG ACCGTGAGGC TGGAGGCTGG CCACGGGAGG      4380

TGTGAGGGGT AGGGGCAGGG TGGGAGGTGG GCTCGCGGGT GGGCTGGGGT CATGAAGGGC      4440

CTCAGGCGCT CTGCTATTGG GTTCCAAGGC TATCCTGAGA ACAGGGGTGA GGGGGGATTG      4500

CCGTGGGGGG TTAAAGCCTT GTCATGTTCG CTTTCGGGAG ATAAAAACAA CAGGTGGCCT      4560

TTATGGAGAC GCTGCCCAGA GCCAGGTCTG TGCCAGGCTC CTGTTGGGGG TCGTCATGCG      4620

GAATCCTGAC TCTGACCATC CGAGGCATAG GGACCGTGGA GATTTGCATT TCACAGATGA      4680

GGAAACAGGT TTGGAGAGGT GACACGACCT GTCCCAGGCA TCACAGCCGG GATGTGCATA      4740

GCAGGGGTTT GGAACTATGA GGTGCCCAGG ACCCAGGGTT GGATTGAAAA GGGCGGAGGG      4800

GACTAAGATA AGCAGACAGT TGTCCCCAGC GCTGGGGAGA GTCTTGGGAC CAGTCTGATG      4860

CCTTGTATTT CCCAGGCTCC AGGCTCCTCG CCGGGACAGT GTCTCCTTGG GTGCGTGCTG      4920

GATCCCTGGG GGACGTGGCA CATCCCCAGG CTTGCTAAAC ATTGGGTGGG TTCTGGCATT      4980

TGGTTTTGTA ACGTTTCTGG GTCACTCCCG CCTGTGCCA CCCTTCCTTA GGGGAGCCGT       5040

GTGTCCTTGG GGCTTTGCTG GGTGGTCTCG AGGGTGGGAG AAGAATGGGT TCTCCTGGAC      5100

CAATGGAGCC CGTGCCCCTC GGGGCCACAT TGCTCCTGCG CTCCCTGACT GCGGACGCGT      5160

GTGTCTCGCG GCTGTCTCTG TGGAGATGGC CTCCTCCTGC CTGGCAACAG CACCCACAGA      5220

ATTGCATCAG ACCTACCCCA CCCGTTGTTT GTGATGCTGT AGCTGAGGGC TCCTCTGTCT      5280

GCCAGGCCGG TCACTGGGGA CTCTGTCCAG GGCCTGGTGG TTCCTGCTTC CCAGCACCTG      5340

ATGGTGTCCA TGAGAGCAGC CCCTCAGGAG CTGTCCGGGA GAGAAGGGCG CTGGTGGCTG      5400

CTGAGCGGAG AGCAAGGCCC GTGTTCTCCA GGCCCTTGGC ACAGCAGTGG AGCCCCCGCC      5460

CCTGCCTTGT GTTGTCCTCT TAGGCTCTGG TCCTGGGGTT TGGAGGAGGG GGACCCTGGG      5520

AGTTGGTGGC CTGTCCCAGC CTGAGCTGGC AAGATTCCGA ATGCCAGGCC CCCCAAGTGT      5580

GCAACAGGGC ACAGGGTGAC CTCATGTGGG CAGGTGGGTG CTGTTCTGTA CACACCTGGG      5640

GCCGCCGCTG GGAGAGTTCT GGAAGGTGGG GTGAGGGGAC CCATGGCAAA CTAGGGCCTT      5700

AGGAAGGATG TGAAGGCCCT GGCTGGCCCC CCAGGCCACC CTCTGTGCTG TGGGCAGCC      5760

CAGCCATTTT GCTGTCTACC CTGCAAACTC CTCCTCGGGG AGACGGCTGG GTTTTCCCCA      5820

GGGAAGAGGG GTCAAGCTGG GAGAGGTGAA GGACACAGAT CACAGCTGCT GGCAGGTGTT      5880

CAAGGGTCCA AGAGCGTTGC TGTCTGGGTG TCACCAGTAG CCTTCCTGGG GGGCTCACGC      5940

AGGTGCCTCT CCACTTGTGG CTCCCTGGCT GCTGAAGCTC AGCAGGGACA GCTGTGTCCA      6000

GTTCCAGGTG GAGGACAGCC GGGGCTTCTG AGGCCACAGC CTGCCTTGGG TTAATGATGC      6060

TGCCGAGAGG TGGTGGCTTT TGGAAAAGAT GGCGTACTGC AAAACGTGCT GCTCTGCGTG      6120
```

-continued

```
GCTCGAAGCT TCGTGGGGAG ACGTGGGCAG AGCCGTGGCT GACTCACAGA CCCCCCACCC    6180

CAGAGCCTGC CCTGCCCTCC CTGCCCCGAC CCTTCTCCCT CCTGACCCAT GTGTTTTTTT    6240

TTTTTTTTTT TTTTTTTGAG ACAGAGTTCA CTCTTGTTGC CAAGGCTGGA GTGCAATGGC    6300

ACGATCTCGG CTCATGGCAA CCTCCGCCTC CTGGGTTCAA GCGCTTTTTC CTGCCTCAGC    6360

CTCCCGAGTA GCTGGGATTA CAGGCGTGCA CCACCATGCC TGGCTAATTT TGTATTTTTA    6420

GTAGAGACAG GGTTTCTCCA TATTGGTCAG GCTGGTCTTG AACTCCTGAC CTCAGATGAT    6480

CCGCCCGCCT CGGCCTCCCA AAGTGCTGGG ATTACAGGCA TGAGCCACCA CGCCCAGCCC    6540

TGACCCATGT TTTGAACCAA ATTCCAGCCA CCCTTTTATC TGCAAGCATT TTGGAGGGCA    6600

TCGCAATACT GCAGACCCAC CTAACACAAC AGACAGTTCC TTCATGCCAC CGAAGGCCTG    6660

GTGTGTTCAC ATTTTTGGTT TAATAGTTTG AATTAAGAGC CAAATAAGGT CCACACACTG    6720

CAATTAGTTG ATGTCTTTTT TTTTTTCTTT TTTTTTTTTT TTTTGAGACG GAGTCTTGCT    6780

CTTGTCTCCA GGCCGCAGTG CAGTGGCATG ATCTCAGCTC ACCGCAACCT CCGACTCCCT    6840

GGTTCAAGCG ATTCTCCTGC CTCAGCCTCC CGAGTACCTG GTAGCTGGGT TTACAGGCAT    6900

GCACCACCGT GCCCAGCTAA TTTTTGTATT TTTAGTAGAG ACGGGGTTTT ACTGTGTTGG    6960

CCAGGATGGT CTCGATCTCC TGACCTCGTG ATCTGCCCAC CTCGGCCTCC CAAAGTGCTG    7020

GGATTACAGG CGTGAGCCAC CGCACCCGGC CAATGTCTTT TAAAAATATA TACTTTTTTT    7080

TTTTTTTTGA GACGGAGTTT CGCTCTTGTT GCCCAGGCTG GAGTGCAGTG GCGCGATCTC    7140

ACCTCACGGC AACCTCCGCC TCCCGGGTTC AAGTGATTCT CCTGCCTCAG CCTCTCCAGT    7200

AGCTGGGATT ACAGGCATGT GCCACCATGC CTGGCTAATT TTGTATTTTT AGGAGAGACG    7260

GGGTTTCTCC ACGTTGGTCA GGCTGGTCTC AAACTCCTGA CCTCAGGTGA TCCGCCTGCC    7320

TTGGCCTCCC AAAGTGTTGG GATTACAGGT GTGAGCCAAC GCGCCCAGAC AAAAATATAT    7380

GTGTGTCTTT AAGGCTGGTC AAGCAAAGCA GTAGGACTGG AGAAAGAATG AAGAATTCTA    7440

CCTGGCTGTG ATCAATTCGT TGTGAACACC ACTGTGCTTG GACCAGCTAG CTGATGTCTT    7500

TTGTTTTGTT TTGTTTGAGA CGGAGTCTGG CTCTGTCACC CAGGCTGGAG GACAATGGTG    7560

TGATCTCGGC TCACTGCAGC CTCCATCTCC CGGGTTCAAG CGATTCTCCT GCCTCAGCCT    7620

CCTGAGTAGC TGGGATTAGA GGCGCGCGCC ACCACGCCCG GCTAATTTTT AAAAATATTT    7680

TTAGTAGAGA TGGGGTTTCA CCATGTTGGT CAGGCTGGTC TTGAACTCTT GGCCTTAGGT    7740

GATCTGCTTG CCTCGGCCTC CCAAAGTGCT GGGATTACAG GTGTGAGTGA TGTATTTTAT    7800

TTATTTATTT ATTTATTTAT TTTTATTATT TGAGATGGAG TCTCACTCTG TTGCCCAGGC    7860

TGGAGTGCAG CAGTGCCATC TCAGCTCACT GCAAGCTCCG CCTCCTGGGT TCACGCCATT    7920

CTCCTGCCTC AGCCTCCTGA GTAGCCTGGA CTGGTGCCCG CCACCATGCC CAGCTAATTT    7980

TTTGTATTTT TAGTAGAGAC GGGGTTTCAC CGTGTTAGCC AGGATGGTCT GGATCTCCTG    8040

ACCTCGTGAT CCTCCCGCCT CAGCCTCCCA AAGTGCTGGG ATTACAGGCT TGAGCCACCG    8100

CCTGTCTTTT AAATGTCCGA TGATGTCTAG GAGCTTCCCT TCCTCTCTTT TTCCTTGTGC    8160

AATTTGTTGA AGAAACTGGC TCCTGCAGCC TGGATTTCTC GCTGTGTCTT GGGGGTGCCA    8220

CCTCCATGGT GTCACCTCCG TGGTGCTGTG AGTGTGTGCT TTGTGTTTCT TGTAAATTGG    8280

TCGTTGGAGC CGACATCCCA TTGTCCCAGA GGTTGTCCTG GCTGGCACTG GCCTAGGTGT    8340

AGATGTCATC AGCTCAGGGC CCCCTGCTCT AAAGGCCACT TCTGGTGCTG GTTGCCACTC    8400

ACCCTGGCTG GGGGTCACCT GGGTCTGCTG CTGTCTCGCA AATGCTGGGG TCCAGGACTG    8460
```

```
GGCACATCGA GGGACTTGGT AGGTGCTTGG TTCACTGATG TAAAATATAG GAGCACCCGG    8520

GGCCTTGCCC TTTCCCACCT GCATCCCTGA ATGACAGGAG AGTGTGGGAG AGTGTAGGGA    8580

CAGCAGGCGC AGACCCCGGG GCCCCTGCCT GGGATTGGCG TCGGGAAGA CAGGCATTCT     8640

GGAGCGACCC CTAGGCCTGA TGCCTTAGAG CGCAACTGCC AGAGACACAG CTTCCTTGGG    8700

GGGCTGGCCA GGCCACGGAG GGGCCCTGGC TCCCATTTCT GGTCCCTGGA TCCTGAGAGC    8760

GAGGACTAGG GATTGTCACC AAGGCCTCCA TGAGCCCTCA GCAGAAGGAG GGCCACCCTC    8820

GAGGGCTCCG TTATCACTGG AGCCCGCGTT CAACCAACAC GCAGATGATT CTCCAAGGAC    8880

AGAGATGGAT GATGGGAGG GGGCTGGCCT GGAAGGACCC CCAGTGCAGG TGACATTGAA     8940

GCCAGGTTTC AAAGCTCCCA CAGGGAGCTG CCCAGAGAGA GTCCCAAGG GGCAAGGTGA     9000

CTCGGGGGCA GGGGTAGGGC CTCTGTCAGG AGAGCCTAGG AGAGGCCTGT GTCTTCTAGG    9060

AAGAGCCCTG GCAGCCGAGC GGAGGCAGTG GTGAGGACCT GCATCCTGCA TGTCCAGCTG    9120

GCCTCACCCG GGGTCCCTGA GCCGGGTCTT ACGTGGCTCC CGCACTCGGG CGTTCAGAAC    9180

GTGCCTGCGT GAGAAACGGT AGTTTCTTTA TTAGACGCGG ATGCAAACTC GCCAAACTTG    9240

TGGACAAAAA TGTGGACAAG AAGTCACACG CTCACTCCTG TACGCGATTG CCGGCAGGGG    9300

TGGGGGAAGG GATGGGGAGG CTTTGGTTGT GTCTGCAGCA GTTGGGAATG TGGGGCACCC    9360

GAGCTCCCAC TGCAGAGGCG ACTGTGGAGA CAGAGAGCAC CTGCAGGTCA TCCATGCAGT    9420

ATCGGCTTGC ATCCAGATCA TACAGGGAAC ACTATGATTC AACAACAGAC AGGGACCCCG    9480

TTTAAACATG GACAAGGGGT CACTCACGCC TGGAATCCCA GCAGTTTGGG AGGCCAGGGT    9540

GGGTGGATCG CTTGAGCCCA GGAGTTTGAC ACCAGCCTGG GCAACAGGGT GAGACCCCGG    9600

TCTCTAAAAA ATAAAAGAAC ATTGGCCGGG CGTGGTGGTA TGCATCTGTG GTCCCAGCTA    9660

TTCAGGAGAC TGAGGTGGGA CATCACTTGA GCCGAGGAGG TCAAGGCTGC AGTGAGCTGT    9720

GATCACACCA CTGCACTCCA GGCTGGGTCA CAGAGCAAGA CCCTGTCTCA AAAAAAAAAA    9780

AAAAAAAAAA AAAAAATCAC AGGATCTGAA CAGAGATTTC TCCAAAGAAG ACGCACAGAT    9840

GGCCAACAGC GTGTGAGAAG ATGGTCGGCC TCATTAGTCA TGAGGGAAAC GTAAATCAAA    9900

ACCACTGTCC AGCCGGGCGC GGTGCCTCAC GCCTGTAATC CCAGCACTTT AGGAGAGCAG    9960

ATGGCTTGAG GCCAGGAGTT TGAGGCCAGC CTGGGCAACA TAGCGAGACC AATAAATAGA   10020

TATTAGTGGT GGCGCCTGTA GTCCCAGCTA GTTGGGAGGC TGAGGGGGA GGATTCCCTG    10080

AGTCTATGAG GTTGAGACTG CAGTTAGCTG TGATGGTGCC ACTGCACTCC AGCCTGGGCG   10140

ACTAGGAAAC GGTCTTTAAA AAAAAAAAAA AAAAACAGGG TGGGCGCGGT GGTTCACGCC   10200

TGTAATCTCA GCACTTTGGG AGGCCAAGGT GGGGGGATCA CAAGGTCAGG AGTTTGTGAC   10260

CAGCCTGACC AACATGGTGA AACCCCGTTC TACTAAAAAT ACAAAAATTA GCGAGGTGTG   10320

GTCGTGGGCG CCTGTAATCC CAGCTAATTA GGAGGCTGAG GCAGGAGAAT CACTTGAACC   10380

CGGGAGGCGG AGGTTGCAGT GAGCCAATAT CACACCACTG CACTCTAGCC TGGTCAACAG   10440

AGCGAGACTC TGTCTCAAAA AAAAAAAATG CTGAGCGTGG TGGCGCATGC CTGTAGTCTC   10500

AGCTACTTTG GGGGCTGAGG CAGGAGAATC GCTTGAACCT GGGAGGCAGA GGTCGCAGTG   10560

AGGCAAGATT GCACCATTGC ACTCCAGCCT GGGAGACAGA GTGAAACTCT GTCTCAAAAA   10620

GAAAAGGTCT AGGAAGAGTC CGCACCCTCT CCCCGCGGTG GCCACGCCGG GCTCCGCGCT   10680

GAGCCCTCTG TGTTCTTGTC TCTCCATACC TCATCACGGC ACCGCAGGGT TGCAGCCACT   10740

CCTGGTCTCA TTTTACACAC CAGGAAATTG AGGCTCTTTG AGAAGCCGTG GTGATGATTT   10800

CATCAGCATG CTCTGGGGCA GACCCCTGCA GCCGCACAGG GTGCCTGGGG CCCACACTAG   10860
```

```
TGCCCTGGTT TATAGACAGA CAGAGGTGGC AGTGGCGCTT CCGAGTCGGG CTGCGATGTG    10920

CTTGCACTCC CCGAGGGGCT GAGGGGCCCT GCGCCCAGGT GCAGCTGCTT GGGTGCTGCC    10980

AGCCCCTCCC ACCTCTCCCT CCCTGCCAGC CCCTCCCACC TCTCCCTCCC TGCCAGCCCC    11040

TCCCACCTCT CCCTCCCTGC CAGCCCCTCC CACCTCTCCC TCCCTGCCAG CCCCTCCCAC    11100

CTCTCCCTCC CTGCCAGCCC CTCCCACCTC TCCCTCCCTG CCAGCCCCTC CCACCTCTCC    11160

CTCCCTGCCA GCCCCTCCCA CCTCTCCCTC CCTCCAGCCC CTCCCACCTC TCCCTCCCTG    11220

CCAGCCCCTC CCACCTCTCC CTCCCTGCCA GCCCCTCCCA CCTCTCCCTC CCTGCCAGCC    11280

CCTCCCACCT CTCCCTCCCT GCCAGCCCCT CCCACCTCTC CCTCCCTGCC AGCCCCTCCC    11340

ACCTCTCCCT CCCTGCCAGC CCCTCCCACC TCTCCCTCCC TGGCTCATCC CTGCTGTGTC    11400

CCTTCTCTCT AGTTTCCTGT TCAGTTTCAG GAAGGAGGCT GGGAACCCAG ATGTAGGGAA    11460

TTTGCGCCCT GGAGTCAGAC CTGGGTTCAC GTCCCAGCGC CTCCACCTCT GGTGTGACCT    11520

TGGTCCAGTC TCTCAGCCTC AGTTTCCTCA CCTGTAAAGT GGGCTCCATG ATTAGATGCA    11580

CCCTGCAGGG CAGTGTAGCA GTGACCTGGC TCAGCCACTG GCAGCCCCAA CAATCATACC    11640

TTGTTAAAGT AGCTCTGTCG GTTCCCTCAG GGGTTCCGGG GGCCCATTCC CCTGTCCTCC    11700

ATGCACTGTG AGACCTGCCC TGCCACAGAG CAGAGTGTAA CAGCCTGAGG GTGAGAGCCA    11760

GACACTGTGC CTGTGCTTAG ACCAGACACT GGACGACGGG AGCCAGTGCA GCCTGGGCGG    11820

GTGGACTCCT ATGGACCCCT CAGCACCCAG CCTCGGTGCC TTCAGCGCAG GGCCGCGTGG    11880

CTGTGGGGGC TCACAAGACC CGGCCCACTC CTGCTTGTGC CTACATCTGG GTGTTTGCCC    11940

ATTGGTGCCT TTTGACGCGT TCTGGTGTGT GTGAGACGTG CGGGGCTGGG AAGTGTTGGC    12000

AGAGCCGCGA GTACCGTCCT CACTCCTTTT GTTCTTTTGA CGTAAGCTGG CGAGTGGCAC    12060

TGCCTGAGTT CCGCTCAGTG CCCGCCCTGA TGTGCGGACC CCGCTGCATT CTTGCTGTTA    12120

GGTGGTGGCG GTGTGCGCTG TCGCTGGTGG GCACCGAGAG TCTTTGGGAG CTTTGGGGAG    12180

GTTGTGCCAA GCCTGAGCCT CGACGTCCCC CTTCCCGGCT TTCTGTTGGC TCTTCTGAGG    12240

CCAGGGCATC TCTATGAGGG CCTCCTGCTG GAGCCGTCTC TGTGGATCTC CTCTGCCATC    12300

CTGGCCCATG AGTGGGTGAT GCGCTGGCCA CCATCTGGTG ACAGTGGCCG GGCACCGCTG    12360

CCAAATGTGG GTCCCGCATC TGCAAGCCCC TCCCTGGGTC CCCTAGGGTA TGGGGTGGTT    12420

CTGCCACTGC CCTCGCTCCC CCACCTTGGG GTGCCTCTCC CCCTGCTCGT GGGGGAGACC    12480

CTGCCTGGGA TCTGCTTTCC AGCAAGGAAT ATACTTTGGA GGGAGACACA CATGTTCTTT    12540

TCTGGAGCTC TGCAGTGGCC ACGGCAGCCC AGCCCGCCAA GCACCCTGGA ATGAAAACAT    12600

CCCGCTGCTG TCTGGGCCTG GCCTGCACTC TGCTGCCTGC GCTCCAGCTG GCTGAGGCCG    12660

GGCACGTCTG CGGGCACAGC AGCGGGGGCG CCACAGTCTC CCTGCAGAGT GAGCGCAGCT    12720

GGAAAATGCA GCTCACGCCC TTTCCCAGAA CACCTCGCTC TTCATGGCTT GGCAGCTGTC    12780

CTTGCCTAGG GGCCAGGGTG CCCAGGCACT GGTGGCAGGA GAAGGGCTAC ATCTGGGGCT    12840

GAGGCGGGCT GGGTCCTTTT CTCCCTGCAG CTCCCGAGGC CAGCCCTGG CCCAGCCTGG     12900

CATTCCTGAC CTTAGCAGCG CCATGATCTG AAGACAGGCT GGCTTCTGTG AGGCCACCTC    12960

AGAAAGGGCT TTGTGCCCAG GCAGAGGCGG AAGCCAGCTC TTCCTTCTGG TTGAGGCAGG    13020

AATGAGGCCA GCGCTGGGCA AGCCCATGCC CAGGGAACGT CACAGCTGTG GGAGTACAGG    13080

GGCTCCGGGT TCTGAGCCCG TCCACTGTGC ATCGTGGCCC TGGCCTCAGG ATGGCTCGTA    13140

CCATCATTGG CTGTGCCCAC AGCCGAGTGG GTGATGGGAT TCCGGCTGCC CCGCTGGATC    13200
```

```
TGTGCTGCTG CCCTCTCCAG GGCACTGCTG TGCCCGCACA GCCGGGCGCA GATGGCCAGT    13260

TTGCTTGCCC CCCCCCCCAC CATCCTCTTC CTACCTTGGC TTCCTCCATT GACACACTGG    13320

ACCCTGCTGG CTGCCCGGGG AGGTGTTTGG GGGATGGTGT TGGGGGAGGA GGAGGGCCCC    13380

TTGAGCCTCA GTGTGCCCAT CAGGAGCGTA AGGTCAGTGC AGCACCTGCC CACACAGGCT    13440

GTGAAGGGTG GGAGTGGAGA GGGATGCAAG GGGGTCACAA CGCCTGGCTC CATGTCAGCT    13500

GCGTGCAGGG GCACCAGGAG CCGGCCCTCA TTCTCCCCTT GAACTGGAAG GGTGGCCCCG    13560

ACCCCAGCGG CAGGTAGCAT ACGTATGAAG CGCTCTCCTT CCTACACCCC ACAGGTGGGC    13620

TCGTCTCCAG ACGGCCCTTT TGAGCTGGC  TGTGTTTTTC CATCTGTGTA GGCAAGGACA    13680

TCGCAGACTC CCCTTTCTCA TCTCCCTCGT TCAGCCTCCG AGGCCGGAGT CTCCATCCCT    13740

GTGCCTGCCT GTGGGTCCCG GGAGGACCTG AGGCTGCCCA TGTCACCCCC GGCATCTCAT    13800

CCTGGGACA  GTTCAGCCGT GGGAGGGATC TGTAAGGACA GAATGCCGCT GAGCCTGGGG    13860

CTCCCCAGCT AGTCTCACAC CCCGTGTCTG GGACCCAGAG ACCCTCGTGC AGGGCTCTGT    13920

TGCTTGGGGC CTGGCAGCCT CGTCCTGTAT CAGAGGCTGC CACCCCCACC CCTCGTGGGG    13980

CCAGGGTTGT GGCCGGCCTC CCTGGCCCTC CCCATGGAAG TGGTAGGCGG AGCCAGCAGC    14040

CATCTGCCCA GCCGGGGCT  GCACTGTTTT TTTTCAAATG AGCACCGTCC CAAACTGCAG    14100

CCCGTTAATT TAAACAGGAT CATTTCCGGC CCTGGAAGCC GCCTCACTCT CCTTAAATAG    14160

AAAGGAGCAC AGCGCAGAGG GAAACAGATG AGGTCATGGC TCGGCTGGCC CAGCGAGGAA    14220

GGGGCCGCAG TGGGGTGGC  ACTGCCGCCT GTCCCTGTC  CTCTCCAGCG CCCACACTGC    14280

AGCCCATTTC CTCACCCTGG GCCTGCTCTC GGGAGGGACG GGCCTGGGGG TCCTCTTGCT    14340

GGGCGGAGGG GAACCAGCTC CTCCAGGAGA GGACGGGGCC TGGCAGGGGG CATGGGGCCT    14400

CCCTGGGTCT GGCGTCCTGT CCTGCCCCTG CCGAGGGAGG AGCGGTTACA TAAGCTCCGC    14460

AGGCGGCCCC TCCGAGCCGG TCCCCCCAGC CCAGTTTCCA GTGAGGCGGC CAGCGCGGGC    14520

GGGGGTGCCG GGCCTGGCGC ACACCCGCTG CTGACCACAC GTGTCTGGAA TGTGCAGATG    14580

TTTCTTTGGG GGCTCCGTCC GGCCCCCAGA CCCCACTCAG CATCTGGTCT GGGGAGTGGG    14640

CGCCTGGGGC ACTCAGCTCT GAGTGTGAGA CTCTGAGGCA GGTCTGGTTT GTCTGGGGCC    14700

ATTCCCTCTG CTGTGGATTG GGAGGGCCCC GGGAGCTGCC CCACACCCAG GGAAGTTCTC    14760

CTCAGTCCCA CTGTTGCATT CCCCGACCCC GGCTCCCCCG GCCCAGGAGC GCCTGTGGGG    14820

CAGAAGGCCC AGCCCCAAGA CTTCCCGGCC CTGCCAGCCT CAGGCTTCAC CCACCCTCGC    14880

GCCAACTGTG GGCAGAGCCC AGGGGGAGGG CAGGAGAGCC AGCGCCTGGC TGGGAACACC    14940

CCTGAGGGGC CGAGGCTCCA GGGCGAGGGG GCCCGACCTG GGGTTCACAC GCCCGGGTGG    15000

CGGGCAGACC CGCTGCAGCA TGAGACACGT GTCAGCTACC TCGGGCCGGC AGGCTGGCCC    15060

TGCTGCCCAC AGCCCTGGGA CGTGGCCCCA CCTGTGACGG GTGTGGAGGG GCAGCCTCCA    15120

GGCCTGGCCA CACCCTCTGC TGTTGCTGCT CCTGCTCCAG GATTGGCAAG GGTGCTGGGA    15180

AGGGGTGAAG ACCCGTACTG TGGCCACACA CCTGGGACTT CCTTCTCCAC CCAGTGGTGC    15240

CCCAGCAGCC GCTAAGGAGC CCGCTGGGTC CCACGCTAGG ATGGTCCTAA CTCCTCCCGC    15300

CTTCCAGATC GGACGCTCGG CGCTGGGGAC CCCTTGTGTC CCGGGGCTGG GGCACCGTCC    15360

TGCCCCCATG GGGGTGTACT CCTCCCGACA AGCTTGGCTT CAGCTTCCCT GGGAGCACAT    15420

CCTGGCCCTC GGGCACCCAT CAGGCTGTCC CTGTGCACCT GGCTCCCACC CTTCCAGCTC    15480

ATAGCAGGAA CTGGGGTGAG GAGTGCGTGG GGCAGCAAGG GCCTGGGACC CCAGAGGACC    15540

CTGCACTCTG CTCTGTGCTC TTGCCTGGGC TTAGGGCCGC TCGGTGGTCC TGCTGCCAGA    15600
```

```
TGCCTGGGCC CTGCTGTGTC CCCCATCCTT GCAGGGAACC AGAACGTGGG GGCAGGGCAT   15660

CAGACAGCGG CGATGATGTC ACCTGGCGGG TGCAGAGGAA GCCCGAGGGG CGGGGTGGGG   15720

GGGCTGGCGC GAGGCTGCCT GGCTAGGCCT TGGCGTTCCC CCAGAACGGC GATGGCAAAA   15780

GCAGATGGAG ACGTGAAAAA GTACGGGAGC AAGCGAGGTG AGGACTCCAC GGGGACCCCT   15840

GTGCTGTTCC CTGTCCCTGA AGCCCACACC TGAGTCCTGC CCAGGGCAGA TGCTTCCACA   15900

CCCAGGGGGC ACCTGAGTCC TACCCAGGGC AGACGCTTCC ACACCCTGGG GGCTGGGGGA   15960

CTGCACCTGG CTCCTGTCTG GGCCCCAGCT TCATTCCACT GCCCTGGGCC CTGGGAGCTC   16020

GGCCGAGCGG GGTCCCCAAG ACCTTGCTGC ATTTCTGGGC CTTGGGCTGG GGTGAGGGCC   16080

GGGAGAAGGA GCCAGCCTGG AGCCTGGCAC GCAGGGAGTG CATGGCCAGA ACCGGTGACA   16140

GGCAGGGCTG CCTGCTGGCG TGGAAGAAGT GTCCATGGCA CCCCCAGGCC TGGTTCACAG   16200

TGGGATGGGC GGGGAGCCGG GGGGCTCTGG GGTCCTCGGC TGACCTGCCC CCACCCCTGC   16260

CCTGGCTTGT CAGCTCCCAG CAGCAGCCAC TCTTGATGGA TTTTCCAGAA AATGAGGTGT   16320

GGCCAAACAT CTTCAGGCTT TTCCTTCTTT CCTTTCTCCC GTGGCCTGGG TGGGAGCTGC   16380

TCCCCATGCC TGGGGCAGG TGCGAGAGCC TGTGCCCCTC CCTGGGGCAG TTTCACAGCT   16440

GTGTCCCTTC CAGGGGCCT GCCTGTGTTC ACCGTGGCCT CTGCAGCACC TCTCGCCCCT   16500

TAGGGCTCCT GCGCCTCGGG TCCCGGTGCC TCATTTCTCC CTAAAGCATT GGTTCTGCTG   16560

CCGCCGCAGC CGCTGGAAAG TCCCTCCTCA GGTCTAACTG CAGTTCCTCA CGGCACAGTG   16620

TTCCCCCTCG GGCATGGTGC TTGGGCAGTG GGTGTGAGTC CAGCTGCCTC ACCCTGTCTC   16680

GAGAATGGCC TCTTGCTGGT CTCCCAGCCA CCACCCTGTC CCACCCCACG GCGGGGATGG   16740

TGTGGATGCC TAGCAGCGCG GCTGTGGGCC CACCCATCCT TATGGGCAGT GGGGAGCACC   16800

TCAGCCCGTG TCCCTACCTT GGTGTAGAGG AGGGGACGGC AGAGAAGCAG GGTTCAGTTA   16860

GGGGGGAAGT GGTGGCCCTG CCGGAGGGGC CGTTCCCTGT GTGCCTGGCC CCCAGATCCT   16920

CTCCCCTCCC GGAGCCCAGG GCACAGGCAT AGGCTCTCTG AGTGTCCCAC AGCCCCTGGG   16980

GGAAGGGAAC TGCACCCCCA ACCGTGCCCT CCATCCGCAG ATGGAACGAG AAGCTCCGGG   17040

AGCCAGTGCC CAGCGTCTCA TCTGTCTGGG CACCCAGCCC AGGTGAGGGC CTGGCTCCAC   17100

CGTCCGTGGC TGGTGCTGCT TCCTGGCACG GAGAAGGCCT CGGCTGCTCT GTCCCCTCAG   17160

CTGGGGTGGC CTCTGGTCCC CTTCTTTGTT GGTTCCCTTC TCAAGCTCTT GCCCTGGCCC   17220

CGGGCCCCAC CGGGCAGCCT GTGTGTGCGT CTCTCCTGCG CCGGGTAGGC TCCTGTGGGA   17280

GCGGAGCTCC GGTGGGAGGA GCAGGGCTGG AGGCTGGCAG GGGCTGGGCG GGTGTTCAGG   17340

GATGGAGGCC GCCCCGGCTT GGGGCTGGCT GCCGGGTGGT CATTGCTGGG AAGAGCAAGT   17400

CTAGGCGGAG GCACCTGCTG GGTCACTCGT GGGGAGGGTG ACACCTGGGG AAGTAGAGGC   17460

CCGTGGCAGG AGGTGAGGCC TCGGGGTCCT GGGGAGCAGG GGGGTGGTGT GCAGACCTGC   17520

GGAGCCATAG TCCTGTGCCA GGAGCACTAC TGGGAGTGCG TGGGACCAGG AGGGGTGCCC   17580

AGGGTGGGCG GCAGAGTGAC CCCCGAGGTG CTTGAGGCCG AGGGGAGGTG GAGTTCTCGG   17640

TTTGCCCCAG CTCTCTGTCT ACTCACCTCC GCATCACCAG CTCCAGGACC TGGTTTGTAA   17700

CTCGGGCAGC TCTGAAAAGA GAGACATGCT GCCGCCCTGT GGTTTCTGTT GCTTTTTCTT   17760

CACTGACTAC TGACATGGGA TGTTTTTCCT ACGGCTGTGA CCAATTGTGC TTCTTCTAAT   17820

TGCCTGGTTT TTCTTTTTTT GTTTTTGGAG TTTTCTCTTT CTTTCCTCCC TCCCTCTCAC   17880

CCTCCATCCT TTTTTTTTTT ATTTTTATTT TTTGAGATGG AGCTTCACTC TTGCAGGATG   17940
```

```
GGGTGCTGGA GTGCAGGGGT GCGATCTCAG CTCACTGCAA CCTCTGCCTC GCGGGTTCAA  18000

GTGATTCTCC TGCCTAAGCC TCCTGAGTAG CTGGAATTAC AGGTGCTTGC CACCACGCCC  18060

GACTAATTCT GTAGTTTTGG TAGAGACAGG GTGTCTCCGT GTTGGTCGGT CTGGTCTTGA  18120

ACTCCTGACC TCAGGTGATG CGCCCGCCTC AGCCTCCCAA AGTGCTGGGA TTACAGGCAG  18180

GAGCCATTGC ACCCGGCTCT TTCCCCTTCT CCTTTTCTTC TCTCTCTCCT CCCTTTCTTT  18240

CTTTTCTTTT CTTTTTTTTT TCTTTTGAGA TGGAGTCTCG CTCTGTCACC AGGCTGGATT  18300

GCAGTGGCGT GATCTTGGCT CACTGCAACC TTCGCCTCCC GGGTTCACGT GATTCTCCTG  18360

CCTCAGCCTC CTGAGTGGCT GGCACTACAG GCTCCCGCCG CCATGCCCGG CTAATTTTTG  18420

CATTTTTAGT AGAGACAGGG TTTCACCCTG TTGGCCAGGA TGGTCTCGAT CTCTTGATCT  18480

CATGATCCAC CCACCTTGGC CTCCCAAAGT TCTGGCATTA CAGGAGTGAG CCACCGTGCC  18540

CGGCCATCTT TCTTTCCTTG CTTTCTCTTT GTTTTCTTTC GAGACCGGGT CTTGCTCTGT  18600

CGCCCAGGCT GGACTGCAGT GGCACAATCA TAGCTCACTG CAGCCTCGAC TTCCCTGGCT  18660

CAAGCGATCC TTCCTCCTCA GCCCCCCGAG TAGCTGGAAC TACAGTTACA CACTACCATG  18720

CCTGGCTGAT TCTTTTTTTC CTTGTAGAGA TGGGGTCTTG CTATGCTGTC CATCCTGGTC  18780

TCAAACTCCT GGCCTTCCCA AAGCACTGGG TTTACAGGCA TAAGCCACCA CACCCAGTTT  18840

CCTTTTCTTC TTTTTAACTG GAATAGTTGA CGTTTTCTTT ATTAGCTGTG TGTCAGGAGG  18900

GTATTTTTGG CCTTTAGTAT GTCGTGTAAG TTGCTAGTGC TTTTCTGAGA TTGTAGTTTG  18960

TTTTCTAATT TTATTTATAT TTTGCGTAGA AGTTGTGTAT TTTAGATGGA GTTAGGTCGG  19020

CTGGTCTTTG ATGTTTTATT TATTAATTAT GTATGTATTT ATTTATTTTT GAGGTAGAGT  19080

CTCGCCGTTT CACCCAGGCT GGAGTACAGT GATGCGATCT CAGCTCCCTG TAGCCTTGAC  19140

CTCTCTGGGC TCAAGTGATT TTTCTCTCCT CTACCTCCCG AGTACTTGGG ACCCCAGGCG  19200

CATGCCGCCA TGCCTGGCTA ATGTGTATTT TTTGTAGATA CGGGGTCTCA CTGTGTTGCC  19260

CAGGGTGGTT TCAAAATCCT GGGCCCAGGC GATCCTTCCG TCTCAGCTCC CACGGTGCTG  19320

TGTTACCGGC GTGTGCCCAG TGCCTGGCCG TCTTGGAGGT CTTGTTTCTC TGGGTTTATG  19380

CCTCGAGGTG GCGCCTGCTC CCCTGTGCTC CCTGGTAGCC TGGTAGTGAG CCTGCTTCTC  19440

ACACAGTCAT ACCTGGTTGT GGTCCCACAG TGGGACCACC CTGTTGGGTT CAGAACAGGA  19500

GATGGGGGCC CCTCGAGTCT GTGTGGGGGC TGTGGACAGG GTTGGGAGAC CTTGGCTCTG  19560

TGGGGACTG TGGACAGGGG ATGGGGGCC TTGGCCCTGC GTGGGATGGG TTGGGGGTCC  19620

GTGCCCTTCC TGGCCCTGGG TGGACAGGTC CATGTGGCAC TCGGCATAGG GCTGAGATGG  19680

GTGCAGAGGG CTGAGGCCCC CAGGCCTCTC CTGGCTTGGT TTCCCCAGAT GAGTGTTCAT  19740

TTGGGTCTTC CATCAGAAAG TCCCCTCCTG ACCTCTGGGA GTGGGAGCT CAAGGGTGGG  19800

AGGCCATAGC TTGGGGATGC TGGCAATGTG TGGGATGGGC CCAGGGAAGG CCTCTGGCCT  19860

ACTAGGGGCT CTGGCCCTGA CCCACGGCCA CTCACTCCTC AGAGACGTCT CCCACAACCT  19920

GCTCCGGGCG CTGGACGTTG GGCTCCTGGC GAACCTCTCG GCGCTGGCAG AGCTGTGAGT  19980

GTCCCCCAGT CGTGCCAGCA TGCGGGCTC ACTCCGGGTG GGCTGGCGGC ACCGCCTCTT  20040

GCTGCTCAGC TGTGGGGGCT TCCATCAGCT TTGCCGAATC CCCCGTCTCT TCCAGGGATA  20100

TAAGCAACAA CAAGATTTCT ACGTTAGAAG AAGGAATATT TGCTAATTTA TTTAATTTAA  20160

GTGAAATGTA AGTTGTGGTT CTTTGGGTGG GGTCCTGGCT GGACCCCAGG CCCCCAATAT  20220

CCCTTCTGCC CTCCCAGTTG GTCCGTGTCC CCTTCCAGGG TTGAGACCAG ATCCTGGGGG  20280

CAGTTCACTG CCTGCTTGGA GCCCCCCAGT GCCGGCTTGG TTGGGGCAGG GGAGGCGGTG  20340
```

```
CTGTCAGGGT GGCTCCAGGG CCTGGTTGCC AGTGGGGGGC TGGCATAGAC CCTTCCCACC    20400

AGACCTGGTC CCCAACACCT GCCCCTGCCC TGCAGAAACC TGAGTGGGAA CCCGTTTGAG    20460

TGTGACTGTG GCCTGGCGTG GCTGCCGCGA TGGGCGGAGG AGCAGCAGGT GCGGGTGGTG    20520

CAGCCCGAGG CAGCCACGTG TGCTGGGCCT GGCTCCCTGG CTGGCCAGCC TCTGCTTGGC    20580

ATCCCCTTGC TGGACAGTGG CTGTGGTGAG TGCCGGTGGG TGGGGCCAGC TCTGTCCTTC    20640

CCAGCCAGGT GGGACCTGGG CCCTGCAGAC ACTGGGCAGG GCTCAGGAAG GCCTCTCTGG    20700

GGGGGGCCTC CGGGCCAAGG GAACAGCATG GGAGCCTGTG AGTGCGGCGG GCGGATGTGG    20760

GGGCGTGGGG TGGAGCCAGG AGGAGCAGAA CCCGGGGTCC AGTGGCTGCC TCTTCTAGGT    20820

GAGGAGTATG TCGCCTGCCT CCCTGACAAC AGCTCAGGCA CCGTGGCAGC AGTGTCCTTT    20880

TCAGCTGCCC ACGAAGGCCT GCTTCAGCCA GAGGCCTGCA GCGCCTTCTG CTTCTCCACC    20940

GGCCAGGGCC TCGCAGCCCT CTCGGAGCAG GGCTGGTGCC TGTGTGGGGC GGCCCAGCCC    21000

TCCAGTGCCT CCTTTGCCTG CCTGTCCCTC TGCTCCGGCC CCCGCCACC TCCTGCCCCC     21060

ACCTGTAGGG GCCCCACCCT CCTCCAGCAC GTCTTCCCTG CCTCCCCAGG GGCCACCCTG    21120

GTGGGGCCCC ACGGACCTCT GGCCTCTGGC CAGCTAGCAG CCTTCCACAT CGCTGCCCCG    21180

CTCCCTGTCA CTGCCACACG CTGGGACTTC GGAGACGGCT CCGCCGAGGT GGATGCCGCT    21240

GGGCCGGCTG CCTCGCATCG CTATGTGCTG CCTGGGCGCT ATCACGTGAC GGCCGTGCTG    21300

GCCCTGGGGG CCGGCTCAGC CCTGCTGGGG ACAGACGTGC AGGTGGAAGC GGCACCTGCC    21360

GCCCTGGAGC TCGTGTGCCC GTCCTCGGTG CAGAGTGACG AGAGCCTCGA CCTCAGCATC    21420

CAGAACCGCG GTGGTTCAGG CCTGGAGGCC GCCTACAGCA TCGTGGCCCT GGGCGAGGAG    21480

CCGGCCCGAG GTGAGTGTCT GCTGCCCACT CCCCTTCCTC CCCAGGGCCA TCCAGATGGG    21540

GCAGAGCCTG GTACCCCCGT CTTGGGCCCA CACTGACCGT TGACACCCTC GTTCCCACCG    21600

GTCTCCAGCG GTGCACCCGC TCTGCCCCTC GGACACGGAG ATCTTCCCTG GCAACGGGCA    21660

CTGCTACCGC CTGGTGGTGG AGAAGGCGGC CTGGCTGCAG GCGCAGGAGC AGTGTCAGGC    21720

CTGGGCCGGG GCCGCCCTGG CAATGGTGGA CAGTCCCGCC GTGCAGCGCT TCCTGGTCTC    21780

CCGGGTCACC AGGTGCCTGC CCCCACCCCC CGAGGGGCCA TAGGTTGGGA GATCTCTGAA    21840

GCACTGGGGC AGAGACTGCG GCTGGGGAGT CTCAGGAGGA AGGAGGTGGG AGCTGGGCCG    21900

GCCCTGGTGA GCAGGTGGCG CCGGCCGGTG GGGCCGTTCC TGTCAGCTCT GCAGATGCAG    21960

AGGTGGACAT GAGCTGGGGG CAGCCTCCGG ACACTCCTGG GCACGCCATA CGGGAGGTGG    22020

CCTGCACGGG GATCCCTGCC GGTACCCACA GGCCCCGTGG GTGGGTGCTG CTGTGAGCCT    22080

GGGCTGGTGG GCCCTGGTCT CCGGGCTCTG AGCCTCAGTT TCCCCATCTG GAAAGGGGA     22140

CAGTGATGGG GCTCCCAGCG GGCTGCTGTG AGGGTGGGAG GATGGAGGAG TGCCCTGAGC    22200

CCCCTGCCAT CCCACACCCG CCCCCAGGAG CCTAGACGTG TGGATCGGCT TCTCGACTGT    22260

GCAGGGGGTG GAGGTGGGCC CAGCGCCGCA GGGCGAGGCC TTCAGCCTGG AGAGCTGCCA    22320

GAACTGGCTG CCCGGGGAGC CACACCCAGC CACAGCCGAG CACTGCGTCC GGCTCGGGCC    22380

CACCGGGTGG TGTAACACCG ACCTGTGCTC AGCGCCGCAC AGCTACGTCT GCGAGCTGCA    22440

GCCCGGAGGT GTGCGGGGGG CCAGGCAGGG GCCTGAGACG CTGGCTGTGG TTAGGGGCCT    22500

GCCGAGCGCC CGCGGTGGAG CCTGGGCTGA GGAGGAGGGG CTGGTGGGGG GGTTTTCGGG    22560

CGGCTCGGTC CCCAGTCTGT TCGTCCTGGT GTCCTGGGCC CTGGCCCGGC GCCTCACTGT    22620

GCACTCGCCA CCCCAGGCCC AGTGCAGGAT GCCGAGAACC TCCTCGTGGG AGCGCCCAGT    22680
```

```
                                             -continued

GGGGACCTGC AGGGACCCCT GACGCCTCTG GCACAGCAGG ACGGCCTCTC AGCCCCGCAC    22740

GAGCCCGTGG AGGTAGTCGG CCCCCCACGT TCTACAACCT GCCCTCCTGC CTGCCCCTGG    22800

AGGCCTTGCC TGCCCTGCCC ACTGTGGGTC TCGCCAAAAA ACTTGGGGGC CTTAATGTTG    22860

CTTGTGCCCA GTGAAGATGG TTGGGAAAAT CCAGAGTGCA GAGAGGAAAG CGTTTACTCA    22920

CATTACCTCC AGGCCTTTTC TCTGAGCGTG TGTGAGTTAT TCCTGAAAGG CAGGTCAGGG    22980

GTCCTGCCCC CCATGGACAG TTTCCACCGG AGTCTTCCTC TCGAGCGACA GGAGCCAGGC    23040

CTGTGGGGGT CTGATGGCTC GCTCTCCTTC CCTCCCCTCT TCCTGGGAAG TTCGGGTAGG    23100

GGGAGTCTGG GCTTCAGGCT GGGATGGGGT CTGTGGAGCT GAGGCGGCCC CCTGCCCACC    23160

AGGTCATGGT ATTCCCGGGC CTGCGTCTGA GCCGTGAAGC CTTCCTCACC ACGGCCGAAT    23220

TTGGGACCCA GGAGCTCCGG CGGCCCGCCC AGCTGCGGCT GCAGGTGTAC CGGCTCCTCA    23280

GCACAGCAGG TGGGACTCTG GGTGGTGGGT GGTGGGTGGT GGGCGCCGCA GGACTCGGGG    23340

TGGCCTCTCT GAGCTTTCAC GTCTGCTGGT CCTGTGGCCA CCAGAGTGGT TCCCAGTCTT    23400

AGGTGGACAG AGCAGGGGTT CCAGAGACAC CAGCTCATTC CAGGTGTCCT GGGGGTGGAT    23460

TGGGTGGGGC CTGCCTGGGG GCCGGCCTGG GTCAGTCGGC TGGCCGGAGA CGGACGCAGC    23520

ACTGGGCTGG GAGTGCTGCC CAGGTGGGGA GACCTGTCCT CACAGCAAGG CCAGGATTGC    23580

TGGTGCAGGC AGTTGGGCAT CTCTGACGGT GGCCTGTGGG CAAATCAGGG CCCCAACACC    23640

CTCCCCTCCT CACAGGGACC CCGGAGAACG GCAGCGAGCC TGAGAGCAGG TCCCCGGACA    23700

ACAGGACCCA GCTGGCCCCC GCGTGCATGC CAGGGGGACG CTGGTGCCCT GGAGCCAACA    23760

TCTGCTTGCC GCTGGACGCC TCCTGCCACC CCCAGGCCTG CGCCAATGGC TGCACGTCAG    23820

GGCCAGGGCT ACCCGGGGCC CCCTATGCGC TATGGAGAGA GTTCCTCTTC TCCGTTCCCG    23880

CGGGGCCCCC CGCGCAGTAC TCGGTGTGTG GCCCTGACCT GGGTCTGTTC CCTGCATCTC    23940

CTCAGGCCAC CTTCCTGTCT GCTGCCCAGG GTCTGGGTCT GTGCACCAGA CACACCCAGC    24000

CTGCAGGCCC CTCCCACGTC CTTGCCACCT CTGACCTCCG ACCTCTGCAG TGCCCTCGGC    24060

CCTCTCCCAG TGGGAGAAGC TCTCGCCTGG GCCCTTGGCA CGAGCTGTGC CTCCTCTTCC    24120

TCTCTCCCAG CACAGCTGCT CCTTCCTGTC TGCCAGGTCT TGGCCTGTGT CCTCTCCCCG    24180

TGTGTCCCCC GGTCTGCAAC TGTCCTGCCT GTCCTTGTCA CGAGCACTGT GGGGAGGCTC    24240

CTTGAGGTGT GGCTGACGAA GCGGGGAGCC CTGCGTGTCC ACCCTCATCC GTCGTGCGGG    24300

GGTCCACGGG CCATGACCGT GAGGACGTGA TGCAGCCCTG CCTCCCTCTC ACAGGTCAC    24360

CCTCCACGGC CAGGATGTCC TCATGCTCCC TGGTGACCTC GTTGGCTTGC AGCACGACGC    24420

TGGCCCTGGC GCCCTCCTGC ACTGCTCGCC GGCTCCCGGC CACCCTGGTC CCCGGGCCCC    24480

GTACCTCTCC GCCAACGCCT CGTCATGGCT GCCCCACTTG CCAGCCCAGC TGGAGGGCAC    24540

TTGGGCCTGC CCTGCCTGTG CCCTGCGGCT GCTTGCAGCC ACGGAACAGC TCACCGTGCT    24600

GCTGGGCTTG AGGCCCAACC CTGGACTGCG GCTGCCTGGG CGCTATGAGG TCCGGGCAGA    24660

GGTGGGCAAT GGCGTGTCCA GGCACAACCT CTCCTGCAGC TTTGACGTGG TCTCCCCAGT    24720

GGCTGGGCTG CGGGTCATCT ACCCTGCCCC CCGCGACGGC CGCCTCTACG TGCCCACCAA    24780

CGGCTCAGCC TTGGTGCTCC AGGTGGACTC TGGTGCCAAC GCCACGGCCA CGGCTCGCTG    24840

GCCTGGGGGC AGTGTCAGCG CCCGCTTTGA GAATGTCTGC CCTGCCCTGG TGGCCACCTT    24900

CGTGCCCGGC TGCCCCTGGG AGACCAACGA TACCCTGTTC TCAGTGGTAG CACTGCCGTG    24960

GCTCAGTGAG GGGGAGCACG TGGTGGACGT GGTGGTGGAA AACAGCGCCA GCCGGGCCAA    25020

CCTCAGCCTG CGGGTGACGG CGGAGGAGCC CATCTGTGGC CTCCGCGCCA CGCCCAGCCC    25080
```

```
CGAGGCCCGT GTACTGCAGG GAGTCCTAGT GGTGAGTATG GCCGAGGCTC CACCACCAGC    25140

CCCCAGGCAG GTGCCTGCAG ACAGGGTGCT CACACAGGGC GTGAGGCCTG GCTTCCCAGT    25200

GAGGGCAGCA GCCCAGTTAC TGGGGACGTC GGCCCCGGGC AGGTCCTGCT GGCTGGCTCC    25260

TCGGGCTACC TGGTGGGCTT TAAATTCCTG GAAAGTCACG GCTCTGACAG TGGCTCCGCT    25320

AACTCATTCC ACTGTCTCAT TTCACAAAAT GAATTTAAAA CTCTGCTCCC TGACCTCACA    25380

CGAGCCCCCG TGAGTCTCTC ACGCCCTCTG CTGTGTTCTC GCCTGGCTAA AGCGAGTGGC    25440

TTTTGAGGTG GAGTCTGAAC CCCTGATGGG AAACTGCGGG CTGCCCGCGG TGCCACCATG    25500

CTGGGTACAT GGGGGACAGG GCTGTCTCCA TCTTGCGGGT ACCTGCCTCT TCACCAGGGG    25560

CCTTGGGAGG GGCCATCAGA AATGGCGTGA CCTGTGCAGC CTGTCCTGGG TTCTGTAAGC    25620

CAGTGTAGGT GCCTCCCCTC ACTGCTCCGA GCTCTCTGGG TGAGGAGCTG GGCAAGAGC    25680

GCCGGGAGGG TCTGAGAAGA CTCAGAGAGA GGTGGACTCT TTGTAGCTGG TACTAGGTTT    25740

GCTTTACAGA TGGGAAACT GAGGCACAGA GAGGTTGAGG CATTAGTAGT ACTACATGGC    25800

TGGCTGGAGA GCCGGACAGT GAGTGTCCCA GCCCGGGCTT GGCTCCCATG GCATGCAGAG    25860

CCCCGGGCAC CTCCTCTCCT CTGTGCCCCG CGTGGGACTC TCCAGCCCGA CGGGAGGTGT    25920

GTCCAGGAGG CGACAGGCTA AGGGCAGAGT CCTCCACAGA GCCCAGGCTG ACACCATTCC    25980

CCCCGCAGAG GTACAGCCCC GTGGTGGAGG CCGGCTCGGA CATGGTCTTC CGGTGGACCA    26040

TCAACGACAA GCAGTCCCTG ACCTTCCAGA ACGTGGTCTT CAATGTCATT TATCAGAGCG    26100

CGGCGGTCTT CAAGCTCTCA GTAGGTGGGC GGGGGTGGGG AGGGGAGGGG ATGGGCGGG    26160

GCAGGGCGGG GGCGGGCTCC ACCTTCACCT CTGCCTTCTG CTCTGCTTCA TGCTGCCCGA    26220

GGACGCTGCC ATGGCTGTGG GTGAGTGGAG GGAGGGACGC CAATCAGGGC CAGGCCTCTC    26280

ACCTGCCACC TGGGCTCACT GACGCCTGTC CCTGCAGCTG ACGGCCTCCA ACCACGTGAG    26340

CAACGTCACC GTGAACTACA ACGTAACCGT GGAGCGGATG AACAGGATGC AGGGTCTGCA    26400

GGTCTCCACA GTGCCGGCCG TGCTGTCCCC CAATGCCACG CTAGCACTGA CGGCGGGCGT    26460

GCTGGTGGAC TCGGCCGTGG AGGTGGCCTT CCTGTGAGTG ACTCGGGGGC CGGTTTGGGG    26520

TGGGCACCAG GCTCTTGTCC CAGCCCCAGC CTCAGCCGAG GGACCCCCAC ATCACGGGGT    26580

TGCTTTTCTG AGCCTCGGTT TCCCTGTCTG TTGGGAGGTA ACTGGGTGCA CAGGAGCCCT    26640

GAGGCTGCAC GGGAGCCGGG AGAGGCCTCA GCACAGCCGG GTGGGCCCTG AATGGAGGCC    26700

CGGGGCGTGA CTGCAGAGTG GAGCCTCGGC TGGGTCCCAA GCACCCCCTG CCCCGCCACC    26760

GCCCACCCCT GTCCCGGTTC ACTCACTGCG TCCCACCGCC CCGGCAGGTG GACCTTTGGG    26820

GATGGGGAGC AGGCCCTCCA CCAGTTCCAG CCTCCGTACA ACGAGTCCTT CCCGGTTCCA    26880

GACCCCTCGG TGGCCCAGGT GCTGGTGGAG CACAATGTCA TGCACACCTA CGCTGCCCCA    26940

GGTGAGGGAT GAGGGGTGA GGGGGCCACT GCCTTTCAGG CTCTGAGCAC GGGTCCCCCC    27000

AGCTCCCCAG TCAAGCTGCC CCCCTTCCTC CCCAACAGCC CTCACTGTGA CCTCACCTGG    27060

GCTGATGGCT TAGGCCCTAC TGGGGTGAGG GAGGGGCCAG GCGTGGGGGG AGTGGACAGG    27120

GAAGCTGGGC CCCTGAACTG CGCCCCCCGC CCTCCCCGGG CCTGGCTCTT GCTGCTCTGC    27180

TGCCCCGAGT GCAGCTGCAC TTGGAGGCGG TGCCGTCCTC GCCAGGCAGC CCTCAGTGCT    27240

GCTACACCTG TGCTCCGTCC CGCACGTGGC TTGGGAGCCT GGGACCCTTA AGGCTGGGCC    27300

GCAGGTGCAG CCGTTCACCC CGGGCTCCTC AGGCGGGGGG CTTCTGCCGA GCGGGTGGGG    27360

AGCAGGTGGG GGTGCCGCGG CTGCCCCACT CGGGCCTGTC CCCACAGGTG AGTACCTCCT    27420
```

-continued

```
GACCGTGCTG GCATCTAATG CCTTCGAGAA CCTGACGCAG CAGGTGCCTG TGAGCGTGCG   27480
CGCCTCCCTG CCCTCCGTGG CTGTGGGTGT GAGTGACGGC GTCCTGGTGG CCGGCCGGCC   27540
CGTCACCTTC TACCCGCACC CGCTGCCCTC GCCTGGGGGT GTTCTTTACA CGTGGGACTT   27600
CGGGGACGGC TCCCCTGTCC TGACCCAGAG CCAGCCGGCT GCCAACCACA CCTATGCCTC   27660
GAGGGGCACC TACCACGTGC GCCTGGAGGT CAACAACACG GTGAGCGGTG CGGCGGCCCA   27720
GGCGGATGTG CGCGTCTTTG AGGAGCTCCG CGGACTCAGC GTGGACATGA GCCTGGCCGT   27780
GGAGCAGGGC GCCCCCGTGG TGGTCAGCGC CGCGGTGCAG ACGGGCGACA ACATCACGTG   27840
GACCTTCGAC ATGGGGACG GCACCGTGCT GTCGGGCCCG GAGGCAACAG TGGAGCATGT   27900
GTACCTGCGG GCACAGAACT GCACAGTGAC CGTGGGTGCG GCCAGCCCG CCGGCCACCT   27960
GGCCCGGAGC CTGCACGTGC TGGTCTTCGT CCTGGAGGTG CTGCGCGTTG AACCCGCCGC   28020
CTGCATCCCC ACGCAGCCTG ACGCGCGGCT CACGGCCTAC GTCACCGGGA ACCCGGCCCA   28080
CTACCTCTTC GACTGGACCT TCGGGGATGG CTCCTCCAAC ACGACCGTGC GGGGGTGCCC   28140
GACGGTGACA CACAACTTCA CGCGGAGCGG CACGTTCCCC CTGGCGCTGG TGCTGTCCAG   28200
CCGCGTGAAC AGGGCGCATT ACTTCACCAG CATCTGCGTG GAGCCAGAGG TGGGCAACGT   28260
CACCCTGCAG CCAGAGAGGC AGTTTGTGCA GCTCGGGGAC GAGGCCTGGC TGGTGGCATG   28320
TGCCTGGCCC CCGTTCCCCT ACCGCTACAC CTGGGACTTT GGCACCGAGG AAGCCGCCCC   28380
CACCCGTGCC AGGGGCCCTG AGGTGACGTT CATCTACCGA GACCCAGGCT CCTATCTTGT   28440
GACAGTCACC GCGTCCAACA ACATCTCTGC TGCCAATGAC TCAGCCCTGG TGGAGGTGCA   28500
GGAGCCCGTG CTGGTCACCA GCATCAAGGT CAATGGCTCC CTTGGGCTGG AGCTGCAGCA   28560
GCCGTACCTG TTCTCTGCTG TGGGCCGTGG GCGCCCCGCC AGCTACCTGT GGGATCTGGG   28620
GGACGGTGGG TGGCTCGAGG GTCCGGAGGT CACCCACGCT TACAACAGCA CAGGTGACTT   28680
CACCGTTAGG GTGGCCGGCT GGAATGAGGT GAGCCGCAGC GAGGCCTGGC TCAATGTGAC   28740
GGTGAAGCGG CGCGTGCGGG GGCTCGTCGT CAATGCAAGC CGCACGGTGG TGCCCCTGAA   28800
TGGGAGCGTG AGCTTCAGCA CGTCGCTGGA GGCCGGCAGT GATGTGCGCT ATTCCTGGGT   28860
GCTCTGTGAC CGCTGCACGC CCATCCCTGG GGGTCCTACC ATCTCTTACA CCTTCCGCTC   28920
CGTGGGCACC TTCAATATCA TCGTCACGGC TGAGAACGAG GTGGGCTCCG CCCAGGACAG   28980
CATCTTCGTC TATGTCCTGC AGCTCATAGA GGGGCTGCAG GTGGTGGGCG GTGGCCGCTA   29040
CTTCCCCACC AACCACACGG TACAGCTGCA GGCCGTGGTT AGGGATGGCA CCAACGTCTC   29100
CTACAGCTGG ACTGCCTGGA GGGACAGGGG CCCGGCCCTG GCCGGCAGCG GCAAAGGCTT   29160
CTCGCTCACC GTGCTCGAGG CCGGCACCTA CCATGTGCAG CTGCGGGCCA CCAACATGCT   29220
GGGCAGCGCC TGGGCCGACT GCACCATGGA CTTCGTGGAG CCTGTGGGGT GGCTGATGGT   29280
GGCCGCCTCC CCGAACCCAG CTGCCGTCAA CACAAGCGTC ACCCTCAGTG CCGAGCTGGC   29340
TGGTGGCAGT GGTGTCGTAT ACACTTGGTC CTTGGAGGAG GGGCTGAGCT GGGAGACCTC   29400
CGAGCCATTT ACCACCCATA GCTTCCCCAC ACCCGGCCTG CACTTGGTCA CCATGACGGC   29460
AGGGAACCCG CTGGGCTCAG CCAACGCCAC CGTGGAAGTG GATGTGCAGG TGCCTGTGAG   29520
TGGCCTCAGC ATCAGGGCCA GCGAGCCCGG AGGCAGCTTC GTGGCGGCCG GGTCCTCTGT   29580
GCCCTTTTGG GGGCAGCTGG CCACGGGCAC CAATGTGAGC TGGTGCTGGG CTGTGCCCGG   29640
CGGCAGCAGC AAGCGTGGCC CTCATGTCAC CATGGTCTTC CCGGATGCTG GCACCTTCTC   29700
CATCCGGCTC AATGCCTCCA ACGCAGTCAG CTGGGTCTCA GCCACGTACA ACCTCACGGC   29760
GGAGGAGCCC ATCGTGGGCC TGGTGCTGTG GGCCAGCAGC AAGGTGGTGG CGCCCGGGCA   29820
```

```
GCTGGTCCAT TTTCAGATCC TGCTGGCTGC CGGCTCAGCT GTCACCTTCC GCCTGCAGGT    29880

CGGCGGGGCC AACCCCGAGG TGCTCCCCGG GCCCCGTTTC TCCCACAGCT TCCCCCGCGT    29940

CGGAGACCAC GTGGTGAGCG TGCGGGGCAA AAACCACGTG AGCTGGGCCC AGGCGCAGGT    30000

GCGCATCGTG GTGCTGGAGG CCGTGAGTGG GCTGCAGGTG CCCAACTGCT GCGAGCCTGG    30060

CATCGCCACG GGCACTGAGA GGAACTTCAC AGCCCGCGTG CAGCGCGGCT CTCGGGTCGC    30120

CTACGCCTGG TACTTCTCGC TGCAGAAGGT CCAGGGCGAC TCGCTGGTCA TCCTGTCGGG    30180

CCGCGACGTC ACCTACACGC CCGTGGCCGC GGGGCTGTTG GAGATCCAGG TGCGCGCCTT    30240

CAACGCCCTG GCAGTGAGA ACCGCACGCT GGTGCTGGAG GTTCAGGACG CCGTCCAGTA    30300

TGTGGCCCTG CAGAGCGGCC CCTGCTTCAC CAACCGCTCG GCGCAGTTTG AGGCCGCCAC    30360

CAGCCCCAGC CCCCGGCGTG TGGCCTACCA CTGGGACTTT GGGGATGGGT CGCCAGGGCA    30420

GGACACAGAT GAGCCCAGGG CCGAGCACTC CTACCTGAGG CCTGGGGACT ACCGCGTGCA    30480

GGTGAACGCC TCCAACCTGG TGAGCTTCTT CGTGGCGCAG GCCACGGTGA CCGTCCAGGT    30540

GCTGGCCTGC CGGGAGCCGG AGGTGGACGT GGTCCTGCCC CTGCAGGTGC TGATGCGGCG    30600

ATCACAGCGC AACTACTTGG AGGCCCACGT TGACCTGCGC GACTGCGTCA CCTACCAGAC    30660

TGAGTACCGC TGGGAGGTGT ATCGCACCGC CAGCTGCCAG CGGCCGGGGC GCCCAGCGCG    30720

TGTGGCCCTG CCCGGCGTGG ACGTGAGCCG GCCTCGGCTG GTGCTGCCGC GGCTGGCGCT    30780

GCCTGTGGGG CACTACTGCT TTGTGTTTGT CGTGTCATTT GGGGACACGC CACTGACACA    30840

GAGCATCCAG GCCAATGTGA CGGTGGCCCC CGAGCGCCTG GTGCCCATCA TTGAGGGTGG    30900

CTCATACCGC GTGTGGTCAG ACACACGGGA CCTGGTGCTG GATGGGAGCG AGTCCTACGA    30960

CCCCAACCTG GAGGACGGCG ACCAGACGCC GCTCAGTTTC CACTGGGCCT GTGTGGCTTC    31020

GACACAGGTC AGTGCGTGGC AGGGCCGTCC TCCATGCCCC TCACCCGTCC ACACCCATGA    31080

GCCCAGAGAA CACCCAGCTT GCCACCAGGG CTGGCCCGTC CTCAGTGCCT GGTGGGCCCC    31140

GTCCCAGCAT GGGGAGGGGG TCTCCCGCGC TGTCTCCTGG GCCGGGCTCT GCTTTAAAAC    31200

TGGATGGGGC TCTCAGGCCA CGTCGCCCCT TGTTCTCGGC CTGCAGAGGG AGGCTGGCGG    31260

GTGTGCGCTG AACTTTGGGC CCCGCGGGAG CAGCACGGTC ACCATTCCAC GGGAGCGGCT    31320

GGCGGCTGGC GTGGAGTACA CCTTCAGCCT GACCGTGTGG AAGGCCGGCC GCAAGGAGGA    31380

GGCCACCAAC CAGACGGTGG GTGCCGCCCG CCCCTCGGCC ACTTGCCTTG GACAGCCCAG    31440

CCTCCCTGGT CATCTACTGT TTTCCGTGTT TTAGTGCTGG TGGAGGCCGC ACGCTCTCCC    31500

CTCTCTGTTT CTGATGCAAA TTCTATGTAA CACGACAGCC TGCTTCAGCT TTGCTTCCTT    31560

CCAAACCTGC CACAGTTCCA CGTACAGTCT TCAAGCCACA TATGCTCTAG TGGCAAAAGC    31620

TACACAGTCC CCTAGCAATA CCAACAGTGA GGAAGAGCCC CTTCCCACCC CAGAGGTAGC    31680

CACTGTCCCC AGCCCATGTC CCTGTTGCTG GATGTGGTGG GCCGGTTCTC ACCCTCACGC    31740

TCCCCTCTCT GGACCGGCCA GGAGGCTTGG TGACCCTGAG CCCGTGGTGG CTGCTCCTGC    31800

TGCTGTCAGG CGGGGCCTGC TGGTGCCCCA GAGTGGGCGT CTGTTCCCCA GTCCCTGCTT    31860

TCCTCAGCTG GCCTGATTGG GGGTCTTCCC AGAGGGGTCG TCTGAGGGGA GGGTGTGGGA    31920

GCAGGTTCCA TCCCAGCTCA GCCTCCTGAC CCAGGCCCTG GCTAAGGGCT GCAGGAGTCT    31980

GTGAGTCAGG CCTACGTGGC AGCTGCGGTC CTCACACCCA CACATACGTC TCTTCTCACA    32040

CGCATCCCCC CAGGGGCCCT CAGTGAGCAT TGCCTGCCTC CTGCTAGGGT CCAGCTGGGT    32100

CCAGTACACC AGAACGCACA CTCCAGTGTC CTCTGCCCTG TGTATGCCCT TCCGCCGTCC    32160
```

-continued

```
AAGTTGGAAG GTGGCAAACC GGATGAGTAT CCTGGGAGGG AGTGAGCTCA CCGGCAGTGG    32220

CCAGGCCCCT GGGAAACCTG GAGTTTGGGA GCAGCATCCT CCATGGGTCC CCCAGTCCTT    32280

CCAGCAGGCC AAATAGACCT GTGTTGGAGG TAACCCCACT CCCACGCCAG GTGCTGATCC    32340

GGAGTGGCCG GGTGCCCATT GTGTCCTTGG AGTGTGTGTC CTGCAAGGCA CAGGCCGTGT    32400

ACGAAGTGAG CCGCAGCTCC TACGTGTACT TGGAGGGCCG CTGCCTCAAT TGCAGCAGCG    32460

GCTCCAAGCG AGGGGTGAGT GTTGAGCGGG GTGTGGGCGG GCTGGGATG GGTCCCATGG     32520

CCGAGGGGAC GGGGCCTGCA GGCAGAAGTG GGGCTGACAG GGCAGAGGGT TGCGCCCCCT    32580

CACCACCCCT TCTGCCTGCA GCGGTGGGCT GCACGTACGT TCAGCAACAA GACGCTGGTG    32640

CTGGATGAGA CCACCACATC CACGGGCAGT GCAGGCATGC GACTGGTGCT GCGGCGGGGC    32700

GTGCTGCGGG ACGGCGAGGG ATACACCTTC ACGCTCACGG TGCTGGGCCG CTCTGGCGAG    32760

GAGGAGGGCT GCGCCTCCAT CCGCCTGTCC CCCAACCGCC CGCCGCTGGG GGGCTCTTGC    32820

CGCCTCTTCC CACTGGGCGC TGTGCACGCC CTCACCACCA AGGTGCACTT CGAATGCACG    32880

GGTGAGTGCA GGCCTGCGTG GGGGGAGCAG CGGGATCCCC CGACTCTGTG ACGTCACGGA    32940

GCCCTCCCGT GATGCCGTGG GGACCGTCCC TCAGGCTGGC ATGACGCGGA GGATGCTGGC    33000

GCCCCGCTGG TGTACGCCCT GCTGCTGCGG CGCTGTCGCC AGGGCCACTG CGAGGAGTTC    33060

TGTGTCTACA AGGGCAGCCT CTCCAGCTAC GGAGCCGTGC TGCCCCCGGG TTTCAGGCCA    33120

CACTTCGAGG TGGGCCTGGC CGTGGTGGTG CAGGACCAGC TGGGAGCCGC TGTGGTCGCC    33180

CTCAACAGGT GAGCCAGGCC GTGGGAGGGC GCCCCCGAGA CTGCCACCTG CTCACCACCC    33240

CCTCTGCTCG TAGGTCTTTG GCCATCACCC TCCCAGAGCC CAACGGCAGC GCAACGGGGC    33300

TCACAGTCTG GCTGCACGGG CTCACCGCTA GTGTGCTCCC AGGGCTGCTG CGGCAGGCCG    33360

ATCCCCAGCA CGTCATCGAG TACTCGTTGG CCCTGGTCAC CGTGCTGAAC GAGGTGAGTG    33420

CAGCCTGGGA GGGGACGTCA CATCTGCTGC ATGCGTGCTT GGGACCAAGA CCTGTACCCC    33480

TGCCTGGAGC TTTGCAGAGG GCTCATCCCG GGCCCCAGAG ATAAATCCCA GTGACCCTGA    33540

AGCAGCACCC CGACCTTCCG CTCCCAGCAG CCACACCCAC CGGGCCCTCT CCGGCGTCTG    33600

CTTTCCACAA TGCAGCCCCC GCCCAGGAGG GCCCATGTGC TTACCCTGTT TTGCCCATGA    33660

AGAAACAGCT CAGTGTTGTG GGTCAGTGCC CGCATCACAC AGCGTCTAGC ACGTAACTGC    33720

ACCCCGGGAG TCGTGGGCAT CTGCTGGCCT CCTGCCGGCC TCCTGCGCTG CTGACAGCTT    33780

GCTGTGCCCC CTGCCTGCCC CAGTACGAGC GGGCCCTGGA CGTGGCGGCA GAGCCCAAGC    33840

ACGAGCGGCA GCACCGAGCC CAGATACGCA AGAACATCAC GGAGACTCTG GTGTCCCTGA    33900

GGGTCCACAC TGTGGATGAC ATCCAGCAGA TCGCTGCTGC GCTGGCCCAG TGCATGGTAG    33960

GATGGCCCCA CCTGCTCACC CTGCCCCGCA TGCCTGCCAG GGCACTGGGT TCAGCCCCCC    34020

AGGGCAGACG GGCAGCTTGG CCGAGGAGCT GAGCCTCCAG CCTGGGCTCC TTCCTGCCAT    34080

GGCGTTCCTC GGTCTCTGAC CTGCTTCAGT AGCCTCAGCC GTTCTGTCCT GTGTGAACGC    34140

AGGGTGCCTC TCGGGGACC CAGGGTGTAA AGAGGGGCCC AGATGTGGGG AGGGACTAAG     34200

AAGATGCTGC TCTGTGCCCT CCACTCTCCC CTCCCCTCCC CTCCCCCTTC CCTCCCCTAG    34260

CCCCTCCCCT CCTCCCCTCC CCTAGCCCTT CCCCTCCTCC CCTCCCCTAG CCCTTTCCCT    34320

TCTTCCCCCC CAGCCCTTCC CCTCCTCCCC TCCCCTAGCC CTTCCCCTCC TCCCCTCCCC    34380

TACCCCTTCC CCTCCTCCCC TCCCCTAGAC CTTCCCCTCA CCTCCTCCCG CTGAGCCCCT    34440

CCACTCGTCC CCCAGCCCCT CCCTCCCCTA GCCCCTCCCC TCCCCCTTCC TCCCCTCCTC    34500

CCCCTCCCCT CCTCCCCCTC CCTCTTCCTC CCCCTCCCCT CCTCCCCCTT CCTCCCCTCT    34560
```

```
CCTCCCCCTC CCCTCCTGTC CCCCCTCCTC CCCTCCTCCC TCCTCCCCTC CTCCCCCCTC    34620

CTCCTCCCCC TCCTCCCTCC TCCCTCCTCC CCCTCCTCCT CCTCCCCTCC TCCCTCCTCC    34680

CCTCCTCCCC TCCCCTCCTC CCCCTCCCCC CTCCCTTCCT CCCCCTCCCC CCTCCCCTCC    34740

TCCCCCTCTC CTCCTCCCAT CCCTCCTCCC ATCCCTCCTC CCCGTTCCCA TTCTCTCCCC    34800

TCCCCCTTCC ATTTCTCCCT CCTCCCCCTG CCCTCCTCTC CTCCTCACCT CCCCTTCTCC    34860

GCTCCTTTCT TCTCCTCCCT CCCTTTCTCT CCTCCCTCCC CTTCTCCCCT TCTCCTCTTC    34920

TCCCCTTCTC CTCTCTTTTC ATCCTTCCCT TCTTCCCTCC TTTCCTCCTC TTTTCCCTCT    34980

TCTCCCCCCT CCTCCCCTCC TTCCTCCTCC CATTCCCCCT CCTCCCCCCT CCCATTCCCC    35040

CTCCTCCCCT CCTTCCTCCT CCCATTACCC TCCTCTCCCT CCCCTCCTCC CACCCCCCTC    35100

TCCTCCCGGC TCCTCTCCTC CCCTCCTCAT CCCCCTCCTC TCCTTCCCTC CTAACCCCCC    35160

TCCTCTCCTC CCCTCCTCAT CCCCCTCCTC TCCTTCCCTC CTCCTATCCC CCCTCCTCTC    35220

CTCCCCTCCT CCTATTCCCC CTCCTCTCCT CCCCTCCTTC CTCCTCCTCT CCTCCCATGC    35280

CCCCTCCTCC CCTCCTCCCA TCCCCCTCCT CCCCTCCTCC CTCCTCCCAT CCCATCCCCC    35340

TCCTCTCCTC CCCTTCTCTC CCTCCTCTCC CTCCCCTCCT CTCCTCTCCT CCTCTCCTCC    35400

CCTCCTCCCA TCCCCCCTCC TCCCATCCCC CCTCCTCTCC TCCCCACTCC TCTCCTCCCC    35460

ACTCCTCTCC TCCCCTCATC CCCCTCCTCT CTCCTCCCCT CCCCCTCCTC TCCTTCCCTC    35520

CTCCTTTCCT CCCCTCCCCC TCCTTCCCCC TCCTCCCCCT CCTTCTCCCC ATCCCCCTTC    35580

CCCTTCTCCT CCTCTCCCCT CCCCCTTCTC TTTTTCCCTC CTCCTCCCTT CCTCCTCCCC    35640

TCTTCTCCCC TTTTCCCTTT TCTCTTCCTC TCCTCCCCTT CTCCCCTCCT GTCCTCCCTC    35700

CCTTTCTCTC TTTCTTTCCT CCCCTTTCCTT CTCCCCTGTT CTCCTCCCTT CCCTTCTCCC    35760

CTTTTCTTCC CTCCTCCTTT CCTCCCCTCC TCCTTTTCTC TGTTTCTCTT CCTTTCCCCT    35820

CCACTTTCCC CTTCCTTTCC CCTCTCCTTT CTCCTTCCTT TCCTCTCCCC TTCTCTTCCT    35880

TTTCCTCTCT CCCCTTCTTT TCCCTCTTCC CCTCCCCTCC TCTTCCCCTC CCCTCCTCTT    35940

CCCCTCCCCT CCTCTTCCCC TCCCCTCCTC TTCCCCTCTC CTCCTCTTCC CCTCCCCTCC    36000

TCTTTCCCTC CCCTCTTCTC CTCCCCTCCT CTCCCCTCTT CCCCTCCCCT CCTCTTCCCT    36060

CCCCTTCCCC TCCCCTCCTC TTCCCTCCCC TTCCCCTCCC CTCCTCTTCC CTCCCCTTCC    36120

CCTCCTCTTC CTTCCTCTCT TCCCCTCCCC TCCTCTTCCC TCCCCTCTTC CCCTCCCCTT    36180

CTCTTCTCCT CCCCTTCTCT TCCCCTCCCC TTTTCTTCCC TCTCCTTGTC TTCCCTGCCC    36240

TCCTCTTCCC TCCCCTCCTC TTCCCTCCCC TCTTCCCCTC TCCTCCTCTT CCCTCCCCTC    36300

TTCCTCTTTC CTCTTCCCCT CCCCTCCTCC TCCCTCCCCT TTCCCCTCTT CCCCTCCCCT    36360

CCGCTTCCCT CCCCTTTCTC CCCCTTCTCT CCCCTCCCCT CTCCCCCCTT CTCTCCCCTC    36420

CCCTCTCCCC CTTCTCTCCC CTCCCCTCTC CCCCTTCTCT CCCCTCTCCT CTCCCCCTTC    36480

TCTCCCCCTT CTCTCCCCCT TCTCTCTCCC CTTCTCTCCC CCTTCTCTCC CCTCCCCCCT    36540

TCTCTCCCCT CCCCTCTCCC CCTTCTCTCC CCTCCCCTCT CCCCTGTCCT CTCCTCTCCA    36600

CCCTTCTCTC CCCTCCCCTC TCCTCTCCCC CTTCCCTCTC CTCTCCCCCT TCTCTCCCCT    36660

CCCCTCTCCT CTCCCCCCTT TTCTCCACTC CCCTCTCCTC TCTCCCCTCC TCCTCCGCTC    36720

TCATGTGAAG AGGTGCCTTG TGTGGTCGGT GGGCTGCATC ACGTGGTCCC CAGGTGGAGG    36780

CCCTGGGTCA TGCAGAGCCA CAGAAAATGC TTAGTGAGGA GGCTGTGGGG GTCCAGTCAA    36840

GTGGGCTCTC CAGCTGCAGG GCTGGGGGTG GGAGCCAGGT GAGGACCCGT GTAGAGAGGA    36900
```

-continued

```
GGGCGTGTGC AAGGAGTGGG GCCAGGAGCG GGGCTGGACA CTGCTGGCTC CACACAGGGG    36960
CCCAGCAGGG AGCTCGTATG CCGCTCGTGC CTGAAGCAGA CGCTGCACAA GCTGGAGGCC    37020
ATGATGCTCA TCCTGCAGGC AGAGACCACC GCGGGCACCG TGACGCCCAC CGCCATCGGA    37080
GACAGCATCC TCAACATCAC AGGTGCCGCG GCCCGTGCCC CATGCCACCC GCCCGCCCCG    37140
TGCGGCCCTT TCCTCTGCCT CCCTCCTCCC CCCAACCGCG TCGCCTTTGC CCCATCCCAT    37200
CTTCGTCCCC CTCCCCTCCC CCCAATTCCC ATCCTCATCC CCCTCCCCCA ATTCCCATTC    37260
TCCTCCCCCT CCCCCTTCCC TATTACCATC CCTTTTCTCC ATCTCTCTCC CCTTTTCTCC    37320
ATTTCCCCCC CCGTCCTCCC CGTCCTTTTG TCCATTCCCC TCATCTTCCT CATCCCCCTC    37380
ATCCCCCTTC CCCTCCCTTA TCCCCCTTCC CCTCCCTTTC CCCCTGCTCC TCTTCTTCTC    37440
CCTTCTCTTT TCTCTACCCT TTTCCTTCCT TTTTCCTCCC TCTCCCCATC ATCCCCCTCA    37500
TCTTCGTCCT CATCCCCATC ACCTTCCCCC TCCCCCCTCC ACCACTCTCT CTCCAGCTTC    37560
CCCCTTCCTT CTGCCTGCAC CTCGCTCTCT GCCCCCTCAG GTTCCCCCTT TCTCCCAGCC    37620
CCCACCCTCC GGCTCCCCCT TTTTGCCTGC CCCCACCCTC CCTCTACCTC CCTGTCTCTG    37680
CACTGACCTC ACGCATGTCT GCAGGAGACC TCATCCACCT GGCCAGCTCG GACGTGCGGG    37740
CACCACAGCC CTCAGAGCTG GGAGCCGAGT CACCATCTCG GATGGTGGCG TCCCAGGCCT    37800
ACAACCTGAC CTCTGCCCTC ATGCGCATCC TCATGCGCTC CCGCGTGCTC AACGAGGAGC    37860
CCCTGACGCT GGCGGGCGAG GAGATCGTGG CCCAGGGCAA GCGCTCGGAC CCGCGGAGCC    37920
TGCTGTGCTA TGGCGGCGCC CCAGGGCCTG GCTGCCACTT CTCCATCCCC GAGGCTTTCA    37980
GCGGGGCCCT GGCCAACCTC AGTGACGTGG TGCAGCTCAT CTTTCTGGTG GACTCCAATC    38040
CCTTTCCCTT TGGCTATATC AGCAACTACA CCGTCTCCAC CAAGGTGGCC TCGATGGCAT    38100
TCCAGACACA GGCCGGCGCC CAGATCCCCA TCGAGCGGCT GGCCTCAGAG CGCGCCATCA    38160
CCGTGAAGGT GCCCAACAAC TCGGACTGGG CTGCCCGGGG CCACCGCAGC TCCGCCAACT    38220
CCGCCAACTC CGTTGTGGTC CAGCCCCAGG CCTCCGTCGG TGCTGTGGTC ACCCTGGACA    38280
GCAGCAACCC TGCGGCCGGG CTGCATCTGC AGCTCAACTA TACGCTGCTG GACGGTGCGT    38340
GCAGCGGGTG GGGCACACGC GGCCCCCTGG CCTTGTTCTT GGGGGGAAGG CGTTTCTCGT    38400
AGGGCTTCCA TGGGTGTCTC TGGTGAAATT TGCTTTCTGT TTCATGGGCT GCTGGGGGCC    38460
TGGCCAGAGA GGAGCTGGGG GCCACGGAGA AGCAGGTGCC AGCTCTGGTG CAGAGGCTCC    38520
TATGCTTTCA GGCCCGTGGC AGAGGGTGGG CTCAGGAGGG CCATCGTGGG TGTCCCCCGG    38580
GTGGTTGAGC TTCCCGGCAG GCGTGTGACC TGCGCGTTCT GCCCCAGGCC ACTACCTGTC    38640
TGAGGAACCT GAGCCCTACC TGGCAGTCTA CCTACACTCG GAGCCCCGGC CCAATGAGCA    38700
CAACTGCTCG GCTAGCAGGA GGATCCGCCC AGAGTCACTC CAGGGTGCTG ACCACCGGCC    38760
CTACACCTTC TTCATTTCCC CGGGGTGAGC TCTGCGGGCC AGCCTGGCAG GGCAGGGCAG    38820
GGCATCATGG GTCAGCATTG CCTGGGTTAC TGGCCCCATG GGGACGGCAG GCAGCGAGGG    38880
GACTGGACCG GGTATGGGCT CTGAGACTGC GACATCCAAC CTGGCGGAGC CTGGGCTCAC    38940
GTCCGCTACC CCTTCCCTGC CCAGGAGCAG AGACCCAGCG GGGAGTTACC ATCTGAACCT    39000
CTCCAGCCAC TTCCGCTGGT CGGCGCTGCA GGTGTCCGTG GGCCTGTACA CGTCCCTGTG    39060
CCAGTACTTC AGCGAGGAGG ACATGGTGTG GCGGACAGAG GGGCTGCTGC CCCTGGAGGA    39120
GACCTCGCCC CGCCAGGCCG TCTGCCTCAC CCGCCACCTC ACCGCTTCG GCGCCAGCCT     39180
CTTCGTGCCC CCAAGCCATG TCCGCTTTGT GTTTCCTGTG AGTGACCCTG TGCTCCTGGG    39240
AGCCTCTGCA GAGTCGAGGA GGGCCTGGGT GGGCTCGGCT CTATCCTGAG AAGGCACAGC    39300
```

```
TTGCACGTGA CCTCCTGGGC CCGGCGGCTG TGTCCTCACA GGAGCCGACA GCGGATGTAA    39360

ACTACATCGT CATGCTGACA TGTGCTGTGT GCCTGGTGAC CTACATGGTC ATGGCCGCCA    39420

TCCTGCACAA GCTGGACCAG TTGGATGCCA GCCGGGGCCG CGCCATCCCT TTCTGTGGGC    39480

AGCGGGGCCG CTTCAAGTAC GAGATCCTCG TCAAGACAGG CTGGGCCGG GGCTCAGGTG     39540

AGGGGCGCAG CGGGGTGGCA GGGCCTCCCC TGCTCTCACT GGCTGTGCTG GTTGCACCCT    39600

CTGGGAGTGA GTCTCGTCGC AGGCGTCAGA ACAAGGCAGT TTTTGCAGTG CTGTGTGAAG    39660

GGCTCGTGTG TTCATCCTGG GAATGACCTC GTGAGCACTC ACTGTCCCTG AGGACTAGGA    39720

CAGCTCCTAG CTGGAAGTAG GTGCCAGTCA GTCAGGGTGG GCAGCCCACG TTCTGCACAG    39780

TAGCGTGGCC CCACAAGTGA CGTGAGCATC GCTACCACTG TGGGAGACTG TGCATCCACC    39840

CGCGATCCTG ACTGCATAGC TCGTCTCTCA GACGGAGGCG CCAGCACCCT CCCCGTGGCT    39900

GTTTCTTCAG TACCTCCATT TTCCTTTCAT TGGAATTGCC CTTCTGGCAT TCCCTTTTTG    39960

TTTTCGTTTT TCTTTTTTTA GAGACGGAGT CTCACTCTGT TGCCCAGGCT GGAGTGCAAT    40020

GGCATGATCT TGGCTCACAG CAACTTCCAG CTCCCGGGTT TAAGCCATTC CCCTTAAGCG    40080

ATTCTCCTGA GTAGCTGGGA GTACAGGTGC ACACCACCAC ACCCAGTTAA TTTTTCACCA    40140

TGTCAGCCAG GCGAACTCCT GACCTCAGGT GATCCGCCTG CCTCGGCCTG CCAGAGTGCT    40200

GGGATGACAG GTGTGAGCCA CCACACCTGG CTGTGTTCCC ATTTTTTATC TCTGTGCTGC    40260

TTTCCTCTTC ATTGCCCAGT TCTTTCTTTT GATTACCTAC TTTTAAAAAC TGTCGGCCGG    40320

GCGCGGTGGC TCACACCTGT AATCCGAGCA CTTTGGGAGG CCAGGCAGGC AAATCACGGG    40380

GTCAGGAGAT CGAGACCATC CTGGCTAACG GTGAAACCCT GTCTCTAATA AAAGTACAA    40440

AAAAATTAGC CCGGCGTAGT GGCAGGCGCC TGTAGTCCCA GCTCCTTGGG AGACTGAGGC    40500

AGGAGAATGG CGTGAACCCG GGAGGCGGAG CTTGCAGTGA GCTGAGATTG CGCCACTGCA    40560

CTCCAGCCTG GGTGACACAG CAAGACTCCA TCTCAAAAAA AAAAGAAAAA AAATACTGTC    40620

ACCTGGGTCT GTCACTGGGA GAGGAGGTGA CACAGCTTCA CGCTTTGCAG TCTGTGCATG    40680

AACTGAGGGA CGGGTGTGTG GTGCGGGTCA CCGGTTGTGG CATGACTGAG GCGTGGACAG    40740

GTGTGCAGTG CGGGTCACTG GTTGTGGTGT GGACTGAGGC GTGTGCAGCC ATGTTTGCAT    40800

GTCACAAGTT ACAGTTCTTT CCATGTAACT TAATCATGTC CTTGAGGTCC TGCTGTTAAT    40860

TGGACAAATT GCAGTAACCG CAGCTCCTTG TGTATGGCAG AGCCGTGCAA AGCCGGGACT    40920

GCCTGTGTGG CTCCTTGAGT GCGCACAGGC CAAAGCTGAG ATGACTTGCC TGGGATGCCA    40980

CACGTGTTGG GCAGCAGACC GAGCCTCCCA CCCCTCCCTC TTGCCTCCCA GGTACCACGG    41040

CCCACGTGGG CATCATGCTG TATGGGGTGG ACAGCCGGAG CGGCCACCGG CACCTGGACG    41100

GCGACAGAGC CTTCCACCGC AACAGCCTGG ACATCTTCCG GATCGCCACC CCGCACAGCC    41160

TGGGTAGCGT GTGGAAGATC CGAGTGTGGC ACGACAACAA AGGTTTGTGC GGACCCTGCC    41220

AAGCTCTGCC CCTCTGCCCC CGCATTGGGG CGCCCTGCGA GCCTGACCTC CCTCCTGCGC    41280

CTCTGCAGGG CTCAGCCCTG CCTGGTTCCT GCAGCACGTC ATCGTCAGGG ACCTGCAGAC    41340

GGCACGCAGC GCCTTCTTCC TGGTCAATGA CTGGCTTTCG GTGGAGACGG AGGCCAACGG    41400

GGGCCTGGTG GAGAAGGAGG TGCTGGCCGC GAGTAAGGCC TCGTTCCATG GTCCCACTCC    41460

GTGGGAGGTT GGGCAGGGTG GTCCTGCCCC GTGGCCTCCT GCAGTGCGGC CCTCCCTGCC    41520

TTCTAGGCGA CGCAGCCCTT TTGCGCTTCC GGCGCCTGCT GGTGGCTGAG CTGCAGCGTG    41580

GCTTCTTTGA CAAGCACATC TGGCTCTCCA TATGGGACCG GCCGCCTCGT AGCCGTTTCA    41640
```

```
CTCGCATCCA GAGGGCCACC TGCTGCGTTC TCCTCATCTG CCTCTTCCTG GGCGCCAACG    41700

CCGTGTGGTA CGGGGCTGTT GGCGACTCTG CCTACAGGTG GGTGCCGTAG GGGTCGGGGC    41760

AGCCTCTTCC TGCCCAGCCC TTCCTGCCCC TCAGCCTCAC CTGTGTGGCC TCCTCTCCTC    41820

CACACAGCAC GGGGCATGTG TCCAGGCTGA GCCCGCTGAG CGTCGACACA GTCGCTGTTG    41880

GCCTGGTGTC CAGCGTGGTT GTCTATCCCG TCTACCTGGC CATCCTTTTT CTCTTCCGGA    41940

TGTCCCGGAG CAAGGTGGGC TGGGGCTGGG GACCCGGGAG TACTGGGAAT GGAGCCTGGG    42000

CCTCGGCACC ATGCCTAGGG CCGCCACTTT CCAGTGCTGC AGCCAGAGGG AAAGGCGTCC    42060

ACCAAAGGCT GCTCGGGAAG GGTCAACACA CTTGAGCAGC CTTAGCTAGA CTGACCAGGG    42120

AGAAAGAGAG AAGACTCAGA AGCCAGAATG GTGAAAGAAC GAGGGCACTT TGCTAAGCAG    42180

ACGCCACGGA CGACTGCACA GCAGCACGCC AGATAACTCA GAAGAAGCAA GCACGCGGCT    42240

GTGCACGCTT CCGAAATGCA CTCCAGAAGA AAATCTCAGT ACATCTATAG GAAGTGAAGA    42300

GGCTGAGTTA GTCCCTTAGA AACGTCCCAG TGGCCGGGCC GGGTGTGGTG GCTCACGCCT    42360

GTAATCCCAA CACTTCAGGT GGCCGAGGTG GGCGGATCTG AGTCCAGGAG TTTGAGACCA    42420

GCCTGGGCAA CATAGCAAGA CCCCATCTAT ATAAAACATT AAAAAGGGCC AGGCGCGGTG    42480

GCTCACGCCT GTAATCCCAG CACTTTGGGA GGCCGAGGCG GGCAGATCAC TTGAGGTCAG    42540

GAGTTCGAGA CCAGCCTGGC CAACACAATG AAACCCCGAC TCTACTACAA ATACAAAAAC    42600

TTAGCTGGGC ATGGTGGCGG GCGCCTGTAG TCCCAGCTAC TCGAGAGGCT GAGGCAGGAG    42660

AATGGCATGA ACCCAGGAGG CGGAGCTTGC AGTGAGCCGA GATTGCGCCA CTGCACTCCA    42720

TCCTGGGCAA CGGAGCAAGA CTCCATCTCC AAAAAAAAAA AAAAAAAATC CCACAAAGAA    42780

AAGCTCAGGC TCAGAGCCTT CACGATAGAA TTTTTCTAAG CAGTTAAGGA AGAATTAACA    42840

CCAATCCTTC ACAGACTCTT TCCAAGAATA CAGCAGGTGG GAACGCTTCC CATTCATACG    42900

GAAACGGGAG GCCGCACCCC TTAGGAATGC ACACGTGGGG TCCTCAAGAG GTTACATGCA    42960

AACTAACCCC AGCAGCACAC AGAGAAGGCG CATAAGCCGC GACCAGGAGG GGTTGCTCCC    43020

GAGTCCGTGG CAGGAACCAG AGGCCACATG TGGCTGCTCG TATTTAAGTT AATTAAAATG    43080

GAACGATGGC CGGGTGTGGT GGCTCACACC TGTAATCCCA GCACTTTGGG AGGCGGAGGC    43140

GGGCAGATCA CTTGAGGTCA GGAGTTCCAA GACCAGCCTG GCCAACACAG TGAAACCCCG    43200

TCTCTACTAA AAATACAAAA AATTAGCTGG GCATGGTGGC AGGCACCTGT AATCCCAGCT    43260

ACTCAGGAGG CTGAGCCAGG ACAATCGCCT GAACGCGGGA GGTGGAGGTT GCAGTGAGCT    43320

GAGATTGCGC CATTGCACTC CAGCCTGGGT GACAGCGAGA CTCCATCTAA AAAAGAAAAT    43380

ATGAAATTTA AAACTCTGTT CCTTAGCTGC ACCAGTCTGC TGTCAAGTGT TCAGTGGCAC    43440

ACGTCGCGAG GGGCTGCCAT CACGGACGGT GCAGATGTCC CATATATCCA GCATTCTAGG    43500

ACATTCTGTC AGATGGCACC GGGCTCTGTC CTGTCTGCTG AGGAGGTGGC TTCTCATCCC    43560

TGTCCTGAGC AGGTCTGAGC TGCCGCCCGC TGACCACTGC CCTCGTCCTG CAGGTGGCTG    43620

GGAGCCCGAG CCCCACACCT GCCGGGCAGC AGGTGCTGGA CATCGACAGC TGCCTGGACT    43680

CGTCCGTGCT GGACAGCTCC TTCCTCACGT TCTCAGGCCT CCACGCTGAG GTGAGGACTC    43740

TACTGGGGGT CCTGGGCTGG GCTGGGGGTC CTGCCGCCTT GGCGCAGCTT GGACTCAAGA    43800

CACTGTGCAC CTCTCAGCAG GCCTTTGTTG GACAGATGAA GAGTGACTTG TTTCTGGATG    43860

ATTCTAAGAG GTGGGTTCCC TAGAGAAACC TCGAGCCCTG GTGCAGGTCA CTGTGTCTGG    43920

GGTGCCGGGG GTGTGCGGGC TGCGTGTCCT TGCTGGGTGT CTGTGGCTCC ATGTGGTCAC    43980

ACCACCCGGG AGCAGGTTTG CTCGGAAGCC CAGGGTGTCC GTGCGTGACT GGACGGGGGT    44040
```

```
GGGCTGTGTG TGTGACACAT CCCCTGGTAC CTTGCTGACC CGCGCCACCT GCAGTCTGGT    44100

GTGCTGGCCC TCCGGCGAGG GAACGCTCAG TTGGCCGGAC CTGCTCAGTG ACCCGTCCAT    44160

TGTGGGTAGC AATCTGCGGC AGCTGGCACG GGGCCAGGCG GGCCATGGGC TGGGCCCAGA    44220

GGAGGACGGC TTCTCCCTGG CCAGCCCCTA CTCGCCTGCC AAATCCTTCT CAGCATCAGG    44280

TGAGCTGGGG TGAGAGGAGG GGGCTCTGAA GCTCACCCTT GCAGCTGGGC CCACCCTATG    44340

CCTCCTGTAC CTCTAGATGA AGACCTGATC CAGCAGGTCC TTGCCGAGGG GGTCAGCAGC    44400

CCAGCCCCTA CCCAAGACAC CCACATGGAA ACGGACCTGC TCAGCAGCCT GTGAGTGTCC    44460

GGCTCTCGGG GGAGGGGGGA TTGCCAGAGG AGGGGCCGGG ACTCAGGCCA GGCAGCCGTG    44520

GTTCCCGCCT GGGGTAGGGT GGGGTGGGGT GCCAGGGCAG GGCTGTGGCT GCACCACTTC    44580

ACTTCTCTGA ACCTCTGTTG TCTGTGGAAA GAGCCTCATG GGATCCCCAG GGCCCCAGAA    44640

CCTTCCCTCT AGGGAGGGAG CAGGCTCATG GGGCTTTGTA GGAGCAGAAA GGCTCCTGTG    44700

TGAGGCTGGC CGGGGCCACG TTTTTATCTT GGTCTCAGAG CAGTGAGAAA TTATGGGCGG    44760

GTTTTTAAAT ACCCCATTTT TGGCCGGGCG CGGTGGCTCA CACGTGTAAT CCCAGCACTT    44820

TGGGAGGCCG AGGTGGGCAG ATGACCTGAG GTCAGCAGTT CGAGACCAGC CTGGCCAACA    44880

TGGCGAAACC CCGTCTCTAC TAAAAATACA AAAAATTAGC CGGGCATGCT GGCAGGCGCC    44940

TGTAGTCCCA GTTACTCGGG AGACTGAGGT AGGAGAATCG ATTGAACCTG GTAGGTGAAG    45000

GTTGTAGTGA GCCGAGATCG CGCCACTGCA CTCCAGCCTG GCAACAAGA GCGAAACTCC    45060

GTCTCAAAAA CAAAAAAATT CCTCAATTTC TTGGTTGTTT TGTAACTTAT CAACAAATGG    45120

TCATATAGAG GTTACCTTGT ATGTAGTCAC GCACATAGTC ACGCACATGG CAGCCGGCGG    45180

CGGAGCGCAC CCACGGCGTG TTCCCACGCG TGTGACCCCG GGCTCTGCCA TGCCCTCCTA    45240

TGCTCAGGTG TGCTGAGGTC CACACGGCCC TGCCGTTGCA CTGCAGCTGC CTGCAGGATT    45300

CAGTGCAGTG GCATGCAGTG CAGGTGCGGT GCCCCGGAGC CACAGGCCAC ACCACAGGGC    45360

CTGCATGCAC AGGGGCTGCG GTGTCTGGGT TTGGGTAACT ACGCCCTGTG ACATTTGCAC    45420

AGCAACAGAA TTACCTAATG ACGCATTTCT CAGAACACAT CCCTGGCACT AAGTGGTGCG    45480

TGACTGCTGC TTTTGCATCC ACATCTAGTT TGATTTGTGT GTTATTCCTT TGAGTGCTTC    45540

TCATTGTTAA GCAACCAAGA ACTAAAGAGG TATGAACTGC CCCTGGACTC AAACAAAAAG    45600

GAAAACTTCC TGATTTACAA AAGGCAGATA ACCATCACAT GAGGGCATCT TTATGAATAA    45660

ATTGCTGGTT GGTTTTAAAA ATACAGAGTA TGGGGAAATC CAGGGGTAGT CACTACATGC    45720

TGACCAGCCC CAGGTATCTC CGGCCCAAAG CTCTGTGAAA TCCAGATTCA GTGCTTCCGC    45780

GGGGATTTCT GACGGCAGCT CAGACTCCGC ATCCACACAG AGCGCGTGGC CCTCACCCTC    45840

CCGGCTTCCT CAACCCTTGG CCGTCCCTTG CTCGGACAGT GCTTCGGGCT GACCAGGTCG    45900

GAGGCTTGGG TTTGTCCTGG ACCCCTCTGC GTCCTTCCTC ACTGCAGCCT CCAGCGCGTC    45960

CCGTGGCTCC TTTCCCAACG CAGAGCACGG CCTTCCCTGC GCCTGAGCCT GCACCCTCCG    46020

TCCTGGCGGC GCCTCTGCCC TGGCATTCCC TGCCACTCCA TGCCTCCCTA TTGGCCATTC    46080

TCCGTCTCTG CCAGCGAGAG CCTGCTCCCT GAGTCAGACC CTGAGTCATT TGTGTTGCTA    46140

TAAAGGAATA GTTGAGGCTG GGTTATTTTT TATTTTATT TATTTTTTG AGATGGAGTC    46200

TCTGTTGCCC AGACTGGAGT GCAGTCGCAT GATCTCGGCT CACTGCAAAG TCTGCCTCCC    46260

ACGTTCAAGC AGTTATCTGC CTCAGCCTCC CAAGTAGCTA AGATTACAGG CGCCCGCCGC    46320

CACAGCCGGC TAATTTTTTG TGTGTGTGTT TTAGTAGAGA GGAGGTTTCA CCATCTTAGC    46380
```

```
CAGGCTGGTC TTGAACTCCT GACCTCGTGA TCCACCCATC TCAGCCTCCC AAAATGCTGA    46440

GATTACAGGC GTGAGCCACC ACGCCTGACC AAGTTGAGGC TAGGTCATTT TTTAATTTTT    46500

TGTAAAGACA GGGTCTCACT GTCTCCAACT CCTGAGCTCA AGTGATCCTC CTGCCTCAGC    46560

CTCCTGAAGT GCTGGGATTA CAGGCTTGAG ACACTGCGCC CAGCCAAGAG TGTCTTTTAT    46620

CCTCCGAGAG ACAGCAAAAC AGGAAGCATT CAGTGCAGTG TGACCCTGGG TCAGGCCGTT    46680

CTTTCGGTGA TGGGCTGACG AGGGCGCAGG TACGGGAGAG CGTCCTGAGA GCCCGGGACT    46740

CGGCGTCTCG CAGTTGGTCT CGTCCTCCCC CTCAACGTGT CTTCGCTGCC TCTGTACCTC    46800

TTCTCTAGCA GCTCTGGGAC CGGGCATATC AGCATGGTGG CCCGATGCAG TGGCACAGCC    46860

TCGGTGGTCA CTGGCTCCTG GAGACACAAG CAGATCTCTG GCCTCAGGGA GCCCTACACA    46920

CTGTTGGGAT TTGAAAGGCA TTCATATGTT TCCTTGTCCA GAAGTTAATT TTAGGCCATA    46980

AACCTGCATG GGACAGACAC ACTGGCGTCT CTAGATTGTA GAGATGCTTG TTGGATGGTT    47040

GAGACCCAAT CATAGTTTGC AGGGTTGAAG GGGGGCTCAT TGCACCCTGA GAGACTGTGC    47100

ACTGCTGTAA GGGCAGCTGG TCAGGCTGTG GGCGATGGGT TTATCAGCAG CAAGCGGGCG    47160

GGAGAGGGAC GCAGGCGGAC GCCTGACTTC GGTGCCTGGA GTGGCTCTTG GTTCCCTGGC    47220

TCCCAGCACC ACTCCCACTC TCGTTTGGGG TAGGGTCTTC CGGCTTTTTG TCGGGGGAC    47280

CCTGTGACCC AAGAGGCTCA AGAAACTGCC CGCCCAGGTT AACATGGGCT TGGCTGCAAC    47340

TGCCTCCTGG AGGCCGGGAT GAATTCACAG CCTACCATGT CCCTCAGGTC CAGCACTCCT    47400

GGGGAGAAGA CAGAGACGCT GGCGCTGCAG AGGCTGGGGG AGCTGGGGCC ACCCAGCCCA    47460

GGCCTGAACT GGGAACAGCC CCAGGCAGCG AGGCTGTCCA GGACAGGTGT GCTTGCGTAG    47520

CCCCGGGATG CCCCTAGCCC CTCCCTGTGA GCTGCCTCTC ACAGGTCTGT CTCTGCTTCC    47580

CCAGGACTGG TGGAGGGTCT GCGGAAGCGC CTGCTGCCGG CCTGGTGTGC CTCCCTGGCC    47640

CACGGGCTCA GCCTGCTCCT GGTGGCTGTG GCTGTGGCTG TCTCAGGGTG GGTGGGTGCG    47700

AGCTTCCCCC CGGGCGTGAG TGTTGCGTGG CTCCTGTCCA GCAGCGCCAG CTTCCTGGCC    47760

TCATTCCTCG GCTGGGAGCC ACTGAAGGTG AGGGGGCTGC CAGGGGTAGG CTACAGGCCT    47820

CCATCACGGG GGACCCCTCT GAAGCCACCC CCTCCCCAGG TCTTGCTGGA AGCCCTGTAC    47880

TTCTCACTGG TGGCCAAGCG GCTGCACCCG GATGAAGATG ACACCCTGGT AGAGAGCCCG    47940

GCTGTGACGC CTGTGAGCGC ACGTGTGCCC CGCGTACGGC CACCCCACGG CTTTGCACTC    48000

TTCCTGGCCA AGGAAGAAGC CCGCAAGGTC AAGAGGCTAC ATGGCATGCT GCGGGTGAGC    48060

CTGGGTGCGG CCTGTGCCCC TGCCACCTCC GTCTCTTGTC TCCCACCTCC CACCCATGCA    48120

CGCAGGACAC TCCTGTCCCC CTTTCCTCAC CTCAGAAGGC CCTTAGGGGT TCAATGCTCT    48180

GCAGCCTTTG CCCGGTCTCC CTCCTACCCC ACGCCCCCCA CTTGCTGCCC CAGTCCCTGC    48240

CAGGGCCCAG CTCCAATGCC CACTCCTGCC TGGCCCTGAA GGCCCCTAAG CACCACTGCA    48300

GTGGCCTGTG TGTCTGCCCC CAGGTGGGGT TCCGGGCAGG GTGTGTGCTG CCATTACCCT    48360

GGCCAGGTAG AGTCTTGGGG CGCCCCCTGC CAGCTCACCT TCCTGCAGCC ACACCTGCCG    48420

CAGCCATGGC TCCAGCCGTT GCCAAAGCCC TGCTGTCACT GTGGGCTGGG GCCAGGCTGA    48480

CCACAGGGCC CCCCCGTCCA CCAGAGCCTC CTGGTGTACA TGCTTTTTCT GCTGGTGACC    48540

CTGCTGGCCA GCTATGGGGA TGCCTCATGC CATGGGCACG CCTACCGTCT GCAAAGCGCC    48600

ATCAAGCAGG AGCTGCACAG CCGGGCCTTC CTGGCCATCA CGCGGTACGG GCATCCGGTG    48660

CACTGGTCTG TCTTCTGGGC TTTAGTTTTG CCTTTAGTCC AGCCAGACCC TAGGGGACAT    48720

GTGGACATGT GTAGATACCT TTGTGGCTGC TAGAACTGGA GGTAGGTGCT GCTGGCATCA    48780
```

```
GTAGGCAGAG GGGAGGGACA CAGGTCCGTG TCTTGCAGTG CACAGGACGG GCCCATGACA    48840

GACAACTGTC TGCCCCAGAA CATCCCCAGG ATAAGGCTGA GAAGCCCAGG TCTAGCCGTG    48900

GCCAGCAGGG CAGTGGGAGC CATGTTCCCT GGGTCTCTGG TGGCCGCTCA CTCGAGGCGG    48960

GCATGGGGCA GTAGGGGCTG GAGCGTGTGA CTGATGCTGT GGCAGGTCTG AGGAGCTCTG    49020

GCCATGGATG GCCCACGTGC TGCTGCCCTA CGTCCACGGG AACCAGTCCA GCCCAGAGCT    49080

GGGGCCCCCA CGGCTGCGGC AGGTGCGGCT GCAGGAAGGT GAGCTGGCAG GGCGTGCCCC    49140

AAGACTTAAA TCGTTCCTCT TGTTGAGAGA GCAGCCTTTA GCGGAGCTCT GGCATCAGCC    49200

CTGCTCCCTA GCTGTGTGAC CTTTGCCCTC TTAACACCGC CGTTTCCTTC TCTGTATATG    49260

AGAGATGGTA ACGTTGTCTA ATTGATGGCT GCTGGGAGGG TTCCCTGGGG TGGCGCCGAA    49320

CCAGAGCTCA GGCGAGCTGG CCAGCAGGAA ACACTCCTGT TGGGTTTTGA TGAGGCCCTG    49380

GCCCCGGCCT GGGGCTCTGT GTGTTTCAGC ACTCTACCCA GACCCTCCCG GCCCCAGGGT    49440

CCACACGTGC TCGGCCGCAG GAGGCTTCAG CACCAGCGAT TACGACGTTG CTGGGAGAG    49500

TCCTCACAAT GGCTCGGGGA CGTGGGCCTA TTCAGCGCCG GATCTGCTGG GGTGAGCAGA    49560

GCGAGGGCCC CGGGCGTCTA CGCCAAGGAC AAGGGAGTAG TTCTCCAGGA GTGCCGCGGC    49620

CTCCTGACCA GCCTGGCTCC GGGGTGCCGG AAGGGCTGGG GTGCGGCACC CACGCCACCC    49680

CTCTCCGGCA GGGCATGGTC CTGGGGCTCC TGTGCCGTGT ATGACAGCGG GGGCTACGTG    49740

CAGGAGCTGG GCCTGAGCCT GGAGGAGAGC CGCGACCGGC TGCGCTTCCT GCAGCTGCAC    49800

AACTGGCTGG ACAACAGGTG GGAGCTCCCT CCCCTGCCCT CTCCGGGGTG GCCGCAGTCA    49860

CCAGCCAGGA GCCCACCCTC ACTCCTCCGG CCCCGCTGG CCTAGGCGGC TTCCACAGCC    49920

CCTCAGCCAC GCCTGCACTG CGCGGTCCCC GCAGCTCCCG CCCTGCCACC CGCTCCTACT    49980

GACCCGCACC CTCTGCGCAG GAGCCGCGCT GTGTTCCTGG AGCTCACGCG CTACAGCCCG    50040

GCCGTGGGGC TGCACGCCGC CGTCACGCTG CGCCTCGAGT TCCCGGCGGC CGGCCGCGCC    50100

CTGGCCGCCC TCAGCGTCCG CCCCTTTGCG CTGCGCCGCC TCAGCGCGGG CCTCTCGCTG    50160

CCTCTGCTCA CCTCGGTACG CCCGTCCCCG GCCAGACCCC GCGCCTCCCA CCGGCAGCGT    50220

CCCGCCCCCT CGCGGGGCCC CGCCCGGCAG CGTCTCACCC CTCGCAGCGC CCCGCCCCCT    50280

CGCAGCGTCC CGCCCCCTCG CAGGGCCCCG CCCCGGCAGC GTCCCGCCCC CTCGTAGGGC    50340

CCCGCCCCGG CAGCGTCCCG CCCCCTCGCA GGGCCCCGCC CCGGCAGCGT CCCTCCCGCC    50400

CTCCTGACCG CGCCCCCCAC AGGTGTGCCT GCTGCTGTTC GCCGTGCACT TCGCCGTGGC    50460

CGAGGCCCGT ACTTGGCACA GGGAAGGGCG CTGGCGCGTG CTGCGGCTCG GAGCCTGGGC    50520

GCGGTGGCTG CTGGTGGCGC TGACGGCGGC CACGGCACTG GTACGCCTCG CCCAGCTGGG    50580

TGCCGCTGAC CGCCAGTGGA CCCGTTTCGT GCGCGGCCGC CCGCGCCGCT TCACTAGCTT    50640

CGACCAGGTG GCGCAGCTGA GCTCCGCAGC CCGTGGCCTG GCGGCCTCGC TGCTCTTCCT    50700

GCTTTTGGTC AAGGTGAGGG CTGGGCCGGT GGGCGCGGGG CTGGGCGCAC ACCCCAGGGC    50760

TGCAAGCAGA CAGATTTCTC GTCCGCAGGC TGCCCAGCAG CTACGCTTCG TGCGCCAGTG    50820

GTCCGTCTTT GGCAAGACAT TATGCCGAGC TCTGCCAGAG CTCCTGGGGG TCACCTTGGG    50880

CCTGGTGGTC CTCGGGGTAG CCTACGCCCA GCTGGCCATC CTGGTAGGTG ACTGCGCGGC    50940

CGGGGAGGGC GTCTTAGCTC AGCTCAGCTC AGCTGTACGC CCTCACTGGT GTCGCCTTCC    51000

CCGCAGCTCG TGTCTTCCTG TGTGGACTCC CTCTGGAGCG TGGCCCAGGC CCTGTTGGTG    51060

CTGTGCCCTG GGACTGGGCT CTCTACCCTG TGTCCTGCCG AGTCCTGGCA CCTGTCACCC    51120
```

```
CTGCTGTGTG TGGGGCTCTG GGCACTGCGG CTGTGGGGCG CCCTACGGCT GGGGGCTGTT    51180
ATTCTCCGCT GGCGCTACCA CGCCTTGCGT GGAGAGCTGT ACCGGCCGGC CTGGGAGCCC    51240
CAGGACTACG AGATGGTGGA GTTGTTCCTG CGCAGGCTGC GCCTCTGGAT GGGCCTCAGC    51300
AAGGTCAAGG AGGTGGGTAC GGCCCAGTGG GGGGGAGAGG GACACGCCCT GGGCTCTGCC    51360
CAGGGTGCAG CCGGACTGAC TGAGCCCCTG TGCCGCCCCC AGTTCCGCCA CAAAGTCCGC    51420
TTTGAAGGGA TGGAGCCGCT GCCCTCTCGC TCCTCCAGGG GCTCCAAGGT ATCCCCGGAT    51480
GTGCCCCCAC CCAGCGCTGG CTCCGATGCC TCGCACCCCT CCACCTCCTC CAGCCAGCTG    51540
GATGGGCTGA GCGTGAGCCT GGGCCGGCTG GGACAAGGT GTGAGCCTGA GCCCTCCCGC    51600
CTCCAAGCCG TGTTCGAGGC CCTGCTCACC CAGTTTGACC GACTCAACCA GGCCACAGAG    51660
GACGTCTACC AGCTGGAGCA GCAGCTGCAC AGCCTGCAAG GCCGCAGGAG CAGCCGGGCG    51720
CCCGCCGGAT CTTCCCGTGG CCCATCCCCG GGCCTGCGGC CAGCACTGCC CAGCCGCCTT    51780
GCCCGGGCCA GTCGGGGTGT GGACCTGGCC ACTGGCCCCA GCAGGACACC CCTTCGGGCC    51840
AAGAACAAGG TCCACCCCAG CAGCACTTAG TCCTCCTTCC TGGCGGGGGT GGGCCGTGGA    51900
GTCGGAGTGG ACACCGCTCA GTATTACTTT CTGCCGCTGT CAAGGCCGAG GGCCAGGCAG    51960
AATGGCTGCA CGTAGGTTCC CCAGAGAGCA GGCAGGGGCA TCTGTCTGTC TGTGGGCTTC    52020
AGCACTTTAA AGAGGCTGTG TGGCCAACCA GGACCCAGGG TCCCCTCCCC AGCTCCCTTG    52080
GGAAGGACAC AGCAGTATTG GACGGTTTCT AGCCTCTGAG ATGCTAATTT ATTTCCCCGA    52140
GTCCTCAGGT ACAGCGGGCT GTGCCCGGCC CCACCCCCTG GGCAGATGTC CCCCACTGCT    52200
AAGGCTGCTG GCTTCAGGGA GGGTTAGCCT GCACCGCCGC CACCCTGCCC CTAAGTTATT    52260
ACCTCTCCAG TTCCTACCGT ACTCCCTGCA CCGTCTCACT GTGTGTCTCG TGTCAGTAAT    52320
TTATATGGTG TTAAAATGTG TATATTTTTG TATGTCACTA TTTTCACTAG GGCTGAGGGG    52380
CCTGCGCCCA GAGCTGGCCT CCCCCAACAC CTGCTGCGCT TGGTAGGTGT GGTGGCGTTA    52440
TGGCAGCCCG GCTGCTGCTT GGATGCGAGC TTGGCCTTGG GCCGGTGCTG GGGGCACAGC    52500
TGTCTGCCAG GCACTCTCAT CACCCCAGAG GCCTTGTCAT CCTCCCTTGC CCCAGGCCAG    52560
GTAGCAAGAG AGCAGCGCCC AGGCCTGCTG GCATCAGGTC TGGGCAAGTA GCAGGACTAG    52620
GCATGTCAGA GGACCCCAGG GTGGTTAGAG GAAAAGACTC CTCCTGGGGG CTGGCTCCCA    52680
GGGTGGAGGA AGGTGACTGT GTGTGTGTGT GTGTGCGCGC GCGCACGCGC GAGTGTGCTG    52740
TATGGCCCAG GCAGCCTCAA GGCCCTCGGA GCTGGCTGTG CCTGCTTCTG TGTACCACTT    52800
CTGTGGGCAT GGCCGCTTCT AGAGCCTCGA CACCCCCCCA ACCCCGCAC CAAGCAGACA    52860
AAGTCAATAA AAGAGCTGTC TGACTGCAAT CTGTGCCTCT ATGTCTGTGC ACTGGGGTCA    52920
GGACTTTATT TATTTCACTG ACAGGCAATA CCGTCCAAGG CCAGTGCAGG AGGGAGGGCC    52980
CCGGCCTCAC ACAAACTCGG TGAAGTCCTC CACCGAGGAG ATGAGGCGCT TCCGCTGGCC    53040
CACCTCATAG CCAGGTGTGG GCTCGGCTGG AGTCTGTGCA GGGGCTTTGC TATGGGACGG    53100
AGGGTGCACC AGAGGTAGGC TGGGGTTGGA GTAGGCGGCT TCCTCGCAGA TCTGAAGGCA    53160
GAGGCGGCTT GGGCAGTAAG TCTGGGAGGC GTGGCAACCG CTCTGCCCAC ACACCCGCCC    53220
CACAGCTTGG GCAGCCAGCA CACCCCGCTG AGGGAGCCCC ATATTCCCTA CCCGCTGGCG    53280
GAGCGCTTGA TGTGGCGGAG CGGGCAATCC ACTTGGAGGG GTAGATATCG GTGGGGTTGG    53340
AGCGGCTATG ATGCACCTGT GAGGCCATCT GGGGACGTAG GCAGGGGGTG AGCTCACTAT    53400
CAGGTGGCAC CTGGGCCTGT CCCACCAGCT CACGCCTGGA CCCACCCCCA CTCACATTTG    53460
CGTGCAGGGC CATCTGGCGG GCCACGAAGG GCAGGTTGCG GTCAGACACG ATCTTGGCCA    53520
```

| | |
|---|---|
| CGCTGG | 53526 |

(2) INFORMATION FOR SEQ ID NO:3:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | |
|---|---:|
| GGTGTGAGGG GTAGGGGCAG GGTGGGAGGT GGGCTCGCGG GTGGGCTGGG GTCATGAAGG | 60 |
| GCCTCAGGCG CTCTGCTATT GGGTTCCAAG GCTATCCTGA AACAGGGGT GAGGGGGAT | 120 |
| TGCCGTGGGG GGTTAAAGCC TTGTCATGTT CGCTTTCGGG AGATAAAAAC AACAGGTGGC | 180 |
| CTTTATGGAG ACGCTGCCCA GAGCCAGGTC TGTGCCAGGC TCCTGTTGGG GGTCGTCATG | 240 |
| CGGAATCCTG ACTCTGACCA TCCGAGGCAT AGGGACCGTG GAGATTTGCA TTTCACAGAT | 300 |
| GAGGAAACAG GTTTGGAGAG GTGACACGAC CTGTCCCAGG CATCACAGCC GGGATGTGCA | 360 |
| TAGCAGGGGT TTGGAACTAT GAGGTGCCCA GGACCCAGGG TTGGATTGAA AAGGGCGGAG | 420 |
| GGGACTAAGA TAAGCAGACA GTTGTCCCCA GCGCTGGGGA GAGTCTTGGG ACCAGTCTGA | 480 |
| TGCCTTGTAT TTCCCAGGCT CCAGGCTCCT CGCCGGACA GTGTCTCCTT GGGTGCGTGC | 540 |
| TGGATCCCTG GGGGACGTGG CACATCCCCA GGCTTGCTAA ACATTGGGTG GGTTCTGGCA | 600 |
| TTTGGTTTTG TAACGTTTCT GGGTCACTCC CGCCTGTGGC CACCCTTCCT TAGGGGAGCC | 660 |
| GTGTGTCCTT GGGGCTTTGC TGGGTGGTCT CGAGGGTGGG AGAAGAATGG GTTCTCCTGG | 720 |
| ACCAATGGAG CCCGTGCCCC TCGGGCCAC ATTGCTCCTG CGCTCCCTGA CTGCGGACGC | 780 |
| GTGTGTCTCG CGGCTGTCTC TGTGGAGATG GCCTCCTCCT GCCTGGCAAC AGCACCCACA | 840 |
| GAATTGCATC AGACCTACCC CACCCGTTGT TTGTGATGCT GTAGCTGAGG GCTC | 894 |

(2) INFORMATION FOR SEQ ID NO:4:

(i) SEQUENCE CHARACTERISTICS:
        (A) LENGTH: 14060 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 135..13040

(xi) SEQUENCE DESCRIPTION: SEQ ID NO:4:

| | |
|---|---:|
| GCTCAGCAGC AGGTCGCGGC CGCAGCCCCA TCCAGCCCGC GCCCGCCATG CCGTCCGCGG | 60 |
| GCCCCGCCTG AGCTGCGGCC TCCGCGCGCG GGCGGGCCTG GGGACGGCGG GGCCATGCGC | 120 |

| GCGCTGCCCT AACG ATG CCG CCC GCC GCG CCC GCC CGC CTG GCG CTG GCC | 170 |
|---|---:|
|               Met Pro Pro Ala Ala Pro Ala Arg Leu Ala Leu Ala | |
|                1                5                   10 | |

| CTG GGC CTG GGC CTG TGG CTC GGG GCG CTG GCG GGG GGC CCC GGG CGC | 218 |
|---|---:|
| Leu Gly Leu Gly Leu Trp Leu Gly Ala Leu Ala Gly Gly Pro Gly Arg | |
|  15               20                  25 | |

| GGC TGC GGG CCC TGC GAG CCC CCC TGC CTC TGC GGC CCA GCG CCC GGC | 266 |
|---|---:|
| Gly Cys Gly Pro Cys Glu Pro Pro Cys Leu Cys Gly Pro Ala Pro Gly | |
|      30                  35                  40 | |

```
GCC GCC TGC CGC GTC AAC TGC TCG GGC CGC GGG CTG CGG ACG CTC GGT        314
Ala Ala Cys Arg Val Asn Cys Ser Gly Arg Gly Leu Arg Thr Leu Gly
 45              50                  55                  60

CCC GCG CTG CGC ATC CCC GCG GAC GCC ACA GCG CTA GAC GTC TCC CAC        362
Pro Ala Leu Arg Ile Pro Ala Asp Ala Thr Ala Leu Asp Val Ser His
                 65                  70                  75

AAC CTG CTC CGG GCG CTG GAC GTT GGG CTC CTG GCG AAC CTC TCG GCG        410
Asn Leu Leu Arg Ala Leu Asp Val Gly Leu Leu Ala Asn Leu Ser Ala
             80                  85                  90

CTG GCA GAG CTG GAT ATA AGC AAC AAC AAG ATT TCT ACG TTA GAA GAA        458
Leu Ala Glu Leu Asp Ile Ser Asn Asn Lys Ile Ser Thr Leu Glu Glu
         95                 100                 105

GGA ATA TTT GCT AAT TTA TTT AAT TTA AGT GAA ATA AAC CTG AGT GGG        506
Gly Ile Phe Ala Asn Leu Phe Asn Leu Ser Glu Ile Asn Leu Ser Gly
    110                 115                 120

AAC CCG TTT GAG TGT GAC TGT GGC CTG GCG TGG CTG CCG CGA TGG GCG        554
Asn Pro Phe Glu Cys Asp Cys Gly Leu Ala Trp Leu Pro Arg Trp Ala
125                 130                 135                 140

GAG GAG CAG CAG GTG CGG GTG GTG CAG CCC GAG GCA GCC ACG TGT GCT        602
Glu Glu Gln Gln Val Arg Val Val Gln Pro Glu Ala Ala Thr Cys Ala
                145                 150                 155

GGG CCT GGC TCC CTG GCT GGC CAG CCT CTG CTT GGC ATC CCC TTG CTG        650
Gly Pro Gly Ser Leu Ala Gly Gln Pro Leu Leu Gly Ile Pro Leu Leu
            160                 165                 170

GAC AGT GGC TGT GGT GAG GAG TAT GTC GCC TGC CTC CCT GAC AAC AGC        698
Asp Ser Gly Cys Gly Glu Glu Tyr Val Ala Cys Leu Pro Asp Asn Ser
        175                 180                 185

TCA GGC ACC GTG GCA GCA GTG TCC TTT TCA GCT GCC CAC GAA GGC CTG        746
Ser Gly Thr Val Ala Ala Val Ser Phe Ser Ala Ala His Glu Gly Leu
    190                 195                 200

CTT CAG CCA GAG GCC TGC AGC GCC TTC TGC TTC TCC ACC GGC CAG GGC        794
Leu Gln Pro Glu Ala Cys Ser Ala Phe Cys Phe Ser Thr Gly Gln Gly
205                 210                 215                 220

CTC GCA GCC CTC TCG GAG CAG GGC TGG TGC CTG TGT GGG GCG GCC CAG        842
Leu Ala Ala Leu Ser Glu Gln Gly Trp Cys Leu Cys Gly Ala Ala Gln
                225                 230                 235

CCC TCC AGT GCC TCC TTT GCC TGC CTG TCC CTC TGC TCC GGC CCC CCG        890
Pro Ser Ser Ala Ser Phe Ala Cys Leu Ser Leu Cys Ser Gly Pro Pro
            240                 245                 250

CCA CCT CCT GCC CCC ACC TGT AGG GGC CCC ACC CTC CTC CAG CAC GTC        938
Pro Pro Pro Ala Pro Thr Cys Arg Gly Pro Thr Leu Leu Gln His Val
        255                 260                 265

TTC CCT GCC TCC CCA GGG GCC ACC CTG GTG GGG CCC CAC GGA CCT CTG        986
Phe Pro Ala Ser Pro Gly Ala Thr Leu Val Gly Pro His Gly Pro Leu
    270                 275                 280

GCC TCT GGC CAG CTA GCA GCC TTC CAC ATC GCT GCC CCG CTC CCT GTC       1034
Ala Ser Gly Gln Leu Ala Ala Phe His Ile Ala Ala Pro Leu Pro Val
285                 290                 295                 300

ACT GCC ACA CGC TGG GAC TTC GGA GAC GGC TCC GCC GAG GTG GAT GCC       1082
Thr Ala Thr Arg Trp Asp Phe Gly Asp Gly Ser Ala Glu Val Asp Ala
                305                 310                 315

GCT GGG CCG GCT GCC TCG CAT CGC TAT GTG CTG CCT GGG CGC TAT CAC       1130
Ala Gly Pro Ala Ala Ser His Arg Tyr Val Leu Pro Gly Arg Tyr His
            320                 325                 330

GTG ACG GCC GTG CTG GCC CTG GGG GCC GGC TCA GCC CTG CTG GGG ACA       1178
Val Thr Ala Val Leu Ala Leu Gly Ala Gly Ser Ala Leu Leu Gly Thr
        335                 340                 345

GAC GTG CAG GTG GAA GCG GCA CCT GCC GCC CTG GAG CTC GTG TGC CCG       1226
Asp Val Gln Val Glu Ala Ala Pro Ala Ala Leu Glu Leu Val Cys Pro
    350                 355                 360
```

```
TCC TCG GTG CAG AGT GAC GAG AGC CTC GAC CTC AGC ATC CAG AAC CGC    1274
Ser Ser Val Gln Ser Asp Glu Ser Leu Asp Leu Ser Ile Gln Asn Arg
365             370                 375                 380

GGT GGT TCA GGC CTG GAG GCC GCC TAC AGC ATC GTG GCC CTG GGC GAG    1322
Gly Gly Ser Gly Leu Glu Ala Ala Tyr Ser Ile Val Ala Leu Gly Glu
                385                 390                 395

GAG CCG GCC CGA GCG GTG CAC CCG CTC TGC CCC TCG GAC ACG GAG ATC    1370
Glu Pro Ala Arg Ala Val His Pro Leu Cys Pro Ser Asp Thr Glu Ile
            400                 405                 410

TTC CCT GGC AAC GGG CAC TGC TAC CGC CTG GTG GTG GAG AAG GCG GCC    1418
Phe Pro Gly Asn Gly His Cys Tyr Arg Leu Val Val Glu Lys Ala Ala
        415                 420                 425

TGG CTG CAG GCG CAG GAG CAG TGT CAG GCC TGG GCC GGG GCC GCC CTG    1466
Trp Leu Gln Ala Gln Glu Gln Cys Gln Ala Trp Ala Gly Ala Ala Leu
    430                 435                 440

GCA ATG GTG GAC AGT CCC GCC GTG CAG CGC TTC CTG GTC TCC CGG GTC    1514
Ala Met Val Asp Ser Pro Ala Val Gln Arg Phe Leu Val Ser Arg Val
445                 450                 455                 460

ACC AGG TGC CTA GAC GTG TGG ATC GGC TTC TCG ACT GTG CAG GGG GTG    1562
Thr Arg Cys Leu Asp Val Trp Ile Gly Phe Ser Thr Val Gln Gly Val
                465                 470                 475

GAG GTG GGC CCA GCG CCG CAG GGC GAG GCC TTC AGC CTG GAG AGC TGC    1610
Glu Val Gly Pro Ala Pro Gln Gly Glu Ala Phe Ser Leu Glu Ser Cys
            480                 485                 490

CAG AAC TGG CTG CCC GGG GAG CCA CAC CCA GCC ACA GCC GAG CAC TGC    1658
Gln Asn Trp Leu Pro Gly Glu Pro His Pro Ala Thr Ala Glu His Cys
        495                 500                 505

GTC CGG CTC GGG CCC ACC GGG TGG TGT AAC ACC GAC CTG TGC TCA GCG    1706
Val Arg Leu Gly Pro Thr Gly Trp Cys Asn Thr Asp Leu Cys Ser Ala
    510                 515                 520

CCG CAC AGC TAC GTC TGC GAG CTG CAG CCC GGA GGC CCA GTG CAG GAT    1754
Pro His Ser Tyr Val Cys Glu Leu Gln Pro Gly Gly Pro Val Gln Asp
525                 530                 535                 540

GCC GAG AAC CTC CTC GTG GGA GCG CCC AGT GGG GAC CTG CAG GGA CCC    1802
Ala Glu Asn Leu Leu Val Gly Ala Pro Ser Gly Asp Leu Gln Gly Pro
                545                 550                 555

CTG ACG CCT CTG GCA CAG CAG GAC GGC CTC TCA GCC CCG CAC GAG CCC    1850
Leu Thr Pro Leu Ala Gln Gln Asp Gly Leu Ser Ala Pro His Glu Pro
            560                 565                 570

GTG GAG GTC ATG GTA TTC CCG GGC CTG CGT CTG AGC CGT GAA GCC TTC    1898
Val Glu Val Met Val Phe Pro Gly Leu Arg Leu Ser Arg Glu Ala Phe
        575                 580                 585

CTC ACC ACG GCC GAA TTT GGG ACC CAG GAG CTC CGG CGG CCC GCC CAG    1946
Leu Thr Thr Ala Glu Phe Gly Thr Gln Glu Leu Arg Arg Pro Ala Gln
    590                 595                 600

CTG CGG CTG CAG GTG TAC CGG CTC CTC AGC ACA GCA GGG ACC CCG GAG    1994
Leu Arg Leu Gln Val Tyr Arg Leu Leu Ser Thr Ala Gly Thr Pro Glu
605                 610                 615                 620

AAC GGC AGC GAG CCT GAG AGC AGG TCC CCG GAC AAC AGG ACC CAG CTG    2042
Asn Gly Ser Glu Pro Glu Ser Arg Ser Pro Asp Asn Arg Thr Gln Leu
                625                 630                 635

GCC CCC GCG TGC ATG CCA GGG GGA CGC TGG TGC CCT GGA GCC AAC ATC    2090
Ala Pro Ala Cys Met Pro Gly Gly Arg Trp Cys Pro Gly Ala Asn Ile
            640                 645                 650

TGC TTG CCG CTG GAC GCC TCC TGC CAC CCC CAG GCC TGC GCC AAT GGC    2138
Cys Leu Pro Leu Asp Ala Ser Cys His Pro Gln Ala Cys Ala Asn Gly
        655                 660                 665

TGC ACG TCA GGG CCA GGG CTA CCC GGG GCC CCC TAT GCG CTA TGG AGA    2186
Cys Thr Ser Gly Pro Gly Leu Pro Gly Ala Pro Tyr Ala Leu Trp Arg
```

```
                670                 675                 680
GAG TTC CTC TTC TCC GTT CCC GCG GGG CCC CCC GCG CAG TAC TCG GTC      2234
Glu Phe Leu Phe Ser Val Pro Ala Gly Pro Pro Ala Gln Tyr Ser Val
685                 690                 695                 700

ACC CTC CAC GGC CAG GAT GTC CTC ATG CTC CCT GGT GAC CTC GTT GGC      2282
Thr Leu His Gly Gln Asp Val Leu Met Leu Pro Gly Asp Leu Val Gly
                705                 710                 715

TTG CAG CAC GAC GCT GGC CCT GGC GCC CTC CTG CAC TGC TCG CCG GCT      2330
Leu Gln His Asp Ala Gly Pro Gly Ala Leu Leu His Cys Ser Pro Ala
                720                 725                 730

CCC GGC CAC CCT GGT CCC CGG GCC CCG TAC CTC TCC GCC AAC GCC TCG      2378
Pro Gly His Pro Gly Pro Arg Ala Pro Tyr Leu Ser Ala Asn Ala Ser
                735                 740                 745

TCA TGG CTG CCC CAC TTG CCA GCC CAG CTG GAG GGC ACT TGG GCC TGC      2426
Ser Trp Leu Pro His Leu Pro Ala Gln Leu Glu Gly Thr Trp Ala Cys
        750                 755                 760

CCT GCC TGT GCC CTG CGG CTG CTT GCA GCC ACG GAA CAG CTC ACC GTG      2474
Pro Ala Cys Ala Leu Arg Leu Leu Ala Ala Thr Glu Gln Leu Thr Val
765                 770                 775                 780

CTG CTG GGC TTG AGG CCC AAC CCT GGA CTG CGG CTG CCT GGG CGC TAT      2522
Leu Leu Gly Leu Arg Pro Asn Pro Gly Leu Arg Leu Pro Gly Arg Tyr
                785                 790                 795

GAG GTC CGG GCA GAG GTG GGC AAT GGC GTG TCC AGG CAC AAC CTC TCC      2570
Glu Val Arg Ala Glu Val Gly Asn Gly Val Ser Arg His Asn Leu Ser
                800                 805                 810

TGC AGC TTT GAC GTG GTC TCC CCA GTG GCT GGG CTG CGG GTC ATC TAC      2618
Cys Ser Phe Asp Val Val Ser Pro Val Ala Gly Leu Arg Val Ile Tyr
        815                 820                 825

CCT GCC CCC CGA GAC GGC CGC CTC TAC GTG CCC ACC AAC GGC TCA GCC      2666
Pro Ala Pro Arg Asp Gly Arg Leu Tyr Val Pro Thr Asn Gly Ser Ala
830                 835                 840

TTG GTG CTC CAG GTG GAC TCT GGT GCC AAC GCC ACG GCC ACG GCT CGC      2714
Leu Val Leu Gln Val Asp Ser Gly Ala Asn Ala Thr Ala Thr Ala Arg
845                 850                 855                 860

TGG CCT GGG GGC AGT GTC AGC GCC CGC TTT GAG AAT GTC TGC CCT GCC      2762
Trp Pro Gly Gly Ser Val Ser Ala Arg Phe Glu Asn Val Cys Pro Ala
                865                 870                 875

CTG GTG GCC ACC TTC GTG CCC GGC TGC CCC TGG GAG ACC AAC GAT ACC      2810
Leu Val Ala Thr Phe Val Pro Gly Cys Pro Trp Glu Thr Asn Asp Thr
                880                 885                 890

CTG TTC TCA GTG GTA GCA CTG CCG TGG CTC AGT GAG GGG GAG CAC GTG      2858
Leu Phe Ser Val Val Ala Leu Pro Trp Leu Ser Glu Gly Glu His Val
        895                 900                 905

GTG GAC GTG GTG GTG GAA AAC AGC GCC AGC CGG GCC AAC CTC AGC CTG      2906
Val Asp Val Val Val Glu Asn Ser Ala Ser Arg Ala Asn Leu Ser Leu
910                 915                 920

CGG GTG ACG GCG GAG GAG CCC ATC TGT GGC CTC CGC GCC ACG CCC AGC      2954
Arg Val Thr Ala Glu Glu Pro Ile Cys Gly Leu Arg Ala Thr Pro Ser
925                 930                 935                 940

CCC GAG GCC CGT GTA CTG CAG GGA GTC CTA GTG AGG TAC AGC CCC GTG      3002
Pro Glu Ala Arg Val Leu Gln Gly Val Leu Val Arg Tyr Ser Pro Val
                945                 950                 955

GTG GAG GCC GGC TCG GAC ATG GTC TTC CGG TGG ACC ATC AAC GAC AAG      3050
Val Glu Ala Gly Ser Asp Met Val Phe Arg Trp Thr Ile Asn Asp Lys
                960                 965                 970

CAG TCC CTG ACC TTC CAG AAC GTG GTC TTC AAT GTC ATT TAT CAG AGC      3098
Gln Ser Leu Thr Phe Gln Asn Val Val Phe Asn Val Ile Tyr Gln Ser
                975                 980                 985

GCG GCG GTC TTC AAG CTC TCA CTG ACG GCC TCC AAC CAC GTG AGC AAC      3146
```

```
        Ala Ala Val Phe Lys Leu Ser Leu Thr Ala Ser Asn His Val Ser Asn
            990                 995                 1000

GTC ACC GTG AAC TAC AAC GTA ACC GTG GAG CGG ATG AAC AGG ATG CAG            3194
Val Thr Val Asn Tyr Asn Val Thr Val Glu Arg Met Asn Arg Met Gln
1005                1010                1015                1020

GGT CTG CAG GTC TCC ACA GTG CCG GCC GTG CTG TCC CCC AAT GCC ACG            3242
Gly Leu Gln Val Ser Thr Val Pro Ala Val Leu Ser Pro Asn Ala Thr
                    1025                1030                1035

CTA GCA CTG ACG GCG GGC GTG CTG GTG GAC TCG GCC GTG GAG GTG GCC            3290
Leu Ala Leu Thr Ala Gly Val Leu Val Asp Ser Ala Val Glu Val Ala
                1040                1045                1050

TTC CTG TGG ACC TTT GGG GAT GGG GAG CAG GCC CTC CAC CAG TTC CAG            3338
Phe Leu Trp Thr Phe Gly Asp Gly Glu Gln Ala Leu His Gln Phe Gln
            1055                1060                1065

CCT CCG TAC AAC GAG TCC TTC CCG GTT CCA GAC CCC TCG GTG GCC CAG            3386
Pro Pro Tyr Asn Glu Ser Phe Pro Val Pro Asp Pro Ser Val Ala Gln
        1070                1075                1080

GTG CTG GTG GAG CAC AAT GTC ATG CAC ACC TAC GCT GCC CCA GGT GAG            3434
Val Leu Val Glu His Asn Val Met His Thr Tyr Ala Ala Pro Gly Glu
1085                1090                1095                1100

TAC CTC CTG ACC GTG CTG GCA TCT AAT GCC TTC GAG AAC CTG ACG CAG            3482
Tyr Leu Leu Thr Val Leu Ala Ser Asn Ala Phe Glu Asn Leu Thr Gln
                1105                1110                1115

CAG GTG CCT GTG AGC GTG CGC GCC TCC CTG CCC TCC GTG GCT GTG GGT            3530
Gln Val Pro Val Ser Val Arg Ala Ser Leu Pro Ser Val Ala Val Gly
            1120                1125                1130

GTG AGT GAC GGC GTC CTG GTG GCC GGC CGG CCC GTC ACC TTC TAC CCG            3578
Val Ser Asp Gly Val Leu Val Ala Gly Arg Pro Val Thr Phe Tyr Pro
        1135                1140                1145

CAC CCG CTG CCC TCG CCT GGG GGT GTT CTT TAC ACG TGG GAC TTC GGG            3626
His Pro Leu Pro Ser Pro Gly Gly Val Leu Tyr Thr Trp Asp Phe Gly
1150                1155                1160

GAC GGC TCC CCT GTC CTG ACC CAG AGC CAG CCG GCT GCC AAC CAC ACC            3674
Asp Gly Ser Pro Val Leu Thr Gln Ser Gln Pro Ala Ala Asn His Thr
1165                1170                1175                1180

TAT GCC TCG AGG GGC ACC TAC CAC GTG CGC CTG GAG GTC AAC AAC ACG            3722
Tyr Ala Ser Arg Gly Thr Tyr His Val Arg Leu Glu Val Asn Asn Thr
                1185                1190                1195

GTG AGC GGT GCG GCG GCC CAG GCG GAT GTG CGC GTC TTT GAG GAG CTC            3770
Val Ser Gly Ala Ala Ala Gln Ala Asp Val Arg Val Phe Glu Glu Leu
            1200                1205                1210

CGC GGA CTC AGC GTG GAC ATG AGC CTG GCC GTG GAG CAG GGC GCC CCC            3818
Arg Gly Leu Ser Val Asp Met Ser Leu Ala Val Glu Gln Gly Ala Pro
        1215                1220                1225

GTG GTG GTC AGC GCC GCG GTG CAG ACG GGC GAC AAC ATC ACG TGG ACC            3866
Val Val Val Ser Ala Ala Val Gln Thr Gly Asp Asn Ile Thr Trp Thr
1230                1235                1240

TTC GAC ATG GGG GAC GGC ACC GTG CTG TCG GGC CCG GAG GCA ACA GTG            3914
Phe Asp Met Gly Asp Gly Thr Val Leu Ser Gly Pro Glu Ala Thr Val
1245                1250                1255                1260

GAG CAT GTG TAC CTG CGG GCA CAG AAC TGC ACA GTG ACC GTG GGT GCG            3962
Glu His Val Tyr Leu Arg Ala Gln Asn Cys Thr Val Thr Val Gly Ala
                1265                1270                1275

GCC AGC CCC GCC GGC CAC CTG GCC CGG AGC CTG CAC GTG CTG GTC TTC            4010
Ala Ser Pro Ala Gly His Leu Ala Arg Ser Leu His Val Leu Val Phe
            1280                1285                1290

GTC CTG GAG GTG CTG CGC GTT GAA CCC GCC GCC TGC ATC CCC ACG CAG            4058
Val Leu Glu Val Leu Arg Val Glu Pro Ala Ala Cys Ile Pro Thr Gln
        1295                1300                1305
```

```
CCT GAC GCG CGG CTC ACG GCC TAC GTC ACC GGG AAC CCG GCC CAC TAC      4106
Pro Asp Ala Arg Leu Thr Ala Tyr Val Thr Gly Asn Pro Ala His Tyr
    1310                1315                1320

CTC TTC GAC TGG ACC TTC GGG GAT GGC TCC TCC AAC ACG ACC GTG CGG      4154
Leu Phe Asp Trp Thr Phe Gly Asp Gly Ser Ser Asn Thr Thr Val Arg
1325                1330                1335                1340

GGG TGC CCG ACG GTG ACA CAC AAC TTC ACG CGG AGC GGC ACG TTC CCC      4202
Gly Cys Pro Thr Val Thr His Asn Phe Thr Arg Ser Gly Thr Phe Pro
                1345                1350                1355

CTG GCG CTG GTG CTG TCC AGC CGC GTG AAC AGG GCG CAT TAC TTC ACC      4250
Leu Ala Leu Val Leu Ser Ser Arg Val Asn Arg Ala His Tyr Phe Thr
    1360                1365                1370

AGC ATC TGC GTG GAG CCA GAG GTG GGC AAC GTC ACC CTG CAG CCA GAG      4298
Ser Ile Cys Val Glu Pro Glu Val Gly Asn Val Thr Leu Gln Pro Glu
1375                1380                1385

AGG CAG TTT GTG CAG CTC GGG GAC GAG GCC TGG CTG GTG GCA TGT GCC      4346
Arg Gln Phe Val Gln Leu Gly Asp Glu Ala Trp Leu Val Ala Cys Ala
                1390                1395                1400

TGG CCC CCG TTC CCC TAC CGC TAC ACC TGG GAC TTT GGC ACC GAG GAA      4394
Trp Pro Pro Phe Pro Tyr Arg Tyr Thr Trp Asp Phe Gly Thr Glu Glu
1405                1410                1415                1420

GCC GCC CCC ACC CGT GCC AGG GGC CCT GAG GTG ACG TTC ATC TAC CGA      4442
Ala Ala Pro Thr Arg Ala Arg Gly Pro Glu Val Thr Phe Ile Tyr Arg
                1425                1430                1435

GAC CCA GGC TCC TAT CTT GTG ACA GTC ACC GCG TCC AAC AAC ATC TCT      4490
Asp Pro Gly Ser Tyr Leu Val Thr Val Thr Ala Ser Asn Asn Ile Ser
    1440                1445                1450

GCT GCC AAT GAC TCA GCC CTG GTG GAG GTG CAG GAG CCC GTG CTG GTC      4538
Ala Ala Asn Asp Ser Ala Leu Val Glu Val Gln Glu Pro Val Leu Val
1455                1460                1465

ACC AGC ATC AAG GTC AAT GGC TCC CTT GGG CTG GAG CTG CAG CAG CCG      4586
Thr Ser Ile Lys Val Asn Gly Ser Leu Gly Leu Glu Leu Gln Gln Pro
    1470                1475                1480

TAC CTG TTC TCT GCT GTG GGC CGT GGG CGC CCC GCC AGC TAC CTG TGG      4634
Tyr Leu Phe Ser Ala Val Gly Arg Gly Arg Pro Ala Ser Tyr Leu Trp
1485                1490                1495                1500

GAT CTG GGG GAC GGT GGG TGG CTC GAG GGT CCG GAG GTC ACC CAC GCT      4682
Asp Leu Gly Asp Gly Gly Trp Leu Glu Gly Pro Glu Val Thr His Ala
                1505                1510                1515

TAC AAC AGC ACA GGT GAC TTC ACC GTT AGG GTG GCC GGC TGG AAT GAG      4730
Tyr Asn Ser Thr Gly Asp Phe Thr Val Arg Val Ala Gly Trp Asn Glu
    1520                1525                1530

GTG AGC CGC AGC GAG GCC TGG CTC AAT GTG ACG GTG AAG CGG CGC GTG      4778
Val Ser Arg Ser Glu Ala Trp Leu Asn Val Thr Val Lys Arg Arg Val
1535                1540                1545

CGG GGG CTC GTC GTC AAT GCA AGC CGC ACG GTG GTG CCC CTG AAT GGG      4826
Arg Gly Leu Val Val Asn Ala Ser Arg Thr Val Val Pro Leu Asn Gly
    1550                1555                1560

AGC GTG AGC TTC AGC ACG TCG CTG GAG GCC GGC AGT GAT GTG CGC TAT      4874
Ser Val Ser Phe Ser Thr Ser Leu Glu Ala Gly Ser Asp Val Arg Tyr
1565                1570                1575                1580

TCC TGG GTG CTC TGT GAC CGC TGC ACG CCC ATC CCT GGG GGT CCT ACC      4922
Ser Trp Val Leu Cys Asp Arg Cys Thr Pro Ile Pro Gly Gly Pro Thr
                1585                1590                1595

ATC TCT TAC ACC TTC CGC TCC GTG GGC ACC TTC AAT ATC ATC GTC ACG      4970
Ile Ser Tyr Thr Phe Arg Ser Val Gly Thr Phe Asn Ile Ile Val Thr
    1600                1605                1610

GCT GAG AAC GAG GTG GGC TCC GCC CAG GAC AGC ATC TTC GTC TAT GTC      5018
Ala Glu Asn Glu Val Gly Ser Ala Gln Asp Ser Ile Phe Val Tyr Val
1615                1620                1625
```

```
CTG CAG CTC ATA GAG GGG CTG CAG GTG GTG GGC GGT GGC CGC TAC TTC       5066
Leu Gln Leu Ile Glu Gly Leu Gln Val Val Gly Gly Gly Arg Tyr Phe
         1630             1635              1640

CCC ACC AAC CAC ACG GTA CAG CTG CAG GCC GTG GTT AGG GAT GGC ACC       5114
Pro Thr Asn His Thr Val Gln Leu Gln Ala Val Val Arg Asp Gly Thr
1645              1650              1655              1660

AAC GTC TCC TAC AGC TGG ACT GCC TGG AGG GAC AGG GGC CCG GCC CTG       5162
Asn Val Ser Tyr Ser Trp Thr Ala Trp Arg Asp Arg Gly Pro Ala Leu
              1665              1670              1675

GCC GGC AGC GGC AAA GGC TTC TCG CTC ACC GTG CTC GAG GCC GGC ACC       5210
Ala Gly Ser Gly Lys Gly Phe Ser Leu Thr Val Leu Glu Ala Gly Thr
         1680             1685              1690

TAC CAT GTG CAG CTG CGG GCC ACC AAC ATG CTG GGC AGC GCC TGG GCC       5258
Tyr His Val Gln Leu Arg Ala Thr Asn Met Leu Gly Ser Ala Trp Ala
         1695             1700              1705

GAC TGC ACC ATG GAC TTC GTG GAG CCT GTG GGG TGG CTG ATG GTG GCC       5306
Asp Cys Thr Met Asp Phe Val Glu Pro Val Gly Trp Leu Met Val Ala
         1710             1715              1720

GCC TCC CCG AAC CCA GCT GCC GTC AAC ACA AGC GTC ACC CTC AGT GCC       5354
Ala Ser Pro Asn Pro Ala Ala Val Asn Thr Ser Val Thr Leu Ser Ala
1725              1730              1735              1740

GAG CTG GCT GGT GGC AGT GGT GTC GTA TAC ACT TGG TCC TTG GAG GAG       5402
Glu Leu Ala Gly Gly Ser Gly Val Val Tyr Thr Trp Ser Leu Glu Glu
              1745              1750              1755

GGG CTG AGC TGG GAG ACC TCC GAG CCA TTT ACC ACC CAT AGC TTC CCC       5450
Gly Leu Ser Trp Glu Thr Ser Glu Pro Phe Thr Thr His Ser Phe Pro
         1760             1765              1770

ACA CCC GGC CTG CAC TTG GTC ACC ATG ACG GCA GGG AAC CCG CTG GGC       5498
Thr Pro Gly Leu His Leu Val Thr Met Thr Ala Gly Asn Pro Leu Gly
         1775             1780              1785

TCA GCC AAC GCC ACC GTG GAA GTG GAT GTG CAG GTG CCT GTG AGT GGC       5546
Ser Ala Asn Ala Thr Val Glu Val Asp Val Gln Val Pro Val Ser Gly
1790              1795              1800

CTC AGC ATC AGG GCC AGC GAG CCC GGA GGC AGC TTC GTG GCG GCC GGG       5594
Leu Ser Ile Arg Ala Ser Glu Pro Gly Gly Ser Phe Val Ala Ala Gly
1805              1810              1815              1820

TCC TCT GTG CCC TTT TGG GGG CAG CTG GCC ACG GGC ACC AAT GTG AGC       5642
Ser Ser Val Pro Phe Trp Gly Gln Leu Ala Thr Gly Thr Asn Val Ser
              1825              1830              1835

TGG TGC TGG GCT GTG CCC GGC GGC AGC AGC AAG CGT GGC CCT CAT GTC       5690
Trp Cys Trp Ala Val Pro Gly Gly Ser Ser Lys Arg Gly Pro His Val
         1840             1845              1850

ACC ATG GTC TTC CCG GAT GCT GGC ACC TTC TCC ATC CGG CTC AAT GCC       5738
Thr Met Val Phe Pro Asp Ala Gly Thr Phe Ser Ile Arg Leu Asn Ala
         1855             1860              1865

TCC AAC GCA GTC AGC TGG GTC TCA GCC ACG TAC AAC CTC ACG GCG GAG       5786
Ser Asn Ala Val Ser Trp Val Ser Ala Thr Tyr Asn Leu Thr Ala Glu
         1870             1875              1880

GAG CCC ATC GTG GGC CTG GTG CTG TGG GCC AGC AGC AAG GTG GTG GCG       5834
Glu Pro Ile Val Gly Leu Val Leu Trp Ala Ser Ser Lys Val Val Ala
1885              1890              1895              1900

CCC GGG CAG CTG GTC CAT TTT CAG ATC CTG CTG GCT GCC GGC TCA GCT       5882
Pro Gly Gln Leu Val His Phe Gln Ile Leu Leu Ala Ala Gly Ser Ala
              1905              1910              1915

GTC ACC TTC CGC CTG CAG GTC GGC GGG GCC AAC CCC GAG GTG CTC CCC       5930
Val Thr Phe Arg Leu Gln Val Gly Gly Ala Asn Pro Glu Val Leu Pro
              1920              1925              1930

GGG CCC CGT TTC TCC CAC AGC TTC CCC CGC GTC GGA GAC CAC GTG GTG       5978
Gly Pro Arg Phe Ser His Ser Phe Pro Arg Val Gly Asp His Val Val
```

-continued

```
            1935                1940                1945
AGC GTG CGG GGC AAA AAC CAC GTG AGC TGG GCC CAG GCG CAG GTG CGC    6026
Ser Val Arg Gly Lys Asn His Val Ser Trp Ala Gln Ala Gln Val Arg
        1950                1955                1960

ATC GTG GTG CTG GAG GCC GTG AGT GGG CTG CAG GTG CCC AAC TGC TGC    6074
Ile Val Val Leu Glu Ala Val Ser Gly Leu Gln Val Pro Asn Cys Cys
1965                1970                1975                1980

GAG CCT GGC ATC GCC ACG GGC ACT GAG AGG AAC TTC ACA GCC CGC GTG    6122
Glu Pro Gly Ile Ala Thr Gly Thr Glu Arg Asn Phe Thr Ala Arg Val
            1985                1990                1995

CAG CGC GGC TCT CGG GTC GCC TAC GCC TGG TAC TTC TCG CTG CAG AAG    6170
Gln Arg Gly Ser Arg Val Ala Tyr Ala Trp Tyr Phe Ser Leu Gln Lys
        2000                2005                2010

GTC CAG GGC GAC TCG CTG GTC ATC CTG TCG GGC CGC GAC GTC ACC TAC    6218
Val Gln Gly Asp Ser Leu Val Ile Leu Ser Gly Arg Asp Val Thr Tyr
    2015                2020                2025

ACG CCC GTG GCC GCG GGG CTG TTG GAG ATC CAG GTG CGC GCC TTC AAC    6266
Thr Pro Val Ala Ala Gly Leu Leu Glu Ile Gln Val Arg Ala Phe Asn
        2030                2035                2040

GCC CTG GGC AGT GAG AAC CGC ACG CTG GTG CTG GAG GTT CAG GAC GCC    6314
Ala Leu Gly Ser Glu Asn Arg Thr Leu Val Leu Glu Val Gln Asp Ala
2045                2050                2055                2060

GTC CAG TAT GTG GCC CTG CAG AGC GGC CCC TGC TTC ACC AAC CGC TCG    6362
Val Gln Tyr Val Ala Leu Gln Ser Gly Pro Cys Phe Thr Asn Arg Ser
            2065                2070                2075

GCG CAG TTT GAG GCC GCC ACC AGC CCC AGC CCC CGG CGT GTG GCC TAC    6410
Ala Gln Phe Glu Ala Ala Thr Ser Pro Ser Pro Arg Arg Val Ala Tyr
        2080                2085                2090

CAC TGG GAC TTT GGG GAT GGG TCG CCA GGG CAG GAC ACA GAT GAG CCC    6458
His Trp Asp Phe Gly Asp Gly Ser Pro Gly Gln Asp Thr Asp Glu Pro
            2095                2100                2105

AGG GCC GAG CAC TCC TAC CTG AGG CCT GGG GAC TAC CGC GTG CAG GTG    6506
Arg Ala Glu His Ser Tyr Leu Arg Pro Gly Asp Tyr Arg Val Gln Val
        2110                2115                2120

AAC GCC TCC AAC CTG GTG AGC TTC TTC GTG GCG CAG GCC ACG GTG ACC    6554
Asn Ala Ser Asn Leu Val Ser Phe Phe Val Ala Gln Ala Thr Val Thr
2125                2130                2135                2140

GTC CAG GTG CTG GCC TGC CGG GAG CCG GAG GTG GAC GTG GTC CTG CCC    6602
Val Gln Val Leu Ala Cys Arg Glu Pro Glu Val Asp Val Val Leu Pro
            2145                2150                2155

CTG CAG GTG CTG ATG CGG CGA TCA CAG CGC AAC TAC TTG GAG GCC CAC    6650
Leu Gln Val Leu Met Arg Arg Ser Gln Arg Asn Tyr Leu Glu Ala His
            2160                2165                2170

GTT GAC CTG CGC GAC TGC GTC ACC TAC CAG ACT GAG TAC CGC TGG GAG    6698
Val Asp Leu Arg Asp Cys Val Thr Tyr Gln Thr Glu Tyr Arg Trp Glu
            2175                2180                2185

GTG TAT CGC ACC GCC AGC TGC CAG CGG CCG GGG CGC CCA GCG CGT GTG    6746
Val Tyr Arg Thr Ala Ser Cys Gln Arg Pro Gly Arg Pro Ala Arg Val
        2190                2195                2200

GCC CTG CCC GGC GTG GAC GTG AGC CGG CCT CGG CTG GTG CTG CCG CGG    6794
Ala Leu Pro Gly Val Asp Val Ser Arg Pro Arg Leu Val Leu Pro Arg
2205                2210                2215                2220

CTG GCG CTG CCT GTG GGG CAC TAC TGC TTT GTG TTT GTC GTG TCA TTT    6842
Leu Ala Leu Pro Val Gly His Tyr Cys Phe Val Phe Val Val Ser Phe
            2225                2230                2235

GGG GAC ACG CCA CTG ACA CAG AGC ATC CAG GCC AAT GTG ACG GTG GCC    6890
Gly Asp Thr Pro Leu Thr Gln Ser Ile Gln Ala Asn Val Thr Val Ala
        2240                2245                2250

CCC GAG CGC CTG GTG CCC ATC ATT GAG GGT GGC TCA TAC CGC GTG TGG    6938
```

```
                            Pro Glu Arg Leu Val Pro Ile Ile Glu Gly Gly Ser Tyr Arg Val Trp
                                    2255                2260                2265

TCA GAC ACA CGG GAC CTG GTG CTG GAT GGG AGC GAG TCC TAC GAC CCC              6986
Ser Asp Thr Arg Asp Leu Val Leu Asp Gly Ser Glu Ser Tyr Asp Pro
    2270                2275                2280

AAC CTG GAG GAC GGC GAC CAG ACG CCG CTC AGT TTC CAC TGG GCC TGT              7034
Asn Leu Glu Asp Gly Asp Gln Thr Pro Leu Ser Phe His Trp Ala Cys
2285                2290                2295                2300

GTG GCT TCG ACA CAG AGG GAG GCT GGC GGG TGT GCG CTG AAC TTT GGG              7082
Val Ala Ser Thr Gln Arg Glu Ala Gly Gly Cys Ala Leu Asn Phe Gly
                2305                2310                2315

CCC CGC GGG AGC AGC ACG GTC ACC ATT CCA CGG GAG CGG CTG GCG GCT              7130
Pro Arg Gly Ser Ser Thr Val Thr Ile Pro Arg Glu Arg Leu Ala Ala
            2320                2325                2330

GGC GTG GAG TAC ACC TTC AGC CTG ACC GTG TGG AAG GCC GGC CGC AAG              7178
Gly Val Glu Tyr Thr Phe Ser Leu Thr Val Trp Lys Ala Gly Arg Lys
        2335                2340                2345

GAG GAG GCC ACC AAC CAG ACG GTG CTG ATC CGG AGT GGC CGG GTG CCC              7226
Glu Glu Ala Thr Asn Gln Thr Val Leu Ile Arg Ser Gly Arg Val Pro
    2350                2355                2360

ATT GTG TCC TTG GAG TGT GTG TCC TGC AAG GCA CAG GCC GTG TAC GAA              7274
Ile Val Ser Leu Glu Cys Val Ser Cys Lys Ala Gln Ala Val Tyr Glu
2365                2370                2375                2380

GTG AGC CGC AGC TCC TAC GTG TAC TTG GAG GGC CGC TGC CTC AAT TGC              7322
Val Ser Arg Ser Ser Tyr Val Tyr Leu Glu Gly Arg Cys Leu Asn Cys
                2385                2390                2395

AGC AGC GGC TCC AAG CGA GGG CGG TGG GCT GCA CGT ACG TTC AGC AAC              7370
Ser Ser Gly Ser Lys Arg Gly Arg Trp Ala Ala Arg Thr Phe Ser Asn
            2400                2405                2410

AAG ACG CTG GTG CTG GAT GAG ACC ACC ACA TCC ACG GGC AGT GCA GGC              7418
Lys Thr Leu Val Leu Asp Glu Thr Thr Thr Ser Thr Gly Ser Ala Gly
        2415                2420                2425

ATG CGA CTG GTG CTG CGG CGG GGC GTG CTG CGG GAC GGC GAG GGA TAC              7466
Met Arg Leu Val Leu Arg Arg Gly Val Leu Arg Asp Gly Glu Gly Tyr
    2430                2435                2440

ACC TTC ACG CTC ACG GTG CTG GGC CGC TCT GGC GAG GAG GAG GGC TGC              7514
Thr Phe Thr Leu Thr Val Leu Gly Arg Ser Gly Glu Glu Glu Gly Cys
2445                2450                2455                2460

GCC TCC ATC CGC CTG TCC CCC AAC CGC CCG CCG CTG GGG GGC TCT TGC              7562
Ala Ser Ile Arg Leu Ser Pro Asn Arg Pro Pro Leu Gly Gly Ser Cys
                2465                2470                2475

CGC CTC TTC CCA CTG GGC GCT GTG CAC GCC CTC ACC ACC AAG GTG CAC              7610
Arg Leu Phe Pro Leu Gly Ala Val His Ala Leu Thr Thr Lys Val His
            2480                2485                2490

TTC GAA TGC ACG GGC TGG CAT GAC GCG GAG GAT GCT GGC GCC CCG CTG              7658
Phe Glu Cys Thr Gly Trp His Asp Ala Glu Asp Ala Gly Ala Pro Leu
        2495                2500                2505

GTG TAC GCC CTG CTG CTG CGG CGC TGT CGC CAG GGC CAC TGC GAG GAG              7706
Val Tyr Ala Leu Leu Leu Arg Arg Cys Arg Gln Gly His Cys Glu Glu
    2510                2515                2520

TTC TGT GTC TAC AAG GGC AGC CTC TCC AGC TAC GGA GCC GTG CTG CCC              7754
Phe Cys Val Tyr Lys Gly Ser Leu Ser Ser Tyr Gly Ala Val Leu Pro
2525                2530                2535                2540

CCG GGT TTC AGG CCA CAC TTC GAG GTG GGC CTG GCC GTG GTG GTG CAG              7802
Pro Gly Phe Arg Pro His Phe Glu Val Gly Leu Ala Val Val Val Gln
                2545                2550                2555

GAC CAG CTG GGA GCC GCT GTG GTC GCC CTC AAC AGG TCT TTG GCC ATC              7850
Asp Gln Leu Gly Ala Ala Val Val Ala Leu Asn Arg Ser Leu Ala Ile
            2560                2565                2570
```

```
                                          -continued

ACC CTC CCA GAG CCC AAC GGC AGC GCA ACG GGG CTC ACA GTC TGG CTG    7898
Thr Leu Pro Glu Pro Asn Gly Ser Ala Thr Gly Leu Thr Val Trp Leu
        2575                2580                2585

CAC GGG CTC ACC GCT AGT GTG CTC CCA GGG CTG CTG CGG CAG GCC GAT    7946
His Gly Leu Thr Ala Ser Val Leu Pro Gly Leu Leu Arg Gln Ala Asp
2590                2595                2600

CCC CAG CAC GTC ATC GAG TAC TCG TTG GCC CTG GTC ACC GTG CTG AAC    7994
Pro Gln His Val Ile Glu Tyr Ser Leu Ala Leu Val Thr Val Leu Asn
2605                2610                2615                2620

GAG TAC GAG CGG GCC CTG GAC GTG GCG GCA GAG CCC AAG CAC GAG CGG    8042
Glu Tyr Glu Arg Ala Leu Asp Val Ala Ala Glu Pro Lys His Glu Arg
        2625                2630                2635

CAG CAC CGA GCC CAG ATA CGC AAG AAC ATC ACG GAG ACT CTG GTG TCC    8090
Gln His Arg Ala Gln Ile Arg Lys Asn Ile Thr Glu Thr Leu Val Ser
        2640                2645                2650

CTG AGG GTC CAC ACT GTG GAT GAC ATC CAG CAG ATC GCT GCT GCG CTG    8138
Leu Arg Val His Thr Val Asp Asp Ile Gln Gln Ile Ala Ala Ala Leu
        2655                2660                2665

GCC CAG TGC ATG GGG CCC AGC AGG GAG CTC GTA TGC CGC TCG TGC CTG    8186
Ala Gln Cys Met Gly Pro Ser Arg Glu Leu Val Cys Arg Ser Cys Leu
        2670                2675                2680

AAG CAG ACG CTG CAC AAG CTG GAG GCC ATG ATG CTC ATC CTG CAG GCA    8234
Lys Gln Thr Leu His Lys Leu Glu Ala Met Met Leu Ile Leu Gln Ala
2685                2690                2695                2700

GAG ACC ACC GCG GGC ACC GTG ACG CCC ACC GCC ATC GGA GAC AGC ATC    8282
Glu Thr Thr Ala Gly Thr Val Thr Pro Thr Ala Ile Gly Asp Ser Ile
        2705                2710                2715

CTC AAC ATC ACA GGA GAC CTC ATC CAC CTG GCC AGC TCG GAC GTG CGG    8330
Leu Asn Ile Thr Gly Asp Leu Ile His Leu Ala Ser Ser Asp Val Arg
        2720                2725                2730

GCA CCA CAG CCC TCA GAG CTG GGA GCC GAG TCA CCA TCT CGG ATG GTG    8378
Ala Pro Gln Pro Ser Glu Leu Gly Ala Glu Ser Pro Ser Arg Met Val
        2735                2740                2745

GCG TCC CAG GCC TAC AAC CTG ACC TCT GCC CTC ATG CGC ATC CTC ATG    8426
Ala Ser Gln Ala Tyr Asn Leu Thr Ser Ala Leu Met Arg Ile Leu Met
        2750                2755                2760

CGC TCC CGC GTG CTC AAC GAG GAG CCC CTG ACG CTG GCG GGC GAG GAG    8474
Arg Ser Arg Val Leu Asn Glu Glu Pro Leu Thr Leu Ala Gly Glu Glu
2765                2770                2775                2780

ATC GTG GCC CAG GGC AAG CGC TCG GAC CCG CGG AGC CTG CTG TGC TAT    8522
Ile Val Ala Gln Gly Lys Arg Ser Asp Pro Arg Ser Leu Leu Cys Tyr
        2785                2790                2795

GGC GGC GCC CCA GGG CCT GGC TGC CAC TTC TCC ATC CCC GAG GCT TTC    8570
Gly Gly Ala Pro Gly Pro Gly Cys His Phe Ser Ile Pro Glu Ala Phe
        2800                2805                2810

AGC GGG GCC CTG GCC AAC CTC AGT GAC GTG GTG CAG CTC ATC TTT CTG    8618
Ser Gly Ala Leu Ala Asn Leu Ser Asp Val Val Gln Leu Ile Phe Leu
        2815                2820                2825

GTG GAC TCC AAT CCC TTT CCC TTT GGC TAT ATC AGC AAC TAC ACC GTC    8666
Val Asp Ser Asn Pro Phe Pro Phe Gly Tyr Ile Ser Asn Tyr Thr Val
        2830                2835                2840

TCC ACC AAG GTG GCC TCG ATG GCA TTC CAG ACA CAG GCC GGC GCC CAG    8714
Ser Thr Lys Val Ala Ser Met Ala Phe Gln Thr Gln Ala Gly Ala Gln
2845                2850                2855                2860

ATC CCC ATC GAG CGG CTG GCC TCA GAG CGC GCC ATC ACC GTG AAG GTG    8762
Ile Pro Ile Glu Arg Leu Ala Ser Glu Arg Ala Ile Thr Val Lys Val
        2865                2870                2875

CCC AAC AAC TCG GAC TGG GCT GCC CGG GGC CAC CGC AGC TCC GCC AAC    8810
Pro Asn Asn Ser Asp Trp Ala Ala Arg Gly His Arg Ser Ser Ala Asn
        2880                2885                2890
```

```
TCC GCC AAC TCC GTT GTG GTC CAG CCC CAG GCC TCC GTC GGT GCT GTG         8858
Ser Ala Asn Ser Val Val Val Gln Pro Gln Ala Ser Val Gly Ala Val
            2895                2900                2905

GTC ACC CTG GAC AGC AGC AAC CCT GCG GCC GGG CTG CAT CTG CAG CTC         8906
Val Thr Leu Asp Ser Ser Asn Pro Ala Ala Gly Leu His Leu Gln Leu
    2910                2915                2920

AAC TAT ACG CTG CTG GAC GGC CAC TAC CTG TCT GAG GAA CCT GAG CCC         8954
Asn Tyr Thr Leu Leu Asp Gly His Tyr Leu Ser Glu Glu Pro Glu Pro
2925                2930                2935                2940

TAC CTG GCA GTC TAC CTA CAC TCG GAG CCC CGG CCC AAT GAG CAC AAC         9002
Tyr Leu Ala Val Tyr Leu His Ser Glu Pro Arg Pro Asn Glu His Asn
                2945                2950                2955

TGC TCG GCT AGC AGG AGG ATC CGC CCA GAG TCA CTC CAG GGT GCT GAC         9050
Cys Ser Ala Ser Arg Arg Ile Arg Pro Glu Ser Leu Gln Gly Ala Asp
            2960                2965                2970

CAC CGG CCC TAC ACC TTC TTC ATT TCC CCG GGG AGC AGA GAC CCA GCG         9098
His Arg Pro Tyr Thr Phe Phe Ile Ser Pro Gly Ser Arg Asp Pro Ala
        2975                2980                2985

GGG AGT TAC CAT CTG AAC CTC TCC AGC CAC TTC CGC TGG TCG GCG CTG         9146
Gly Ser Tyr His Leu Asn Leu Ser Ser His Phe Arg Trp Ser Ala Leu
    2990                2995                3000

CAG GTG TCC GTG GGC CTG TAC ACG TCC CTG TGC CAG TAC TTC AGC GAG         9194
Gln Val Ser Val Gly Leu Tyr Thr Ser Leu Cys Gln Tyr Phe Ser Glu
3005                3010                3015                3020

GAG GAC ATG GTG TGG CGG ACA GAG GGG CTG CTG CCC CTG GAG GAG ACC         9242
Glu Asp Met Val Trp Arg Thr Glu Gly Leu Leu Pro Leu Glu Glu Thr
                3025                3030                3035

TCG CCC CGC CAG GCC GTC TGC CTC ACC CGC CAC CTC ACC GCC TTC GGC         9290
Ser Pro Arg Gln Ala Val Cys Leu Thr Arg His Leu Thr Ala Phe Gly
            3040                3045                3050

GCC AGC CTC TTC GTG CCC CCA AGC CAT GTC CGC TTT GTG TTT CCT GAG         9338
Ala Ser Leu Phe Val Pro Pro Ser His Val Arg Phe Val Phe Pro Glu
        3055                3060                3065

CCG ACA GCG GAT GTA AAC TAC ATC GTC ATG CTG ACA TGT GCT GTG TGC         9386
Pro Thr Ala Asp Val Asn Tyr Ile Val Met Leu Thr Cys Ala Val Cys
    3070                3075                3080

CTG GTG ACC TAC ATG GTC ATG GCC GCC ATC CTG CAC AAG CTG GAC CAG         9434
Leu Val Thr Tyr Met Val Met Ala Ala Ile Leu His Lys Leu Asp Gln
3085                3090                3095                3100

TTG GAT GCC AGC CGG GGC CGC GCC ATC CCT TTC TGT GGG CAG CGG GGC         9482
Leu Asp Ala Ser Arg Gly Arg Ala Ile Pro Phe Cys Gly Gln Arg Gly
                3105                3110                3115

CGC TTC AAG TAC GAG ATC CTC GTC AAG ACA GGC TGG GGC CGG GGC TCA         9530
Arg Phe Lys Tyr Glu Ile Leu Val Lys Thr Gly Trp Gly Arg Gly Ser
            3120                3125                3130

GGT ACC ACG GCC CAC GTG GGC ATC ATG CTG TAT GGG GTG GAC AGC CGG         9578
Gly Thr Thr Ala His Val Gly Ile Met Leu Tyr Gly Val Asp Ser Arg
        3135                3140                3145

AGC GGC CAC CGG CAC CTG GAC GGC GAC AGA GCC TTC CAC CGC AAC AGC         9626
Ser Gly His Arg His Leu Asp Gly Asp Arg Ala Phe His Arg Asn Ser
    3150                3155                3160

CTG GAC ATC TTC CGG ATC GCC ACC CCG CAC AGC CTG GGT AGC GTG TGG         9674
Leu Asp Ile Phe Arg Ile Ala Thr Pro His Ser Leu Gly Ser Val Trp
3165                3170                3175                3180

AAG ATC CGA GTG TGG CAC GAC AAC AAA GGG CTC AGC CCT GCC TGG TTC         9722
Lys Ile Arg Val Trp His Asp Asn Lys Gly Leu Ser Pro Ala Trp Phe
                3185                3190                3195

CTG CAG CAC GTC ATC GTC AGG GAC CTG CAG ACG GCA CGC AGC GCC TTC         9770
Leu Gln His Val Ile Val Arg Asp Leu Gln Thr Ala Arg Ser Ala Phe
```

-continued

```
           3200            3205            3210
TTC CTG GTC AAT GAC TGG CTT TCG GTG GAG ACG GAG GCC AAC GGG GGC     9818
Phe Leu Val Asn Asp Trp Leu Ser Val Glu Thr Glu Ala Asn Gly Gly
        3215            3220            3225

CTG GTG GAG AAG GAG GTG CTG GCC GCG AGC GAC GCA GCC CTT TTG CGC     9866
Leu Val Glu Lys Glu Val Leu Ala Ala Ser Asp Ala Ala Leu Leu Arg
        3230            3235            3240

TTC CGG CGC CTG CTG GTG GCT GAG CTG CAG CGT GGC TTC TTT GAC AAG     9914
Phe Arg Arg Leu Leu Val Ala Glu Leu Gln Arg Gly Phe Phe Asp Lys
3245            3250            3255            3260

CAC ATC TGG CTC TCC ATA TGG GAC CGG CCG CCT CGT AGC CGT TTC ACT     9962
His Ile Trp Leu Ser Ile Trp Asp Arg Pro Pro Arg Ser Arg Phe Thr
            3265            3270            3275

CGC ATC CAG AGG GCC ACC TGC TGC GTT CTC CTC ATC TGC CTC TTC CTG    10010
Arg Ile Gln Arg Ala Thr Cys Cys Val Leu Leu Ile Cys Leu Phe Leu
        3280            3285            3290

GGC GCC AAC GCC GTG TGG TAC GGG GCT GTT GGC GAC TCT GCC TAC AGC    10058
Gly Ala Asn Ala Val Trp Tyr Gly Ala Val Gly Asp Ser Ala Tyr Ser
        3295            3300            3305

ACG GGG CAT GTG TCC AGG CTG AGC CCG CTG AGC GTC GAC ACA GTC GCT    10106
Thr Gly His Val Ser Arg Leu Ser Pro Leu Ser Val Asp Thr Val Ala
        3310            3315            3320

GTT GGC CTG GTG TCC AGC GTG GTT GTC TAT CCC GTC TAC CTG GCC ATC    10154
Val Gly Leu Val Ser Ser Val Val Val Tyr Pro Val Tyr Leu Ala Ile
3325            3330            3335            3340

CTT TTT CTC TTC CGG ATG TCC CGG AGC AAG GTG GCT GGG AGC CCG AGC    10202
Leu Phe Leu Phe Arg Met Ser Arg Ser Lys Val Ala Gly Ser Pro Ser
            3345            3350            3355

CCC ACA CCT GCC GGG CAG CAG GTG CTG GAC ATC GAC AGC TGC CTG GAC    10250
Pro Thr Pro Ala Gly Gln Gln Val Leu Asp Ile Asp Ser Cys Leu Asp
        3360            3365            3370

TCG TCC GTG CTG GAC AGC TCC TTC CTC ACG TTC TCA GGC CTC CAC GCT    10298
Ser Ser Val Leu Asp Ser Ser Phe Leu Thr Phe Ser Gly Leu His Ala
        3375            3380            3385

GAG GCC TTT GTT GGA CAG ATG AAG AGT GAC TTG TTT CTG GAT GAT TCT    10346
Glu Ala Phe Val Gly Gln Met Lys Ser Asp Leu Phe Leu Asp Asp Ser
        3390            3395            3400

AAG AGT CTG GTG TGC TGG CCC TCC GGC GAG GGA ACG CTC AGT TGG CCG    10394
Lys Ser Leu Val Cys Trp Pro Ser Gly Glu Gly Thr Leu Ser Trp Pro
3405            3410            3415            3420

GAC CTG CTC AGT GAC CCG TCC ATT GTG GGT AGC AAT CTG CGG CAG CTG    10442
Asp Leu Leu Ser Asp Pro Ser Ile Val Gly Ser Asn Leu Arg Gln Leu
            3425            3430            3435

GCA CGG GGC CAG GCG GGC CAT GGG CTG GGC CCA GAG GAG GAC GGC TTC    10490
Ala Arg Gly Gln Ala Gly His Gly Leu Gly Pro Glu Glu Asp Gly Phe
        3440            3445            3450

TCC CTG GCC AGC CCC TAC TCG CCT GCC AAA TCC TTC TCA GCA TCA GAT    10538
Ser Leu Ala Ser Pro Tyr Ser Pro Ala Lys Ser Phe Ser Ala Ser Asp
        3455            3460            3465

GAA GAC CTG ATC CAG CAG GTC CTT GCC GAG GGG GTC AGC AGC CCA GCC    10586
Glu Asp Leu Ile Gln Gln Val Leu Ala Glu Gly Val Ser Ser Pro Ala
        3470            3475            3480

CCT ACC CAA GAC ACC CAC ATG GAA ACG GAC CTC CTC AGC AGC CTG TCC    10634
Pro Thr Gln Asp Thr His Met Glu Thr Asp Leu Leu Ser Ser Leu Ser
3485            3490            3495            3500

AGC ACT CCT GGG GAG AAG ACA GAG ACG CTG GCG CTG CAG AGG CTG GGG    10682
Ser Thr Pro Gly Glu Lys Thr Glu Thr Leu Ala Leu Gln Arg Leu Gly
            3505            3510            3515

GAG CTG GGG CCA CCC AGC CCA GGC CTG AAC TGG GAA CAG CCC CAG GCA    10730
```

```
                    -continued

Glu Leu Gly Pro Pro Ser Pro Gly Leu Asn Trp Glu Gln Pro Gln Ala
            3520                3525                3530

GCG AGG CTG TCC AGG ACA GGA CTG GTG GAG GGT CTG CGG AAG CGC CTG            10778
Ala Arg Leu Ser Arg Thr Gly Leu Val Glu Gly Leu Arg Lys Arg Leu
        3535                3540                3545

CTG CCG GCC TGG TGT GCC TCC CTG GCC CAC GGG CTC AGC CTG CTC CTG            10826
Leu Pro Ala Trp Cys Ala Ser Leu Ala His Gly Leu Ser Leu Leu Leu
3550                3555                3560

GTG GCT GTG GCT GTG GCT GTC TCA GGG TGG GTG GGT GCG AGC TTC CCC            10874
Val Ala Val Ala Val Ala Val Ser Gly Trp Val Gly Ala Ser Phe Pro
3565                3570                3575                3580

CCG GGC GTG AGT GTT GCG TGG CTC CTG TCC AGC AGC GCC AGC TTC CTG            10922
Pro Gly Val Ser Val Ala Trp Leu Leu Ser Ser Ser Ala Ser Phe Leu
        3585                3590                3595

GCC TCA TTC CTC GGC TGG GAG CCA CTG AAG GTC TTG CTG GAA GCC CTG            10970
Ala Ser Phe Leu Gly Trp Glu Pro Leu Lys Val Leu Leu Glu Ala Leu
        3600                3605                3610

TAC TTC TCA CTG GTG GCC AAG CGG CTG CAC CCG GAT GAA GAT GAC ACC            11018
Tyr Phe Ser Leu Val Ala Lys Arg Leu His Pro Asp Glu Asp Asp Thr
        3615                3620                3625

CTG GTA GAG AGC CCG GCT GTG ACG CCT GTG AGC GCA CGT GTG CCC CGC            11066
Leu Val Glu Ser Pro Ala Val Thr Pro Val Ser Ala Arg Val Pro Arg
        3630                3635                3640

GTA CGG CCA CCC CAC GGC TTT GCA CTC TTC CTG GCC AAG GAA GAA GCC            11114
Val Arg Pro Pro His Gly Phe Ala Leu Phe Leu Ala Lys Glu Glu Ala
3645                3650                3655                3660

CGC AAG GTC AAG AGG CTA CAT GGC ATG CTG CGG AGC CTC CTG GTG TAC            11162
Arg Lys Val Lys Arg Leu His Gly Met Leu Arg Ser Leu Leu Val Tyr
        3665                3670                3675

ATG CTT TTT CTG CTG GTG ACC CTG CTG GCC AGC TAT GGG GAT GCC TCA            11210
Met Leu Phe Leu Leu Val Thr Leu Leu Ala Ser Tyr Gly Asp Ala Ser
        3680                3685                3690

TGC CAT GGG CAC GCC TAC CGT CTG CAA AGC GCC ATC AAG CAG GAG CTG            11258
Cys His Gly His Ala Tyr Arg Leu Gln Ser Ala Ile Lys Gln Glu Leu
        3695                3700                3705

CAC AGC CGG GCC TTC CTG GCC ATC ACG CGG TCT GAG GAG CTC TGG CCA            11306
His Ser Arg Ala Phe Leu Ala Ile Thr Arg Ser Glu Glu Leu Trp Pro
        3710                3715                3720

TGG ATG GCC CAC GTG CTG CTG CCC TAC GTC CAC GGG AAC CAG TCC AGC            11354
Trp Met Ala His Val Leu Leu Pro Tyr Val His Gly Asn Gln Ser Ser
3725                3730                3735                3740

CCA GAG CTG GGG CCC CCA CGG CTG CGG CAG GTG CGG CTG CAG GAA GCA            11402
Pro Glu Leu Gly Pro Pro Arg Leu Arg Gln Val Arg Leu Gln Glu Ala
            3745                3750                3755

CTC TAC CCA GAC CCT CCC GGC CCC AGG GTC CAC ACG TGC TCG GCC GCA            11450
Leu Tyr Pro Asp Pro Pro Gly Pro Arg Val His Thr Cys Ser Ala Ala
        3760                3765                3770

GGA GGC TTC AGC ACC AGC GAT TAC GAC GTT GGC TGG GAG AGT CCT CAC            11498
Gly Gly Phe Ser Thr Ser Asp Tyr Asp Val Gly Trp Glu Ser Pro His
        3775                3780                3785

AAT GGC TCG GGG ACG TGG GCC TAT TCA GCG CCG GAT CTG CTG GGG GCA            11546
Asn Gly Ser Gly Thr Trp Ala Tyr Ser Ala Pro Asp Leu Leu Gly Ala
        3790                3795                3800

TGG TCC TGG GGC TCC TGT GCC GTG TAT GAC AGC GGG GGC TAC GTG CAG            11594
Trp Ser Trp Gly Ser Cys Ala Val Tyr Asp Ser Gly Gly Tyr Val Gln
3805                3810                3815                3820

GAG CTG GGC CTG AGC CTG GAG GAG AGC CGC GAC CGG CTG CGC TTC CTG            11642
Glu Leu Gly Leu Ser Leu Glu Glu Ser Arg Asp Arg Leu Arg Phe Leu
        3825                3830                3835
```

-continued

```
CAG CTG CAC AAC TGG CTG GAC AAC AGG AGC CGC GCT GTG TTC CTG GAG        11690
Gln Leu His Asn Trp Leu Asp Asn Arg Ser Arg Ala Val Phe Leu Glu
            3840                3845                3850

CTC ACG CGC TAC AGC CCG GCC GTG GGG CTG CAC GCC GCC GTC ACG CTG        11738
Leu Thr Arg Tyr Ser Pro Ala Val Gly Leu His Ala Ala Val Thr Leu
            3855                3860                3865

CGC CTC GAG TTC CCG GCG GCC GGC CGC GCC CTG GCC GCC CTC AGC GTC        11786
Arg Leu Glu Phe Pro Ala Ala Gly Arg Ala Leu Ala Ala Leu Ser Val
            3870                3875                3880

CGC CCC TTT GCG CTG CGC CGC CTC AGC GCG GGC CTC TCG CTG CCT CTG        11834
Arg Pro Phe Ala Leu Arg Arg Leu Ser Ala Gly Leu Ser Leu Pro Leu
3885                3890                3895                3900

CTC ACC TCG GTG TGC CTG CTG CTG TTC GCC GTG CAC TTC GCC GTG GCC        11882
Leu Thr Ser Val Cys Leu Leu Leu Phe Ala Val His Phe Ala Val Ala
            3905                3910                3915

GAG GCC CGT ACT TGG CAC AGG GAA GGG CGC TGG CGC GTG CTG CGG CTC        11930
Glu Ala Arg Thr Trp His Arg Glu Gly Arg Trp Arg Val Leu Arg Leu
            3920                3925                3930

GGA GCC TGG GCG CGG TGG CTG CTG GTG GCG CTG ACG GCG GCC ACG GCA        11978
Gly Ala Trp Ala Arg Trp Leu Leu Val Ala Leu Thr Ala Ala Thr Ala
            3935                3940                3945

CTG GTA CGC CTC GCC CAG CTG GGT GCC GCT GAC CGC CAG TGG ACC CGT        12026
Leu Val Arg Leu Ala Gln Leu Gly Ala Ala Asp Arg Gln Trp Thr Arg
            3950                3955                3960

TTC GTG CGC GGC CGC CCG CGC CGC TTC ACT AGC TTC GAC CAG GTG GCG        12074
Phe Val Arg Gly Arg Pro Arg Arg Phe Thr Ser Phe Asp Gln Val Ala
3965                3970                3975                3980

CAG CTG AGC TCC GCA GCC CGT GGC CTG GCG GCC TCG CTG CTC TTC CTG        12122
Gln Leu Ser Ser Ala Ala Arg Gly Leu Ala Ala Ser Leu Leu Phe Leu
            3985                3990                3995

CTT TTG GTC AAG GCT GCC CAG CAG CTA CGC TTC GTG CGC CAG TGG TCC        12170
Leu Leu Val Lys Ala Ala Gln Gln Leu Arg Phe Val Arg Gln Trp Ser
            4000                4005                4010

GTC TTT GGC AAG ACA TTA TGC CGA GCT CTG CCA GAG CTC CTG GGG GTC        12218
Val Phe Gly Lys Thr Leu Cys Arg Ala Leu Pro Glu Leu Leu Gly Val
            4015                4020                4025

ACC TTG GGC CTG GTG GTG CTC GGG GTA GCC TAC GCC CAG CTG GCC ATC        12266
Thr Leu Gly Leu Val Val Leu Gly Val Ala Tyr Ala Gln Leu Ala Ile
            4030                4035                4040

CTG CTC GTG TCT TCC TGT GTG GAC TCC CTC TGG AGC GTG GCC CAG GCC        12314
Leu Leu Val Ser Ser Cys Val Asp Ser Leu Trp Ser Val Ala Gln Ala
4045                4050                4055                4060

CTG TTG GTG CTG TGC CCT GGG ACT GGG CTC TCT ACC CTG TGT CCT GCC        12362
Leu Leu Val Leu Cys Pro Gly Thr Gly Leu Ser Thr Leu Cys Pro Ala
            4065                4070                4075

GAG TCC TGG CAC CTG TCA CCC CTG CTG TGT GTG GGG CTC TGG GCA CTG        12410
Glu Ser Trp His Leu Ser Pro Leu Leu Cys Val Gly Leu Trp Ala Leu
            4080                4085                4090

CGG CTG TGG GGC GCC CTA CGG CTG GGG GCT GTT ATT CTC CGC TGG CGC        12458
Arg Leu Trp Gly Ala Leu Arg Leu Gly Ala Val Ile Leu Arg Trp Arg
            4095                4100                4105

TAC CAC GCC TTG CGT GGA GAG CTG TAC CGG CCG GCC TGG GAG CCC CAG        12506
Tyr His Ala Leu Arg Gly Glu Leu Tyr Arg Pro Ala Trp Glu Pro Gln
            4110                4115                4120

GAC TAC GAG ATG GTG GAG TTG TTC CTG CGC AGG CTG CGC CTC TGG ATG        12554
Asp Tyr Glu Met Val Glu Leu Phe Leu Arg Arg Leu Arg Leu Trp Met
4125                4130                4135                4140

GGC CTC AGC AAG GTC AAG GAG TTC CGC CAC AAA GTC CGC TTT GAA GGG        12602
Gly Leu Ser Lys Val Lys Glu Phe Arg His Lys Val Arg Phe Glu Gly
            4145                4150                4155
```

-continued

```
ATG GAG CCG CTG CCC TCT CGC TCC TCC AGG GGC TCC AAG GTA TCC CCG        12650
Met Glu Pro Leu Pro Ser Arg Ser Ser Arg Gly Ser Lys Val Ser Pro
            4160                4165                4170

GAT GTG CCC CCA CCC AGC GCT GGC TCC GAT GCC TCG CAC CCC TCC ACC        12698
Asp Val Pro Pro Pro Ser Ala Gly Ser Asp Ala Ser His Pro Ser Thr
        4175                4180                4185

TCC TCC AGC CAG CTG GAT GGG CTG AGC GTG AGC CTG GGC CGG CTG GGG        12746
Ser Ser Ser Gln Leu Asp Gly Leu Ser Val Ser Leu Gly Arg Leu Gly
        4190                4195                4200

ACA AGG TGT GAG CCT GAG CCC TCC CGC CTC CAA GCC GTG TTC GAG GCC        12794
Thr Arg Cys Glu Pro Glu Pro Ser Arg Leu Gln Ala Val Phe Glu Ala
4205                4210                4215                4220

CTG CTC ACC CAG TTT GAC CGA CTC AAC CAG GCC ACA GAG GAC GTC TAC        12842
Leu Leu Thr Gln Phe Asp Arg Leu Asn Gln Ala Thr Glu Asp Val Tyr
                4225                4230                4235

CAG CTG GAG CAG CAG CTG CAC AGC CTG CAA GGC CGC AGG AGC AGC CGG        12890
Gln Leu Glu Gln Gln Leu His Ser Leu Gln Gly Arg Arg Ser Ser Arg
                4240                4245                4250

GCG CCC GCC GGA TCT TCC CGT GGC CCA TCC CCG GGC CTG CGG CCA GCA        12938
Ala Pro Ala Gly Ser Ser Arg Gly Pro Ser Pro Gly Leu Arg Pro Ala
            4255                4260                4265

CTG CCC AGC CGC CTT GCC CGG GCC AGT CGG GGT GTG GAC CTG GCC ACT        12986
Leu Pro Ser Arg Leu Ala Arg Ala Ser Arg Gly Val Asp Leu Ala Thr
        4270                4275                4280

GGC CCC AGC AGG ACA CCC CTT CGG GCC AAG AAC AAG GTC CAC CCC AGC        13034
Gly Pro Ser Arg Thr Pro Leu Arg Ala Lys Asn Lys Val His Pro Ser
4285                4290                4295                4300

AGC ACT TAGTCCTCCT TCCTGGCGGG GGTGGGCCGT GGAGTCGGAG TGGACACCGC         13090
Ser Thr

TCAGTATTAC TTTCTGCCGC TGTCAAGGCC GAGGGCCAGG CAGAATGGCT GCACGTAGGT      13150

TCCCCAGAGA GCAGGCAGGG GCATCTGTCT GTCTGTGGGC TTCAGCACTT TAAAGAGGCT      13210

GTGTGGCCAA CCAGGACCCA GGGTCCCCTC CCCAGCTCCC TTGGGAAGGA CACAGCAGTA      13270

TTGGACGGTT TCTAGCCTCT GAGATGCTAA TTTATTTCCC CGAGTCCTCA GGTACAGCGG      13330

GCTGTGCCCG GCCCCACCCC CTGGGCAGAT GTCCCCCACT GCTAAGGCTG CTGGCTTCAG      13390

GGAGGGTTAG CCTGCACCGC CGCCACCCTG CCCCTAAGTT ATTACCTCTC CAGTTCCTAC      13450

CGTACTCCCT GCACCGTCTC ACTGTGTGTC TCGTGTCAGT AATTTATATG GTGTTAAAAT      13510

GTGTATATTT TTGTATGTCA CTATTTTCAC TAGGGCTGAG GGGCCTGCGC CCAGAGCTGG      13570

CCTCCCCCAA CACCTGCTGC GCTTGGTAGG TGTGGTGGCG TTATGGCAGC CCGGCTGCTG      13630

CTTGGATGCG AGCTTGGCCT TGGGCCGGTG CTGGGGGCAC AGCTGTCTGC CAGGCACTCT      13690

CATCACCCCA GAGGCCTTGT CATCCTCCCT TGCCCCAGGC CAGGTAGCAA GAGAGCAGCG      13750

CCCAGGCCTG CTGGCATCAG GTCTGGGCAA GTAGCAGGAC TAGGCATGTC AGAGGACCCC      13810

AGGGTGGTTA GAGGAAAAGA CTCCTCCTGG GGGCTGGCTC CCAGGGTGGA GGAAGGTGAC      13870

TGTGTGTGTG TGTGTGTGCG CGCGCGCACG CGCGAGTGTG CTGTATGGCC CAGGCAGCCT      13930

CAAGGCCCTC GGAGCTGGCT GTGCCTGCTT CTGTGTACCA CTTCTGTGGG CATGGCCGCT      13990

TCTAGAGCCT CGACACCCCC CCAACCCCCG CACCAAGCAG ACAAAGTCAA TAAAAGAGCT      14050

GTCTGACTGC                                                             14060
```

(2) INFORMATION FOR SEQ ID NO:5:

(i) SEQUENCE CHARACTERISTICS:
        (A) LENGTH: 4302 amino acids

```
        (B) TYPE: amino acid
        (D) TOPOLOGY: linear (ii) MOLECULE TYPE: protein (xi) SEQUENCE DESCRIPTION: SEQ ID NO:5:

Met Pro Pro Ala Ala Pro Ala Arg Leu Ala Leu Ala Leu Gly Leu Gly
  1               5                  10                  15

Leu Trp Leu Gly Ala Leu Ala Gly Gly Pro Gly Arg Gly Cys Gly Pro
                 20                  25                  30

Cys Glu Pro Pro Cys Leu Cys Gly Pro Ala Pro Gly Ala Ala Cys Arg
             35                  40                  45

Val Asn Cys Ser Gly Arg Gly Leu Arg Thr Leu Gly Pro Ala Leu Arg
         50                  55                  60

Ile Pro Ala Asp Ala Thr Ala Leu Asp Val Ser His Asn Leu Leu Arg
 65                  70                  75                  80

Ala Leu Asp Val Gly Leu Leu Ala Asn Leu Ser Ala Leu Ala Glu Leu
                     85                  90                  95

Asp Ile Ser Asn Asn Lys Ile Ser Thr Leu Glu Glu Gly Ile Phe Ala
                100                 105                 110

Asn Leu Phe Asn Leu Ser Glu Ile Asn Leu Ser Gly Asn Pro Phe Glu
            115                 120                 125

Cys Asp Cys Gly Leu Ala Trp Leu Pro Arg Trp Ala Glu Glu Gln Gln
        130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                    165                 170                 175

Gly Glu Glu Tyr Val Ala Cys Leu Pro Asp Asn Ser Ser Gly Thr Val
                180                 185                 190

Ala Ala Val Ser Phe Ser Ala His Glu Gly Leu Leu Gln Pro Glu
            195                 200                 205

Ala Cys Ser Ala Phe Cys Phe Ser Thr Gly Gln Gly Leu Ala Ala Leu
        210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
370                 375                 380
```

```
Leu Glu Ala Ala Tyr Ser Ile Val Ala Leu Gly Glu Pro Ala Arg
385                 390                 395                 400

Ala Val His Pro Leu Cys Pro Ser Asp Thr Glu Ile Phe Pro Gly Asn
            405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
        435                 440                 445

Ser Pro Ala Val Gln Arg Phe Leu Val Ser Arg Val Thr Arg Cys Leu
450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
                500                 505                 510

Pro Thr Gly Trp Cys Asn Thr Asp Leu Cys Ser Ala Pro His Ser Tyr
            515                 520                 525

Val Cys Glu Leu Gln Pro Gly Gly Pro Val Gln Asp Ala Glu Asn Leu
530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
                580                 585                 590

Glu Phe Gly Thr Gln Glu Leu Arg Arg Pro Ala Gln Leu Arg Leu Gln
            595                 600                 605

Val Tyr Arg Leu Leu Ser Thr Ala Gly Thr Pro Glu Asn Gly Ser Glu
            610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
            660                 665                 670

Pro Gly Leu Pro Gly Ala Pro Tyr Ala Leu Trp Arg Glu Phe Leu Phe
            675                 680                 685

Ser Val Pro Ala Gly Pro Pro Ala Gln Tyr Ser Val Thr Leu His Gly
690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
                725                 730                 735

Gly Pro Arg Ala Pro Tyr Leu Ser Ala Asn Ala Ser Ser Trp Leu Pro
            740                 745                 750

His Leu Pro Ala Gln Leu Glu Gly Thr Trp Ala Cys Pro Ala Cys Ala
        755                 760                 765

Leu Arg Leu Leu Ala Ala Thr Glu Gln Leu Thr Val Leu Leu Gly Leu
770                 775                 780

Arg Pro Asn Pro Gly Leu Arg Leu Pro Gly Arg Tyr Glu Val Arg Ala
785                 790                 795                 800

Glu Val Gly Asn Gly Val Ser Arg His Asn Leu Ser Cys Ser Phe Asp
```

```
                     805                 810                 815
Val Val Ser Pro Val Ala Gly Leu Arg Val Ile Tyr Pro Ala Pro Arg
                820                 825                 830
Asp Gly Arg Leu Tyr Val Pro Thr Asn Gly Ser Ala Leu Val Leu Gln
            835                 840                 845
Val Asp Ser Gly Ala Asn Ala Thr Ala Thr Ala Arg Trp Pro Gly Gly
850                 855                 860
Ser Val Ser Ala Arg Phe Glu Asn Val Cys Pro Ala Leu Val Ala Thr
865                 870                 875                 880
Phe Val Pro Gly Cys Pro Trp Glu Thr Asn Asp Thr Leu Phe Ser Val
                885                 890                 895
Val Ala Leu Pro Trp Leu Ser Glu Gly Glu His Val Val Asp Val Val
                900                 905                 910
Val Glu Asn Ser Ala Ser Arg Ala Asn Leu Ser Leu Arg Val Thr Ala
            915                 920                 925
Glu Glu Pro Ile Cys Gly Leu Arg Ala Thr Pro Ser Pro Glu Ala Arg
            930                 935                 940
Val Leu Gln Gly Val Leu Val Arg Tyr Ser Pro Val Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
            980                 985                 990
Lys Leu Ser Leu Thr Ala Ser Asn His Val Ser Asn Val Thr Val Asn
            995                1000                1005
Tyr Asn Val Thr Val Glu Arg Met Asn Arg Met Gln Gly Leu Gln Val
        1010                1015                1020
Ser Thr Val Pro Ala Val Leu Ser Pro Asn Ala Thr Leu Ala Leu Thr
1025                1030                1035                1040
Ala Gly Val Leu Val Asp Ser Ala Val Glu Val Ala Phe Leu Trp Thr
            1045                1050                1055
Phe Gly Asp Gly Glu Gln Ala Leu His Gln Phe Gln Pro Pro Tyr Asn
            1060                1065                1070
Glu Ser Phe Pro Val Pro Asp Pro Ser Val Ala Gln Val Leu Val Glu
        1075                1080                1085
His Asn Val Met His Thr Tyr Ala Ala Pro Gly Glu Tyr Leu Leu Thr
        1090                1095                1100
Val Leu Ala Ser Asn Ala Phe Glu Asn Leu Thr Gln Gln Val Pro Val
1105                1110                1115                1120
Ser Val Arg Ala Ser Leu Pro Ser Val Ala Val Gly Val Ser Asp Gly
            1125                1130                1135
Val Leu Val Ala Gly Arg Pro Val Thr Phe Tyr Pro His Pro Leu Pro
        1140                1145                1150
Ser Pro Gly Gly Val Leu Tyr Thr Trp Asp Phe Gly Asp Gly Ser Pro
        1155                1160                1165
Val Leu Thr Gln Ser Gln Pro Ala Ala Asn His Thr Tyr Ala Ser Arg
        1170                1175                1180
Gly Thr Tyr His Val Arg Leu Glu Val Asn Asn Thr Val Ser Gly Ala
1185                1190                1195                1200
Ala Ala Gln Ala Asp Val Arg Val Phe Glu Glu Leu Arg Gly Leu Ser
                1205                1210                1215
Val Asp Met Ser Leu Ala Val Glu Gln Gly Ala Pro Val Val Val Ser
        1220                1225                1230
```

```
Ala Ala Val Gln Thr Gly Asp Asn Ile Thr Trp Thr Phe Asp Met Gly
            1235                1240                1245

Asp Gly Thr Val Leu Ser Gly Pro Glu Ala Thr Val Glu His Val Tyr
        1250                1255                1260

Leu Arg Ala Gln Asn Cys Thr Val Thr Val Gly Ala Ala Ser Pro Ala
1265                1270                1275                1280

Gly His Leu Ala Arg Ser Leu His Val Leu Val Phe Val Leu Glu Val
                1285                1290                1295

Leu Arg Val Glu Pro Ala Ala Cys Ile Pro Thr Gln Pro Asp Ala Arg
            1300                1305                1310

Leu Thr Ala Tyr Val Thr Gly Asn Pro Ala His Tyr Leu Phe Asp Trp
        1315                1320                1325

Thr Phe Gly Asp Gly Ser Ser Asn Thr Thr Val Arg Gly Cys Pro Thr
            1330                1335                1340

Val Thr His Asn Phe Thr Arg Ser Gly Thr Phe Pro Leu Ala Leu Val
1345                1350                1355                1360

Leu Ser Ser Arg Val Asn Arg Ala His Tyr Phe Thr Ser Ile Cys Val
                1365                1370                1375

Glu Pro Glu Val Gly Asn Val Thr Leu Gln Pro Glu Arg Gln Phe Val
            1380                1385                1390

Gln Leu Gly Asp Glu Ala Trp Leu Val Ala Cys Ala Trp Pro Pro Phe
        1395                1400                1405

Pro Tyr Arg Tyr Thr Trp Asp Phe Gly Thr Glu Glu Ala Ala Pro Thr
            1410                1415                1420

Arg Ala Arg Gly Pro Glu Val Thr Phe Ile Tyr Arg Asp Pro Gly Ser
1425                1430                1435                1440

Tyr Leu Val Thr Val Thr Ala Ser Asn Asn Ile Ser Ala Ala Asn Asp
                1445                1450                1455

Ser Ala Leu Val Glu Val Gln Glu Pro Val Leu Val Thr Ser Ile Lys
            1460                1465                1470

Val Asn Gly Ser Leu Gly Leu Glu Leu Gln Gln Pro Tyr Leu Phe Ser
        1475                1480                1485

Ala Val Gly Arg Gly Arg Pro Ala Ser Tyr Leu Trp Asp Leu Gly Asp
        1490                1495                1500

Gly Gly Trp Leu Glu Gly Pro Glu Val Thr His Ala Tyr Asn Ser Thr
1505                1510                1515                1520

Gly Asp Phe Thr Val Arg Val Ala Gly Trp Asn Glu Val Ser Arg Ser
                1525                1530                1535

Glu Ala Trp Leu Asn Val Thr Val Lys Arg Arg Val Arg Gly Leu Val
            1540                1545                1550

Val Asn Ala Ser Arg Thr Val Val Pro Leu Asn Gly Ser Val Ser Phe
                1555                1560                1565

Ser Thr Ser Leu Glu Ala Gly Ser Asp Val Arg Tyr Ser Trp Val Leu
        1570                1575                1580

Cys Asp Arg Cys Thr Pro Ile Pro Gly Gly Pro Thr Ile Ser Tyr Thr
1585                1590                1595                1600

Phe Arg Ser Val Gly Thr Phe Asn Ile Ile Val Thr Ala Glu Asn Glu
                1605                1610                1615

Val Gly Ser Ala Gln Asp Ser Ile Phe Val Tyr Val Leu Gln Leu Ile
            1620                1625                1630

Glu Gly Leu Gln Val Val Gly Gly Arg Tyr Phe Pro Thr Asn His
        1635                1640                1645
```

```
Thr Val Gln Leu Gln Ala Val Val Arg Asp Gly Thr Asn Val Ser Tyr
    1650                1655                1660

Ser Trp Thr Ala Trp Arg Asp Arg Gly Pro Ala Leu Ala Gly Ser Gly
1665            1670                1675                1680

Lys Gly Phe Ser Leu Thr Val Leu Glu Ala Gly Thr Tyr His Val Gln
                1685                1690                1695

Leu Arg Ala Thr Asn Met Leu Gly Ser Ala Trp Ala Asp Cys Thr Met
        1700                1705                1710

Asp Phe Val Glu Pro Val Gly Trp Leu Met Val Ala Ala Ser Pro Asn
            1715                1720                1725

Pro Ala Ala Val Asn Thr Ser Val Thr Leu Ser Ala Glu Leu Ala Gly
        1730                1735                1740

Gly Ser Gly Val Val Tyr Thr Trp Ser Leu Glu Gly Leu Ser Trp
1745                1750                1755                1760

Glu Thr Ser Glu Pro Phe Thr Thr His Ser Phe Pro Thr Pro Gly Leu
                1765                1770                1775

His Leu Val Thr Met Thr Ala Gly Asn Pro Leu Gly Ser Ala Asn Ala
                1780                1785                1790

Thr Val Glu Val Asp Val Gln Val Pro Val Ser Gly Leu Ser Ile Arg
        1795                1800                1805

Ala Ser Glu Pro Gly Gly Ser Phe Val Ala Ala Gly Ser Ser Val Pro
    1810                1815                1820

Phe Trp Gly Gln Leu Ala Thr Gly Thr Asn Val Ser Trp Cys Trp Ala
1825            1830                1835                1840

Val Pro Gly Gly Ser Ser Lys Arg Gly Pro His Val Thr Met Val Phe
                1845                1850                1855

Pro Asp Ala Gly Thr Phe Ser Ile Arg Leu Asn Ala Ser Asn Ala Val
            1860                1865                1870

Ser Trp Val Ser Ala Thr Tyr Asn Leu Thr Ala Glu Glu Pro Ile Val
        1875                1880                1885

Gly Leu Val Leu Trp Ala Ser Ser Lys Val Val Ala Pro Gly Gln Leu
    1890                1895                1900

Val His Phe Gln Ile Leu Leu Ala Ala Gly Ser Ala Val Thr Phe Arg
1905            1910                1915                1920

Leu Gln Val Gly Gly Ala Asn Pro Glu Val Leu Pro Gly Pro Arg Phe
                1925                1930                1935

Ser His Ser Phe Pro Arg Val Gly Asp His Val Val Ser Val Arg Gly
                1940                1945                1950

Lys Asn His Val Ser Trp Ala Gln Ala Gln Val Arg Ile Val Val Leu
        1955                1960                1965

Glu Ala Val Ser Gly Leu Gln Val Pro Asn Cys Cys Glu Pro Gly Ile
    1970                1975                1980

Ala Thr Gly Thr Glu Arg Asn Phe Thr Ala Arg Val Gln Arg Gly Ser
1985            1990                1995                2000

Arg Val Ala Tyr Ala Trp Tyr Phe Ser Leu Gln Lys Val Gln Gly Asp
                2005                2010                2015

Ser Leu Val Ile Leu Ser Gly Arg Asp Val Thr Tyr Thr Pro Val Ala
            2020                2025                2030

Ala Gly Leu Leu Glu Ile Gln Val Arg Ala Phe Asn Ala Leu Gly Ser
        2035                2040                2045

Glu Asn Arg Thr Leu Val Leu Glu Val Gln Asp Ala Val Gln Tyr Val
    2050                2055                2060

Ala Leu Gln Ser Gly Pro Cys Phe Thr Asn Arg Ser Ala Gln Phe Glu
```

```
2065                2070                2075                2080
Ala Ala Thr Ser Pro Ser Pro Arg Arg Val Ala Tyr His Trp Asp Phe
            2085                2090                2095
Gly Asp Gly Ser Pro Gly Gln Asp Thr Asp Glu Pro Arg Ala Glu His
            2100                2105                2110
Ser Tyr Leu Arg Pro Gly Asp Tyr Arg Val Gln Val Asn Ala Ser Asn
            2115                2120                2125
Leu Val Ser Phe Phe Val Ala Gln Ala Thr Val Thr Val Gln Val Leu
            2130                2135                2140
Ala Cys Arg Glu Pro Glu Val Asp Val Val Leu Pro Leu Gln Val Leu
2145                2150                2155                2160
Met Arg Arg Ser Gln Arg Asn Tyr Leu Glu Ala His Val Asp Leu Arg
            2165                2170                2175
Asp Cys Val Thr Tyr Gln Thr Glu Tyr Arg Trp Glu Val Tyr Arg Thr
            2180                2185                2190
Ala Ser Cys Gln Arg Pro Gly Arg Pro Ala Arg Val Ala Leu Pro Gly
            2195                2200                2205
Val Asp Val Ser Arg Pro Arg Leu Val Leu Pro Arg Leu Ala Leu Pro
            2210                2215                2220
Val Gly His Tyr Cys Phe Val Phe Val Val Ser Phe Gly Asp Thr Pro
2225                2230                2235                2240
Leu Thr Gln Ser Ile Gln Ala Asn Val Thr Val Ala Pro Glu Arg Leu
            2245                2250                2255
Val Pro Ile Ile Glu Gly Gly Ser Tyr Arg Val Trp Ser Asp Thr Arg
            2260                2265                2270
Asp Leu Val Leu Asp Gly Ser Glu Ser Tyr Asp Pro Asn Leu Glu Asp
            2275                2280                2285
Gly Asp Gln Thr Pro Leu Ser Phe His Trp Ala Cys Val Ala Ser Thr
            2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Glu Arg Leu Ala Ala Gly Val Glu Tyr
            2325                2330                2335
Thr Phe Ser Leu Thr Val Trp Lys Ala Gly Arg Lys Glu Glu Ala Thr
            2340                2345                2350
Asn Gln Thr Val Leu Ile Arg Ser Gly Arg Val Pro Ile Val Ser Leu
            2355                2360                2365
Glu Cys Val Ser Cys Lys Ala Gln Ala Val Tyr Glu Val Ser Arg Ser
            2370                2375                2380
Ser Tyr Val Tyr Leu Glu Gly Arg Cys Leu Asn Cys Ser Ser Gly Ser
2385                2390                2395                2400
Lys Arg Gly Arg Trp Ala Ala Arg Thr Phe Ser Asn Lys Thr Leu Val
            2405                2410                2415
Leu Asp Glu Thr Thr Thr Ser Thr Gly Ser Ala Gly Met Arg Leu Val
            2420                2425                2430
Leu Arg Arg Gly Val Leu Arg Asp Gly Glu Gly Tyr Thr Phe Thr Leu
            2435                2440                2445
Thr Val Leu Gly Arg Ser Gly Glu Glu Glu Gly Cys Ala Ser Ile Arg
            2450                2455                2460
Leu Ser Pro Asn Arg Pro Pro Leu Gly Gly Ser Cys Arg Leu Phe Pro
2465                2470                2475                2480
Leu Gly Ala Val His Ala Leu Thr Thr Lys Val His Phe Glu Cys Thr
            2485                2490                2495
```

```
Gly Trp His Asp Ala Glu Asp Ala Gly Ala Pro Leu Val Tyr Ala Leu
            2500                2505                2510

Leu Leu Arg Arg Cys Arg Gln Gly His Cys Glu Glu Phe Cys Val Tyr
        2515                2520                2525

Lys Gly Ser Leu Ser Ser Tyr Gly Ala Val Leu Pro Pro Gly Phe Arg
    2530                2535                2540

Pro His Phe Glu Val Gly Leu Ala Val Val Gln Asp Gln Leu Gly
2545                2550                2555                2560

Ala Ala Val Val Ala Leu Asn Arg Ser Leu Ala Ile Thr Leu Pro Glu
            2565                2570                2575

Pro Asn Gly Ser Ala Thr Gly Leu Thr Val Trp Leu His Gly Leu Thr
            2580                2585                2590

Ala Ser Val Leu Pro Gly Leu Leu Arg Gln Ala Asp Pro Gln His Val
            2595                2600                2605

Ile Glu Tyr Ser Leu Ala Leu Val Thr Val Leu Asn Glu Tyr Glu Arg
            2610                2615                2620

Ala Leu Asp Val Ala Ala Glu Pro Lys His Glu Arg Gln His Arg Ala
2625                2630                2635                2640

Gln Ile Arg Lys Asn Ile Thr Glu Thr Leu Val Ser Leu Arg Val His
            2645                2650                2655

Thr Val Asp Asp Ile Gln Gln Ile Ala Ala Ala Leu Ala Gln Cys Met
            2660                2665                2670

Gly Pro Ser Arg Glu Leu Val Cys Arg Ser Cys Leu Lys Gln Thr Leu
            2675                2680                2685

His Lys Leu Glu Ala Met Met Leu Ile Leu Gln Ala Glu Thr Thr Ala
            2690                2695                2700

Gly Thr Val Thr Pro Thr Ala Ile Gly Asp Ser Ile Leu Asn Ile Thr
2705                2710                2715                2720

Gly Asp Leu Ile His Leu Ala Ser Ser Asp Val Arg Ala Pro Gln Pro
            2725                2730                2735

Ser Glu Leu Gly Ala Glu Ser Pro Ser Arg Met Val Ala Ser Gln Ala
            2740                2745                2750

Tyr Asn Leu Thr Ser Ala Leu Met Arg Ile Leu Met Arg Ser Arg Val
            2755                2760                2765

Leu Asn Glu Glu Pro Leu Thr Leu Ala Gly Glu Glu Ile Val Ala Gln
    2770                2775                2780

Gly Lys Arg Ser Asp Pro Arg Ser Leu Leu Cys Tyr Gly Gly Ala Pro
2785                2790                2795                2800

Gly Pro Gly Cys His Phe Ser Ile Pro Glu Ala Phe Ser Gly Ala Leu
            2805                2810                2815

Ala Asn Leu Ser Asp Val Val Gln Leu Ile Phe Leu Val Asp Ser Asn
            2820                2825                2830

Pro Phe Pro Phe Gly Tyr Ile Ser Asn Tyr Thr Val Ser Thr Lys Val
            2835                2840                2845

Ala Ser Met Ala Phe Gln Thr Gln Ala Gly Ala Gln Ile Pro Ile Glu
            2850                2855                2860

Arg Leu Ala Ser Glu Arg Ala Ile Thr Val Lys Val Pro Asn Asn Ser
2865                2870                2875                2880

Asp Trp Ala Ala Arg Gly His Arg Ser Ser Ala Asn Ser Ala Asn Ser
            2885                2890                2895

Val Val Val Gln Pro Gln Ala Ser Val Gly Ala Val Val Thr Leu Asp
            2900                2905                2910
```

```
Ser Ser Asn Pro Ala Ala Gly Leu His Leu Gln Leu Asn Tyr Thr Leu
        2915                2920                2925

Leu Asp Gly His Tyr Leu Ser Glu Glu Pro Glu Pro Tyr Leu Ala Val
    2930                2935                2940

Tyr Leu His Ser Glu Pro Arg Pro Asn Glu His Asn Cys Ser Ala Ser
2945                2950                2955                2960

Arg Arg Ile Arg Pro Glu Ser Leu Gln Gly Ala Asp His Arg Pro Tyr
            2965                2970                2975

Thr Phe Phe Ile Ser Pro Gly Ser Arg Asp Pro Ala Gly Ser Tyr His
                2980                2985                2990

Leu Asn Leu Ser Ser His Phe Arg Trp Ser Ala Leu Gln Val Ser Val
            2995                3000                3005

Gly Leu Tyr Thr Ser Leu Cys Gln Tyr Phe Ser Glu Glu Asp Met Val
        3010                3015                3020

Trp Arg Thr Glu Gly Leu Leu Pro Leu Glu Glu Thr Ser Pro Arg Gln
3025                3030                3035                3040

Ala Val Cys Leu Thr Arg His Leu Thr Ala Phe Gly Ala Ser Leu Phe
                3045                3050                3055

Val Pro Pro Ser His Val Arg Phe Val Phe Pro Glu Pro Thr Ala Asp
            3060                3065                3070

Val Asn Tyr Ile Val Met Leu Thr Cys Ala Val Cys Leu Val Thr Tyr
        3075                3080                3085

Met Val Met Ala Ala Ile Leu His Lys Leu Asp Gln Leu Asp Ala Ser
    3090                3095                3100

Arg Gly Arg Ala Ile Pro Phe Cys Gly Gln Arg Gly Arg Phe Lys Tyr
3105                3110                3115                3120

Glu Ile Leu Val Lys Thr Gly Trp Gly Arg Gly Ser Gly Thr Thr Ala
                3125                3130                3135

His Val Gly Ile Met Leu Tyr Gly Val Asp Ser Arg Ser Gly His Arg
            3140                3145                3150

His Leu Asp Gly Asp Arg Ala Phe His Arg Asn Ser Leu Asp Ile Phe
        3155                3160                3165

Arg Ile Ala Thr Pro His Ser Leu Gly Ser Val Trp Lys Ile Arg Val
    3170                3175                3180

Trp His Asp Asn Lys Gly Leu Ser Pro Ala Trp Phe Leu Gln His Val
3185                3190                3195                3200

Ile Val Arg Asp Leu Gln Thr Ala Arg Ser Ala Phe Phe Leu Val Asn
                3205                3210                3215

Asp Trp Leu Ser Val Glu Thr Glu Ala Asn Gly Gly Leu Val Glu Lys
            3220                3225                3230

Glu Val Leu Ala Ala Ser Asp Ala Ala Leu Leu Arg Phe Arg Arg Leu
        3235                3240                3245

Leu Val Ala Glu Leu Gln Arg Gly Phe Phe Asp Lys His Ile Trp Leu
    3250                3255                3260

Ser Ile Trp Asp Arg Pro Pro Arg Ser Arg Phe Thr Arg Ile Gln Arg
3265                3270                3275                3280

Ala Thr Cys Cys Val Leu Leu Ile Cys Leu Phe Leu Gly Ala Asn Ala
                3285                3290                3295

Val Trp Tyr Gly Ala Val Gly Asp Ser Ala Tyr Ser Thr Gly His Val
            3300                3305                3310

Ser Arg Leu Ser Pro Leu Ser Val Asp Thr Val Ala Val Gly Leu Val
        3315                3320                3325

Ser Ser Val Val Val Tyr Pro Val Tyr Leu Ala Ile Leu Phe Leu Phe
```

```
              3330           3335           3340
Arg Met Ser Arg Ser Lys Val Ala Gly Ser Pro Ser Pro Thr Pro Ala
3345           3350           3355           3360
Gly Gln Gln Val Leu Asp Ile Asp Ser Cys Leu Asp Ser Val Leu
              3365           3370           3375
Asp Ser Ser Phe Leu Thr Phe Ser Gly Leu His Ala Glu Ala Phe Val
              3380           3385           3390
Gly Gln Met Lys Ser Asp Leu Phe Leu Asp Asp Ser Lys Ser Leu Val
              3395           3400           3405
Cys Trp Pro Ser Gly Glu Gly Thr Leu Ser Trp Pro Asp Leu Leu Ser
              3410           3415           3420
Asp Pro Ser Ile Val Gly Ser Asn Leu Arg Gln Leu Ala Arg Gly Gln
3425           3430           3435           3440
Ala Gly His Gly Leu Gly Pro Glu Glu Asp Gly Phe Ser Leu Ala Ser
              3445           3450           3455
Pro Tyr Ser Pro Ala Lys Ser Phe Ser Ala Ser Asp Glu Asp Leu Ile
              3460           3465           3470
Gln Gln Val Leu Ala Glu Gly Val Ser Ser Pro Ala Thr Gln Asp
              3475           3480           3485
Thr His Met Glu Thr Asp Leu Leu Ser Ser Leu Ser Ser Thr Pro Gly
              3490           3495           3500
Glu Lys Thr Glu Thr Leu Ala Leu Gln Arg Leu Gly Glu Leu Gly Pro
3505           3510           3515           3520
Pro Ser Pro Gly Leu Asn Trp Glu Gln Pro Gln Ala Ala Arg Leu Ser
              3525           3530           3535
Arg Thr Gly Leu Val Glu Gly Leu Arg Lys Arg Leu Leu Pro Ala Trp
              3540           3545           3550
Cys Ala Ser Leu Ala His Gly Leu Ser Leu Leu Leu Val Ala Val Ala
              3555           3560           3565
Val Ala Val Ser Gly Trp Val Gly Ala Ser Phe Pro Pro Gly Val Ser
              3570           3575           3580
Val Ala Trp Leu Leu Ser Ser Ser Ala Ser Phe Leu Ala Ser Phe Leu
3585           3590           3595           3600
Gly Trp Glu Pro Leu Lys Val Leu Leu Glu Ala Leu Tyr Phe Ser Leu
              3605           3610           3615
Val Ala Lys Arg Leu His Pro Asp Glu Asp Asp Thr Leu Val Glu Ser
              3620           3625           3630
Pro Ala Val Thr Pro Val Ser Ala Arg Val Pro Arg Val Arg Pro Pro
              3635           3640           3645
His Gly Phe Ala Leu Phe Leu Ala Lys Glu Glu Ala Arg Lys Val Lys
              3650           3655           3660
Arg Leu His Gly Met Leu Arg Ser Leu Leu Val Tyr Met Leu Phe Leu
3665           3670           3675           3680
Leu Val Thr Leu Leu Ala Ser Tyr Gly Asp Ala Ser Cys His Gly His
              3685           3690           3695
Ala Tyr Arg Leu Gln Ser Ala Ile Lys Gln Glu Leu His Ser Arg Ala
              3700           3705           3710
Phe Leu Ala Ile Thr Arg Ser Glu Glu Leu Trp Pro Trp Met Ala His
              3715           3720           3725
Val Leu Leu Pro Tyr Val His Gly Asn Gln Ser Ser Pro Glu Leu Gly
              3730           3735           3740
Pro Pro Arg Leu Arg Gln Val Arg Leu Gln Glu Ala Leu Tyr Pro Asp
3745           3750           3755           3760
```

-continued

```
Pro Pro Gly Pro Arg Val His Thr Cys Ser Ala Ala Gly Gly Phe Ser
            3765                3770                3775

Thr Ser Asp Tyr Asp Val Gly Trp Glu Ser Pro His Asn Gly Ser Gly
            3780                3785                3790

Thr Trp Ala Tyr Ser Ala Pro Asp Leu Leu Gly Ala Trp Ser Trp Gly
            3795                3800                3805

Ser Cys Ala Val Tyr Asp Ser Gly Gly Tyr Val Gln Glu Leu Gly Leu
            3810                3815                3820

Ser Leu Glu Glu Ser Arg Asp Arg Leu Arg Phe Leu Gln Leu His Asn
3825                3830                3835                3840

Trp Leu Asp Asn Arg Ser Arg Ala Val Phe Leu Glu Leu Thr Arg Tyr
            3845                3850                3855

Ser Pro Ala Val Gly Leu His Ala Ala Val Thr Leu Arg Leu Glu Phe
            3860                3865                3870

Pro Ala Ala Gly Arg Ala Leu Ala Ala Leu Ser Val Arg Pro Phe Ala
            3875                3880                3885

Leu Arg Arg Leu Ser Ala Gly Leu Ser Leu Pro Leu Leu Thr Ser Val
            3890                3895                3900

Cys Leu Leu Leu Phe Ala Val His Phe Ala Val Ala Glu Ala Arg Thr
3905                3910                3915                3920

Trp His Arg Glu Gly Arg Trp Arg Val Leu Arg Leu Gly Ala Trp Ala
            3925                3930                3935

Arg Trp Leu Leu Val Ala Leu Thr Ala Ala Thr Ala Leu Val Arg Leu
            3940                3945                3950

Ala Gln Leu Gly Ala Ala Asp Arg Gln Trp Thr Arg Phe Val Arg Gly
            3955                3960                3965

Arg Pro Arg Arg Phe Thr Ser Phe Asp Gln Val Ala Gln Leu Ser Ser
            3970                3975                3980

Ala Ala Arg Gly Leu Ala Ala Ser Leu Leu Phe Leu Leu Val Lys
3985                3990                3995                4000

Ala Ala Gln Gln Leu Arg Phe Val Arg Gln Trp Ser Val Phe Gly Lys
            4005                4010                4015

Thr Leu Cys Arg Ala Leu Pro Glu Leu Leu Gly Val Thr Leu Gly Leu
            4020                4025                4030

Val Val Leu Gly Val Ala Tyr Ala Gln Leu Ala Ile Leu Leu Val Ser
            4035                4040                4045

Ser Cys Val Asp Ser Leu Trp Ser Val Ala Gln Ala Leu Leu Val Leu
            4050                4055                4060

Cys Pro Gly Thr Gly Leu Ser Thr Leu Cys Pro Ala Glu Ser Trp His
4065                4070                4075                4080

Leu Ser Pro Leu Leu Cys Val Gly Leu Trp Ala Leu Arg Leu Trp Gly
            4085                4090                4095

Ala Leu Arg Leu Gly Ala Val Ile Leu Arg Trp Arg Tyr His Ala Leu
            4100                4105                4110

Arg Gly Glu Leu Tyr Arg Pro Ala Trp Glu Pro Gln Asp Tyr Glu Met
            4115                4120                4125

Val Glu Leu Phe Leu Arg Arg Leu Arg Leu Trp Met Gly Leu Ser Lys
            4130                4135                4140

Val Lys Glu Phe Arg His Lys Val Arg Phe Glu Gly Met Glu Pro Leu
4145                4150                4155                4160

Pro Ser Arg Ser Ser Arg Gly Ser Lys Val Ser Pro Asp Val Pro Pro
            4165                4170                4175
```

-continued

```
Pro Ser Ala Gly Ser Asp Ala Ser His Pro Ser Thr Ser Ser Ser Gln
            4180            4185            4190

Leu Asp Gly Leu Ser Val Ser Leu Gly Arg Leu Gly Thr Arg Cys Glu
        4195            4200            4205

Pro Glu Pro Ser Arg Leu Gln Ala Val Phe Glu Ala Leu Leu Thr Gln
    4210            4215            4220

Phe Asp Arg Leu Asn Gln Ala Thr Glu Asp Val Tyr Gln Leu Glu Gln
4225            4230            4235            4240

Gln Leu His Ser Leu Gln Gly Arg Arg Ser Ser Arg Ala Pro Ala Gly
                4245            4250            4255

Ser Ser Arg Gly Pro Ser Pro Gly Leu Arg Pro Ala Leu Pro Ser Arg
            4260            4265            4270

Leu Ala Arg Ala Ser Arg Gly Val Asp Leu Ala Thr Gly Pro Ser Arg
        4275            4280            4285

Thr Pro Leu Arg Ala Lys Asn Lys Val His Pro Ser Ser Thr
    4290            4295            4300
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CACGACCTGT CCCAGGCAT                                      19

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTGGCGGGCG AGGAGAT                                        17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTTTGACAAG CACATCT                                        17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CAACTGGCTG GACAACA                     17

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGGACCTGTC CAGGCATC                    18

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTGCACTGAC CTCACGCATG T                21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ACGTTGGGCT CCTGGCGAAC C                21

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGGTCAACGT GGGCCTCCAA GTAGT            25

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCGCTTTGCA GACGGTAGGC G                21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AGCGCAACTA CTTGGAGGCC C                                              21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GCCAAAGGGA AAGGGATTGG A                                              21

(2) INFORMATION FOR SEQ ID NO:17:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:17:

Cys Ser Arg Thr Pro Leu Arg Ala Lys Asn Lys Val His Pro Ser Ser
1               5                   10                  15

Thr (2) INFORMATION FOR SEQ ID NO:18:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GGAAACAGGT TTGGAGAGGT GACACGACCT GTCCCAGGCA TCACAGCCAG GACAGGACCT     60

GTCCAGGCAT CACAGCCGGG ATGTGCATAG CAGGGGTTTG GAACTATGAG GTGCCCAGGA    120

CCCAGGGTTG GATTGAAAAG GGCGCAGGGG ACTAAGATAA                         160

(2) INFORMATION FOR SEQ ID NO:19:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
GGAAACAGGT TTGGAGAGGT GACACGACCT GTCCCAGGCA TCACAGCCGG GATGTGCATA      60

GCAGGGGTTT GGAACTATGA GGTGCCCAGG ACCCAGGGTT GGATTGAAAA GGGCGCAGGG     120

GACTAAGATA A                                                          131
```

(2) INFORMATION FOR SEQ ID NO:20:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:20:

```
CGC CCG CGC CGC TTC ACT AGC TTC GAC CAG GTG GCG CAC GTG AGC TCC       48
Arg Pro Arg Arg Phe Thr Ser Phe Asp Gln Val Ala His Val Ser Ser
 1               5                  10                  15

GCA GCC CGT GGC                                                       60
Ala Ala Arg Gly
            20
```

(2) INFORMATION FOR SEQ ID NO:21:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:21:

```
Arg Pro Arg Arg Phe Thr Ser Phe Asp Gln Val Ala His Val Ser Ser
 1               5                  10                  15

Ala Ala Arg Gly
            20
```

(2) INFORMATION FOR SEQ ID NO:22:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..60

(xi) SEQUENCE DESCRIPTION: SEQ ID NO:22:

```
CGC CCG CGC CGC TTC ACT AGC TTC GAC CAG GTG GCG CAG CTG AGC TCC       48
Arg Pro Arg Arg Phe Thr Ser Phe Asp Gln Val Ala Gln Leu Ser Ser
 1               5                  10                  15

GCA GCC CGT GGC                                                       60
Ala Ala Arg Gly
            20
```

(2) INFORMATION FOR SEQ ID NO:23:

(i) SEQUENCE CHARACTERISTICS:

(A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO:23:

Arg Pro Arg Arg Phe Thr Ser Phe Asp Gln Val Ala Gln Leu Ser Ser
1               5                   10                  15

Ala Ala Arg Gly
            20

(2) INFORMATION FOR SEQ ID NO:24:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..60

(xi) SEQUENCE DESCRIPTION: SEQ ID NO:24:

GCT GCC CAG CAC GTA CGC TTC GTG CGC CAG TGG TCC GTC TTT GGC AAG        48
Ala Ala Gln His Val Arg Phe Val Arg Gln Trp Ser Val Phe Gly Lys
1               5                   10                  15

ACA TTA TGC CGA                                                        60
Thr Leu Cys Arg
            20

(2) INFORMATION FOR SEQ ID NO:25:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO:25:

Ala Ala Gln His Val Arg Phe Val Arg Gln Trp Ser Val Phe Gly Lys
1               5                   10                  15

Thr Leu Cys Arg
            20

(2) INFORMATION FOR SEQ ID NO:26:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..60

(xi) SEQUENCE DESCRIPTION: SEQ ID NO:26:

GCT GCC CAG CAG CTA CGC TTC GTG CGC CAG TGG TCC GTC TTT GGC AAG        48
Ala Ala Gln Gln Leu Arg Phe Val Arg Gln Trp Ser Val Phe Gly Lys
1               5                   10                  15

ACA TTA TGC CGA                                                        60

(2) INFORMATION FOR SEQ ID NO:27:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:27:

```
Ala Ala Gln Gln Leu Arg Phe Val Arg Gln Trp Ser Val Phe Gly Lys
 1               5                  10                  15
Thr Leu Cys Arg
            20
```

(2) INFORMATION FOR SEQ ID NO:28:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..81

(xi) SEQUENCE DESCRIPTION: SEQ ID NO:28:

```
CTG GCC ACT GGC CCC AGC AGG ACA CCT TCG GGC CAA GAA CAA GGT CCA      48
Leu Ala Thr Gly Pro Ser Arg Thr Pro Ser Gly Gln Glu Gln Gly Pro
 1               5                  10                  15
CCC CAG CAG CAC TTA GTC CTC CTT CCT GGC GGG                          81
Pro Gln Gln His Leu Val Leu Leu Pro Gly Gly
                20                  25
```

(2) INFORMATION FOR SEQ ID NO:29:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:29:

```
Leu Ala Thr Gly Pro Ser Arg Thr Pro Ser Gly Gln Glu Gln Gly Pro
 1               5                  10                  15
Pro Gln Gln His Leu Val Leu Leu Pro Gly Gly
                20                  25
```

(2) INFORMATION FOR SEQ ID NO:30:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..64

(xi) SEQUENCE DESCRIPTION: SEQ ID NO:30:

```
CTG GCC ACT GGC CCC AGC AGG ACA CCC CTT CGG GCC AAG AAC AAG GTC           48
Leu Ala Thr Gly Pro Ser Arg Thr Pro Leu Arg Ala Lys Asn Lys Val
 1               5                  10                  15

CAC CCC AGC AGC ACT T AGTCCTCCTT CCTGGCG                                  81
His Pro Ser Ser Thr
             20
```

(2) INFORMATION FOR SEQ ID NO:31:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:31:

```
Leu Ala Thr Gly Pro Ser Arg Thr Pro Leu Arg Ala Lys Asn Lys Val
 1               5                  10                  15

His Pro Ser Ser Thr
             20
```

(2) INFORMATION FOR SEQ ID NO:32:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:32:

```
Ala Leu Thr His Gly His Ser Leu Leu Arg Asp Val Ser His Asn Leu
 1               5                  10                  15

Leu Arg Ala Leu Asp Val Gly Leu Leu Ala Asn Leu Ser Ala Leu Ala
                20                  25                  30

Glu Leu
```

(2) INFORMATION FOR SEQ ID NO:33:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:33:

```
Leu His Gly Leu Lys Ala Leu Gly His Leu Asp Leu Ser Gly Asn Arg
 1               5                  10                  15

Leu Arg Lys Leu Pro Pro Gly Leu Leu Ala Asn Phe Thr Leu Leu Arg
                20                  25                  30

Thr Leu
```

(2) INFORMATION FOR SEQ ID NO:34:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:34:

```
Pro Ala Leu Pro Ala Arg Thr Arg His Leu Leu Leu Ala Asn Asn Ser
1               5                   10                  15

Leu Gln Ser Val Pro Pro Gly Ala Phe Asp His Leu Pro Gln Leu Gln
                20                  25                  30

Thr Leu
```

(2) INFORMATION FOR SEQ ID NO:35:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:35:

```
Gly Gln Thr Leu Pro Ala Leu Thr Val Leu Asp Val Ser Phe Asn Arg
1               5                   10                  15

Leu Thr Ser Leu Pro Leu Gly Ala Leu Arg Gly Leu Gly Glu Leu Gln
                20                  25                  30

Glu Leu
```

(2) INFORMATION FOR SEQ ID NO:36:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:36:

```
Thr Ala Phe Pro Val Asp Thr Thr Glu Leu Val Leu Thr Gly Asn Asn
1               5                   10                  15

Leu Thr Ala Leu Pro Pro Gly Leu Leu Asp Ala Leu Pro Ala Leu Arg
                20                  25                  30

Thr Ala
```

(2) INFORMATION FOR SEQ ID NO:37:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:37:

```
Leu Glu His Gln Val Asn Leu Leu Ser Leu Asp Leu Ser Asn Asn Ala
1               5                   10                  15

Leu Thr His Leu Pro Asp Ser Leu Phe Ala His Thr Thr Asn Leu Thr
                20                  25                  30

Asp Leu
```

(2) INFORMATION FOR SEQ ID NO:38:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:38:

Ile Arg His Leu Arg Ser Leu Thr Arg Leu Asp Leu Ser Asn Asn Gln
1               5                  10                  15

Ile Thr Ile Leu Ser Asn Tyr Thr Phe Ala Asn Leu Thr Lys Leu Ser
                20                  25                  30

Thr Leu (2) INFORMATION FOR SEQ ID NO:39:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:39:

Phe Gly Asn Met Pro His Leu Gln Trp Leu Asp Leu Ser Tyr Asn Trp
1               5                  10                  15

Ile His Glu Leu Asp Phe Asp Ala Phe Lys Asn Thr Lys Gln Leu Gln
                20                  25                  30

Leu Val (2) INFORMATION FOR SEQ ID NO:40:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:40:

Leu Asp Leu Ser Asn Leu Thr Leu Pro Gly Leu Leu Ala Leu Leu Thr
1               5                  10                  15

Leu (2) INFORMATION FOR SEQ ID NO:41:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:41:

Gly Pro Gln His Leu Pro Leu Pro Cys Arg Asn Leu Ser Gly Asn Pro
1               5                  10                  15

Phe Glu Cys Asp Cys Gly Leu Ala Trp Leu Pro Arg Trp Ala Glu Glu
                20                  25                  30

(2) INFORMATION FOR SEQ ID NO:42:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:42:

Gln Pro Asn Trp Asp Met Arg Asp Gly Phe Asp Ile Ser Gly Asn Pro
1               5                  10                  15

```
Trp Ile Cys Asp Gln Asn Leu Ser Asp Leu Tyr Arg Trp Leu Gln Ala
            20                  25                  30
```

(2) INFORMATION FOR SEQ ID NO:43:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:43:

```
Thr Val Gln Gly Leu Ser Leu Gln Glu Leu Val Leu Ser Gly Asn Pro
1               5                   10                  15

Leu His Cys Ser Cys Ala Leu Arg Trp Leu Gln Arg Trp Glu Glu Glu
            20                  25                  30
```

(2) INFORMATION FOR SEQ ID NO:44:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:44:

```
Phe Asp His Leu Pro Gln Leu Gln Thr Leu Asp Val Thr Gln Asn Pro
1               5                   10                  15

Trp His Cys Asp Cys Ser Leu Thr Tyr Leu Arg Leu Trp Leu Glu Asp
            20                  25                  30
```

(2) INFORMATION FOR SEQ ID NO:45:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:45:

```
Phe Phe Gly Ser His Leu Leu Pro Phe Ala Phe Leu His Gly Asn Pro
1               5                   10                  15

Trp Leu Cys Asn Cys Glu Ile Leu Tyr Phe Arg Arg Trp Leu Gln Asp
            20                  25                  30
```

(2) INFORMATION FOR SEQ ID NO:46:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:46:

```
Leu Asp Ala Leu Pro Ala Leu Arg Thr Ala His Leu Gly Ala Asn Pro
1               5                   10                  15

Trp Arg Cys Asp Cys Arg Leu Val Pro Leu Arg Ala Trp Leu Ala Gly
            20                  25                  30
```

(2) INFORMATION FOR SEQ ID NO:47:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:47:

```
Leu Asn Arg Thr Met Lys Trp Arg Ser Val Lys Leu Ser Gly Asn Pro
1               5                   10                  15

Trp Met Cys Asp Cys Thr Ala Lys Pro Leu Leu Leu Phe Thr Gln Asp
            20                  25                  30
```

(2) INFORMATION FOR SEQ ID NO:48:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:48:

```
Phe Glu Asp Leu Lys Ser Leu Thr His Ile Ala Leu Gly Ser Asn Pro
1               5                   10                  15

Leu Tyr Cys Asp Cys Gly Leu Lys Trp Phe Ser Asp Trp Ile Lys Leu
            20                  25                  30
```

(2) INFORMATION FOR SEQ ID NO:49:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:49:

```
Leu Leu Ser Gly Asn Pro Trp Cys Asp Cys Leu Trp Leu Arg Trp
1               5                   10                  15
```

(2) INFORMATION FOR SEQ ID NO:50:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:50:

```
Thr Ala Thr Arg Trp Asp Phe Gly Asp Gly Ser Ala Glu Val Asp Ala
1               5                   10                  15

Ala Gly Pro Ala Ala Ser His Arg Tyr Val Leu Pro Gly Arg Tyr His
            20                  25                  30

Val Thr Ala
        35
```

(2) INFORMATION FOR SEQ ID NO:51:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:51:

Val Leu Tyr Thr Trp Asp Phe Gly Asp Gly Ser Pro Val Leu Thr Gln
1               5                  10                 15

Ser Gln Pro Ala Ala Asn His Thr Tyr Ala Ser Arg Gly Thr Tyr His
            20                  25                  30

Val Arg Leu
        35

(2) INFORMATION FOR SEQ ID NO:52:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:52:

Val Ala Tyr His Trp Asp Phe Gly Asp Gly Ser Pro Gly Gln Asp Thr
1               5                  10                 15

Asp Glu Pro Arg Ala Glu His Ser Tyr Leu Arg Pro Gly Asp Tyr Arg
            20                  25                  30

Val Gln Val
        35

(2) INFORMATION FOR SEQ ID NO:53:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:53:

Leu Ser Tyr Thr Trp Asp Phe Gly Asp Ser Ser Gly Thr Leu Ile Ser
1               5                  10                 15

Arg Ala Pro Val Val Thr His Thr Tyr Leu Glu Pro Gly Pro Val Thr
            20                  25                  30

Ala Gln Val
        35

(2) INFORMATION FOR SEQ ID NO:54:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:54:

Leu Ser Tyr Thr Trp Asp Phe Gly Asp Ser Thr Gly Thr Leu Ile Ser
1               5                  10                 15

Arg Ala Leu Thr Val Thr His Thr Tyr Leu Glu Ser Gly Pro Val Thr
            20                  25                  30

Ala Gln Val
        35

(2) INFORMATION FOR SEQ ID NO:55:

(i) SEQUENCE CHARACTERISTICS:
        (A) LENGTH: 22 amino acids

-continued

```
            (B) TYPE: amino acid
            (D) TOPOLOGY: linear (ii) MOLECULE TYPE: peptide (xi) SEQUENCE DESCRIPTION: SEQ ID NO:55:

Tyr Thr Trp Asp Phe Gly Asp Gly Ser Leu Pro Ala His Thr Tyr Leu
1               5                   10                  15

Pro Gly Tyr Val Gln Val
            20

(2) INFORMATION FOR SEQ ID NO:56:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:56:

ATCTCCTCGC CCGCCAG                                                17

(2) INFORMATION FOR SEQ ID NO:57:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:57:

AGATGTGCTT GTCAAAG                                                17

(2) INFORMATION FOR SEQ ID NO:58:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:58:

TGTTGTCCAG CCAGTTG                                                17
```